United States Patent
Stansfield et al.

(10) Patent No.: US 11,136,311 B2
(45) Date of Patent: Oct. 5, 2021

(54) HETEROAROMATIC DERIVATIVES AS NIK INHIBITORS

(71) Applicant: Janssen Pharmaceutica NV, Beerse (BE)

(72) Inventors: Ian Stansfield, Issy-les Moulineaux (FR); Olivier Alexis Georges Querolle, Issy-les Moulineaux (FR); Yannick Aime Eddy Ligny, Issy-les Moulineaux (FR); Gerhard Max Gross, Beerse (BE); Edgar Jacoby, Beerse (BE); Lieven Meerpoel, Beerse (BE); Simon Richard Green, Harlow (GB); George Hynd, Harlow (GB); Janusz Jozef Kulagowski, Harlow (GB); Calum Macleod, Harlow (GB); Samuel Edward Mann, Harlow (GB)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 16/309,059

(22) PCT Filed: Jun. 29, 2017

(86) PCT No.: PCT/EP2017/066120
§ 371 (c)(1),
(2) Date: Dec. 11, 2018

(87) PCT Pub. No.: WO2018/002217
PCT Pub. Date: Jan. 4, 2018

(65) Prior Publication Data
US 2019/0359598 A1   Nov. 28, 2019

(30) Foreign Application Priority Data

Jun. 30, 2016   (EP) .................................... 16177104

(51) Int. Cl.
C07D 403/14 (2006.01)
C07D 405/12 (2006.01)
C07D 417/14 (2006.01)

(52) U.S. Cl.
CPC ......... *C07D 403/14* (2013.01); *C07D 405/12* (2013.01); *C07D 417/14* (2013.01)

(58) Field of Classification Search
CPC .................................................. C07D 403/14
See application file for complete search history.

(56) References Cited

U.S. PATENT DOCUMENTS

2019/0119299 A1   4/2019 Stansfield et al.

FOREIGN PATENT DOCUMENTS

| JP | 2003511378 | 3/2003 |
|---|---|---|
| JP | 2014510794 A | 5/2014 |
| WO | WO 2001/025220 A1 | 4/2001 |
| WO | WO-0160816 A1 | 8/2001 |
| WO | WO-0164643 A2 | 9/2001 |
| WO | WO-02079197 A1 | 10/2002 |
| WO | WO-02102313 A2 | 12/2002 |
| WO | WO-03030909 A1 | 4/2003 |
| WO | WO-2009158011 A1 | 12/2009 |
| WO | WO-2009158571 A1 | 12/2009 |
| WO | WO-2010042337 A1 | 4/2010 |
| WO | WO-2011022440 A2 | 2/2011 |
| WO | WO-2011153553 A2 | 12/2011 |
| WO | WO-2012016217 A1 | 2/2012 |
| WO | WO 2012/142329 A1 | 10/2012 |
| WO | WO-2014174021 A1 | 10/2014 |
| WO | WO-2015030847 A1 | 3/2015 |
| WO | WO-2015044267 A1 | 4/2015 |
| WO | WO-2015044269 A1 | 4/2015 |
| WO | WO-2015154039 A2 | 10/2015 |
| WO | WO-2015176135 A1 | 11/2015 |
| WO | WO-2016022645 A1 | 2/2016 |
| WO | WO 2016/049211 A1 | 3/2016 |
| WO | WO-2017114510 A1 | 7/2017 |
| WO | WO-2017125530 A1 | 7/2017 |
| WO | WO-2017125534 A1 | 7/2017 |
| WO | WO-2017161028 A1 | 9/2017 |
| WO | WO-2018002217 A1 | 1/2018 |
| WO | WO-2018002219 A1 | 1/2018 |

OTHER PUBLICATIONS

Pinedo et al. (2000).*
McMahon et al. (2000).*
Allen et al. NLRP12 suppresses colon inflammation and tumorigenesis through the negative regulation of noncanonical NF-kB signaling. Immunity. 36: 742-754 (2012).
Annuziata et al. Frequent engagement of the classical and alternative NF-kB pathways by diverse genetic abnormalities in multiple myeloma. Cancer Cell. 12: 115-130 (2007).
Aya et al. NF-κB-inducing kinase controls lymphocyte and osteoclast activities in inflammatory arthritis. J. Clin. Invest. 115: 1848-1854 (2005).
Bhattacharyya et al. Tumor necrosis factor alpha-induced inflammation is increased but apoptosis is inhibited by common food additive carrageenan. J Biol. Chem. 285: 39511-39522 (2011).
Bitar et al. Inflammation and apoptosis in aortic tissues of aged type II diabetes: Amelioration with α-lipoic acid through phosphatidylinositol 3-kinase/Akt-dependent mechanism. Life Sci. 86: 844-853 (2010).
Bushell et al., Genetic inactivation of TRAF3 in canine and human B-cell lymphoma. Blood. 125: 999-1005 (2015).

(Continued)

*Primary Examiner* — Paul V Ward

(57) ABSTRACT

The present invention relates to pharmaceutical agents useful for therapy and/or prophylaxis in a mammal, and in particular to inhibitors of NF-κB-inducing kinase (NIK—also known as MAP3K14) useful for treating diseases such as cancer, inflammatory disorders, metabolic disorders and autoimmune disorders. The invention is also directed to pharmaceutical compositions comprising such compounds, and to the use of such compounds or pharmaceutical compositions for the prevention or treatment of diseases such as cancer, inflammatory disorders, metabolic disorders including obesity and diabetes, and autoimmune disorders.

15 Claims, No Drawings

(56) References Cited

OTHER PUBLICATIONS

Cancer [online]; Retrieved from the Internet, URL: http://www.nim.nih.gov/medlineplus/cancer.html (2007).
Choudhary et al. NF-kB-Inducing Kinase (NIK) mediates skeletal muscle insulin resistance: blockade by adiponectin. Endocrinology. 152: 3622-3627 (2011).
Chung et al. NF-kB Inducing Kinase, NIK mediates cigarette smoke/ TNFa-induced histone acetylation and inflammation through differential activation of IKKs. PLoS One. 6(8): e23488. doi:10.1371/journal.pone.0023488 (2011).
Demchenko et al. Classical and/or alternative NF-κB pathway activation in multiple myeloma. Blood. 115: 3541-3552 (2010).
Gennaro et al. Remington's Pharmaceutical Sciences (18th ed., Mack Publishing Company, 1990, see especially Part 8 : Pharmaceutical preparations and their Manufacture (1990).
Golub et al.: Molecular Classification of Cancer: Class Discovery and Class Prediction by Gene Expression Monitoring; Science 286; 531-537 (1999).
Hughes et al., 4-Aryl-5-cyano-2-aminopyrimidines as VEGF-R2 inhibitors: synthesis and biological evaluation.Bioorg Med Chem Lett. 17(12):3266-3270 (2007).
International Application No. PCT/EP2017/066120 International Preliminary Report on Patentability dated Jan. 1, 2019.
Keats et al. Promiscuous mutations activate the noncanonical NF-kB pathway in multiple myeloma. Cancer Cell. 12: 131-144 (2007).
Lala et al.: Role of nitric oxide in tumor progression: Lessons from experimental tumors; Cancer and Metastasis Reviews; 17; 91-106 (1999).
Nishina et al. NIK is involved in constitutive activation of the alternative NF-jB pathway and proliferation of pancreatic cancer cells. Biochemical and Biophysical Research Communications. 388: 96-101 (2009).
Pham et al. Constitutive BR3 receptor signaling in diffuse, large B-cell lymphomas stabilizes nuclear factor-B-inducing kinase while activating both canonical and alternative nuclear factor-B pathways. Blood. 117: 200-210 (2011).
Rahal et al., Pharmacological and genomic profiling identifies NF-κB-targeted treatment strategies for mantle cell lymphoma. Nature Medicine. 20(1): 87-92 (2014).
Ranuncolo et al. Hodgkin lymphoma requires stabilized NIK and constitutive RelB expression for survival. Blood First Edition Paper. DOI 10.1182/blood-2012-01-405951; 120(18): 3756-3763 (2012).
Rosebeck et al. Cleavage of NIK by the API2-MALT1 fusion oncoprotein leads to noncanonical NF-kB activation. Science. 331: 468-472 (2011).
Saitoh et al. Overexpressed NF-B-inducing kinase contributes to the tumorigenesis of adult T-cell leukemia and Hodgkin Reed-Sternberg cells. Blood. 111: 5118-5129 (2008).
Shuto et al. Activation of NF-kB by nontypeable Hemophilus influenzae is mediated by toll-like receptor 2-TAK1-dependent NIK-IKKayb-IkBa and MKK3y6-p38 MAP kinase signaling pathways in epithelial cells. PNAS. 98: 8774-8779 (2001).
International Application No. PCT/EP2017/066125 International Preliminary Report on Patentability dated Jan. 1, 2019.
PCT/EP2017/066125 International Search Report and Written Opinion dated Jul. 27, 2017.
PCT/EP2017/051150 International Preliminary Report on Patentability dated Jul. 24, 2018.
PCT/EP2017/051150 International Search Report and Written Opinion dated Mar. 2, 2017.
PCT/EP2017/051160 International Preliminary Report on Patentability dated Jul. 24, 2018.
PCT/EP2017/051160 International Search Report and Written Opinion dated Mar. 9, 2017.
PCT/EP2017/066120 International Search Report and Written Opinion dated Aug. 23, 2017.
Thu and Richmond, NF-κB inducing kinase: a key regulator in the immune system and in cancer. Cytokine Growth F. R. 21: 213-226 (2010).
Thu et al. NF-kB inducing kinase (NIK) modulates melanoma tumorigenesis by regulating expression of pro-survival factors through the b-catenin pathway. Oncogene. 31(20), 2580-2592 (2012).
U.S. Appl. No. 16/309,080 Office Action dated May 29, 2019.
Wixted et al. A model to identify novel targets involved in oxidative stress-induced apoptosis in human lung epithelial cells by RNA interference. Toxicology in Vitro. 24: 310-318 (2010).
Yamamoto et al. Epigenetic alteration of the NF-kB-inducing kinase (NIK) gene is involved in enhanced NIK expression in basal-like breast cancer. Cancer Science. 101: 2391-2397 (2010).
Yang et al. NIK stabilization in osteoclasts results in osteoporosis and enhanced inflammatory osteolysis. PLoS One. 5(11): e15383. doi:10.1371/journal.pone.0015383 (2010).
Zhao et al. NF-κB-Inducing kinase increases renal tubule epithelial inflammation associated with diabetes. Exp. Diabetes Res. 2011: 1-9 (2011).
F. Herrington, et al., "Modulation of NF-κB Signaling as a Therapeutic Target in Autoimmunity", Journal of Biomolecular Screening, (2016), vol. 21, No. 3, pp. 223-242.
T.W. Greene and P.G.M. Wuts, Protective Groups in Organic Synthesis, 4th ed., Wiley, Hoboken, New Jersey, 2007.
D. Vrabel, et al., "The impact of NF-κB signaling on pathogenesis and current treatment strategies in multiple myeloma", Blood Reviews, (2019), vol. 34, pp. 56-66.

* cited by examiner

HETEROAROMATIC DERIVATIVES AS NIK INHIBITORS

FIELD OF THE INVENTION

The present invention relates to pharmaceutical agents useful for therapy and/or prophylaxis in a mammal, and in particular to inhibitors of NF-κB-inducing kinase (NIK—also known as MAP3K14) useful for treating diseases such as cancer (in particular B-cell malignancies including leukemias, lymphomas and myeloma), inflammatory disorders, metabolic disorders including obesity and diabetes, and autoimmune disorders. The invention is also directed to pharmaceutical compositions comprising such compounds, and to the use of such compounds or pharmaceutical compositions for the prevention or treatment of diseases such as cancer, inflammatory disorders, metabolic disorders including obesity and diabetes, and autoimmune disorders.

BACKGROUND OF THE INVENTION

The present invention relates to pharmaceutical agents useful for therapy and/or prophylaxis in a mammal, and in particular to inhibitors of NF-κB-inducing kinase (NIK—also known as MAP3K14) useful for treating diseases such as cancer and inflammatory disorders. Nuclear factor-kappa B (NF-κB) is a transcription factor regulating the expression of various genes involved in the immune response, cell proliferation, adhesion, apoptosis, and carcinogenesis. NF-κB dependent transcriptional activation is a tightly controlled signaling pathway, through sequential events including phosphorylation and protein degradation. NIK is a serine/threonine kinase which regulates NF-κB pathway activation. There are two NF-κB signaling pathways, the canonical and the non-canonical. NIK is indispensable for the non-canonical signaling pathway where it phosphorylates IKKα, leading to the partial proteolysis of p100; liberating p52 which then heterodimerizes with RelB, translocates to the nucleus and mediates gene expression. The non-canonical pathway is activated by only a handful of ligands such as CD40 ligands, B-cell activating factor (BAFF), lymphotoxin β receptor ligands and TNF-related weak inducer of apoptosis (TWEAK) and NIK has been shown to be required for activation of the pathway by these ligands. Because of its key role, NIK expression is tightly regulated. Under normal non-stimulated conditions NIK protein levels are very low, this is due to its interaction with a range of TNF receptor associated factors (TRAF2 and TRAF3), which are ubiquitin ligases and result in degradation of NIK. It is believed that when the non-canonical pathway is stimulated by ligands, the activated receptors now compete for TRAFs, dissociating the TRAF-NIK complexes and thereby increasing the levels of NIK. (Thu and Richmond, *Cytokine Growth F. R.* 2010, 21, 213-226)

Research has shown that blocking the NF-κB signaling pathway in cancer cells can cause cells to stop proliferating, to die and to become more sensitive to the action of other anti-cancer therapies. A role for NIK has been shown in the pathogenesis of both hematological malignancies and solid tumours.

The NF-κB pathway is dysregulated in multiple myeloma due to a range of diverse genetic abnormalities that lead to the engagement of the canonical and non-canonical pathways (Annuziata et al. *Cancer Cell* 2007, 12, 115-130; Keats et al. *Cancer Cell* 2007, 12, 131-144; Demchenko et al. *Blood* 2010, 115, 3541-3552). Myeloma patient samples frequently have increased levels of NIK activity. This can be due to chromosomal amplification, translocations (that result in NIK proteins that have lost TRAF binding domains), mutations (in the TRAF binding domain of NIK) or TRAF loss of function mutations. Researchers have shown that myeloma cell lines can be dependent on NIK for proliferation; in these cell lines if NIK activity is reduced by either shRNA or compound inhibition, this leads to a failure in NF-κB signaling and the induction of cell death (Annuziata 2007).

In a similar manner, mutations in TRAF and increased levels of NIK have also been seen in samples from Hodgkin lymphoma (HL) patients. Once again proliferation of cell lines derived from HL patients is susceptible to inhibition of NIK function by both shRNA and compounds (Ranuncolo et al. *Blood* First Edition Paper, 2012, DOI 10.1182/blood-2012-01-405951).

NIK levels are also enhanced in adult T cell leukemia (ATL) cells and targeting NIK with shRNA reduced ATL growth in vivo (Saitoh et al. *Blood* 2008, 111, 5118-5129).

It has been demonstrated that the API2-MALT 1 fusion oncoprotein created by the recurrent translocation t(11;18)(q21; q21) in mucosa-associated lymphoid tissue (MALT) lymphoma induces proteolytic cleavage of NF-κB-inducing kinase (NIK) at arginine 325. NIK cleavage generates a C-terminal NIK fragment that retains kinase activity and is resistant to proteasomal degradation (due to loss of TRAF binding region). The presence of this truncated NIK leads to constitutive non-canonical NF-κB signaling, enhanced B cell adhesion, and apoptosis resistance. Thus NIK inhibitors could represent a new treatment approach for refractory t(11; 18)-positive MALT lymphoma (Rosebeck et al. *Science* 2011, 331, 468-472).

NIK aberrantly accumulates in diffuse large B-cell lymphoma (DLBCL) cells due to constitutive activation of B-cell activation factor (BAFF) through interaction with autochthonous B-lymphocyte stimulator (BLyS) ligand. NIK accumulation in human DLBCL cell lines and patient tumor samples suggested that constitutive NIK kinase activation is likely to be a key signaling mechanism involved in abnormal lymphoma tumor cell proliferation. Growth assays showed that using shRNA to inhibit NIK kinase protein expression in GCB- and ABC-like DLBCL cells decreased lymphoma cell growth in vitro, implicating NIK-induced NF-κB pathway activation as having a significant role in DLBCL proliferation (Pham et al. *Blood* 2011, 117, 200-210). More recently, also loss-of-function mutations in TRAF3 have been characterized in human and canine DLBCL (Bushell et al., *Blood* 2015, 125, 999-1005).

Recently, similar mutations in the non-canonical NFkB signaling pathway (TRAF2, TRAF3, NIK, BIRC3) were found in ibrutinib-refractory mantle cell lymphoma cell lines (Rahal et al., *Nat Med* 2014, 1, 87-92).

As mentioned a role of NIK in tumour cell proliferation is not restricted to hematological cells, there are reports that NIK protein levels are stabilised in some pancreatic cancer cell lines and as seen in blood cells proliferation of these pancreatic cancer lines are susceptible to NIK siRNA treatment (Nishina et al. *Biochem. Bioph. Res. Co.* 2009, 388, 96-101). Constitutive activation of NF-κB, is preferentially involved in the proliferation of basal-like subtype breast cancer cell lines, including elevated NIK protein levels in specific lines (Yamamoto et al. *Cancer Sci.* 2010, 101, 2391-2397). In melanoma tumours, tissue microarray analysis of NIK expression revealed that there was a statistically significant elevation in NIK expression when compared with benign tissue. Moreover, shRNA techniques were used to knock-down NIK, the resultant NIK-depleted melanoma cell lines exhibited decreased proliferation, increased apoptosis, delayed cell cycle progression and reduced tumor growth in a mouse xenograft model (Thu et al. *Oncogene* 2012, 31(20), 2580-92). A wealth of evidence showed that NF-κB is often constitutively activated in non-small cell lung cancer tissue specimens and cell lines. Depletion of NIK by RNAi induced apoptosis and affected efficiency of anchorage-independent NSCLC cell growth.

In addition research has shown that NF-κB controls the expression of many genes involved in inflammation and that NF-κB signaling is found to be chronically active in many inflammatory diseases, such as rheumatoid arthritis, inflammatory bowel disease, sepsis and others. Thus pharmaceutical agents capable of inhibiting NIK and thereby reducing NF-κB signaling pathway can have a therapeutic benefit for the treatment of diseases and disorders for which over-activation of NF-κB signaling is observed.

Dysregulated NF-κB activity is associated with colonic inflammation and cancer, and it has been shown that Nlrp12 deficient mice were highly susceptible to colitis and colitis-associated colon cancer. In this context work showed that NLRP12 functions as a negative regulator of the NF-κB pathway through its interaction and regulation of NIK and TRAF3, and as a checkpoint of critical pathways associated with inflammation and inflammation-associated tumorigenesis (Allen et al. *Immunity* 2012, 36, 742-754).

Tumor necrosis factor (TNF)-α, is secreted in response to inflammatory stimuli in diseases such as rheumatoid arthritis and inflammatory bowel disease. In a series of experiments in colonic epithelial cells and mouse embryonic fibroblasts, TNF-α mediates both apoptosis and inflammation, stimulating an inflammatory cascade through the non-canonical pathway of NF-κB activation, leading to increased nuclear RelB and p52. TNF-α induced the ubiquitination of TRAFs, which interacts with NIK, leading to increased levels of phospho-NIK (Bhattacharyya et al. *J Biol. Chem.* 2011, 285, 39511-39522).

Inflammatory responses are a key component of chronic obstructive pulmonary disease (COPD) as such it has been shown that NIK plays a key role in exacerbating the disease following infection with the Gram-negative bacterium non-typeable Hemophilus influenza (Shuto et al. *PNAS* 2001, 98, 8774-8779). Likewise cigarette smoke (CS) contains numerous reactive oxygen/nitrogen species, reactive aldehydes, and quinones, which are considered to be some of the most important causes of the pathogenesis of chronic inflammatory lung diseases, such as COPD and lung cancer. Increased levels of NIK and p-IKKα have been observed in peripheral lungs of smokers and patients with COPD. In addition it has been shown that endogenous NIK is recruited to promoter sites of pro-inflammatory genes to induce post-translational modification of histones, thereby modifying gene expression profiles, in response to CS or TNFα (Chung et al. *PLoS ONE* 2011, 6(8): e23488. doi:10.1371/journal.pone.0023488). A shRNA screen was used in an in vitro model of oxidative stress induced cell death (as a model of COPD) to interrogate a human drugable genome siRNA library in order to identify genes that modulate the cellular response to stress. NIK was one of the genes identified in this screen as a potential new therapeutic target to modulate epithelial apoptosis in chronic lung diseases (Wixted et al. *Toxicol. In Vitro* 2010, 24, 310-318).

Diabetic individuals can be troubled by a range of additional manifestations associated with inflammation. One such complication is cardiovascular disease and it has been shown that there are elevated levels of p-NIK, p-IKK-α/β and p-IκB-α in diabetic aortic tissues (Bitar et al. *Life Sci.* 2010, 86, 844-853). In a similar manner, NIK has been shown to regulate proinflammatory responses of renal proximal tubular epithelial cells via mechanisms involving TRAF3. This suggests a role for NF-κB noncanonical pathway activation in modulating diabetes-induced inflammation in renal tubular epithelium (Zhao et al. *Exp. Diabetes Res.* 2011, 1-9. doi: 10.1155/2011/192564). The same group has shown that NIK plays a critical role in noncanonical NF-κB pathway activation, induced skeletal muscle insulin resistance in vitro, suggesting that NIK could be an important therapeutic target for the treatment of insulin resistance associated with inflammation in obesity and type 2 diabetes (Choudhary et al. *Endocrinology* 2011, 152, 3622-3627).

NF-κB is an important component of both autoimmunity and bone destruction in rheumatoid arthritis (RA). Mice lacking functional NIK have no peripheral lymph nodes, defective B and T cells, and impaired receptor activator of NF-κB ligand-stimulated osteoclastogenesis. Aya et al. (*J. Clin. Invest.* 2005, 115, 1848-1854) investigated the role of NIK in murine models of inflammatory arthritis using Nik−/− mice. The serum transfer arthritis model was initiated by preformed antibodies and required only intact neutrophil and complement systems in recipients. While Nik−/− mice had inflammation equivalent to that of Nik+/+ controls, they showed significantly less periarticular osteoclastogenesis and less bone erosion. In contrast, Nik−/− mice were completely resistant to antigen-induced arthritis (AIA), which requires intact antigen presentation and lymphocyte function but not lymph nodes. Additionally, transfer of Nik+/+ splenocytes or T cells to Rag2−/− mice conferred susceptibility to AIA, while transfer of Nik−/− cells did not. Nik−/− mice were also resistant to a genetic, spontaneous form of arthritis, generated in mice expressing both the KRN T cell receptor and H-2 g7. The same group used transgenic mice with OC-lineage expression of NIK lacking its TRAF3 binding domain (NT3), to demonstrate that constitutive activation of NIK drives enhanced osteoclastogenesis and bone resorption, both in basal conditions and in response to inflammatory stimuli (Yang et al. *PLoS ONE* 2010, 5(11): e15383. doi:10.1371/journal.pone.0015383). Thus this group concluded that NIK is important in the immune and bone-destructive components of inflammatory arthritis and represents a possible therapeutic target for these diseases.

It has also been hypothesized that manipulating levels of NIK in T cells may have therapeutic value. Decreasing NIK activity in T cells might significantly ameliorate autoimmune responses and alloresponses, like GVHD (Graft Versus Host Disease) and transplant rejection, without crippling the immune system as severely as do inhibitors of canonical NF-κB activation.

WO2003030909 describes the preparation of 2- and 4-aminopyrimidines N-substituted by a bicyclic ring for use as kinase inhibitors in the treatment of cancer.

WO2002079197 describes 4-aryl-substituted 2-pyrimidinamines and 2-pyridinamines, useful as inhibitors of c-Jun N-terminal kinases (JNK) and other protein kinases.

DESCRIPTION OF THE INVENTION

The present invention concerns novel compounds of Formula (I):

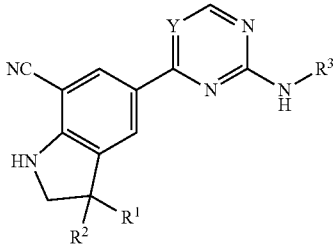

tautomers and stereoisomeric forms thereof, wherein
$R^1$ represents $C_{1-4}$alkyl;
$R^2$ represents $C_{1-6}$alkyl, $C_{1-6}$alkyl substituted with one $R^5$, or $C_{1-6}$alkyl substituted with one, two or three fluoro atoms;
Y represents $CR^4$ or N;
$R^4$ represents hydrogen or halo;
$R^5$ represents $Het^{3a}$, $-NR^{6a}R^{6b}$, or $-OR^7$;
$R^{6a}$ represents hydrogen or $C_{1-4}$alkyl;
$R^{6b}$ represents hydrogen; $C_{1-4}$alkyl; $C_{3-6}$cycloalkyl; $-C(=O)-C_{1-4}$alkyl; $-C(=O)-Het^4$; $-S(=O)_2-C_{1-4}$alkyl; $-C(=O)-C_{1-4}$alkyl substituted with one substituent selected from the group consisting of $-OH$ and $-NR^{16a}R^{6b}$; or $C_{1-4}$alkyl substituted with one substituent selected from the group consisting of $-OH$ and $-S(=O)_2-C_{1-4}$alkyl;
$R^7$ represents hydrogen, $C_{1-4}$alkyl, $-C_{1-4}$akyl-$NR^{8a}R^{8b}$, $-C(=O)-R^9$, $-S(=O)_2-OH$, $-P(=O)_2-OH$, $-(C=O)-CH(NH_2)-C_{1-4}$alkyl-$Ar^1$, or $-C_{1-4}$alkyl-$Het^{3b}$;
$R^{8a}$ represents hydrogen or $C_{1-4}$alkyl;
$R^{8b}$ represents hydrogen, $C_{1-4}$alkyl, or $C_{3-6}$cycloalkyl;
$R^9$ represents $C_{1-6}$alkyl, or $C_{1-6}$alkyl substituted with one substituent selected from the group consisting of $-NH_2$, $-COOH$, and $Het^6$;
$R^{16a}$ and $R^{16b}$ each independently represents hydrogen, $C_{1-4}$alkyl or $C_{3-6}$cycloalkyl;
$R^3$ represents a 5-membered heteroaromatic ring containing one, two or three heteroatoms each independently selected from O, S, and N;
wherein said 5-membered heteroaromatic ring may optionally be substituted, where possible, on one ring N-atom with a substituent selected from the group consisting of $C_{1-6}$alkyl; $C_{3-6}$cycloalkyl; $Het^{1a}$; $R^{18}$; $R^{21}$; $C_{1-4}$alkyl substituted with one, two or three halo atoms; $C_{1-5}$alkyl substituted with one, two or three $-OH$ substituents; $C_{1-6}$alkyl substituted with one $R^{13}$; $-C_4$alkyl-$O-C_{1-4}$alkyl substituted with one or two $-OH$ substituents; $C_{1-4}$alkyl substituted with one $R^{18}$; $C_{2-6}$alkenyl; and $C_{2-6}$alkenyl substituted with one $R^{13}$; provided that when $Het^{1a}$ or $R^{18}$ are directly attached to the N-atom of the 5-membered heteroaromatic ring, said $Het^{1a}$ or $R^{18}$ are attached to the N-atom via a ring carbon atom; and
wherein said 5-membered heteroaromatic ring may optionally be substituted on the ring carbon atoms with in total one or two substituents each independently selected from the group consisting of halo; cyano; $C_{1-6}$alkyl; $-O-C_{1-4}$alkyl; $-C(=O)-R^{10}$; $-S(=O)_2-C_{1-4}$alkyl; $-S(=O)(=N-R^{20a})-C_{1-4}$alkyl; $-O-C_{1-4}$alkyl substituted with one, two or three halo atoms; $-O-C_{1-4}$alkyl-$R^{12}$; $C_{3-6}$cycloalkyl; $-O-C_{3-6}$cycloalkyl; $Het^{1a}$; $-O-Het^{1b}$; $R^{18}$; $R^{21}$; $-P(=O)-(C_{1-4}$alkyl$)_2$; $-NH-C(=O)-C_{1-4}$alkyl; $-NH-C(=O)-Het^{1g}$; $-NR^{17a}R^{17b}$; $C_{1-4}$alkyl substituted with one, two or three halo atoms; $C_{1-4}$alkyl substituted with one, two or three $-OH$ substituents; $C_{1-6}$alkyl substituted with one $R^{13}$; $C_{1-4}$alkyl substituted with one $R^{18}$; $C_{2-6}$alkenyl; and $C_{2-6}$alkenyl substituted with one $R^{13}$;

$R^{10}$ represents $-OH$, $-O-C_{1-4}$alkyl, $-NR^{11a}R^{11b}$ or $Het^2$;

$R^{18}$ represents a 5-membered aromatic ring containing one, two or three N-atoms; wherein said 5-membered aromatic ring may optionally be substituted with one substituent selected from the group consisting of $C_{1-4}$alkyl and $C_{3-6}$cycloalkyl;

$R^{21}$ represents 3,6-dihydro-2H-pyran-4-yl or 1,2,3,6-tetrahydro-4-pyridinyl, wherein 1,2,3,6-tetrahydro-4-pyridinyl may optionally be substituted on the N-atom with $C_{1-4}$alkyl or $C_{3-6}$cycloalkyl;

$Het^{1a}$, $Het^{1c}$ and $Het^{1d}$ each independently represents a 4- to 7-membered monocyclic saturated heterocyclyl containing one or two heteroatoms each independently selected from O, S, $S(=O)_p$ and N; or a 6- to 11-membered bicyclic saturated heterocyclyl, including fused, spiro and bridged cycles, containing one, two or three heteroatoms each independently selected from O, S, $S(=O)_p$ and N;

wherein said 4- to 7-membered monocyclic saturated heterocyclyl or said 6- to 11-membered bicyclic saturated heterocyclyl may optionally be substituted, where possible, on one, two or three ring N-atoms with a substituent each independently selected from the group consisting of $C_{1-4}$alkyl, $C_{3-6}$cycloalkyl, $C_{1-4}$alkyl substituted with one, two or three halo atoms, and $C_{1-4}$alkyl substituted with one substituent selected from the group consisting of $-OH$, $-C(=O)-OH$, $-C(=O)-NR^{22a}R^{22b}$ and $-O-C_{1-4}$alkyl; and wherein said 4- to 7-membered monocyclic saturated heterocyclyl or said 6- to 11-membered bicyclic saturated heterocyclyl may optionally be substituted on one, two or three ring C-atoms with one or two substituents each independently selected from the group consisting of $-OH$, oxo, halo, $C_{1-4}$alkyl, cyano, $-C(=O)-C_{1-4}$alkyl, $-O-C_{1-4}$alkyl, $-NH_2$, $-NH(C_{1-4}$alkyl$)$, and $-N(C_{1-4}$alkyl$)_2$;

$Het^{1b}$, $Het^{1e}$, $Het^{1g}$ and $Het^4$ each independently represents a 4- to 7-membered monocyclic saturated heterocyclyl, attached to the remainder of the molecule of Formula (I) through any available ring carbon atom, said $Het^{1b}$, $Het^{1e}$, $Het^{1g}$ and $Het^4$ containing one or two heteroatoms each independently selected from O, S, $S(=O)_p$ and N;

wherein said 4- to 7-membered monocyclic saturated heterocyclyl may optionally be substituted, where possible, on one or two ring N-atoms with a substituent each independently selected from the group consisting of $C_{1-4}$alkyl, $C_{3-6}$cycloalkyl, and $C_{1-4}$alkyl substituted with one substituent selected from the group consisting of $-OH$ and $-O-C_{1-4}$alkyl; and wherein said 4- to 7-membered monocyclic saturated heterocyclyl may optionally be substituted on one, two or three ring C-atoms with one or two substituents each independently selected from the group consisting of $-OH$, halo, $C_{1-4}$alkyl, cyano, $-C(=O)-C_{1-4}$alkyl, $-O-C_{1-4}$alkyl, $-NH_2$, $-NH(C_{1-4}$alkyl$)$, and $-N(C_{1-4}$alkyl$)_2$;

Het² represents a heterocyclyl of formula (b-1):

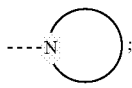

(b-1)

(b-1) represents a N-linked 4- to 7-membered monocyclic saturated heterocyclyl optionally containing one additional heteroatom selected from O, S, S(=O)$_p$ and N, or a N-linked 6- to 11-membered bicyclic saturated heterocyclyl, including fused, spiro and bridged cycles, optionally containing one or two additional heteroatoms each independently selected from O, S, S(=O)$_p$ and N;
wherein in case (b-1) contains one or two additional N-atoms, said one or two N-atoms may optionally be substituted with $C_{1-4}$alkyl; and
wherein (b-1) may optionally be substituted on one, two or three ring C-atoms with one or two substituents each independently selected from the group consisting of halo, —OH, cyano, $C_{1-4}$alkyl, —O—$C_{1-4}$alkyl, —NH$_2$, —NH($C_{1-4}$alkyl), —N($C_{1-4}$alkyl)$_2$, and $C_{1-4}$alkyl-OH;
$R^{11b}$ represents hydrogen; Het$^{1e}$; $C_{1-4}$alkyl; $C_{1-4}$alkyl-Het; $C_{1-4}$alkyl substituted with one, two or three substituents each independently selected from the group consisting of halo, —OH and —O—$C_{1-4}$alkyl; $C_{3-6}$cycloalkyl; or $C_{3-6}$cycloalkyl substituted with one, two or three substituents each independently selected from the group consisting of halo, —OH and —O—$C_{1-4}$alkyl;
$R^{13}$ represents —O—$C_{1-4}$alkyl, —C(=O)OH, —C(=O)NR$^{15a}$R$^{15b}$, —NR$^{19a}$R$^{19b}$, $C_{3-6}$cycloalkyl, Het$^{1d}$, Het$^7$, —S(=O)$_2$—$C_{1-4}$alkyl, —S(=O)(=N—R$^{20c}$)—$C_{1-4}$alkyl, or —C(=O)—Het$^{1f}$;
$R^{12}$ represents —OH, —O—$C_{1-4}$alkyl, —NR$^{14a}$R$^{14b}$, —C(=O)NR$^{14c}$R$^{14d}$, —S(=O)$_2$—$C_{1-4}$alkyl, —S(=O)(=N—R$^{20b}$)—$C_{1-4}$alkyl, $C_{3-6}$cycloalkyl, Ar², or Het$^{1e}$;
Ar¹ represents phenyl optionally substituted with one hydroxy;
Ar² represents phenyl optionally substituted with one $C_{1-4}$alkyl;
Het$^{3a}$, Het$^{3b}$, Het$^5$, Het$^6$ and Het$^{1f}$ each independently represents a heterocyclyl of formula (c-1):

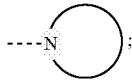

(c-1)

(c-1) represents a N-linked 4- to 7-membered monocyclic saturated heterocyclyl optionally containing one additional heteroatom selected from O, S, S(=O)$_p$ and N; wherein in case (c-1) contains one additional N-atom, said additional N-atom may optionally be substituted with $C_{1-4}$alkyl or $C_{3-6}$cycloalkyl; and
wherein (c-1) may optionally be substituted on one or two ring C-atoms atoms with one or two substituents each independently selected from the group consisting of halo, $C_{1-4}$alkyl, and $C_{3-6}$cycloalkyl;
Het$^7$ represents 5,6,7,8-tetrahydro-imidazo[1,2-a]pyridinyl;
$R^{11a}$, $R^{14a}$, $R^{14c}$, $R^{15a}$, $R^{17a}$, $R^{19a}$ and $R^{22a}$ each independently represents hydrogen, $C_{1-4}$alkyl, or $C_{3-6}$cycloalkyl;
$R^{14b}$, $R^{14d}$, $R^{15b}$, $R^{17b}$, $R^{19b}$ and $R^{22b}$ each independently represents hydrogen; $C_{1-4}$alkyl; $C_{3-6}$cycloalkyl; or $C_{1-4}$alkyl substituted with one substituent selected from the group consisting of halo, —OH and —O—$C_{1-4}$alkyl;
$R^{20a}$, $R^{20b}$ and $R^{20c}$ each independently represents hydrogen; $C_{1-4}$alkyl; $C_{3-6}$cycloalkyl; or $C_{1-4}$alkyl substituted with one substituent selected from the group consisting of —OH and —O—$C_{1-4}$alkyl;
p represents 1 or 2;
and the pharmaceutically acceptable addition salts, and the solvates thereof.

The present invention also relates to a pharmaceutical composition comprising a therapeutically effective amount of a compound of Formula (I), a pharmaceutically acceptable addition salt, or a solvate thereof, and a pharmaceutically acceptable carrier or excipient.

Additionally, the invention relates to a compound of Formula (I), a pharmaceutically acceptable addition salt, or a solvate thereof, for use as a medicament, and to a compound of Formula (I), a pharmaceutically acceptable addition salt, or a solvate thereof, for use in the treatment or in the prevention of cancer, inflammatory disorders, autoimmune disorders, and metabolic disorders such as diabetes and obesity.

In a particular embodiment, the invention relates to a compound of Formula (I), a pharmaceutically acceptable addition salt, or a solvate thereof, for use in the treatment or in the prevention of a haematological malignancy or solid tumour.

In a specific embodiment said haematological malignancy is selected from the group consisting of multiple myeloma, Hodgkin lymphoma, T-cell leukaemia, mucosa-associated lymphoid tissue lymphoma, diffuse large B-cell lymphoma and mantle cell lymphoma. In another specific embodiment of the present invention, the solid tumour is selected from the group consisting of pancreatic cancer, breast cancer, melanoma and non-small cell lung cancer.

The invention also relates to the use of a compound of Formula (I), a pharmaceutically acceptable addition salt, or a solvate thereof, in combination with an additional pharmaceutical agent for use in the treatment or prevention of cancer, inflammatory disorders, autoimmune disorders, and metabolic disorders such as diabetes and obesity. Furthermore, the invention relates to a process for preparing a pharmaceutical composition according to the invention, characterized in that a pharmaceutically acceptable carrier is intimately mixed with a therapeutically effective amount of a compound of Formula (I), a pharmaceutically acceptable addition salt, or a solvate thereof.

The invention also relates to a product comprising a compound of Formula (I), a pharmaceutically acceptable addition salt, or a solvate thereof, and an additional pharmaceutical agent, as a combined preparation for simultaneous, separate or sequential use in the treatment or prevention of cancer, inflammatory disorders, autoimmune disorders, and metabolic disorders such as diabetes and obesity.

Additionally, the invention relates to a method of treating or preventing a cell proliferative disease in a warm-blooded animal which comprises administering to the said animal an effective amount of a compound of Formula (I), a pharmaceutically acceptable addition salt, or a solvate thereof, as defined herein, or a pharmaceutical composition or combination as defined herein.

Some of the compounds of the present invention may undergo metabolism to a more active form in vivo (prodrugs).

DETAILED DESCRIPTION OF THE INVENTION

The term 'halo' or 'halogen' as used herein represents fluoro, chloro, bromo and iodo.

The prefix '$C_{x-y}$' (where x and y are integers) as used herein refers to the number of carbon atoms in a given group. Thus, a $C_{1-6}$alkyl group contains from 1 to 6 carbon atoms, a $C_{3-6}$cycloalkyl group contains from 3 to 6 carbon atoms, and so on.

The term '$C_{1-4}$alkyl' as used herein as a group or part of a group represents a straight or branched chain saturated hydrocarbon radical having from 1 to 4 carbon atoms, such as methyl, ethyl, n-propyl, isopropyl, n-butyl, s-butyl, t-butyl and the like.

The term '$C_{1-6}$alkyl' as used herein as a group or part of a group represents a straight or branched chain saturated hydrocarbon radical having from 1 to 6 carbon atoms such as the groups defined for $C_{1-4}$alkyl and n-pentyl, n-hexyl, 2-methylbutyl and the like.

The term "$C_{2-6}$alkenyl" as used herein as a group or part of a group represents a straight or branched chain hydrocarbon group containing from 2 to 6 carbon atoms and containing a carbon carbon double bond such as, but not limited to, ethenyl, propenyl, butenyl, pentenyl, 1-propen-2-yl, hexenyl and the like.

The term '$C_{3-6}$cycloalkyl' as used herein as a group or part of a group represents cyclic saturated hydrocarbon radicals having from 3 to 6 carbon atoms such as cyclopropyl, cyclobutyl, cyclopentyl or cyclohexyl.

In general, whenever the term "substituted" is used in the present invention, it is meant, unless otherwise is indicated or is clear from the context, to indicate that one or more hydrogens, in particular from 1 to 4 hydrogens, more in particular from 1 to 3 hydrogens, preferably 1 or 2 hydrogens, more preferably 1 hydrogen, on the atom or radical indicated in the expression using "substituted" are replaced with a selection from the indicated group, provided that the normal valency is not exceeded, and that the substitution results in a chemically stable compound, i.e. a compound that is sufficiently robust to survive isolation to a useful degree of purity from a reaction mixture, and formulation into a therapeutic agent.

Combinations of substituents and/or variables are permissible only if such combinations result in chemically stable compounds. "Stable compound" is meant to indicate a compound that is sufficiently robust to survive isolation to a useful degree of purity from a reaction mixture, and formulation into a therapeutic agent.

The skilled person will understand that the term "optionally substituted" means that the atom or radical indicated in the expression using "optionally substituted" may or may not be substituted (this means substituted or unsubstituted respectively).

When two or more substituents are present on a moiety they may, where possible and unless otherwise is indicated or is clear from the context, replace hydrogens on the same atom or they may replace hydrogen atoms on different atoms in the moiety.

It will be clear for the skilled person that, unless otherwise is indicated or is clear from the context, a substituent on a heterocyclyl group may replace any hydrogen atom on a ring carbon atom or on a ring heteroatom (e.g. a hydrogen on a nitrogen atom may be replaced by a substituent), for example in saturated heterocyclyl groups or 5-membered aromatic rings as used in the definition of $R^{is}$.

C(O) or C(=O) represents a carbonyl moiety.
S(=O)$_2$ or SO$_2$ represents a sulfonyl moiety.
"oxo" means O: for example piperidine substituted with oxo in position 2 is represented by the following structure:

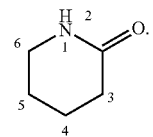

The skilled person will understand that —S(=O)(=N—$R^{20a}$)—$C_{1-4}$alkyl corresponds with

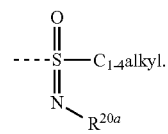

Within the context of this invention 'saturated' means 'fully saturated', if not otherwise specified.

Het$^{1a}$, Het$^{1c}$ and Het$^{1d}$, may be attached to the remainder of the molecule of Formula (I) through any available ring carbon or nitrogen atom as appropriate, if not otherwise specified.

The 5-membered aromatic ring containing one, two or three N-atoms as referred to in the definition of $R^{18}$, may be attached to the remainder of the molecule of Formula (I) through any available ring carbon or nitrogen atom as, if not otherwise specified.

It will be clear that in case a saturated cyclic moiety is substituted on two ring carbon atoms with one substituent, in total two carbon-linked substituents are present on the saturated cyclic moiety (one substituent on each carbon atom).

It will be clear that in case a saturated cyclic moiety is substituted on two ring carbon atoms with two substituents, in total four carbon-linked substituents are present on the saturated cyclic moiety (two substituents on each carbon atom).

It will be clear that in case a saturated cyclic moiety is substituted on three ring carbon atoms with two substituents, in total six carbon-linked substituents are present on the saturated cyclic moiety (two substituents on each carbon atom).

It will be clear that in case a saturated cyclic moiety is substituted on two ring N-atoms with a substituent, in total two N-linked substituents are present on the saturated cyclic moiety (a substituent on each N-atom).

It will be clear that a saturated cyclic moiety may, where possible, have substituents on both carbon and N-atoms, unless otherwise is indicated or is clear from the context.

Within the context of this invention, bicyclic saturated heterocyclyl groups include fused, spiro and bridged saturated heterocycles.

Fused bicyclic groups are two cycles that share two atoms and the bond between these atoms.

Spiro bicyclic groups are two cycles that are joined at a single atom.

Bridged bicyclic groups are two cycles that share more than two atoms.

Examples of N-linked 6- to 11-membered fused bicyclic saturated heterocyclyl groups, include, but are not limited to,

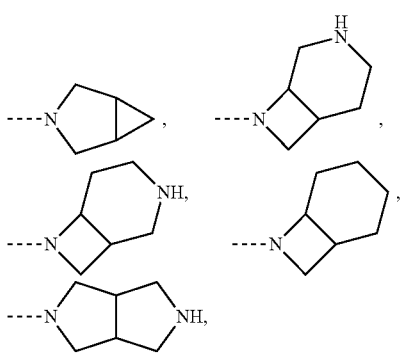

and the like.

Examples of N-linked 6- to 11-membered spiro bicyclic saturated heterocyclyl groups, include, but are not limited to

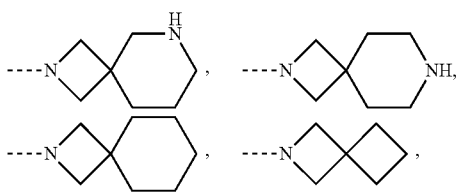

and the like.

Examples of N-linked 6- to 11-membered bridged bicyclic saturated heterocyclyl groups, include, but are not limited to

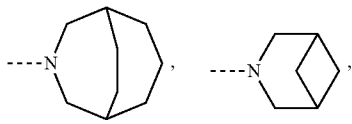

and the like.

The skilled person will realize that the definition of Het$^{1a}$, Het$^{1c}$ and Het$^{1d}$ also includes C-linked bicycles (attached to the remainder of the molecule of Formula (I) through any available ring carbon atom).

It should be understood that the exemplified bicyclic saturated heterocyclyl groups referred to above may optionally be substituted, where possible, on carbon and/or nitrogen atoms according to any of the embodiments.

Non-limiting examples of 4- to 7-membered monocyclic saturated heterocyclyl moieties containing one or two heteroatoms each independently selected from O, S, S(=O)$_p$ and N (as in the definition of Het$^{1a}$, Het$^{1c}$, and Het$^{1d}$) are shown below:

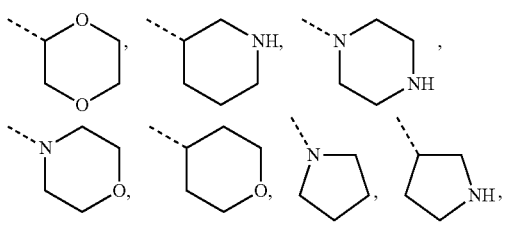

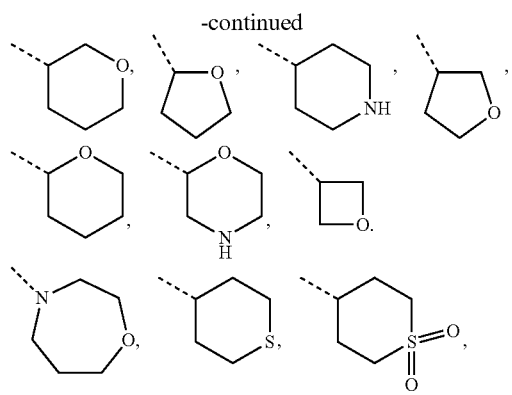

and the like.

Each of which may optionally be substituted, where possible, on carbon and/or nitrogen atoms according to any of the embodiments.

Non-limiting examples of 4- to 7-membered monocyclic saturated heterocyclyl moieties, attached to the remainder of the molecule of Formula (I) through any available ring carbon atom (C-linked), and containing one or two heteroatoms each independently selected from O, S, S(=O)$_p$ and N (as in the definition of Het$^{1b}$, Het$^{1e}$, Het$^{1g}$ and Het$^4$) are shown below:

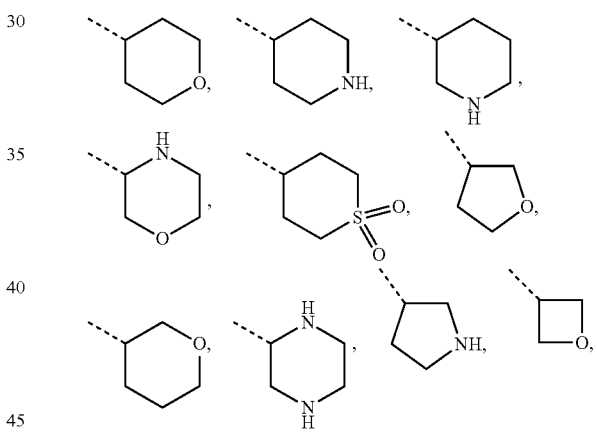

and the like.

Each of which may optionally be substituted, where possible, on carbon and/or nitrogen atoms according to any of the embodiments.

Non-limiting examples of N-linked 4- to 7-membered monocyclic saturated heterocyclyl moieties optionally containing one additional heteroatom selected from O, S, S(=O), and N (as in the definition of (b-1) and (c-1)) are shown below:

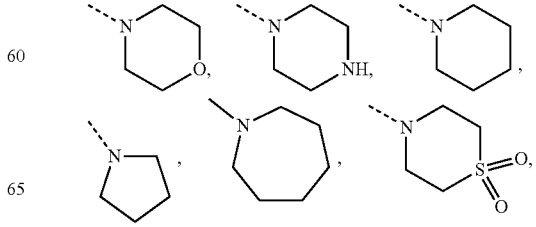

and the like.

Each of which may optionally be substituted, where possible, on carbon and/or nitrogen atoms according to any of the embodiments.

Non-limiting examples of 5-membered aromatic ring containing one, two or three N-atoms as referred to in the definition of $R^8$ are shown below:

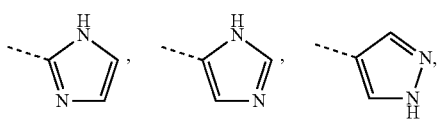

and the like.

Each of which may optionally be substituted, where possible, on carbon and/or nitrogen atoms according to any of the embodiments.

Non-limiting examples of 5-membered heteroaromatic ring containing one, two or three heteroatoms each independently selected from O, S, and N (as in the definition of $R^3$) are shown below:

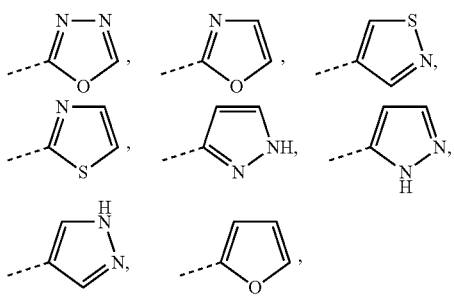

and the like.

Each of which may optionally be substituted, where possible, on carbon atoms and/or one nitrogen atom according to any of the embodiments.

The skilled person will understand that $R^3$ is attached to the remainder of the molecule of Formula (I) (—NH— moiety) via a ring carbon atom.

Whenever substituents are represented by chemical structure, " - - - " represents the bond of attachment to the remainder of the molecule of Formula (I).

Lines (such as " - - - ") drawn into ring systems indicate that the bond may be attached to any of the suitable ring atoms.

When any variable occurs more than one time in any constituent, each definition is independent.

When any variable occurs more than one time in any formula (e.g. Formula (I)), each definition is independent.

The term "subject" as used herein, refers to an animal, preferably a mammal (e.g. cat, dog, primate or human), more preferably a human, who is or has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medicinal doctor or other clinician, which includes alleviation or reversal of the symptoms of the disease or disorder being treated.

The term "composition" is intended to encompass a product comprising the specified ingredients in the specified amounts, as well as any product which results, directly or indirectly, from combinations of the specified ingredients in the specified amounts.

The term "treatment", as used herein, is intended to refer to all processes wherein there may be a slowing, interrupting, arresting or stopping of the progression of a disease, but does not necessarily indicate a total elimination of all symptoms.

The term "compound(s) of the (present) invention" or "compound(s) according to the (present) invention" as used herein, is meant to include the compounds of Formula (I) and the pharmaceutically acceptable addition salts, and the solvates thereof.

As used herein, any chemical formula with bonds shown only as solid lines and not as solid wedged or hashed wedged bonds, or otherwise indicated as having a particular configuration (e.g. R, S) around one or more atoms, contemplates each possible stereoisomer, or mixture of two or more stereoisomers.

Hereinbefore and hereinafter, the term "compound(s) of Formula (I)" is meant to include the tautomers thereof and the stereoisomeric forms thereof.

The terms "stereoisomers", "stereoisomeric forms" or "stereochemically isomeric forms" hereinbefore or hereinafter are used interchangeably.

The invention includes all stereoisomers of the compounds of the invention either as a pure stereoisomer or as a mixture of two or more stereoisomers.

Enantiomers are stereoisomers that are non-superimposable mirror images of each other. A 1:1 mixture of a pair of enantiomers is a racemate or racemic mixture.

Atropisomers (or atropoisomers) are stereoisomers which have a particular spatial configuration, resulting from a restricted rotation about a single bond, due to large steric hindrance. All atropisomeric forms of the compounds of Formula (I) are intended to be included within the scope of the present invention.

Diastereomers (or diastereoisomers) are stereoisomers that are not enantiomers, i.e. they are not related as mirror images. If a compound contains a double bond, the substituents may be in the E or the Z configuration.

Substituents on bivalent cyclic saturated or partially saturated radicals may have either the cis- or trans-configuration; for example if a compound contains a disubstituted cycloalkyl group, the substituents may be in the cis or trans configuration.

Therefore, the invention includes enantiomers, atropisomers, diastereomers, racemates, E isomers, Z isomers, cis isomers, trans isomers and mixtures thereof, whenever chemically possible.

The meaning of all those terms, i.e. enantiomers, atropisomers, diastereomers, racemates, E isomers, Z isomers, cis isomers, trans isomers and mixtures thereof are known to the skilled person.

The absolute configuration is specified according to the Cahn-Ingold-Prelog system.

The configuration at an asymmetric atom is specified by either R or S. Resolved stereoisomers whose absolute configuration is not known can be designated by (+) or (−) depending on the direction in which they rotate plane polarized light. For instance, resolved enantiomers whose absolute configuration is not known can be designated by (+) or (−) depending on the direction in which they rotate plane polarized light.

When a specific stereoisomer is identified, this means that said stereoisomer is substantially free, i.e. associated with less than 50%, preferably less than 20%, more preferably less than 10%, even more preferably less than 5%, in particular less than 2% and most preferably less than 1%, of the other stereoisomers. Thus, when a compound of Formula (I) is for instance specified as (R), this means that the compound is substantially free of the (S) isomer; when a compound of Formula (I) is for instance specified as E, this means that the compound is substantially free of the Z isomer; when a compound of Formula (I) is for instance specified as cis, this means that the compound is substantially free of the trans isomer.

Some of the compounds according to Formula (I) may also exist in their tautomeric form. Such forms in so far as they may exist, although not explicitly indicated in the above Formula (I) are intended to be included within the scope of the present invention. It follows that a single compound may exist in both stereoisomeric and tautomeric form.

Pharmaceutically-acceptable addition salts include acid addition salts and base addition salts. Such salts may be formed by conventional means, for example by reaction of a free acid or a free base form with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound of the invention in the form of a salt with another counter-ion, for example using a suitable ion exchange resin.

The pharmaceutically acceptable addition salts as mentioned hereinabove or hereinafter are meant to comprise the therapeutically active non-toxic acid and base addition salt forms which the compounds of Formula (I) and solvates thereof, are able to form.

Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds of Formula (I) and solvates thereof containing an acidic proton may also be converted into their non-toxic metal or amine addition salt forms by treatment with appropriate organic and inorganic bases.

Appropriate base salt forms comprise, for example, the ammonium salts, the alkali and earth alkaline metal salts, e.g. the lithium, sodium, potassium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline; the benzathine, N-methyl-D-glucamine, hydrabamine salts, and salts with amino acids such as, for example, arginine, lysine and the like. Conversely the salt form can be converted by treatment with acid into the free acid form.

The term solvate comprises the solvent addition forms as well as the salts thereof, which the compounds of Formula (I) are able to form. Examples of such solvent addition forms are e.g. hydrates, alcoholates and the like.

The compounds of the invention as prepared in the processes described below may be synthesized in the form of mixtures of enantiomers, in particular racemic mixtures of enantiomers, that can be separated from one another following art-known resolution procedures. A manner of separating the enantiomeric forms of the compounds of Formula (I), and pharmaceutically acceptable addition salts, and solvates thereof, involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound would be synthesized by stereospecific methods of preparation. These methods will advantageously employ enantiomerically pure starting materials.

The present invention also embraces isotopically-labeled compounds of the present invention which are identical to those recited herein, but for the fact that one or more atoms are replaced by an atom having an atomic mass or mass number different from the atomic mass or mass number usually found in nature (or the most abundant one found in nature).

All isotopes and isotopic mixtures of any particular atom or element as specified herein are contemplated within the scope of the compounds of the invention, either naturally occurring or synthetically produced, either with natural abundance or in an isotopically enriched form. Exemplary isotopes that can be incorporated into compounds of the invention include isotopes of hydrogen, carbon, nitrogen, oxygen, phosphorus, sulfur, fluorine, chlorine and iodine, such as $^{2}H$, $^{3}H$, $^{11}C$, $^{13}C$, $^{14}C$, $^{13}N$, $^{15}O$, $^{17}O$, $^{18}O$, $^{32}P$, $^{33}P$, $^{35}S$, $^{18}F$, $^{36}Cl$, $^{122}I$, $^{123}I$, $^{125}I$, $^{131}I$, $^{75}Br$, $^{76}Br$, $^{77}Br$ and $^{82}Br$. Preferably, the radioactive isotope is selected from the group of $^{2}H$, $^{3}H$, $^{11}C$ and $^{18}F$. More preferably, the radioactive isotope is $^{2}H$. In particular, deuterated compounds are intended to be included within the scope of the present invention.

Certain isotopically-labeled compounds of the present invention (e.g., those labeled with $^{3}H$ and $^{14}C$) are useful in compound and for substrate tissue distribution assays. Tritiated ($^{3}H$) and carbon-14 ($^{14}C$) isotopes are useful for their ease of preparation and detectability. Further, substitution with heavier isotopes such as deuterium (i.e., $^{2}H$ may afford certain therapeutic advantages resulting from greater metabolic stability (e.g., increased in vivo half-life or reduced dosage requirements) and hence may be preferred in some circumstances. Positron emitting isotopes such as $^{15}O$, $^{13}N$, C and $^{18}F$ are useful for positron emission tomography (PET) studies to examine substrate receptor occupancy.

The present invention relates in particular to compounds of Formula (I) as defined herein, tautomers and stereoisomeric forms thereof, wherein $R^1$ represents $C_{1-4}$alkyl;
$R^2$ represents $C_{1-6}$alkyl, or $C_{1-6}$alkyl substituted with one $R^5$; Y represents $CR^4$;
$R^4$ represents hydrogen or halo;
$R^5$ represents $Het^{3a}$, $-NR^{6a}R^{6b}$, or $-OR^7$;
$R^{6a}$ represents hydrogen or $C_{1-4}$alkyl;

R$^{6b}$ represents hydrogen; C$_{1-4}$alkyl; C$_{3-6}$cycloalkyl; —C(=O)—C$_{1-4}$alkyl; —C(=O)—Het$^4$; —S(=O)$_2$—C$_{1-4}$alkyl; —C(=O)—C$_{1-4}$alkyl substituted with one substituent selected from the group consisting of —OH and —NR$^{6a}$R$^{16b}$; or C$_{1-4}$alkyl substituted with one substituent selected from the group consisting of —OH and —S(=O)$_2$—C$_{1-4}$alkyl;

R$^7$ represents hydrogen, C$_{1-4}$alkyl, —C$_{1-4}$alkyl-NR$^{8a}$R$^{8b}$, —C(=O)—R$^9$, —S(=O)$_2$—OH, —P(=O)$_2$—OH, —(C=O)—CH(NH$_2$)—C$_{1-4}$alkyl-Ar$^1$, or —C$_4$alkyl-Het$^{3b}$;

R$^{8a}$ represents hydrogen or C$_{1-4}$alkyl;

R$^{8b}$ represents hydrogen, C$_{1-4}$alkyl, or C$_{3-6}$cycloalkyl;

R$^9$ represents C$_{1-6}$alkyl, or C$_{1-6}$alkyl substituted with one substituent selected from the group consisting of —NH$_2$, —COOH, and Het$^6$;

R$^{16a}$ and R$^{16b}$ each independently represents hydrogen, C$_{1-4}$alkyl or C$_{3-6}$cycloalkyl;

R$^3$ represents a 5-membered heteroaromatic ring containing one, two or three heteroatoms each independently selected from O, S, and N;

wherein said 5-membered heteroaromatic ring may optionally be substituted, where possible, on one ring N-atom with a substituent selected from the group consisting of C$_{1-6}$alkyl; C$_{3-6}$cycloalkyl; Het$^{1a}$; R$^{18}$; R$^{21}$; C$_{1-4}$alkyl substituted with one, two or three halo atoms; C$_{1-4}$alkyl substituted with one, two or three —OH substituents; C$_{1-6}$alkyl substituted with one R$^{13}$; C$_{1-4}$alkyl substituted with one R$^{18}$; C$_{2-6}$alkenyl; and C$_{2-6}$alkenyl substituted with one R$^{13}$; provided that when Het$^{1a}$ or R$^{18}$ are directly attached to the N-atom of the 5-membered heteroaromatic ring, said Het$^{1a}$ or R$^{18}$ are attached to the N-atom via a ring carbon atom; and wherein said 5-membered heteroaromatic ring may optionally be substituted on the ring carbon atoms with in total one or two substituents each independently selected from the group consisting of halo; cyano; C$_{1-6}$alkyl; —O—C$_{1-4}$alkyl; —C(=O)—R$^{10}$; —S(=O)$_2$—C$_{1-4}$alkyl; —S(=O)(=N—R$^{20a}$)—C$_{1-4}$alkyl; —O—C$_{1-4}$alkyl substituted with one, two or three halo atoms; —O—C$_{1-4}$alkyl-R$^{12}$; C$_{3-6}$cycloalkyl; —O—C$_{3-6}$cycloalkyl; Het$^{1a}$; —O-Het$^{1b}$; R$^{18}$; R$^{21}$; —P(=O)—(C$_{1-4}$alkyl)$_2$; —NH—C(=O)—C$_{1-4}$alkyl; —NH—C(=O)—Het$^{1g}$; —NR$^{17a}$R$^{17b}$; C$_{1-4}$alkyl substituted with one, two or three halo atoms; C$_{1-4}$alkyl substituted with one, two or three —OH substituents; C$_{1-6}$alkyl substituted with one R$^{13}$; C$_{1-4}$allyl substituted with one R$^{18}$; C$_{2-6}$alkenyl; and C$_{2-6}$alkenyl substituted with one R$^{13}$;

R$^{10}$ represents —OH, —O—C$_{1-4}$alkyl, —NR$^{11a}$R$^{11b}$ or Het$^2$;

R$^{18}$ represents a 5-membered aromatic ring containing one, two or three N-atoms; wherein said 5-membered aromatic ring may optionally be substituted with one substituent selected from the group consisting of C$_{1-4}$alkyl and C$_{3-6}$cycloalkyl;

R$^{21}$ represents 3,6-dihydro-2H-pyran-4-yl or 1,2,3,6-tetrahydro-4-pyridinyl, wherein 1,2,3,6-tetrahydro-4-pyridinyl may optionally be substituted on the N-atom with C$_{1-4}$alkyl or C$_{3-6}$cycloalkyl;

Het$^{1a}$, Het$^{1c}$ and Het$^{1d}$ each independently represents a 4- to 7-membered monocyclic saturated heterocyclyl containing one or two heteroatoms each independently selected from O, S, S(=O)$_p$ and N; or a 6- to 11-membered bicyclic saturated heterocyclyl, including fused, spiro and bridged cycles, containing one, two or three heteroatoms each independently selected from O, S, S(=O)$_p$ and N;

wherein said 4- to 7-membered monocyclic saturated heterocyclyl or said 6- to 11-membered bicyclic saturated heterocyclyl may optionally be substituted, where possible, on one, two or three ring N-atoms with a substituent each independently selected from the group consisting of C$_{1-4}$alkyl, C$_{3-6}$cycloalkyl, C$_{1-4}$alkyl substituted with one, two or three halo atoms, and C$_{1-4}$alkyl substituted with one substituent selected from the group consisting of —OH, —C(=O)—OH, —C(=O)—NR$^{22a}$R$^{22b}$ and —O—C$_{1-4}$alkyl; and wherein said 4- to 7-membered monocyclic saturated heterocyclyl or said 6- to 11-membered bicyclic saturated heterocyclyl may optionally be substituted on one, two or three ring C-atoms with one or two substituents each independently selected from the group consisting of —OH, oxo, halo, C$_{1-4}$alkyl, cyano, —C(=O)—C$_{1-4}$alkyl, —O—C$_{1-4}$alkyl, —NH$_2$, —NH(C$_{1-4}$alkyl), and —N(C$_{1-4}$alkyl)$_2$;

Het$^{1b}$, Het$^{1c}$, Het$^{1g}$ and Het$^4$ each independently represents a 4- to 7-membered monocyclic saturated heterocyclyl, attached to the remainder of the molecule of Formula (I) through any available ring carbon atom, said Het$^{1b}$, Het$^{1e}$, Het$^{1g}$ and Het$^4$ containing one or two heteroatoms each independently selected from O, S, S(=O)$_p$ and N;

wherein said 4- to 7-membered monocyclic saturated heterocyclyl may optionally be substituted, where possible, on one or two ring N-atoms with a substituent each independently selected from the group consisting of C$_{1-4}$alkyl, C$_{3-6}$cycloalkyl, and C$_{1-4}$alkyl substituted with one substituent selected from the group consisting of —OH and —O—C$_{1-4}$alkyl; and wherein said 4- to 7-membered monocyclic saturated heterocyclyl may optionally be substituted on one, two or three ring C-atoms with one or two substituents each independently selected from the group consisting of —OH, halo, C$_{1-4}$alkyl, cyano, —C(=O)—C$_{1-4}$alkyl, —O—C$_{1-4}$alkyl, —NH$_2$, —NH(C$_{1-4}$alkyl), and —N(C$_{1-4}$alkyl)$_2$;

Het$^2$ represents a heterocyclyl of formula (b-1):

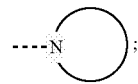

(b-1)

(b-1) represents a N-linked 4- to 7-membered monocyclic saturated heterocyclyl optionally containing one additional heteroatom selected from O, S, S(=O)$_p$ and N, or a N-linked 6- to 11-membered bicyclic saturated heterocyclyl, including fused, spiro and bridged cycles, optionally containing one or two additional heteroatoms each independently selected from O, S, S(=O)$_p$ and N;

wherein in case (b-1) contains one or two additional N-atoms, said one or two N-atoms may optionally be substituted with C$_{1-4}$alkyl; and wherein (b-1) may optionally be substituted on one, two or three ring C-atoms with one or two substituents each independently selected from the group consisting of halo, —OH, cyano, C$_{1-4}$alkyl, —O—C$_{1-4}$alkyl, —NH$_2$, —NH(C$_{1-4}$alkyl), —N(C$_{1-4}$alkyl)$_2$, and C$_{1-4}$alkyl-OH;

R$^{11b}$ represents hydrogen; Het$^{1e}$; C$_{1-4}$alkyl; C$_{1-4}$alkyl-Het$^5$; C$_{1-4}$alkyl substituted with one, two or three substituents each independently selected from the group consisting of halo, —OH and —O—C$_{1-4}$alkyl; C$_{3-6}$cycloalkyl; or C$_{3-6}$cycloalkyl substituted with one, two or three substituents each independently selected from the group consisting of halo, —OH and —O—C$_{1-4}$alkyl;

R$^{13}$ represents —O—C$_{1-4}$alkyl, —C(=O)OH, —C(=O)NR$^{1a}$R$^{5b}$, —NR$^{19a}$R$^{19b}$, C$_{3-6}$cycloalkyl, Het$^{1d}$, —S(=O)$_2$—C$_{1-4}$alkyl, —S(=O)(=N—R$^{20c}$)—C$_{1-4}$alkyl, or —C(=O)—Het$^f$;

$R^{12}$ represents —OH, —O—$C_{1-4}$alkyl, —NR$^{14a}$R$^{14b}$, —C(=O)NR$^{14c}$R$^{14d}$, —S(=O)$_2$—C$_4$alkyl, —S(=O)(=N—R$^{20b}$)—$C_{1-4}$alkyl, $C_{3-6}$cycloalkyl, Ar$^2$, or Het$^{1e}$;

Ar$^1$ represents phenyl optionally substituted with one hydroxy;

Ar$^2$ represents phenyl optionally substituted with one $C_{1-4}$alkyl;

Het$^{3a}$, Het$^{3b}$, Het$^5$, Het$^6$ and Het$^{1f}$ each independently represents a heterocyclyl of formula (c-1):

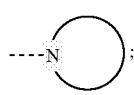

(c-1)

(c-1) represents a N-linked 4- to 7-membered monocyclic saturated heterocyclyl optionally containing one additional heteroatom selected from O, S, S(=O)$_p$ and N; wherein in case (c-1) contains one additional N-atom, said additional N-atom may optionally be substituted with $C_{1-4}$alkyl or $C_{3-6}$cycloalkyl; and wherein (c-1) may optionally be substituted on one or two ring C-atoms atoms with one or two substituents each independently selected from the group consisting of halo, $C_{1-4}$alkyl, and $C_{3-6}$cycloalkyl;

$R^{11a}$, $R^{14a}$, $R^{14c}$, $R^{15a}$, $R^{17a}$, $R^{19a}$ and $R^{22a}$ each independently represents hydrogen, $C_{1-4}$alkyl, or $C_{3-6}$cycloalkyl;

$R^{14b}$, $R^{14d}$, $R^{15b}$, $R^{17b}$, $R^{19b}$ and $R^{22b}$ each independently represents hydrogen; $C_{1-4}$alkyl; $C_{3-6}$cycloalkyl; or $C_{1-4}$alkyl substituted with one substituent selected from the group consisting of halo, —OH and —O—$C_{1-4}$alkyl;

$R^{20a}$, $R^{20b}$ and $R^{20c}$ each independently represents hydrogen; $C_{1-4}$alkyl; $C_{3-6}$cycloalkyl; or $C_{1-4}$alkyl substituted with one substituent selected from the group consisting of —OH and —O—$C_{1-4}$alkyl;

p represents 1 or 2;

and the pharmaceutically acceptable addition salts, and the solvates thereof.

The present invention relates in particular to compounds of Formula (I) as defined herein, tautomers and stereoisomeric forms thereof, wherein $R^1$ represents $C_{1-4}$alkyl;

$R^2$ represents $C_{1-6}$alkyl substituted with one $R^5$;

Y represents CR$^4$ or N;

$R^4$ represents hydrogen or halo;

$R^5$ represents Het$^{3a}$, —NR$^{6a}$R$^{6b}$, or —OR$^7$;

$R^{6a}$ represents hydrogen or $C_{1-4}$alkyl;

$R^{6b}$ represents hydrogen; or $C_{1-4}$alkyl substituted with one —OH substituent;

$R^7$ represents hydrogen or —C(=O)—R$^9$;

$R^9$ represents $C_{1-6}$alkyl;

$R^3$ represents a 5-membered heteroaromatic ring containing one, two or three heteroatoms each independently selected from O, S, and N;

wherein said 5-membered heteroaromatic ring may optionally be substituted, where possible, on one ring N-atom with a substituent selected from the group consisting of $C_{1-6}$alkyl; $C_{3-6}$cycloalkyl; Het$^{1a}$; $C_{1-4}$alkyl substituted with one, two or three halo atoms; $C_{1-5}$alkyl substituted with one, two or three —OH substituents; $C_{1-6}$alkyl substituted with one $R^{13}$; —$C_{1-4}$alkyl-O—$C_{1-4}$alkyl substituted with one or two —OH substituents; $C_{1-4}$alkyl substituted with one $R^{18}$; and $C_{2-6}$alkenyl; provided that when Het$^{1a}$ is directly attached to the N-atom of the 5-membered heteroaromatic ring, said Het$^{1a}$ is attached to the N-atom via a ring carbon atom; and wherein said 5-membered heteroaromatic ring may optionally be substituted on the ring carbon atoms with in total one or two substituents each independently selected from the group consisting of halo; cyano; $C_{1-6}$alkyl; —O—$C_{1-4}$alkyl; —C(=O)—R$^{10}$; —O—$C_{1-4}$alkyl-R$^{12}$; $C_{3-6}$cycloalkyl; —O—$C_{3-6}$cycloalkyl; Het$^{1a}$; —O-Het$^{1b}$; —P(=O)—($C_{1-4}$alkyl)$_2$; $C_{1-4}$alkyl substituted with one, two or three halo atoms; $C_{1-4}$alkyl substituted with one, two or three —OH substituents; and $C_{1-6}$alkyl substituted with one $R^{13}$;

$R^{10}$ represents —NR$^{11a}$R$^{11b}$ or Het$^2$;

$R^{18}$ represents a 5-membered aromatic ring containing one, two or three N-atoms; wherein said 5-membered aromatic ring may optionally be substituted with one substituent selected from the group consisting of $C_{1-4}$alkyl and $C_{3-6}$cycloalkyl;

Het$^{1a}$, Het$^{1c}$ and Het$^{1d}$ each independently represents a 4- to 7-membered monocyclic saturated heterocyclyl containing one or two heteroatoms each independently selected from O, S, S(=O)$_p$ and N; or a 6- to 11-membered bicyclic saturated heterocyclyl, including fused cycles, containing one, two or three heteroatoms each independently selected from O and N;

wherein said 4- to 7-membered monocyclic saturated heterocyclyl or said 6- to 11-membered bicyclic saturated heterocyclyl may optionally be substituted, where possible, on one, two or three ring N-atoms with a substituent each independently selected from the group consisting of $C_{1-4}$alkyl, $C_{1-4}$alkyl substituted with one, two or three halo atoms, and $C_{1-4}$alkyl substituted with one substituent selected from the group consisting of —C(=O)—OH, —C(=O)—NR$^{22a}$R$^{22b}$ and —O—$C_{1-4}$alkyl; and wherein said 4- to 7-membered monocyclic saturated heterocyclyl or said 6- to 11-membered bicyclic saturated heterocyclyl may optionally be substituted on one, two or three ring C-atoms with one or two substituents each independently selected from the group consisting of oxo, halo and $C_{1-4}$alkyl;

Het$^{1b}$ and Het$^{1e}$ each independently represents a 4- to 7-membered monocyclic saturated heterocyclyl, attached to the remainder of the molecule of Formula (I) through any available ring carbon atom, said Het$^b$ and Het$^{1e}$ containing one or two O-atoms;

Het$^2$ represents a heterocyclyl of formula (b-1):

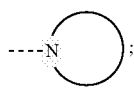

(b-1)

(b-1) represents a N-linked 4- to 7-membered monocyclic saturated heterocyclyl optionally containing one additional N-atom;

wherein in case (b-1) contains one additional N-atom, said N-atom may optionally be substituted with $C_{1-4}$alkyl;

$R^{11b}$ represents Het$^{1e}$; $C_{1-4}$alkyl; or $C_{3-6}$cycloalkyl;

$R^{13}$ represents —O—$C_{1-4}$alkyl, —C(=O)OH, —C(=O)NR$^{1a}$R$^{15b}$, —NR$^{19a}$R$^{19b}$, $C_{3-6}$cycloalkyl, Het$^{1d}$, Het$^7$, —S(=O)$_2$—$C_{1-4}$alkyl, or —C(=O)—Het$^{1f}$;

$R^{12}$ represents —O—$C_{1-4}$alkyl or Het$^{1c}$;

Het$^{3a}$ and Het$^{1f}$ each independently represents a heterocyclyl of formula (c-1):

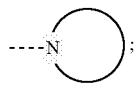

(c-1) represents a N-linked 4- to 7-membered monocyclic saturated heterocyclyl optionally containing one additional N-atom;

wherein in case (c-1) contains one additional N-atom, said additional N-atom may optionally be substituted with $C_{3-6}$cycloalkyl; and wherein (c-1) may optionally be substituted on one or two ring C-atoms atoms with one or two halo substituents;

Het$^7$ represents 5,6,7,8-tetrahydro-imidazo[1,2-a]pyridinyl;

$R^{11a}$, $R^{15a}$, $R^{19a}$ and $R^{22a}$ each independently represents hydrogen, $C_{1-4}$alkyl, or $C_{3-6}$cycloalkyl;

$R^{15b}$, $R^{19b}$ and $R^{22b}$ each independently represents $C_{1-4}$alkyl or $C_{3-6}$cycloalkyl;

p represents 2;

and the pharmaceutically acceptable addition salts, and the solvates thereof.

The present invention relates in particular to compounds of Formula (I) as defined herein, tautomers and stereoisomeric forms thereof, wherein $R^1$ represents $C_{1-4}$alkyl;

$R^2$ represents $C_{1-6}$alkyl, or $C_{1-6}$alkyl substituted with one $R^5$;

Y represents $CR^4$;

$R^4$ represents hydrogen or halo;

$R^5$ represents Het$^{3a}$, —NR$^{6a}$R$^{6b}$, or —OR$^7$;

$R^{6a}$ represents hydrogen or $C_{1-4}$alkyl;

$R^{6b}$ represents hydrogen; $C_{1-4}$alkyl; $C_{3-6}$cycloalkyl; —C(=O)—$C_{1-4}$alkyl; —C(=O)—$C_{1-4}$alkyl substituted with one substituent selected from the group consisting of —OH and —NR$^{16a}$R$^{16b}$; or $C_{1-4}$alkyl substituted with one —OH substituent;

$R^7$ represents hydrogen, $C_{1-4}$alkyl, —$C_{1-4}$alkyl-NR$^{8a}$R$^b$, or —C(=O)—R$^9$;

$R^{8a}$ represents hydrogen or $C_{1-4}$alkyl;

$R^{8b}$ represents hydrogen, $C_{1-4}$alkyl, or $C_{3-6}$cycloalkyl;

$R^9$ represents $C_{1-6}$alkyl, or $C_{1-6}$alkyl substituted with one substituent selected from the group consisting of —NH$_2$, and —COOH;

$R^{16a}$ and $R^{16b}$ each independently represents hydrogen, $C_{1-4}$alkyl or $C_{3-6}$cycloalkyl;

$R^3$ represents a 5-membered heteroaromatic ring containing one, two or three heteroatoms each independently selected from O, S, and N;

wherein said 5-membered heteroaromatic ring may optionally be substituted, where possible, on one ring N-atom with a substituent selected from the group consisting of $C_{1-6}$alkyl; $C_{3-6}$cycloalkyl; Het$^{1a}$; $R^{18}$; $C_{1-4}$alkyl substituted with one, two or three halo atoms; $C_{1-4}$alkyl substituted with one, two or three —OH substituents; $C_{1-6}$alkyl substituted with one $R^{13}$; $C_{1-4}$alkyl substituted with one $R^{18}$; $C_{2-6}$alkenyl; and $C_{2-6}$alkenyl substituted with one $R^{13}$; provided that when Het$^{1a}$ or $R^{18}$ are directly attached to the N-atom of the 5-membered heteroaromatic ring, said Het$^{1a}$ or $R^{18}$ are attached to the N-atom via a ring carbon atom; and wherein said 5-membered heteroaromatic ring may optionally be substituted on the ring carbon atoms with in total one or two substituents each independently selected from the group consisting of halo; cyano; $C_{1-6}$alkyl; —O—$C_{1-4}$alkyl; —C(=O)—$R^{10}$; —O—$C_{1-4}$alkyl substituted with one, two or three halo atoms; —O—$C_{1-4}$alkyl-$R^{12}$; $C_{3-6}$cycloalkyl; —O—$C_{3-6}$cycloalkyl; Het a; —O-Het$^{1b}$; $R^{18}$; —P(=O)—(C$_{1-4}$alkyl)$_2$; —NH—C(=O)—$C_{1-4}$alkyl; —NH—C(=O)—Het$^{1g}$; —NR$^{17a}$R$^{17b}$; $C_{1-4}$alkyl substituted with one, two or three halo atoms; $C_{1-4}$alkyl substituted with one, two or three —OH substituents; $C_{1-6}$alkyl substituted with one $R^{13}$; $C_{1-4}$alkyl substituted with one $R^{18}$; $C_{2-6}$alkenyl; and $C_{2-6}$alkenyl substituted with one $R^{13}$;

$R^{10}$ represents —OH, —O—$C_{1-4}$alkyl, —NR$^{11a}$R$^{11b}$ or Het$^2$;

$R^{18}$ represents a 5-membered aromatic ring containing one, two or three N-atoms; wherein said 5-membered aromatic ring may optionally be substituted with one substituent selected from the group consisting of $C_{1-4}$alkyl and $C_{3-6}$cycloalkyl;

Het$^{1a}$, and Het$^{1d}$ each independently represents a 4- to 7-membered monocyclic saturated heterocyclyl containing one or two heteroatoms each independently selected from O, S, S(=O)$_p$ and N;

wherein said 4- to 7-membered monocyclic saturated heterocyclyl may optionally be substituted, where possible, on one, two or three ring N-atoms with a substituent each independently selected from the group consisting of $C_{1-4}$alkyl, $C_{3-6}$cycloalkyl, $C_{1-4}$alkyl substituted with one, two or three halo atoms, and $C_{1-4}$alkyl substituted with one substituent selected from the group consisting of —OH, —C(=O)—OH, —C(=O)—NR$^{22a}$R$^{22b}$ and —O—$C_{1-4}$alkyl; and wherein said 4- to 7-membered monocyclic saturated heterocyclyl may optionally be substituted on one, two or three ring C-atoms with one or two substituents each independently selected from the group consisting of —OH, oxo, halo, $C_{1-4}$alkyl, cyano, —C(=O)—$C_{1-4}$alkyl, —O—$C_{1-4}$alkyl, —NH$_2$, —NH(C$_{1-4}$alkyl), and —N(C$_{1-4}$alkyl)$_2$;

Het$^{1b}$, Het$^{1e}$, and Het$^{1g}$ each independently represents a 4- to 7-membered monocyclic saturated heterocyclyl, attached to the remainder of the molecule of Formula (I) through any available ring carbon atom, said Het$^{1b}$, Het$^{1e}$, and Het$^{1g}$ containing one or two heteroatoms each independently selected from O, S, S(=O)$_p$ and N;

wherein said 4- to 7-membered monocyclic saturated heterocyclyl may optionally be substituted, where possible, on one or two ring N-atoms with a substituent each independently selected from the group consisting of $C_{1-4}$alkyl, $C_{3-6}$cycloalkyl, and $C_{1-4}$alkyl substituted with one substituent selected from the group consisting of —OH and —O—$C_{1-4}$alkyl; and wherein said 4- to 7-membered monocyclic saturated heterocyclyl may optionally be substituted on one, two or three ring C-atoms with one or two substituents each independently selected from the group consisting of —OH, halo, $C_{1-4}$alkyl, cyano, —C(=O)—$C_{1-4}$alkyl, —O—$C_{1-4}$alkyl, —NH$_2$, —NH(C$_{1-4}$alkyl), and —N(C$_{1-4}$alkyl)$_2$;

Het$^2$ represents a heterocyclyl of formula (b-1):

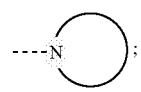

(b-1) represents a N-linked 4- to 7-membered monocyclic saturated heterocyclyl optionally containing one additional heteroatom selected from O, S, S(=O)$_p$ and N; wherein in case (b-1) contains one additional N-atom, said N-atom may optionally be substituted with $C_{1-4}$alkyl; and wherein (b-1) may optionally be substituted on one, two or three ring C-atoms with one or two substituents each independently selected from the group consisting of halo, —OH, cyano, $C_{1-4}$alkyl, —O—$C_{1-4}$alkyl, —NH$_2$, —NH($C_{1-4}$alkyl), —N($C_{1-4}$alkyl)$_2$, and $C_{1-4}$alkyl-OH;

$R^{11b}$ represents hydrogen; Het$^{1e}$; $C_{1-4}$alkyl; $C_{1-4}$alkyl substituted with one, two or three substituents each independently selected from the group consisting of halo, —OH and —O—$C_{1-4}$alkyl; $C_{3-6}$cycloalkyl; or $C_{3-6}$cycloalkyl substituted with one, two or three substituents each independently selected from the group consisting of halo, —OH and —O—$C_{1-4}$alkyl;

$R^{13}$ represents —O—$C_{1-4}$alkyl, —C(=O)OH, —C(=O)NR$^{1a}$R$^{15b}$, —NR$^{19a}$R$^{19b}$, $C_{3-6}$cycloalkyl, Het$^{1d}$, —S(=O)$_2$—$C_{1-4}$alkyl, or —C(=O)—Het$^{1f}$;

$R^{12}$ represents —OH, —O—$C_{1-4}$alkyl, —NR$^{14a}$R$^{14b}$, —C(=O)NR$^{14c}$R$^{14d}$, —S(=O)$_2$—$C_{1-4}$alkyl, $C_{3-6}$cycloalkyl;

Het$^{3a}$, and Het$^{1f}$ each independently represents a heterocyclyl of formula (c-1):

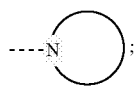
(c-1)

(c-1) represents a N-linked 4- to 7-membered monocyclic saturated heterocyclyl optionally containing one additional heteroatom selected from O, S, S(=O)$_p$ and N; wherein in case (c-1) contains one additional N-atom, said additional N-atom may optionally be substituted with $C_{1-4}$alkyl or $C_{3-6}$cycloalkyl; and wherein (c-1) may optionally be substituted on one or two ring C-atoms atoms with one or two substituents each independently selected from the group consisting of halo, $C_{1-4}$alkyl, and $C_{3-6}$cycloalkyl;

$R^{11a}$, $R^{14a}$, $R^{14c}$, $R^{15a}$, $R^{17a}$, $R^{19a}$ and $R^{22a}$ each independently represents hydrogen, $C_{1-4}$alkyl, or $C_{3-6}$cycloalkyl;

$R^{14b}$, $R^{14d}$, $R^{15b}$, $R^{17b}$, $R^{19b}$ and $R^{22b}$ each independently represents hydrogen; $C_{1-4}$alkyl; $C_{3-6}$cycloalkyl; or $C_{1-4}$alkyl substituted with one substituent selected from the group consisting of halo, —OH and —O—$C_{1-4}$alkyl;

p represents 1 or 2;

and the pharmaceutically acceptable addition salts, and the solvates thereof.

The present invention relates in particular to compounds of Formula (I) as defined herein, tautomers and stereoisomeric forms thereof, wherein $R^1$ represents $C_{1-4}$alkyl;
$R^2$ represents $C_{1-6}$alkyl substituted with one $R^5$;
Y represents CR$^4$;
$R^4$ represents hydrogen or halo;
$R^5$ represents Het$^{3a}$, —NR$^{6a}$R$^{6b}$, or —OR$^7$;
$R^{6a}$ represents $C_{1-4}$alkyl;
$R^{6b}$ represents $C_{1-4}$alkyl substituted with one —OH substituent;
$R^7$ represents hydrogen, or —C(=O)—R$^9$;
$R^9$ represents $C_{1-6}$alkyl;
$R^3$ represents a 5-membered heteroaromatic ring containing two or three heteroatoms each independently selected from O, S, and N;

wherein said 5-membered heteroaromatic ring may optionally be substituted, where possible, on one ring N-atom with a substituent selected from the group consisting of $C_{1-6}$alkyl; Het$^{1a}$; $C_{1-4}$alkyl substituted with one, two or three halo atoms; $C_{1-4}$alkyl substituted with one, two or three —OH substituents; $C_{1-6}$alkyl substituted with one R$^{13}$; $C_{1-4}$alkyl substituted with one R$^{18}$; and $C_{2-6}$alkenyl; provided that when Het$^{1a}$ is directly attached to the N-atom of the 5-membered heteroaromatic ring, said Het$^1$a is attached to the N-atom via a ring carbon atom; and wherein said 5-membered heteroaromatic ring may optionally be substituted on the ring carbon atoms with in total one or two substituents each independently selected from the group consisting of halo; cyano; $C_{1-6}$alkyl; —O—$C_{1-4}$alkyl; —C(=O)—R$^{10}$; $C_{3-6}$cycloalkyl; Het$^{1a}$; —P(=O)—($C_{1-4}$alkyl)$_2$; $C_{1-4}$alkyl substituted with one, two or three halo atoms; $C_{1-4}$alkyl substituted with one, two or three —OH substituents; and $C_{1-6}$alkyl substituted with one R$^{13}$;

$R^{10}$ represents —NR$^{11a}$R$^{11b}$ or Het$^2$;
$R^{18}$ represents a 5-membered aromatic ring containing one, two or three N-atoms; wherein said 5-membered aromatic ring may optionally be substituted with one $C_{1-4}$alkyl;

Het$^{1a}$, and Het$^{1d}$ each independently represents a 4- to 7-membered monocyclic saturated heterocyclyl containing one or two heteroatoms each independently selected from O, S, S(=O)$_p$ and N;

wherein said 4- to 7-membered monocyclic saturated heterocyclyl may optionally be substituted, where possible, on one ring N-atom with a substituent each independently selected from the group consisting of $C_{1-4}$alkyl, $C_{1-4}$alkyl substituted with one, two or three halo atoms, and $C_{1-4}$alkyl substituted with one substituent selected from the group consisting of —C(=O)—NR$^{22a}$R$^{22b}$ and —O—$C_{1-4}$alkyl; and wherein said 4- to 7-membered monocyclic saturated heterocyclyl may optionally be substituted on one, two or three ring C-atoms with one or two substituents each independently selected from the group consisting of oxo, halo, and $C_{1-4}$alkyl;

Het$^{1e}$ represents a 4- to 7-membered monocyclic saturated heterocyclyl, attached to the remainder of the molecule of Formula (I) through any available ring carbon atom, said Het$^{1e}$ containing one or two O-atoms;

Het$^2$ represents 1-piperidinyl;
$R^{11b}$ represents Het$^{1e}$; $C_{1-4}$alkyl; $C_{3-6}$cycloalkyl;
$R^{13}$ represents —O—$C_{1-4}$alkyl, —C(=O)OH, —C(=O)NR$^{5a}$R$^{15b}$, —NR$^{19a}$R$^{19b}$, $C_{3-6}$cycloalkyl, Het$^{1d}$, —S(=O)$_2$—$C_{1-4}$alkyl, or —C(=O)—Het$^{1f}$;

Het$^{3a}$, and Het$^{1f}$ each independently represents a heterocyclyl of formula (c-1):

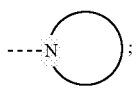
(c-1)

(c-1) represents a N-linked 4- to 7-membered monocyclic saturated heterocyclyl optionally containing one additional N-atom;

wherein in case (c-1) contains one additional N-atom, said additional N-atom may optionally be substituted with $C_{3-6}$cycloalkyl; and wherein (c-1) may optionally be substituted on one or two ring C-atoms atoms with one or two halo substituents;

$R^{11a}$, $R^{15a}$, $R^{19a}$ and $R^{22a}$ each independently represents hydrogen, $C_{1-4}$alkyl, or $C_{3-6}$cycloalkyl;

$R^{15b}$, $R^{19b}$ and $R^{22b}$ each independently represents $C_{1-4}$alkyl; or $C_{3-6}$cycloalkyl; p represents 2;

and the pharmaceutically acceptable addition salts, and the solvates thereof.

The present invention relates in particular to compounds of Formula (I) as defined herein, tautomers and stereoisomeric forms thereof, wherein $R^1$ represents $C_{1-4}$alkyl;

$R^2$ represents $C_{1-6}$alkyl substituted with one $R^5$;

Y represents $CR^4$;

$R^4$ represents hydrogen or halo;

$R^5$ represents $Het^{3a}$, $-NR^{6a}R^{6b}$, or $-OR^7$;

$R^{6a}$ represents $C_{1-4}$alkyl;

$R^{6b}$ represents $C_{1-4}$alkyl substituted with one $-OH$ substituent;

$R^7$ represents hydrogen, or $-C(=O)-R^9$;

$R^9$ represents $C_{1-6}$alkyl;

$R^3$ represents a 5-membered heteroaromatic ring containing two or three heteroatoms each independently selected from O, S, and N;

wherein said 5-membered heteroaromatic ring may optionally be substituted, where possible, on one ring N-atom with a substituent selected from the group consisting of $C_{1-6}$alkyl; $Het^{1a}$; $C_{1-4}$alkyl substituted with one, two or three halo atoms; $C_{1-5}$alkyl substituted with one, two or three $-OH$ substituents; $C_{1-6}$alkyl substituted with one $R^{13}$; $C_{1-4}$alkyl substituted with one $R^{18}$; and $C_{2-6}$alkenyl; provided that when $Het^{1a}$ is directly attached to the N-atom of the 5-membered heteroaromatic ring, said $Het^{1a}$ is attached to the N-atom via a ring carbon atom; and wherein said 5-membered heteroaromatic ring may optionally be substituted on the ring carbon atoms with in total one or two substituents each independently selected from the group consisting of halo; cyano; $C_{1-6}$alkyl; $-O-C_{1-4}$alkyl; $-C(=O)-R^{10}$; $C_{3-6}$cycloalkyl; $Het^{1a}$; $-P(=O)-(C_{1-4}$alkyl$)_2$; $C_{1-4}$alkyl substituted with one, two or three halo atoms; $C_{1-4}$alkyl substituted with one, two or three $-OH$ substituents; and $C_{1-4}$alkyl substituted with one $R^{13}$;

$R^{10}$ represents $-NR^{11a}R^{11b}$ or $Het^2$;

$R^{18}$ represents a 5-membered aromatic ring containing one, two or three N-atoms; wherein said 5-membered aromatic ring may optionally be substituted with one $C_{1-4}$alkyl;

$Het^{1a}$, and $Het^{1d}$ each independently represents a 4- to 7-membered monocyclic saturated heterocyclyl containing one or two heteroatoms each independently selected from O, S, $S(=O)_p$ and N;

wherein said 4- to 7-membered monocyclic saturated heterocyclyl may optionally be substituted, where possible, on one ring N-atom with a substituent each independently selected from the group consisting of $C_{1-4}$alkyl, $C_{1-4}$alkyl substituted with one, two or three halo atoms, and $C_{1-4}$alkyl substituted with one substituent selected from the group consisting of $-C(=O)-NR^{22a}R^{22b}$ and $-O-C_{1-4}$alkyl; and wherein said 4- to 7-membered monocyclic saturated heterocyclyl may optionally be substituted on one two or three ring C-atoms with one or two substituents each independently selected from the group consisting of oxo, halo, and $C_{1-4}$alkyl;

$Het^{1e}$ represents a 4- to 7-membered monocyclic saturated heterocyclyl, attached to the remainder of the molecule of Formula (I) through any available ring carbon atom, said $Het^{1e}$ containing one or two O-atoms;

$Het^2$ represents 1-piperidinyl;

$Het^7$ represents 5,6,7,8-tetrahydro-imidazo[1,2-a]pyridinyl;

$R^{11b}$ represents $Het^{1e}$; $C_{1-4}$alkyl; $C_{3-6}$cycloalkyl;

$R^{13}$ represents $-O-C_{1-4}$alkyl, $-C(=O)OH$, $-C(=O)NR^{15a}R^{15b}$, $-NR^{19a}R^{19b}$, $C_{3-6}$cycloalkyl, $Het^{1d}$, $Het^7$, $-S(=O)_2-C_{1-4}$alkyl, or $-C(=O)-Het^{1f}$;

$Het^{3a}$, and $Het^{1f}$ each independently represents a heterocyclyl of formula (c-1):

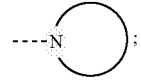

(c-1) represents a N-linked 4- to 7-membered monocyclic saturated heterocyclyl optionally containing one additional N-atom;

wherein in case (c-1) contains one additional N-atom, said additional N-atom may optionally be substituted with $C_{3-6}$cycloalkyl; and wherein (c-1) may optionally be substituted on one or two ring C-atoms atoms with one or two halo substituents;

$R^{11a}$, $R^{15a}$, $R^{19a}$ and $R^{22a}$ each independently represents hydrogen, $C_{1-4}$alkyl, or $C_{3-6}$cycloalkyl;

$R^{15b}$, $R^{19b}$ and $R^{22b}$ each independently represents $C_{1-4}$alkyl; or $C_{3-6}$cycloalkyl; p represents 2;

and the pharmaceutically acceptable addition salts, and the solvates thereof.

The present invention relates in particular to compounds of Formula (I) as defined herein, tautomers and stereoisomeric forms thereof, wherein $R^1$ represents $C_{1-4}$alkyl;

$R^2$ represents $C_{1-6}$alkyl substituted with one, two or three fluoro atoms;

Y represents $CR^4$;

$R^4$ represents hydrogen or halo;

$R^3$ represents a 5-membered heteroaromatic ring containing two or three heteroatoms each independently selected from O, S, and N;

wherein said 5-membered heteroaromatic ring may optionally be substituted, where possible, on one ring N-atom with a substituent selected from the group consisting of $C_{1-6}$alkyl; $Het^{1a}$; $C_{1-4}$alkyl substituted with one, two or three halo atoms; $C_{1-5}$alkyl substituted with one, two or three $-OH$ substituents; $C_{1-6}$alkyl substituted with one $R^{13}$; $C_{1-4}$alkyl substituted with one $R^{18}$; and $C_{2-6}$alkenyl; provided that when $Het^{1a}$ is directly attached to the N-atom of the 5-membered heteroaromatic ring, said $Het^{1a}$ is attached to the N-atom via a ring carbon atom; and wherein said 5-membered heteroaromatic ring may optionally be substituted on the ring carbon atoms with in total one or two substituents each independently selected from the group consisting of halo; cyano; $C_{1-6}$alkyl; $-O-C_{1-4}$alkyl; $-C(=O)-R^{10}$; $C_{3-6}$cycloalkyl; $Het^{1a}$; $-P(=O)-(C_{1-4}$alkyl$)_2$; $C_{1-4}$alkyl substituted with one, two or three halo atoms; $C_{1-4}$alkyl substituted with one, two or three $-OH$ substituents; and $C_{1-6}$alkyl substituted with one $R^{13}$;

$R^{10}$ represents $-NR^{11a}R^{11b}$ or $Het^2$;

$R^{18}$ represents a 5-membered aromatic ring containing one, two or three N-atoms; wherein said 5-membered aromatic ring may optionally be substituted with one $C_{1-4}$alkyl;

$Het^{1a}$, and $Het^{1d}$ each independently represents a 4- to 7-membered monocyclic saturated heterocyclyl containing one or two heteroatoms each independently selected from O, S, $S(=O)_p$ and N;

wherein said 4- to 7-membered monocyclic saturated heterocyclyl may optionally be substituted, where possible, on one ring N-atom with a substituent each independently selected from the group consisting of $C_{1-4}$alkyl, $C_{1-4}$alkyl substituted with one, two or three halo atoms, and $C_{1-4}$alkyl substituted with one substituent selected from the group consisting of —C(=O)—NR$^{22a}$R$^{2b}$ and —O—$C_{1-4}$alkyl; and wherein said 4- to 7-membered monocyclic saturated heterocyclyl may optionally be substituted on one, two or three ring C-atoms with one or two substituents each independently selected from the group consisting of oxo, halo, and $C_{1-4}$alkyl;

Het$^{1e}$ represents a 4- to 7-membered monocyclic saturated heterocyclyl, attached to the remainder of the molecule of Formula (I) through any available ring carbon atom, said Het$^{1e}$ containing one or two O-atoms;

Het$^2$ represents 1-piperidinyl;

Het$^7$ represents 5,6,7,8-tetrahydro-imidazo[1,2-a]pyridinyl;

R$^{11b}$ represents Het$^{1e}$; $C_{1-4}$alkyl; $C_{3-6}$cycloalkyl;

R$^{13}$ represents —O—$C_{1-4}$alkyl, —C(=O)OH, —C(=O)NR$^{15a}$R$^{15b}$, —NR$^{19a}$R$^{19b}$, $C_{3-6}$cycloalkyl, Het$^{1d}$, Het$^7$, —S(=O)$_2$—$C_{1-4}$alkyl, or —C(=O)—Het$^f$;

Het$^{3a}$, and Het$^{1f}$ each independently represents a heterocyclyl of formula (c-1):

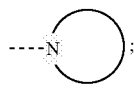 (c-1)

(c-1) represents a N-linked 4- to 7-membered monocyclic saturated heterocyclyl optionally containing one additional N-atom;

wherein in case (c-1) contains one additional N-atom, said additional N-atom may optionally be substituted with $C_{3-6}$cycloalkyl; and wherein (c-1) may optionally be substituted on one or two ring C-atoms atoms with one or two halo substituents;

R$^{11a}$, R$^{15a}$, R$^{19a}$ and R$^{22a}$ each independently represents hydrogen, $C_{1-4}$alkyl, or $C_{3-6}$cycloalkyl;

R$^{15b}$, R$^{19b}$ and R$^{22b}$ each independently represents $C_{1-4}$alkyl; or $C_{3-6}$cycloalkyl; p represents 2;

and the pharmaceutically acceptable addition salts, and the solvates thereof.

The present invention relates in particular to compounds of Formula (I) as defined herein, tautomers and stereoisomeric forms thereof, wherein R$^1$ represents $C_{1-4}$alkyl;
R$^2$ represents $C_{1-6}$alkyl substituted with one R$^5$;
Y represents CR$^4$;
R$^4$ represents hydrogen;
R$^5$ represents —OR$^7$;
R$^7$ represents hydrogen, or —C(=O)—R$^9$;
R$^9$ represents $C_{1-6}$alkyl;
R$^3$ represents a 5-membered heteroaromatic ring containing two or three heteroatoms each independently selected from S, and N;

wherein said 5-membered heteroaromatic ring may optionally be substituted, where possible, on one ring N-atom with a substituent selected from the group consisting of $C_{1-6}$alkyl; $C_{1-4}$alkyl substituted with one, two or three halo atoms; $C_{1-6}$alkyl substituted with one R$^{13}$; and $C_{1-4}$alkyl substituted with one R$^{18}$; and wherein said 5-membered heteroaromatic ring may optionally be substituted on the ring carbon atoms with in total one or two substituents each independently selected from the group consisting of halo; $C_{1-6}$alkyl; —C(=O)—R$^{10}$; and $C_{1-4}$alkyl substituted with one, two or three —OH substituents;

R$^{10}$ represents —NR$^{11a}$R$^{11b}$;

R$^{18}$ represents a 5-membered aromatic ring containing two N-atoms; wherein said 5-membered aromatic ring may optionally be substituted with one $C_{1-4}$alkyl;

Het$^{1d}$ represents a 4- to 7-membered monocyclic saturated heterocyclyl containing one or O-atom;

R$^{11b}$ represents $C_{1-4}$alkyl or $C_{3-6}$cycloalkyl;

R$^{13}$ represents —O—$C_{1-4}$alkyl, —C(=O)NR$^{15a}$R$^{15b}$, or Het$^{1d}$;

R$^{11a}$ and R$^{15a}$ each independently represents hydrogen or $C_{1-4}$alkyl;

R$^{15b}$ represents $C_{3-6}$cycloalkyl;

and the pharmaceutically acceptable addition salts, and the solvates thereof.

The present invention relates in particular to compounds of Formula (I) as defined herein, tautomers and stereoisomeric forms thereof, wherein R$^1$ represents $C_{1-4}$alkyl;
R$^2$ represents $C_{1-6}$alkyl substituted with one R$^5$;
Y represents CR$^4$;
R$^4$ represents hydrogen;
R$^5$ represents —OR$^7$;
R$^7$ represents hydrogen, or —C(=O)—R$^9$;
R$^9$ represents $C_{1-6}$alkyl;
R$^3$ represents a 5-membered heteroaromatic ring containing two or three heteroatoms each independently selected from S, and N;

wherein said 5-membered heteroaromatic ring may optionally be substituted, where possible, on one ring N-atom with a substituent selected from the group consisting of $C_{1-6}$alkyl; $C_{1-4}$alkyl substituted with one, two or three halo atoms; $C_{1-6}$alkyl substituted with one R$^{13}$; and $C_{1-4}$alkyl substituted with one R$^{18}$; and wherein said 5-membered heteroaromatic ring may optionally be substituted on the ring carbon atoms with in total one or two substituents each independently selected from the group consisting of halo; $C_{1-6}$alkyl; —C(=O)—R$^{10}$; and $C_{1-4}$alkyl substituted with one, two or three —OH substituents;

R$^{10}$ represents —NR$^{11a}$R$^{11b}$;

R$^{18}$ represents a 5-membered aromatic ring containing two N-atoms; wherein said 5-membered aromatic ring may optionally be substituted with one $C_{1-4}$alkyl;

Het$^7$ represents 5,6,7,8-tetrahydro-imidazo[1,2-a]pyridinyl;

R$^{11b}$ represents $C_{1-4}$alkyl or $C_{3-6}$cycloalkyl;

R$^{13}$ represents Het$^7$;

and the pharmaceutically acceptable addition salts, and the solvates thereof.

The present invention relates in particular to compounds of Formula (I) as defined herein, tautomers and stereoisomeric forms thereof, wherein R$^1$ represents $C_{1-4}$alkyl;
R$^2$ represents $C_{1-6}$alkyl substituted with one R$^5$;
Y represents N;
R$^4$ represents hydrogen;
R$^5$ represents —OR$^7$;
R$^7$ represents hydrogen, or —C(=O)—R$^9$;
R$^9$ represents $C_{1-6}$alkyl;

$R^3$ represents a 5-membered heteroaromatic ring containing two or three heteroatoms each independently selected from S, and N;

wherein said 5-membered heteroaromatic ring may optionally be substituted, where possible, on one ring N-atom with a substituent selected from the group consisting of $C_{1-6}$alkyl; $C_{1-4}$alkyl substituted with one, two or three halo atoms; $C_{1-6}$alkyl substituted with one $R^{13}$; and $C_{1-4}$alkyl substituted with one $R^{18}$; and wherein said 5-membered heteroaromatic ring may optionally be substituted on the ring carbon atoms with in total one or two substituents each independently selected from the group consisting of halo; $C_{1-6}$alkyl; —C(=O)—$R^{10}$; and $C_{1-4}$alkyl substituted with one, two or three —OH substituents;

$R^{10}$ represents —$NR^{11a}R^{11b}$;

$R^{18}$ represents a 5-membered aromatic ring containing two N-atoms; wherein said 5-membered aromatic ring may optionally be substituted with one $C_{1-4}$alkyl;

$Het^{1d}$ represents a 4- to 7-membered monocyclic saturated heterocyclyl containing one or O-atom;

$R^{11b}$ represents $C_{1-4}$alkyl or $C_{3-6}$cycloalkyl;

$R^{13}$ represents —O—$C_{1-4}$alkyl, —C(=O)$NR^{15a}R^{15b}$, or $Het^{1d}$;

$R^{11a}$ and $R^{15a}$ each independently represents hydrogen or $C_{1-4}$alkyl;

$R^{15b}$ represents $C_{3-6}$cycloalkyl;

and the pharmaceutically acceptable addition salts, and the solvates thereof.

The present invention relates in particular to compounds of Formula (I) as defined herein, tautomers and stereoisomeric forms thereof, wherein $R^1$ represents methyl;

$R^2$ represents methyl substituted with one $R^5$;

Y represents $CR^4$;

$R^4$ represents hydrogen;

$R^5$ represents —$OR^7$;

$R^7$ represents hydrogen;

$R^3$ represents pyrazolyl optionally substituted on one ring N-atom with a substituent selected from the group consisting of $C_{1-6}$alkyl; $C_{1-4}$alkyl substituted with one, two or three halo atoms; $C_{1-6}$alkyl substituted with one $R^{13}$; and $C_{1-4}$alkyl substituted with one $R^{18}$; and wherein said 5-membered heteroaromatic ring may optionally be substituted on the ring carbon atoms with in total one or two substituents each independently selected from the group consisting of halo; $C_{1-6}$alkyl; —C(=O)—$R^{10}$; and $C_{1-4}$alkyl substituted with one, two or three —OH substituents;

$R^{10}$ represents —$NR^{11a}R^{11b}$; $R^{18}$ represents

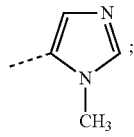

$Het^{1d}$ represents tetrahydrofuranyl;

$R^{11b}$ represents $C_{1-4}$alkyl or $C_{3-6}$cycloalkyl;

$R^{13}$ represents —O—$C_{1-4}$alkyl, —C(=O)$NR^{15a}R^{15b}$, or $Het^{1d}$;

$R^{11a}$ and $R^{15a}$ each independently represents hydrogen or $C_{1-4}$alkyl;

$R^{15b}$ represents $C_{3-6}$cycloalkyl;

and the pharmaceutically acceptable addition salts, and the solvates thereof.

Another embodiment of the present invention relates to those compounds of Formula (I) and the pharmaceutically acceptable addition salts, and the solvates thereof, or any subgroup thereof as mentioned in any of the other embodiments wherein one or more of the following restrictions apply:

(a) $R^2$ represents $C_{1-6}$alkyl substituted with one $R^5$;

(b) $R^{6a}$ represents $C_{1-4}$alkyl;

(c) $R^{6b}$ represents $C_{1-4}$alkyl substituted with one —OH substituent;

(d) $R^7$ represents hydrogen, or —C(=O)—$R^9$;

(e) $R^9$ represents $C_{1-6}$alkyl;

(f) $R^3$ represents a 5-membered heteroaromatic ring containing two or three heteroatoms each independently selected from O, S, and N;

wherein said 5-membered heteroaromatic ring may optionally be substituted, where possible, on one ring N-atom with a substituent selected from the group consisting of $C_{1-6}$alkyl; $Het^1a$; $C_{1-4}$alkyl substituted with one, two or three halo atoms; $C_{1-4}$alkyl substituted with one, two or three —OH substituents; $C_{1-6}$alkyl substituted with one $R^{13}$; $C_{1-4}$alkyl substituted with one $R^{18}$; and $C_{2-6}$alkenyl; provided that when $Het^1a$ is directly attached to the N-atom of the 5-membered heteroaromatic ring, said $Het^{1a}$ is attached to the N-atom via a ring carbon atom; and wherein said 5-membered heteroaromatic ring may optionally be substituted on the ring carbon atoms with in total one or two substituents each independently selected from the group consisting of halo; cyano; $C_{1-6}$alkyl; —O—$C_{1-4}$alkyl; —C(=O)—$R^{10}$; $C_{3-6}$cycloalkyl; $Het^1a$; —P(=O)—($C_{1-4}$alkyl)$_2$; $C_{1-4}$alkyl substituted with one, two or three halo atoms; $C_{1-4}$alkyl substituted with one, two or three —OH substituents; and $C_{1-6}$alkyl substituted with one $R^{13}$;

(g) $R^{10}$ represents —$NR^{11a}R^{11b}$ or $Het^2$;

(h) $R^{18}$ represents a 5-membered aromatic ring containing one, two or three N-atoms; wherein said 5-membered aromatic ring may optionally be substituted with one $C_{1-4}$alkyl;

(i) $Het^{1a}$, and $Het^1$-d each independently represents a 4- to 7-membered monocyclic saturated heterocyclyl containing one or two heteroatoms each independently selected from O, S, S(=O)$_p$ and N;

wherein said 4- to 7-membered monocyclic saturated heterocyclyl may optionally be substituted, where possible, on one ring N-atom with a substituent each independently selected from the group consisting of $C_{1-4}$alkyl, $C_{1-4}$alkyl substituted with one, two or three halo atoms, and $C_{1-4}$alkyl substituted with one substituent selected from the group consisting of —C(=O)—$NR^{22a}R^{22b}$ and —O—$C_{1-4}$alkyl; and wherein said 4- to 7-membered monocyclic saturated heterocyclyl may optionally be substituted on one, two or three ring C-atoms with one or two substituents each independently selected from the group consisting of oxo, halo, and $C_{1-4}$alkyl;

(j) $Het^{1e}$ represents a 4- to 7-membered monocyclic saturated heterocyclyl, attached to the remainder of the molecule of Formula (I) through any available ring carbon atom, said $Het^{1e}$ containing one or two O-atoms;

(k) $Het^2$ represents 1-piperidinyl;

(l) $R^{1b}$ represents $Het^{1e}$; $C_{1-4}$alkyl; $C_{3-6}$cycloalkyl;

(m) $R^{13}$ represents —O—$C_{1-4}$alkyl, —C(=O)OH, —C(=O)$NR^{15a}R^{15b}$, —$NR^{19a}R^{19b}$$C_{3-6}$cycloalkyl, $Het^{1d}$, —S(=O)$_2$—$C_{1-4}$alkyl, or —C(=O)—$Het^f$;

(n) Het$^{3a}$, and Het$^{1f}$ each independently represents a heterocyclyl of formula (c-1):

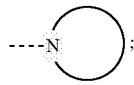

(c-1) represents a N-linked 4- to 7-membered monocyclic saturated heterocyclyl optionally containing one additional N-atom;
wherein in case (c-1) contains one additional N-atom, said additional N-atom may optionally be substituted with $C_{3-6}$cycloalkyl; and
wherein (c-1) may optionally be substituted on one or two ring C-atoms atoms with one or two halo substituents;
(o) $R^{11a}$, $R^{15a}$, $R^{19a}$ and $R^{22a}$ each independently represents hydrogen, $C_{1-4}$alkyl, or $C_{3-6}$cycloalkyl;
(p) $R^{15b}$, $R^{19b}$ and $R^{22b}$ each independently represents $C_{1-4}$alkyl; or $C_{3-6}$cycloalkyl; (q) p represents 2.

Another embodiment of the present invention relates to those compounds of Formula (I) and the pharmaceutically acceptable addition salts, and the solvates thereof, or any subgroup thereof as mentioned in any of the other embodiments wherein one or more of the following restrictions apply:
(a) $R^2$ represents $C_{1-6}$alkyl substituted with one $R^5$;
(b) $R^{6a}$ represents $C_{1-4}$alkyl;
(c) $R^{6b}$ represents $C_{1-4}$alkyl substituted with one —OH substituent;
(d) $R^7$ represents hydrogen, or —C(=O)—$R^9$;
(e) $R^9$ represents $C_{1-6}$alkyl;
(f) $R^3$ represents a 5-membered heteroaromatic ring containing two or three heteroatoms each independently selected from O, S, and N;
wherein said 5-membered heteroaromatic ring may optionally be substituted, where possible, on one ring N-atom with a substituent selected from the group consisting of $C_{1-6}$alkyl; Het$^{1a}$; $C_{1-4}$alkyl substituted with one, two or three halo atoms; $C_{1-5}$alkyl substituted with one, two or three —OH substituents; $C_{1-6}$alkyl substituted with one $R^{13}$; $C_{1-4}$alkyl substituted with one $R^{18}$; and $C_{2-6}$alkenyl; provided that when Het$^{1a}$ is directly attached to the N-atom of the 5-membered heteroaromatic ring, said Het a is attached to the N-atom via a ring carbon atom; and
wherein said 5-membered heteroaromatic ring may optionally be substituted on the ring carbon atoms with in total one or two substituents each independently selected from the group consisting of halo; cyano; $C_{1-6}$alkyl; —O—$C_{1-4}$alkyl; —C(=O)—$R^{10}$; $C_{3-6}$cycloalkyl; Het$^{1a}$; —P(=O)—($C_{1-4}$alkyl)$_2$; $C_{1-4}$alkyl substituted with one, two or three halo atoms; $C_{1-4}$alkyl substituted with one, two or three —OH substituents; and $C_{1-6}$alkyl substituted with one $R^{13}$;
(g) $R^{10}$ represents —NR$^{11a}$R$^{11b}$ or Het$^2$;
(h) $R^{18}$ represents a 5-membered aromatic ring containing one, two or three N-atoms; wherein said 5-membered aromatic ring may optionally be substituted with one $C_{1-4}$alkyl;
(i) Het$^{1a}$, and Het$^{1d}$ each independently represents a 4- to 7-membered monocyclic saturated heterocyclyl containing one or two heteroatoms each independently selected from O, S, S(=O)$_p$, and N;
wherein said 4- to 7-membered monocyclic saturated heterocyclyl may optionally be substituted, where possible, on one ring N-atom with a substituent each independently selected from the group consisting of $C_{1-4}$alkyl, $C_{1-4}$alkyl substituted with one, two or three halo atoms, and $C_{1-4}$alkyl substituted with one substituent selected from the group consisting of —C(=O)—NR$^{22a}$R$^{22b}$ and —O—$C_{1-4}$alkyl; and
wherein said 4- to 7-membered monocyclic saturated heterocyclyl may optionally be substituted on one, two or three ring C-atoms with one or two substituents each independently selected from the group consisting of oxo, halo, and $C_{1-4}$alkyl;
(j) Het$^{1e}$ represents a 4- to 7-membered monocyclic saturated heterocyclyl, attached to the remainder of the molecule of Formula (I) through any available ring carbon atom, said Het$^{1e}$ containing one or two O-atoms;
(k) Het$^2$ represents 1-piperidinyl;
(l) $R^{11b}$ represents Het$^{1e}$; $C_{1-4}$alkyl; $C_{3-6}$cycloalkyl;
(m) $R^{13}$ represents —O—$C_{1-4}$alkyl, —C(=O)OH, —C(=O)NR$^{5a}$R$^{15b}$, —NR$^{19a}$R$^{19b}$, $C_{3-6}$cycloalkyl, Het$^{1d}$, —S(=O)$_2$—$C_{1-4}$alkyl, or —C(=O)—Het$^f$;
(n) Het$^{3a}$, and Het$^{1f}$ each independently represents a heterocyclyl of formula (c-1):

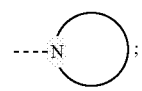

(c-1) represents a N-linked 4- to 7-membered monocyclic saturated heterocyclyl optionally containing one additional N-atom;
wherein in case (c-1) contains one additional N-atom, said additional N-atom may optionally be substituted with $C_{3-6}$cycloalkyl; and
wherein (c-1) may optionally be substituted on one or two ring C-atoms atoms with one or two halo substituents;
(o) $R^{11a}$, $R^{15a}$, $R^{19a}$ and $R^{22a}$ each independently represents hydrogen, $C_{1-4}$alkyl, or $C_{3-6}$cycloalkyl;
(p) $R^{15b}$, $R^{19b}$ and $R^{22b}$ each independently represents $C_{1-4}$alkyl; or $C_{3-6}$cycloalkyl; (q) p represents 2.

Another embodiment of the present invention relates to those compounds of Formula (I) and the pharmaceutically acceptable addition salts, and the solvates thereof, or any subgroup thereof as mentioned in any of the other embodiments wherein one or more of the following restrictions apply:
(a) $R^2$ represents $C_{1-6}$alkyl substituted with one $R^5$;
(b) $R^4$ represents hydrogen;
(c) $R^5$ represents —OR$^7$;
(d) $R^7$ represents hydrogen, or —C(=O)—$R^9$;
(e) $R^9$ represents $C_{1-6}$alkyl;
(f) $R^3$ represents a 5-membered heteroaromatic ring containing two or three heteroatoms each independently selected from S, and N;
wherein said 5-membered heteroaromatic ring may optionally be substituted, where possible, on one ring N-atom with a substituent selected from the group consisting of $C_{1-6}$alkyl; $C_{1-4}$alkyl substituted with one, two or three halo atoms; $C_{1-6}$alkyl substituted with one $R^{13}$; and $C_{1-4}$alkyl substituted with one $R^{18}$; and
wherein said 5-membered heteroaromatic ring may optionally be substituted on the ring carbon atoms with in total one or two substituents each independently selected from the group consisting of halo; $C_{1-6}$alkyl; —C(=O)—$R^{10}$; and $C_{1-4}$alkyl substituted with one, two or three —OH substituents;

(g) $R^{10}$ represents —$NR^{11a}R^{11b}$;

(h) $R^{18}$ represents a 5-membered aromatic ring containing two N-atoms; wherein said 5-membered aromatic ring may optionally be substituted with one $C_{1-4}$alkyl;

(i) $Het^{1d}$ represents a 4- to 7-membered monocyclic saturated heterocyclyl containing one or O-atom;

(j) $R^{11b}$ represents $C_{1-4}$alkyl or $C_{3-6}$cycloalkyl;

(k) $R^{13}$ represents —O—$C_{1-4}$alkyl, —C(=O)$NR^{15a}R^{15b}$, or $Het^{1d}$;

(l) $R^{11a}$ and $R^{15a}$ each independently represents hydrogen or $C_{1-4}$alkyl;

(m) $R^{15b}$ represents $C_{3-6}$cycloalkyl.

In an embodiment, the present invention relates to those compounds of Formula (I) and the pharmaceutically acceptable addition salts, and the solvates thereof, or any subgroup thereof as mentioned in any of the other embodiments, wherein $R^{6b}$ represents hydrogen; $C_{1-4}$alkyl; $C_{3-6}$cycloalkyl; —C(=O)—$C_{1-4}$alkyl; —C(=O)—$C_{1-4}$alkyl substituted with one substituent selected from the group consisting of —OH and —$NR^{16a}R^{6b}$; or $C_{1-4}$alkyl substituted with one —OH substituent;

$R^7$ represents hydrogen, $C_{1-4}$alkyl, —$C_{1-4}$alkyl-$NR^{8a}R^{8b}$, or —C(=O)—$R^9$;

$R^9$ represents $C_{1-6}$alkyl, or $C_{1-6}$alkyl substituted with one substituent selected from the group consisting of —$NH_2$, and —COOH;

$R^3$ represents a 5-membered heteroaromatic ring containing one, two or three heteroatoms each independently selected from O, S, and N;

wherein said 5-membered heteroaromatic ring may optionally be substituted, where possible, on one ring N-atom with a substituent selected from the group consisting of $C_{1-6}$alkyl; $C_{3-6}$cycloalkyl; $Het^{1a}$; $R^{18}$; $C_{1-4}$alkyl substituted with one, two or three halo atoms; $C_{1-4}$alkyl substituted with one, two or three —OH substituents; $C_{1-6}$alkyl substituted with one $R^{13}$; $C_{1-4}$alkyl substituted with one $R^{18}$; $C_{2-6}$alkenyl; and $C_{2-6}$alkenyl substituted with one $R^{13}$; provided that when $Het^{1a}$ or $R^{18}$ are directly attached to the N-atom of the 5-membered heteroaromatic ring, said Het a or $R^{18}$ are attached to the N-atom via a ring carbon atom; and wherein said 5-membered heteroaromatic ring may optionally be substituted on the ring carbon atoms with in total one or two substituents each independently selected from the group consisting of halo; cyano; $C_{1-6}$alkyl; —O—$C_{1-4}$alkyl; —C(=O)—$R^{10}$; —O—$C_{1-4}$alkyl substituted with one, two or three halo atoms; —O—$C_{1-4}$alkyl-$R^{12}$; $C_{3-6}$cycloalkyl; —O—$C_{3-6}$cycloalkyl; $Het^{1a}$; —O-$Het^{1b}$; $R^{18}$; —P(=O)—$(C_{1-4}$alkyl$)_2$; —NH—C(=O)—$C_{1-4}$alkyl; —NH—C(=O)—$Het^{1g}$; —$NR^{17a}R^{17b}$; $C_{1-4}$alkyl substituted with one, two or three halo atoms; $C_{1-4}$alkyl substituted with one, two or three —OH substituents; $C_{1-6}$alkyl substituted with one $R^{13}$; $C_{1-4}$alkyl substituted with one $R^{18}$; $C_{2-6}$alkenyl; and $C_{2-6}$alkenyl substituted with one $R^{13}$;

$Het^{1a}$, and $Het^{1d}$ each independently represents a 4- to 7-membered monocyclic saturated heterocyclyl containing one or two heteroatoms each independently selected from O, S, S(=O)$_p$ and N;

wherein said 4- to 7-membered monocyclic saturated heterocyclyl may optionally be substituted, where possible, on one, two or three ring N-atoms with a substituent each independently selected from the group consisting of $C_{1-4}$alkyl, $C_{3-6}$cycloalkyl, $C_{1-4}$alkyl substituted with one, two or three halo atoms, and $C_{1-4}$alkyl substituted with one substituent selected from the group consisting of —OH, —C(=O)—OH, —C(=O)—$NR^{22a}R^{22b}$ and —O—$C_{1-4}$alkyl; and wherein said 4- to 7-membered monocyclic saturated heterocyclyl may optionally be substituted on one, two or three ring C-atoms with one or two substituents each independently selected from the group consisting of —OH, oxo, halo, $C_{1-4}$alkyl, cyano, —C(=O)—$C_{1-4}$alkyl, —O—$C_{1-4}$alkyl, —$NH_2$, —NH($C_{1-4}$alkyl), and —N($C_{1-4}$alkyl$)_2$;

$Het^{1b}$, $Het^{1e}$, and $Het^{1g}$ each independently represents a 4- to 7-membered monocyclic saturated heterocyclyl, attached to the remainder of the molecule of Formula (I) through any available ring carbon atom, said $Het^{1b}$, $Het^{1e}$, and $Het^{1g}$ containing one or two heteroatoms each independently selected from O, S, S(=O)$_p$ and N; wherein said 4- to 7-membered monocyclic saturated heterocyclyl may optionally be substituted, where possible, on one or two ring N-atoms with a substituent each independently selected from the group consisting of $C_{1-4}$alkyl, $C_{3-6}$cycloalkyl, and $C_{1-4}$alkyl substituted with one substituent selected from the group consisting of —OH and —O—$C_{1-4}$alkyl; and wherein said 4- to 7-membered monocyclic saturated heterocyclyl may optionally be substituted on one, two or three ring C-atoms with one or two substituents each independently selected from the group consisting of —OH, halo, $C_{1-4}$alkyl, cyano, —C(=O)—$C_{1-4}$alkyl, —O—$C_{1-4}$alkyl, —$NH_2$, —NH($C_{1-4}$alkyl), and —N($C_{1-4}$alkyl$)_2$; $Het^2$ represents a heterocyclyl of formula (b-1):

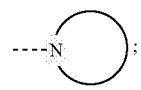

(b-1) represents a N-linked 4- to 7-membered monocyclic saturated heterocyclyl optionally containing one additional heteroatom selected from O, S, S(=O)$_p$ and N; wherein in case (b-1) contains one additional N-atom, said N-atom may optionally be substituted with $C_{1-4}$alkyl; and wherein (b-1) may optionally be substituted on one, two or three ring C-atoms with one or two substituents each independently selected from the group consisting of halo, —OH, cyano, $C_{1-4}$alkyl, —O—$C_{1-4}$alkyl, —$NH_2$, —NH($C_{1-4}$alkyl), —N($C_{1-4}$alkyl$)_2$, and $C_{1-4}$alkyl-OH; $R^{11b}$ represents hydrogen; $Het^{1e}$; $C_{1-4}$alkyl; $C_{1-4}$alkyl substituted with one, two or three substituents each independently selected from the group consisting of halo, —OH and —O—$C_{1-4}$alkyl; $C_{3-6}$cycloalkyl; or $C_{3-6}$cycloalkyl substituted with one, two or three substituents each independently selected from the group consisting of halo, —OH and —O—$C_{1-4}$alkyl;

$R^{13}$ represents —O—$C_{1-4}$alkyl, —C(=O)OH, —C(=O)$NR^{15a}R^{15b}$, —$NR^{19a}R^{19b}$, $C_{3-6}$cycloalkyl, $Het^{1d}$, —S(=O)$_2$—$C_{1-4}$alkyl, or —C(=O)—$Het^f$;

$R^{12}$ represents —OH, —O—$C_{1-4}$alkyl, —$NR^{4a}R^{14b}$, —C(=O)$NR^{14c}R^{14d}$, —S(=O)$_2$—$C_4$alkyl, $C_{3-6}$cycloalkyl;

$Het^{3a}$, and $Het^{1f}$ each independently represents a heterocyclyl of formula (c-1):

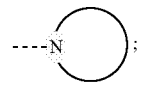

(c-1) represents a N-linked 4- to 7-membered monocyclic saturated heterocyclyl optionally containing one additional heteroatom selected from O, S, S(=O)$_p$ and N; wherein in case (c-1) contains one additional N-atom, said additional N-atom may optionally be substituted with $C_{1-4}$alkyl or $C_{3-6}$cycloalkyl; and wherein (c-1) may optionally be substituted on one or two ring C-atoms atoms with one or two substituents each independently selected from the group consisting of halo, $C_{1-4}$alkyl, and $C_{3-6}$cycloalkyl.

In an embodiment, the present invention relates to those compounds of Formula (I) and the pharmaceutically acceptable addition salts, and the solvates thereof, or any subgroup thereof as mentioned in any of the other embodiments, wherein $R^2$ represents $C_{1-6}$alkyl substituted with one $R^5$;
$R^4$ represents hydrogen;
$R^5$ represents —$OR^7$;
$R^7$ represents hydrogen, or —C(=O)—$R^9$;
$R^9$ represents $C_{1-6}$alkyl;
$R^3$ represents a 5-membered heteroaromatic ring containing two or three heteroatoms each independently selected from S, and N;
wherein said 5-membered heteroaromatic ring may optionally be substituted, where possible, on one ring N-atom with a substituent selected from the group consisting of $C_{1-6}$alkyl; $C_{1-4}$alkyl substituted with one, two or three halo atoms; $C_{1-6}$alkyl substituted with one $R^{13}$; and $C_{1-4}$alkyl substituted with one $R^{18}$; and
wherein said 5-membered heteroaromatic ring may optionally be substituted on the ring carbon atoms with in total one or two substituents each independently selected from the group consisting of halo; $C_{1-6}$alkyl; —C(=O)—$R^{10}$; and $C_{1-4}$alkyl substituted with one, two or three —OH substituents;
$R^{10}$ represents —$NR^{11a}R^{11b}$;
$R^{18}$ represents a 5-membered aromatic ring containing two N-atoms; wherein said 5-membered aromatic ring may optionally be substituted with one $C_{1-4}$alkyl; $Het^{1d}$ represents a 4- to 7-membered monocyclic saturated heterocyclyl containing one or O-atom;
$R^{11b}$ represents $C_{1-4}$alkyl or $C_{3-6}$cycloalkyl;
$R^{13}$ represents —O—$C_{1-4}$alkyl, —C(=O)$NR^{15a}R^{15b}$, or $Het^{1d}$;
$R^{11a}$ and $R^{15a}$ each independently represents hydrogen or $C_{1-4}$alkyl;
$R^{15b}$ represents $C_{3-6}$cycloalkyl.

In an embodiment, the present invention relates to a subgroup of Formula (I), hereby named compounds of Formula (I'):

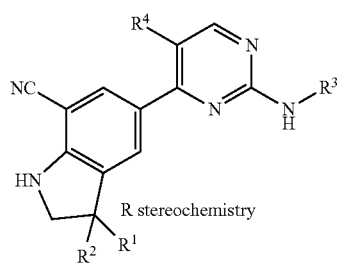

(I')

wherein $R^1$ represents $C_{1-4}$alkyl;
$R^2$ represents $C_{1-6}$alkyl substituted with one $R^5$;
in particular wherein $R^1$ represents $C_{1-4}$alkyl;
$R^2$ represents $C_{1-6}$alkyl substituted with one $R^5$;
$R^5$ represents —$OR^7$;
more in particular wherein $R^1$ represents $C_{1-4}$alkyl;

$R^2$ represents $C_{1-6}$alkyl substituted with one $R^5$;
$R^5$ represents —$OR^7$;
$R^7$ represents hydrogen;
and wherein all other variables are defined according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein
$R^1$ represents methyl;
$R^2$ represents methyl or —$CH_2$—OH.

In an embodiment, the present invention relates to those compounds of Formula (I) and the pharmaceutically acceptable addition salts, and the solvates thereof, or any subgroup thereof as mentioned in any of the other embodiments, wherein $R^1$ represents methyl; $R^2$ represents —$CH_2$—OH.

In an embodiment, the present invention relates to those compounds of Formula (I) and the pharmaceutically acceptable addition salts, and the solvates thereof, or any subgroup thereof as mentioned in any of the other embodiments, wherein $R^4$ represents hydrogen or fluoro.

In an embodiment, the present invention relates to those compounds of Formula (I) and the pharmaceutically acceptable addition salts, and the solvates thereof, or any subgroup thereof as mentioned in any of the other embodiments, wherein $R^4$ represents hydrogen.

In an embodiment, the present invention relates to those compounds of Formula (I) and the pharmaceutically acceptable addition salts, and the solvates thereof, or any subgroup thereof as mentioned in any of the other embodiments, wherein
$R^7$ represents hydrogen.

In an embodiment, the present invention relates to those compounds of Formula (I) and the pharmaceutically acceptable addition salts, and the solvates thereof, or any subgroup thereof as mentioned in any of the other embodiments, wherein
$R^5$ represents —$OR^7$; and
$R^7$ represents hydrogen.

In an embodiment, the present invention relates to those compounds of Formula (I) and the pharmaceutically acceptable addition salts, and the solvates thereof, or any subgroup thereof as mentioned in any of the other embodiments, wherein $R^{18}$ is attached to the remainder of the molecule of Formula (I) via a carbon atom.

In an embodiment, the present invention relates to those compounds of Formula (I) and the pharmaceutically acceptable addition salts, and the solvates thereof, or any subgroup thereof as mentioned in any of the other embodiments, wherein $R^{18}$ represents

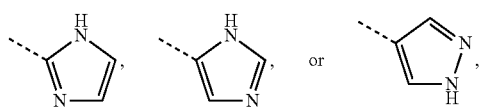

each optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein $R^{18}$ represents

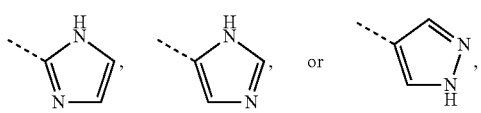

each substituted on the NH with $C_{1-4}$alkyl.

In an embodiment, the present invention relates to those compounds of Formula (I) and the pharmaceutically acceptable addition salts, and the solvates thereof, or any subgroup thereof as mentioned in any of the other embodiments, wherein $Het^{1a}$, $Het^{1c}$ and $Het^{1d}$ each independently represents morpholinyl, piperidinyl, pyrrolidinyl, oxetanyl, azetidinyl, piperazinyl, tetrahydro-2H-pyranyl, tetrahydrofuranyl, or hexahydro-1,4-oxazepinyl, each optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein $Het^{1a}$, $Het^{1c}$ and $Het^{1d}$ represent morpholinyl, in particular 1-morpholinyl, optionally substituted where possible on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein $Het^{1a}$, $Het^{1c}$ and $Het^{1d}$ each independently represents

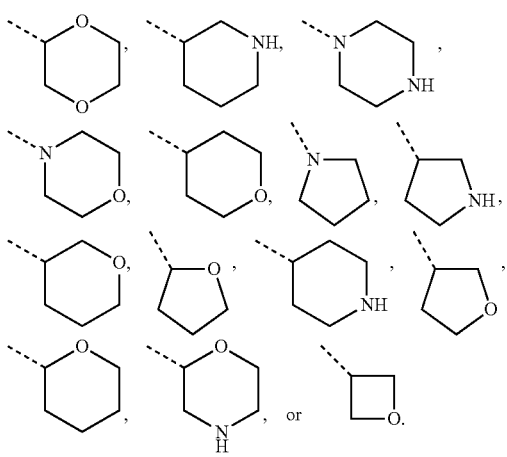

each optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein $Het^{1d}$ represents morpholinyl, in particular 1-morpholinyl, optionally substituted where possible on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein $Het^{1b}$, $Het^{1e}$, $Het^{1g}$ and $Het^4$ each independently represents morpholinyl, piperidinyl, pyrrolidinyl, oxetanyl, azetidinyl, piperazinyl, tetrahydro-2H-pyranyl, tetrahydrofuranyl, or hexahydro-1,4-oxazepinyl, attached to the remainder of the molecule of Formula (I) through any available ring carbon atom, each optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein $Het^{1b}$, $Het^{1e}$, $Het^{1g}$ and $Het^4$ each independently represents piperidinyl, tetrahydro-2H-pyranyl, or pyrrolidinyl, attached to the remainder of the molecule of Formula (I) through any available ring carbon atom, each optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein $Het^{1b}$, $Het^{1e}$, $Het^{1g}$ and $Het^4$ each independently represents

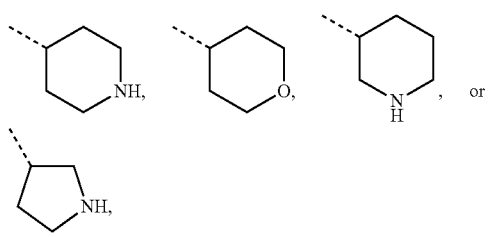

each optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein $Het^{1b}$, $Het^{1e}$, $Het^{1g}$ and $Het^4$ represent

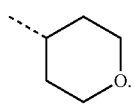

In an embodiment, the present invention relates to those compounds of Formula (I) and the pharmaceutically acceptable addition salts, and the solvates thereof, or any subgroup thereof as mentioned in any of the other embodiments, wherein $Het^{1e}$ represents

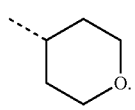

In an embodiment, the present invention relates to those compounds of Formula (I) and the pharmaceutically acceptable addition salts, and the solvates thereof, or any subgroup thereof as mentioned in any of the other embodiments, wherein $Het^{1g}$ represents

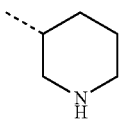

optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein Het$^{1e}$ represents

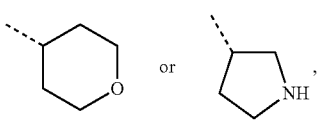

each optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein Het$^b$ represents

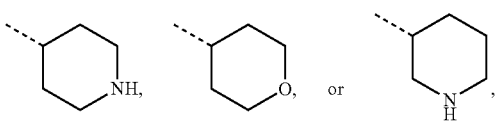

each optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein Het$^2$ represents

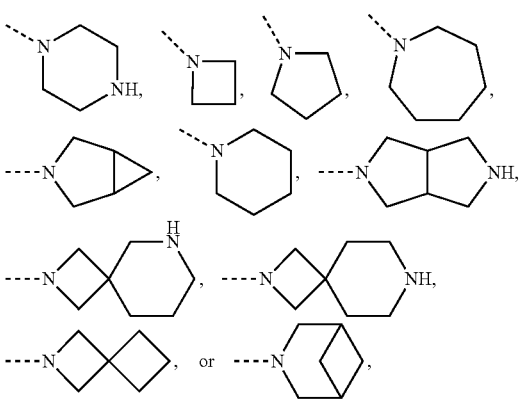

each optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein Het$^2$ represents

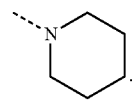

In an embodiment, the present invention relates to those compounds of Formula (I) and the pharmaceutically acceptable addition salts, and the solvates thereof, or any subgroup thereof as mentioned in any of the other embodiments, wherein Het$^{3a}$, Het$^{3b}$, Het$^5$, Het$^6$ and Het$^{1f}$ each independently represents

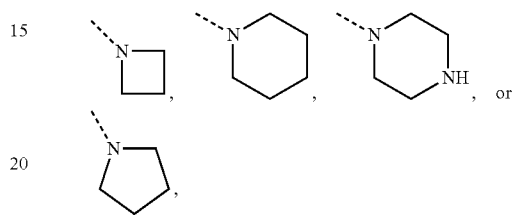

each optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein Het$^4$ represents pyrrolidinyl, piperidinyl, tetrahydropyranyl, azetidinyl, or 1,1-dioxidethiopyranyl;

each optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein Het$^5$ represents

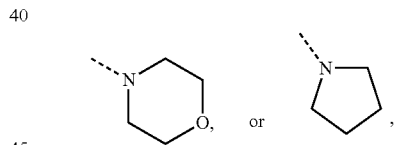

each optionally substituted according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein Het$^6$ represents

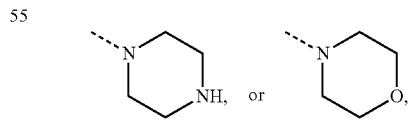

each optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein Het$^{3a}$, and Het$^{1f}$ each independently represents

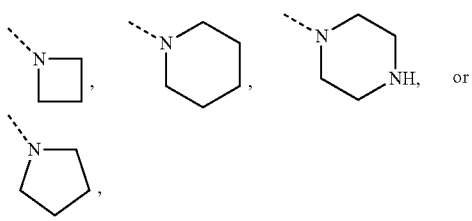

each optionally substituted on carbon and/or nitrogen atoms according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein $Het^{1a}$, $Het^{1c}$ and $Het^{1d}$ each independently represents a 4- to 7-membered monocyclic saturated heterocyclyl containing one or two heteroatoms each independently selected from O, S, $S(=O)_p$ and N;

wherein said 4- to 7-membered monocyclic saturated heterocyclyl may optionally be substituted, where possible, on one, two or three ring N-atoms with a substituent each independently selected from the group consisting of $C_{1-4}$alkyl, $C_{3-6}$cycloalkyl, $C_{1-4}$alkyl substituted with one, two or three halo atoms, and $C_{1-4}$alkyl substituted with one substituent selected from the group consisting of —OH, —C(=O)—OH, —C(=O)—$NR^{22a}R^{22b}$ and —O—$C_{1-4}$alkyl; and wherein said 4- to 7-membered monocyclic saturated heterocyclyl may optionally be substituted on one, two or three ring C-atoms with one or two substituents each independently selected from the group consisting of —OH, oxo, halo, $C_{1-4}$alkyl, cyano, —C(=O)—$C_{1-4}$alkyl, —O—$C_{1-4}$alkyl, —$NH_2$, —NH($C_{1-4}$alkyl), and —N($C_{1-4}$alkyl)$_2$;

In an embodiment, the present invention relates to those compounds of Formula (I) and the pharmaceutically acceptable addition salts, and the solvates thereof, or any subgroup thereof as mentioned in any of the other embodiments, wherein $Het^2$ represents a heterocyclyl of formula (b-1):

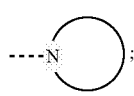

(b-1)

(b-1) represents a N-linked 4- to 7-membered monocyclic saturated heterocyclyl optionally containing one additional heteroatom selected from O, S, $S(=O)_p$ and N; wherein in case (b-1) contains one additional N-atom, said N-atom may optionally be substituted with $C_{1-4}$alkyl; and wherein (b-1) may optionally be substituted on one, two or three ring C-atoms with one or two substituents each independently selected from the group consisting of halo, —OH, cyano, $C_{1-4}$alkyl, —O—$C_{1-4}$alkyl, —$NH_2$, —NH($C_{1-4}$alkyl), —N($C_{1-4}$alkyl)$_2$, and $C_{1-4}$alkyl-OH.

In an embodiment, the present invention relates to those compounds of Formula (I) and the pharmaceutically acceptable addition salts, and the solvates thereof, or any subgroup thereof as mentioned in any of the other embodiments, wherein $Het^{1a}$ represents a 4- to 7-membered monocyclic saturated heterocyclyl containing one or two heteroatoms each independently selected from O, S, $S(=O)_p$ and N; or a 6- to 11-membered bicyclic saturated heterocyclyl, including fused, spiro and bridged cycles, containing one, two or three heteroatoms each independently selected from O, S, $S(=O)_p$ and N;

wherein said 4- to 7-membered monocyclic saturated heterocyclyl or said 6- to 11-membered bicyclic saturated heterocyclyl may optionally be substituted, where possible, on one, two or three ring N-atoms with a substituent each independently selected from the group consisting of $C_{1-4}$alkyl, $C_{3-6}$cycloalkyl, $C_{1-4}$alkyl substituted with one, two or three halo atoms, and $C_{1-4}$alkyl substituted with one substituent selected from the group consisting of —OH, —C(=O)—OH, —C(=O)—$NR^{22a}R^{22b}$ and —O—$C_{1-4}$alkyl; and wherein said 4- to 7-membered monocyclic saturated heterocyclyl or said 6- to 11-membered bicyclic saturated heterocyclyl may optionally be substituted on one, two or three ring C-atoms with one or two substituents each independently selected from the group consisting of —OH, oxo, halo, $C_{1-4}$alkyl, cyano, —C(=O)—$C_{1-4}$alkyl, —O—$C_{1-4}$alkyl, —$NH_2$, —NH($C_{1-4}$alkyl), and —N($C_{1-4}$alkyl)$_2$;

$Het^{1c}$ and $Het^{1d}$ each independently represents a 4- to 7-membered monocyclic saturated heterocyclyl containing one or two heteroatoms each independently selected from O, S, $S(=O)_p$ and N; or in case $Het^1C$ and $Het^{1d}$ are attached to the remainder of the molecule of Formula (I) through an N-atom, $Het^{1c}$ and $Het^{1d}$ may also represent a N-linked 6- to 11-membered bicyclic saturated heterocyclyl, including fused, spiro and bridged cycles, optionally containing one or two additional heteroatoms each independently selected from O, S, $S(=O)_p$ and N;

wherein said 4- to 7-membered monocyclic saturated heterocyclyl or said N-linked 6- to 11-membered bicyclic saturated heterocyclyl may optionally be substituted, where possible, on one or two ring N-atoms with a substituent each independently selected from the group consisting of $C_{1-4}$alkyl, $C_{3-6}$cycloalkyl, $C_{1-4}$alkyl substituted with one, two or three halo atoms, and $C_{1-4}$alkyl substituted with one substituent selected from the group consisting of —OH, —C(=O)—OH, —C(=O)—$NR^{22a}R^{22b}$ and —O—$C_{1-4}$alkyl; and wherein said 4- to 7-membered monocyclic saturated heterocyclyl or said N-linked 6- to 11-membered bicyclic saturated heterocyclyl may optionally be substituted on one, two or three ring C-atoms with one or two substituents each independently selected from the group consisting of —OH, oxo, halo, $C_{1-4}$alkyl, cyano, —C(=O)—$C_{1-4}$alkyl, —O—$C_{1-4}$alkyl, —$NH_2$, —NH($C_{1-4}$alkyl), and —N($C_{1-4}$alkyl)$_2$.

In an embodiment, the present invention relates to those compounds of Formula (I) and the pharmaceutically acceptable addition salts, and the solvates thereof, or any subgroup thereof as mentioned in any of the other embodiments, wherein $R^3$ represents pyrazolyl optionally substituted according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein $R^3$ represents a 5-membered heteroaromatic ring selected from the following structures

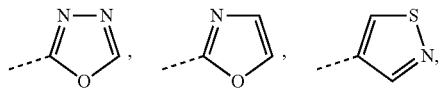

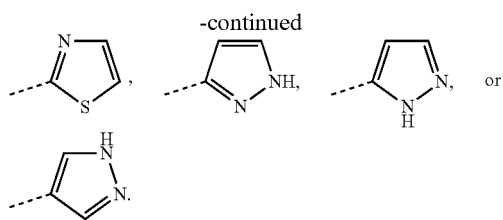

each optionally substituted according to any of the other embodiments (on the carbon and/or nitrogen atoms).

In an embodiment, the present invention relates to those compounds of Formula (I) and the pharmaceutically acceptable addition salts, and the solvates thereof, or any subgroup thereof as mentioned in any of the other embodiments, wherein $R^3$ represents pyrazolyl optionally substituted on one ring N-atom with a substituent selected from the group consisting of $C_{1-6}$alkyl; $C_{3-6}$cycloalkyl; Het$^{1a}$; $R^{18}$; $R^{21}$; $C_{1-4}$alkyl substituted with one, two or three halo atoms; $C_{1-4}$alkyl substituted with one, two or three —OH substituents; $C_{1-6}$alkyl substituted with one $R^{13}$; $C_{1-4}$alkyl substituted with one $R^{18}$; $C_{2-6}$alkenyl; and $C_{2-6}$alkenyl substituted with one $R^{13}$; provided that when Het$^{1a}$ or $R^{18}$ are directly attached to the N-atom of the 5-membered heteroaromatic ring, said Het$^{1a}$ or $R^{18}$ are attached to the N-atom via a ring carbon atom; and wherein said 5-membered heteroaromatic ring may optionally be substituted on the ring carbon atoms with in total one or two substituents each independently selected from the group consisting of halo; cyano; $C_{1-6}$alkyl; —O—$C_{1-4}$alkyl; —C(=O)—$R^{10}$; —S(=O)$_2$—$C_{1-4}$alkyl; —S(=O)(=N—$R^{20a}$)—$C_{1-4}$alkyl; —O—$C_{1-4}$alkyl substituted with one, two or three halo atoms; —O—$C_{1-4}$alkyl-$R^{12}$; $C_{3-6}$cycloalkyl; —O—$C_{3-6}$cycloalkyl; Het$^{1a}$; —O-Het$^{1b}$; $R^{18}$; $R^{21}$; —P(=O)—($C_{1-4}$alkyl)$_2$; —NH—C(=O)—$C_{1-4}$alkyl; —NH—C(=O)—Het$^{1g}$; —NR$^{17a}$R$^{17b}$; $C_{1-4}$alkyl substituted with one, two or three halo atoms; $C_{1-4}$alkyl substituted with one, two or three —OH substituents; $C_{1-6}$alkyl substituted with one $R^{13}$; $C_{1-4}$alkyl substituted with one $R^{18}$; $C_{2-6}$alkenyl; and $C_{2-6}$alkenyl substituted with one $R^{13}$.

In an embodiment, the present invention relates to those compounds of Formula (I) and the pharmaceutically acceptable addition salts, and the solvates thereof, or any subgroup thereof as mentioned in any of the other embodiments, wherein $R^3$ represents pyrazolyl optionally substituted on one ring N-atom with a substituent selected from the group consisting of $C_{1-6}$alkyl; $C_{3-6}$cycloalkyl; Het$^{1a}$; $R^{18}$; $R^{21}$; $C_{1-4}$alkyl substituted with one, two or three halo atoms; $C_{1-6}$alkyl substituted with one or two or three —OH substituents; $C_{1-6}$alkyl substituted with one $R^{13}$; —$C_{1-4}$alkyl-O—$C_{1-4}$alkyl substituted with one or two —OH substituents; $C_{1-4}$alkyl substituted with one $R^{18}$; $C_{2-6}$alkenyl; and $C_{2-6}$alkenyl substituted with one $R^{13}$; provided that when Het$^{1a}$ or $R^{18}$ are directly attached to the N-atom of the 5-membered heteroaromatic ring, said Het$^{1a}$ or $R^{18}$ are attached to the N-atom via a ring carbon atom; and wherein said 5-membered heteroaromatic ring may optionally be substituted on the ring carbon atoms with in total one or two substituents each independently selected from the group consisting of halo; cyano; $C_{1-6}$alkyl; —O—$C_{1-4}$alkyl; —C(=O)—$R^{10}$; —S(=O)$_2$—$C_{1-4}$alkyl; —S(=O)(=N—$R^{20a}$)—$C_{1-4}$alkyl; —O—$C_{1-4}$alkyl substituted with one, two or three halo atoms; —O—$C_{1-4}$alkyl-$R^{12}$; $C_{3-6}$cycloalkyl; —O—$C_{3-6}$cycloalkyl; Het$^{1a}$; —O-Het$^{1b}$; $R^1$; $R^{21}$; —P(=O)—($C_{1-4}$alkyl)$_2$; —NH—C(=O)—$C_{1-4}$alkyl; —NH—C(=O)—Het$^{1g}$; —NR$^{17a}$R$^{17b}$; $C_{1-4}$alkyl substituted with one, two or three halo atoms; $C_{1-4}$alkyl substituted with one, two or three —OH substituents; $C_{1-6}$alkyl substituted with one $R^{13}$; $C_{1-4}$alkyl substituted with one $R^{18}$; $C_{2-6}$alkenyl; and $C_{2-6}$alkenyl substituted with one $R^{13}$.

In an embodiment, the present invention relates to those compounds of Formula (I) and the pharmaceutically acceptable addition salts, and the solvates thereof, or any subgroup thereof as mentioned in any of the other embodiments, wherein $R^{13}$ represents —O—$C_{1-4}$alkyl, —C(=O)NR$^{15a}$R$^{15b}$, —NR$^{19a}$R$^{19b}$, $C_{3-6}$cycloalkyl, Het$^{1d}$, —S(=O)$_2$—$C_{1-4}$alkyl, —S(=O)(=N—$R^{20c}$)—$C_{1-4}$alkyl, or —C(=O)—Het$^{1f}$.

In an embodiment, the present invention relates to those compounds of Formula (I) and the pharmaceutically acceptable addition salts, and the solvates thereof, or any subgroup thereof as mentioned in any of the other embodiments, wherein $R^{13}$ represents —O—$C_{1-4}$alkyl, —C(=O)NR$^{15a}$R$^{15b}$, —NR$^{19a}$R$^{19b}$, $C_{3-6}$cycloalkyl, Het$^{1d}$, Het$^7$, —S(=O)$_2$—$C_{1-4}$alkyl, —S(=O)(=N—$R^{20c}$)—$C_{1-4}$alkyl, or —C(=O)—Het$^{1f}$.

In an embodiment, the present invention relates to those compounds of Formula (I) and the pharmaceutically acceptable addition salts, and the solvates thereof, or any subgroup thereof as mentioned in any of the other embodiments, wherein $R^{18}$ represents

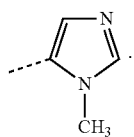

In an embodiment, the present invention relates to those compounds of Formula (I) and the pharmaceutically acceptable addition salts, and the solvates thereof, or any subgroup thereof as mentioned in any of the other embodiments, wherein Y represents CR$^4$.

In an embodiment, the present invention relates to a subgroup of Formula (I), hereby named compounds of Formula (I-x), and the pharmaceutically acceptable addition salts, and the solvates thereof:

(I-x)

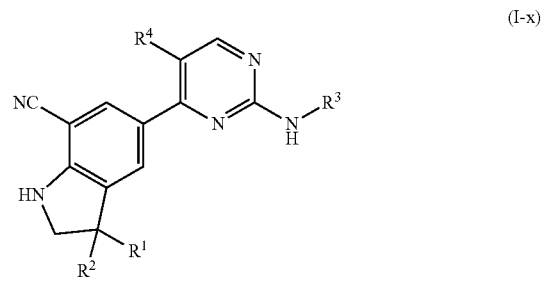

wherein all variables are defined according to any of the other embodiments.

In an embodiment, the present invention relates to those compounds of Formula (I) and the pharmaceutically acceptable addition salts, and the solvates thereof, or any subgroup thereof as mentioned in any of the other embodiments, wherein Y represents N.

In an embodiment, the present invention relates to a subgroup of Formula (I), hereby named compounds of Formula (I-y), and the pharmaceutically acceptable addition salts, and the solvates thereof:

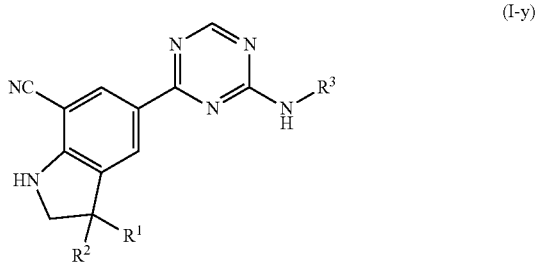

(I-y)

wherein all variables are defined according to any of the other embodiments.

In an embodiment, the present invention relates to a subgroup of Formula (I), hereby named compounds of Formula (I″), and the pharmaceutically acceptable addition salts, and the solvates thereof:

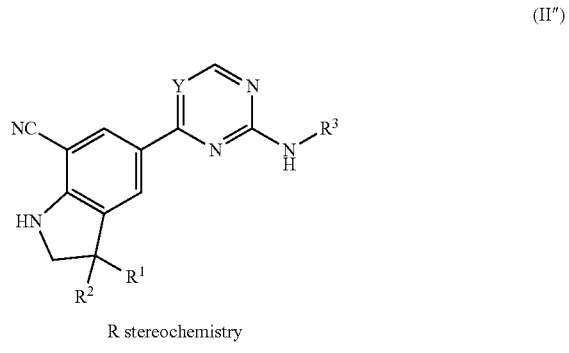

(II″)

R stereochemistry wherein all variables are defined according to any of the other embodiments.

In an embodiment, the present invention relates to a subgroup of Formula (I) as defined in the general reaction schemes.

In an embodiment the compound of Formula (I) is selected from the group consisting of compounds 19, 42, 49, 107, 113, 114, 118, 120, 132, 145, 156, 164, 183 and 177, tautomers and stereoisomeric forms thereof, and the pharmaceutically acceptable addition salts, and the solvates thereof.

In an embodiment the compound of Formula (I) is selected from the group consisting of compounds 19, 42, 49, 107, 113, 114, 118, 120, 132, 145, 156, 164, 183 and 177.

In an embodiment the compound of Formula (I) is selected from the group consisting of any of the exemplified compounds,
tautomers and stereoisomeric forms thereof,
and the free bases, the pharmaceutically acceptable addition salts, and the solvates thereof.

All possible combinations of the above-indicated embodiments are considered to be embraced within the scope of this invention.

Methods for the Preparation of Compounds of Formula (I)

In this section, as in all other sections unless the context indicates otherwise, references to Formula (I) also include all other sub-groups and examples thereof as defined herein.

The general preparation of some typical examples of the compounds of Formula (I) is described hereunder and in the specific examples, and are generally prepared from starting materials which are either commercially available or prepared by standard synthetic processes commonly used by those skilled in the art. The following schemes are only meant to represent examples of the invention and are in no way meant to be a limit of the invention.

Alternatively, compounds of the present invention may also be prepared by analogous reaction protocols as described in the general schemes below, combined with standard synthetic processes commonly used by those skilled in the art of organic chemistry.

The skilled person will realise that functionalization reactions illustrated in the Schemes below for compounds of Formula (I) wherein Y is $CR^4$, may also be carried out for compounds wherein Y is N. The skilled person will realise this applies, for example and without limitation, to steps 3 and 4 of scheme 2 and scheme 20.

The skilled person will realize that in the reactions described in the Schemes, although this is not always explicitly shown, it may be necessary to protect reactive functional groups (for example hydroxy, amino, or carboxy groups) where these are desired in the final product, to avoid their unwanted participation in the reactions. For example in Scheme 6, the NH moiety on the pyrimidinyl or the cyanoindoline moiety can be protected with a t-butoxycarbonyl protecting group. In general, conventional protecting groups can be used in accordance with standard practice. The protecting groups may be removed at a convenient subsequent stage using methods known from the art. This is illustrated in the specific examples.

The skilled person will realize that in the reactions described in the Schemes, it may be advisable or necessary to perform the reaction under an inert atmosphere, such as for example under $N_2$-gas atmosphere.

It will be apparent for the skilled person that it may be necessary to cool the reaction mixture before reaction work-up (refers to the series of manipulations required to isolate and purify the product(s) of a chemical reaction such as for example quenching, column chromatography, extraction).

The skilled person will realize that heating the reaction mixture under stirring may enhance the reaction outcome. In some reactions microwave heating may be used instead of conventional heating to shorten the overall reaction time.

The skilled person will realize that another sequence of the chemical reactions shown in the Schemes below, may also result in the desired compound of formula (I).

The skilled person will realize that intermediates and final compounds shown in the schemes below may be further functionalized according to methods well-known by the person skilled in the art.

It will be clear for a skilled person that in case a variable in a specific general scheme is not defined, the variable is defined according to the scope of the present invention, or as defined in any one of the other general schemes.

In general, compounds of Formula (I) wherein $R^2$ is $R^{2a}$ being $C_{1-6}$alkyl, and wherein all the other variables are defined according to the scope of the present invention, hereby named compounds of Formula (Ia), can be prepared according to the following reaction Scheme 1. In Scheme 1 $halo^1$ is defined as Cl, Br or I; and $PG^1$ represents a suitable protecting group, such as for example tert-(butoxycarbonyl). All other variables in Scheme 1 are defined according to the scope of the present invention.

In Scheme 1, the following reaction conditions apply:
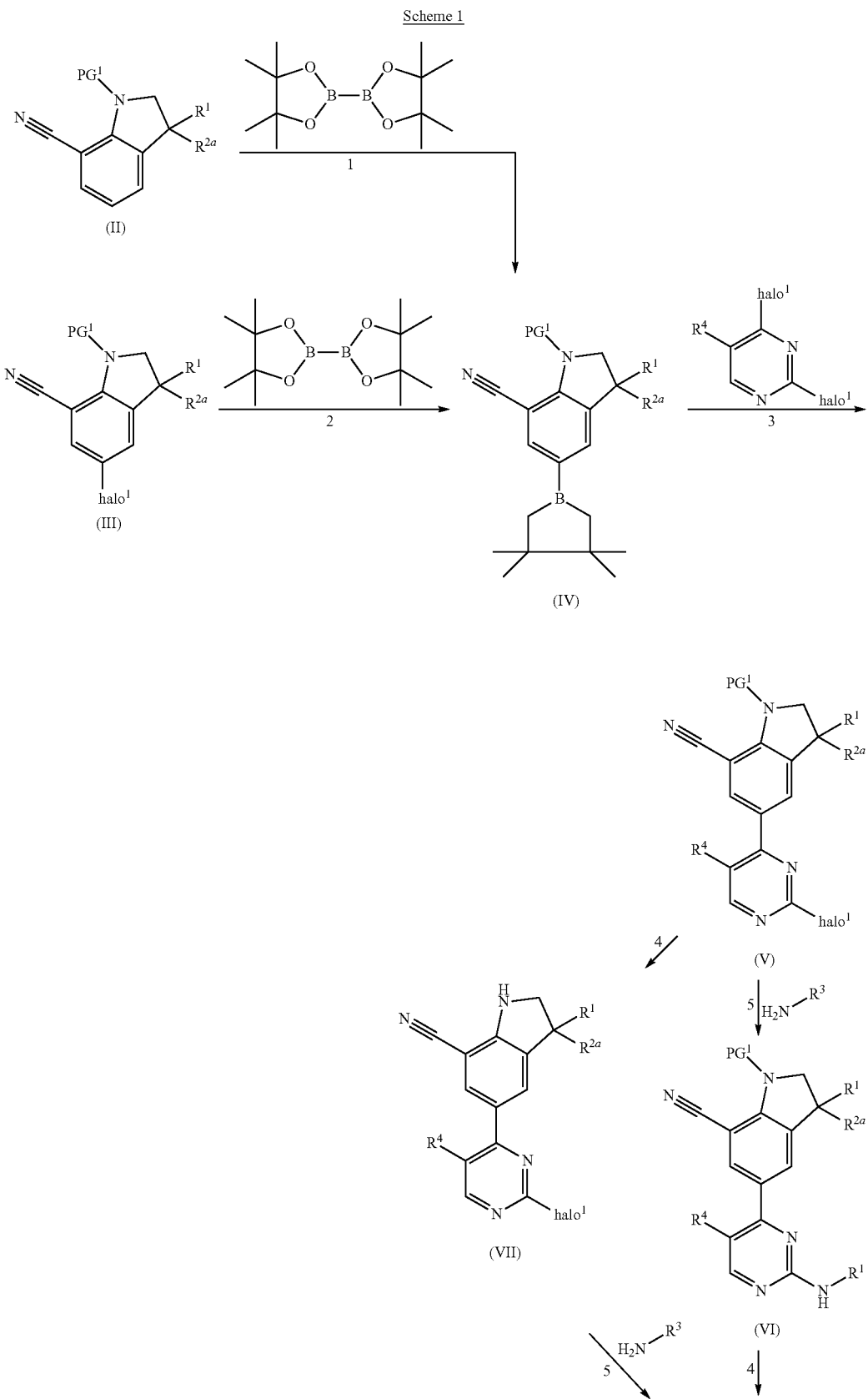

-continued

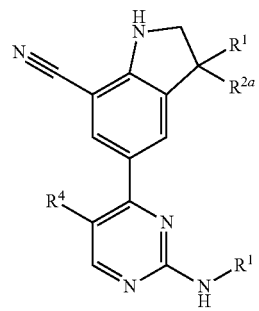

(Ia)

1: at a suitable temperature such as for example 80° C., in the presence of a suitable ligand such as for example 4,4'-di-tert-butyl-2,2'-dipyridyl, a suitable catalyst such as for example bis(1,5-cyclooctadiene)-di-μ-merhoxydiiridium (I) ([Ir(OCH₃)(C₈H₁₂)]₂), and a suitable solvent such as for example heptane;
2: at a suitable temperature such as for example 85° C., in the presence of a suitable catalyst such as for example [1,1'-bis(diphenylphosphino)ferrocene] dichloropalladium (II), optionally with dichloromethane complex, a suitable base such as for example potassium acetate and a suitable solvent such as for example 1,4-dioxane;
3: at a suitable temperature such as for example 85° C., in the presence of a suitable catalyst such as for example palladium tetrakis (Pd(PPh₃)₄ or [1,1'-Bis(diphenylphosphino)ferrocene]-dichloropalladium(II). Dichloromethane (Pd(dppf)Cl₂·CH₂Cl₂), a suitable base such as for example sodium carbonate, and a suitable solvent such as for example 1,4-dioxane;
4: at a suitable temperature such as for example 0° C. or room temperature or reflux, in presence of a suitable acid such as for example trifluoroacetic acid or aqueous hydrochorlic acid with a suitable solvent such as for example dichloromethane, methanol, ethyl acetate or 1,4-dioxane or alternatively in the presence of silica in a suitable solvent such as for example toulene a a suitable temperature such as for example 125° C., and a suitable time such as for example 3 hours;
5: at a suitable temperature such as for example ranged between 100° C. and 140° C., in the presence of a suitable catalyst such a for example palladium acetate (Pd(OAc)₂) or chloro[2-(dicyclohexylphosphino)-3,6-dimethyl-2',4',6'-triisopropyl-1,1'-biphenyl][2-(2-aminoethyl)phenyl]palladium(II) (Brettphos palladacycle), a suitable ligand such as for example 2,2'-bis(diphenylphophino)-1,1'-binaphthyl (BINAP) or chloro[2-(dicyclohexylphosphino)-3,6-dimethoxy-2',4',6'-triisopropyl-1,1'-biphenyl][2-(2-aminoethyl)phenyl] (Brettphos), a suitable base such as for example cesium carbonate, and a suitable solvent such as for example 1,4-dioxane, optionally under microwave irradiation.

The skilled person will understand that the reactions described in Scheme 1 will also be applicable starting from an intermediate of formula (III-a) (as described in Scheme 23).

In general, compounds of Formula (I) wherein $R^2$ is $R^{2a}$ being $C_{1-6}$alkyl, a-1 is a 5-membered heteroaromatic ring containing one, two or three heteroatoms each independently selected from O, S, and N, substituted with —C(=O)—$R^{10}$ and additionally optionally substituted with other substituents according to the scope of the present invention, and wherein all the other variables are as defined according to the scope of the present invention, hereby named compounds of Formula (Ib), can be prepared according to the following reaction Scheme 2. In Scheme 2, halo¹ is defined as Cl, Br or I; $PG^1$ represents a suitable protecting group, such as for example tert-(butoxycarbonyl). All other variables in Scheme 2 are defined as before or according to the scope of the present invention.

In Scheme 2, the following reaction conditions apply:

Scheme 2

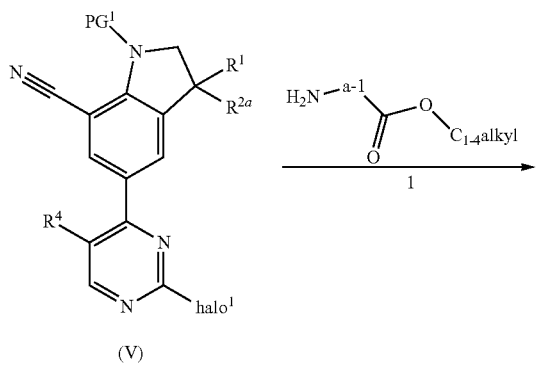

(V)

-continued

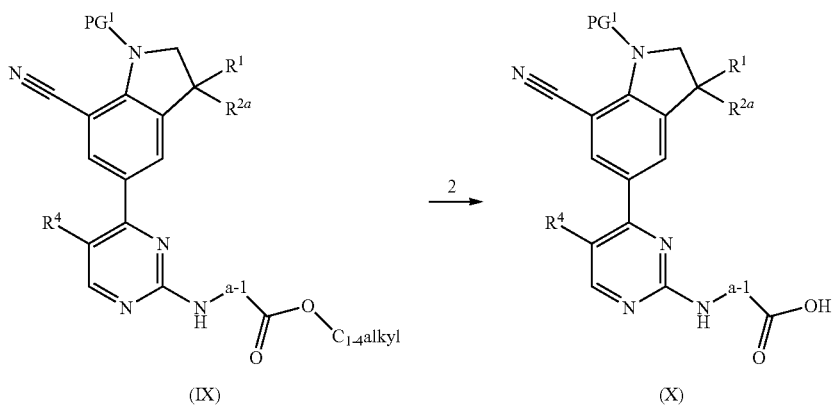

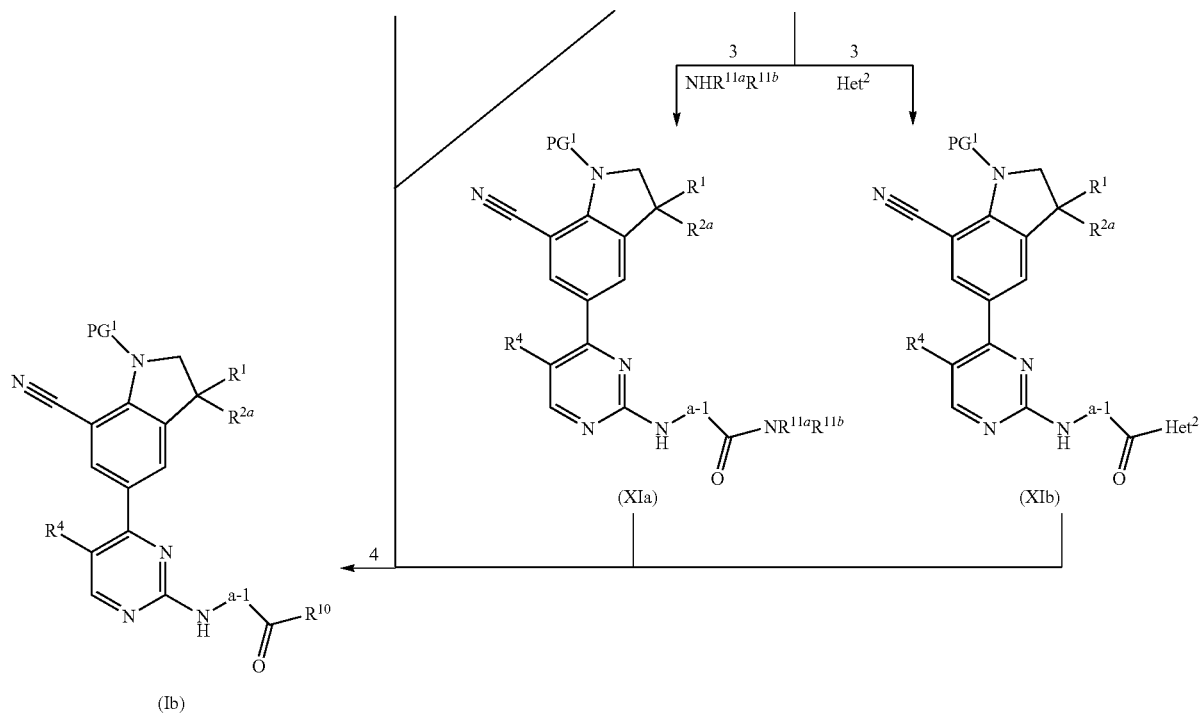

1: at a suitable temperature such as for example 100° C., in the presence of a suitable catalyst such as for example palladium acetate (Pd(OAc)$_2$), a suitable ligand such as for example 2,2'-bis(diphenylphosphino)-1,1'-binaphthyl (BINAP), a suitable base such as for example cesium carbonate, and a suitable solvent such as for example 1,4-dioxane, optionally under microwave activation;
2: at a suitable temperature such as for example 70° C., in presence of a suitable base such as for example lithium hydroxide, and a suitable solvent such as for example a mixture of tetrahydrofuran and water;
3: at a suitable temperature such as for example room temperature, in presence of a suitable coupling reagent such as for example 1-[bis(dimethylamino)methylene]-1H-1,2,3-triazolo[4,5-b]pyridinium 3-oxid hexafluorophosphate (HATU), a suitable base such as for example N,N-diisopropylethylamine, and a suitable solvent such as for example dimethylformamide;
4: at a suitable temperature such as for example 0° C. or room temperature or reflux, in presence of a suitable acid such as for example trifluoroacetic acid or aqueous hydrochloric acid with a suitable solvent such as for example dichloromethane, methanol, ethylacetate, or 1,4-dioxane, and a suitable time such as for example 3 hours.

In general, compounds of Formula (I) wherein $R^2$ is $R^{2b}$ being $C_{1-6}$alkyl substituted with one OH, and wherein all the other variables are as defined according to the scope of the present invention, hereby named compounds of Formula (Ic), can be prepared according to the following reaction Scheme 3. In Scheme 3 halo$^1$ is defined as Cl, Br or I; PG$^1$ represents a suitable protecting group, such as for example tert-(butoxycarbonyl) and PG$^2$ represents a suitable protecting group, such as for example tert-butyl-dimethylsilyl. All other variables in Scheme 3 are defined as before or according to the scope of the present invention.

In Scheme 3, the following reaction conditions apply:

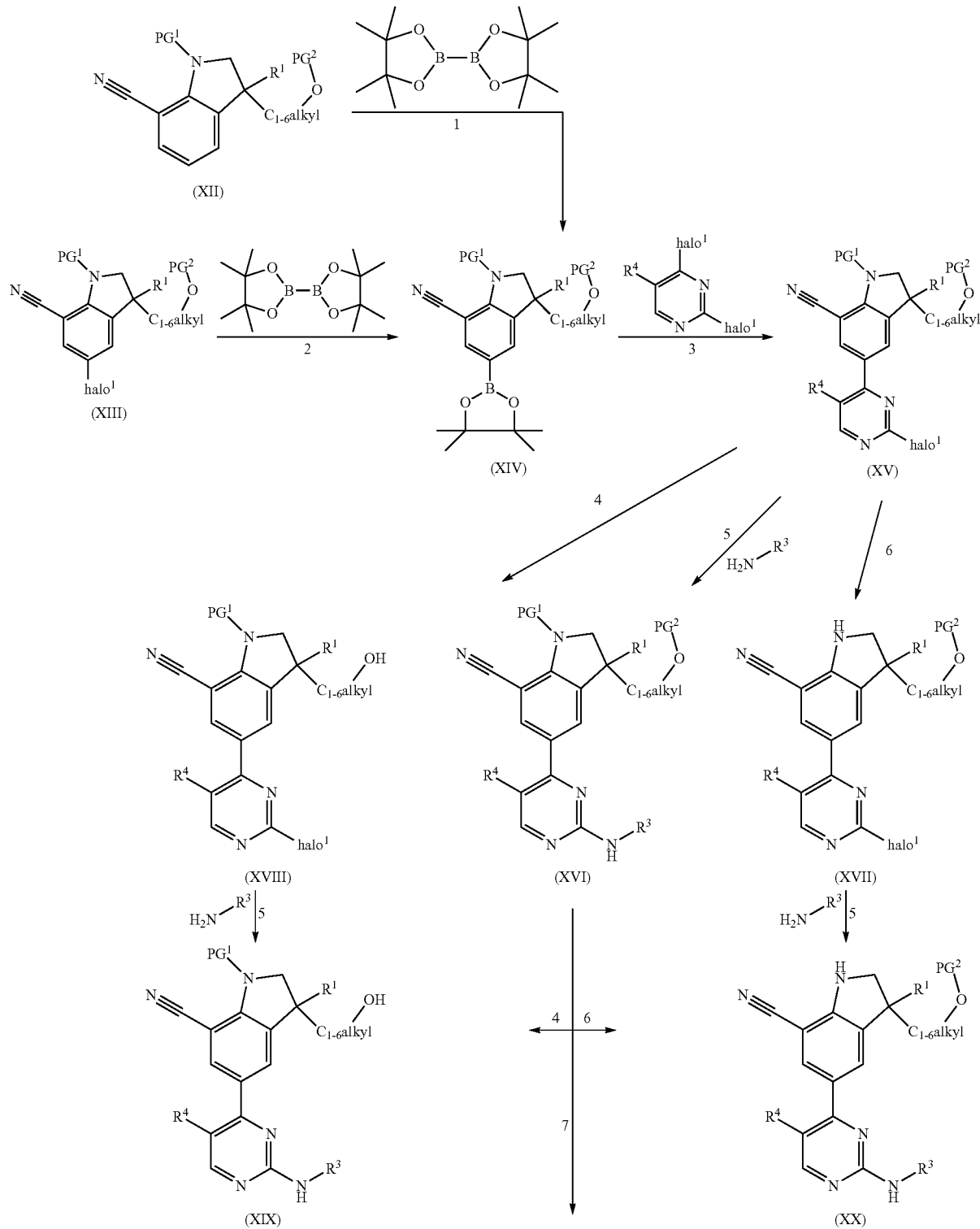

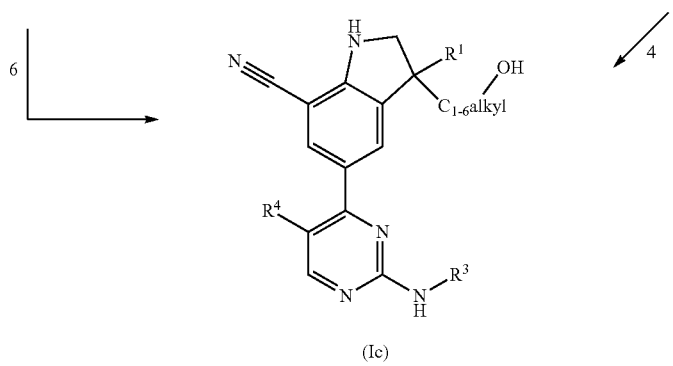

(Ic)

1: at a suitable temperature such as for example 80° C., in the presence of a suitable ligand such as for example 4,4'-di-tert-butyl-2,2'-dipyridyl, a suitable catalyst such as for example bis(1,5-cyclooctadiene)di-μ-methoxydiiridium (I) ([Ir(OCH$_3$(C$_8$H$_{12}$)]$_2$), and suitable solvent such as for example heptane;

2: at a suitable temperature such as for example 85° C., in the presence of a suitable catalyst such as for example [1,1'-bis(diphenylphosphino)ferrocene]dichloropalladium (II), optionally with dichloromethane complex, a suitable base such as for example potassium acetate and a suitable solvent such as for example 1,4-dioxane;

3: at a suitable temperature such as for example 85° C., in the presence of a suitable catalyst such as for example palladium tetrakis (Pd(PPh$_3$)$_4$), a suitable base such as for example sodium carbonate, and a suitable solvent such as for example 1,4-dioxane;

4: at a suitable temperature such as for example room temperature, in presence of a suitable desilylating agent such as for example tetra-n-butylammonium fluoride and a suitable solvent such as for example 2-methyltetrahydrofuran or tetrahydrofuran;

5: at a suitable temperature such as for example ranged between 100° C. and 140° C., in the presence of a suitable catalyst such as for example palladium acetate (Pd(OAc)$_2$) or chloro[2-(dicyclohexylphosphino)-3,6-dimethoxy-2',4'6'-triisopropyl-1,1'-biphenyl][2-(2-aminoethyl)phenyl]palladium(II) (Brettphos palladacycle), a suitable ligand such as for example 2,2'-bis(diphenylphosphino)-1,1'-chloro[2-(dicyclohexylphosphino)-3,6-dimethoxy-2',4',6'-triisoproyl-1,1'-biphenyl][2-(2-aminoethyl)phenyl] (Brettphos), a suitable base such as for example cesium carbonate, and a suitable solvent such as for example 1,4-dioxane, optionally under microwave irradiation.

6: at a suitable temperature such as example 0° C. or room temperature or reflux, in presence of a suitable acid such as for example trifluoroacetic acid and aqueous hydrochloric acid with a suitable solvent such as for example dichloromethane, methanol solvent such as for example toluene at a suitable temperature such as for example 125° C., and a suitable time such as for example 3 hours;

7: at a suitable temperature such as for example reflux, in presence of a suitable acid such as for example aqueous hydrochloric acid with a suitable solvent such as for example dichloromethane, methanol, ethyl acetate or 1,4-dioxane, and a suitable time such as for example 6 hours.

In general, compounds of Formula (I) wherein $R^2$ is $R^{2b}$ being $C_{1-6}$alkyl substituted with one OH, $R^3$ is 5-membered heteroaromatic ring containing one, two or three heteroatoms each independently selected from O, S, and N, substituted with —C(═O)—R$^{10}$ and additionally optionally substituted with other substituents according to the scope of the present invention, and wherein all the other variables are as defined according to the scope of the present invention, hereby named compounds of Formula (Id), can be prepared according to the following reaction Scheme 4. In Scheme 4, halo$^1$ is defined as Cl, Br or I; PG$^1$ represents a suitable protecting group, such as for example tert-(butoxycarbonyl) and PG$^2$ represents a suitable protecting group, such as for example tert-butyl-dimethylsilyl. All other variables in Scheme 4 are defined as before or according to the scope of the present invention.

In Scheme 4, the following reaction conditions apply:

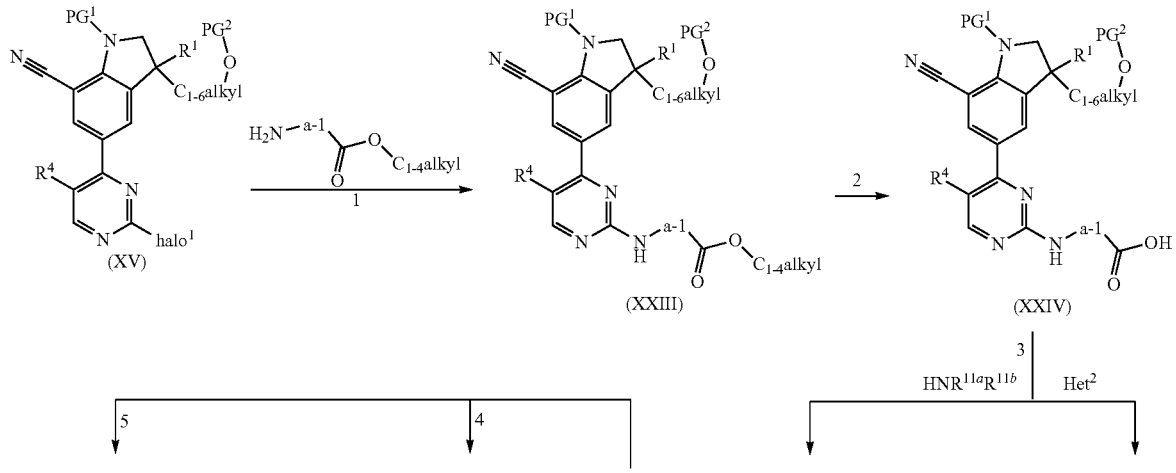

Scheme 4

-continued

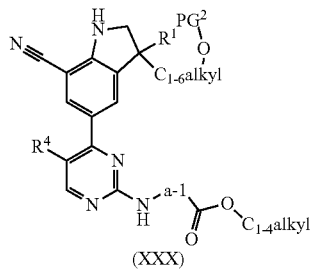 (XXX)

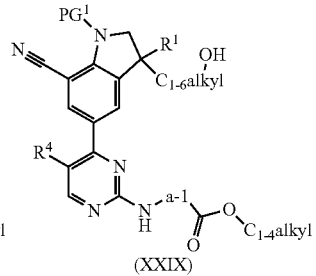 (XXIX)

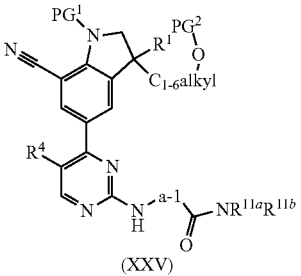 (XXV)

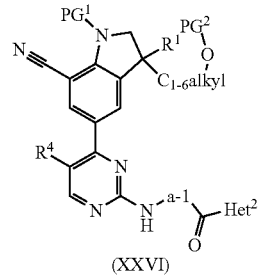 (XXVI)

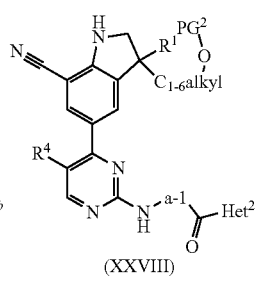 (XXVII) (XXVIII)

(Id)

1: at a suitable temperature such as for example 100° C., in the presence of a suitable catalyst such as for example paladium acetate (Pd(OAc)₂), a suitable ligand such as for example 2,2′-bis(diphenylphosphino)-1,1′-binaphthyl (BINAP), a suitable base such as for example cesium carbonate, and a suitable solvent such as for example 1,4-dioxane, optionally under microwave activation;
2: at a suitable temperature such as for example 70° C., in presence of a suitable base such as for example lithium hydroxide, and a suitable solvent such as for example a mixture of tetrahydrofuran and water;
3: at a suitable temperature such as for example room temperature, in presence of a suitable coupling reagent such as for example 1-[bis(dimethylamino)methylene]-1H-1,2,3-triazolo[4,5-b]pyridinium 3-oxid hexafluorophosphate (HATU), a suitable base such as for example N,N-diisopropylethylamine, and a suitable solvent such as for example dimethylformamide;
4: at a suitable temperature such as for example room temperature, in presence of a suitable desilylating agent such as for example tetra-n-butylammonium fluoride and a suitable solvent such as for example 2-methyltetrahydrofuran or tetrahydrofuran;
5: at a suitable temperature such as for example 0° C. or room temperature or reflux, in presence of a suitable acid such as for example trifluoroacetic acid or aqueous hydrochloric acid with a suitable solvent such as for example dichloromethane, methanol, ethyl acetate or 1,4-dioxane or alternatively in the presence of silica in a suitable solvent such as for example toluene at a suitable temperature such as for example 125° C., and a suitable time such as for example 3 hours;
6: at a suitable temperature such as for example reflux, in presence of a suitable acid such as for example aqueous hydrochloric acid with suitable solvent such as for example dichloromethane, methanol, ethyl acetate or 1,4-dioxane, and a suitable time such as for example 6 hours.

In general, compounds of Formula (I) wherein $R^2$ is $R^{2c}$ being $C_{1-6}$alkyl substituted with one $Het^{3a}$ or $-NR^{6a}R^{6b}$, wherein $R^{6b}$ is $R^{6b}a$ being H, $C_{1-4}$alkyl and $C_{3-6}$cycloalkyl and wherein all the other variables are as defined according to the scope of the present invention, hereby named compounds of Formula (Ie) and Formula (If), can be prepared according to the following reaction Scheme 5. In Scheme 5 $PG^1$ represents a suitable protecting group, such as for example tert-(butoxycarbonyl). All other variables in Scheme 5 are defined according to the scope of the present invention.

In Scheme 5, the following reaction conditions apply:

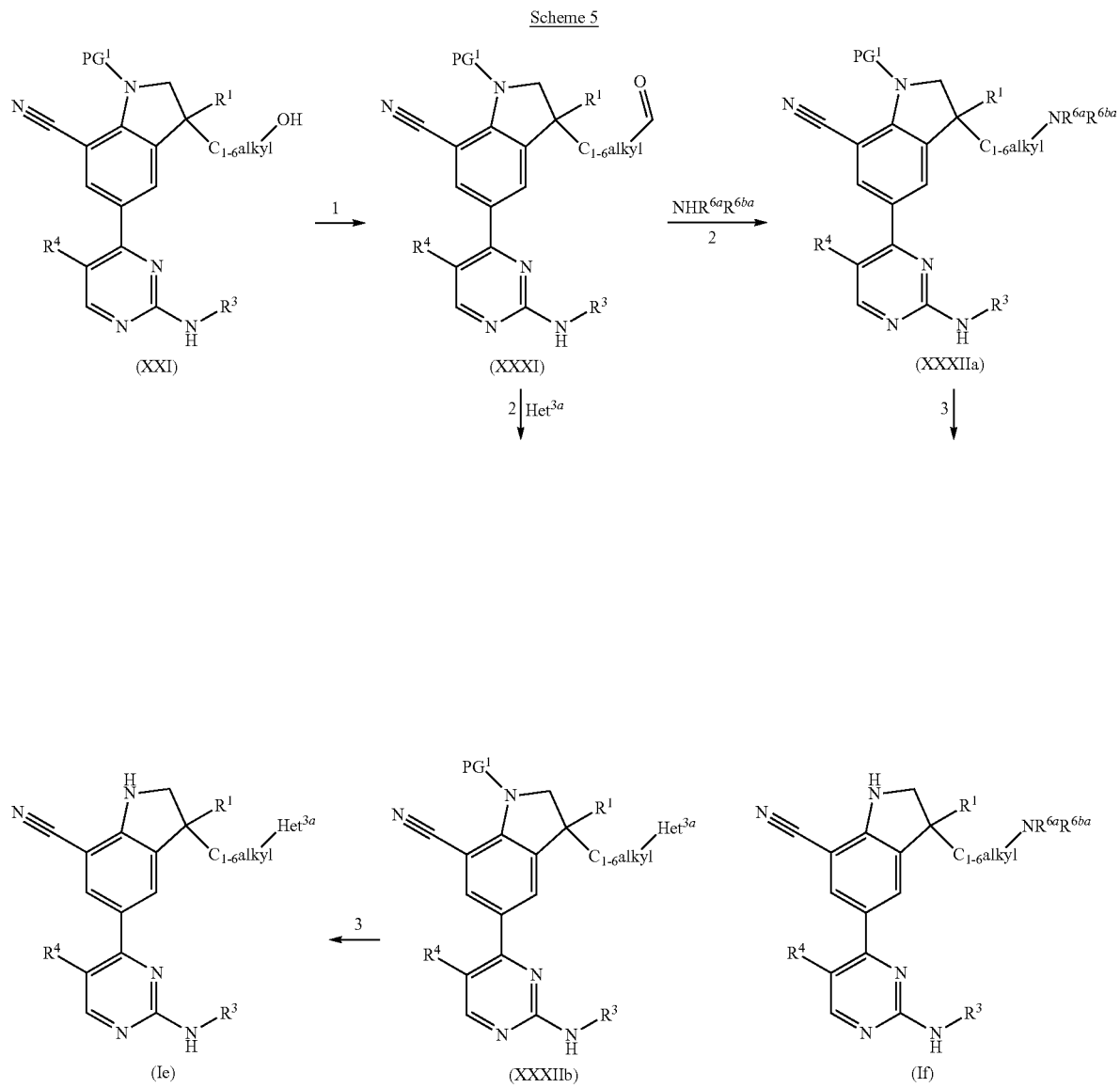

Scheme 5

1: at a suitable temperature such as for example -78° C., in the presence of oxalyl chloride and demithyl sulfoxide as reagents, a suitable base such as for example N,N-diisopropylethylamine, and a suitable solvent such as for example dichloromethane;
2: at a suitable temperature such as for example room temperature, in the presence of a suitable acid such as for example acetic acid, a suitable reducing agent such as for example sodium tricetoxyborohydride, and a suitable solvent such as for example dichloroethane;
3: at a suitable temperature such as for example 0° C. or room temperature or reflux, in presence of a suitable acid such as for example trifluoroacetic acid or aqueous hydrochloric acid with a suitable solvent such as for example dichloromethane, methanol, ethyl acetate or 1,4-dioxane or alternatively in the presence of silica in a suitable solvent such as for example toluene at a suitable temperature such as for example 125° C., and a suitable time such as for example 3 hours.

In general, compounds of Formula (I) wherein $R^2$ is $C_{1-6}$alkyl substituted with one $OR^{7a}$, $R^{7a}$ being —C(=O)—$R^9$ or —(C=O)—CH(NH$_2$)—$C_{1-4}$alkyl-Art), and wherein all the other variables are as defined according to the scope of the present invention, hereby named compounds of Formula (Ig), can be prepared according to the following reaction Scheme 6. In Scheme 6 PG$^3$ represents a suitable protecting group, such as for example a tert-(butoxycarbonyl), a tert-butyl or a benzyl. All other variables in Scheme 6 are defined according to the scope of the present invention.

In Scheme 6, the following reaction conditions apply:

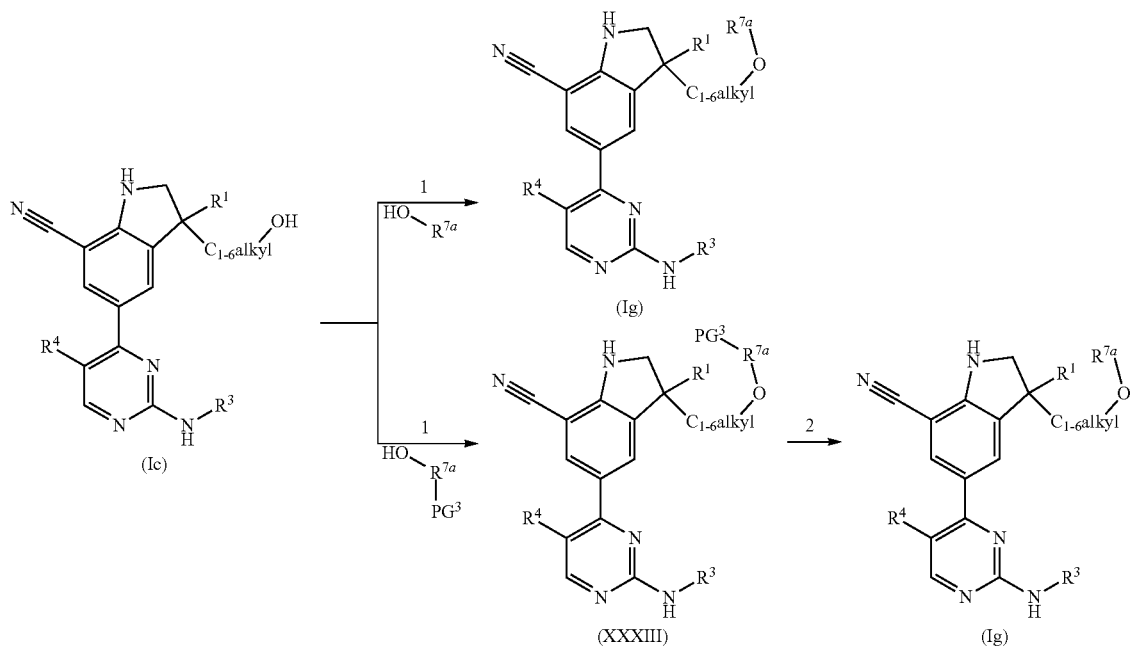

1: at a suitable temperature such as for example room temperature, in the presence of a suitable coupling reagent such as for example 1-[bis(dimethylamino)methylene]-1H-1,2,3-triazolo[4,5-b]pyridinium 3-oxid hexafluorophosphate (HATU), in the presence of a suitable base as for example N,N-diisopropylethylamine, and a suitable solvent such as for example a mixture of tetrahydrofuran and dimethylformamide, and optionally followed by a deprotection step using a suitable acid such as for example hydrochloric acid in a suitable solvent such as for example, 1,4-dioxane;
2: at a suitable temperature such as for example 0° C. or room temperature, in presence of a suitable acid such as for example trifluoroacetic acid or awueous hydrochloric acid with a suitable solvent such as for example dichloromethane, methanol, ethyl acetate or 1,4-dioxane or alternatively in the presence of silica in a suitable solvent such as for example toluene at a suitable temperature such as for example 125° C., and a suitable time such as for example 3 hours.

In general, compounds of Formula (I) wherein $R^2$ is $C_{1-6}$alkyl substituted with one $OR^{7b}$, $R^{7b}$ being $C_{1-4}$alkyl, and wherein all the other variables are as defined according to the scope of the present invention, hereby named compounds of Formula (Ih), can be prepared according to the following reaction Scheme 7. In Scheme 7 halo$^1$ is defined as Cl, Br or I; PG$^1$ represents a suitable protecting group, such as for example tert-(butoxycarbonyl) and PG$^2$ represents a suitable protecting group, such as for example tert-butyl-dimethylsilyl; W represents a leaving group, such as for example a methane sulfonate or toluene sulfonate or an halogen (Cl, Br or I). All other variables in Scheme 7 are defined as before or according to the scope of the present invention.

In Scheme 7, the following reaction conditions apply:

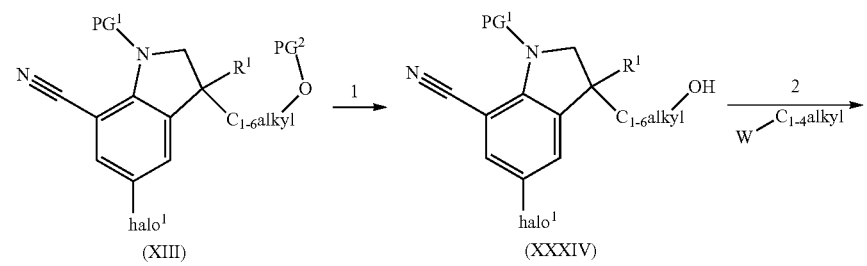

-continued

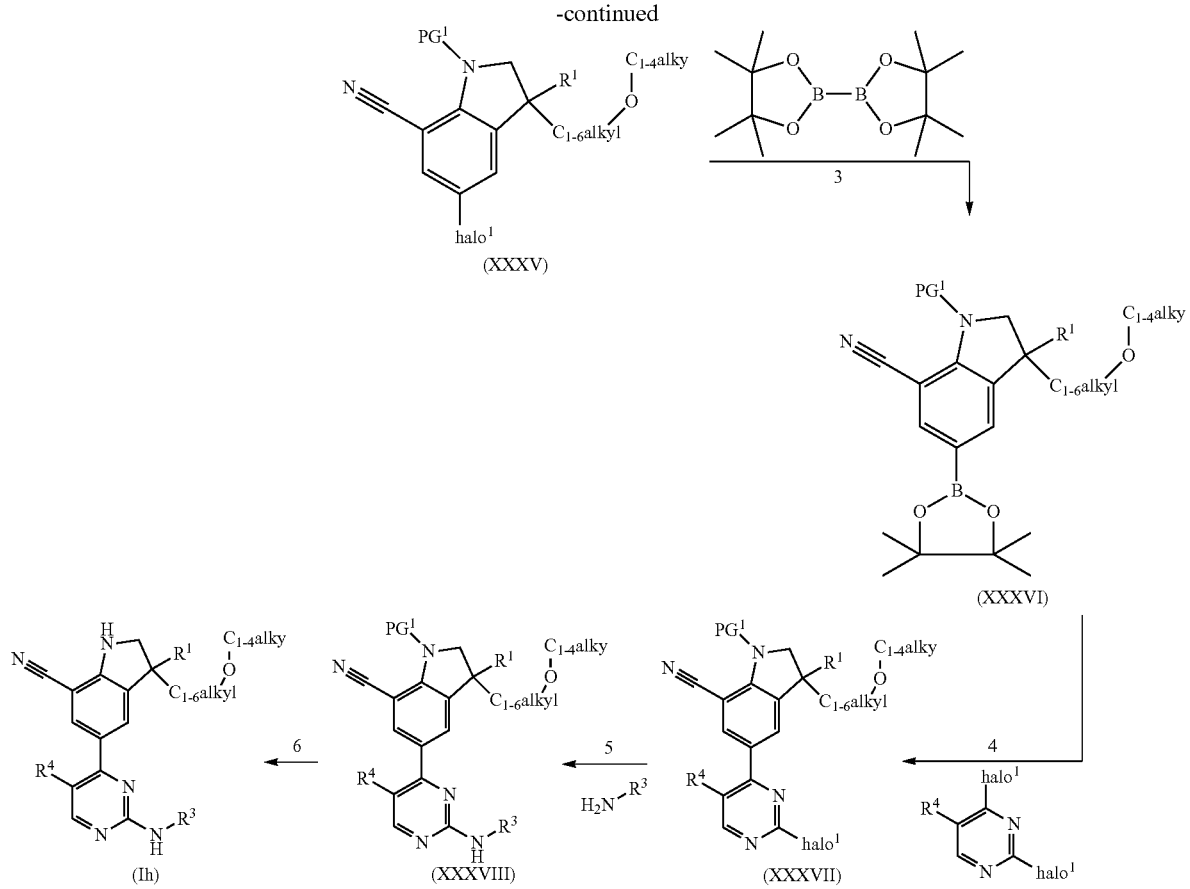

1: at a suitable temperature such as for example room temperature, inpresence of a suitable desilylating agent such as for example tetra-n-butylammonium fluoride and a suitable solvent such as for example 2-methyltetrahydrofuran or tetrahydrofuran;
2: at a suitable temperature such as for example room temperature, in the presence of a suitable base as for example sodium hydride, and a suitable solvent such as for example dimethylformamide;
3: at a suitable temperature such as for example 85° C., in the presence of a suitable catalyst such as for example [1,1′-bis(diphenylphosphino)ferrocene] dichloropalladium (II), optionally with dichloromethane complex, a suitable base such as for example potassium acetate and a suitable solvent such as for example 1,4-dioxane;
4: at a suitable temperature such as for example 80° C., in the presence of a suitable catalyst such as for example palladium tetrakis (Pd(PPh$_3$)$_4$), a suitable base such as for example sodium carbonate, and a suitable solvent such as for example 1,4-dioxane;
5: at a suitable temperature such as for example 100° C., in the presence of a suitable catalyst such as for example palladium acetate (Pd(OAc)$_2$), a suitable ligand such as for example 2,2′-bis(diphenylphosphino)-1-1′-binaphthyl (BINAP), a suitable base such as for example cesium carbonate, and a suitable solvent such as for example 1,4-dioxane, optionally under microwave activation;

In general, compounds of Formula (I) wherein $R^2$ is $C_{1-6}$alkyl substituted with one $OR^{7c}$, $R^{7c}$ being $C_{1-4}$alkyl-$NR^{8a}R^{8b}$ or $C_{1-4}$alkyl-Het$^{3b}$, and wherein all the other variables are as defined according to the scope of the present invention, hereby named compounds of Formula (Ii) and Formula (Ij), can be prepared according to the following reaction Scheme 8. In Scheme 8 halo$^1$ is defined as Cl, Br or I; PG$^1$ represents a suitable protecting group, such as for example tert-(butoxycarbonyl); W$^1$ represents a leaving group, such as for example a methane sulfonate or toluene sulfonate or an halogen (Cl, Br or I); W$^2$ represents a leaving group, such as for example a mesyl or a tosyl. All other variables in Scheme 8 are defined as before or according to the scope of the present invention.

In Scheme 8, the following reaction conditions apply:

Scheme 8

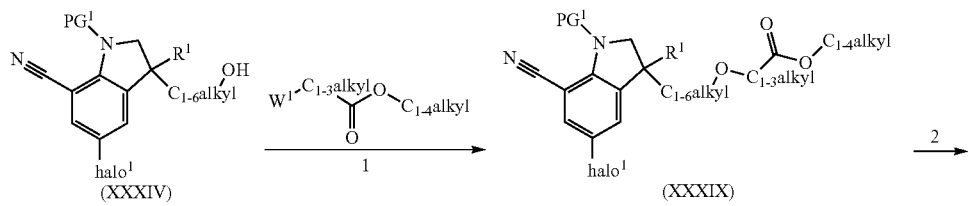

-continued

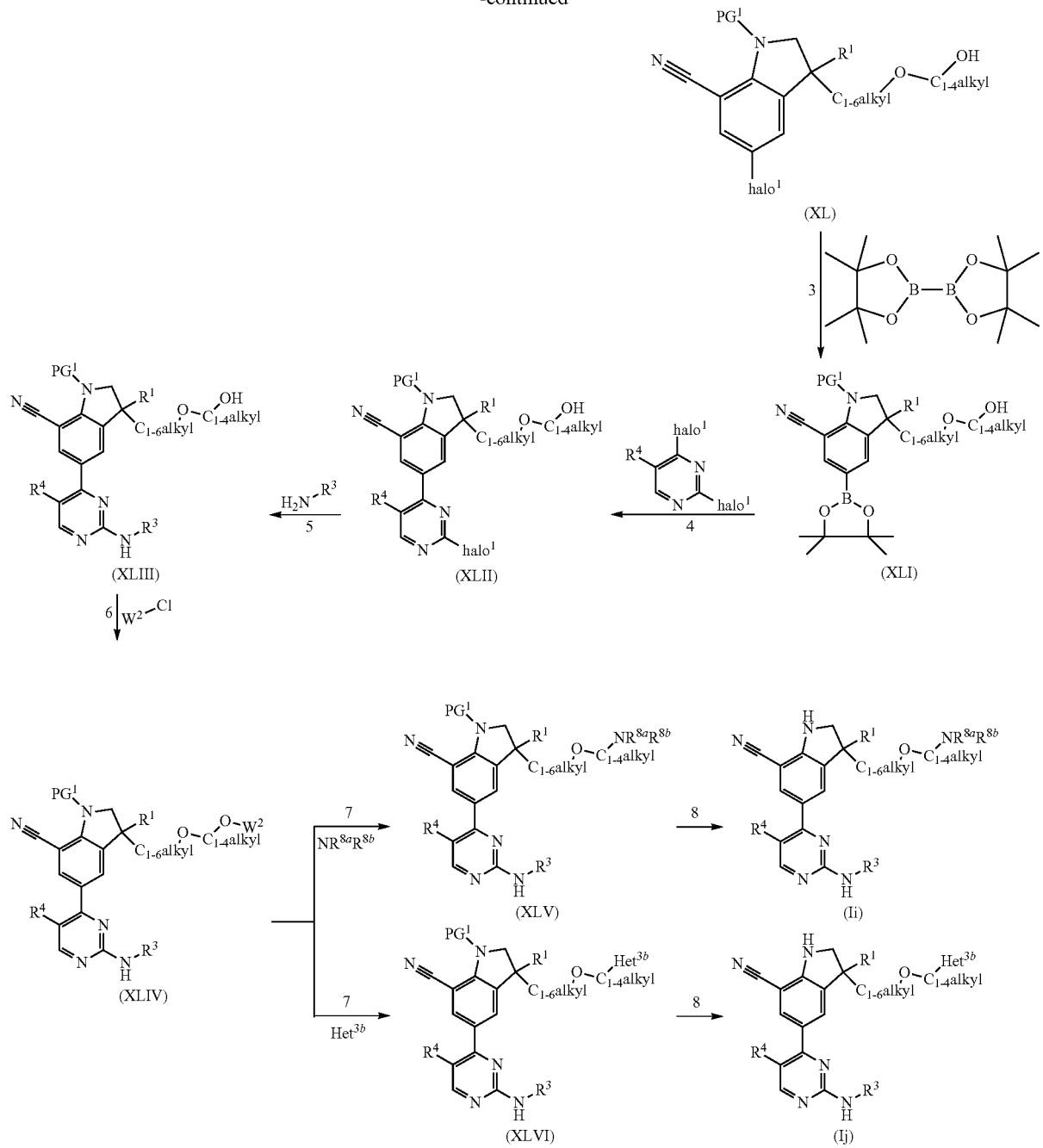

1: at a suitable temperature such as for example room temperature, in the presence of a suitable base as for example sodium hydride, and a suitable solvent such as for example dimethylformamide;
2: at a suitable temperature such as for example 55° C., in presence of reducing agent such as for example sodium borohydride and a suitable solvent such as for example a mixture of tetrahydrofuran and methanol;
3: at a suitable temperature such as for example 100° C., in the presence of a suitable catalyst such as for example [1,1'-bis(diphenylphosphino)ferrocene]dichloropalladium (II), optionally with dichloromethane complex, a suitable base such as for example potassium acetate and a suitable solvent such as for example 1,4-dioxane;
4: at a suitable temperature such as for example 85° C., in the presence of a suitable catalyst such as for example palladium tetrakis (Pd(PPh₃)₄), a suitable base such as for example sodium carbonate, and a suitable solvent such as for example 1,4-dioxane;
5: at a suitable temperature such as for example 120° C., in the presence of a suitable catalyst such as for example palloadium acetate (Pd(OAc)₂), a suitable ligand such as for example 2,2'-bis(diphenylphosphino)1,1'-binaphthyl (BINAP), a suitable base such as for example cesium carbonate, and a suitable solvent such as for example 1,4-dioxane, optionally under microwave activation;
6: at a suitable temperature such as for examplt 5° C., in the presence of a suitable base such as for example triethylamine, and a suitable solvent such as for example dichloromethane;
7: at a suitable temperature such as for example 80° C., and a suitable solvent such as for example acetonitrile;
8: at a suitable temperature such as for example 0° C. or room temperature or reflux, in presence of a suitable acid such as for example trifluoroacetic acid or aqueous hydrochloric acid with a suitable solvent such as for example dichloromethane, methanol, ethyl acetate or 1,4-dioxane or alternatively in the presence of silica in a suitable solvent such as for example toluene at a suitable temperature such as for example 125° C., and a suitable time such as for example 3 hours.

In general, intermediates of Formula (II) and (III) wherein $R^2$ is $R^{2a}$ being $C_{1-6}$alkyl, and wherein all the other variables are as defined according to the scope of the present invention, hereby named compounds of Formula (II) and (III), can be prepared according to the following reaction Scheme 9. In Scheme 9 halo$^1$ is defined as Cl, Br, I; halo$^2$ is defined as Cl, Br, I; PG$^1$ represents a suitable protecting group, such as for example tert-(butoxycarbonyl), W$^1$ represents a leaving group, such as for example a methane sulfonate or toluene sulfonate or an halogen (Cl, Br or I). All other variables in Scheme 9 are defined as before or according to the scope of the present invention.

In Scheme 9, the following reaction conditions apply:

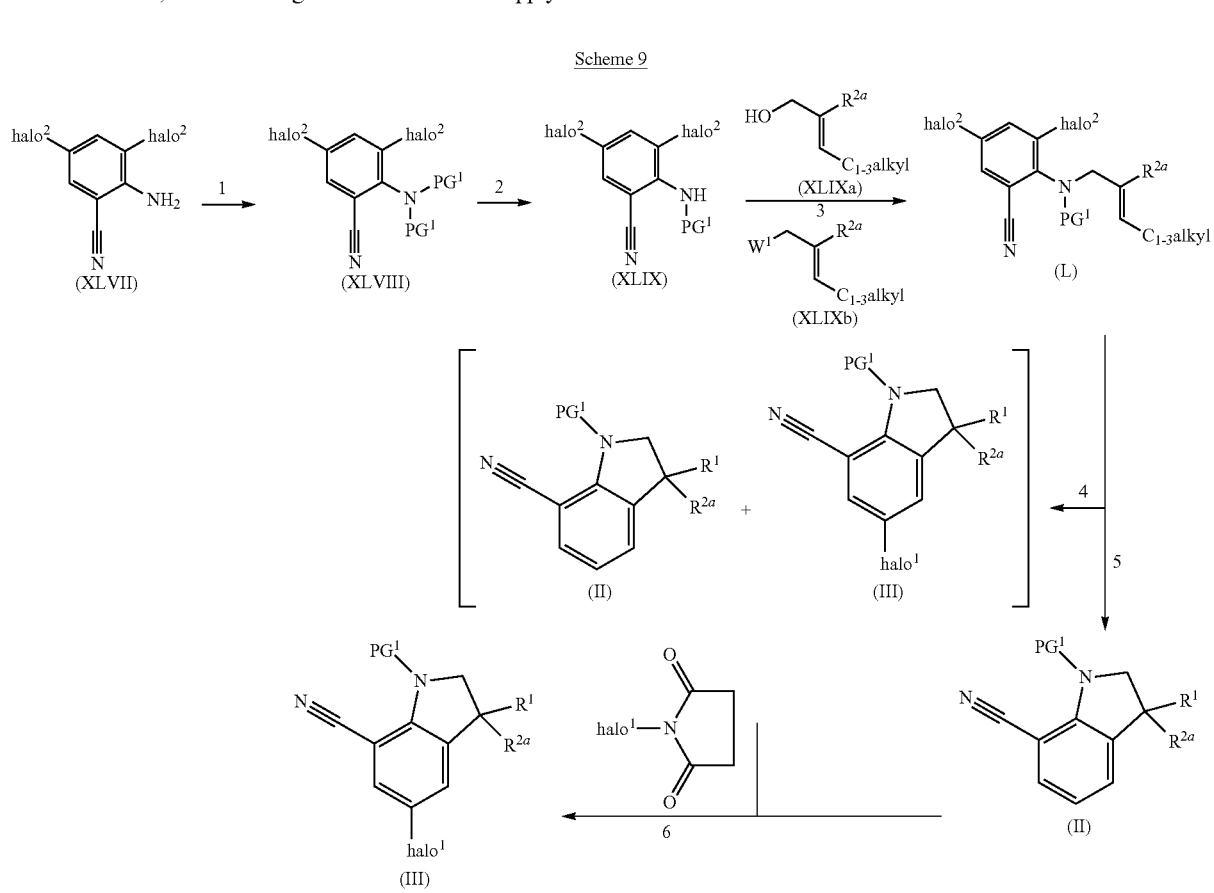

Scheme 9

1: at a suitable temperature such as for example 45° C., in the presence of a suitable reagent such as for example di-tert-butyldicarbonate, in the presence of a suitable catalyst such as for example 4-dimethylaminopyridine (DMAP), and a suitable solvent such as for example dichloromethane;
2: at a suitable temperature such as for example 65° C. and a suitable solvent such as for example methanol;
3: in case of (XLIXa), at a suitable temperature such as for example at room temperature, in the presence of tri-n-butylphosphine and 1,1′-(azodicarbonyl)piperidine and a suitable solvent such as for example 2-methyltetrahydrofuran; In case of (XLIXb), at a suitable temperature such as for example 80° C., in the presence of a suitable base such as for example potassium carbonate, a suitable additive such as for example sodium iodide, in a suitable solvent such as for example acetonitrile;
4: at a suitable temperature such as for example 85° C., in the presence of sodium acetate, sodium formate and tetraethylammonium chloride, a suitable catalyst such as for example palladium acetate (Pd(OAc)$_2$), and a suitable solvent such as for example dimethylformamide;
5: at a suitable temperature such as for example 60° C., in the presence of sodium acetate, sodium formate dehydrate and tetraethylammonium chloride, a suitable catalyst such as for example [1,1′-bis(diphenylphosphino) ferrocene] palladium, (II) chloride optionally with dichloromethane complex, and a suitable solvent such as for example dimethylformamide;
6: at a suitable temperature such as for example 40° C., in the presence of N-halogeno-succinimide, and a suitable solven such as for example acetonitrile Alternatively, in the presence of a suitable reagent such as for example 1,3-dibromo-5,5-dimethylhydantoin, in a suitable solvent such as for example acetonitrile.

In general, intermediates of Formula (XII) and (XIII) wherein $R^2$ is $R^{2b}$ being $C_{1-6}$alkyl substituted with one OH, and wherein all the other variables are as defined according to the scope of the present invention, hereby named compounds of Formula (XII) and (XIII), can be prepared according to the following reaction Scheme 10. In Scheme 10 halo$^1$ is defined as Cl, Br, I; halo$^2$ is defined as Cl, Br, I; PG$^1$ represents a suitable protecting group, such as for example tert-(butoxycarbonyl) and PG$^2$ represents a suitable protecting group, such as for example tert-butyl-dimethylsilyl; W$^1$ represents a leaving group, such as for example a methane sulfonate or toluene sulfonate or an halogen (Cl, Br or I). All other variables in Scheme 10 are defined as before or according to the scope of the present invention.

In Scheme 10, the following reaction conditions apply:

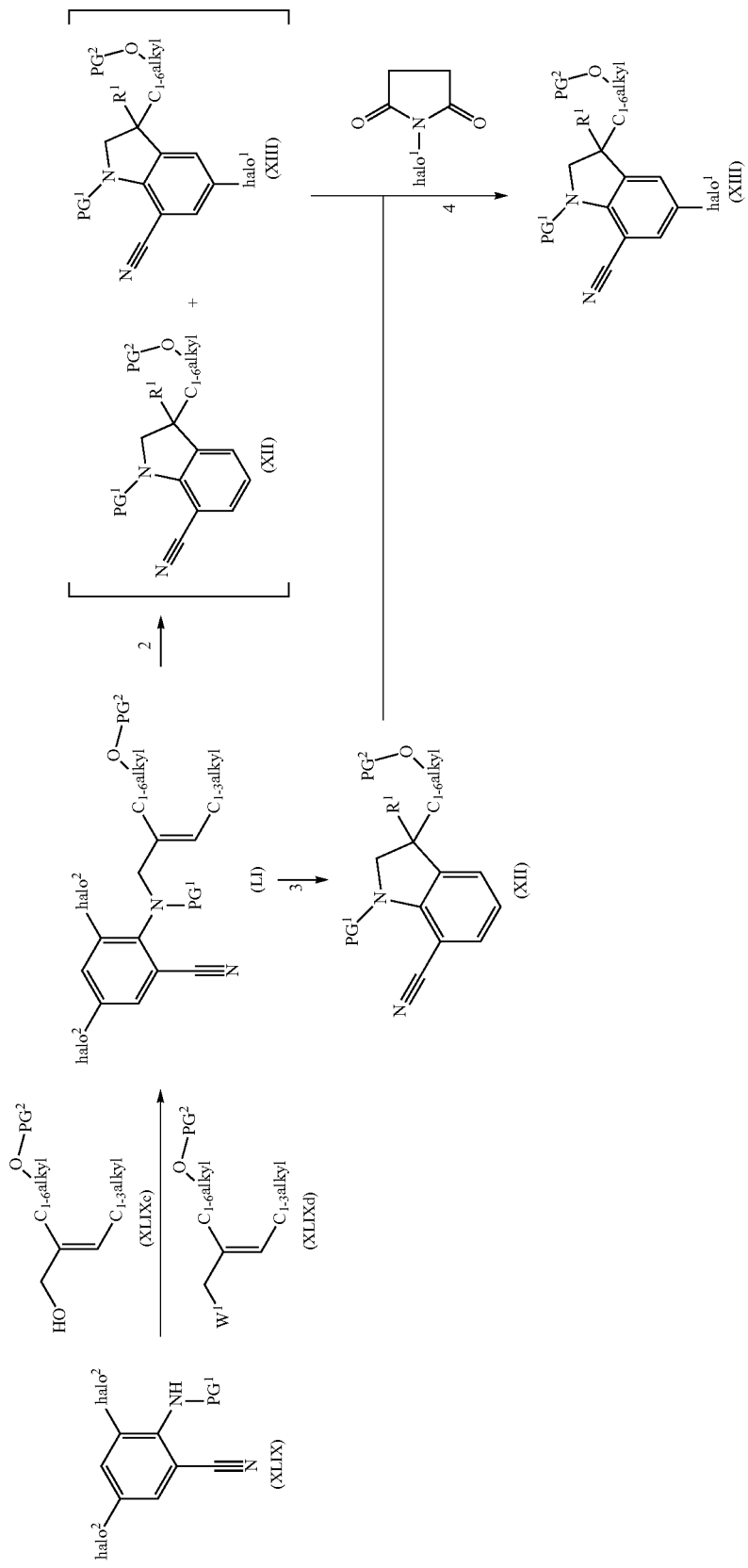

In general, compounds of Formula (I) wherein $R^2$ is as shown in the scheme 11, and wherein all the other variables are as defined according to the scope of the present invention, hereby named compounds of Formula (Ik) can be prepared according to the following reaction Scheme 11. In Scheme 11 $PG^1$ represents a suitable protecting group, such as for example tert-(butoxycarbonyl). All other variables in Scheme 11 are defined as before or according to the scope of the present invention.

In Scheme 11, the following reaction conditions apply:

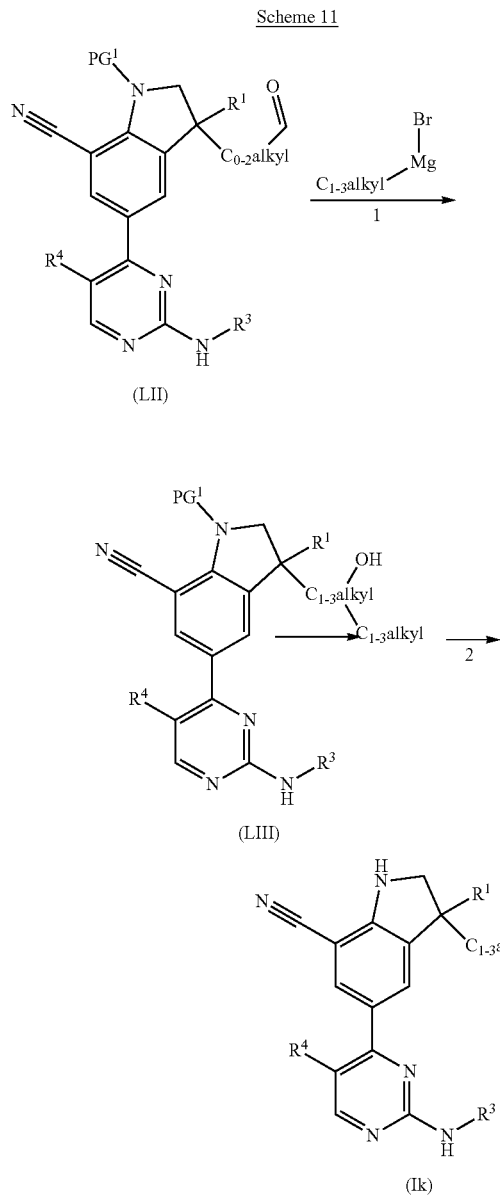

1: at a suitable temperature such as for example at room temperature, and a suitable solvent such as for example tetrahydrofuran;
2: at a suitable temperature such as for example 0° C. or room temperature or reflux, in presence of a suitable acid such as for example trifluoroacetic acid or aqueous hydrochloric acid with a suitable solvent such as for example dichloromethane, methanol, ethyl acetate or 1,4-dioxane or alternatively in the presence of silica in a suitable solvent such as for example toluene at a suitable temperature such as for example 125° C. and a suitable time such as for example 3 hours.

In general, compounds of Formula (I) wherein $R^2$ is as shown in the scheme 12, and wherein all the other variables are as defined according to the scope of the present invention, hereby named compounds of Formula (Il) can be prepared according to the following reaction Scheme 12. In Scheme 12 $PG^1$ represents a suitable protecting group, such as for example tert-(butoxycarbonyl). All other variables in Scheme 12 are defined as before or according to the scope of the present invention.

In Scheme 12, the following reaction conditions apply:

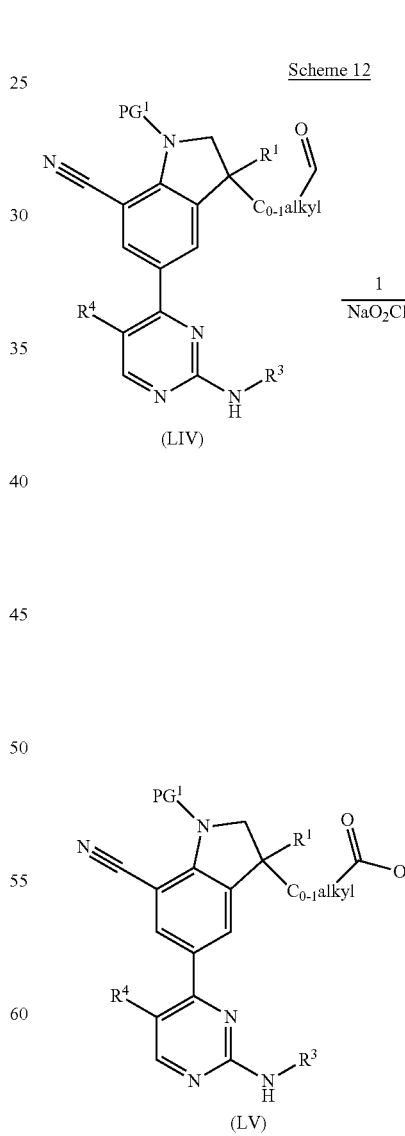

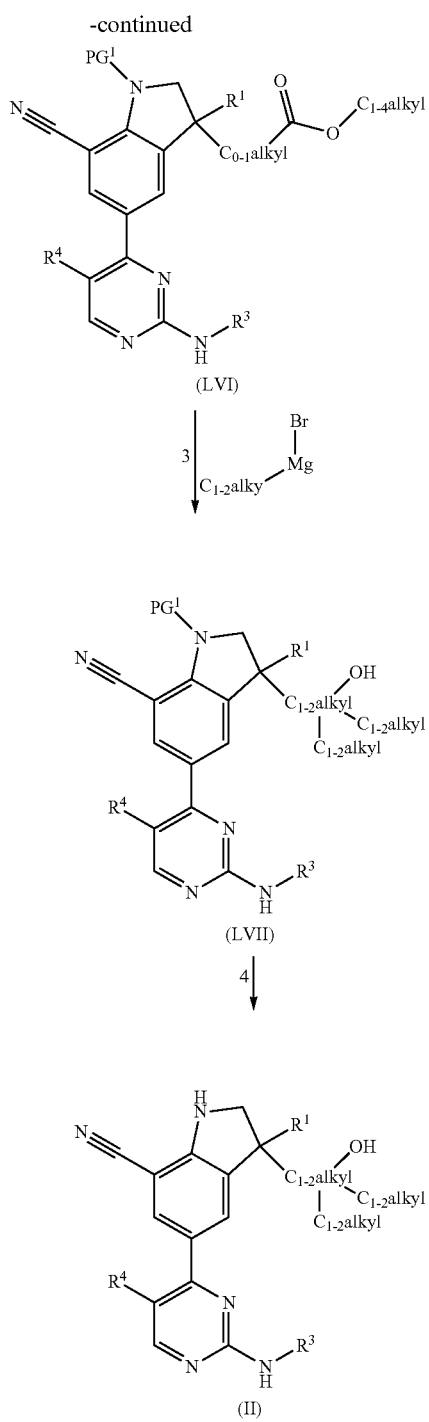

In general, compounds of Formula (I) wherein $R^2$ is as shown in the scheme 13 and wherein all the other variables are as defined according to the scope of the present invention, hereby named compounds of Formula (Im) can be prepared according to the following reaction Scheme 13. In Scheme 13 $PG^1$ represents a suitable protecting group, such as for example tert-(butoxycarbonyl). All other variables in Scheme 13 are defined as before or according to the scope of the present invention.

In Scheme 13, the following reaction conditions apply:

Scheme 13

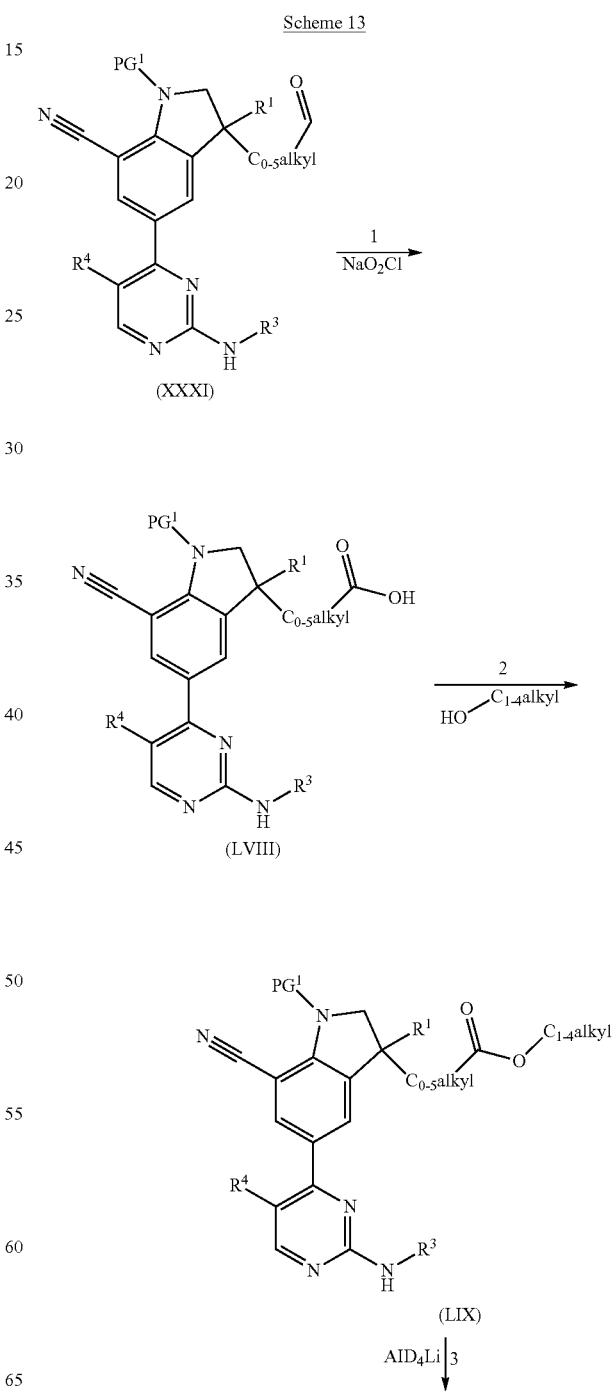

1: at a suitable temperature such as for example at room temperature, in the presence of tert-butyl alcohol, 2-methyl-2-butene, sodium dihydrogenophosphate and distilled water;
2: at a suitable temperature such as for example at room temperature, in presence of 1-[bis(dimethylamino)methylene]-1H-1,2,3-triazolo[4,5-b]pyridinium 3-oxid hexafluorophosphate (HATU) and dimethyl aminopyridine (DMAP), a suitable base such as for example DIPEA and a suitable solvent such as for example dimethylformamide;
3: at a suitable temperature such as for example at room temperature, and a suitable solvent such as for example tetrahydrofuran;
4: at a suitable temperature such as for example 0° C. or room temperature or reflux, in presence of a suitable acid such as for example trifluoroacetic acid or aqueous hydrochloric acid with a suitable solvent such as for example dichloromethane, methanol, ethyl acetate or 1,4-dioxane or alternatively in the presence of silica in a suitable solvent such as for example toluene at a suitable temperature such as for example 125° C. and a suitable time such as for example 3 hours.

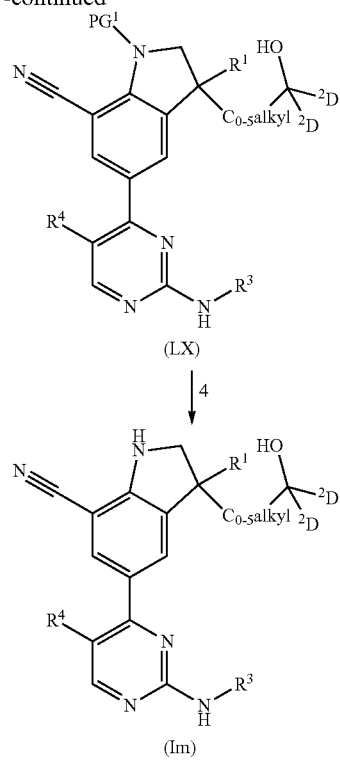

1: at a suitable temperature such as for example at room temperature, in the presence of tert-butyl alcohol, 2-methyl-2-butene, sodium dihydrogenophosphate and distilled water;
2: at a suitable temperature such as for example at room temperature, in presence of 1-[bis(dimethylamino)methylene]-1H-1,2,3-triazolo[4,5-b]pyridinium 3-oxid hexafluorophosphate (HATU) and dimethyl aminopyridine (DMAP), a suitable base such as for example DIPEA and a suitable solvent such as for example dimethylformamide;
3: at a suitable temperature such as for example at 0° C., and a suitable solvent such as for example tetrahydrofuran;
4: at a suitable temperature such as for example 0° C. or room temperature or reflux, in presence of a suitable acid such as for example trifluoroacetic acid or aqueous hydrochloric acid with a suitable solvent such as for example dichloromethane, methanol, ethyl acetate or 1,4-dioxane or alternatively in the presence of silica in a suitable solvent such as for example toluene at a suitable temperature such as for example 125° C. and a suitable time such as for example 3 hours.

In general, compounds of Formula (I) wherein $R^2$ is being $C_{1-6}$alkyl substituted with one $Het^{3a}$ or $-NR^{6a}R^{6b}$, wherein $R^{6a}$ is being H, R is being $-C(=O)-C_{1-4}$alkyl; $-C(=O)$-$Het^4$; $-S(=O)_2-C_{1-4}$alkyl and wherein all the other variables are as defined according to the scope of the present invention, hereby named compounds of Formula (In), Formula (Io) and Formula (Ip), can be prepared according to the following reaction Scheme 14. In Scheme 14, $PG^1$ represents a suitable protecting group, such as for example tert-(butoxycarbonyl). All other variables in Scheme 14 are defined as before or according to the scope of the present invention.

In Scheme 14, the following reaction conditions apply:

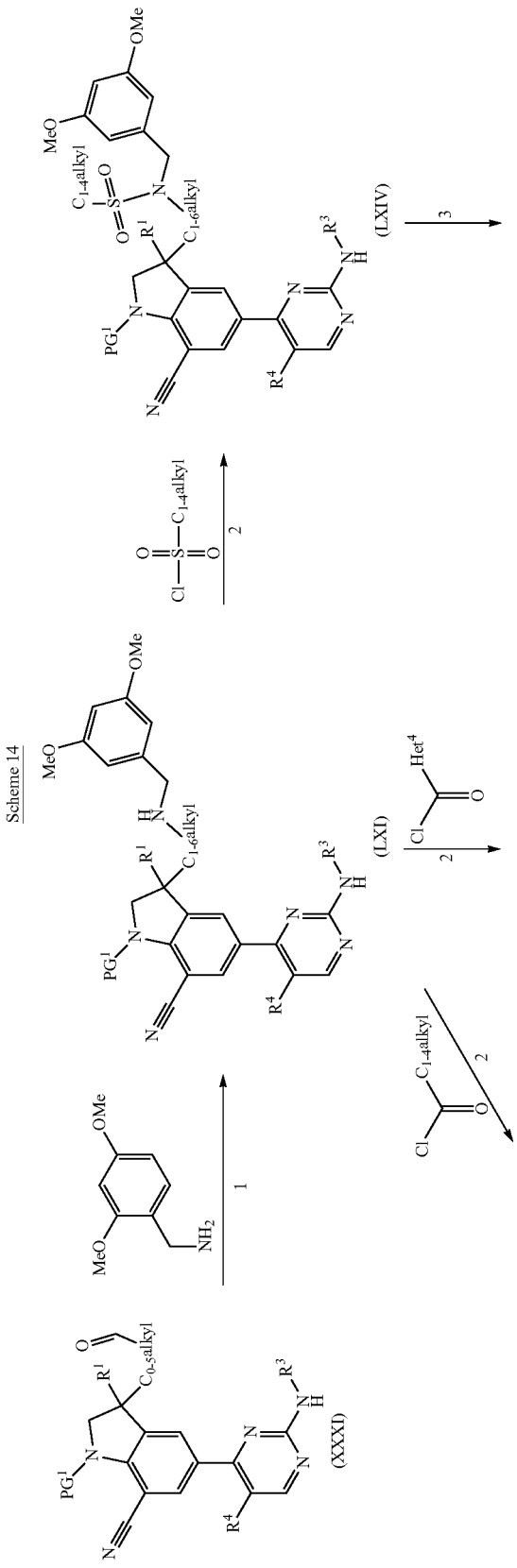

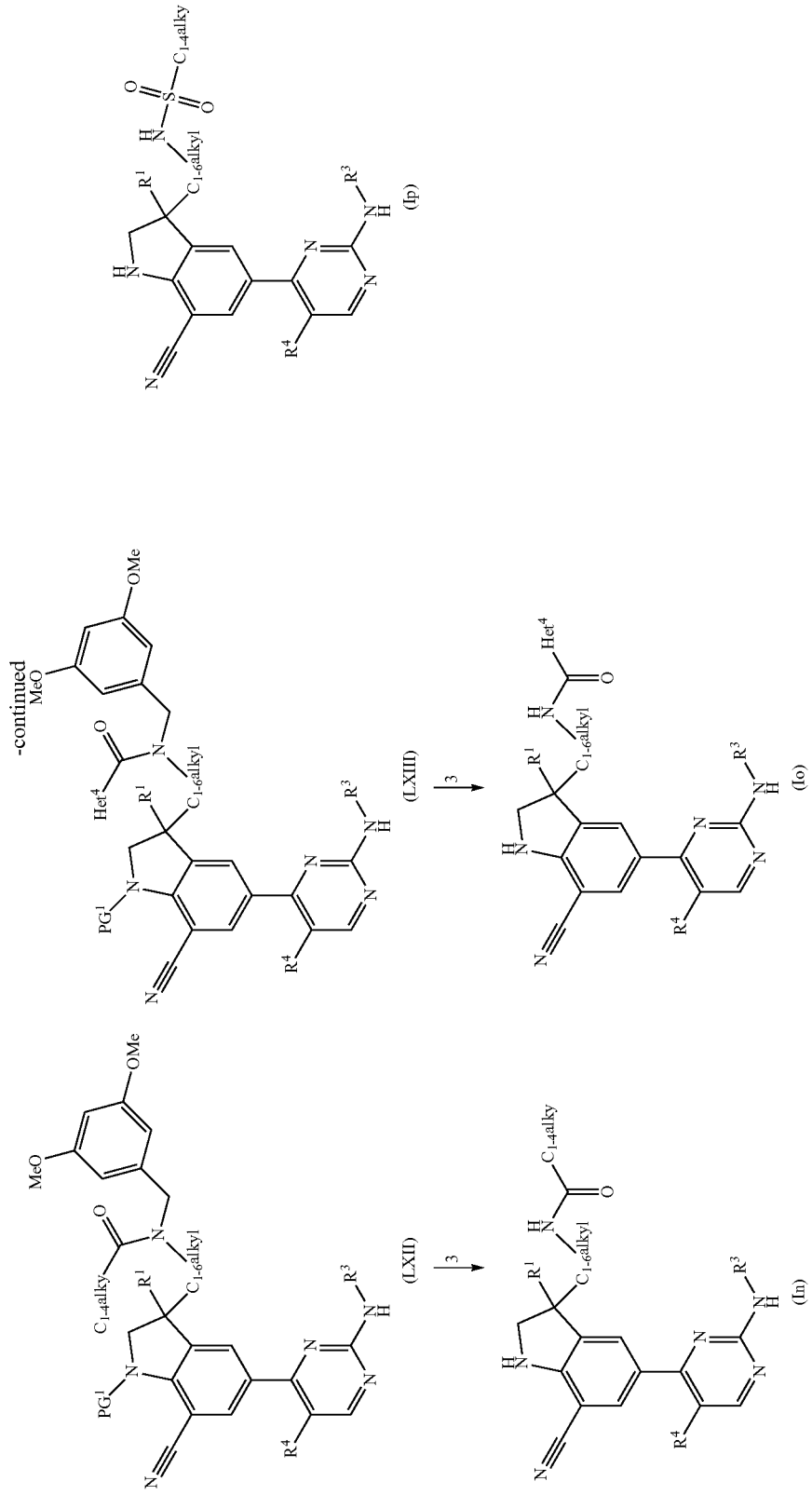

In general, compounds of Formula (I) wherein $R^2$ is being $C_{1-6}$alkyl substituted with one $Het^{3a}$ or $-NR^{6a}R^{6b}$, wherein $R^{6a}$ is being $C_{1-4}$alkyl, $R^{6b}$ is being $-C(=O)-C_{1-4}$alkyl; $-C(=O)-Het^4$; $-S(=O)_2-C_{1-4}$alkyl and wherein all the other variables are as defined according to the scope of the present invention, hereby named compounds of Formula (Iq), Formula (Ir) and Formula (Is), can be prepared according to the following reaction Scheme 15. In Scheme 15, $PG^1$ represents a suitable protecting group, such as for example tert-(butoxycarbonyl). All other variables in Scheme 15 are defined as before or according to the scope of the present invention.

In Scheme 15, the following reaction conditions apply:

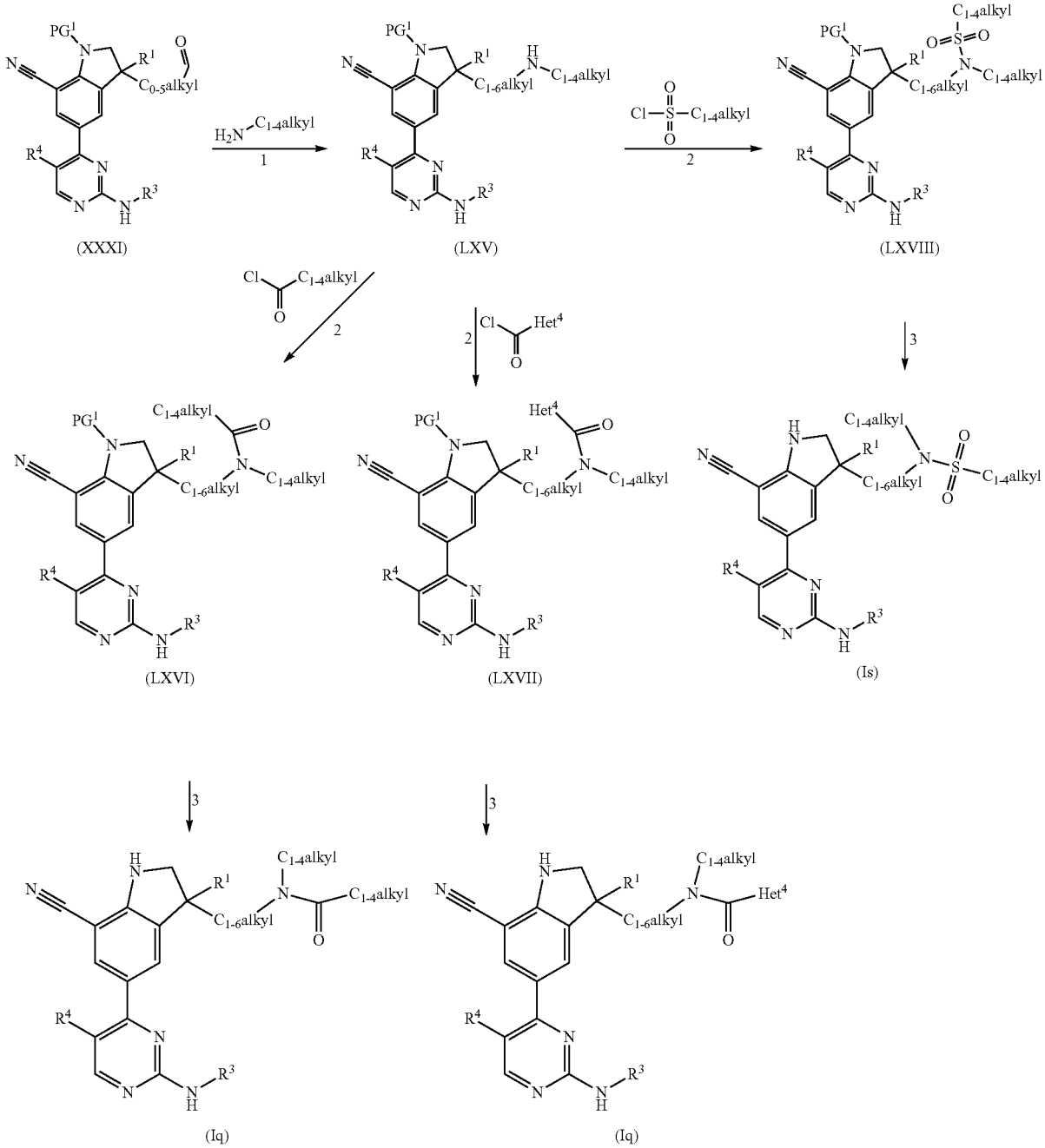

Scheme 15

1: at a suitable temperature such as for example at room temperature, in the presence of a suitable acid such as for example acetic acid, in the presence of a suitable reducing agent such as for example sodium triacetoxyborohydride, in a suitable solvent such as for example dichloroethane;
2: at a suitable temperature such as for example at room temperature, in the presence of a suitable base such as for example triethylamine, in a suitable solvent such as for example tetrahydrofuran;
3: at a suitable temperature such as for example at room temperature, in the presence of a suitable acid such as for example trifluoroacetic acid, in a suitable solvent such as for example dichlormethane.

In general, compounds of Formula (I) wherein $R^2$ is $C_{1-6}$alkyl substituted with one $OR^{7d}$, $R^{7d}$ being —S(=O)$_2$—OH or —P(=O)—(OH)$_2$, and wherein all the other variables are as defined according to the scope of the present invention, hereby named compounds of Formula (It) and Formula (Iu), can be prepared according to the following reaction Scheme 16. All other variables in Scheme 16 are defined as before or according to the scope of the present invention. In Scheme 16, the following reaction conditions apply:

Scheme 16

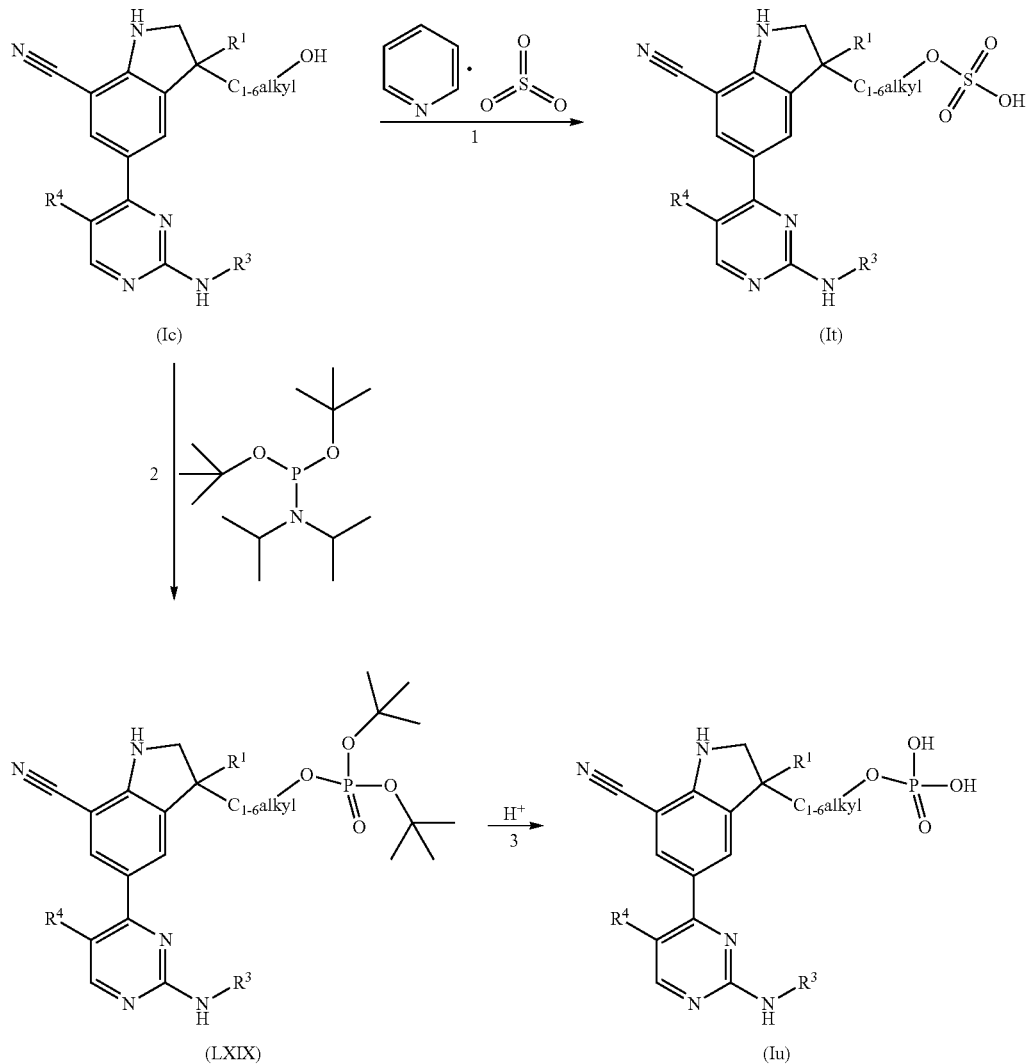

1: at a suitable temperature such as for example at room temperature, in a suitable solvent such as for example tetrahydrofuran, in the presence of a suitable base such as for example sodium hydroxyde;
2: in the presence of a suitable reagent such as for example tetrazole, in the presence of a suitable oxidizing agent such as for example meta-chloroperbenzoic acid, in a suitable solvent such as for example acetonitrile;
3: at a suitable temperature such as for example at room temperature, in the presence of a suitable acid such as for example hydrochloric acid, in a suitable solvent such as for example acetonitrile.

In general, compounds of Formula (I) wherein $R^2$ is $R^{2a}$ being $C_{1-6}$alkyl, $R^3$ is restricted to a-2 being a pyrazolyl substituted on one ring N-atom with a group consisting of $C_{1-4}$alkyl substituted with —C(=O)NR$^{15a}$R$^{1b}$ or —C(=O)—Het$^{1f}$, and additionally optionally substituted with other substituents according to the scope of the present invention, and wherein all the other variables are as defined according to the scope of the present invention, hereby named compounds of Formula (Iv), can be prepared according to the following reaction Scheme 17. In Scheme 17, PG$^1$ represents a suitable protecting group, such as for example tert-(butoxycarbonyl). All other variables in Scheme 17 are defined as before or according to the scope of the present invention.

In Scheme 17, the following reaction conditions apply:
Scheme 17
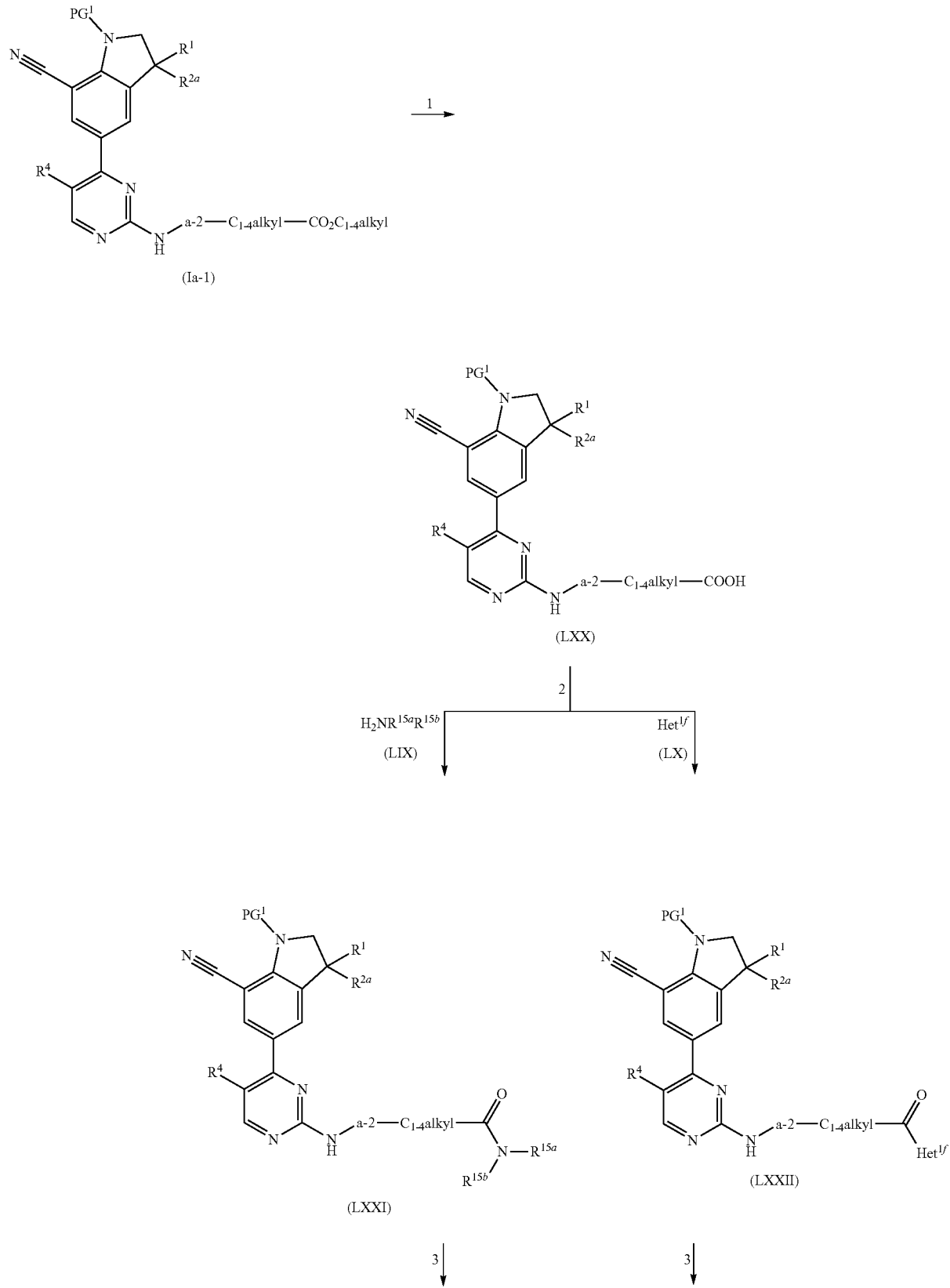

-continued

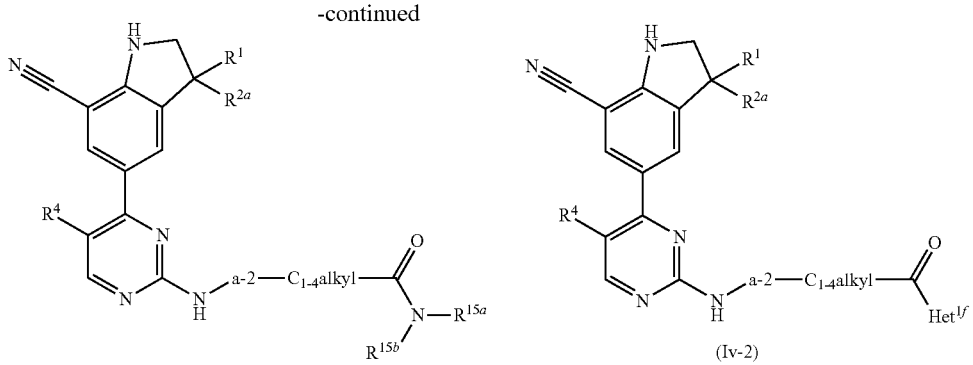

(Iv-1)  (Iv-2)

1: at a suitable temperature such as for example room temperature, in the presence of a suitable base such as for example lithium hydroxide monohydrate, and a suitable solvent such as for example a mixture of water and 1,4-dioxane;
2: at a suitable temperature such as for example room temperature, in presence of a suitable coupling reagent such as for example 1-[bis(dimethylamino)methylene]1H-1,2,3-triazolo[4,5-b]pyridinium 3-oxid hexafluorophosphate (HATU), a suitable base such as for example N,N-dissopropylethylamine, and a suitable solvent such as for example dimethylformamide;
3: at a suitable temperature such as for example 0° C. or room temperature or reflux, in presence of a suitable acid such as for example trifluoroacetic acid or aqueous hydrochloric acid with a suitable solvent such as for example dichloromethane, methanol, ethylacetate, or 1,4-dioxane, and a suitable time such as for example 3 hours.

In general, compounds of Formula (I) wherein $R^2$ is $R^{2b}$ being $C_{1-6}$alkyl substituted with one OH, $R^3$ is restricted to a-2 being a pyrazolyl substituted on one ring N-atom with a group consisting of $C_{1-4}$alkyl substituted with —C(=O)NR$^{15a}$R$^{15b}$ or —C(=O)—Het$^{1f}$ and additionally optionally substituted with other substituents according to the scope of the present invention, and wherein all the other variables are as defined according to the scope of the present invention, hereby named compounds of Formula (Ix), can be prepared according to the following reaction Scheme 18. In Scheme 18, PG$^1$ represents a suitable protecting group, such as for example tert-(butoxycarbonyl) and PG$^2$ represents a suitable protecting group, such as for example tert-butyl-dimethyl-silyl. All other variables in Scheme 18 are defined according to the scope of the present invention. In Scheme 18, the following reaction conditions apply:

Scheme 18

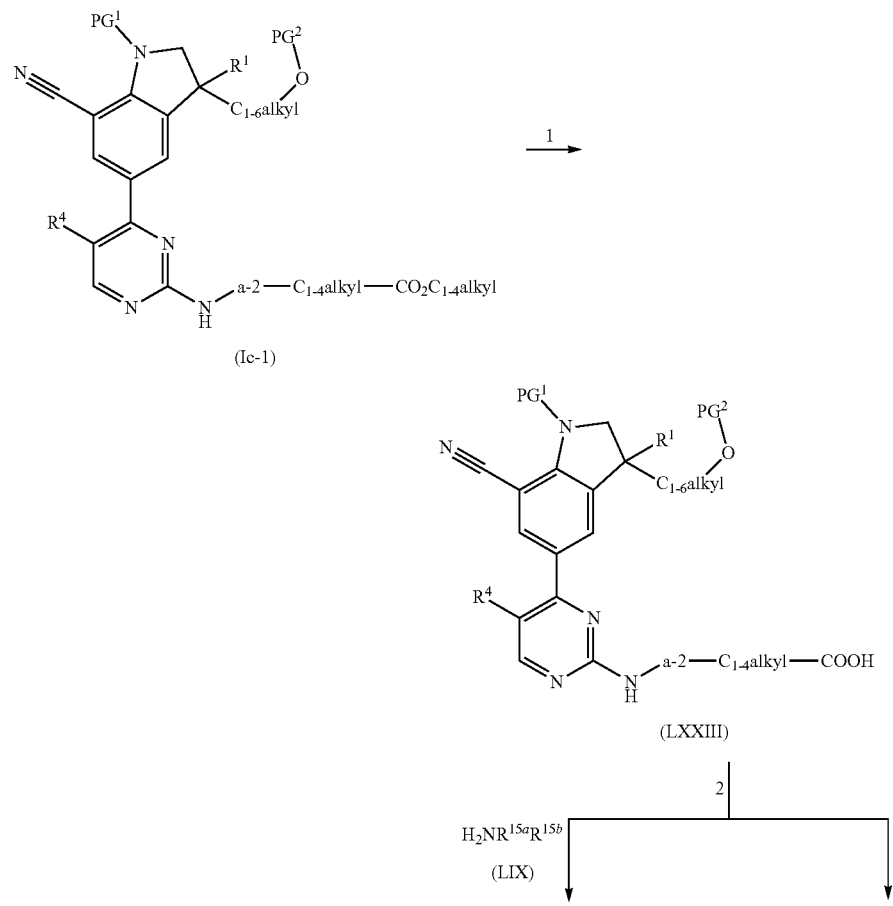

(Ic-1)

(LXXIII)

H$_2$NR$^{15a}$R$^{15b}$  Het$^{1f}$
(LIX)  (LX)

89 90

-continued

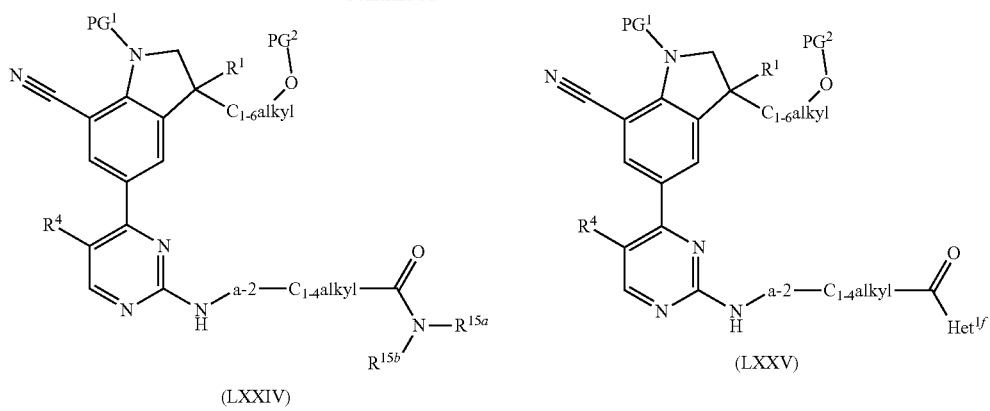

(LXXIV)

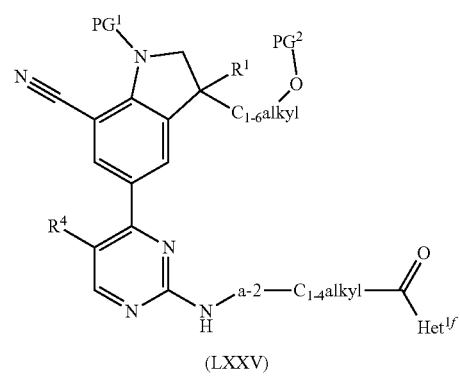

(LXXV)

3 ↓   3 ↓

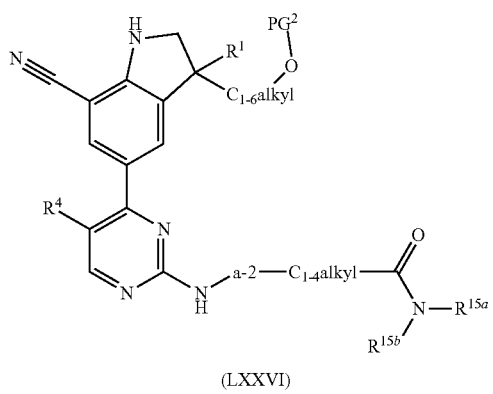

(LXXVI)

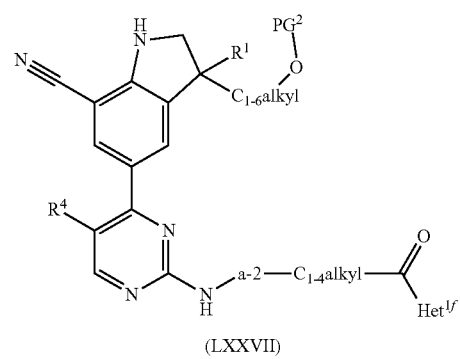

(LXXVII)

4 ↓   4 ↓

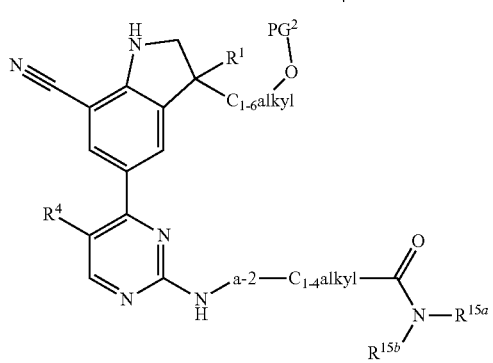

(Ix-1)

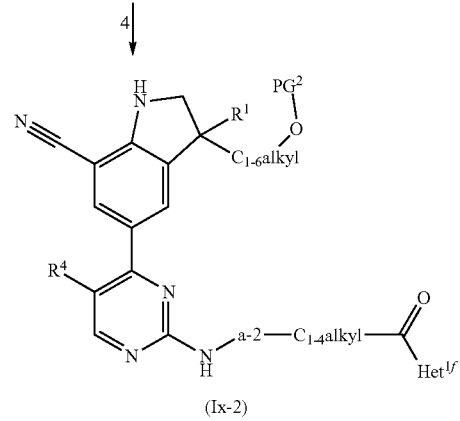

(Ix-2)

1: at a suitable temperature such as for example room temperature, in the presence of a suitable base such as for example lithium hydroxide monohydrate, and a suitable solvent such as for example a mixture of water and 1,4-dioxane;
2: at a suitable temperature such as for example room temperature, in presence of a suitable coupling reagent such as for example 1-[bis(dimethylamino)methylene]-1H-1,2,3-triazolo[4,5-b]pyridinium 3-oxid hexafluorophosphate (HATU),
 a suitable base such as for example N,N-diisopropylethylamine, and a suitable solvent such as for example dimethylformamide;3: at a suitable temperature such as for example 0° C. or room temperature or reflux, in presence of a suitable acid such as for example trifluoroacetic acid or aqueous hydrochloric acid with a suitable solvent such as for example dichloromethane, methanol, ethylacetate, or 1,4-dioxane, and a suitable time such as for example 3 hours.
4: at a suitable temperature such as for example room temperature, in presence of a suitable desilylating agent such as for example tetra-n-butylammonium fluoride and a suitable solvent such as for example 2-methyltetrahydrofuran or tetrahydrofuran.

In general, intermediates of Formula (XII) wherein all the variables are as defined according to the scope of the present invention or as defined before, can be prepared according to the following reaction Scheme 19. All other variables in Scheme 19 are as defined before.

In Scheme 19, the following reaction conditions apply:

In general, compounds of Formula (I) wherein $R^2$ is $R^{2d}$ being $C_{1-6}$alkyl substituted one fluorine, Y is $CR^4$, and wherein all the other variables are as defined according to the scope of the present invention, hereby named compounds of Formula (Iz), can be prepared according to the following reaction Scheme 18.

In Scheme 20, the following reaction conditions apply:

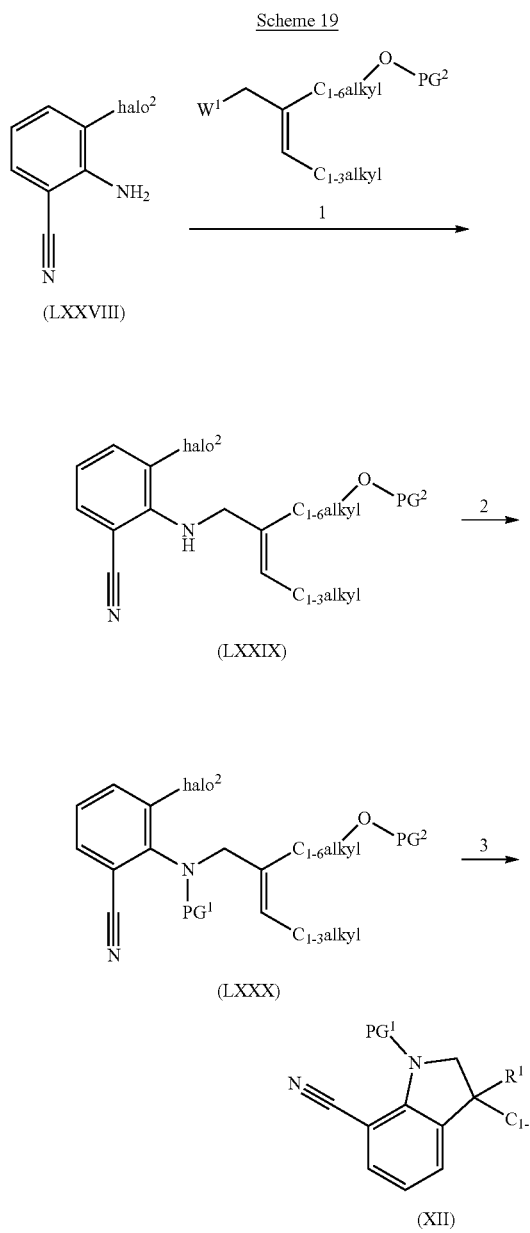

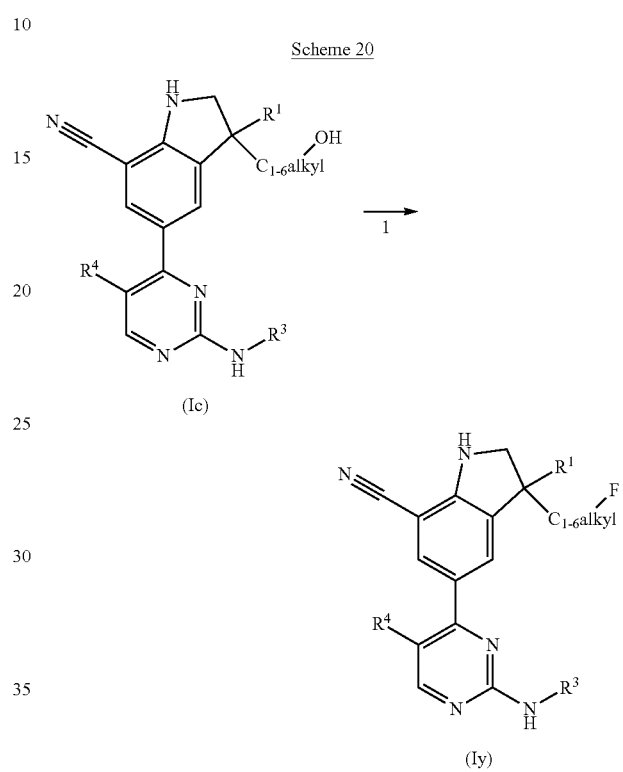

1: in the presence of a suitable fluorinating reagent such as for example diethylaminosulfur trifluoride, a suitable solvent such as for example dichloromethane, at a suitable temperature such as for example room temperature.

In general, compounds of Formula (I) wherein $R^2$ is $R^{2b}$ being $C_{1-6}$alkyl substituted with one OH, Y is N, and wherein all the other variables are as defined according to the scope of the present invention, hereby named compounds of Formula (Iz), can be prepared according to the following reaction Scheme 21. In Scheme 21, halo¹ is defined as Cl, Br or I; $PG^1$ represents a suitable protecting group, such as for example tert-(butoxycarbonyl) and $PG^2$ represents a suitable protecting group, such as for example tert-butyl-dimethylsilyl. All other variables in Scheme 21 are defined according to the scope of the present invention.

In Scheme 21, the following reaction conditions apply:

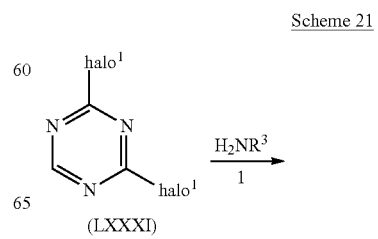

1. At a suitable temperature range between -5° C. and 5° C., in the presence of a suitable base such as for example sodium tert-butoxide in a suitable solvent such as for example tetrahydrofuran;
2. at a suitable temperature ranged between 65 and 70° C., in the presence of a suitable reagent such as for example di-tert-butyl dicarbonate, in the presence of a suitable catalyst such as for example 4-dimethylaminopyridine (DMAP), and a suitable solvent such as for example tetrahydrofuran;
3: at a suitable temperature ranged between 45 and 50° C., in the presence of sodium acetate, sodium formate dehydrate and tetraethylammonium chloride, a suitable catalyst such as for example palladium acetate or [1,1'-bis(diphenylphosphino) ferrocene] palladium, (II) chloride optionally with dichloromethane complex, and a suitable solvent such as for example dimethylformamide.

-continued

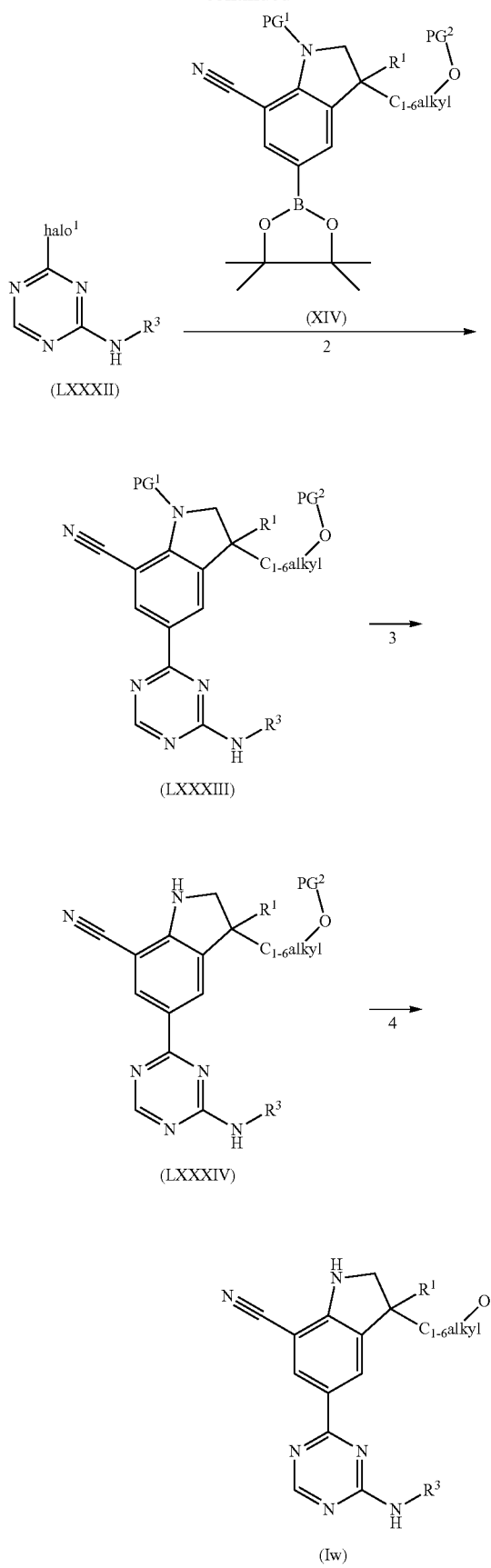

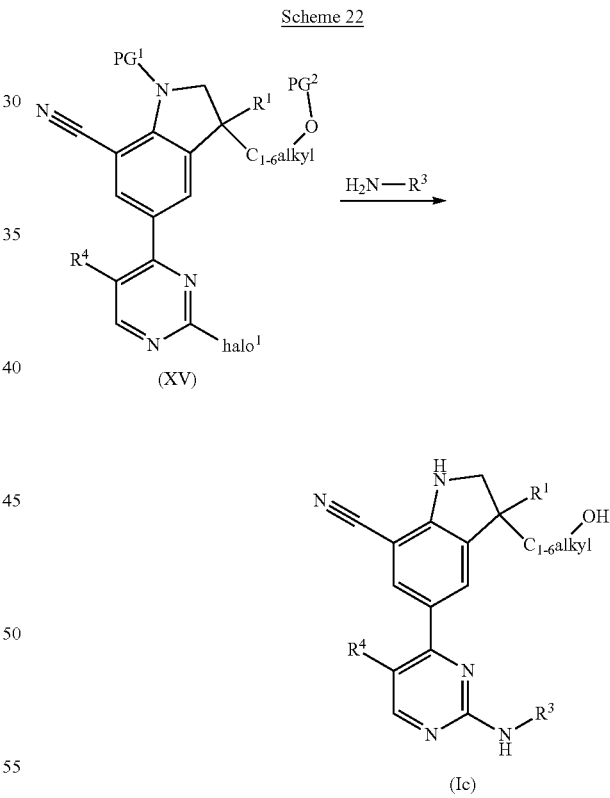

1. in the presence of a suitable base such as for example diisopropylethylamine, in asuitable solvent such as for example acetonitrile;
2. in the presence of a suitable catalyst such as for example [1,1'-bis(diphenylphosphino)ferrocene] dichloropalladium (II), optionally with dichloromethane complex, a suitable base such as an aqueous solution of hydrogenocarbonate at a suitable temperature such as 80° C.;
3. at a suitable temperature such as for example 0° C. or room temperature or reflux, in presence of a suitable acid such as for example trifluoroacetic acid or aqueous hydrochloric acid with a suitable solvent such as for example dichloromethane, methanol, ethyl acetate or 1,4-dioxane or alternatively in the presence of silica in a suitable solvent such as for example toluene at a suitable temperature such as for example 125° C., and at a suitable time such as for example 3 hours;
4. at a suitable temperature such as for example room temperature, in presence of a suitable desilylating agent such as for example tetra-n-butylammonium fluoride and a suitable solvent such as for example 2-methyltetrahydrofuran or tetrahydrofuran.

In general, compounds of Formula (I) wherein $R^2$ is $R^{2b}$ being $C_{1-6}$alkyl substituted with one OH, Y is $CR^4$, and wherein all the other variables are as defined according to the scope of the present invention, hereby named compounds of Formula (Ic), can be prepared according to the following reaction Scheme 22. All other variables in Scheme 22 are defined according to the scope of the present invention or as above.

In Scheme 22, the following reaction conditions apply:

Scheme 22

1: at a suitable temperature such as for example 90° C., in the presence of a suitable acid such as for example p-toluenesulfonic acid and a suitable solvent such as for example 1,4-dioxane.

Intermediate of Formula (IIIa) wherein $R^2$ is $R^{2e}$ being $C_{1-6}$alkyl or $C_{1-6}$alkyl substituted with one, two or three fluoro atoms, and wherein all the other variables are defined according to the scope of the present invention, can be prepared according to the following reaction All other variables in Scheme 23 are defined according to the scope of the present invention.

Scheme 23

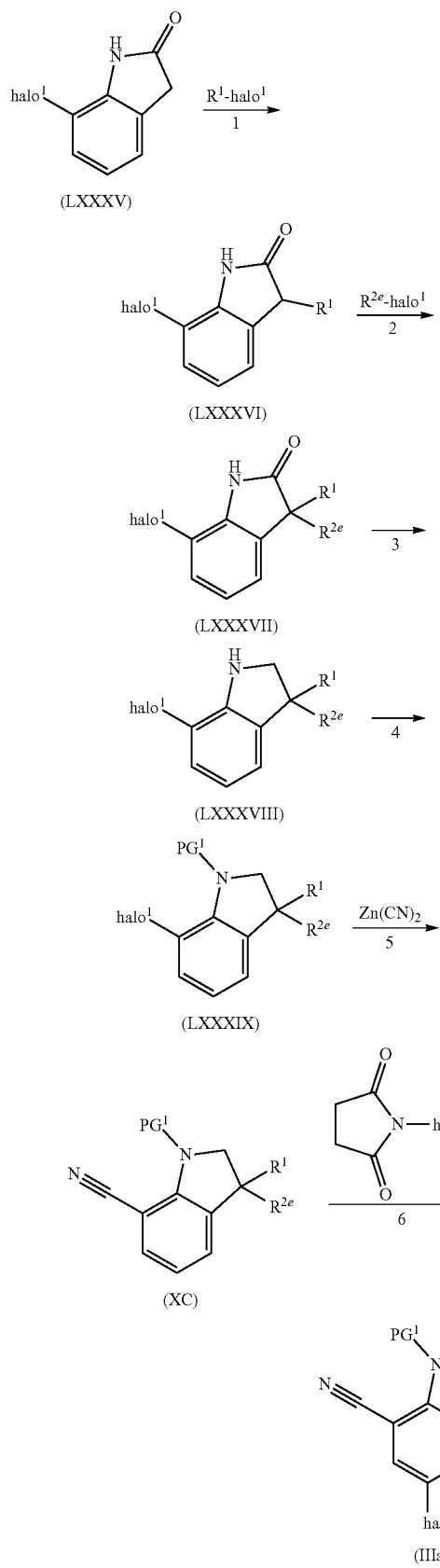

-continued

In Scheme 23, the following reaction conditions apply:
1: at a suitable temperature ranged between for example -20° C. and -78° C., in the presence of a chelating agent such as for example N,N,N',N'-tetramethylethylenediamine, a suitable deprotonating agent such as Butyl Lithium, in a suitable solvent such as for example tetrahydrofurane;
2: at a suitable temperature ranged between for example -20° C. and -78° C., in the presence of a chelating agent such as for example N,N,N',N'-tetramethylethylenediamine, a suitable deprotonating agent such as Butyl Lithium, in a suitable solvent such as for example tetrahydrofurane;
3: at a suitable temperature such as for example 70° C., in the presence of a suitable reducing agent such as for example Borane dimethyl sulfide complex, in a suitable solvent such as for example tetrahydrofurane;
4. at a suitable temperature such as for example room temperature, in the presence of a suitable reagent such as for example di-tert-butyldicarbonate, a suitable catalyst such as for example 4-dimethylaminopyridine (DMAP), a suitable base such as for example triethylamine and a suitable solvent such as for example tetrahydrofuran;
5. at a suitable temperature such as for example 100° C., in the presence of a suitable catalyst such as for example Tetrakis(triphenylphosphine)palladium(0), and a suitable solvent such as for example anhydrous dimethylformamide;
6: at a suitable temperature such as for example solvent reflux, and in a suitable solvent such as for example acetonitrile.

In general, compounds of Formula (I) wherein $R^2$ is $R^{2c}$ being $C_{1-6}$alkyl substituted with $NH_2$ and wherein all the other variables are as defined according to the scope of the present invention, hereby named compounds of Formula (If-a), can be prepared according to the following reaction Scheme 24. In Scheme 24, $PG^1$ represents a suitable protecting group, such as for example tert-(butoxycarbonyl). All other variables in Scheme 24 are defined according to the scope of the present invention.

In Scheme 24, the following reaction conditions apply:

Scheme 24

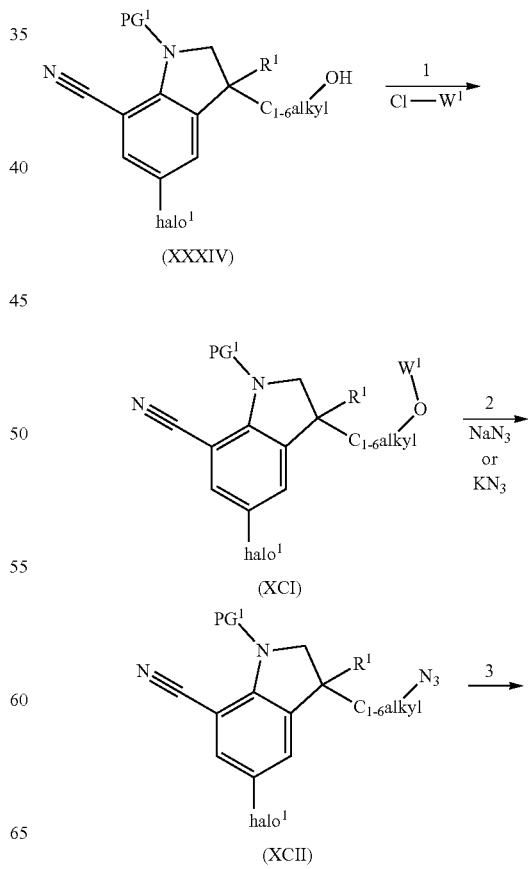

-continued

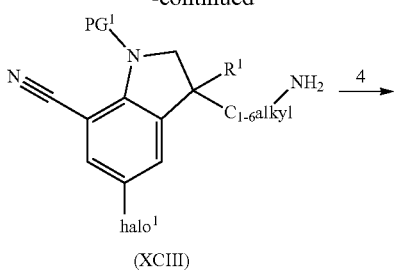
(XCIII)

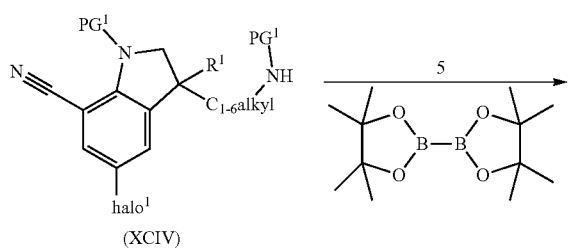
(XCIV)

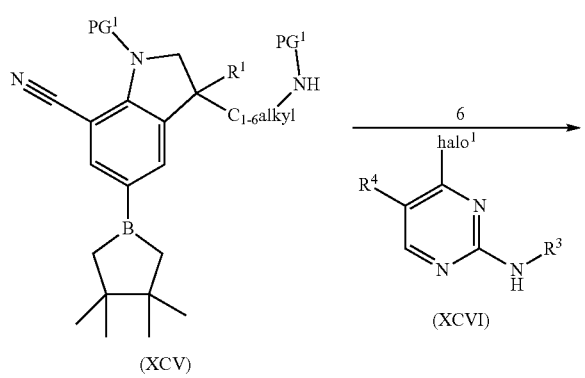
(XCV)

(XCVI)

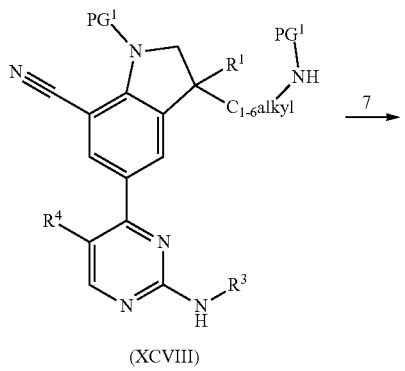
(XCVIII)

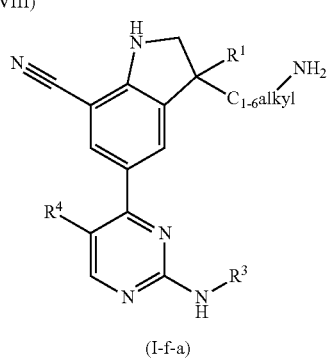
(I-f-a)

-continued 1. at a suitable temperature such as for example 0° C. to room temperature, in the presence of a suitable reagent such as for example methanesulfonyl chloride, a suitable base such as for example diisopropylethylamine and a suitable solvent such as for example dichloromethane;
2: at a suitable temperature such as for example 115° C°., in the presence of a suitable reagent such as for example sodium azide, and a suitable solvent such as for example dimethylformamide;
3: at a suitable temperature such as for example 50° C., in the presence of a suitable reagent such as for example triphenylphospine, and a suitable solvent such as for example tetrahydrofurane;
4: at a suitable temperature such as for example room temperature, in the presence of a suitable reagent such as for example ditertbutyl dicarbonate, and a suitable solvent such as for example dichloromethane;
5: at a suitable temperature such as for example 80° C., in the presence of a suitable base such as for example potassium acetate, a suitable catalyst such as for example (chloro(2-dicyclohexylphosphino-2',4',6'-triisoprophyl-1,1'-biphenyl)[2-(2'-amino-1,1'-biphenyl)]palladium(II)) and a suitable solvent such as for example 1,4-dioxane;
6: at a suitable temperature such as for example 80° C., in the presence of a suitable base such as for example potassium phospate (tribasic), a suitable catalyst such as for example ((chloro(2-dicyclohexylphosphino-2',4',6'-triisopropyl-1,1'-biphenyl)[2-(2'-amino-1,1'-biphenyl)]palladium(II)) and a suitable solvent such as for example a mixture of 1,4-dioxane and water;
7: at a suitable temperature such as for example 0° C. or room temperature or reflux, in presence of a suitable acid such as for example trifluoroacetic acid or aqueous hydrochloric acid with a suitable solvent such as for example dichloromethane, methanol, ethyl acetate or 1,4-dioxane or alternatively in the presence of silica in a suitable solvent such as for example toluene at a suitable temperature such as for example 120° C., and a suitable time such as for example 3 hours.

In general, intermediate of formula C wherein all the variables are as defined according to the scope of the present invention or as defined above can be prepared according to the following reaction Scheme 25.

Scheme 25

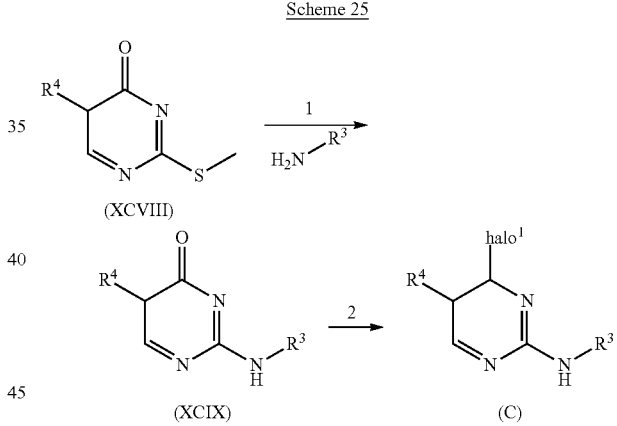

In Scheme 25, the following reaction conditions apply:
1: at a suitable temperature such as for example 180° C.;
2: at a suitable temperature such as for example 180° C. and in the presence of a suitable chlorinated reagent such as for example phosphoryl trichloride.

It will be appreciated that where appropriate functional groups exist, compounds of various formulae or any intermediates used in their preparation may be further derivatised by one or more standard synthetic methods employing condensation, substitution, oxidation, reduction, or cleavage reactions. Particular substitution approaches include conventional alkylation, arylation, heteroarylation, acylation, sulfonylation, halogenation, nitration, formylation and coupling procedures.

The compounds of Formula (I) may be synthesized in the form of racemic mixtures of enantiomers which can be separated from one another following art-known resolution procedures. The racemic compounds of Formula (I) containing a basic nitrogen atom may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of Formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically.

In the preparation of compounds of the present invention, protection of remote functionality (e.g., primary or secondary amine) of intermediates may be necessary. The need for such protection will vary depending on the nature of the remote functionality and the conditions of the preparation methods. Suitable amino-protecting groups (NH-Pg) include acetyl, trifluoroacetyl, t-butoxycarbonyl (Boc), benzyloxycarbonyl (CBz) and 9-fluorenylmethyleneoxycarbonyl (Fmoc). The need for such protection is readily determined by one skilled in the art. For a general description of protecting groups and their use, see T. W. Greene and P. G. M. Wuts, Protective Groups in Organic Synthesis, 4th ed., Wiley, Hoboken, N.J., 2007.

Pharmacology

It has been found that the compounds of the present invention inhibit NF-κB-inducing kinase (NIK—also known as MAP3K14). Some of the compounds of the present invention may undergo metabolism to a more active form in vivo (prodrugs). Therefore the compounds according to the invention and the pharmaceutical compositions comprising such compounds may be useful for treating or preventing diseases such as cancer, inflammatory disorders, metabolic disorders including obesity and diabetes, and autoimmune disorders. In particular, the compounds according to the present invention and the pharmaceutical compositions thereof may be useful in the treatment of a haematological malignancy or solid tumour. In a specific embodiment said haematological malignancy is selected from the group consisting of multiple myeloma, non-Hodgkin's lymphoma, Hodgkin lymphoma, T-cell leukaemia, mucosa-associated lymphoid tissue lymphoma, diffuse large B-cell lymphoma and mantle cell lymphoma, in a particular embodiment mantle cell lymphoma. In another specific embodiment of the present invention, the solid tumour is selected from the group consisting of pancreatic cancer, breast cancer, melanoma and non-small cell lung cancer.

Examples of cancers which may be treated (or inhibited) include, but are not limited to, a carcinoma, for example a carcinoma of the bladder, breast, colon (e.g. colorectal carcinomas such as colon adenocarcinoma and colon adenoma), kidney, urothelial, uterus, epidermis, liver, lung (for example adenocarcinoma, small cell lung cancer and non-small cell lung carcinomas, squamous lung cancer), oesophagus, head and neck, gall bladder, ovary, pancreas (e.g. exocrine pancreatic carcinoma), stomach, gastrointestinal (also known as gastric) cancer (e.g. gastrointestinal stromal tumours), cervix, endometrium, thyroid, prostate, or skin (for example squamous cell carcinoma or dermatofibrosarcoma protuberans); pituitary cancer, a hematopoietic tumour of lymphoid lineage, for example leukemia, acute lymphocytic leukemia, chronic lymphocytic leukemia, B-cell lymphoma (e.g. diffuse large B-cell lymphoma, mantle cell lymphoma), T-cell leukaemia/lymphoma, Hodgkin's lymphoma, non-Hodgkin's lymphoma, hairy cell lymphoma, or Burkett's lymphoma; a hematopoietic tumour of myeloid lineage, for example leukemias, acute and chronic myelogenous leukemias, chronic myelomonocytic leukemia (CMML), myeloproliferative disorder, myeloproliferative syndrome, myelodysplastic syndrome, or promyelocytic leukemia; multiple myeloma; thyroid follicular cancer; hepatocellular cancer, a tumour of mesenchymal origin (e.g. Ewing's sarcoma), for example fibrosarcoma or rhabdomyosarcoma; a tumour of the central or peripheral nervous system, for example astrocytoma, neuroblastoma, glioma (such as glioblastoma multiforme) or schwannoma; melanoma; seminoma; teratocarcinoma; osteosarcoma; xeroderma pigmentosum; keratoctanthoma; thyroid follicular cancer; or Kaposi's sarcoma.

Particular examples of cancers which may be treated (or inhibited) include B-cell malignancies, such as multiple myeloma, hodgkins lymphoma, mantle cell lymphoma, diffuse large B-cell lymphoma or chronic lymphocytic leukemia, with mutations in the non-canonical NFkB signalling pathway (eg in NIK (MAP3K14), TRAF3, TRAF2, BIRC2 or BIRC3 genes).

Hence, the invention relates to compounds of Formula (I), the tautomers and the stereoisomeric forms thereof, and the pharmaceutically acceptable addition salts, and the solvates thereof, for use as a medicament.

The invention also relates to the use of a compound of Formula (I), a tautomer or a stereoisomeric form thereof, or a pharmaceutically acceptable addition salt, or a solvate thereof, or a pharmaceutical composition according to the invention, for the manufacture of a medicament.

The present invention also relates to a compound of Formula (I), a tautomer or a stereoisomeric form thereof, or a pharmaceutically acceptable addition salt, or a solvate thereof, or a pharmaceutical composition according to the invention, for use in the treatment, prevention, amelioration, control or reduction of the risk of disorders associated with NF-κB-inducing kinase dysfunction in a mammal, including a human, the treatment or prevention of which is affected or facilitated by inhibition of NF-κB-inducing kinase.

Also, the present invention relates to the use of a compound of Formula (I), a tautomer or a stereoisomeric form thereof, or a pharmaceutically acceptable addition salt, or a solvate thereof, or a pharmaceutical composition according to the invention, for the manufacture of a medicament for treating, preventing, ameliorating, controlling or reducing the risk of disorders associated with NF-κB-inducing kinase dysfunction in a mammal, including a human, the treatment or prevention of which is affected or facilitated by inhibition of NF-κB-inducing kinase.

The invention also relates to a compound of Formula (I), a tautomer or a stereoisomeric form thereof, or a pharmaceutically acceptable addition salt, or a solvate thereof, for use in the treatment or prevention of any one of the diseases mentioned hereinbefore. The invention also relates to a compound of Formula (I), a tautomer or a stereoisomeric form thereof, or a pharmaceutically acceptable addition salt, or a solvate thereof, for use in treating or preventing any one of the diseases mentioned hereinbefore.

The invention also relates to the use of a compound of Formula (I), a tautomer or a stereoisomeric form thereof, or a pharmaceutically acceptable addition salt, or a solvate thereof, for the manufacture of a medicament for the treatment or prevention of any one of the disease conditions mentioned hereinbefore.

The compounds of the present invention can be administered to mammals, preferably humans, for the treatment or prevention of any one of the diseases mentioned hereinbefore.

In view of the utility of the compounds of Formula (I), a tautomer or a stereoisomeric form thereof, or a pharmaceutically acceptable addition salt, or a solvate thereof, there is provided a method of treating warm-blooded animals, including humans, suffering from any one of the diseases mentioned hereinbefore.

Said method comprises the administration, i.e. the systemic or topical administration, preferably oral administration, of a therapeutically effective amount of a compound of Formula (I), a tautomer or a stereoisomeric form thereof, or a pharmaceutically acceptable addition salt, or a solvate thereof, to warm-blooded animals, including humans.

Therefore, the invention also relates to a method for the treatment of any one of the diseases mentioned hereinbefore comprising administering a therapeutically effective amount of compound according to the invention to a patient in need thereof.

One skilled in the art will recognize that a therapeutically effective amount of the compounds of the present invention is the amount sufficient to have therapeutic activity and that this amount varies inter alias, depending on the type of disease, the concentration of the compound in the therapeutic formulation, and the condition of the patient. Generally, the amount of a compound of the present invention to be administered as a therapeutic agent for treating the disorders referred to herein will be determined on a case by case by an attending physician.

Those of skill in the treatment of such diseases could determine the effective therapeutic daily amount from the test results presented hereinafter. An effective therapeutic daily amount would be from about 0.005 mg/kg to 50 mg/kg, in particular 0.01 mg/kg to 50 mg/kg body weight, more in particular from 0.01 mg/kg to 25 mg/kg body weight, preferably from about 0.01 mg/kg to about 15 mg/kg, more preferably from about 0.01 mg/kg to about 10 mg/kg, even more preferably from about 0.01 mg/kg to about 1 mg/kg, most preferably from about 0.05 mg/kg to about 1 mg/kg body weight. A particular effective therapeutic daily amount might be from about 10 mg/kg body weight to 40 mg/kg body weight. A particular effective therapeutic daily amount might be 1 mg/kg body weight, 2 mg/kg body weight, 4 mg/kg body weight, or 8 mg/kg body weight. The amount of a compound according to the present invention, also referred to here as the active ingredient, which is required to achieve a therapeutically effect may vary on case-by-case basis, for example with the particular compound, the route of administration, the age and condition of the recipient, and the particular disorder or disease being treated. A method of treatment may also include administering the active ingredient on a regimen of between one and four intakes per day. In these methods of treatment the compounds according to the invention are preferably formulated prior to administration. As described herein below, suitable pharmaceutical formulations are prepared by known procedures using well known and readily available ingredients.

The present invention also provides compositions for preventing or treating the disorders referred to herein. Said compositions comprising a therapeutically effective amount of a compound of Formula (I), a tautomer or a stereoisomeric form thereof, or a pharmaceutically acceptable addition salt, or a solvate thereof, and a pharmaceutically acceptable carrier or diluent.

While it is possible for the active ingredient to be administered alone, it is preferable to present it as a pharmaceutical composition. Accordingly, the present invention further provides a pharmaceutical composition comprising a compound according to the present invention, together with a pharmaceutically acceptable carrier or diluent. The carrier or diluent must be "acceptable" in the sense of being compatible with the other ingredients of the composition and not deleterious to the recipients thereof.

The pharmaceutical compositions of this invention may be prepared by any methods well known in the art of pharmacy, for example, using methods such as those described in Gennaro et al. Remington's Pharmaceutical Sciences (18$^{th}$ ed., Mack Publishing Company, 1990, see especially Part 8: Pharmaceutical preparations and their Manufacture). A therapeutically effective amount of the particular compound, in base form or addition salt form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for systemic administration such as oral, percutaneous or parenteral administration; or topical administration such as via inhalation, a nose spray, eye drops or via a cream, gel, shampoo or the like. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions: or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g., as a transdermal patch, as a spot-on or as an ointment.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The present compounds can be used for systemic administration such as oral, percutaneous or parenteral administration; or topical administration such as via inhalation, a nose spray, eye drops or via a cream, gel, shampoo or the like. The compounds are preferably orally administered. The exact dosage and frequency of administration depends on the particular compound of Formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention.

The compounds of the present invention may be administered alone or in combination with one or more additional therapeutic agents. Combination therapy includes administration of a single pharmaceutical dosage formulation which contains a compound according to the present invention and one or more additional therapeutic agents, as well as administration of the compound according to the present invention and each additional therapeutic agent in its own separate pharmaceutical dosage formulation. For example, a compound according to the present invention and a therapeutic agent may be administered to the patient together in a single oral dosage composition such as a tablet or capsule, or each agent may be administered in separate oral dosage formulations.

Therefore, an embodiment of the present invention relates to a product containing as first active ingredient a compound according to the invention and as further active ingredient one or more medicinal agent, more particularly, with one or more anticancer agent or adjuvant, as a combined preparation for simultaneous, separate or sequential use in the treatment of patients suffering from cancer.

Accordingly, for the treatment of the conditions mentioned hereinbefore, the compounds of the invention may be advantageously employed in combination with one or more other medicinal agents (also referred to as therapeutic agents), more particularly, with other anti-cancer agents or adjuvants in cancer therapy. Examples of anti-cancer agents or adjuvants (supporting agents in the therapy) include but are not limited to:

platinum coordination compounds for example cisplatin optionally combined with amifostine, carboplatin or oxaliplatin;

taxane compounds for example paclitaxel, paclitaxel protein bound particles (Abraxane™) or docetaxel;

topoisomerase I inhibitors such as camptothecin compounds for example irinotecan, SN-38, topotecan, topotecan hcl;

topoisomerase II inhibitors such as anti-tumour epipodophyllotoxins or podophyllotoxin derivatives for example etoposide, etoposide phosphate or teniposide;

anti-tumour vinca alkaloids for example vinblastine, vincristine or vinorelbine;

anti-tumour nucleoside derivatives for example 5-fluorouracil, leucovorin, gemcitabine, gemcitabine hcl, capecitabine, cladribine, fludarabine, nelarabine;

alkylating agents such as nitrogen mustard or nitrosourea for example cyclophosphamide, chlorambucil, carmustine, thiotepa, mephalan (melphalan), lomustine, altretamine, busulfan, dacarbazine, estramustine, ifosfamide optionally in combination with mesna, pipobroman, procarbazine, streptozocin, temozolomide, uracil;

anti-tumour anthracycline derivatives for example daunorubicin, doxorubicin optionally in combination with dexrazoxane, doxil, idarubicin, mitoxantrone, epirubicin, epirubicin hcl, valrubicin;

molecules that target the IGF-1 receptor for example picropodophilin;

tetracarcin derivatives for example tetrocarcin A;

glucocorticoiden for example prednisone;

antibodies for example trastuzumab (HER2 antibody), rituximab (CD20 antibody), gemtuzumab, gemtuzumab ozogamicin, cetuximab, pertuzumab, bevacizumab, alemtuzumab, eculizumab, ibritumomab tiuxetan, nofetumomab, panitumumab, tositumomab, CNTO 328;

estrogen receptor antagonists or selective estrogen receptor modulators or inhibitors of estrogen synthesis for example tamoxifen, fulvestrant, toremifene, droloxifene, faslodex, raloxifene or letrozole;

aromatase inhibitors such as exemestane, anastrozole, letrazole, testolactone and vorozole;

differentiating agents such as retinoids, vitamin D or retinoic acid and retinoic acid metabolism blocking agents (RAMBA) for example accutane;

DNA methyl transferase inhibitors for example azacytidine or decitabine;

antifolates for example pemetrexed disodium;

antibiotics for example antinomycin D, bleomycin, mitomycin C, dactinomycin, carminomycin, daunomycin, levamisole, plicamycin, mithramycin;

antimetabolites for example clofarabine, aminopterin, cytosine arabinoside or methotrexate, azacytidine, cytarabine, floxuridine, pentostatin, thioguanine;

apoptosis inducing agents and antiangiogenic agents such as Bcl-2 inhibitors for example YC 137, BH 312, ABT 737, gossypol, HA 14-1, TW 37 or decanoic acid;

tubuline-binding agents for example combrestatin, colchicines or nocodazole;

kinase inhibitors (e.g. EGFR (epithelial growth factor receptor) inhibitors, MTKI (multi target kinase inhibitors), mTOR inhibitors) for example flavoperidol, imatinib mesylate, erlotinib, gefitinib, dasatinib, lapatinib, lapatinib ditosylate, sorafenib, sunitinib, sunitinib maleate, temsirolimus;

farnesyltransferase inhibitors for example tipifarnib;

histone deacetylase (HDAC) inhibitors for example sodium butyrate, suberoylanilide hydroxamic acid (SAHA), depsipeptide (FR 901228), NVP-LAQ824, R306465, quisinostat, trichostatin A, vorinostat;

Inhibitors of the ubiquitin-proteasome pathway for example PS-341, Velcade (MLN-341) or bortezomib;

Yondelis;

Telomerase inhibitors for example telomestatin;

Matrix metalloproteinase inhibitors for example batimastat, marimastat, prinostat or metastat;

Recombinant interleukins for example aldesleukin, denileukin diftitox, interferon alfa 2a, interferon alfa 2b, peginterferon alfa 2b;

MAPK inhibitors;

Retinoids for example alitretinoin, bexarotene, tretinoin;

Arsenic trioxide;

Asparaginase;

Steroids for example dromostanolone propionate, megestrol acetate, nandrolone (decanoate, phenpropionate), dexamethasone;

Gonadotropin releasing hormone agonists or antagonists for example abarelix, goserelin acetate, histrelin acetate, leuprolide acetate;

Thalidomide, lenalidomide;

Mercaptopurine, mitotane, pamidronate, pegademase, pegaspargase, rasburicase;

BH3 mimetics for example ABT-199;

MEK inhibitors for example PD98059, AZD6244, CI-1040;

colony-stimulating factor analogs for example filgrastim, pegfilgrastim, sargramostim; erythropoietin or analogues thereof (e.g. darbepoetin alfa); interleukin 11; oprelvekin; zoledronate, zoledronic acid; fentanyl; bisphosphonate; palifermin;

a steroidal cytochrome P450 17alpha-hydroxylase-17,20-lyase inhibitor (CYP17), e.g. abiraterone, abiraterone acetate.

The one or more other medicinal agents and the compound according to the present invention may be administered simultaneously (e.g. in separate or unitary compositions) or sequentially in either order. In the latter case, the two or more compounds will be administered within a period and in an amount and manner that is sufficient to ensure that an advantageous or synergistic effect is achieved. It will be appreciated that the preferred method and order of administration and the respective dosage amounts and regimes for each component of the combination will depend on the particular other medicinal agent and compound of the present invention being administered, their route of administration, the particular tumour being treated and the particular host being treated. The optimum method and order of administration and the dosage amounts and regime can be readily determined by those skilled in the art using conventional methods and in view of the information set out herein.

The weight ratio of the compound according to the present invention and the one or more other anticancer agent(s) when given as a combination may be determined by the person skilled in the art. Said ratio and the exact dosage and frequency of administration depends on the particular compound according to the invention and the other anticancer agent(s) used, the particular condition being treated, the severity of the condition being treated, the age, weight, gender, diet, time of administration and general physical condition of the particular patient, the mode of administration as well as other medication the individual may be taking, as is well known to those skilled in the art. Furthermore, it is evident that the effective daily amount may be lowered or increased depending on the response of the treated subject and/or depending on the evaluation of the physician prescribing the compounds of the instant invention. A particular weight ratio for the present compound of Formula (I) and another anticancer agent may range from 1/10 to 10/1, more in particular from 1/5 to 5/1, even more in particular from 1/3 to 3/1.

The platinum coordination compound is advantageously administered in a dosage of 1 to 500 mg per square meter ($mg/m^2$) of body surface area, for example 50 to 400 $mg/m^2$, particularly for cisplatin in a dosage of about 75 $mg/m^2$ and for carboplatin in about 300 $mg/m^2$ per course of treatment.

The taxane compound is advantageously administered in a dosage of 50 to 400 mg per square meter ($mg/m^2$) of body surface area, for example 75 to 250 $mg/m^2$, particularly for paclitaxel in a dosage of about 175 to 250 $mg/m^2$ and for docetaxel in about 75 to 150 $mg/m^2$ per course of treatment.

The camptothecin compound is advantageously administered in a dosage of 0.1 to 400 mg per square meter ($mg/m^2$) of body surface area, for example 1 to 300 $mg/m^2$, particularly for irinotecan in a dosage of about 100 to 350 $mg/m^2$ and for topotecan in about 1 to 2 $mg/m^2$ per course of treatment.

The anti-tumour podophyllotoxin derivative is advantageously administered in a dosage of 30 to 300 mg per square meter ($mg/m^2$) of body surface area, for example 50 to 250 $mg/m^2$, particularly for etoposide in a dosage of about 35 to 100 $mg/m^2$ and for teniposide in about 50 to 250 $mg/m^2$ per course of treatment.

The anti-tumour vinca alkaloid is advantageously administered in a dosage of 2 to 30 mg per square meter ($mg/m^2$) of body surface area, particularly for vinblastine in a dosage of about 3 to 12 $mg/m^2$, for vincristine in a dosage of about 1 to 2 $mg/m^2$, and for vinorelbine in dosage of about 10 to 30 $mg/m^2$ per course of treatment.

The anti-tumour nucleoside derivative is advantageously administered in a dosage of 200 to 2500 mg per square meter ($mg/m^2$) of body surface area, for example 700 to 1500 $mg/m^2$, particularly for 5-FU in a dosage of 200 to 500 $mg/m^2$, for gemcitabine in a dosage of about 800 to 1200 $mg/m^2$ and for capecitabine in about 1000 to 2500 $mg/m^2$ per course of treatment.

The alkylating agents such as nitrogen mustard or nitrosourea is advantageously administered in a dosage of 100 to 500 mg per square meter ($mg/m^2$) of body surface area, for example 120 to 200 $mg/m^2$, particularly for cyclophosphamide in a dosage of about 100 to 500 $mg/m^2$, for chlorambucil in a dosage of about 0.1 to 0.2 mg/kg, for carmustine in a dosage of about 150 to 200 $mg/m^2$, and for lomustine in a dosage of about 100 to 150 $mg/m^2$ per course of treatment.

The anti-tumour anthracycline derivative is advantageously administered in a dosage of 10 to 75 mg per square meter ($mg/m^2$) of body surface area, for example 15 to 60 $mg/m^2$, particularly for doxorubicin in a dosage of about 40 to 75 $mg/m^2$, for daunorubicin in a dosage of about 25 to 45 $mg/m^2$, and for idarubicin in a dosage of about 10 to 15 $mg/m^2$ per course of treatment.

The antiestrogen agent is advantageously administered in a dosage of about 1 to 100 mg daily depending on the particular agent and the condition being treated. Tamoxifen is advantageously administered orally in a dosage of 5 to 50 mg, preferably 10 to 20 mg twice a day, continuing the therapy for sufficient time to achieve and maintain a therapeutic effect. Toremifene is advantageously administered orally in a dosage of about 60 mg once a day, continuing the therapy for sufficient time to achieve and maintain a therapeutic effect. Anastrozole is advantageously administered orally in a dosage of about 1 mg once a day. Droloxifene is advantageously administered orally in a dosage of about 20-100 mg once a day. Raloxifene is advantageously administered orally in a dosage of about 60 mg once a day. Exemestane is advantageously administered orally in a dosage of about 25 mg once a day.

Antibodies are advantageously administered in a dosage of about 1 to 5 mg per square meter ($mg/m^2$) of body surface area, or as known in the art, if different. Trastuzumab is advantageously administered in a dosage of 1 to 5 mg per square meter ($mg/m^2$) of body surface area, particularly 2 to 4 $mg/m^2$ per course of treatment.

These dosages may be administered for example once, twice or more per course of treatment, which may be repeated for example every 7, 14, 21 or 28 days.

The following examples further illustrate the present invention.

EXAMPLES

Several methods for preparing the compounds of this invention are illustrated in the following examples. All starting materials were obtained from commercial suppliers and used without further purification, or alternatively, can be easily prepared by a skilled person according to well-known methods.

When a stereocenter is indicated with 'RS' this means that a racemic mixture was obtained.

For intermediates that were used in a next reaction step as a crude or as a partially purified intermediate, theoretical mol amounts are indicated in the reaction protocols described below.

Hereinafter, the terms: 'ACN' means acetonitrile, 'AcOH' means acetic acid, 'Ar' means argon, 'BINAP' means 2,2'-bis(diphenylphosphino)-1,1'-binaphthyl, 'BOC' means tert-butyloxycarbonyl, 'Boc$_2$O' means di-tert-butyl dicarbonate, 'Celite®' means diatomaceous earth, 'Cu(OTf)$_2$' means Copper(II) triflate, 'DCM' means dichloromethane, 'DIPEA' means diisopropylethylamine, 'h' means hours(s), 'min' means minute(s), 'Int.' means intermediate; 'aq.' Means aqueous; 'DMAP' means dimethylaminopyridine, 'DMF' means dimethylformamide, 'DIBAL-H' means diisobutylaluminium hydride, 'EDC hydrochloride' means 1-ethyl-3-(3-dimethylaminopropyl)carbodiimide hydrochloride, 'Et$_2$O' means diethylether, 'Et' means ethyl, 'Me' means methyl, 'EtOAc' or 'AcOEt' means ethyl acetate, 'HPLC' means High-performance Liquid Chromatography, 'iPrOH' means isopropyl alcohol, 'HATU' means 1-[bis(dimethylamino)methylene]-1H-[1,2,3]triazolo[4,5-b]pyridin-1-ium 3-oxide hexafluorophosphate, 'HFIP' means hexafluoroisopropanol, 'HOBT' means 1-Hydroxy-1H-benzotriazole, 'MsCl' means methanesulfonyl chloride, 'LC/MS' means Liquid Chromatography/Mass Spectrometry, 'Me-THF' means methyl-tetrahydrofuran, 'MeOH' means methanol, 'EtOH' means ethanol, 'NBS' means N-bromosuccinimide, 'NCS' means N-chlorosuccinimide, 'NMR' means Nuclear Magnetic Resonance, 'Pd/C 10%' means palladium on carbon loading 10%, 'Pd(OAc)$_2$' means palladium (II) acetate, 'Pd(PPh$_3$)$_4$' means tetrakis(triphenylphosphine)palladium (0), 'Pd(dppf)Cl$_2$' means [1,1'-Bis(diphenylphosphino)ferrocene]-dichloropalladium(II), 'rt' or 'RT' means room temperature, 'SFC' means supercritical fluid chromatography, 'ee' means enantiomeric excess, 'TBAF' means tetrabutylammonium fluoride, 'TBDMS' or 'SMDBT' means tert-butyldimethylsilyl, 'TEA' means triethylamine, 'TFA' means trifluoroacetic acid, 'THF' means tetrahydrofuran, 'CV' means column volumes, 'Quant.' means quantitative, 'equiv.' means equivalent(s), 'M.P.' or 'm.p.' means melting point, 'OR' means optical rotation, 'SFC' means supercritical fluid chromatography, 'DIPE' means diisopropyl ethylether, 'RaNi' means Raney Nickel, 'NaHCO$_3$' means sodium hydrogenocarbonate, 'BRETT-PHOS' means 2-(dicyclohexylphosphino)-3,6-dimethoxy-2', 4', 6'-triisopropyl-1,1'-biphenyl, 'DMSO' means dimethylsulfoxide, 'NaBH$_3$(OAc)$_3$' means sodium triacetoxyborohydride, 'DMA-DMF' means N,N-dimethylformamidedimethylacetal, 'v/v' means volume/volume percent, 'T' means temperature, 'TLC' means thin layer chromatography, 'iPrNH$_2$' means isopropylamine, '2nd generation Xphos precatalyst' means (chloro(2-dicyclohexylphosphino-2',4',6'-triisopropyl-1,1'-biphenyl)[2-(2'-amino-1,1'-biphenyl)]palladium(II)).

It is well known to one skilled in the art that protecting groups such as TBDMS can routinely be removed with TBAF in a variety of solvents such as for example THF. Similarly, conditions for removal of BOC protecting groups are well known to one skilled in the art, commonly including for example TFA in a solvent such as for example DCM, or HCl in a solvent such as for example dioxane.

The skilled person will realize that in some cases where an organic layer was obtained at the end of an experimental protocol, it was necessary to dry the organic layer with a typical drying agent such as for example MgSO$_4$, or by azeotropic distillation, and to evaporate the solvent before using the product as a starting material in the next reaction step.

A. Preparation of the Intermediates

Example A1

Preparation of Intermediate 1

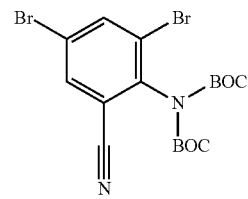 [SMILES: CC(C)(C)OC(=O)N(C(=O)OC(C)(C)C)c1c(Br)cc(Br)cc1C#N]

To a solution of 2,4-dibromo-6-cyanoaniline (200.00 g, 724.82 mmol) and DMAP (17.71 g, 144.96 mmol) in DCM (3 L), Boc$_2$O (474.58 g, 2.17 mol) was added and the reaction mixture was stirred at 45° C. for 4 h. The crude mixture was successively washed with saturated NaHCO$_3$ (2×1 L) and brine (2×1 L), dried over MgSO$_4$, filtered and concentrated under vacuum to give 323 g of intermediate 1 (56% yield, yellow solid, 86% purity evaluated by LC/MS). The product was used in the next step without any further purification.

Preparation of Intermediate 2

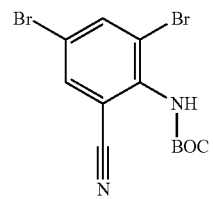 [SMILES: CC(C)(C)OC(=O)Nc1c(Br)cc(Br)cc1C#N]

A mixture of intermediate 1 (620.00 g, 1.30 mol) and K$_2$CO$_3$ (539.02 g, 3.90 mol) in MeOH (6 L) was stirred at 65° C. for 3 h. The reaction mixture was cooled to 25° C. filtered and concentrated under vacuum. Then, the residue was dissolved in EtOAc (4 L) and the organic layer was washed with brine (2 L), dried over MgSO$_4$, and filtered. The filtrate was evaporated under vacuum to 1/8 solvent, filtered to collect the solid and dried under reduced pressure to give 300 g of intermediate 2 (60% yield, yellow solid). The product was used in the next step without any further purification.

Preparation of Intermediate 3

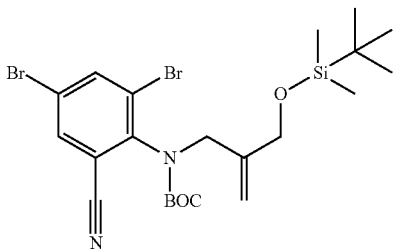 [SMILES: C=C(CO[Si](C)(C)C(C)(C)C)CN(C(=O)OC(C)(C)C)c1c(Br)cc(Br)cc1C#N]

Intermediate 2 (100.00 g, 265.93 mmol), 2-(((tert-butyl-dimethyl-silanyl)oxy) methyl) prop-2-en-1-ol (80.72 g, 398.90 mmol) and tributylphosphane (107.61 g, 531.86 mmol) were dissolved in THF (2 L) and cooled to 0° C. A solution of (NE)-N-(piperidine-1-carbonylimino) piperidine-1-carboxamide (147.61 g, 585.05 mmol) in THF (50 mL) was added dropwise under $N_2$ and stirred at 0° C. for 1 h, then 25° C. for 12 h. The resulting mixture was triturated with petroleum ether (3 L), filtered and concentrated under vacuum. Then, the residue was dissolved in EtOAc (6 L), washed successively with water (2×2 L) and brine (2×2 L), dried over $MgSO_4$, filtered and concentrated under vacuum. Three reactions (each 100 g) were carried out in parallel. The resulting residues were purified by column chromatography on silica gel ($SiO_2$, mobile phase: petroleum ether/EtOAc, 10:1). The desired fractions were collected and the solvent was concentrated to dryness under vacuum to give 350 g of intermediate 3 (78% yield, yellow oil).

Preparation of Intermediate 3a

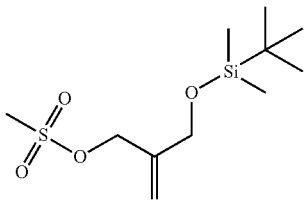 [SMILES: C=C(CO[Si](C)(C)C(C)(C)C)COS(C)(=O)=O]

Triethylamine (196.3 mL; 1.408 mol) was added to a solution of 2-(((tert-butyl-dimethyl-silanyl)oxy) methyl) prop-2-en-1-ol (114 g, 563.3 mmol) in DCM (1L) at 0° C. Methanesulfonylchloride (56.0 mL; 704.2 mmol) was added slowly to the mixture and this mixture was stirred for 2 h at 0° C. The reaction was quenched with saturated aqueous solution of $NaHCO_3$ (100 ml) and extracted with DCM (500 ml*2). The organic layer was dried over $MgSO_4$, filtered, and concentrated under vacuum. The residue was purified by silica gel chromatography (Petroleum ether/ethyl acetate from 0/100 to 5/1) to give 50 g (32%; light yellow oil) of intermediate 3a.

Alternative Preparation of Intermediate 3a

A solution of 1,3-Hydroxy-2-methylenepropane (100 g) in dry THF (200 mL) was added dropwise at 0° C. to a suspension of sodium hydride (0.95 eq.) in dry THF (600 mL). After 30 min a solution of tert-butyldimethylsilylchloride (0.95 eq.) in dry THF (200 mL) was added dropwise to the mixture. After approximately 18 hours at 0-5° C. the reaction was complete by GC and water (500 mL) was added slowly keeping the temperature between 0-5° C. After phase separation, the aqueous layer was back-extracted with ethyl acetate (500 mL) and the combined organic layers were washed with water (500 mL). The organic phase was concentrated to a residue which was azeotropically dried by co-evaporation with THF affording 252.7 g of the crude monoTBDMS-protected diol. A portion of the crude monoT-BDMS-protected diol (152.4 g) was dissolved in dry dichloromethane (610 mL) and triethylamine (1.4 eq.) was added. The mixture was then stirred at 0° C. for 30 min and methanesulfonic anhydride (1.2 eq.) was added as a solution in dichloromethane (950 mL) and the mixture was stirred for 1 h between −5 and 5° C. An additional aliquot of methanesulfonic anhydride (0.1 eq.) and triethylamine (0.2 eq.) were added and, after 1 additional hour, water (500 mL) was added. After phase separation, the organic layer was washed twice with water (500 mL) and concentrated to a residue, which was re-diluted with THF and partially concentrated to obtain a solution of intermediate 3a (311.1 g, 57 weight % intermediate 3a in the solution).

Alternative Preparation of Intermediate 3

Intermediate 2 (140 g; 372.3 mmol) was dissolved in acetonitrile (1.3 L). Intermediate 3a (104.4 g; 372.3 mmol), potassium carbonate (128.6 g; 930.7 mmol), and sodium iodide (5.58 g; 37.2 mmol) were added. The mixture was stirred at 80° C. for 12 h, cooled and concentrated under reduced pressure. The residue was dissolved in water (1 L) and extracted with ethyl acetate (1 L×2). The combined organic phase was washed with brine (1 L), dried over $Na_2SO_4$ and filtered. The filtrate was concentrated under vacuum to give a crude product. The residue was purified by silica gel chromatography (Petroleum ether/ethyl acetate from 100/0 to 40/1) to give 180 g (86%; clear oil) of intermediate 3.

Preparation of Intermediate 4 and intermediate 4'

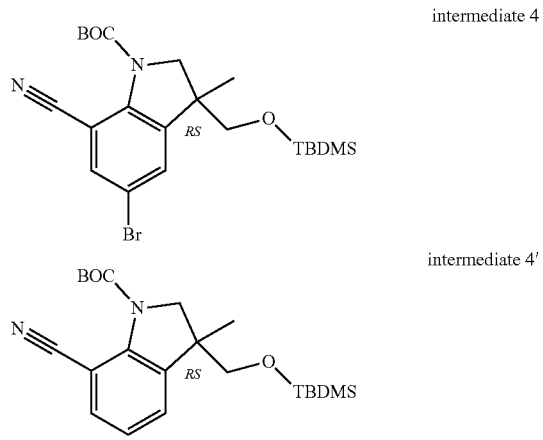

A suspension of intermediate 3 (120.00 g, 214.14 mmol), sodium acetate (45.67 g, 556.76 mmol), sodium formate (37.86 g, 556.76 mmol), $Pd(OAc)_2$ (4.81 g, 21.41 mmol) and tetraethylammonium chloride (44.35 g, 267.67 mmol) in DMF (1.26 L) was degassed under vacuum, purged with Ar three times, and stirred at 85° C. for 2 h. The resulting mixture was filtered through a pad of Celite® and the solid was washed with DCM (2 L). The filtrate was concentrated under vacuum. The residue was dissolved in ethyl acetate (4 L), washed successively with water (2×2 L) and brine (2×2 L), dried over MgSO₄, filtered and concentrated under vacuum. Then, the residue was purified by column chromatography on silica gel (SiO₂, mobile phase: petroleum ether/EtOAc, 15:1). The desired fractions were collected and the solvent was concentrated to dryness under vacuum to give a mixture of intermediates 5 and 5'. Three reactions (each on 100-120 g of intermediate 3) were carried out in parallel which gave in total 160 g of a mixture of intermediates 4 and 4' (38:62).

Alternative Preparation of Intermediate 4

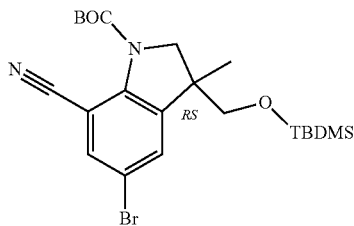

To a mixture of intermediates 4 and 4' in CH₃CN (1.60 L), 1-bromopyrrolidine-2,5-dione (212.20 g, 1.19 mol) was added and stirred at 40° C. for 16 h. The solvent was removed by evaporation under reduced pressure. The residue was dissolved in ethyl acetate (2 L), washed successively with NaHCO₃ (2×1 L) and brine (2×1 L), dried over MgSO₄ and filtered. The filtrate was evaporated under vacuum and purified by column chromatography on silica gel (SiO₂, mobile phase: petroleum ether/EtOAc, 50:1). The desired fractions were collected and the solvent was concentrated to dryness under vacuum to give 110.00 g of intermediate 4 (56% yield, yellow oil, 97% purity evaluated by LC/MS).

Alternative Preparation A of Intermediate 4'

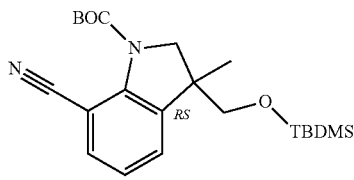

To a solution of intermediate 3 (295.00 g, 473.70 mmol), sodium acetate (101.05 g, 1.23 mol), sodium formate dihydrate (128.15 g, 1.23 mol) and [1,1'-bis(diphenylphosphino)ferrocene] palladium, (II) chloride complex with dichloromethane (19.34 g, 23.70 mmol) in DMF (2 L), tetra-N-butylammonium chloride (164.60 g, 592.20 mmol) was added under N₂ at rt. The reaction mixture was stirred overnight at 60° C., then, filtered through a pad of Celite® and the solid was washed with DCM (400 mL). The filtrate was concentrated under vacuum. The resulting residue was dissolved in EtOAc (4 L) and the organic layer was washed successively with water (2 L) and brine (2 L), dried over Na₂SO₄, filtered and concentrated to give the crude product as black oil. This residue was purified by column chromatography on silica gel (SiO₂, mobile phase: petroleum ether/EtOAc, gradient from 100:0 to 10:1). The desired fractions were collected and the solvent was concentrated to dryness under vacuum to give 155 g of intermediate 4' (70% yield, yellow oil).

Alternative Preparation B of Intermediate 4'

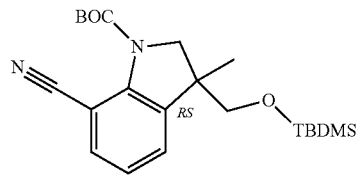

Intermediate 242 (50.0 g) was dissolved in DMF (250 mL). Sodium formate dehydrate (2.6 eq.), sodium acetate (2.6 eq.), tetraethylammonium chloride (1.25 eq.) and palladium acetate (0.05 eq.) were added. The mixture was degassed with nitrogen (3 times) and was then warmed at 45-50° C. until complete conversion (typically 24 hours monitored by HPLC). Water (350 mL) was then added followed by heptane (350 mL). The mixture was filtered and, after phase separation, the aqueous layer was extracted with heptane (350 mL). The combined organic layers were washed with water (250 mL) and then filtered on a diatomite pad (25 g; diatomaceous earth). The filtrate was concentrated to 100-150 mL, cooled to −10 to −5° C. for 2 hours and filtered to afford 37.6 g of intermediate 4'. An additional amount of intermediate 4' could be recovered by filtering the mother liquors on a silica gel pad to remove impurities, and subsequently cool down the filtrate to −10° C. to crystallize out an additional amount of intermediate 4'.

Preparation of Intermediate 4'R

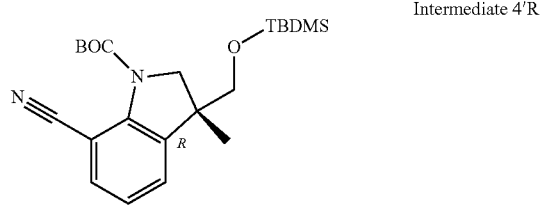

Intermediate 4'R

Intermediates 4'R was obtained from a chiral chromatography separation of intermediate 4' (column CHIRALPAK IC 5 cm*25 cm; mobile phase: hexane/EtOH:80/20; Flow rate: 60.0 mL/min; Wavelength: UV 254 nm; Temperature: 35° C.).

Preparation of Intermediate 4R and intermediate 4S

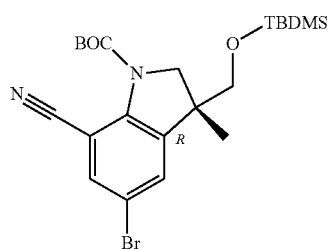
intermediate 4R

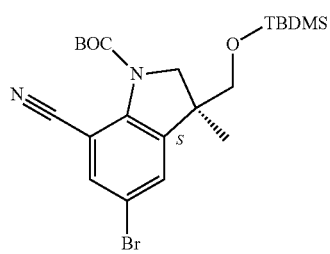
intermediate 4S

Intermediate 4 (500 g) was purified via Normal Phase Chiral separation (Stationary phase: Daicel Chiralpak IC 2000 gram 10 microhm, mobile phase: heptane/EtOH, Isocratic 80% heptane, 20% EtOH). The fractions containing the products were mixed and concentrated to afford 266 g of intermediate 4R (53% yield, ee>98%) and 225 g of intermediate 4S (45% yield, ee>98%).

Alternatively, intermediate 4 (10 g) was purified by chiral SFC (Stationary phase: CHIRALPAK IC 5 m 250×30 mm, mobile phase: 85% $CO_2$, 15% iPrOH). The pure fractions were collected and evaporated to dryness yielding 4.3 g of intermediate 4R (43% yield, ee=100%) and 4.5 g of intermediate 4S (45% yield, ee=100%).

Alternative Preparation of Intermediate 4R

To a solution of intermediate 4'R (10.0 g) in ACN (100 mL) 1,3-dibromo-5,5-dimethylhydantoin (0.75 eq.) was added and the mixture was stirred at 20° C. for 24-28 hours, monitoring the conversion by HPLC. After complete conversion, aqueous 5% $NaHCO_3$ was added (250 mL) and the mixture was stirred for 30 minutes. Toluene (250 mL) was then added and, after 30 min stirring at room temperature, the mixture was allowed to settle and the layers were separated. The organic layer was washed twice with water (100 mL) and used directly in the next step (conversion 99.6%).

Example A2

Preparation of Intermediate 5

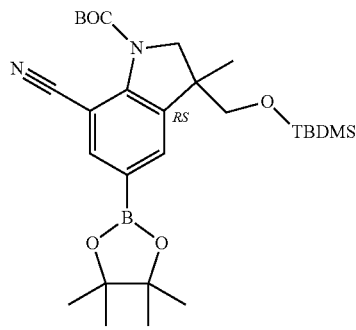

To a solution of intermediate 4 (127.00 g, 234.70 mmol) in 1,4-dioxane (1.2 L), bis(pinacolato)diboron (74.50 g, 293.40 mmol) and potassium acetate (69.11 g, 704.24 mmol) were added. Then, [1,1'-bis(diphenylphosphino) ferrocene] palladium, (II) chloride (8.59 g, 11.74 mmol) was added and stirred for 4 h at 85° C. under $N_2$ atmosphere. The mixture was cooled, partitioned between EtOAc (2 L) and water (500 mL) and filtered through a pad of Celite®. The organic and aqueous layers were separated. The organic layer was washed successively with water (300 mL), brine (300 mL), dried over $Na_2SO_4$ and concentrated under vacuum. The residue was dissolved in a mixture of DCM/EtOAc (90:10, 600 mL), filtered through a plug of flash silica gel, washed with DCM/EtOAc (90:10, 3 L). The filtrate was evaporated to give 125 g of crude intermediate 5 (brown oil) which was directly engaged in the next step.

Preparation of Intermediate 5R

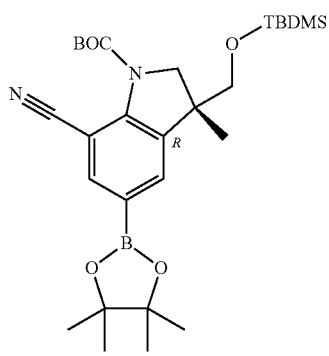

To a solution of intermediate 4R (20.00 g, 41.50 mmol) in 1,4-dioxane (200 mL), bis(pinacolato)diboron (13.20 g, 51.90 mmol) and potassium acetate (12.20 g, 124.60 mmol) were added. Then, [1,1'-bis(diphenylphosphino) ferrocene] palladium, (II) chloride complex with dichloromethane (1.70 g, 2.08 mmol) was added and stirred for 4 h at 85° C. under $N_2$. The mixture was cooled, partitioned between EtOAc (200 mL) and water (100 mL), and filtered through a pad of Celite®. The organic and aqueous layers were separated. The organic layer was washed successively with water (100 mL), brine (100 mL), dried over $Na_2SO_4$, and concentrated under vacuum. The residue was dissolved in a mixture of DCM/EtOAc (90:10, 200 mL), filtered through a plug of flash silica gel and washed with a mixture of DCM/EtOAc (90:10, 1 L). The filtrate was evaporated to give 25 g of crude intermediate 5R (brown oil) which was directly engaged in the next step.

Preparation of Intermediate 6

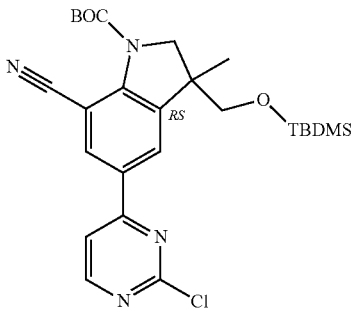

A solution of intermediate 5 (160.00 g, 302.70 mmol) in 1,4-dioxane (1.2 L) was treated with a solution of NaHCO$_3$ (76.30 g, 908.10 mmol) in water (400 mL). Then, 2,4-dichloropyrimidine (67.64 g, 545.06 mmol) and Pd(PPh$_3$)$_4$ (17.50 g, 15.13 mmol) were added under N$_2$. The reaction mixture was stirred at 80° C. under N$_2$. The mixture was cooled, partitioned between EtOAc (2 L) and water (800 mL), and the mixture was filtered through a pad of Celite®. The organic and aqueous layers were separated. The organic layer was washed successively with water (800 mL) and brine (500 mL), dried over Na$_2$SO$_4$ and concentrated under vacuum. The residue was purified by flash column chromatography on silica gel (SiO$_2$, mobile phase: petroleum ether/EtOAc, gradient from 100:0 to 10:1). The desired fractions were collected and the solvent was concentrated to dryness under vacuum to give 100 g of intermediate 6 (71% yield in 2 steps, yellow solid).

Preparation of Intermediate 6R and intermediate 6S

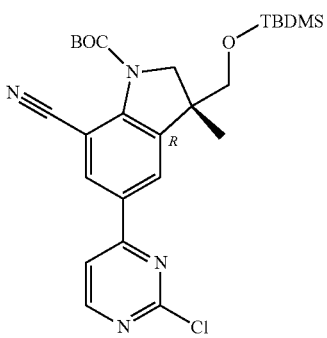

intermediate 6R

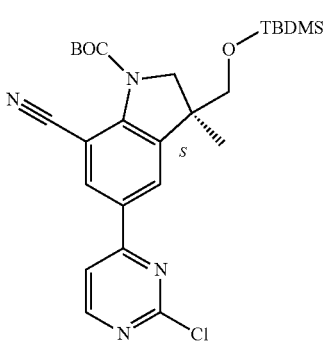

intermediate 6S

Intermediate 6 (52.00 g) was purified by chiral SFC (stationary phase: CHIRALPAK IC 5 m 250×30 mm, mobile phase: 60% CO$_2$, 40% MeOH). The desired fractions were collected and the solvent was concentrated to dryness under vacuum to give 25 g of intermediate 6R (48% yield) and 25.1 g of intermediate 6S (48% yield).

Intermediate 6R (50.10 g) was further purified by chiral SFC (stationary phase: CHIRALPAK IA 5 m 250*20 mm, mobile phase: 87.5% CO$_2$, 12.5% MeOH). The pure fractions were mixed and the solvent was evaporated to afford 49.10 g of intermediate 6R.

Alternative Preparation A of Intermediate 6R

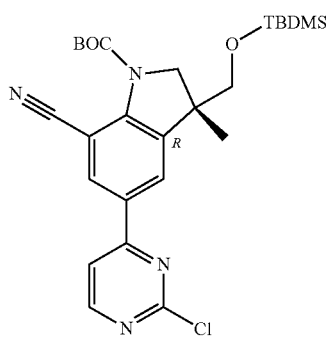

A solution of intermediate 5R (25.00 g, 41.90 mmol) in 1,4-dioxane (1.2 L) was treated with a solution of NaHCO$_3$ (10.50 g, 125.72 mmol) in water (80 mL). Then, 2,4-dichloropyrimidine (9.36 g, 62.86 mmol) and Pd(PPh$_3$)$_4$ (2.42 g, 2.09 mmol) were added under N$_2$. The reaction mixture was stirred at 80° C. under N$_2$. The mixture was cooled, partitioned between EtOAc (300 mL) and water (100 mL), and filtered through a pad of Celite®. The organic layer was washed with water (100 mL), brine (100 mL), dried over Na$_2$SO$_4$ and concentrated under vacuum. The resulting residue was combined with 3 other batches coming from reactions performed on 25 g of intermediate 5R. The residue was purified by flash column chromatography on silica gel (SiO$_2$, mobile phase: petroleum ether/EtOAc, gradient from 100:0 to 10:1). The desired fractions were collected and the solvent was concentrated to dryness under vacuum to give 63 g of intermediate 6R (70% yield over 2 steps, yellow solid).

Alternative Preparation B of Intermediate 6R

To a solution of intermediate 4R (50.0 g) in toluene (400 mL) was added bis(pinacolato)diboron (1.3 eq.), potassium acetate (3.0 eq.) and Pd(dppf)Cl$_2$ (0.05 eq.). The mixture was degassed 3 times with nitrogen and heated to 90° C. for 12-14 hours. Subsequently, the mixture was cooled to room temperature and filtered on a celite pad which was washed with toluene (150 mL). The filtrate was washed with water (250 mL) and was then filtered on a silica pad (10 g) to afford a toluene solution containing 49 g of intermediate 5R. To this solution was added 2,4-dichloropyrimidine (1.5 eq.), NaHCO$_3$ (3.0 eq.), water (25 mL) and Pd(PPh$_3$)$_4$ (0.05 eq.). After degassing three times with nitrogen, the mixture was stirred at 90° C. monitoring the conversion by HPLC. After complete conversion (24-48 hours), the mixture was cooled to room temperature, filtered on a celite pad and washed with water (250 mL). To the organic layer was added silica thiol scavenging resin (10 g) and the mixture was stirred at 90° C. for 3 hours, then cooled to room temperature and filtered. The solvent was switched completely to isopropanol by repeated distillation until about 100 mL of isopropanol solution remained. The solution was warmed to 50° C. and 250 mL of methanol were added. After stirring at 50° C. for 4 hours, the mixture was cooled to 0° C. in 4 h, held at the same temperature for 16 hours and finally filtered to obtain 26 g of intermediate 6R.

Preparation of Intermediate 29

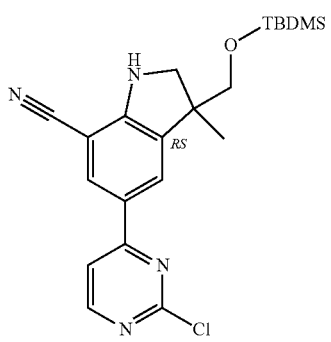

To a solution of intermediate 7 (1.50 g, 2.91 mmol) in DCM (30 mL), TFA (7 mL, 91.50 mmol) was added at 0-5° C. and stirred at 0-5° C. for 1 h, then rt for 1 h. The crude product was poured in a mixture of crushed ice and a saturated aqueous solution of NaHCO$_3$. After extraction with DCM (twice), the organic layers were combined, washed with a saturated solution of NaHCO$_3$, dried over MgSO$_4$ and concentrated under vacuum. The residue was purified by column chromatography on silica gel (Irregular SiOH, 40 m, mobile phase: NH$_4$OH/MeOH/DCM, gradient from 0% NH$_4$OH, 0% MeOH, 100% DCM to 0.1% NH$_4$OH, 2% MeOH, 98% DCM). The desired fractions were collected and the solvent was concentrated to dryness under vacuum to give 524 mg of intermediate 7 (65% yield).

Example A3

Preparation of Intermediate 305

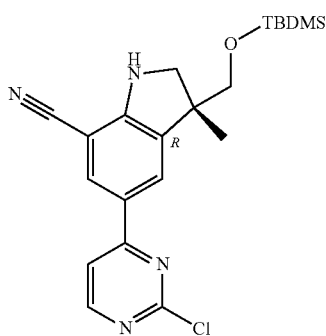

In a three neck round bottom flask, SiO$_2$ (35-70 m) (200 g) was added to a solution of intermediate 6R (45.00 g, 87.36 mmol) in toluene (640 mL) at rt. The reaction mixture was reflux (bath temperature 125° C.) for 6 h under mechanical agitation. Then, SiO$_2$ (35-70 m) was filtered off, washed successively with THF and EtOAc, and the filtrate was evaporated to dryness to give 37.2 g of crude intermediate 305 which was directly engaged in the next steps.

Alternative Preparation of Intermediate 305

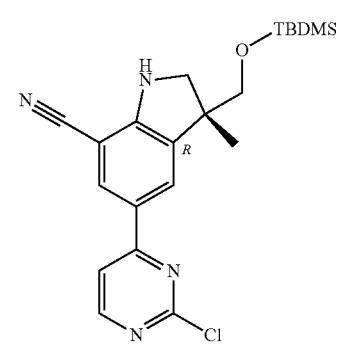

TFA (135 mL, 1.76 mol) was added dropwise at −10° C. (over 50 min) to a solution of intermediate 6R (20.00 g, 38.82 mmol) in DCM (550 mL). The reaction mixture was stirred below 0° C. for 15 min more, then poured in a mixture of crushed ice and a saturated aqueous solution of K$_2$CO$_3$. After extraction with DCM (twice), the organic layers were combined, washed with an aqueous solution of K$_2$CO$_3$, dried over MgSO$_4$ and evaporated to dryness. The residue (17.40 g) was purified by chromatography on silica gel (irregular SiOH, 80 g, mobile phase: NH$_4$OH/MeOH/DCM, gradient from 0% NH$_4$OH, 0% MeOH, 100% DCM to 0.2% NH$_4$OH, 2% MeOH, 98% DCM). The desired fractions were collected and the solvent was concentrated to dryness under vacuum to give 12.1 g of intermediate 305 (75% yield).

Example A4

Preparation of Intermediate 436

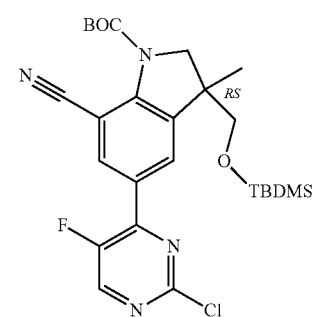

To a solution of intermediate 5 (3.89 g, 4.92 mmol), 5-fluoro-2,4-dichloropyrimidine (1.07 g, 6.40 mmol) and Cs₂CO₃ (4.81 g, 14.80 mmol) in 1,4-dioxane (25 mL) and distilled water (2.5 mL), Pd(PPh₃)₄ (0.28 g, 0.25 mmol) was added and the reaction mixture was heated overnight at 95° C. The mixture was poured into ice and extracted with EtOAc. The organic layer was washed with brine, dried over MgSO₄, filtered and the solvent was evaporated. The residue was purified by column chromatography on silica gel (240 g, 15-40 μm, mobile phase: heptane/EtOAc, gradient from 1:0 to 0:1). The pure fractions were mixed and the solvent was evaporated to give 1.92 g of intermediate 436 (73% yield).

The intermediates in the Table below were prepared by using an analogous starting from the respective starting materials.

| Intermediate number | Structure | Mass (mg) | Yield (%) |
|---|---|---|---|
| Intermediate 439 | From intermediate 5R and 5-fluoro-2,4-dichloropyrimidine | 1820 | 83 |

Example A5

Preparation of Intermediate 7

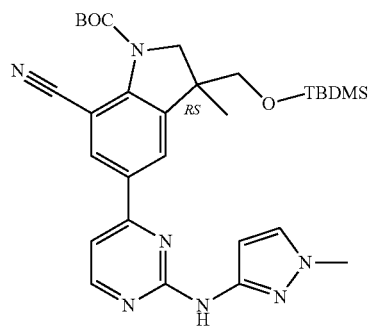

A mixture of intermediate 6 (2.00 g, 3.88 mmol), 1-methyl-1H-pyrazol-3-amine (565.60 mg, 5.82 mmol) and Cs₂CO₃ (3.79 g, 11.65 mmol) in 1,4-dioxane (40 mL) was purged with N₂. Then Pd(OAc)₂ (87.17 mg, 0.39 mmol) and BINAP (241.76 mg, 0.39 mmol) were added. The mixture was purged with N₂ and stirred at 95° C. for 18 h. An extraction was performed with EtOAc and water. The organic layer was washed with brine, dried and evaporated to give 2.96 g of intermediate 7 (quant. yield, 75% purity based on LC/MS, brown foam) and used as it in the next step.

The intermediates in the Table below were prepared by using an analogous method starting from the respective starting materials. The most relevant minor deviations to the referenced method are indicated as additional information in the column 'Yield (%)'.

| Int. number | Structure | Mass (mg) | Yield (%) |
|---|---|---|---|
| Intermediate 9 | 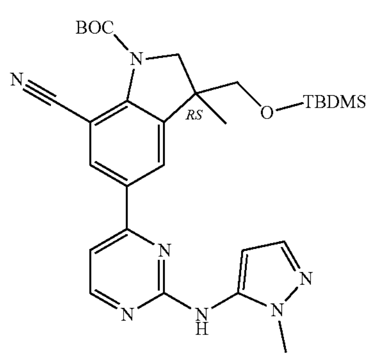 | 574 brown solid | Quant. |

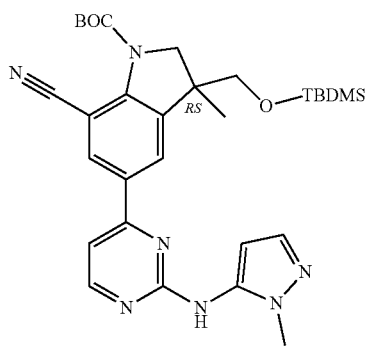

From intermediate 6 and 1-methyl-1H-pyrazole-5-ylamine

| Int. number | Structure | Mass (mg) | Yield (%) |
| --- | --- | --- | --- |
| Intermediate 11 | From intermediate 6 and 1-3-dimethyl-1H-pyrazol-5-amine | 865 (66% purity based on LC/MS) brown solid | Quant. |
| Intermediate 13 | From intermediate 6 and 1-methyl-1H-pyrazole-4-amine, hydrochloride | 650 (86% purity based on LC/MS) brown solid | Quant. |
| Intermediate 16 | From intermediate 6 and intermediate 15 | 350<br>230 (contaminated by impurities) | 56<br>37 |

-continued

| Int. number | Structure | Mass (mg) | Yield (%) |
| --- | --- | --- | --- |
| Intermediate 19 | From intermediate 6 and intermediate 18 | 280 | 44 |
| Intermediate 21 | From intermediate 6 and 1,3-dimethyl-1H-pyrazol-4-amine, hydrochloride | 304 yellow foam | 53 |
| Intermediate 23 | From intermediate 6 and 5-(1,1-dimethylethyl)-1-methyl-1Hpyrazol-3-amine | 272 | 44 |

-continued

| Int. number | Structure | Mass (mg) | Yield (%) |
|---|---|---|---|
| Intermediate 25 | *(structure)* From int. 6 and 5-(amino-β,β,1-trimethyl-1H-Pyrazol-3-ethanol | 311 (78% purity based on LC/MS) | 49 |
| Intermediate 27 | *(structure)* From intermediate 6 and 5-amino-3-(1,1-dimethylethyl)-1H-Pyrazol-1-ethano | 498 (62% purity based on LC/MS) | 48 |
| Intermediate 36 | *(structure)* From intermediate 6 and 1-(2-methoxyethyl)-3-methyl-1H-Pyrazol-5-amine | 477 viscous oil | 78 with T = 90° C. |

-continued
| Int. number | Structure | Mass (mg) | Yield (%) |
| --- | --- | --- | --- |
| Intermediate 38 | 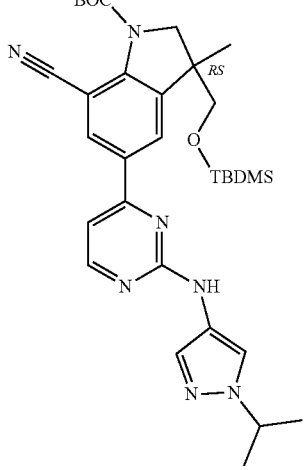<br>From intermediate 6 and 1-(1-methylethyl)-1H-Pyrazol-4-amine | 482 | 82 |
| Intermediate 45 | 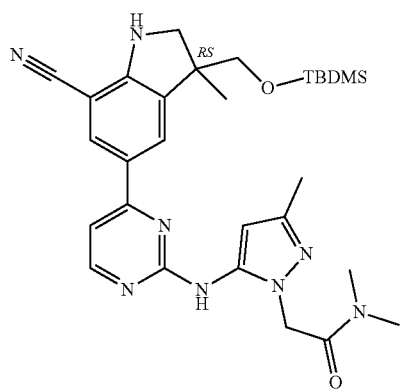<br>From intermediate 6 and intermediate 44 | 208<br>orange solid | 56<br>with T =<br>90° C. |
| Intermediate 46 | 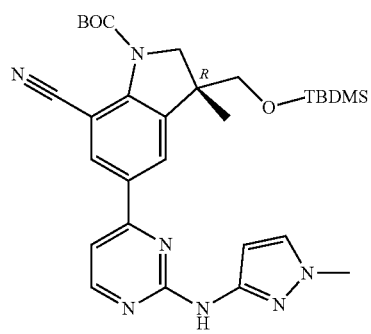<br>From intermediate 6R and 1-methyl-1H-pyrazol-3-amine | 2000<br>(84% purity<br>based on<br>LC/MS)<br>orange foam | Quant. |

-continued

| Int. number | Structure | Mass (mg) | Yield (%) |
|---|---|---|---|
| Intermediate 50 | [Structure: BOC-protected indoline with cyano, methyl, CH₂-O-TBDMS substituents, linked to pyrimidine-NH-pyrazole-N-BOC] *RS*<br>From intermediate 6 and 3-amino-, 1,1-dimethylethyl ester 1H-Pyrazol-1-carboxylic acid | 505 (80% purity based on NMR) | — |
| Intermediate 65 | [Structure: SMDBT-O-CH₂-indoline(BOC, CN, methyl) linked to pyrimidine-NH-pyrazole with methyl-oxetane substituent] *RS*<br>From intermediate 6 and intermediate 15' | 100 | 27 |
| Intermediate 97 | [Structure: BOC-protected indoline with cyano, methyl, CH₂-O-TBDMS substituents, linked to pyrimidine-NH-(3-chloro-1-methyl-pyrazole)] *R*<br>From intermediate 6R and 3-chloro-1-methyl-1H-pyrazol-5-amine dihydrochloride | 365 brown oil | Quant. |

-continued
| Int. number | Structure | Mass (mg) | Yield (%) |
|---|---|---|---|
| Intermediate 99 | 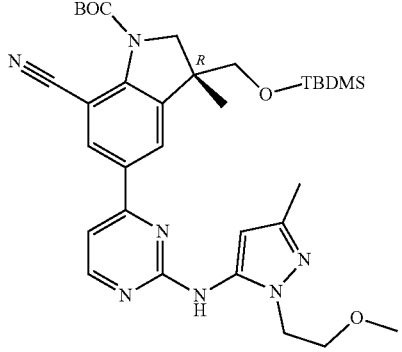 From intermediate 6R and 1-(2-Methoxyethyl)-3-methyl-1H-pyrazol-5-amine | 5530 (85% purity based on LC/MS) | 90 with T = 110° C. |
| Intermediate 116 | 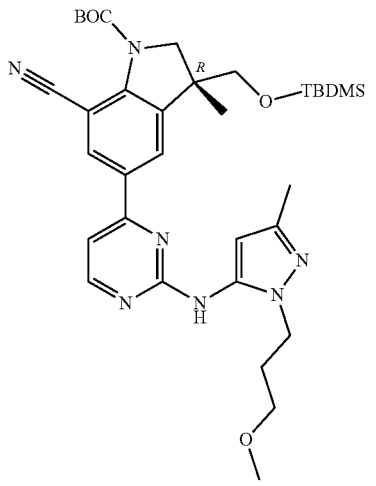 From intermediate 6R and intermediate 115 | 24300 (75% purity based on LC/MS) 11100 | 43 20 T = 120° C. |
| Intermediate 184' (mixture of 2 diastereoisomers) | 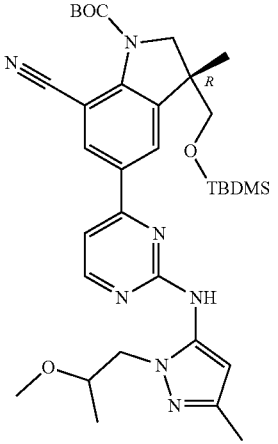 From intermediate 6R and intermediate 184 | 560 (58% purity based on LC/MS) | 45 T = 120° C. |

-continued

| Int. number | Structure | Mass (mg) | Yield (%) |
|---|---|---|---|
| Intermediate 197 | (structure) From intermediate 6R and intermediate 196 | 397 orange powder | 74 with T = 90° C. |
| Intermediate 221 | (structure) From intermediate 6R and intermediate 220 | 3300 | 69 T = 120° C. |
| Intermediate 226 | (structure) From int. 6R and int. 225 | 2800 | 68 T = 120° C. |

-continued
| Int. number | Structure | Mass (mg) | Yield (%) |
|---|---|---|---|
| Intermediate 234 | 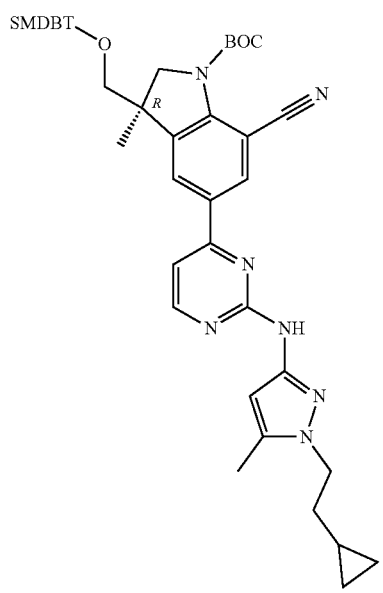<br>From intermediate 6R and intermediate 233 | 445 | 65<br>T = 120° C. |
| Intermediate 237 | 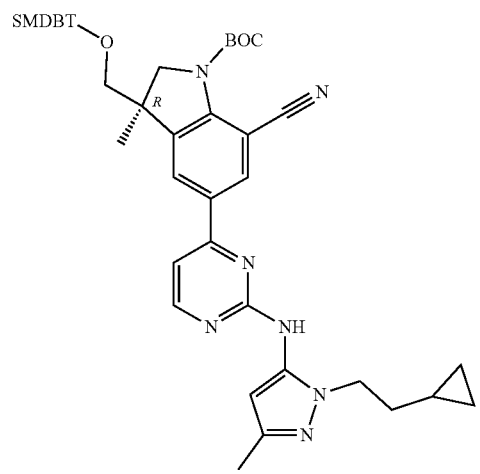<br>From intermediate 6R and intermediate 236 | 2990 | 49<br>T = 120° C. |

-continued
| Int. number | Structure | Mass (mg) | Yield (%) |
|---|---|---|---|
| Intermediate 243 | 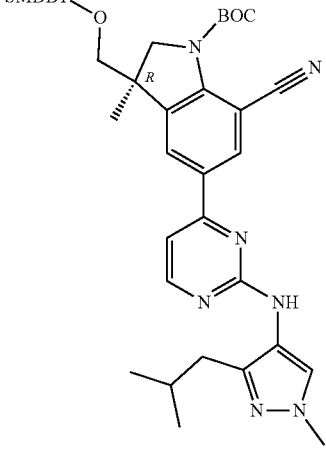<br>From intermediate 6R and intermediate 242 | 5111 | 62<br>T = 120° C. |
| Intermediate 248 | 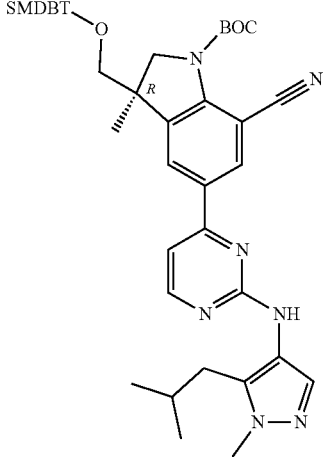<br>From intermediate 6R and intermediate 247 | 4150<br>(86% purity based on LC/MS) | 58<br>T = 120° C. |
| Intermediate 277 | 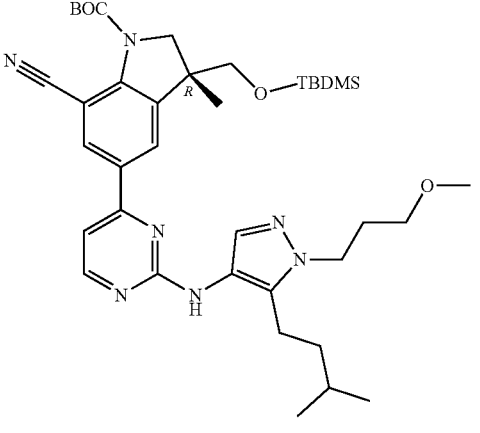<br>From intermediate 6R and intermediate 276 | 2300<br>(64% purity based on LC/MS) | 61<br>T = 120° C. |

-continued

| Int. number | Structure | Mass (mg) | Yield (%) |
|---|---|---|---|
| Intermediate 280 | From intermediate 6R and intermediate 279 | 730 (92% purity based on LC/MS) | 27 T = 120° C. |
| Intermediate 290 | From intermediate 6R and intermediate 289 | 4510 (92% purity based on LC/MS) | 61 T = 90° C. |
| Intermediate 301 | From intermediate 6R and intermediate 300 | 1310 (81% purity based on LC/MS) brown foam | Quant. T = 90° C. |

-continued

| Int. number | Structure | Mass (mg) | Yield (%) |
|---|---|---|---|
| Intermediate 309 | From intermediate 6R and intermediate 308 | 881 brown residue | 76 T = 90° C. |
| Intermediate 313 | From intermediate 6R and intermediate 312 | 760 yellow oil | 94 T = 90° C. |
| Intermediate 317 | From intermediate 6R and intermediate 316 | 765 (84% purity based on LC/MS) brown oil | 63 T = 90° C. |

-continued

| Int. number | Structure | Mass (mg) | Yield (%) |
|---|---|---|---|
| Intermediate 321 | From intermediate 6R and intermediate 320 | 301 brown oil | 56 T = 90° C. |
| Intermediate 325 | From intermediate 6R and intermediate 324 | 534 yellow residue | 84 T = 90° C. |
| Intermediate 329 | From intermediate 6R and intermediate 328 | 578 | 73 T = 120° C. |

-continued

| Int. number | Structure | Mass (mg) | Yield (%) |
| --- | --- | --- | --- |
| Intermediate 333 | From intermediate 6R and intermediate 332 | 244 yellow foam | 51 T = 90° C. |
| Intermediate 339 | From intermediate 6R and intermediate 338 | 178 pale yellow foam | 29 T = 85° C. |
| Intermediate 343 | From intermediate 6R and intermediate 342 | 370 | 40 T = 120° C. |

-continued
| Int. number | Structure | Mass (mg) | Yield (%) |
|---|---|---|---|
| Intermediate 347 | 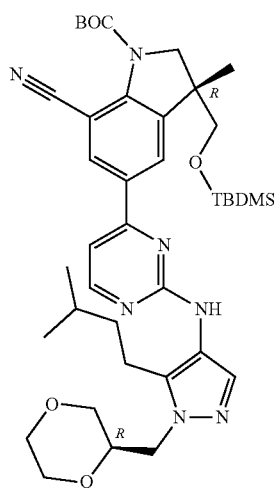<br>From intermediate 6R and intermediate 346 | 615 | 77<br>T = 120° C. |
| Intermediate 360 | 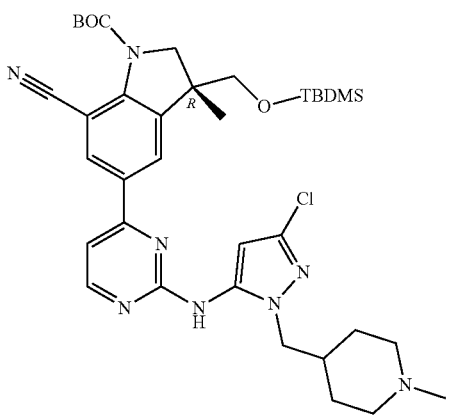<br>From intermediate 6R and intermediate 359 | 250<br>yellow oil | 68<br>T = 90° C. |

-continued
| Int. number | Structure | Mass (mg) | Yield (%) |
|---|---|---|---|
| Intermediate 364 | 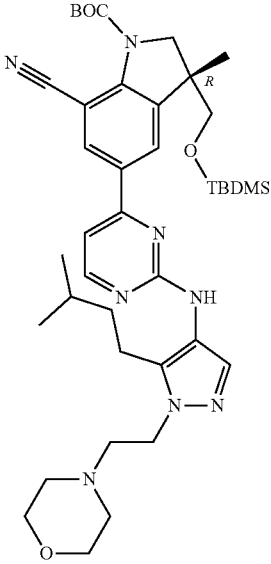<br>From intermediate 6R and intermediate 363 | 578 | 71<br>T = 120° C. |
| Intermediate 368 | 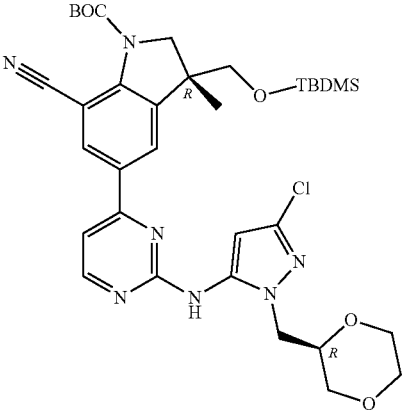<br>From intermediate 6R and intermediate 367 | 475<br>yellow residue | 42<br>T = 90° C. |
| Mixture of Intermediate 372 and intermediate 373 | 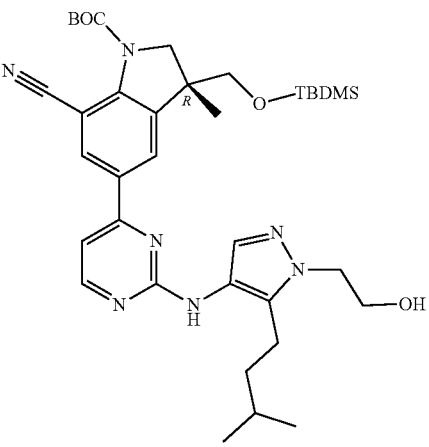<br>intermediate 372 | 400<br>(85% purity based on LC/MS)<br>Ratio 372/373: 56/44 | 37<br>T = 120° C. |

| Int. number | Structure | Mass (mg) | Yield (%) |
|---|---|---|---|
| | intermediate 373<br>From intermediate 6R and<br>intermediate 371 | | |
| Intermediate 377 | From intermediate 6R and<br>intermediate 376 | 3600 | 87<br>T = 120° C. |
| Intermediate 381 | From intermediate 6R and<br>intermediate 380 | 175<br>pale yellow<br>solid | 35<br>T = 90° C. |

| Int. number | Structure | Mass (mg) | Yield (%) |
|---|---|---|---|
| Intermediate 384 | From intermediate 6R and intermediate 383 | 600 (82% purity based on LC/MS) | 65 T = 120° C. |
| Intermediate 388 | 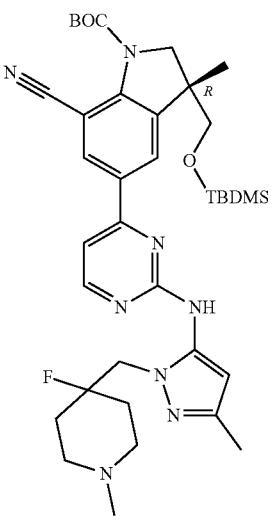 From intermediate 6R and intermediate 387 | 398 | 62 T = 120° C. |

-continued

| Int. number | Structure | Mass (mg) | Yield (%) |
|---|---|---|---|
| Intermediate 402 | (structure) From intermediate 6R and intermediate 401 | 430 yellow solid | 49 T = 90° C. |
| Intermediate 421 | (structure) From intermediate 6R and intermediate 420 | 348 | 50 T = 90° C. |
| Intermediate 425 | (structure) From intermediate 6R and intermediate 424 | 320 | 51 T = 120° C. |

-continued

| Int. number | Structure | Mass (mg) | Yield (%) |
|---|---|---|---|
| Intermediate 429 | *From intermediate 6R and intermediate 428* | 520 | 65<br>T = 120° C. |
| Intermediate 432 | *From intermediate 6R and intermediate 431* | 300 | 37<br>T = 120° C. |
| Intermediate 442 | *From intermediate 6R and 2-amino-4-methylthiazole* | 276<br>(90% purity based on LC/MS)<br>foam | Quant.<br>T = 100° C. |

-continued

| Int. number | Structure | Mass (mg) | Yield (%) |
|---|---|---|---|
| Intermediate 444 | From intermediate 6R and 3-methylisothiazol-4-amine | 412 yellow foam | 89 T = 100° C. |
| Intermediate 446 | From intermediate 6R and 4-methyl-oxazol-2-ylamine | 280 | 50 T = 100° C. |
| Intermediate 448 | From intermediate 6R and 4,5-dimethyl-1,3-thiazol-2-amine | 700 (59% purity based on LC/MS) black foam | Quant. |
| Intermediate 450 | From intermediate 6R and 2-amino-N,N,4-trimethyl-1,3-thiazole-5-carboxamide | 465 yellow solid | 90 T = 100° C. |

-continued
| Int. number | Structure | Mass (mg) | Yield (%) |
|---|---|---|---|
| Intermediate 458 | 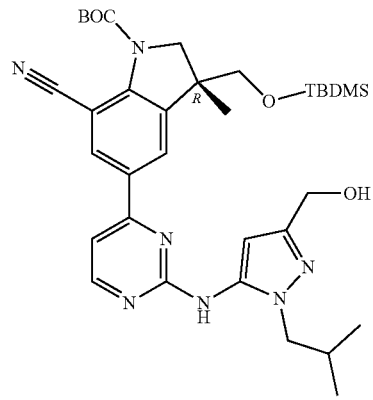<br>From int. 6R and int. 457 | 790 | 88<br>T = 90° C. |
| Intermediate 462 | 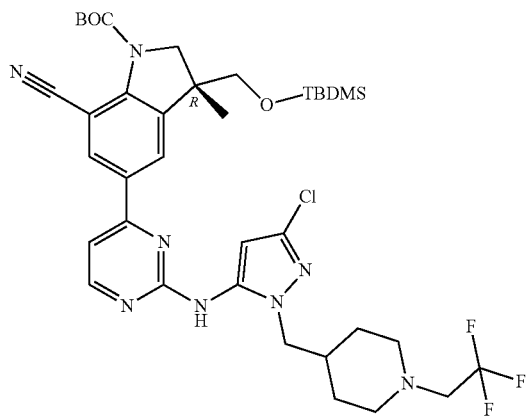<br>From intermediate 6R and intermediate 461 | 376 | 53<br>T = 90° C. |
| Intermediate 466 | 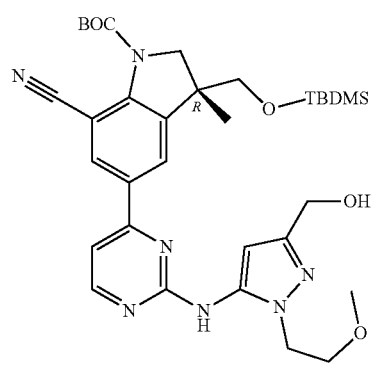<br>From intermediate 6R and intermediate 465 | 435<br>pale yellow<br>foam | 80<br>T = 90° C. |

-continued
| Int. number | Structure | Mass (mg) | Yield (%) |
|---|---|---|---|
| Intermediate 477 | 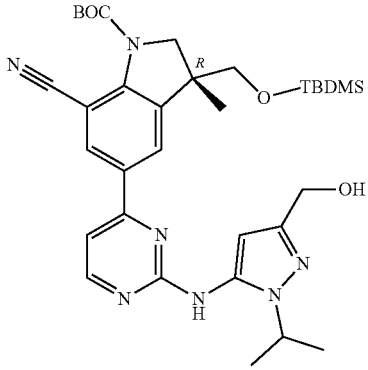<br>From intermediate 6R and intermediate 476 | 452<br>white foam | 75<br>T = 90° C. |
| Intermediate 481 | 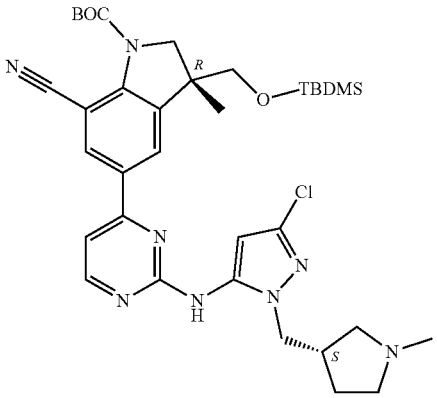<br>From intermediate 6R and intermediate 480 | 580<br>yellow solid | 54<br>T = 90° C. |
| Intermediate 485 | 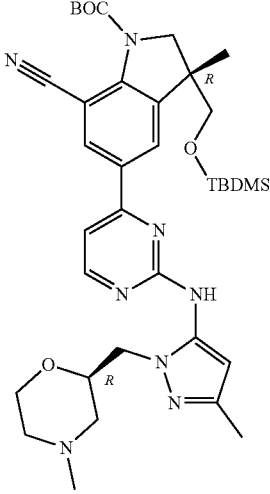<br>From intermediate 6R and intermediate 484 | 377 | 50<br>T = 120° C. |

-continued
| Int. number | Structure | Mass (mg) | Yield (%) |
|---|---|---|---|
| Intermediate 501 | 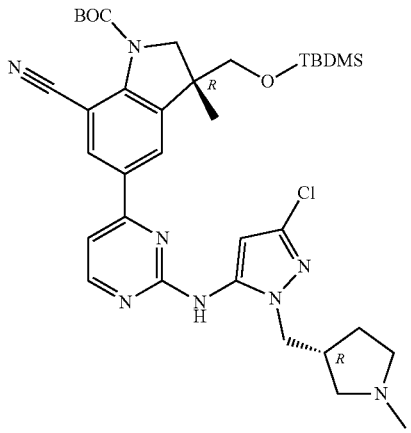<br>From intermediate 6R and intermediate 500 | 674<br>brown residue | 53<br>T = 90° C. |
| Intermediate 552 | 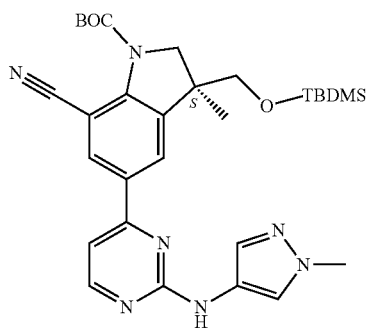<br>From intermediate 6S and 1-methyl-1H-pyrazol-3-amine | 833 | 25<br>T = 90° C. |
| Intermediate 697 | 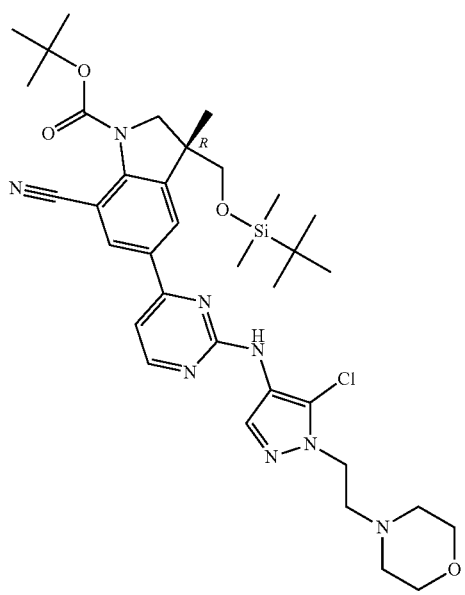<br>From intermediate 6R and intermediate 696 | 200 | 52<br>T = 85° C.<br>48 h |

-continued

| Int. number | Structure | Mass (mg) | Yield (%) |
|---|---|---|---|
| Intermediate 723 | From intermediate 6R and intermediate 722 | 290 | 82<br>T = 100° C.<br>2 h |
| Intermediate 736 | From intermediate 6R and intermediate 735 | 80 | 21 |
| Intermediate 744 | From intermediates 6R and 743 | 4450 | 85<br>Schlenk<br>120° C. for<br>90 min |

Example A6

Preparation of Intermediate 33

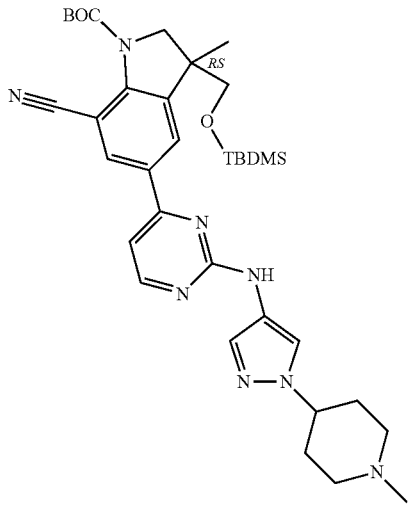

Intermediate 6 (500.00 mg, 0.971 mmol), 1-(1-methyl-4-piperidyl)pyraol-4-amine (279.93 mg, 1.55 mmol), Pd(OAc)$_2$ (21.79 mg, 97.06 µmol), BINAP (60.44 mg, 97.06 mol) and Cs$_2$CO$_3$ (948.76 mg, 2.91 mmol) in 1,4-dioxane (19.87 mL, 232.95 mmol) in a sealed tube were stirred at 120° C. using one single mode microwave (Biotage Initiator EXP 60® with a power output ranging from 0 to 400 W for 30 min). The reaction mixture was poured onto water and DCM, filtered over Celite®. The filtrate was decanted and the organic layer was dried over MgSO$_4$, filtered and evaporated. The residue was purified by column chromatography on silica gel (Irregular SiOH, 40 m, mobile phase: gradient from 100% DCM to 97% DCM, 3% MeOH, 0.1% NH$_4$OH). The pure fractions were combined and the solvent was evaporated to give 375 mg of intermediate 33 (yield 59%).

The intermediates in the Table below were prepared by using an analogous method starting from the respective starting materials. For the synthesis of these intermediates, a one single mode microwave was used (Biotage Initiator EXP 60® with a power output ranging from 0 to 400 W for 30 min or alternatively an Anton Parr monowave 300® with a power output ranging from 0 to 850 W for 30 min).

| Int. number | Structure | Mass (mg) | Yield (%) |
|---|---|---|---|
| Intermediate 40 | 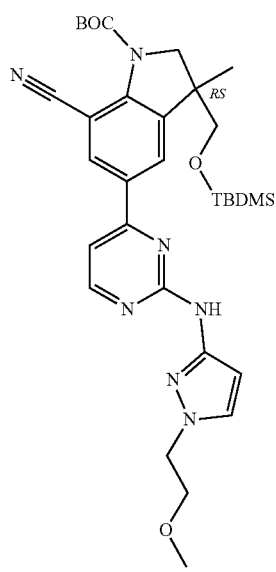<br>From intermediate 6 and 1-(2-methoxyethyl)-1H-Pyrazol-4-amine | 500 | 83 |

-continued

| Int. number | Structure | Mass (mg) | Yield (%) |
|---|---|---|---|
| Intermediate 42 | From intermediate 6 and 3-amino-N,N-dimethyl-1H-pyrazole-1-acetamide | 474 | 75 |
| Intermediate 48 | From intermediate 6 and 1-isopropyl-1H-pyrazol-3-ylamine | 450 (88% purity based on LC/MS) | 68 |
| Intermediate 54 | From intermediate 6 and intermediate 53 | 220 | 36 |

| Int. number | Structure | Mass (mg) | Yield (%) |
|---|---|---|---|
| Intermediate 58 | 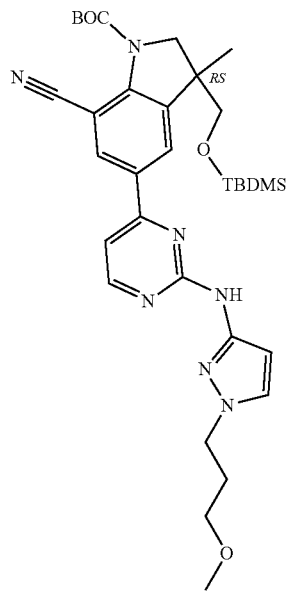 From intermediate 6 and intermediate 57 | 516 | 84 |
| Intermediate 60 | 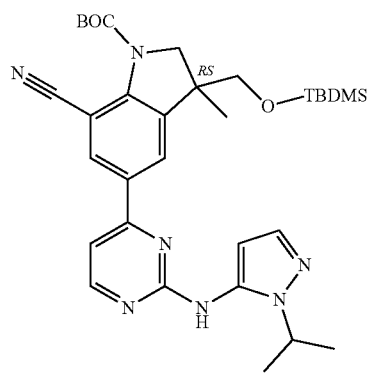 From intermediate 6 and 1-isopropyl-1H-pyrasol-5-amine | 585 | Quant. |

-continued
| Int. number | Structure | Mass (mg) | Yield (%) |
|---|---|---|---|
| Intermediate 63 | 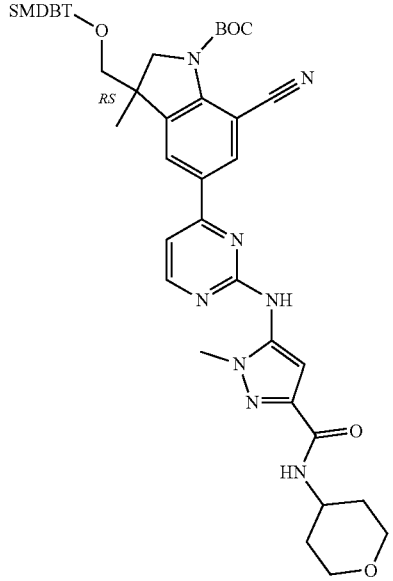<br>From intermediate 6 and intermediate 62 | 305 | 45 |
| Intermediate 68 | 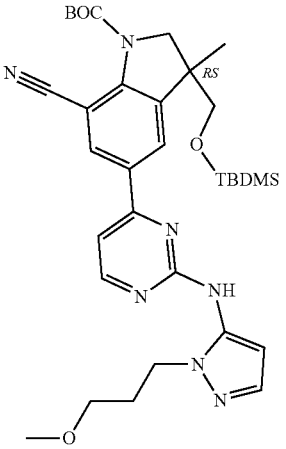<br>From intermediate 6 and intermediate 67 | 369 | 60 |
| Intermediate 71 | 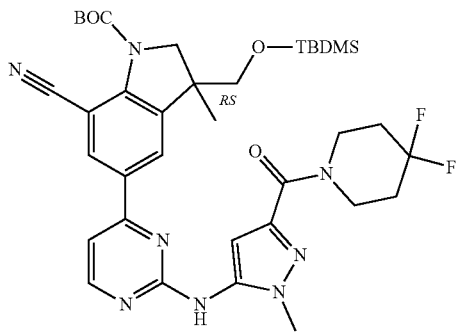<br>From intermediate 6 and intermediate 70 | 212 | 30 |

-continued
| Int. number | Structure | Mass (mg) | Yield (%) |
|---|---|---|---|
| Intermediate 73 | 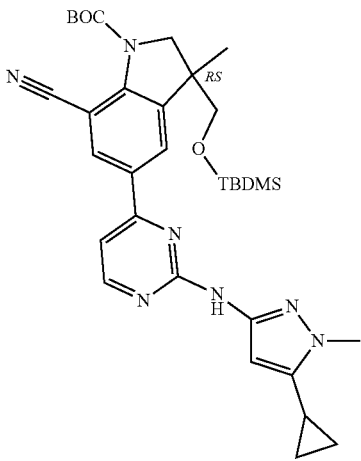 From intermediate 6 and 5-cyclopropyl-1-methyl-1H-pyrazol-3-amine | 610 (93% purity based on LC/MS) | 95 |
| Intermediate 75 | 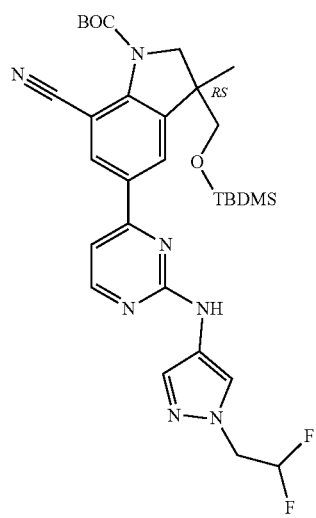 From intermediate 6 and 1-(2,2-difluoroethyl)-1H-Pyrazol-4-amine | 468 | 77 |

-continued

| Int. number | Structure | Mass (mg) | Yield (%) |
|---|---|---|---|
| Intermediate 77 | From intermediate 6S and 1-isopropyl-1H-pyrazol-3-ylamine | 229 | 39 |
| Intermediate 79 | From intermediate 6 and 4-chloro-1-methyl-1H-pyrazol-3-ylamine hydrochloride | 460 | 78 |
| Intermediate 81 (mixture of 2 distereoisomers) | From intermediate 6 and 1-(1,1-dioxidotetrahydro-3-thienyl)-3-methyl-1H-pyrazol-5-amine | 411 (91% purity based on LC/MS) | 61 |

-continued
| Int. number | Structure | Mass (mg) | Yield (%) |
|---|---|---|---|
| Intermediate 85 | 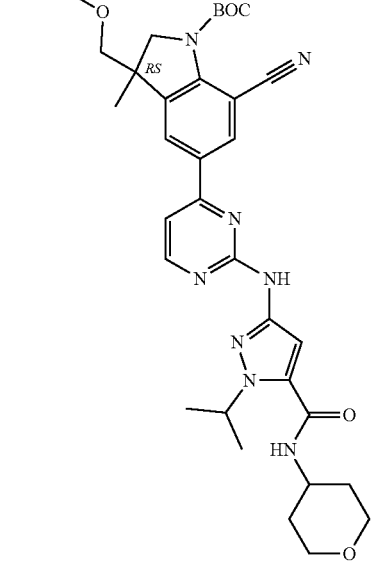<br>From intermediate 6 and intermediate 84 | 386 | 54 |
| Intermediate 87 | 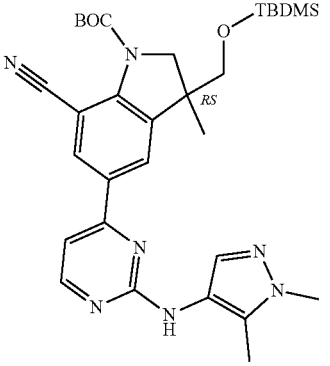<br>From intermediate 6 and 1,5-dimethyl-1H-pyrazol-4-amine hydrochloride | 410 | 72 |
| Intermediate 89 | 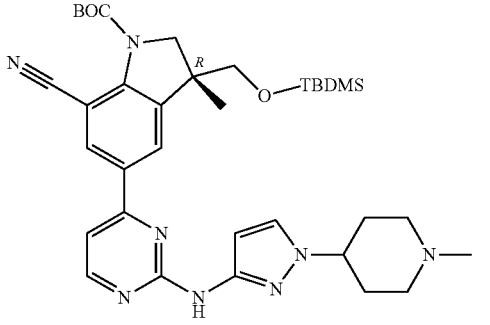<br>From intermediate 6R and 1-(1-methyl-4-piperidinyl)-1H-Pyrazol-3-amine | 410 | 64 |

-continued
| Int. number | Structure | Mass (mg) | Yield (%) |
| --- | --- | --- | --- |
| Intermediate 91 | 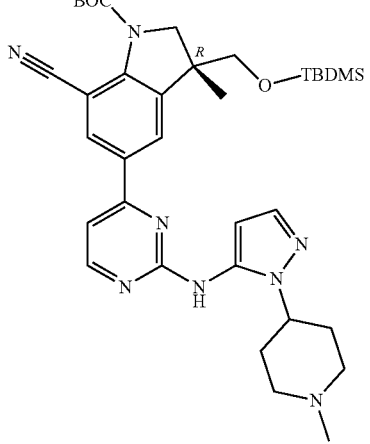<br>From intermediate 6R and 1-(1-methyl-4-piperidinyl)-1H-Pyrazol-5-amine | 130 (88% purity based on LC/MS) | 20 |
| Intermediate 93 | 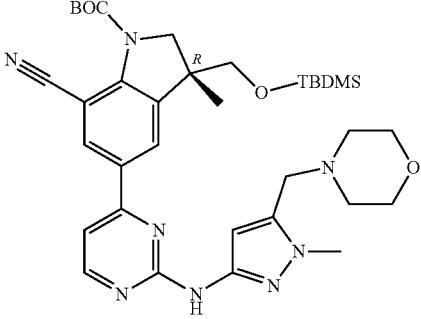<br>From intermediate 6R and 1-methyl-5-(morpholinomethyl)pyrazol-3-amine | 650 | 99 |
| Intermediate 95 | 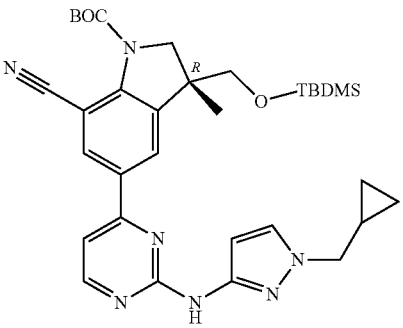<br>From intermediate 6R and 1-(cyclopropylmethyl-1H-pyrazol-3-amine | 544 | 91 |

-continued

| Int. number | Structure | Mass (mg) | Yield (%) |
|---|---|---|---|
| Intermediate 95 | From intermediate 6R and 5-chloro-1-methyl-1H-pyrazol-3-amine | 260 | 44 |
| Intermediate 104 | From intermediate 6R and intermediate 103 | 440 (70% purity based on LC/MS) | 59 |
| Intermediate 106 | From intermediate 6R and 3-amino-N,N,1-trimethyl-1H-Pyrazole-5-carboxamide | 537 (92% purity based on LC/MS) | 86 |

-continued
| Int. number | Structure | Mass (mg) | Yield (%) |
|---|---|---|---|
| Intermediate 108 | 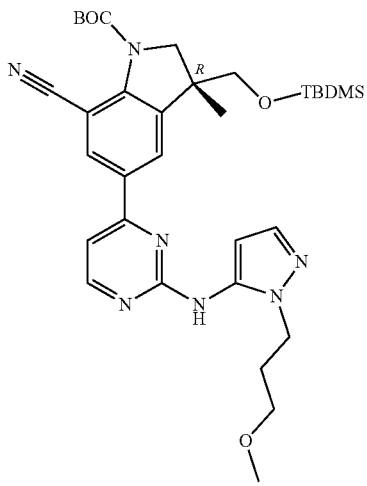<br>From intermediate 6R and intermediate 56' | 2300 (62% purity based on LC/MS) | 47 |
| Intermediate 110 | 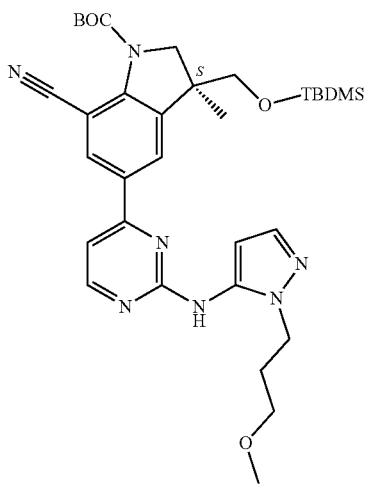<br>From intermediate 6S and intermediate 56' | 980 | 80 |

-continued
| Int. number | Structure | Mass (mg) | Yield (%) |
|---|---|---|---|
| Intermediate 112 | 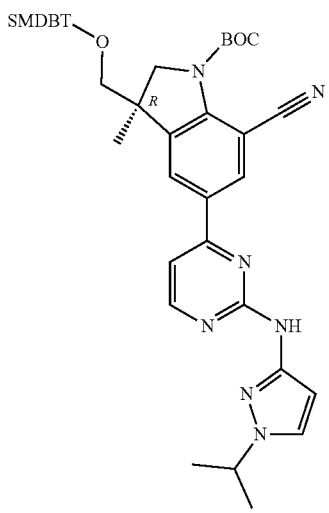<br>From intermediate 6R and 1-isopropyl-1H-pyrazol-3-ylamine | 229 | 39 |
| Intermediate 119 | 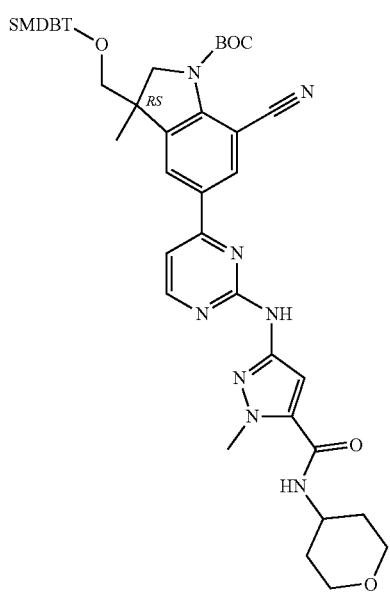<br>From intermediate 6 and intermediate 118 | 287 | 42 |

| Int. number | Structure | Mass (mg) | Yield (%) |
|---|---|---|---|
| Intermediate 122 | From intermediate 6R and intermediate 121 | 1000 | 78 |
| Intermediate 124 | From intermediate 6R and 4-amino_1-methyl-1H-pyrazole-3-carboxylic acid methylamide | 653 | — |
| Intermediate 126 | From intermediate 6S and intermediate 115 | 1310 | Quant. |

-continued
| Int. number | Structure | Mass (mg) | Yield (%) |
|---|---|---|---|
| Intermediate 128 | 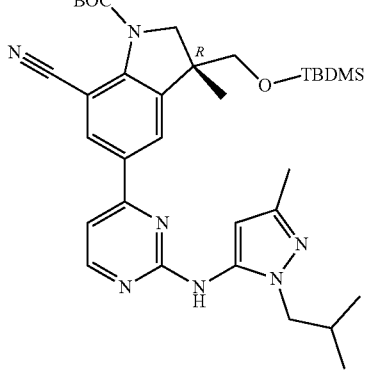<br>From intermediate 6R and 2-isobutyl-5-methyl-2H-pyrazol-3-amine | 370 | 60 |
| Intermediate 130 | 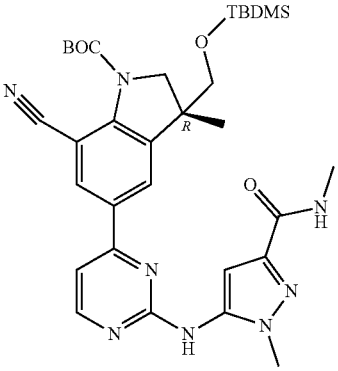<br>From intermediate 6R and 5-amino-N,1-dimethyl-1H-pyrazole-3-carboxamide | 325 | 53 |
| Intermediate 132 | 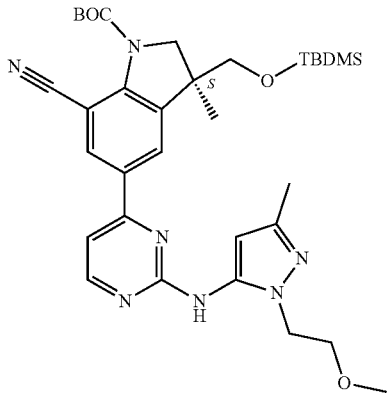<br>From intermediate 6S and 1-(2-Methoxyethyl)-3-methyl-1H-pyrazol-5-amine | 1130 | 92 |

-continued
| Int. number | Structure | Mass (mg) | Yield (%) |
|---|---|---|---|
| Intermediate 136 | 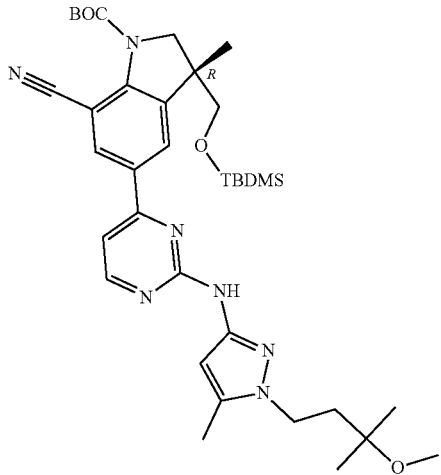<br>From intermediate 6R and intermediate 135 | 540 (88% purity based on LC/MS) | 72 |
| Intermediate 139 | 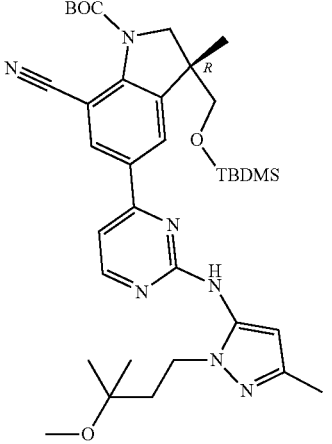<br>From intermediate 6R and intermediate 138 | 395 | 53 |
| Intermediate 143 | 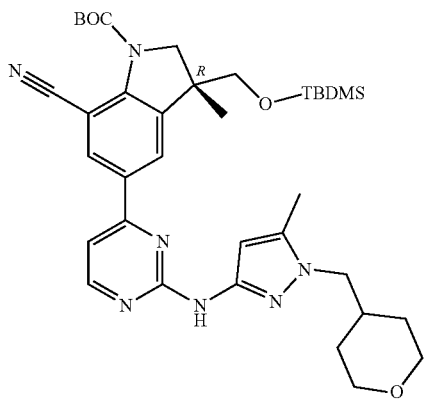<br>From intermediate 6R and intermediate 142 | 600 | 92 |

-continued

| Int. number | Structure | Mass (mg) | Yield (%) |
|---|---|---|---|
| Intermediate 146 | From intermediate 6R and intermediate 145 | 227 | 35 |
| Intermediate 148 | From intermediate 6R and 5-Methyl-2-(1-methyl-piperidine-4-yl)-2H-pyrazol-3-amine | 300 | 46 |
| Intermediate 150 | From intermediate 6R and 5-Methyl-2-(tetrahydropyran-4-yl)-2H-pyrazol-3-amine | 586 | 91 |

-continued
| Int. number | Structure | Mass (mg) | Yield (%) |
|---|---|---|---|
| Intermediate 152 | 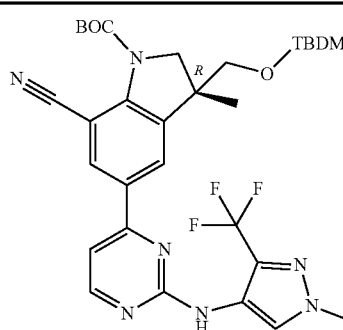<br>From intermediate 6R and 1-methyl-3-trifluoromethyl-1H-pyrazol-4-ylamine | 320 | 21 |
| Intermediate 154 | 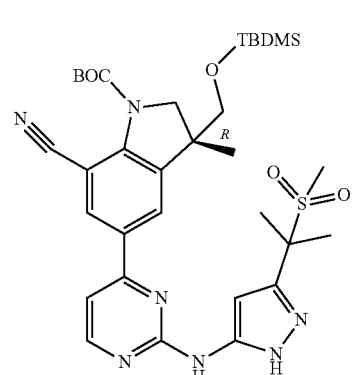<br>From intermediate 6R and 3-[1-methyl-1-(methylsulfonyl)ethyl]-1H-pyrazol-5-amine | 107 | 16 |
| Intermediate 157 | 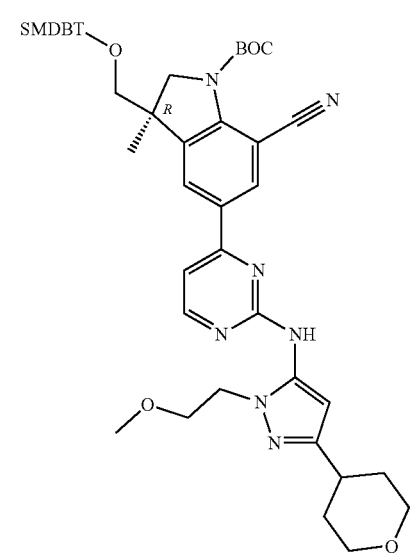<br>From int. 6R and int. 156 | 410 | 94 |

-continued
| Int. number | Structure | Mass (mg) | Yield (%) |
|---|---|---|---|
| Intermediate 160 | 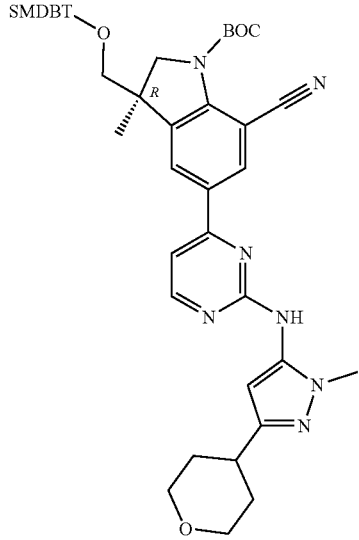<br>From intermediate 6R and intermediate 159 | 618 | 96 |
| Intermediate 164 | 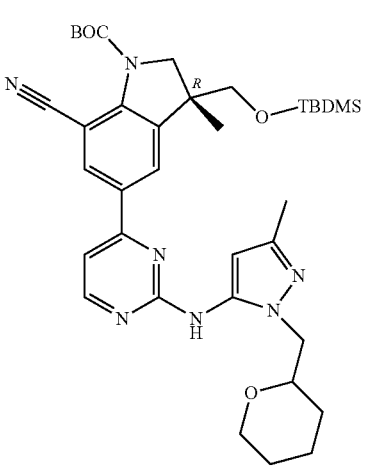<br>From intermediate 6R and intermediate 163 | 830 | 63 |
| Intermediate 167 | 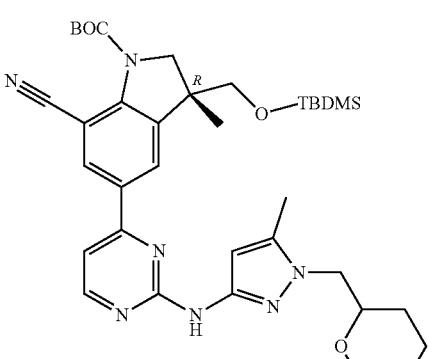<br>From intermediate 6R and intermediate 166 | 814 | 62 |

-continued
| Int. number | Structure | Mass (mg) | Yield (%) |
|---|---|---|---|
| Intermediate 168 | 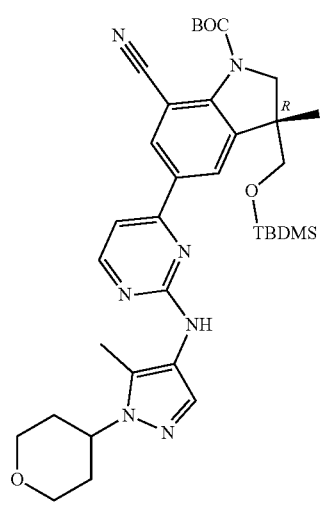<br>From intermediate 6R and 1-methyl-3-(tetrahydro-2H-pyran-4-yl)-1H-pyrazol-5-amine | 350 (47% purity based on LC/MS) | 31 |
| Intermediate 172 | 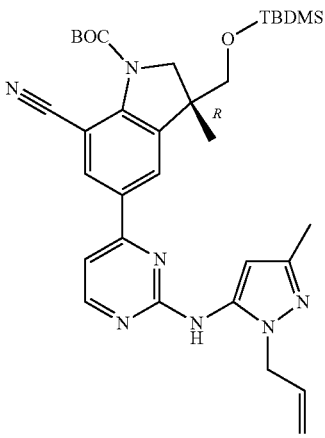<br>From intermediate 6R and intermediate 171 | 545 (63% purity based on LC/MS) | 91 |

| Int. number | Structure | Mass (mg) | Yield (%) |
|---|---|---|---|
| Intermediate 174 | 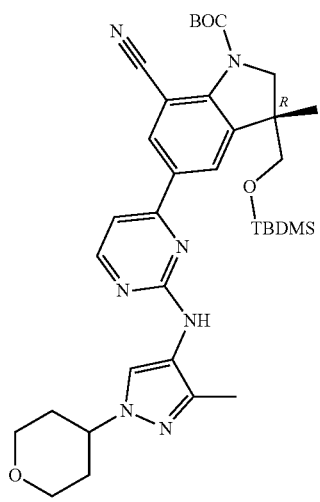 From intermediate 6R and 1-methyl-3-(tetrahydro-2H-pyran-4-yl)-1H-pyrazol-5-amine | 275 | 25 |
| Intermediate 178 | 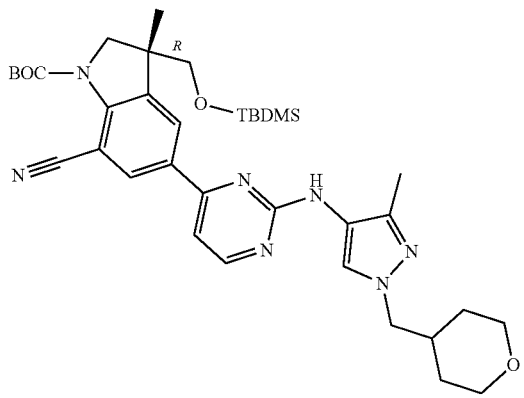 From intermediate 6R and intermediate 177 | 375 (76% purity based on LC/MS) | 25 |

-continued

| Int. number | Structure | Mass (mg) | Yield (%) |
|---|---|---|---|
| Intermediate 180 | From intermediate 6R and intermediate 177' | 455 (44% purity based on LC/MS) | 31 |
| Intermediate 193 Mixture of 2 diastereoisomers | From intermediate 6R and intermediate 192 | 680 | 53 |
| Intermediate 201 Mixture of 2 diastereoisomers | From intermediate 6R and intermediate 200 | 1170 (66% purity based on LC/MS) | 52 |

| Int. number | Structure | Mass (mg) | Yield (%) |
|---|---|---|---|
| Intermediate 203 | 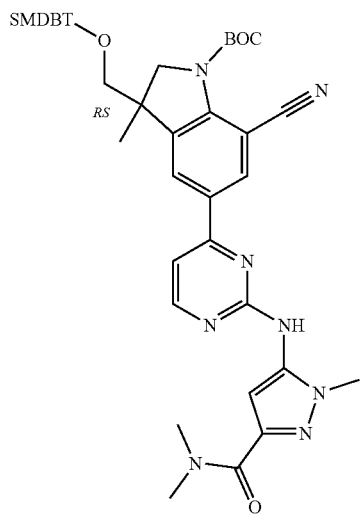<br>From intermediate 6R and 5-amino-N,N,1-trimethyl-1H-pyrazole-3-carboxamide | 365 | 63 |
| Intermediate 215 | 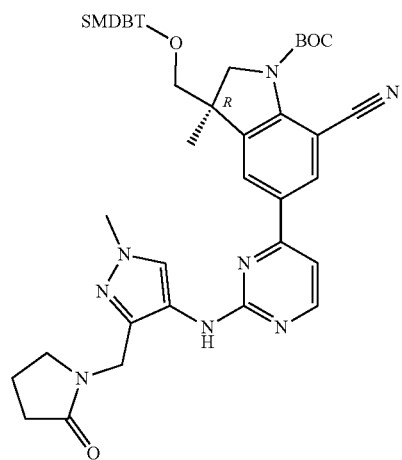<br>From int. 6R and int. 214 | 288 | 55 |

| Int. number | Structure | Mass (mg) | Yield (%) |
|---|---|---|---|
| Intermediate 217 | 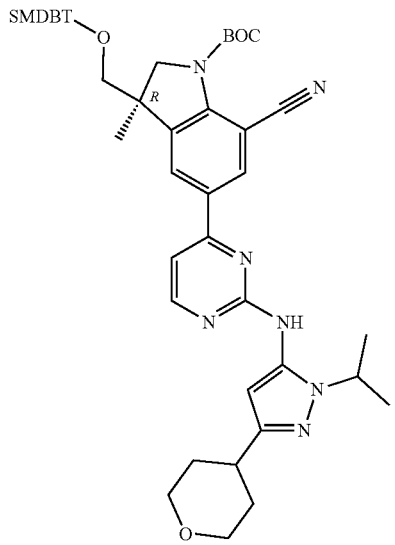<br>From intermediate 6R and 1-(1-methylethyl)-3-(tetrahydro-2H-pyran-4-yl)-1H-pyrazol-5-amine | 380 (89% purity based on LC/MS) | 63 |
| Intermediate 230<br>Mixture of 2 diastereoisomers | 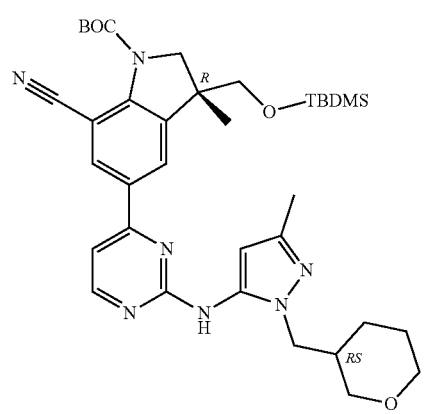<br>From intermediate 6R and intermediate 229 | 1050 (77% purity based on LC/MS) | 80 |
| Intermediate 257 | 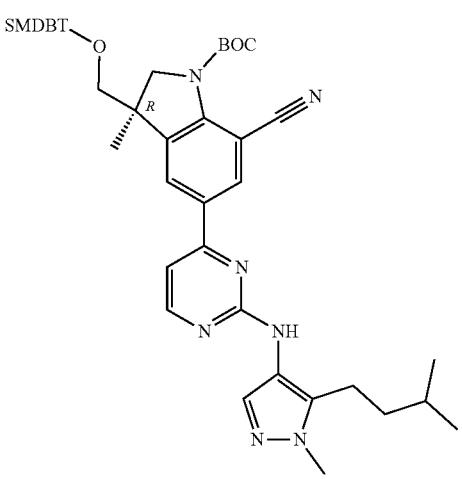<br>From intermediate 6R and intermediate 255 | 75 | 15 |

| Int. number | Structure | Mass (mg) | Yield (%) |
|---|---|---|---|
| Intermediate 259 | 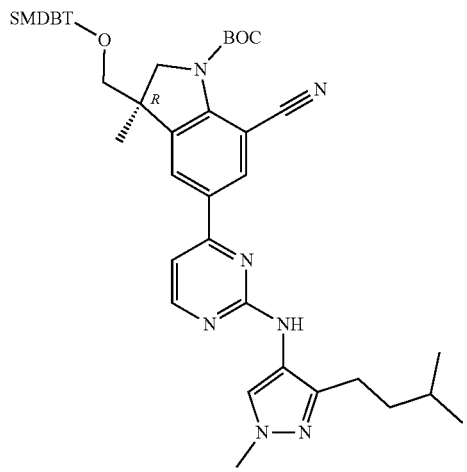 From intermediate 6R and intermediate 256 | 195 | 38 |
| mixture of Intermediate 265 and intermediate 266 | 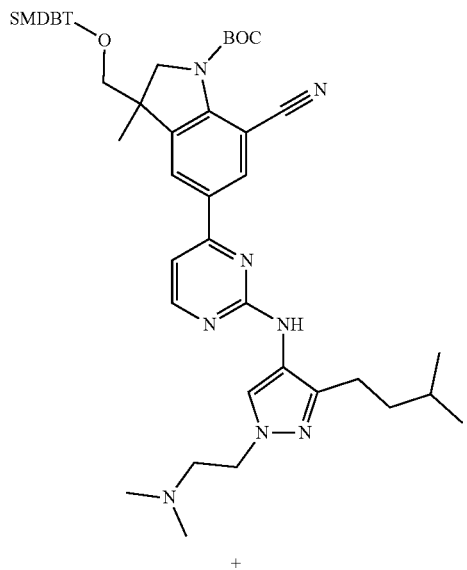 + | 340 | 62 |

| Int. number | Structure | Mass (mg) | Yield (%) |
|---|---|---|---|
| | 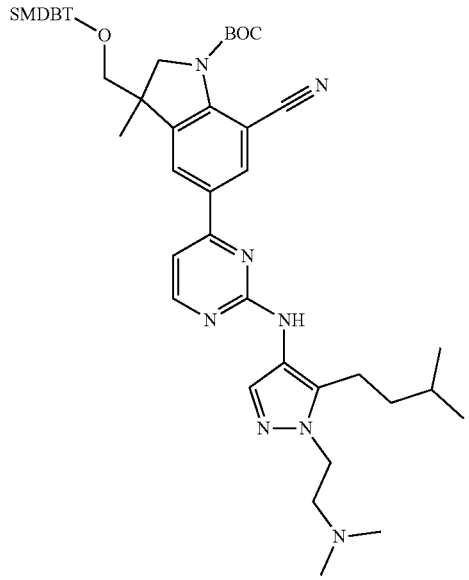 From intermediate 6R and intermediates 263/264 | | |
| Intermediate 271 | 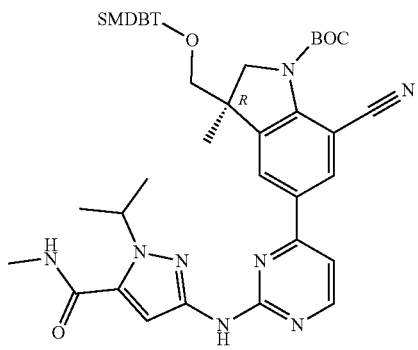 From intermediate 6R and intermediate 270 | 880 | 98 |
| Intermediate 294 | 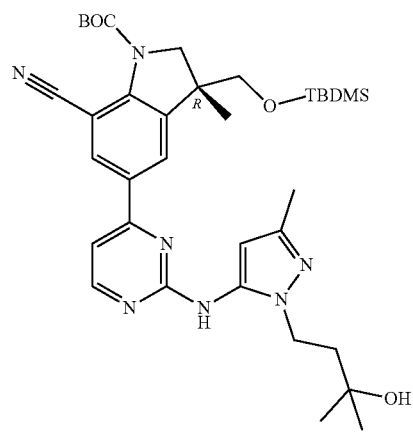 From intermediate 6R and intermediate 293 | 790 | 61 |

-continued
| Int. number | Structure | Mass (mg) | Yield (%) |
|---|---|---|---|
| Intermediate 297 | 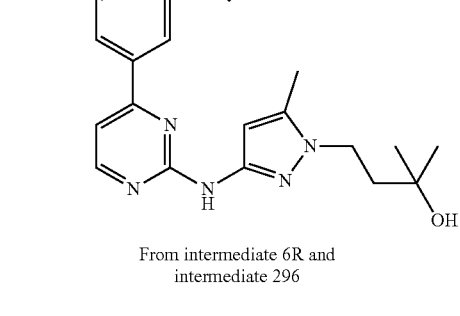<br>From intermediate 6R and intermediate 296 | 430 (75% purity based on LC/MS) | 50 |
| Intermediate 353 | 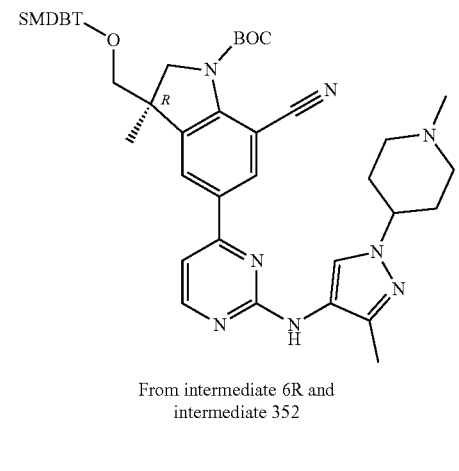<br>From intermediate 6R and intermediate 352 | 245 | 39 |
| Intermediate 356 | 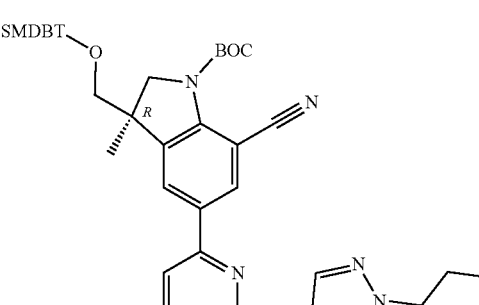<br>From intermediate 6R and intermediate 355 | 290 | 63 |

-continued

| Int. number | Structure | Mass (mg) | Yield (%) |
|---|---|---|---|
| Intermediate 392 | From int. 6R and int. 391 | 630 | 51 |
| Intermediate 396 | From intermediate 6R and intermediate 395 | 1050 brown residue | 71 |
| Intermediate 411 | From intermediate 6R and intermediates 410 | 135 | 31 |

| Int. number | Structure | Mass (mg) | Yield (%) |
|---|---|---|---|
| Intermediate 415 | 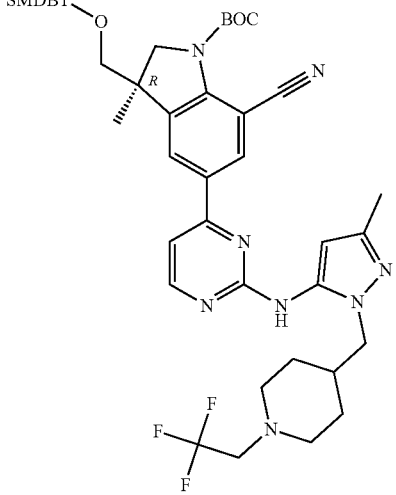<br>From intermediate 6R and intermediates 414 | 711 | 88 |
| Intermediate 437 | 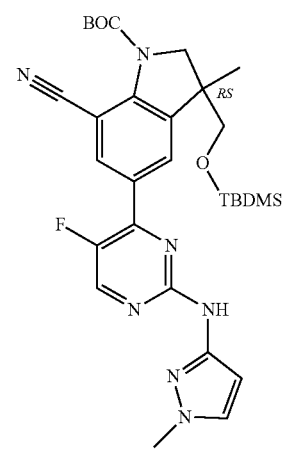<br>From intermediate 436 and 1-methyl-1H-pyrazol-3-amine | 382 | 86 |
| Intermediate 440 | 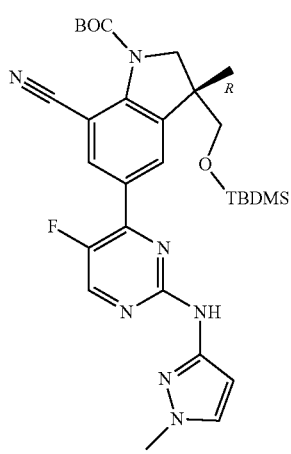<br>From intermediate 439 and 1-methyl-1H-pyrazol-3-amine | 335 | 75 |

-continued

| Int. number | Structure | Mass (mg) | Yield (%) |
|---|---|---|---|
| Intermediate 454 | From intermediate 6R and intermediate 453 | 266 (73% purity based on LC/MS) | 85 |
| Intermediate 473 | From intermediate 6R and intermediate 472 | 517 | 61 |
| Intermediate 493 | From int. 6R and int. 492 | 900 (78% purity based on LC/MS) | 98 |

-continued

| Int. number | Structure | Mass (mg) | Yield (%) |
|---|---|---|---|
| Intermediate 497 | From int. 6R and int. 496 | 120 | 64 |
| Intermediate 510 | From int. 6R and int. 509 | 343 | 59 |
| Intermediate 515 | From int. 6R and int. 514 | 675 | Quant. |

| Int. number | Structure | Mass (mg) | Yield (%) |
|---|---|---|---|
| Intermediate 519 | From int. 6R and int. 518 | 565 | 77 |
| Intermediate 523 | From int. 6 and int. 522 | 247 | 34 |
| Intermediate 527 | From int. 6 and int. 526 | 270 | 34 |

| Int. number | Structure | Mass (mg) | Yield (%) |
|---|---|---|---|
| Intermediate 531 | 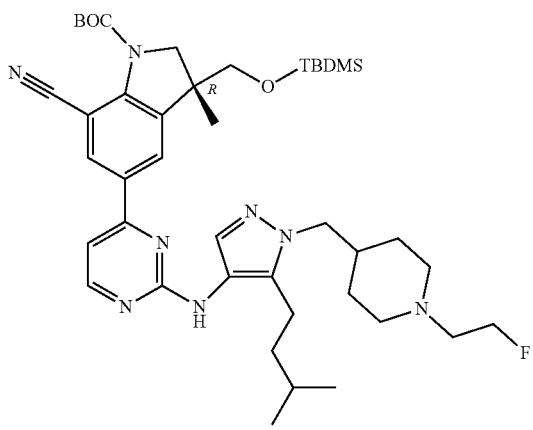 From intermediate 530 | 258 | 25 |
| Intermediate 535 | 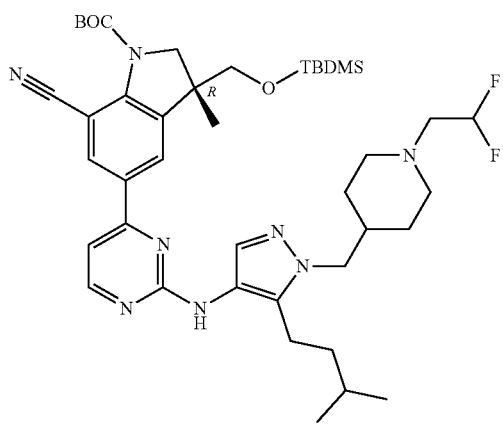 From intermediate 534 | 170 | 50 |
| Intermediate 539 | 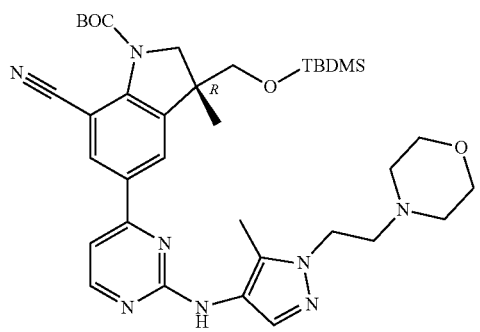 From intermediate 538 | 479 | 64 |

-continued

| Int. number | Structure | Mass (mg) | Yield (%) |
|---|---|---|---|
| Intermediate 543 | From intermediate 542 | 870 | Quant. |
| Intermediate 547 | From intermediate 546 | 368 | 53 |
| Intermediate 570 | From intermediate 6R and intermediate 568 | 3800 | 81 |

| Int. number | Structure | Mass (mg) | Yield (%) |
|---|---|---|---|
| Intermediate 571 | 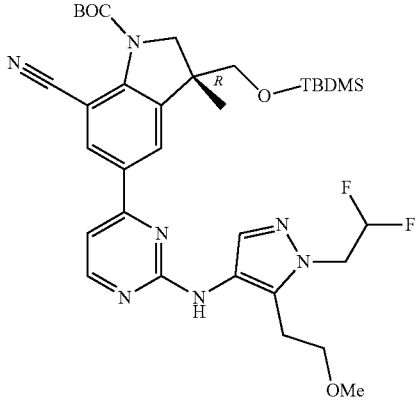 From intermediate 6R and intermediate 569 | 235 | 59 |
| Intermediate 575 | 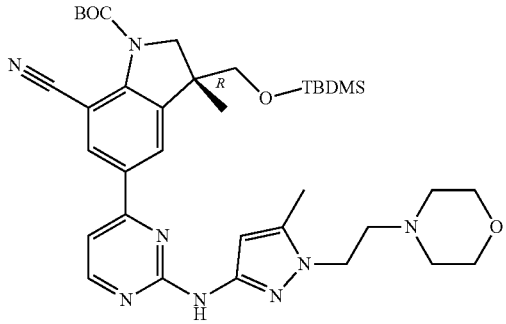 From intermediate 6R and intermediate 576 | 215 | 41 |
| Intermediate 586 | 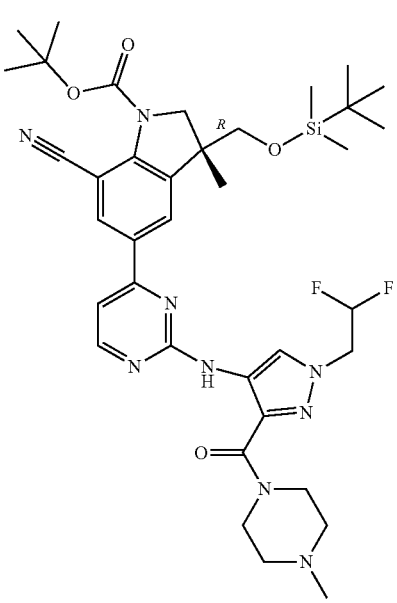 From intermediate 6R and intermediate 585 | 142 | 62 |

| Int. number | Structure | Mass (mg) | Yield (%) |
|---|---|---|---|
| Intermediate 589 | From intermediate 6R and intermediate 588 | 170 (80% purity based on LC/MS) | 66 |
| Intermediate 593 | From intermediate 6R and intermediate 592 | 810 | 83 |
| Intermediate 599 | From intermediate 6R and intermediate 598 | 680 (86% purity based on LC/MS) | 100 |

| Int. number | Structure | Mass (mg) | Yield (%) |
|---|---|---|---|
| Intermediate 603 | 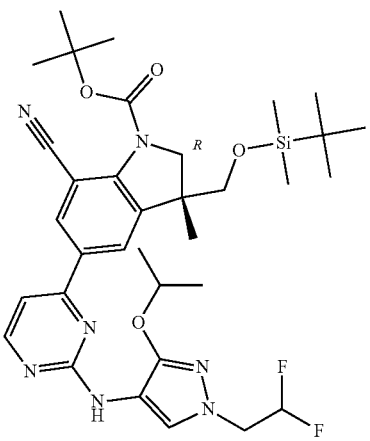<br>From intermediate 6R and intermediate 602 | 440 | 66 |
| Intermediate 608 | 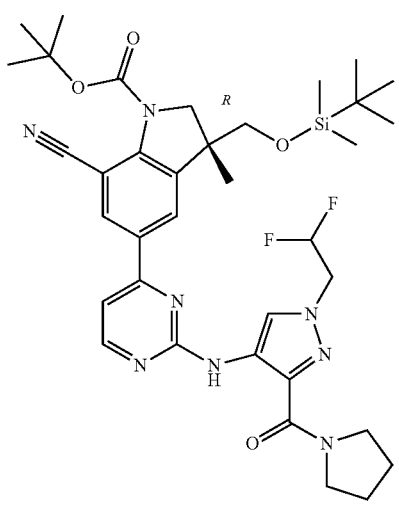<br>From intermediate 6R and intermediate 607 | 350 | 63 |
| Intermediate 614 | 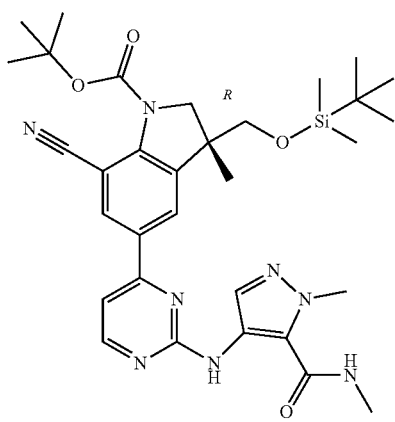<br>From intermediate 6R and intermediate 613 | 280 | 43 |

-continued
| Int. number | Structure | Mass (mg) | Yield (%) |
|---|---|---|---|
| Intermediate 618 | 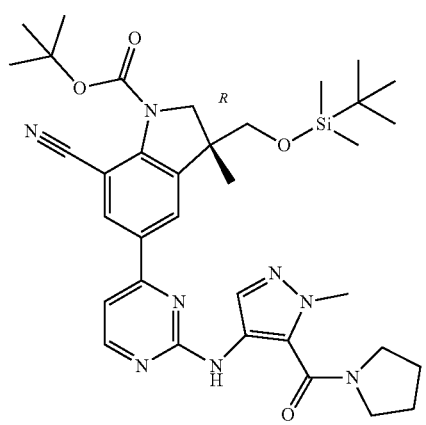<br>From intermediate 6R and intermediate 617 | 293 | 89 |
| Intermediate 622 | 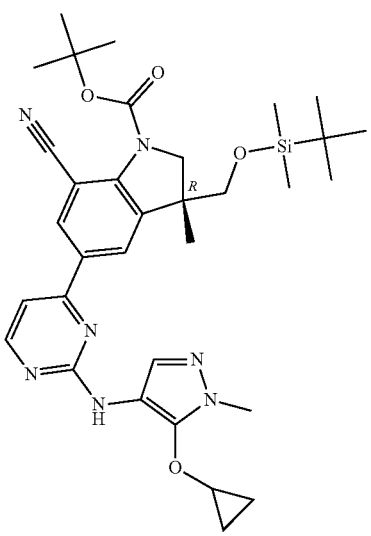<br>From intermediate 6R and intermediate 621 | 230 | 31 |

-continued
| Int. number | Structure | Mass (mg) | Yield (%) |
|---|---|---|---|
| Intermediate 626 | 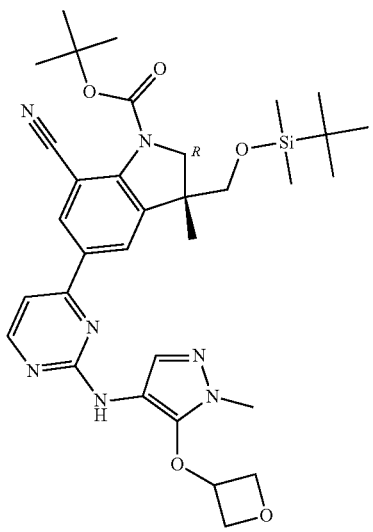<br>From intermediate 6R and intermediate 625 | 80 | 16 |
| Intermediate 630 | 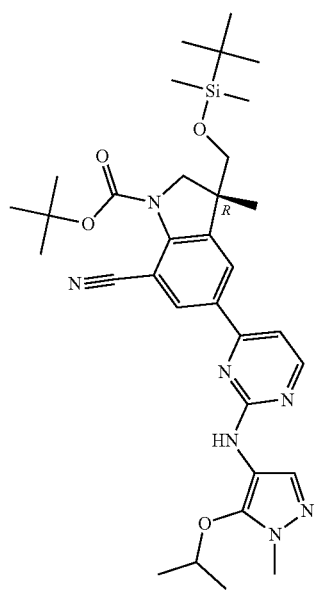<br>From intermediate 6R and intermediate 629 | 720 | 90 |

| Int. number | Structure | Mass (mg) | Yield (%) |
|---|---|---|---|
| Intermediate 638 | From intermediate 6R and intermediate 637 | 233 (92% purity based on LC/MS) | 87 |
| Intermediate 648 | 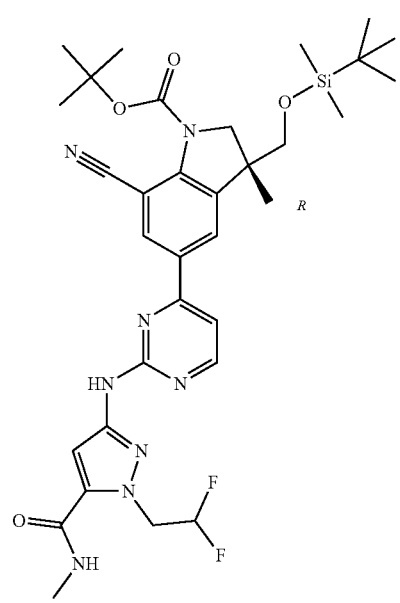<br>From intermediate 6R and intermediate 647 | 819 (53% purity based on LC/MS) | 100 |

-continued
| Int. number | Structure | Mass (mg) | Yield (%) |
|---|---|---|---|
| Intermediate 653 | From intermediate 6R and intermediate 652 | 182 (72% purity based on LC/MS) | 93 |
| Intermediate 660 | 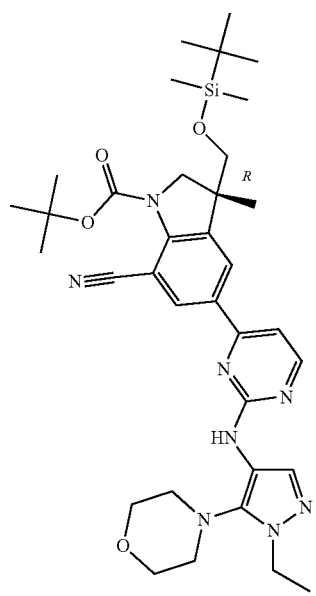<br>From intermediate 6R and intermediate 659 | 540 | 83 |

-continued
| Int. number | Structure | Mass (mg) | Yield (%) |
|---|---|---|---|
| Intermediate 664 | 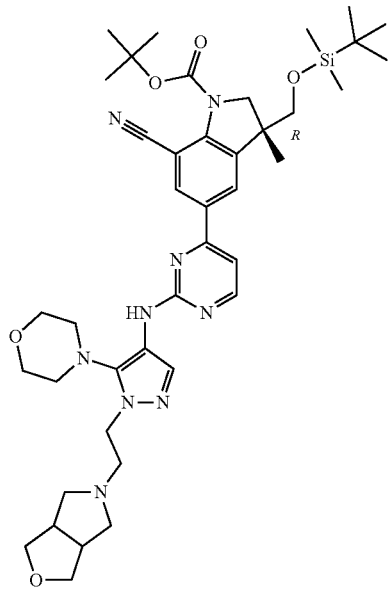<br>From intermediate 6R and intermediate 663 | 420 | 68 |
| Intermediate 670 | 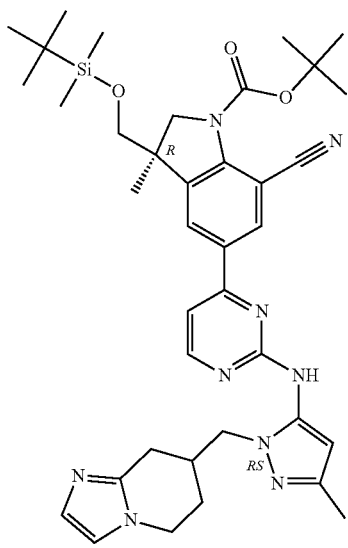<br>From intermediate 6R and intermediate 669 | 240 (85% purity based on LC/MS) | 17 |

| Int. number | Structure | Mass (mg) | Yield (%) |
|---|---|---|---|
| Intermediate 676 | 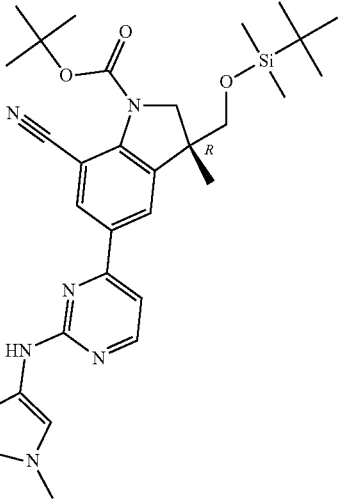<br>From intermediate 6R and intermediate 675 | 510 | 75 |
| Intermediate 682 | 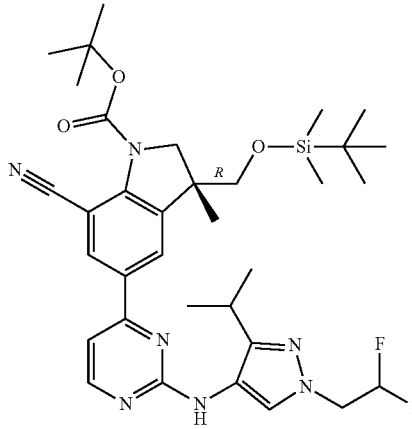<br>From intermediate 6R and intermediate 681 | 816 (81% purity based on LC/MS) | 90 |
| Intermediate 688 | 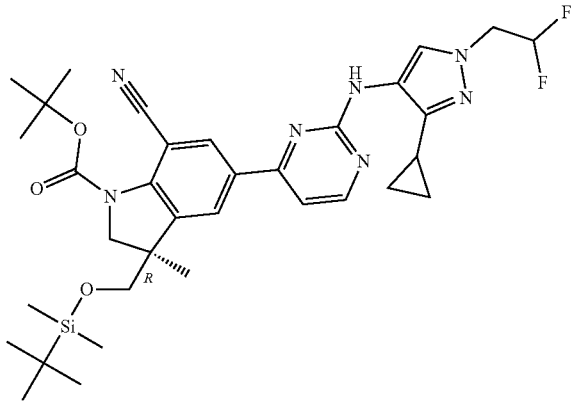<br>From intermediate 6R and intermediate 687 | 227 | 76 |

-continued
| Int. number | Structure | Mass (mg) | Yield (%) |
|---|---|---|---|
| Intermediate 690 | 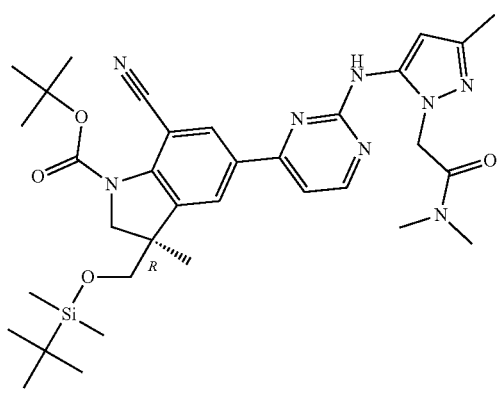<br>From intermediate 6R and intermediate 44 | 600 | 70 |
| Intermediate 694 | 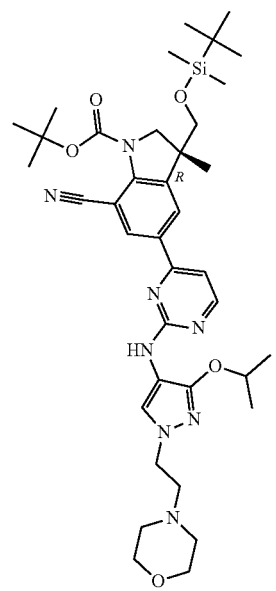<br>From intermediate 6R and intermediate 693 | 440 | 76 |

-continued

| Int. number | Structure | Mass (mg) | Yield (%) |
|---|---|---|---|
| Intermediate 705 | From intermediate 6R and intermediate 704 | 405 | 47 |
| Intermediate 710 | From intermediate 6R and intermediate 709 | 180 | 18 |
| Intermediate 716 | From intermediate 6R and intermediate 715 | 103 | 24 |

-continued
| Int. number | Structure | Mass (mg) | Yield (%) |
|---|---|---|---|
| Intermediate 719 | 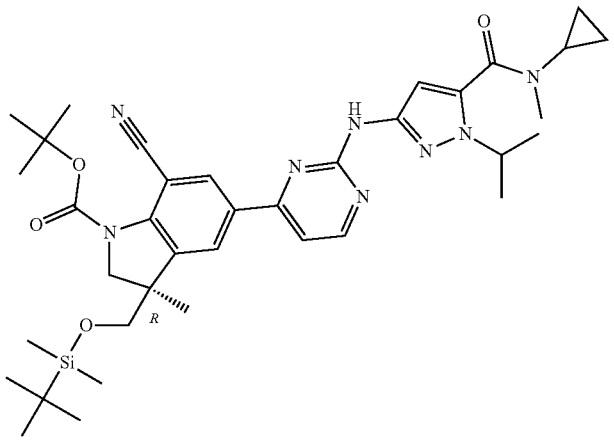 From intermediate 6R and intermediate 718 | 550 | 100 |
| Intermediate 727 | 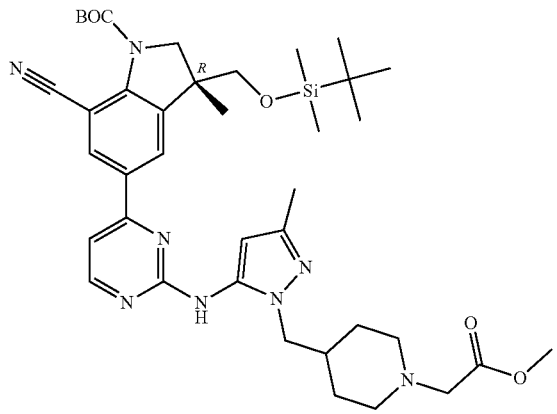 From intermediate 6R and intermediate 726 | 266 | 53 |
| Intermediate 765 | 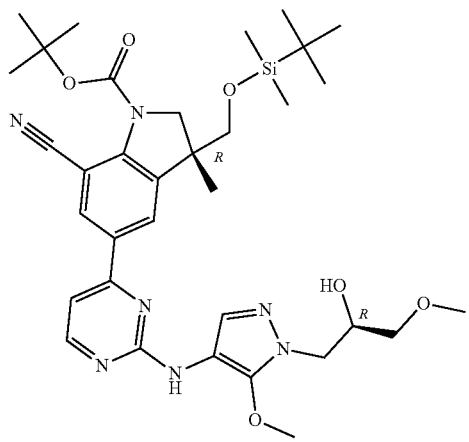 From intermediate 6R and intermediate 764 | 260 (74% purity based on LC/MS) | 92 |

Example A7

Preparation of Intermediate 306

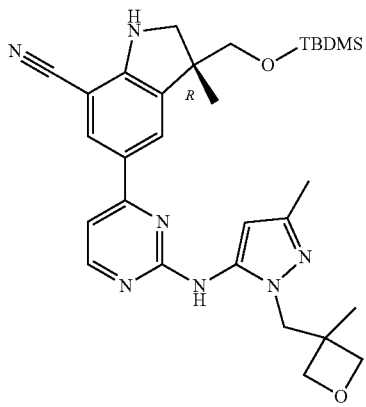

In a sealed tube, a solution of intermediate 305 (350.00 mg, 0.84 mmol), intermediate 304 (275.12 mg, 1.52 mmol) and $Cs_2CO_3$ (686.90 mg, 2.11 mmol) in dry Me-THF (8.40 mL) was purged with $N_2$. $Pd(OAc)_2$ (18.90 mg, 84.30 μmol) and BINAP (52.50 mg, 84.30 μmol) were added. The mixture was purged with $N_2$ and heated at 85° C. for 3 h. After cooling down to rt, the mixture was filtered over a pad of Celite®. The cake was washed with EtOAc and the filtrate was evaporated in vacuo. The residue (752 mg, brown oil) was purified by column chromatography on silica gel (irregular SiOH, 15-40 m, 30 g, mobile phase: DCM/EtOAc, gradient from 100:0 to 50:50). The pure fractions were combined and evaporated to dryness to give 387 mg of intermediate 306 as an orange oil used as it in the next step.

The intermediates in the Table below were prepared by using an analogous method starting from the respective starting materials. The most relevant minor deviations to the referenced method are indicated as additional information in the column 'Yield (%)'

| Int. number | Structure | Mass (mg) | Yield (%) |
|---|---|---|---|
| Intermediate 470 | From intermediate 305 | 323 | 71 |
| Intermediate 505 | 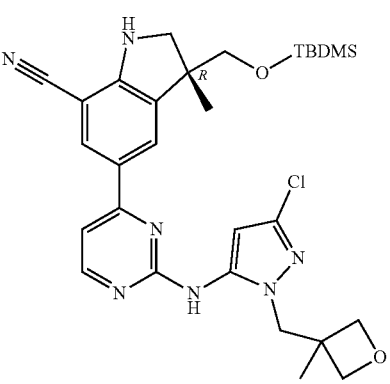<br>From intermediate 504 | 364 | 38 with T = 90° C. |

-continued

| Int. number | Structure | Mass (mg) | Yield (%) |
|---|---|---|---|
| Intermediate 581 | 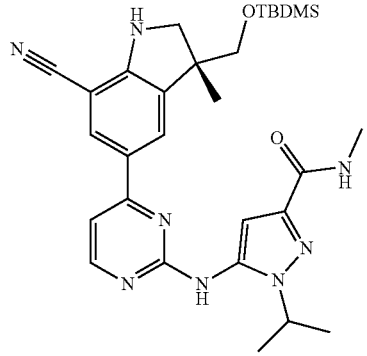<br>From intermediate 580 | 244<br><br>2410 (crude) | With T = 120° C.<br>26<br>25 |
| Intermediate 643 | 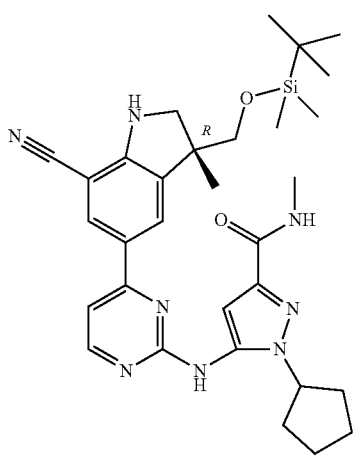<br>From intermediate 642 | 4000 | 54 |

Example A8

Preparation of Intermediate 343

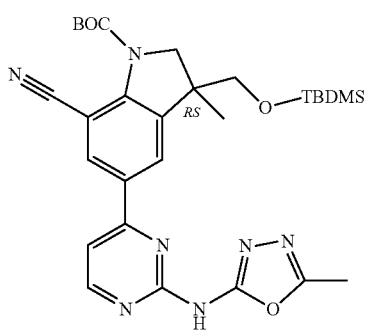

In a sealed tube, a mixture of intermediate 6 (0.30 g, 0.58 mmol), 5-methyl-1,3,4-oxadiazol-2-ylamine (63.50 mg, 0.64 mmol) and $Cs_2CO_3$ (569.00 mg, 1.75 mmol) in THF (6 mL) was purged with $N_2$. Then, chloro[2-(dicyclohexylphosphino)-3,6-dimethoxy-2',4',6'-triisopropyl-1,1'-biphenyl][2-(2-aminoethyl)phenyl] palladium (II) (47.00 mg, 58.20 μmol) and BRETTPHOS (31.00 mg, 58.20 μmol) were added. The mixture was purged with $N_2$ and stirred at 95° C. for 5 h 30 min. Further chloro[2-(dicyclohexylphosphino)-3,6-dimethoxy-2',4',6'-triisopropyl-1,1'-biphenyl][2-(2-aminoethyl)phenyl] palladium (II) (47.00 mg, 58.20 μmol) and BRETTPHOS (31.00 mg, 58.20 μmol) were added and the mixture was purged again with $N_2$ and stirred at 95° C. for 20 h. The reaction mixture was diluted with EtOAc and water. The layers were separated and the aqueous layer was extracted twice with EtOAc. The combined organic layers were dried over $MgSO_4$, filtered and the solvent was removed under reduced pressure to give intermediate 343 as a brown solid used as it in the next step.

The intermediates in the Table below were prepared by using an analogous method starting from the respective starting materials. The most relevant minor deviations to the referenced method are indicated as additional information in the column 'Yield (%)'.

| Int. number | Structure | Mass (mg) | Yield (%) |
|---|---|---|---|
| Intermediate 31 | 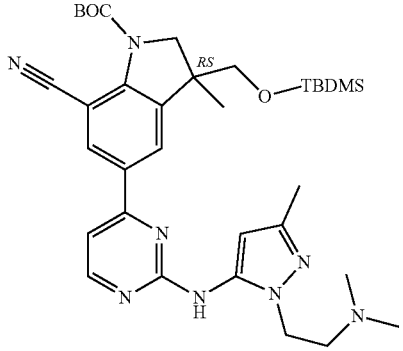 From intermediate 6 and 2-(2-dimethylaminoethyl)-5-methyl-2H-pyrazole-3-ylamine | 259 | 41 with T = 90° C. |

Example A9

Preparation of Intermediate 8

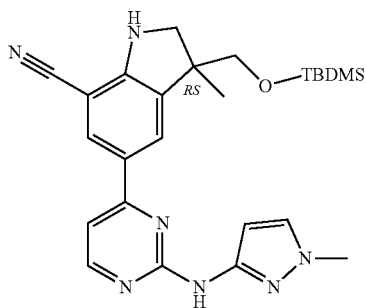

A mixture of intermediate 7 (2.96 g, 3.86 mmol) in a mixture of TFA (7 mL) and DCM (40 mL) was stirred at rt for 1 h and 20 min. The mixture was basified with a saturated aqueous solution of $NaHCO_3$. An extraction was performed with DCM. The organic layer was washed with brine, dried over $MgSO_4$, evaporated and purified by column chromatography on silica gel (irregular SiOH 15-40 m, 120 g, liquid injection with DCM, mobile phase: heptane/EtOAc, gradient from 100:0 to 0:100 in 15 CV). The fractions containing the product were combined and concentrated under vacuum to give 1.09 g of intermediate 8 (59% yield, white solid).

The intermediates in the Table below were prepared by using an analogous method starting from the respective starting materials. The most relevant minor deviations to the referenced method are indicated as additional information in the column 'Yield (%)'.

| Int. number | Structure | Mass (mg) | Yield (%) |
|---|---|---|---|
| Intermediate 14 | 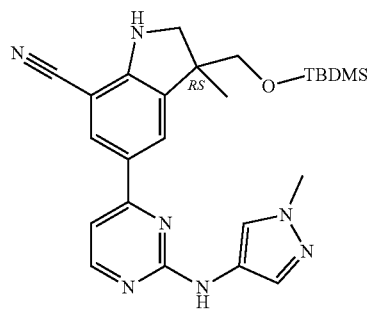 From intermediate 13 | 165 yellow solid | 36 Procedure with DCM/TFA (5:1, v/v) |

-continued

| Int. number | Structure | Mass (mg) | Yield (%) |
| --- | --- | --- | --- |
| Intermediate 22 | From intermediate 21 | 143 yellow solid | 57 Procedure with DCM/TFA (6.5:1, v/v) |
| Intermediate 34 | From intermediate 33 | 370 | — Procedure with DCM/TFA (4:1, v/v) |
| Mixture of Intermediate 37 and compound 14 | From intermediate 36 | 430 (64% purity based on LC/MS; int. 37/ comp. 14 34/66) | — Procedure with DCM/TFA (5:2, v/v) |

-continued

| Int. number | Structure | Mass (mg) | Yield (%) |
| --- | --- | --- | --- |
| Intermediate 41 | From intermediate 40 | 385 (72% purity based on LC/MS) | 92 Procedure with DCM/TFA (5:1, v/v) |
| Intermediate 43 | From intermediate 42 | 333 | 83 Procedure with DCM/TFA (4:1, v/v) |
| Intermediate 47 | From intermediate 46 | 350 white solid | 25 Procedure with DCM/TFA (5:1, v/v) |

-continued

| Int. number | Structure | Mass (mg) | Yield (%) |
| --- | --- | --- | --- |
| Intermediate 49 | From intermediate 48 | 264 (88% purity based on LC/MS) | 62 Procedure with DCM/TFA (4:1, v/v) |
| Intermediate 51 | From intermediate 50 | 256 yellow solid | 82 Procedure with DCM/TFA (3:1, v/v) |
| Intermediate 55 | From intermediate 54 | 107 | 56 Procedure with DCM/TFA (6:1, v/v) |

269                                                                                                    270
-continued
| Int. number | Structure | Mass (mg) | Yield (%) |
|---|---|---|---|
| Intermediate 59 | 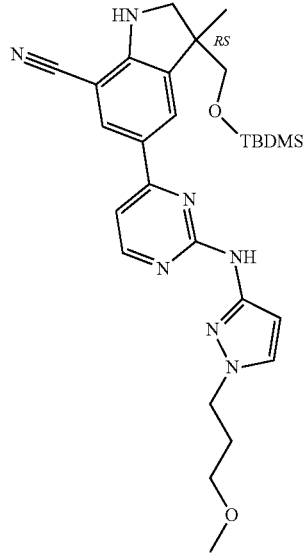<br>From intermediate 58 | 343<br>(87% purity based on LC/MS) | 79<br>Procedure with DCM/TFA (5:1, v/v) |
| Intermediate 61 | 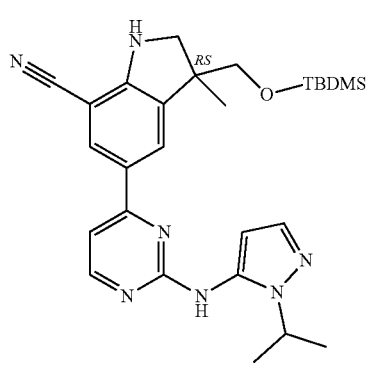<br>From intermediate 60 | 291 | 63 |
| Intermediate 64 | 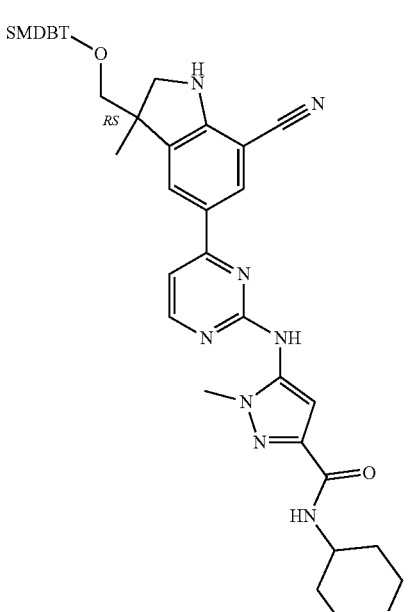<br>From intermediate 63 | 123 | 47<br>Procedure with DCM/TFA (5:2, v/v) |

-continued

| Int. number | Structure | Mass (mg) | Yield (%) |
| --- | --- | --- | --- |
| Intermediate 69 | From intermediate 68 | 225 | 74 |
| Intermediate 72 | From intermediate 71 | 112 | 61<br>Procedure with DCM/TFA (7:1, v/v) |
| Intermediate 74 | From intermediate 73 | 350<br>(82% purity based on LC/MS) | 74<br>Procedure with DCM/TFA (4:1, v/v) |

-continued

| Int. number | Structure | Mass (mg) | Yield (%) |
|---|---|---|---|
| Intermediate 76 | (structure: 7-cyano-3-methyl-3-((TBDMS-oxy)methyl)indoline coupled via phenyl to pyrimidine-NH-pyrazole-N-CH2CHF2, RS) From intermediate 75 | 100 | 27 Procedure with DCM/TFA (4:1, v/v) |
| Intermediate 78 | (structure: SMDBT-O-CH2-3-methyl-indoline(S)-7-cyano, coupled to pyrimidine-NH-pyrazole-N-isopropyl) From intermediate 77 | 112 | 24 |
| Intermediate 80 | (structure: 7-cyano-3-methyl-3-((TBDMS-oxy)methyl)indoline, RS, coupled via phenyl to pyrimidine-NH-(4-chloro-1-methyl-pyrazol-3-yl)) From intermediate 79 | 270 | 73 Procedure with DCM/TFA (4:1, v/v) |

-continued
| Int. number | Structure | Mass (mg) | Yield (%) |
|---|---|---|---|
| Intermediate 82 | 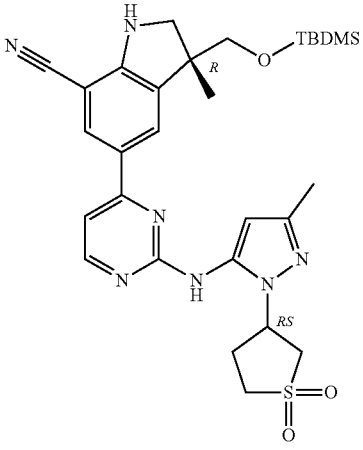<br>From intermediate 81 | 177 | 50<br>Procedure with DCM/TFA (4:1, v/v) |
| Intermediate 86 | 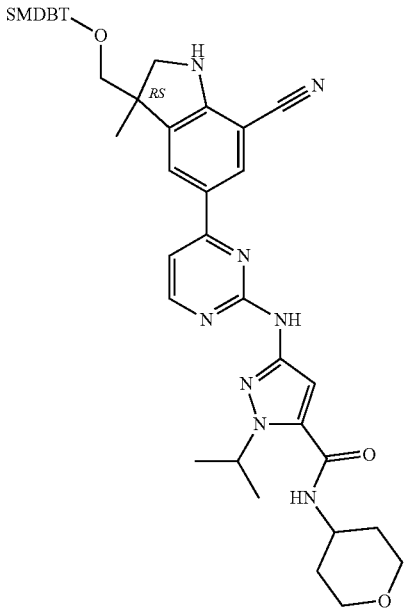<br>From intermediate 85 | 237 | 71 |
| Intermediate 88 | 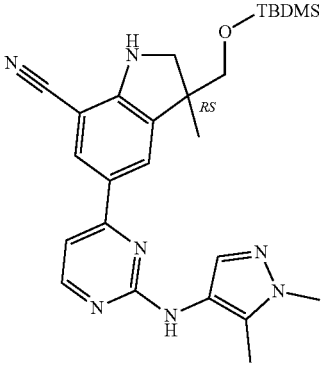<br>From intermediate 87 | 108 | 32<br>Procedure with DCM/TFA (5:1, v/v) |

-continued

| Int. number | Structure | Mass (mg) | Yield (%) |
|---|---|---|---|
| Intermediate 90 | 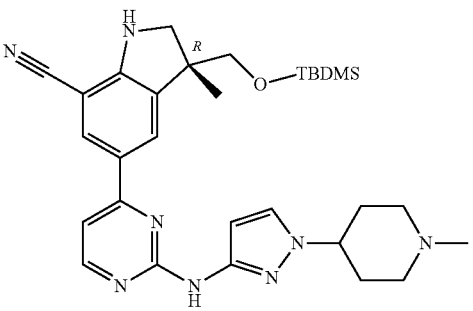 From intermediate 89 | 160 (86% purity based on LC/MS) | 46 Procedure with DCM/TFA (4:1, v/v) |
| Intermediate 91 | 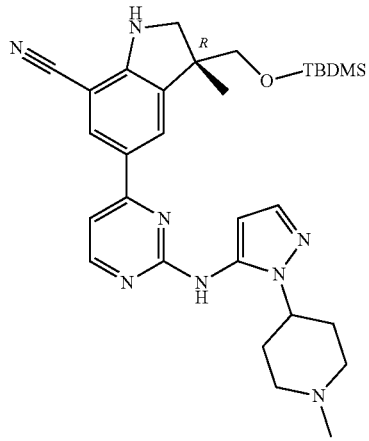 From intermediate 91 | 210 (47% purity based on LC/MS) | — Procedure with DCM/TFA (4:1, v/v) |
| Intermediate 94 | 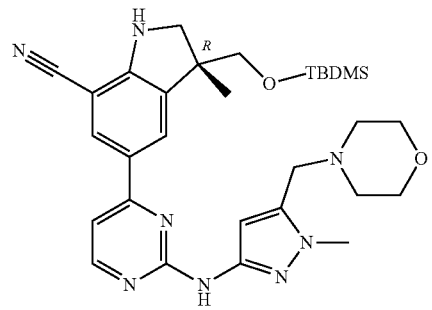 From intermediate 93 | 419 (82% purity based on LC/MS) | 76 Procedure with DCM/TFA (4:1, v/v) |
| Intermediate 96 | 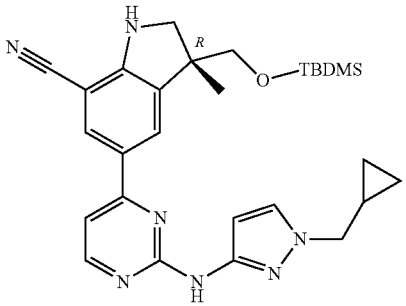 From intermediate 95 | 300 (73% purity based on LC/MS) | 66 Procedure with DCM/TFA (4:1, v/v) |

| Int. number | Structure | Mass (mg) | Yield (%) |
|---|---|---|---|
| Intermediate 98 | From intermediate 97 | 132 yellow oil | 48 Procedure with DCM/TFA (9:2, v/v) |
| Intermediate 100 | From intermediate 99 | 2720 | 58 Procedure with DCM/TFA (9:2, v/v) |
| Intermediate 102 | From intermediate 101 | 220 | Quant. Procedure with DCM/TFA (4:1, v/v) |
| Intermediate 105 | From intermediate 104 | 210 | 81 Procedure with DCM/TFA (4:1, v/v) |

| Int. number | Structure | Mass (mg) | Yield (%) |
|---|---|---|---|
| Intermediate 107 | From intermediate 106 | 349 | 77 Procedure with DCM/TFA (7:1, v/v) |
| Intermediate 109 | From intermediate 108 | 1240 (80% purity based on LC/MS) | 64 Procedure with DCM/TFA (4:1, v/v) |
| Intermediate 111 | From intermediate 110 | 761 | 92 Procedure with DCM/TFA (4:1, v/v) |

-continued

| Int. number | Structure | Mass (mg) | Yield (%) |
|---|---|---|---|
| Intermediate 113 | From intermediate 112 | 146 | 76 Procedure with DCM/TFA (7:1, v/v) |
| Intermediate 117 | From intermediate 116 | 24000 | 80 Procedure with DCM/TFA (4:1, v/v) |

-continued

| Int. number | Structure | Mass (mg) | Yield (%) |
|---|---|---|---|
| Intermediate 120 | From intermediate 119 | 118 | 48 Procedure with DCM/TFA (5:1, v/v) |
| Intermediate 123 | From intermediate 122 | 810 | 95 Procedure with DCM/TFA (4:1, v/v) |
| Intermediate 125 | From intermediate 124 | 273 | 50 Procedure with DCM/TFA (8:1, v/v) |

-continued

| Int. number | Structure | Mass (mg) | Yield (%) |
| --- | --- | --- | --- |
| Intermediate 127 | From intermediate 126 | 676 | 63 Procedure with DCM/TFA (4:1, v/v) |
| Intermediate 129 | From intermediate 128 | 171 | 55 Procedure with DCM/TFA (4:1, v/v) |
| Intermediate 131 | From intermediate 130 | 72 (71% purity based on LC/MS) | 26 |

-continued

| Int. number | Structure | Mass (mg) | Yield (%) |
|---|---|---|---|
| Intermediate 133 | From intermediate 132 | 634 89% purity based on LC/MS) | 67 Procedure with DCM/TFA (4:1, v/v) |
| Intermediate 137 | From intermediate 136 | 370 | 91 Procedure with DCM/TFA (4:1, v/v) |
| Intermediate 140 | From intermediate 139 | 227 | 67 Procedure with DCM/TFA (4:1, v/v) |

| Int. number | Structure | Mass (mg) | Yield (%) |
|---|---|---|---|
| Intermediate 144 | From intermediate 143 | 296 (64% purity based on LC/MS) | 58 Procedure with DCM/TFA (4:1, v/v) |
| Intermediate 147 | From intermediate 146 | 218 | 54 Procedure with DCM/TFA (4:1, v/v) |
| Intermediate 149 | From intermediate 148 | 169 | 66 Procedure with DCM/TFA (4:1, v/v) |

-continued

| Int. number | Structure | Mass (mg) | Yield (%) |
|---|---|---|---|
| Intermediate 151 | From intermediate 150 | 354 | 71 Procedure with DCM/TFA (4:1, v/v) |
| Intermediate 153 | From intermediate 152 | 179 | 66 Procedure with DCM/TFA (13:2, v/v) |
| Intermediate 155 | From intermediate 154 | 65 | 71 Procedure with DCM/TFA (8:1, v/v) |

-continued
| Int. number | Structure | Mass (mg) | Yield (%) |
|---|---|---|---|
| Intermediate 158 | 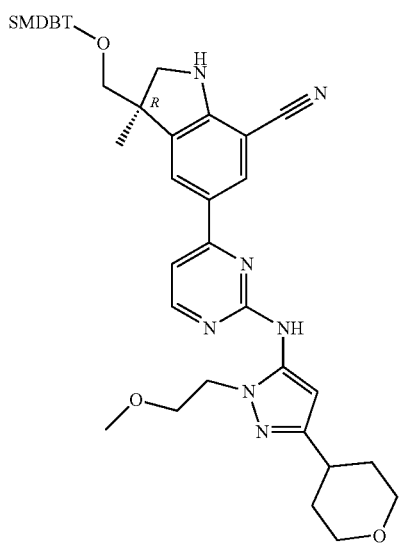<br>From intermediate 157 | 250 | 71<br>Procedure with DCM/TFA (9:1, v/v) |
| Intermediate 161 | 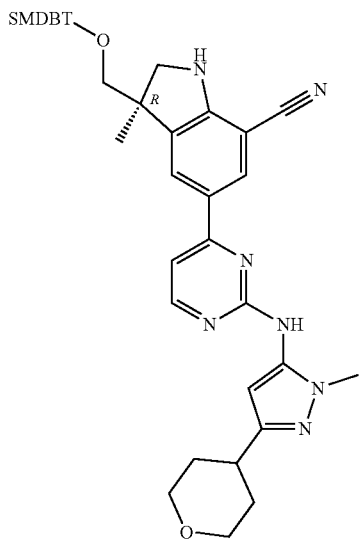<br>From intermediate 160 | 376 | 72<br>Procedure with DCM/TFA (4:1, v/v) |

| Int. number | Structure | Mass (mg) | Yield (%) |
|---|---|---|---|
| Intermediate 165 | From intermediate 164 | 47 | 58 Procedure with DCM/TFA (4:1, v/v) |
| Intermediate 167 | From intermediate 166 | 505 | 73 Procedure with DCM/TFA (4:1, v/v) |
| Intermediate 169 | From intermediate 168 | 110 (74% purity based on LC/MS) | 27 Procedure with DCM/TFA (4:1, v/v) |

-continued

| Int. number | Structure | Mass (mg) | Yield (%) |
|---|---|---|---|
| Intermediate 173 | From intermediate 172 | 195 (88% purity based on LC/MS) | 43 |
| Intermediate 175 | From intermediate 174 | 140 | 60 Procedure with DCM/TFA (4:1, v/v) |
| Intermediate 179 | From intermediate 178 | 205 | 64 Procedure with DCM/TFA (4:1, v/v) |

-continued

| Int. number | Structure | Mass (mg) | Yield (%) |
|---|---|---|---|
| Intermediate 181 | From intermediate 180 | 190 | 49 Procedure with DCM/TFA (4:1, v/v) |
| Intermediate 185 mixture of 2 diastereoisomers | From intermediate 184' | 260 | 55 Procedure with DCM/TFA (4:1, v/v) |
| Intermediate 188 | From intermediate 187 | 150 yellow oil | 41 Procedure with DCM/TFA (5:1, v/v) |

-continued
| Int. number | Structure | Mass (mg) | Yield (%) |
|---|---|---|---|
| Intermediate 190 | 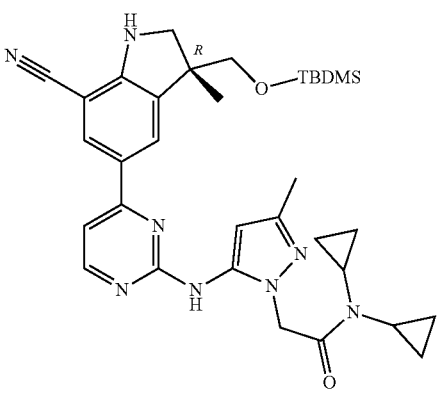<br>From intermediate 189 | 122<br>yellow oil | 82<br>Procedure with DCM/TFA (5:1, v/v) |
| Intermediate 194<br>Mixture of 2 disatereomers | 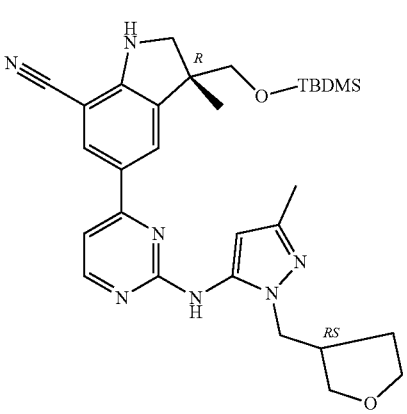<br>From intermediate 193 | 219 | 38<br>Procedure with DCM/TFA (4:1, v/v) |
| Intermediate 198 | 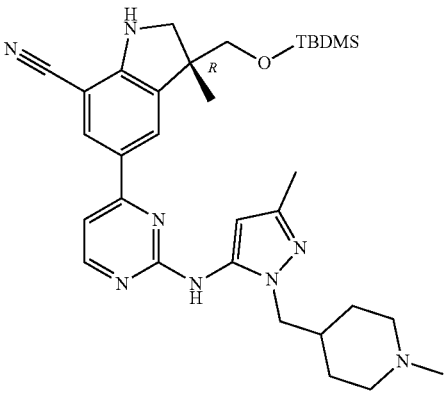<br>From intermediate 197 | 269<br>yellow oil | 81<br>Procedure with DCM/TFA (10:1, v/v) |

| Int. number | Structure | Mass (mg) | Yield (%) |
|---|---|---|---|
| Intermediate 202 | From intermediate 201 | 730 (69% purity based on LC/MS) | 77 Procedure with DCM/TFA (4:1, v/v) |
| Intermediate 204 | From intermediate 203 | 155 | 46 Procedure with DCM/TFA (5:1, v/v) |
| Intermediate 206 | From intermediate 205 | 173 yellow oil | 77 Procedure with DCM/TFA (5:1, v/v) |

| Int. number | Structure | Mass (mg) | Yield (%) |
|---|---|---|---|
| Intermediate 208 | 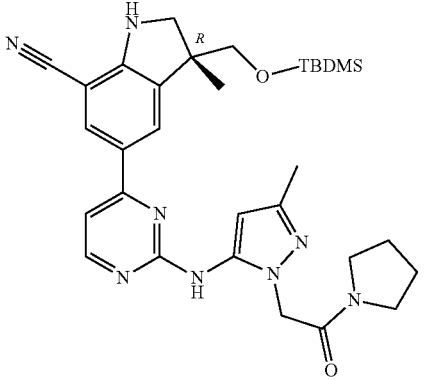<br>From intermediate 207 | 182<br>yellow oil | 75<br>Procedure with DCM/TFA (5:1, v/v) |
| Intermediate 210 | 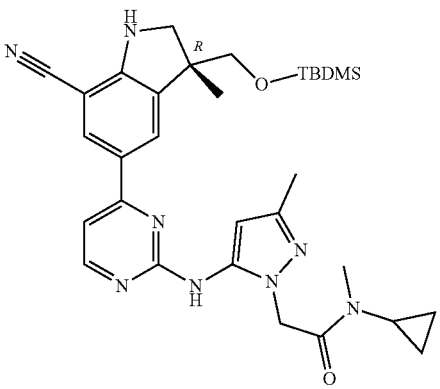<br>From intermediate 209 | 130<br>yellow oil | 60<br>Procedure with DCM/TFA (5:1, v/v) |
| Intermediate 216 | 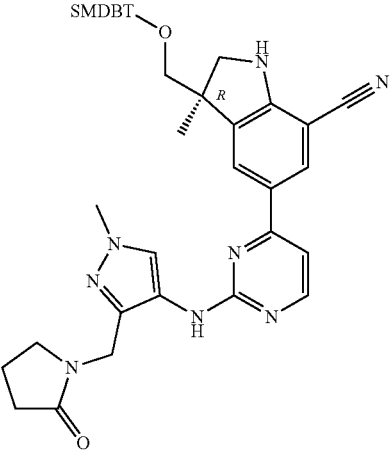<br>From intermediate 215 | 169 | 69<br>Procedure with DCM/TFA (7:1, v/v) |

| Int. number | Structure | Mass (mg) | Yield (%) |
|---|---|---|---|
| Intermediate 218 | From intermediate 217 | 242 | 75 Procedure with DCM/TFA (12:1, v/v) |
| Intermediate 222 | From intermediate 221 | 2000 | 72 Procedure with DCM/TFA (4:1, v/v) |
| Intermediate 227 | From intermediate 226 | 1050 | 44 Procedure with DCM/TFA (12:1, v/v) |

| Int. number | Structure | Mass (mg) | Yield (%) |
|---|---|---|---|
| Intermediate 231 | From intermediate 230 | 531 | 59 Procedure with DCM/TFA (4:1, v/v) |
| Intermediate 235 | From intermediate 234 | 254 | 68 Procedure with DCM/TFA (5:1, v/v) |
| Intermediate 238 | From intermediate 237 | 1530 | 61 Procedure with DCM/TFA (6:1, v/v) |

-continued
| Int. number | Structure | Mass (mg) | Yield (%) |
|---|---|---|---|
| Intermediate 244 | 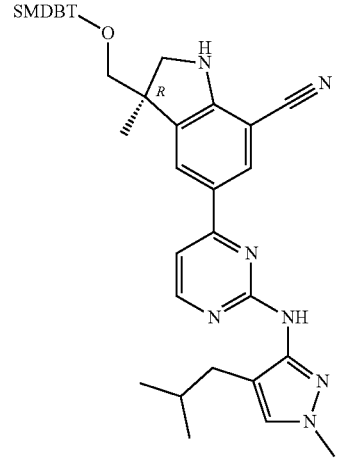<br>From intermediate 243 | 2830 | 66<br>Procedure with DCM/TFA (4:1, v/v) |
| Intermediate 249 | 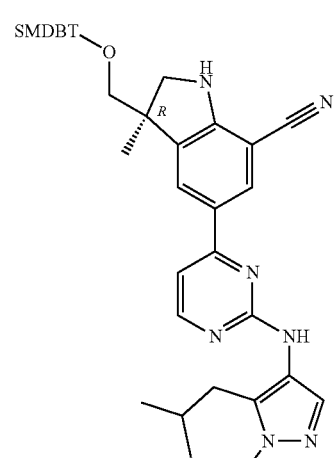<br>From intermediate 248 | 2050 | 59<br>Procedure with DCM/TFA (7:2, v/v) |
| Intermediate 258 | 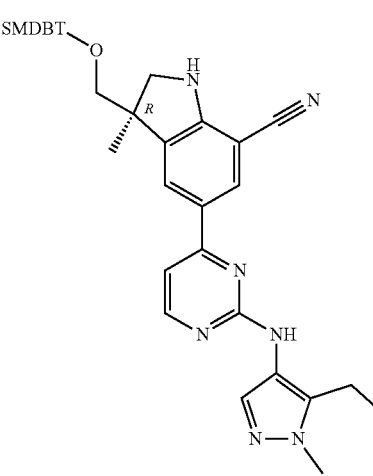<br>From intermediate 257 | 30 | 47<br>Procedure with DCM/TFA (8:1, v/v) |

-continued
| Int. number | Structure | Mass (mg) | Yield (%) |
|---|---|---|---|
| Intermediate 260 | 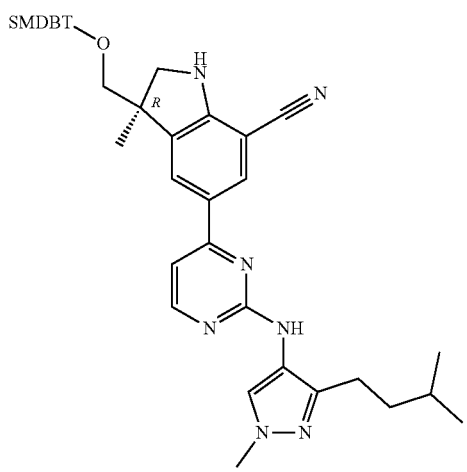<br>From intermediate 259 | 52 | 32<br>Procedure with DCM/TFA (8:1, v/v) |
| mixture of Intermediate 267 and intermediate 268 | 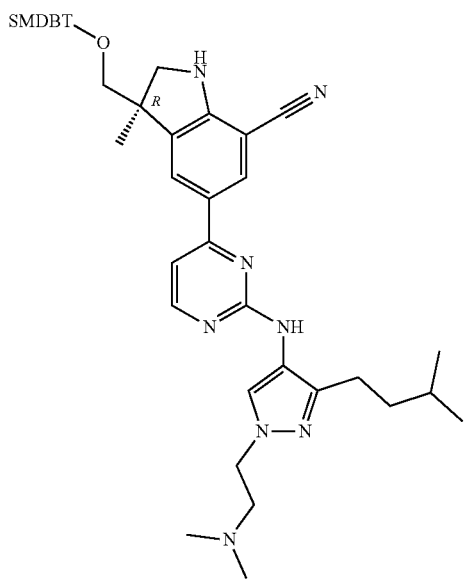<br>+ | 189 | 65<br>Procedure with DCM/TFA (8:1, v/v) |

-continued
| Int. number | Structure | Mass (mg) | Yield (%) |
|---|---|---|---|
| | 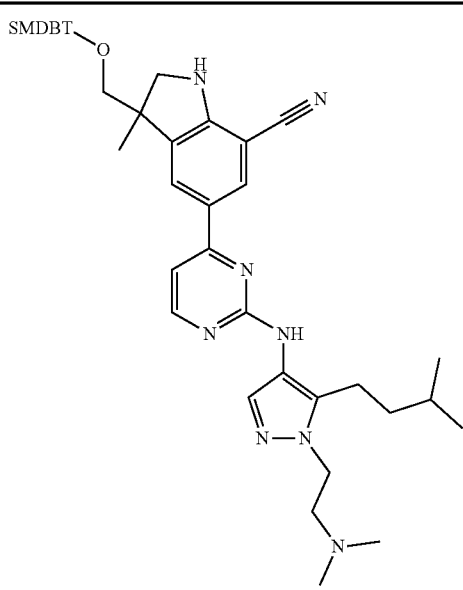<br>From intermediate 265/266 | | |
| Intermediate 278 | 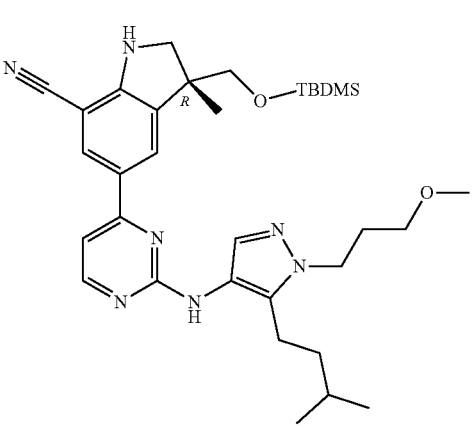<br>From intermediate 277 | 710<br>(30% purity based on LC/MS) | 56<br>Procedure with DCM/TFA (4:1, v/v) |
| Intermediate 281 | 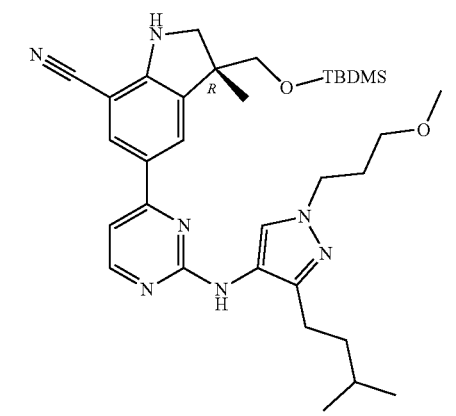<br>From intermediate 280 | 1073<br>(60% purity based on LC/MS) | —<br>Procedure with DCM/TFA (4:1, v/v) |

-continued

| Int. number | Structure | Mass (mg) | Yield (%) |
| --- | --- | --- | --- |
| Intermediate 291 | From intermediate 290 | 2860 (75% purity based on LC/MS) yellow solid | 75 Procedure with DCM/TFA (10:1, v/v) |
| Intermediate 295 | From intermediate 294 | 308 | 46 Procedure with DCM/TFA (4:1, v/v) |
| Intermediate 310 | From intermediate 309 | 530 | 71 Procedure with DCM/TFA (5:1, v/v) |

| Int. number | Structure | Mass (mg) | Yield (%) |
|---|---|---|---|
| Intermediate 314 | From intermediate 313 | 425 yellow oil | 66 Procedure with DCM/TFA (10:1, v/v) |
| Intermediate 318 | From intermediate 317 | 511 orange oil | 78 Procedure with DCM/TFA (5:1, v/v) |
| Intermediate 322 | From intermediate 321 | 119 yellow oil | 47 Procedure with DCM/TFA (5:1, v/v) |

-continued

| Int. number | Structure | Mass (mg) | Yield (%) |
|---|---|---|---|
| Intermediate 326 | From intermediate 325 | 243 (85% purity based on LC/MS) white solid | 55 Procedure with DCM/TFA (10:1, v/v) |
| Intermediate 334 | From intermediate 333 | 209 orange foam | Quant. Procedure with DCM/TFA (10:1, v/v) |
| Intermediate 340 | From intermediate 339 | 114 pale yellow solid | 75 Procedure with DCM/TFA (10:1, v/v) |

| Int. number | Structure | Mass (mg) | Yield (%) |
|---|---|---|---|
| Intermediate 354 | From intermediate 353 | 168 | 81 Procedure with DCM/TFA (7:1, v/v) |
| Intermediate 357 | From intermediate 356 | 116 | 47 Procedure with DCM/TFA (6:1, v/v) |
| Intermediate 361 | From intermediate 360 | 160 yellow residue | 75 Procedure with DCM/TFA (6:1, v/v) |

-continued

| Int. number | Structure | Mass (mg) | Yield (%) |
|---|---|---|---|
| Intermediate 369 | From intermediate 368 | 293 yellow residue | 72 Procedure with DCM/TFA (10:1, v/v) |
| Intermediate 382 | From intermediate 381 | 86 white solid | 58 Procedure with DCM/TFA (10:1, v/v) |
| Intermediate 397 | From intermediate 396 | 582 (65% purity based on LC/MS) yellow residue | 68 (over 2 steps) Procedure with DCM/TFA (5:1, v/v) |

-continued

| Int. number | Structure | Mass (mg) | Yield (%) |
| --- | --- | --- | --- |
| Intermediate 403 | From intermediate 402 | 284 yellow residue | 76 Procedure with DCM/TFA (10:1, v/v) |
| Intermediate 406 | From intermediate 186 | 170 yellow solid | 48 Procedure with DCM/TFA (4:1, v/v) |
| Intermediate 422 | From intermediate 421 | 210 | 70 Procedure with DCM/TFA (5:1, v/v) |

| Int. number | Structure | Mass (mg) | Yield (%) |
|---|---|---|---|
| Intermediate 438 | 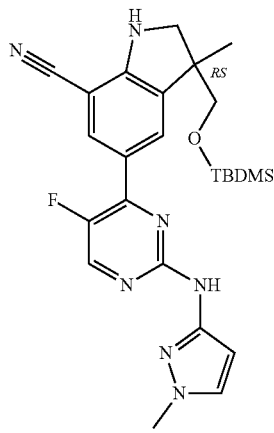<br>From intermediate 437 | 390 | Quant.<br>Procedure with DCM/TFA (9:1, v/v) |
| Intermediate 441 | 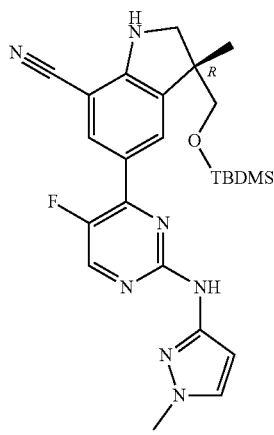<br>From intermediate 440 | 396 | Quant. |
| Intermediate 443 | 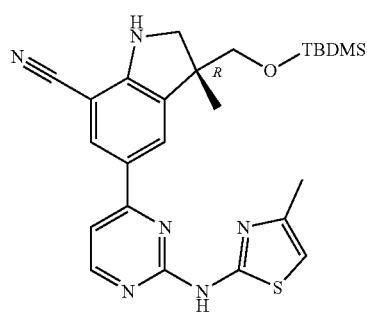<br>From intermediate 442 | 138<br>yellow solid | 60<br>Procedure with DCM/TFA (10:1, v/v) |

| Int. number | Structure | Mass (mg) | Yield (%) |
| --- | --- | --- | --- |
| Intermediate 445 | From intermediate 444 | 245 foam | 72 Procedure with DCM/TFA (10:1, v/v) |
| Intermediate 447 | From intermediate 446 | 220 orange solid | 95 Procedure with DCM/TFA (10:1, v/v) |
| Intermediate 449 | From intermediate 448 | 195 white solid | 56 Procedure with DCM/TFA (7:1, v/v) |
| Intermediate 451 | From intermediate 450 | 394 | Quant. Procedure with DCM/TFA (10:1, v/v) |

-continued
| Int. number | Structure | Mass (mg) | Yield (%) |
|---|---|---|---|
| Intermediate 459 | 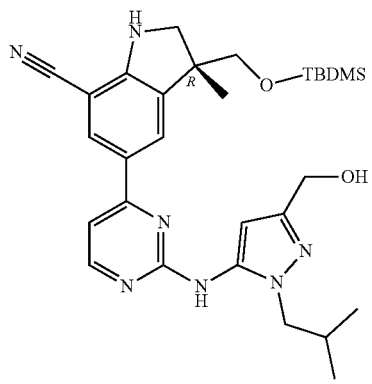<br>From intermediate 458 | 454 | 68<br>Procedure with DCM/TFA (10:1, v/v) |
| Intermediate 463 | 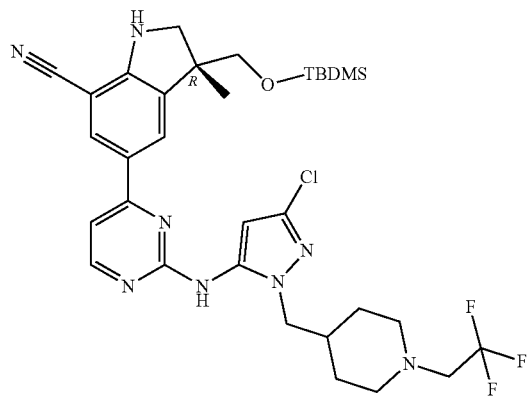<br>From intermediate 462 | 243<br>yellow residue | 74<br>Procedure with DCM/TFA (10:1, v/v) |
| Intermediate 467 | 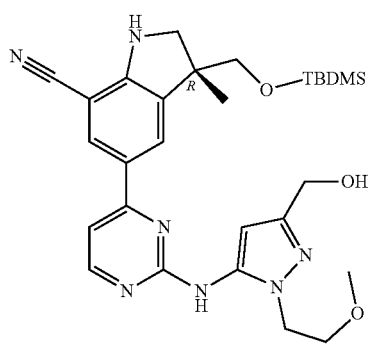<br>From intermediate 466 | 233<br>white foam | 63<br>Procedure with DCM/TFA (10:1, v/v) |

337
-continued
338
| Int. number | Structure | Mass (mg) | Yield (%) |
|---|---|---|---|
| Intermediate 482 | 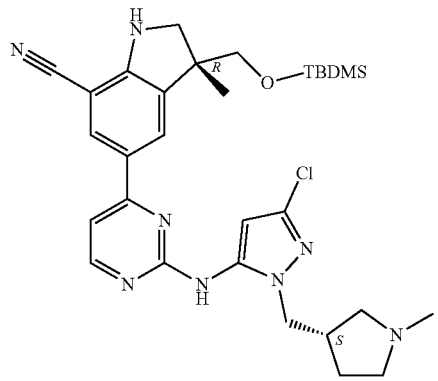<br>From intermediate 481 | 400 yellow residue | 81 Procedure with DCM/TFA (5:1, v/v) |
| Intermediate 498 | 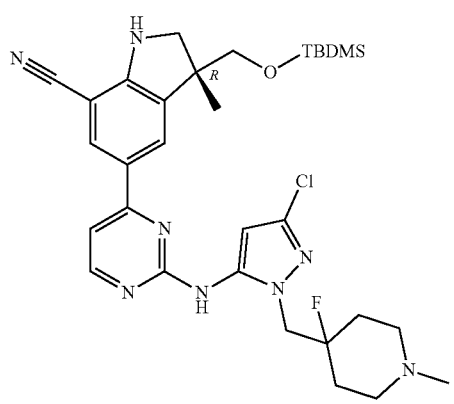<br>From intermediate 497 | 75 | 73 Procedure with DCM/TFA (5:1, v/v) |

| Int. number | Structure | Mass (mg) | Yield (%) |
|---|---|---|---|
| Intermediate 502 | 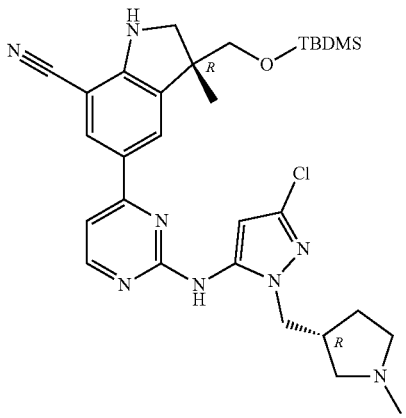<br>From intermediate 501 | 310 | 54<br>Procedure with DCM/TFA (5:1, v/v) |
| Intermediate 520 | 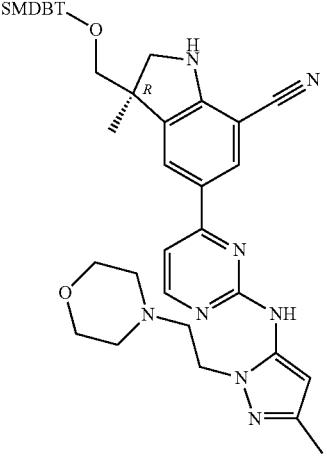<br>From intermediate 519 | 277 | 58<br>Procedure with DCM/TFA (7:1, v/v) |
| Intermediate 740 | 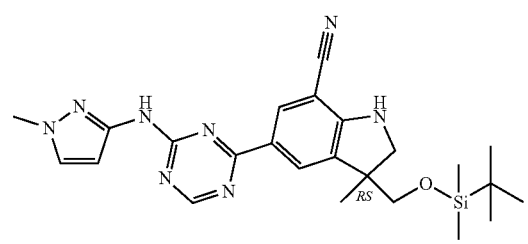<br>From intermediate 739 | 62<br>(80% purity based on LC/MS) | quant<br>Procedure with DCM/TFA (9:1, v/v)<br>5° C. for 1 h |

Example A10

Preparation of Intermediate 10

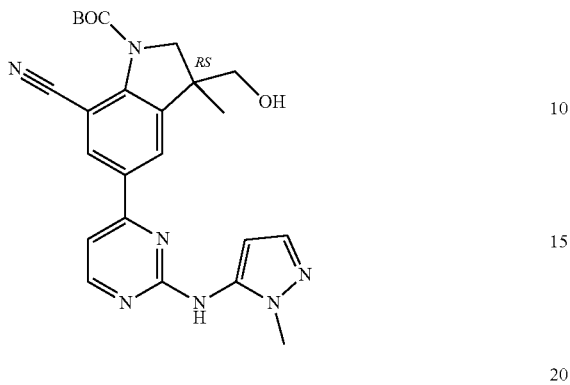

A mixture of intermediate 9 (335.00 mg, 0.58 mmol) and TBAF (1M in THF) (0.64 mL, 0.64 mmol) in THF (5 mL) was stirred at rt for 1 h. An extraction was performed with EtOAc and water. The organic layer was washed with brine, dried over MgSO$_4$ and evaporated to give 355 mg of intermediate 10 (quant. yield, yellow solid) which was used as it for the next step.

The intermediates in the Table below were prepared by using an analogous starting from the respective starting materials. The most relevant minor deviations to the referenced method are indicated as additional information in the column 'Yield (%)'.

| Int. number | Structure | Mass (mg) | Yield (%) |
| --- | --- | --- | --- |
| Intermediate 12 | From intermediate 11 | 950 (48% purity based on LC/MS) yellow solid | 99 |
| Intermediate 17 | From intermediate 16 | 161 | 56 Procedure with 1.2 equiv. of TBAF |

-continued
| Int. number | Structure | Mass (mg) | Yield (%) |
|---|---|---|---|
| Intermediate 20 | 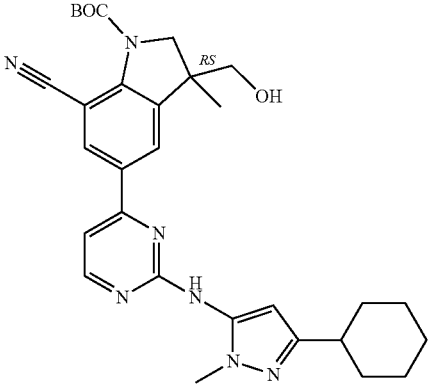 [SMILES: Cn1nc(C2CCCCC2)cc1Nc1nccc(-c2cc(C#N)c3c(c2)C(C)(CO)CN3C(=O)OC(C)(C)C)n1]<br>From intermediate 19 | 180 | 78<br>Procedure with 1.2 equiv. of TBAF |
| Intermediate 24 | 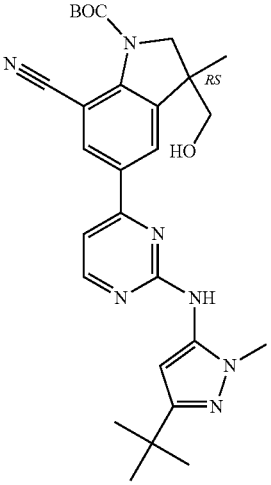 [SMILES: Cn1nc(C(C)(C)C)cc1Nc1nccc(-c2cc(C#N)c3c(c2)C(C)(CO)CN3C(=O)OC(C)(C)C)n1]<br>From intermediate 23 | 171 | 77<br>Procedure with 1.9 equiv. of TBAF |
| Intermediate 26 | 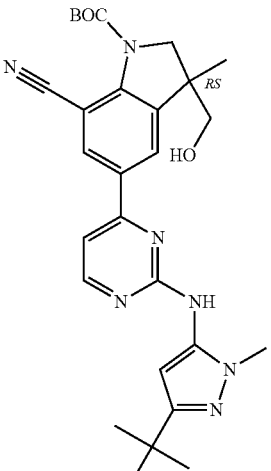<br>From intermediate 25 | 252 | 99<br>Procedure with 1.9 equiv. of TBAF |

-continued

| Int. number | Structure | Mass (mg) | Yield (%) |
|---|---|---|---|
| Intermediate 28 | From intermediate 27 | 219 | 53 Procedure with 1.2 equiv. of TBAF |
| Intermediate 32 | From intermediate 31 | 246 brown oil | — Procedure with 2.2 equiv. of TBAF |
| Intermediate 39 | From intermediate 39 | 170 | 44 Procedure with 1.9 equiv. of TBAF |

| Int. number | Structure | Mass (mg) | Yield (%) |
|---|---|---|---|
| Intermediate 66 | From intermediate 65 | 74 | 90 Procedure with 1.9 equiv. of TBAF |
| Intermediate 272 | From intermediate 271 | 618 | 76 Procedure with 1.5 equiv of TBAF |
| Intermediate 302 | From intermediate 301 | 680 (80% purity based on ¹H NMR) | 62 Procedure with 1.7 equiv of TBAF |
| Intermediate 435 | From intermediate 435 | 270 | Quant. |

| Int. number | Structure | Mass (mg) | Yield (%) |
|---|---|---|---|
| Intermediate 549 | 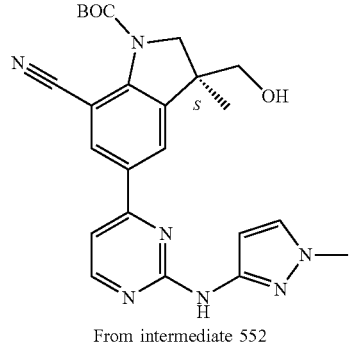<br>From intermediate 552 | 569<br>yellow powder | 85<br>Procedure with 2 equiv. of TBAF |
| Intermediate 553 | 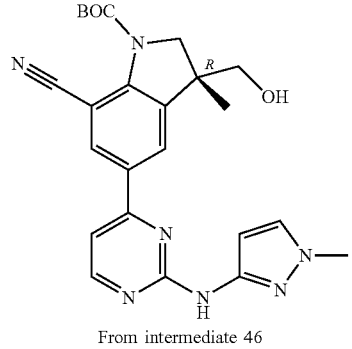<br>From intermediate 46 | 544<br>yellow powder | 85<br>Procedure with 2 equiv. of TBAF |
| Intermediate 728 | 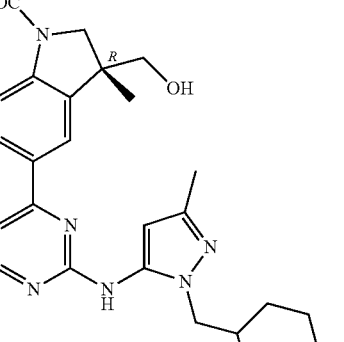<br>From intermediate 727 | 165 | 73 |

Example A11

Preparation of Intermediate 30

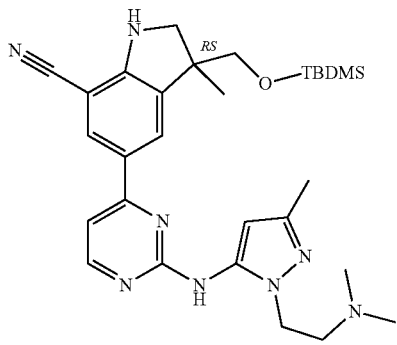

In a sealed glassware, a mixture of intermediate 29 (400.00 mg, 0.96 mmol), 2-(2-dimethylaminoethyl)-5-methyl-2H-pyrazole-3-ylamine (178.37 mg, 1.06 mmol) and $Cs_2CO_3$ (942.10 mg, 2.89 mmol) in dry 1,4-dioxane (20 mL) was purged with $N_2$. Then, $Pd(OAc)_2$ (21.64 mg, 96.40 mol) and BINAP (60.00 mg, 96.40 μmol) were added. The mixture was purged with $N_2$ and stirred at 95° C. for 2 h. The crude was combined with another batch (from 245 mg of intermediate 29) and an extraction was performed with EtOAc and water. The layers were separated and the organic layer was dried over $MgSO_4$, filtered and evaporated under reduced pressure. The residue (958 mg) was purified by column chromatography on silica gel (irregular SiOH 15-40 m, 80 g, dry loading on Celite®, mobile phase: DCM/(MeOH(+aq. 5% $NH_3$)) gradient from 100:0 to 90:10). The fractions containing the product were combined and concentrated to dryness to give 600 mg of intermediate 30 (quant. yield, brown solid) which was used as it in the next step.

The intermediates in the Table below were prepared by using an analogous method starting from the respective starting materials. The most relevant minor deviations to the referenced method are indicated as additional information in the column 'Yield (%)'.

| Int. number | Structure | Mass (mg) | Yield (%) |
|---|---|---|---|
| Intermediate 35 | From intermediate 29 and 1,5-dimethyl-1H-pyrazol-3-ylamine | 255 yellow oil | 72 with T = 100° C. |
| Intermediate 749 | 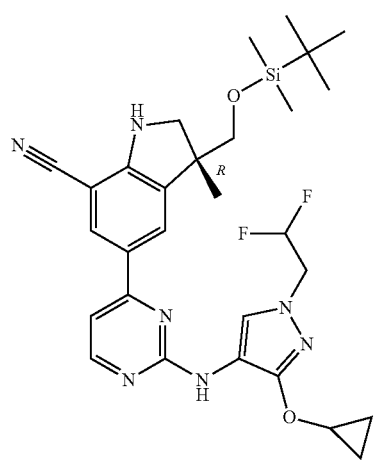 From intermediate 305 and 748 | 340 | 54 μw, 120° C., 30 min |

-continued
| Int. number | Structure | Mass (mg) | Yield (%) |
|---|---|---|---|
| Intermediate 753 | 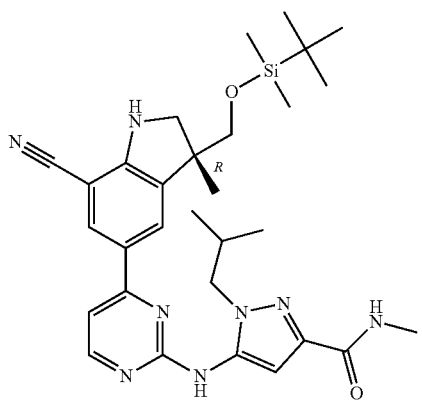<br>From intermediate 305 and 752 | 3380 | 40<br>120° C.,<br>60 min |
| Intermediate 761 | 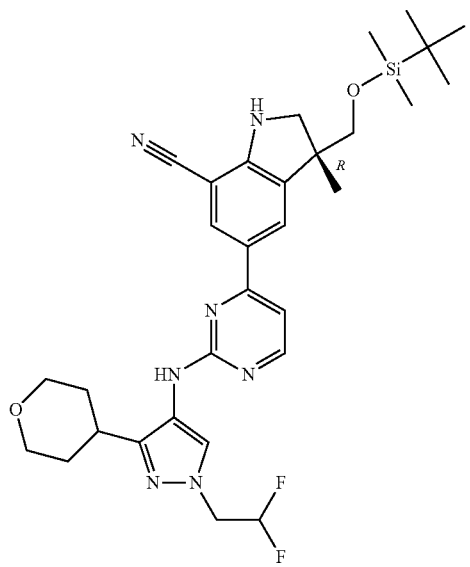<br>From intermediate 305 and 760 | 112 | 59<br>μw,<br>120° C.,<br>30 min |

Example A12

Preparation of Intermediate 186

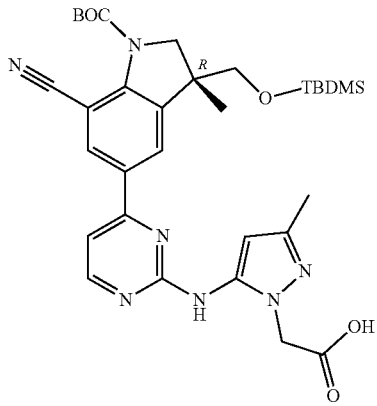

In a sealed glassware, a mixture of intermediate 6R (2.00 g, 3.88 mmol), ethyl-(5-amino-3-methyl-1H-pyrazol-1-yl) acetate hydrochloride (938.20 mg, 4.27 mmol) and $Cs_2CO_3$ (5.10 g, 15.50 mmol) in dry 1,4-dioxane (80 mL) was purged with $N_2$. Then, $Pd(OAc)_2$ (87.20 mg, 0.39 mmol) and BINAP (241.80 mg, 0.39 mmol) were added. The mixture was purged with $N_2$ and stirred at 90° C. for 3 h. Then, lithium hydroxide monohydrate (244.40 mg, 5.82 mmol) and distilled water (11 mL) were added at room temperature for 2 h. The reaction mixture was combined with another batch (from 4 g of intermediate 6R) and the mixture was evaporated under reduced pressure to give a crude. The crude was purified by column chromatography on silica gel (irregular SiOH 15-40 μm, dry load on celiteR, mobile phase: DCM/(MeOH(+10% aq. AcOH)), gradient from 100:0 to 90:10). The fractions containing the product were combined and evaporated to dryness to give 5.98 g of intermediate 186 (81% yield, over 2 steps, brown solid).

Preparation of Intermediate 187

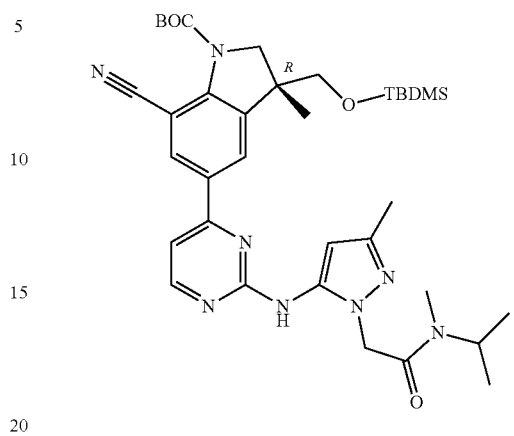

In a sealed tube, intermediate 186 (500.00 mg, 0.79 mmol) and N-isopropylmethylamine (0.14 mL, 1.34 mmol) were diluted in dry DMF (10 mL). Then, HATU (0.81 g, 2.13 mmol) and DIPEA (0.34 mL, 1.97 mmol) were added and the mixture was stirred at rt for 17 h. The reaction mixture was evaporated under reduced pressure and an extraction was performed with EtOAc. The organic layer was washed with brine and the layers were separated. The organic layer was dried over $MgSO_4$, filtered and the solvent was removed under reduced pressure. The residue was purified by column chromatography on silica gel (irregular SiOH, 15-40 m, 30 g, dry load on Celite®, mobile phase: DCM/(MeOH(+10% aq. AcOH)), gradient from 100:0 to 90:10). The fractions containing the product were combined and evaporated to dryness to give 504 mg of intermediate 187 (93% yield, yellow residue).

The intermediates in the Table below were prepared by using an analogous method starting from the respective starting materials. The most relevant minor deviations to the referenced method are indicated as additional information in the column 'Yield (%)'.

| Int. number | Structure | Mass (mg) | Yield (%) |
| --- | --- | --- | --- |
| Intermediate 189 | 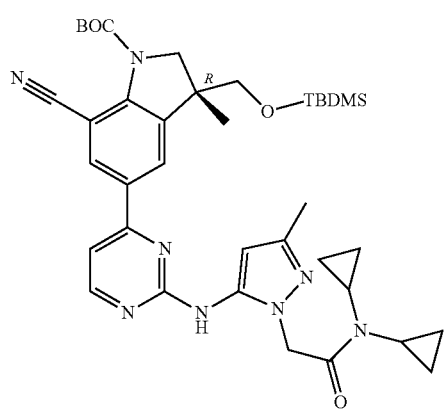<br>From intermediate 186 and dicyclopropylamine hydrochloride | 173 | 31 |

-continued

| Int. number | Structure | Mass (mg) | Yield (%) |
|---|---|---|---|
| Intermediate 205 | From intermediate 186 and 3,3-difluoroazetidine hydrochloride | 260 brown residue | 58 |
| Intermediate 207 | From int. 186 and pyrrolidine | 285 brown oil | 66 |
| Intermediate 209 | From intermediate 186 and N-methylcyclopropanamine | 255 yellow oil | 59 |

Example A13

Preparation of Intermediate 298

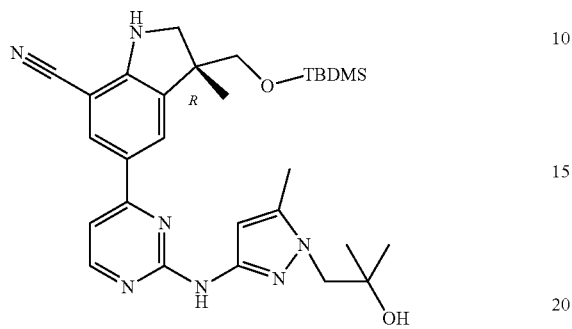

SiO$_2$ (35-70 μm, 1.1 g) was added to a solution of intermediate 298 (400.00 mg, 0.45 mmol) in toluene (3.63 mL, 34.17 mmol) at rt. The resulting mixture was stirred at reflux for 2 h. After cooling down to rt, the reaction mixture was evaporated. The residue was purified by column chromatography on silica gel (Irregular SiOH, 40 m, 40 g, deposited solid, mobile phase gradient from 100% DCM to 96% DCM, 4% MeOH, 0.4% NH$_4$OH). The pure fractions were combined and the solvent was evaporated to give 275 mg of intermediate 298 (Quant. yield).

The intermediates in the Table below were prepared by using an analogous method starting from the respective starting materials. The most relevant minor deviations to the referenced method are indicated as additional information in the column 'Yield (%)'.

| Int. number | Structure | Mass (mg) | Yield (%) |
|---|---|---|---|
| Intermediate 330 | 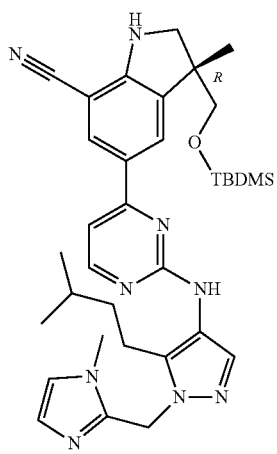  From intermediate 329 | 420 | 85 |

-continued

| Int. number | Structure | Mass (mg) | Yield (%) |
|---|---|---|---|
| Intermediate 340 | From intermediate 339 | 260 | 82 |
| Intermediate 348 | From intermediate 347 | 530 | Quant. |
| Intermediate 365 | From intermediate 364 | 420 | 84 |

-continued
| Int. number | Structure | Mass (mg) | Yield (%) |
|---|---|---|---|
| Intermediate 373 | 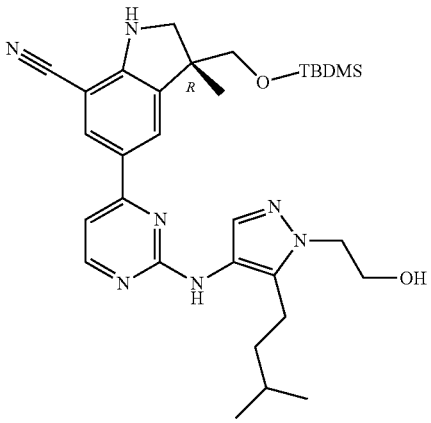<br>From intermediate 372 | 280<br>(51% purity based on LC/MS) | 82 |
| Intermediate 378 | 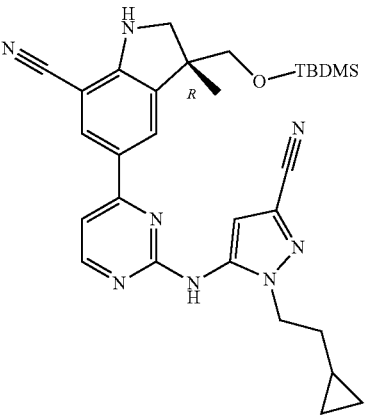<br>From intermediate 377 | 1620<br>(83% purity based on LC/MS) | 53 |
| Intermediate 385 | 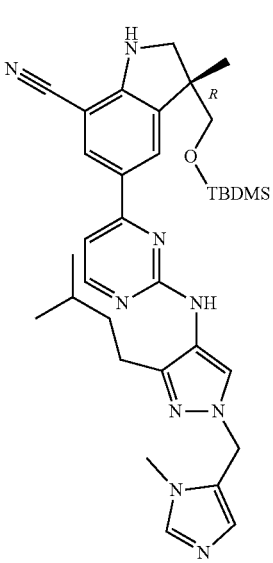<br>From intermediate 384 | 517<br>(85% purity based on LC/MS) | Quant. |

-continued

| Int. number | Structure | Mass (mg) | Yield (%) |
|---|---|---|---|
| Intermediate 389 | From intermediate 388 | 337 | Quant. |
| Intermediate 393 | From intermediate 392 | 313 | 59 |
| Intermediate 412 | From intermediate 411 | 107 | 91 |

-continued

| Int. number | Structure | Mass (mg) | Yield (%) |
|---|---|---|---|
| Intermediate 416 | (structure from intermediate 415) | 452 | 73 |
| Intermediate 426 | (structure from intermediate 425) | 260 | 95 |
| Intermediate 430 | (structure from intermediate 429) | 445 | Quant. |

-continued

| Int. number | Structure | Mass (mg) | Yield (%) |
| --- | --- | --- | --- |
| Intermediate 434 | From intermediate 432 | 260 | Quant. |
| Intermediate 455 | From intermediate 454 | 162 (30% purity based on LC/MS) | 72 |
| Intermediate 474 | From intermediate 473 | 450 | Quant. |

-continued

| Int. number | Structure | Mass (mg) | Yield (%) |
|---|---|---|---|
| Intermediate 478 | From intermediate 477 | 271 | 71 |
| Intermediate 486 | From intermediate 485 | 290 | 90 |
| Intermediate 494 | From intermediate 493 | 664 (74% purity based on LC/MS) | 85 |

-continued

| Int. number | Structure | Mass (mg) | Yield (%) |
|---|---|---|---|
| Intermediate 511 | From intermediate 510 | 279 | 93 |
| Intermediate 516 | From intermediate 515 | 403 (100% purity based on LC/MS) | 70 |
| Intermediate 524 | From intermediate 523 | 263 | 84 |

-continued
| Int. number | Structure | Mass (mg) | Yield (%) |
|---|---|---|---|
| Intermediate 528 | 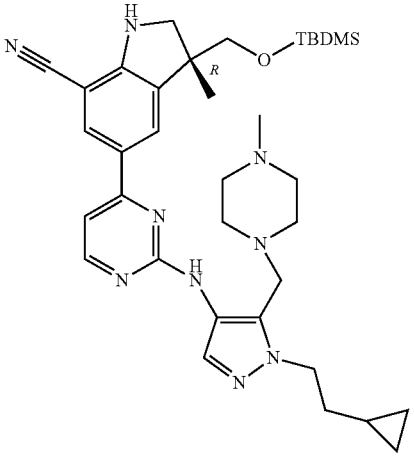<br>From intermediate 527 | 210 | 90 |
| Intermediate 532 | 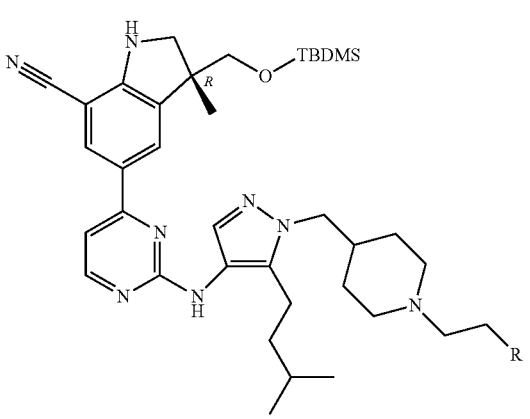<br>From intermediate 531 | 135 | 60 |
| Intermediate 536 | 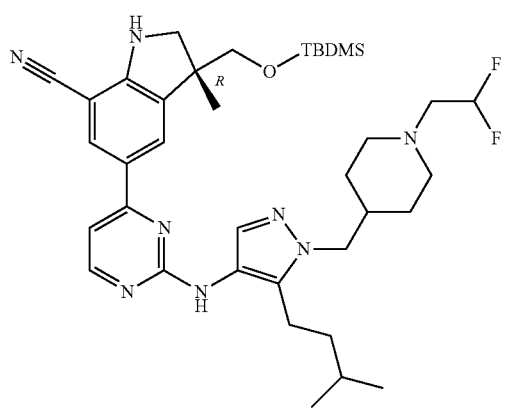<br>From intermediate 535 | 121<br>(45% purity based on LC/MS) | 81 |

-continued
| Int. number | Structure | Mass (mg) | Yield (%) |
|---|---|---|---|
| Intermediate 540 | 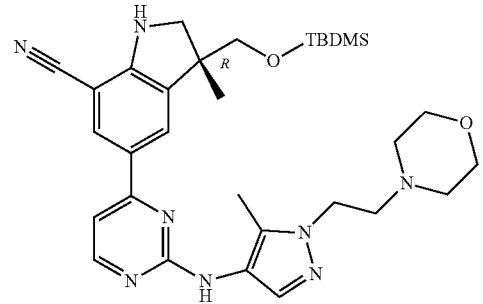<br>From intermediate 539 | 432 (57% purity based on LC/MS) | Quant. |
| Intermediate 544 (mixture of 2 distereoisomers) | 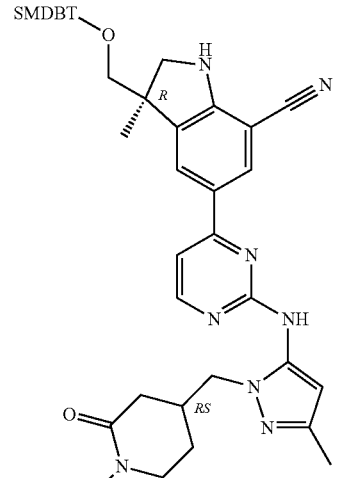<br>From intermediate 543 | 684 | 92 |
| Intermediate 548 | 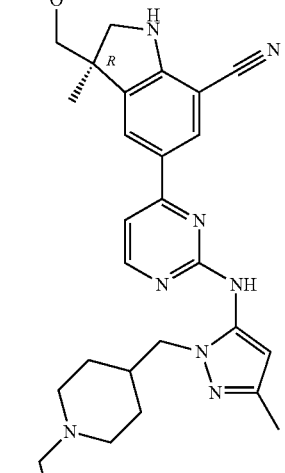<br>From intermediate 547 | 253 | 80 |

-continued
| Int. number | Structure | Mass (mg) | Yield (%) |
|---|---|---|---|
| Intermediate 572 | 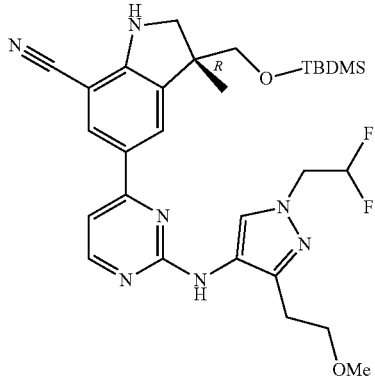<br>From intermediate 570 | 3150 | Quant. |
| Intermediate 573 | 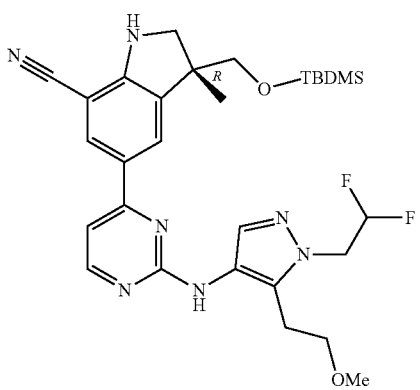<br>From intermediate 571 | 214 | Quant. |
| Intermediate 574 | 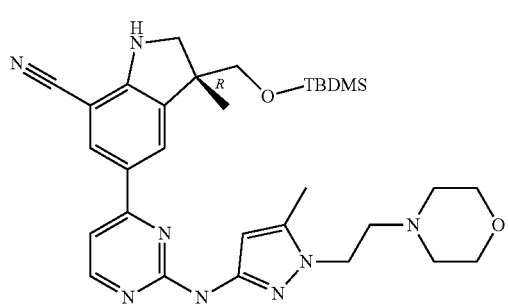<br>From intermediate 575 | 166 | 90 |

-continued
| Int. number | Structure | Mass (mg) | Yield (%) |
|---|---|---|---|
| Intermediate 587 | 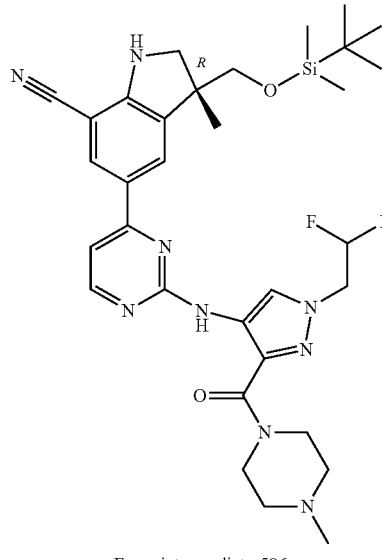<br>From intermediate 586 | 110 | 89<br>Reflux 2 h |
| Intermediate 590 | 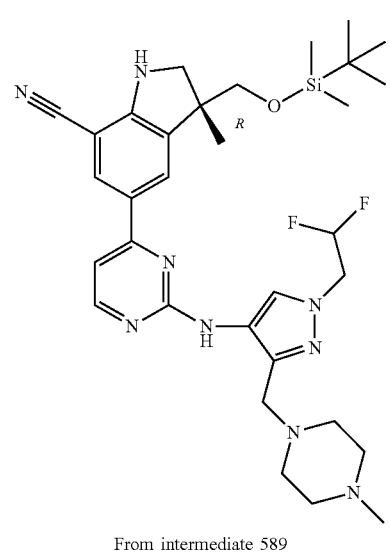<br>From intermediate 589 | 120<br>(80% purity based on LC/MS) | 82<br>Reflux 2 h |
| Intermediate 594 | 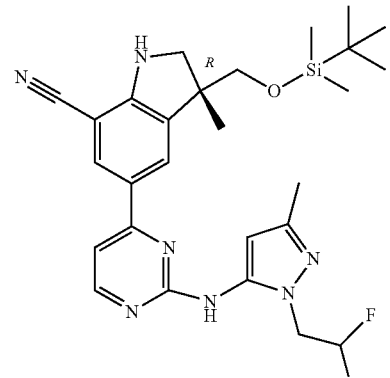<br>From intermediate 593 | 620 | 91 |

-continued

| Int. number | Structure | Mass (mg) | Yield (%) |
|---|---|---|---|
| Intermediate 600 | From intermediate 599 | 580 | 100<br>Reflux 4 h |
| Intermediate 649 | From intermediate 648 | 642<br>(90% purity based on LCMS) | 92<br>Reflux 3 h |
| Intermediate 604 | From intermediate 603 | 375 | 100<br>Reflux 4 h |

-continued
| Int. number | Structure | Mass (mg) | Yield (%) |
|---|---|---|---|
| Intermediate 609 | 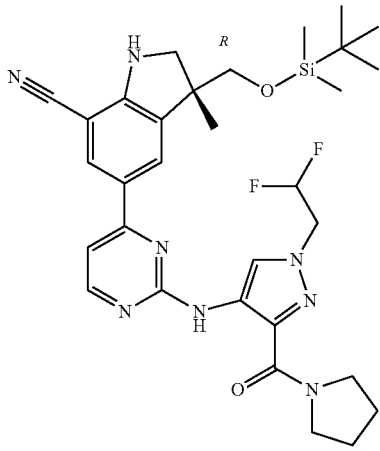<br>From intermediate 608 | 370 | 100<br>Reflux 2 h |
| Intermediate 615 | 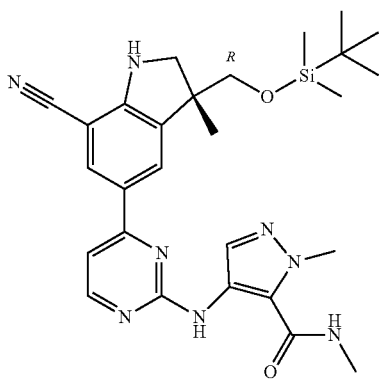<br>From intermediate 614 | 224 | 95<br>Reflux 2 h |
| Intermediate 619 | 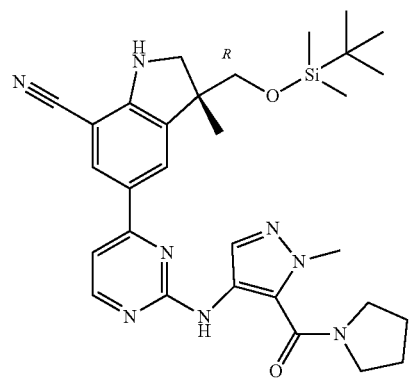<br>From intermediate 618 | 251 | 100<br>Reflux 2 h |

-continued
| Int. number | Structure | Mass (mg) | Yield (%) |
|---|---|---|---|
| Intermediate 623 | 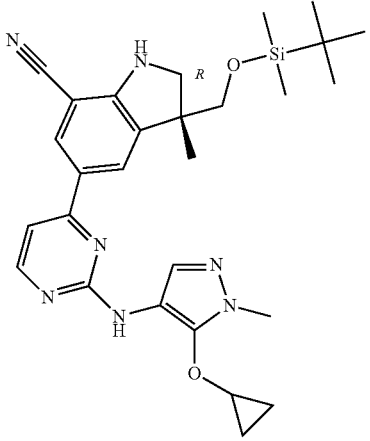<br>From intermediate 622 | 202 | 100 |
| Intermediate 627 | 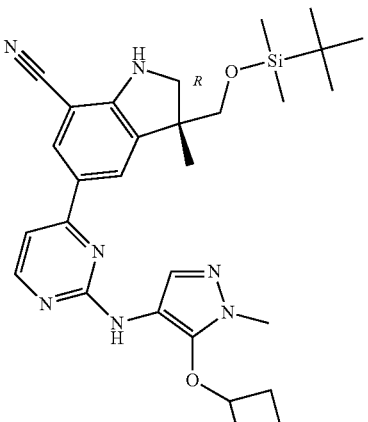<br>From intermediate 626 | 68 | 100<br>Reflux 4 h |
| Intermediate 631 | 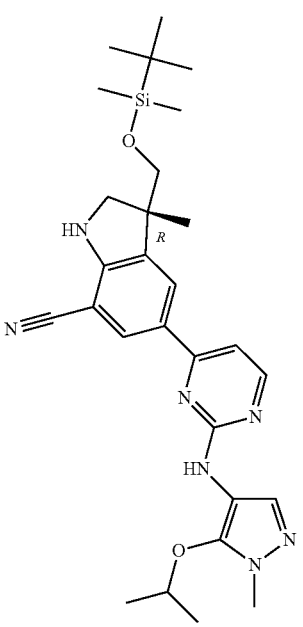<br>From intermediate 630 | 620 | Quant<br>Reflux 4 h |

-continued
| Int. number | Structure | Mass (mg) | Yield (%) |
|---|---|---|---|
| Intermediate 639 | 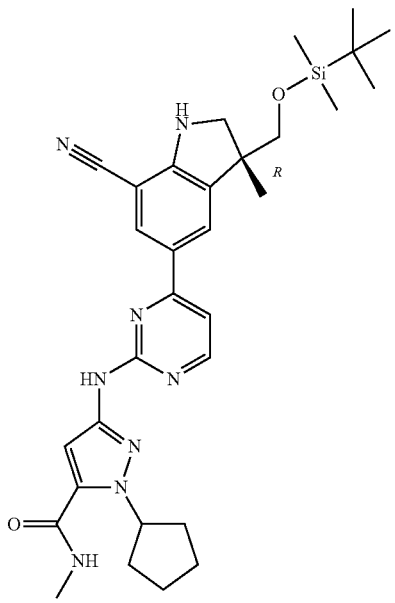<br>From intermediate 638 | 175 | 88<br>Reflux<br>1 h 30 mins |
| Intermediate 655 | 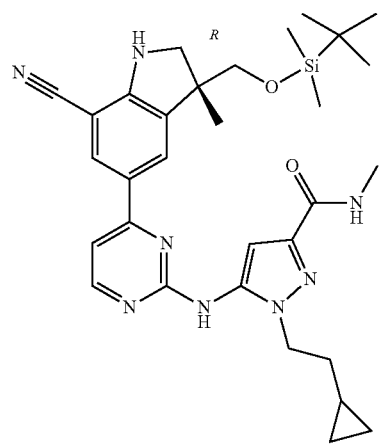<br>From intermediate 654 | 118 | 86<br>90° C. 2 days |

-continued
| Int. number | Structure | Mass (mg) | Yield (%) |
|---|---|---|---|
| Intermediate 661 | 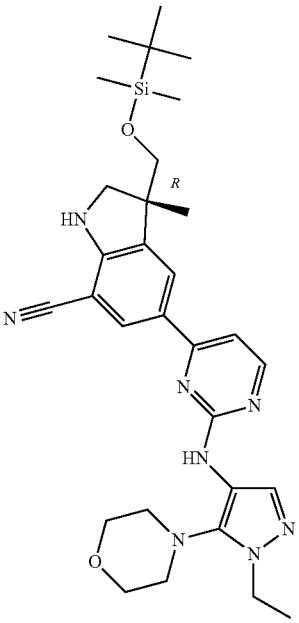<br>From intermediate 660 | 410 | 89<br>Reflux<br>(120° C.)<br>4 h |
| Intermediate 665 | 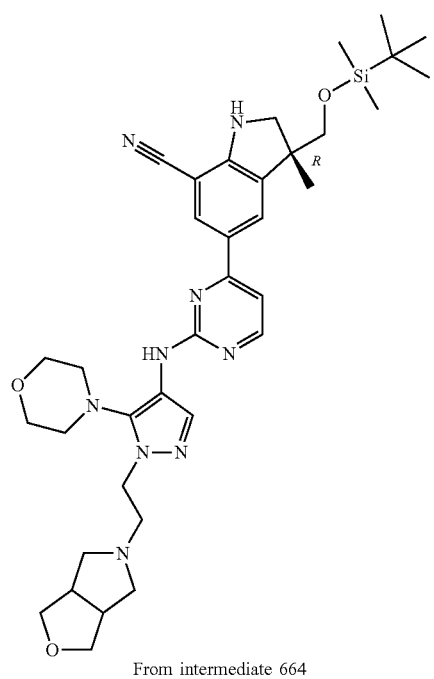<br>From intermediate 664 | 420 | 68<br>Reflux<br>12 h |

-continued

| Int. number | Structure | Mass (mg) | Yield (%) |
| --- | --- | --- | --- |
| Intermediate 671 | From intermediate 670 | 220 (84% purity based on LC/MS) | 88 With T = 120° C. 5 h |
| Intermediate 677 | From intermediate 676 | 510 | 75 Reflux 4 h |
| Intermediate 683 | From intermediate 682 | 605 | 87 With T = 120° C. 4 h |

-continued
| Int. number | Structure | Mass (mg) | Yield (%) |
|---|---|---|---|
| Intermediate 689 | 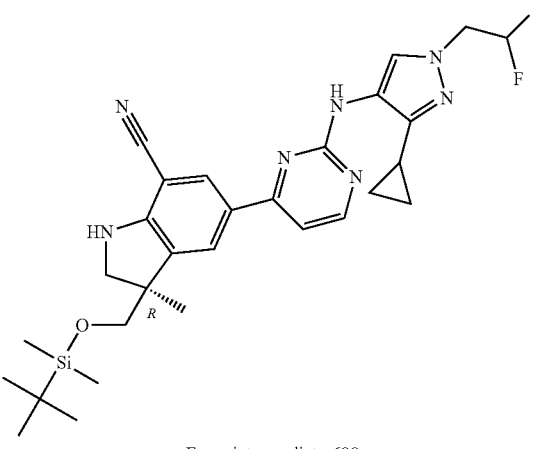<br>From intermediate 688 | 86 | 45<br>With<br>T = 120° C.<br>3 h |
| Intermediate 691 | 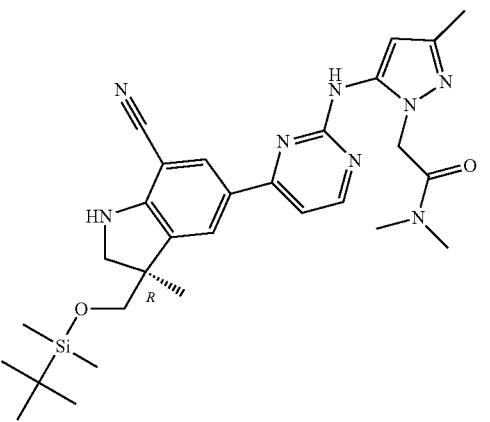<br>From intermediate 690 | 231 | 45<br>With<br>T = 120° C.<br>2 h |
| Intermediate 695 | 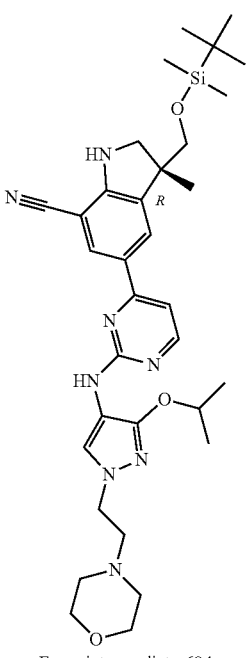<br>From intermediate 694 | 380 | 82<br>Reflux 4 h |

| Int. number | Structure | Mass (mg) | Yield (%) |
|---|---|---|---|
| Intermediate 698 | 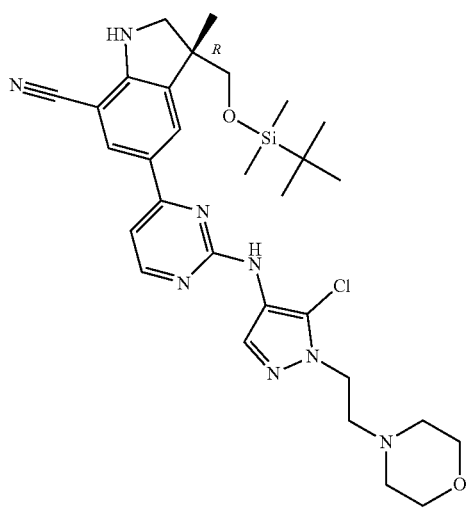<br>From intermediate 697 | 172 | 100<br>Reflux 4 h |
| Intermediate 706 | 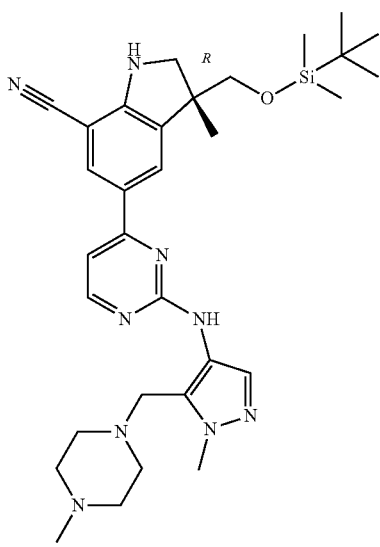<br>From intermediate 705 | 300 | 87<br>Reflux 2 h |
| Intermediate 711 | 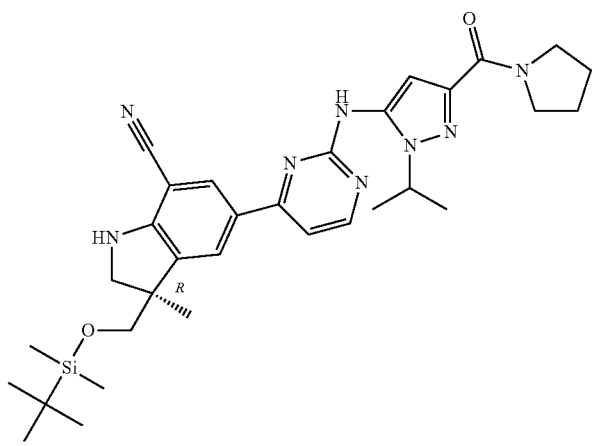<br>From intermediate 710 | 154 | 100<br>With<br>T = 120° C.<br>1 h 30 mins |

-continued

| Int. number | Structure | Mass (mg) | Yield (%) |
|---|---|---|---|
| Intermediate 717 | From intermediate 716 | 83 | 94<br>With<br>T = 120° C.<br>4 h |
| Intermediate 720 | From intermediate 719 | 550 | 100<br>With<br>T = 120° C.<br>3 h 20 mins |
| Intermediate 724 | From intermediate 723 | 170 | 68<br>With<br>T = 90° C.<br>5 h |

-continued

| Int. number | Structure | Mass (mg) | Yield (%) |
|---|---|---|---|
| Intermediate 737 | From intermediate 736 | 45 (91% purity based on LC/MS) | 66 With T = 90° C. 2 days |
| Intermediate 745 | From intermediate 744 | 4450 | 100 |
| Intermediate 766 | From intermediate 765 | 113 LCMS pure at 68% | 51 |

Example A14

Preparation of Intermediate 550

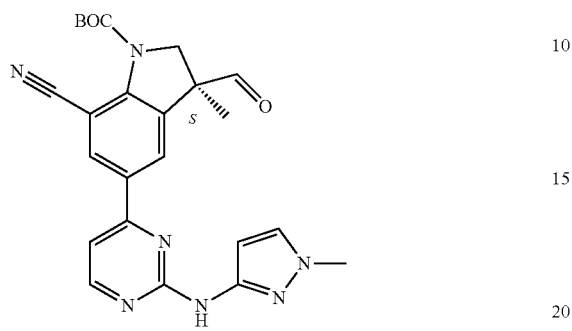

In a dry 25 ml 3 neck round bottom flask, DCM (0.3 mL) was charged and cooled to −78° C., oxalyl chloride (0.92 mL, 1.85 mmol) was added followed by DMSO (0.26 mL, 3.70 mmol). After 1 h, a solution of intermediate 549 (0.57 g, 1.23 mmol) in solution in DCM (1.5 mL) was added dropwise. The mixture was stirred for 1 h at −78° C., before DIPEA (1.27 mL, 7.40 mmol) was added. Stirring was continued and then the mixture was allowed to warm to rt over 5 h. A diluted solution of $NH_4Cl$ was added and the aqueous layer was extracted twice with DCM and the combined layers were dried over $MgSO_4$. After filtration and removal of the solvent in vacuo, 669 mg of intermediate 550 (Quant. yield, orange solid) were obtained and directly used in the next steps without any further treatment.

The intermediates in the Table below were prepared by using an analogous starting from the respective starting materials.

| Int. number | Structure | Mass (mg) | Yield (%) |
| --- | --- | --- | --- |
| Intermediate 554 | 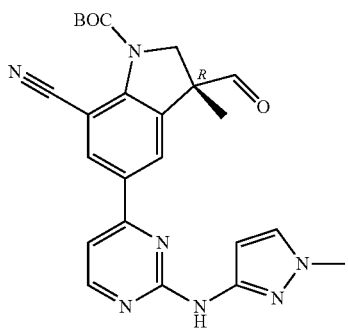<br>From intermediate 553 | 608<br>yellow solid | Quant. |

Preparation of Intermediate 551

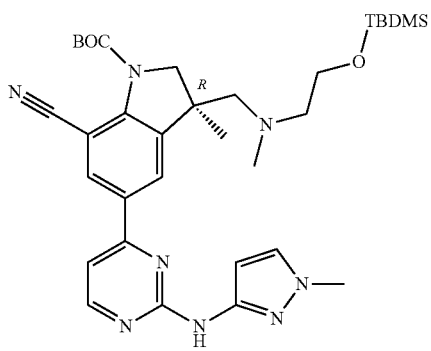

A solution of intermediate 550 (0.30 g, 0.65 mmol), 2-[[(1,1-dimethylethyl) dimethylsilyl]oxy]-N-methyl-ethanamine (0.74 mg, 3.92 mmol), AcOH (224 µl, 3.92 mmol) and NaBH(OAc)$_3$ (1.38 g, 6.53 mmol) in dichloroethane (13.2 ml) was stirred at rt overnight. A saturated solution of NaHCO$_3$ was added and the aqueous layer was extracted with DCM. The organic layer was dried over MgSO$_4$ and evaporated to dryness. The residue (1240 mg, yellow oil) was purified by column chromatography on silica gel (irregular SiOH, 40 g, mobile phase: heptane/EtOAc, gradient from 100:0 to 50:50). The fractions containing the product were combined and evaporated to dryness to provide 152 mg of intermediate 551 (37% yield, yellow oil).

The intermediates in the Table below were prepared by using an analogous starting from the respective starting materials.

| Int. number | Structure | Mass (mg) | Yield (%) |
|---|---|---|---|
| Intermediate 555 | From intermediate 554 | 93 colorless oil | 23 |
| Intermediate 556 | 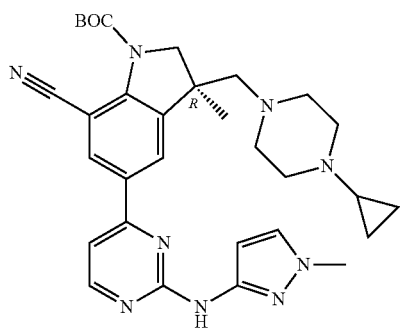 From intermediate 550 and cyploroylpiperazine | 295 (57% purity based on LC/MS) yellow oil | 79 |

| Int. number | Structure | Mass (mg) | Yield (%) |
|---|---|---|---|
| Intermediate 557 | 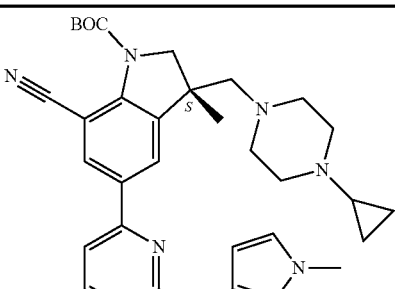<br>From intermediate 554 and cyclopropylpiperazine | 201 (57% purity based on LC/MS) yellow oil | 59 |

Example A15

Preparation of Intermediate 15 and intermediate 15'

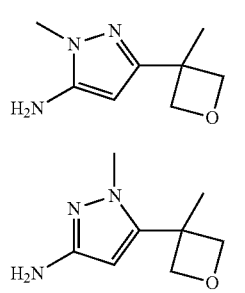

intermediate 15 intermediate 15'

Methylhydrazine (1.14 mL, 21.77 mmol) was added to a stirred solution of 3-methyl-β-oxo-3-oxetanepropanetrile (2.33 g, 16.74 mmol) and TEA (3.23 mL, 23.24 mmol) in toluene (12.22 mL, 115.03 mmol) at rt and stirred at 90° C. for 1 h. The reaction mixture was purified by column chromatography on silica gel (Irregular SiOH 40 μm, mobile phase: DCM/MeOH/NH$_4$OH, gradient from 100% DCM to 95% DCM, 5% MeOH, 0.1% NH$_4$OH. The residue (1.37 g) was purified by achiral SFC (Stationary phase: CHIRAL-CEL OJ-H, 5 μm, 250×20 mm, mobile phase: 90% CO$_2$, 10% MeOH) providing 355 mg of intermediate 15' (13% yield) and 966 mg of intermediate 15 (35% yield).

The intermediates in the Table below were prepared by using an analogous starting from the respective starting materials.

| Int. number | Structure | Mass (mg) | Yield (%) |
|---|---|---|---|
| Intermediate 18 | H$_2$N–[pyrazole]–cyclohexyl<br>From 3-cyclohexyl-3-oxopropanenitrile | 310 | 26 |

Example A16

Preparation of Intermediate 44

[structure of intermediate 44]

In sealed glassware, dimethylamine (1.64 mL, 3.28 mmol) and triazabicyclo[4.4.0]des-5-ene (TBD) (62.02 mg, 0.44 mmol) were added to a solution of ((5-amino-3-methyl-pyrazol-1-yl)-acetic acid ethyl ester (200.00 mg, 1.09 mmol) in dry toluene (19.5 mL). The reaction mixture was stirred at 50° C. for 17 h. The solvent was removed under reduced pressure and the residue was purified by column chromatography on silica gel (irregular SiOH, 15-40 μm, 40 g, liquid loading, mobile phase: DCM/(MeOH(+5% aq NH$_3$)), gradient from 100:0 to 90:10). The fractions containing the product were combined and evaporated to dryness to give 102 mg of intermediate 44 (51% yield, yellow oil).

Example A17

Preparation of Intermediate 52 and intermediate 52'

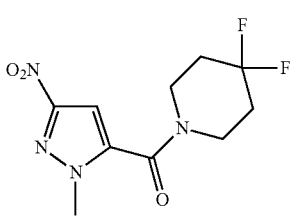

intermediate 52

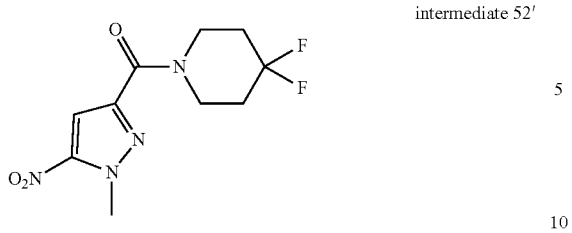

intermediate 52'

A mixture of 1-methyl-3-nitro-1H-pyrazole-5-carboxylic acid (400.00 mg, 2.34 mmol) and 1-methyl-2-nitro-1H-pyrazole-4-carboxylic acid, 4,4-difluoropiperidine (440.00 mg, 2.79 mmol), HATU (1.25 g, 3.29 mmol) in DCM (10 mL) and DIPEA (2.10 mL, 12.19 mmol) was stirred at rt for a weekend. Water was added and this mixture was extracted with DCM. The organic layer was decanted with Chromabond®, the solvent was evaporated until dryness. The residue (773 mg) was purified by column chromatography on silica gel (Stationary phase: irregular bare silica 40 g, mobile phase: 70% heptane, 30% EtOAc). The pure fractions were collected and the solvent was evaporated until dryness to give 270 mg of intermediate 52' (42% yield) and 244 mg of intermediate 52 (38% yield). These intermediates were used as it in the next step.

The intermediates in the Table below were prepared by using an analogous starting from the respective starting materials.

| Int. number | Structure | Mass (mg) | Yield (%) |
|---|---|---|---|
| Intermediate 62 + intermediate 62' | *(structures shown; From 1-methyl-3-nitro-1H-pyrazole-5-carboxylic acid)* | 295 (intermediate 62) <br> 530 (intermediate 62') | 40 <br> 71 |
| Intermediate 83 | *(structure shown; From 2-isopropyl-5-nitro-2H-pyrazol)* | 520 | Quant. |

Preparation of Intermediate 53

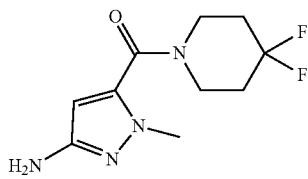 [SMILES: Cn1nc(N)cc1C(=O)N1CCC(F)(F)CC1]

Intermediate 52 (0.24 g, 0.88 mmol) was hydrogenated at rt in MeOH (6 mL) with Pd/C (10 wt. %, 50.00 mg, 0.05 mmol) as a catalyst at atmospheric pressure. After overnight, the catalyst was filtered through a pad of Celite® and the solvent was evaporated until dryness to give 210 mg of intermediate 53 (98% yield) used as it in the next step.

The intermediates in the Table below were prepared by using an analogous starting from the respective starting materials. The most relevant minor deviations to the referenced method are indicated as additional information in the column 'Yield (%)'.

| Int. number | Structure | Mass (mg) | Yield (%) |
|---|---|---|---|
| Intermediate 63 | 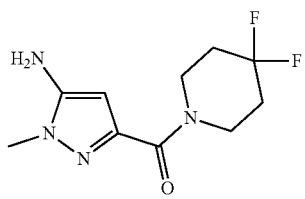<br>From intermediate 62 | 265 | Quant.<br>Procedure with a mixture of MeOH/EtOAc (3:1, v/v) as solvent |
| Intermediate 70 | 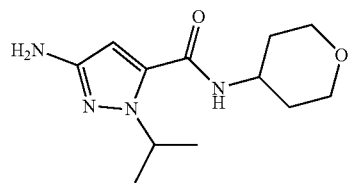<br>From intermediate 52' | 251 | Quant. |
| Intermediate 84 | 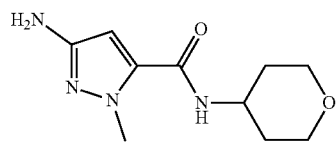<br>From intermediate 83 | 32 | 72<br>Procedure with a mixture of MeOH/EtOAc (5:2, v/v) as solvent |
| Intermediate 118 | <br>From intermediate 62' | 524 | Quant. |

-continued

| Int. number | Structure | Mass (mg) | Yield (%) |
|---|---|---|---|
| Mixture of intermediate 177/intermediate 177' | From mixture of intermediate 176 and 176' | 640 mixture of intermediates 177 and 177' | 43 under 3 bars of H₂ |
| Intermediate 196 | From intermediate 195 | 2140 orange solid | 99 |
| Intermediate 214 | From intermediate 213 | 160 | 23 Procedure with a mixture of MeOH/EtOAc (5:3, v/v) as solvent |
| Intermediate 233 | From intermediate 232 | 297 | Quant. Procedure with a mixture of MeOH/EtOAc (2:1, v/v) as solvent |
| Intermediate 236 | From intermediate 232' | 1950 | Quant. Procedure with a mixture of MeOH/EtOAc (3:1, v/v) as solvent |

-continued

| Int. number | Structure | Mass (mg) | Yield (%) |
|---|---|---|---|
| Intermediate 242 | From intermediate 241 | 1000 | 73 |
| Intermediate 247 | From intermediate 246 | 1610 | 97 Procedure with a mixture of MeOH/EtOAc (2:1, v/v) |
| Mixture of Intermediate 255/ Intermediate 256 | From intermediate 253 and intermediate 254 | 200 (mixture of intermediate 255 and intermediate 256, 50:34) | 98 Procedure with a mixture of MeOH/EtOAc (3:2, v/v) as solvent |
| Mixture of Intermediate 263/ Intermediate 264 | From intermediate 261 and intermediate 262 | 200 | 50 Procedure with a mixture of MeOH/EtOAc (3:2, v/v) as solvent |

-continued

| Int. number | Structure | Mass (mg) | Yield (%) |
| --- | --- | --- | --- |
| Intermediate 270 | From intermediate 269 | 338 | Quant. Procedure with a mixture of MeOH/EtOAc (5:2, v/v) as solvent |
| Intermediate 304 | From intermediate 30 | 2000 off-white solid | 73 Procedure with EtOH as solvent |
| Intermediate 328 | From intermediate 327 | 700 | Quant. Procedure with a mixture of MeOH/EtOAc (3:1, v/v) as solvent |
| Intermediate 342 | From intermediate 341 | 407 | 77 Procedure with a mixture of MeOH/EtOAc (3:1, v/v) as solvent |
| Intermediate 346 | From intermediate 345 | 360 | Quant. Procedure with a mixture of MeOH/EtOAc (3:1, v/v) as solvent |
| Intermediate 352 | From intermediate 351 | 220 | Quant. Procedure with a mixture of MeOH/EtOAc (3:1, v/v) as solvent |

-continued

| Int. number | Structure | Mass (mg) | Yield (%) |
|---|---|---|---|
| Intermediate 355 | From intermediate 351' | 160 | Quant. Procedure with a mixture of MeOH/EtOAc (2:1, v/v) as solvent |
| Intermediate 363 | From intermediate 362 | 380 | Quant. Procedure with a mixture of MeOH/EtOAc (3:1, v/v) as solvent |
| Intermediate 383 | From intermediate 341' | 490 | 71 Procedure with a mixture of MeOH/EtOAc (3:1, v/v) as solvent |
| Intermediate 387 | From intermediate 386 | 270 | Quant. Procedure with a mixture of MeOH/EtOAc (3:1, v/v) as solvent |
| Intermediate 391 | From intermediate 390 | 720 | Quant. with a mixture of MeOH/EtOAc (5:4, v/v) as solvent |
| Intermediate 410 | From intermediate 409 | 187 | Quant. Procedure with a mixture of MeOH/EtOAc (3:2, v/v) as solvent |

-continued

| Int. number | Structure | Mass (mg) | Yield (%) |
|---|---|---|---|
| Intermediate 414 | From intermediate 413 | 440 | 95<br>Procedure with a mixture of MeOH/EtOAc (2:1, v/v) as solvent |
| Intermediate 424 | From intermediate 423 | 495 | 88 |
| Intermediate 428 | From intermediate 427 | 700 | 98 |
| Intermediate 431 | From intermediate 427' | 760 | Quant. |
| Intermediate 469 | From intermediate 468 | 287 | 92<br>Procedure with EtOH as solvent |
| Intermediate 472 | From intermediate 471 | 440 | 93<br>Procedure with a mixture of MeOH/EtOAc (2:1, v/v) as solvent |

-continued

| Int. number | Structure | Mass (mg) | Yield (%) |
|---|---|---|---|
| Intermediate 484 | From intermediate 483 | 940 | Quant. |
| Intermediate 492 | From intermediate 491 | 370 | Quant. Procedure with a mixture of MeOH/EtOAc (2:1, v/v) as solvent |
| Intermediate 509 | From intermediate 508 | 260 | 34 Procedure with a mixture of MeOH/EtOAc (2:1, v/v) as solvent |
| Intermediate 514 | From intermediate 513 | 293 | 96 Procedure with a mixture of MeOH/EtOAc (5:2, v/v) as solvent |
| Intermediate 518 | From intermediate 517 | 750 | Quant. Procedure with a mixture of MeOH/EtOAc (2:1, v/v) as solvent |
| Intermediate 522 | From intermediate 521 | 243 | Quant. Procedure with a mixture of MeOH/EtOAc (2:1, v/v) as solvent |

-continued

| Int. number | Structure | Mass (mg) | Yield (%) |
|---|---|---|---|
| Intermediate 526 | From intermediate 525 | 310 | 93<br>Procedure with a mixture of MeOH/EtOAc (2:1, v/v) as solvent |
| Intermediate 530 | From intermediate 529 | 430 | Quant.<br>Procedure with a mixture of MeOH/EtOAc (2:1, v/v) as solvent |
| Intermediate 534 | From intermediate 533 | 148 | 86<br>Procedure with a mixture of MeOH/EtOAc (2:1, v/v) as solvent |
| Intermediate 538 | From intermediate 537 | 523 | 92<br>Procedure with a mixture of MeOH/EtOAc (2:1, v/v) as solvent |
| Intermediate 542 | From intermediate 541 | 377 | 47<br>Procedure with a mixture of MeOH/EtOAc (2:1, v/v) as solvent |
| Intermediate 546 | From intermediate 545 | 532 | 88<br>Procedure with a mixture of MeOH/EtOAc (2:1, v/v) as solvent |

-continued

| Int. number | Structure | Mass (mg) | Yield (%) |
|---|---|---|---|
| Intermediate 585 | (structure) From intermediate 583 | 97 | 38 |
| Intermediate 588 | (structure) From intermediate 584 | 100 | 99 |
| Intermediate 592 | (structure) From intermediate 591 | 266 | 83 |
| Intermediate 598 | (structure) From intermediate 597 | 340 | 95 |
| Intermediate 602 | (structure) From intermediate 601 | 305 | 100 |
| Intermediate 621 | (structure) From intermediate 620 | 330 | 84 |

-continued

| Int. number | Structure | Mass (mg) | Yield (%) |
|---|---|---|---|
| Intermediate 625 | From intermediate 624 | 199 | 100 |
| Intermediate 629 | From intermediate 628 | 312 | 91 |
| Intermediate 637 | From intermediate 635 | 135 | 74 |
| Intermediate 642 | From intermediate 636 | 3960 | 100 |
| Intermediate 647 | From intermediate 646 | 562 | 96 |
| Intermediate 652 | From intermediate 650 | 65 | 90 |

-continued

| Int. number | Structure | Mass (mg) | Yield (%) |
|---|---|---|---|
| Intermediate 659 | From intermediate 658 | 249 | 100 |
| Intermediate 667 | From intermediate 666 | 308 | Quant. |
| Intermediate 669 | From intermediate 668 | 1010 | 100 |
| Intermediate 675 | From intermediate 674 | 665 | 100 |
| Intermediate 681 | From intermediate 680 | 430 | 100 |
| Intermediate 687 | From intermediate 686 | 115 | 100 |

-continued

| Int. number | Structure | Mass (mg) | Yield (%) |
|---|---|---|---|
| Intermediate 693 | From intermediate 692 | 220 | 63 |
| Intermediate 704 | From intermediate 703 | 290 | 84 |
| Intermediate 709 | From intermediate 708 | 283 | 96 |
| Intermediate 715 | From intermediate 713 | 165 | 80 |
| Intermediate 718 | From intermediate 714 | 252 | 94 |
| Intermediate 726 | From intermediate 725 | 687 | 93 |

| Int. number | Structure | Mass (mg) | Yield (%) |
|---|---|---|---|
| Intermediate 743 | 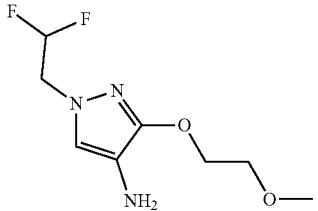<br>From intermediate 742 | 1440<br><br><br><br><br><br>1380 | 51<br>Procedure with a mixture of $^i$PrOH/THF (2:1, v/v) as solvent, 1.5 bars H$_2$, 2days<br>OR<br>49<br>With MeOH as solvent, atmospheric pressure H$_2$, 18 h |
| Intermediate 748 | 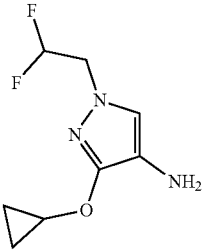<br>From intermediate 747 | 307 | 86<br>Procedure with a mixture of AcOEt/EtOH (4:1, v/v) as solvent, atmospheric pressure H$_2$, 12 h |
| Intermediate 752 | 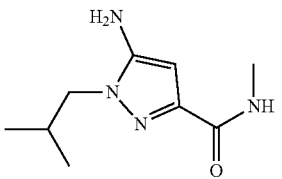<br>From intermediate 750 | 4150 | quant<br>Procedure with a mixture of MeOH/AcOEt (4:1, v/v) as solvent, atmospheric pressure H$_2$, 1 h 30 |
| Intermediate 764 | 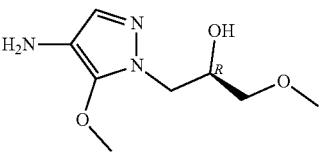<br>From intermediate 763 | 120 | 20 |

Example A18

Preparation of Intermediate 56 and intermediate 56'

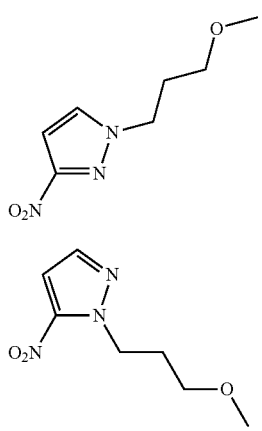

intermediate 56 intermediate 56'

Bromo-3-methoxypropane (1.20 mL, 10.51 mmol) was added at rt to a mixture of 5-nitro-1H-pyrazole (1.00 g, 8.84 mmol), $K_2CO_3$ (2.35 g, 17.00 mmol) in DMF (10 mL). This reaction was stirred in a sealed tube at 120° C. using one single mode microwave (Biotage Initiator EXP 60) with a power output ranging from 0 to 400 W for 30 min. Then, water was added and this mixture was extracted twice with EtOAc. The organic layers were mixed, dried over $MgSO_4$, filtered and the solvent was evaporated until dryness. The residue was purified by column chromatography on silica gel (Irregular SiOH, 40 μm, 80 g, mobile phase: gradient from 70% heptane, 29% EtOAc, 1% MeOH (+10% $NH_4OH$) to 40% heptane, 52% EtOAc, 8% MeOH (+10% $NH_4OH$)). The pure fractions were collected and the solvent was evaporated until dryness to give 1.39 g of intermediate 56 (85% yield) and 267 mg of intermediate 56' (16% yield). These intermediates were used as it in the next step.

The intermediates in the Table below were prepared by using an analogous starting from the respective starting materials. The most relevant minor deviations to the referenced method are indicated as additional information in the column 'Yield (%)'.

| Int. number | Structure | Mass (mg) | Yield (%) |
| --- | --- | --- | --- |
| Intermediate 114 | From 5-methyl-3-nitro-1H-pyrazole and bromo-3-methoxypropane | 20400 (intermediate 114) | 22 without microwave activation |
| Intermediate 134 + intermediate 134' | From 5-methyl-3-nitro-1H-pyrazole and mixture of intermediate 778 and 778' | 880 (intermediate 134) 493 (intermediate 134') | 24 14 without microwave activation |

-continued

| Int. number | Structure | Mass (mg) | Yield (%) |
|---|---|---|---|
| Intermediate 141 + intermediate 141' | 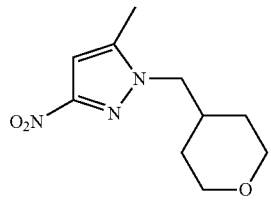 + 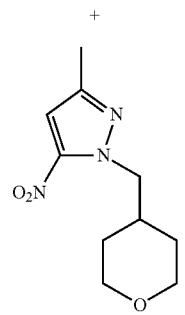<br>From 5-methyl-3-nitro-1H-pyrazole and 4-(bromomethyl)tetrahydro-2H-pyran | 2240 (intermediate 141)<br>2140 (intermediate 141') | 25<br>24 |
| Intermediate 162 + intermediate 162' | 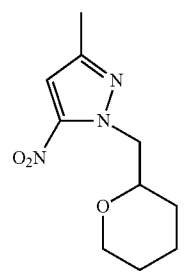 + 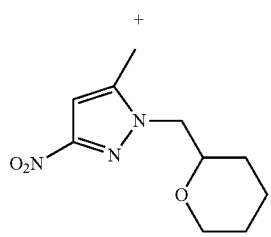<br>From 5-methyl-3-nitro-1H-pyrazole and 2-(bromomethyl)tetrahydro-2H-pyran | 1280 (intermediate 162)<br>3900 (intermediate 162') | 12<br>37 |
| Intermediate 170 | 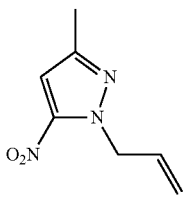<br>From 5-methyl-3-nitro-1H-pyrazole and allyl bromide | 435 (intermediate 170) | 17 |

-continued

| Int. number | Structure | Mass (mg) | Yield (%) |
|---|---|---|---|
| Mixture of Intermediate 176 + intermediate 176' | *(structures shown)* From 3-methyl-4-nitro-1H-pyrazole and 4-(bromomethyl)-tetrahydro-2H-pyran | 1190 (mixture of intermediates 176 and 176' (44:56)) | 67 |
| Intermediate 191 | *(structure shown)* From 5-methyl-3-nitro-1H-pyrazole and 3-(bromomethyl)tetrahydrofuran) | 1300 (intermediate 191) | 24 |
| Intermediate 199 | *(structure shown)* From 5-methyl-3-nitro-1H-pyrazole and 2-(chloromethyl)-1,4-dioxane | 750 | 11 without microwave activation |
| Intermediate 219 | *(structure shown)* From 5-methyl-3-nitro-1H-pyrazole and 3-bromo-1-propanol | 1770 (intermediate 219) | 24 |

| Int. number | Structure | Mass (mg) | Yield (%) |
|---|---|---|---|
| Intermediate 223 | From 1-bromo-3-methylbutane and 5-nitro-1H-pyrazole-3-carboxamide | 2300 | 32 without microwave activation |
| Intermediate 228 | 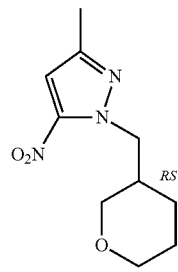 From 5-methyl-3-nitro-1H-pyrazole and 3-(bromomethyl)-tetrahydro-2H-pyran | 1670 (intermediate 228) | 27 |
| Intermediate 275 + Intermediate 275' | 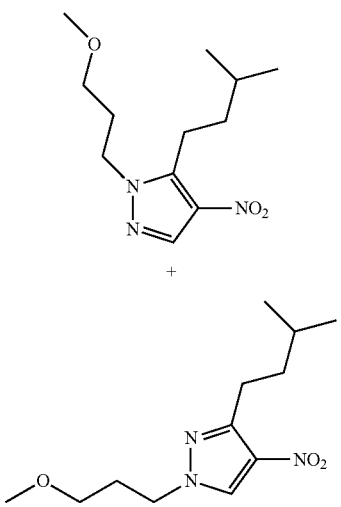 From 1-Bromo-3-methoxypropane and intermediate 252 | 1050 (intermediate 275) 1900 (intermediate 275') | 24 43 |

-continued

| Int. number | Structure | Mass (mg) | Yield (%) |
| --- | --- | --- | --- |
| Intermediate 292 + Intermediate 292' | 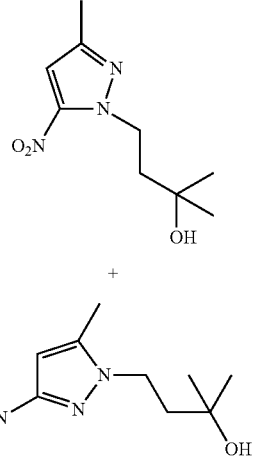<br>+<br>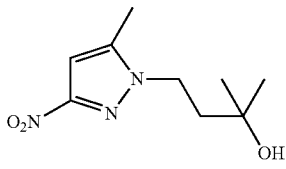<br>From 4-Bromo-2-metylbutan-2-ol and 5-methyl-3-nitro-1H-pyrazole | 1270 (intermediate 292) 1730 (intermediate 292') | 24 32 |
| Intermediate 370 | 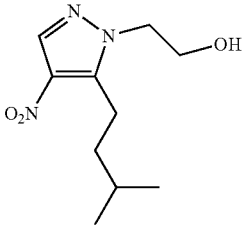<br>From 2-Bromo-ethanol and intermediate 252 | 336 | 14 |
| Intermediate 506 | 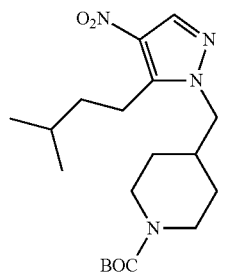<br>From 1-Boc-4-Bromomethylpiperidine and intermediate 252 | 4810 | 23 |
| Intermediate 513 | 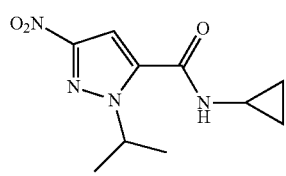<br>From iodopropane and intermediate 512 | 356 (intermediate 513) | 37 without microwave activation and T = 80° C. |

-continued

| Int. number | Structure | Mass (mg) | Yield (%) |
|---|---|---|---|
| Intermediate 650 | From intermediate 730 and (2-iodoethyl)cyclopropane | 83 | 17<br>RT<br>overnight |
| Intermediate 651 | From intermediate 730 and (2-iodoethyl)cyclopropane | 391 | 80<br>RT<br>overnight |
| Intermediate 656 | From 4-nitro-1H-pyrazole and N-(2-chloroethyl)morpholine hydrochloride salt | 4400 | 44<br>without microwave activation<br>T = 120° C.,<br>2 h |
| Intermediate 708 | From intermediate 707 and 2-iodopropane | 335 | 14<br>without microwave activation<br>T = 120° C.,<br>2 h 20 |
| Intermediate 713 | From intermediate 712 and 2-iodopropane<br>Separation from isomer (intermediate 714) by preparative LC (Irregular SiOH 15-40 μm 80 g GraceResolv®, mobile phase Gradient from: 80% Heptane, 20% EtOAc to 65% Heptane, 35% EtOAc) | 235 | 18<br>without microwave activation<br>T = 120° C.,<br>2 h 20 |

-continued

| Int. number | Structure | Mass (mg) | Yield (%) |
|---|---|---|---|
| Intermediate 714 | (structure shown) From intermediate 712 and 2-iodopropane Separation from isomer (intermediate 713) by preparative LC (Irregular SiOH 15-40 μm 80 g GraceResolv®, mobile phase Gradient from: 80% Heptane, 20% EtOAc to 65% Heptane, 35% EtOAc) | 305 | 24 without microwave activation T = 120° C., 2 h 20 |
| Intermediate 633 | (structure shown) From intermediate 730 and cyclopentyl iodide | 675 | 80 rt, overnight |
| Intermediate 731 | (structure shown) From intermediate 730 and methyl iodide | 1220 | 63 |
| Intermediate 750 + 751 | (structure shown) intermediate 750 (structure shown) intermediate 751 From intermediate 578 and 1-iodo-2-methylpropane | 3600 3850 | 32 120° C., 1 h 40 34 |

Example A19

Preparation of Intermediate 57

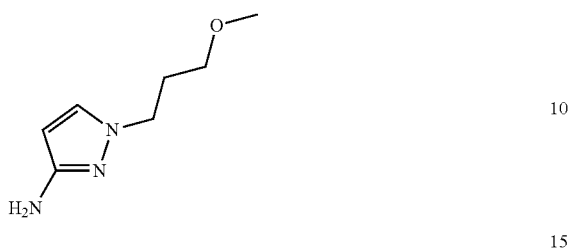

Intermediate 56 (1.30 g, 7.02 mmol) was hydrogenated in MeOH (25 mL) with RaNi (1.00 g, 17.04 mmol) as a catalyst in a pressure vessel reactor with 3 bars of $H_2$ at rt for 2 h. The reaction was filtered over Celite® and the solvent was evaporated until dryness to give 1.03 g of intermediate 57 (95% yield) used as it in the next step.

The intermediates in the Table below were prepared by using an analogous starting from the respective starting materials. The most relevant minor deviations to the referenced method are indicated as additional information in the column 'Yield (%)'.

| Int. number | Structure | Mass (mg) | Yield (%) |
|---|---|---|---|
| Intermediate 67 | 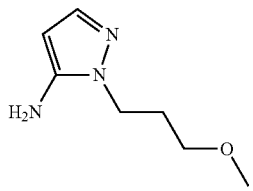<br>From intermediate 56' | 220 | Quant. |
| Intermediate 115 | 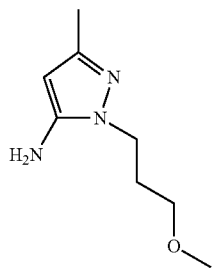<br>From intermediate 114 | 16200 | 95 |
| Intermediate 135 | 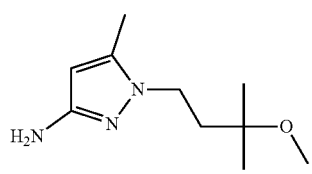<br>From intermediate 134 | 760 | Quant. |

-continued
| Int. number | Structure | Mass (mg) | Yield (%) |
|---|---|---|---|
| Intermediate 138 | 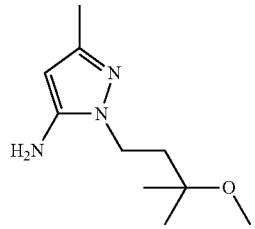<br>From intermediate 134' | 390 | 92 |
| Intermediate 142 | 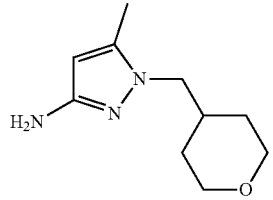<br>From intermediate 141 | 1960 | Quant. |
| Intermediate 145 | 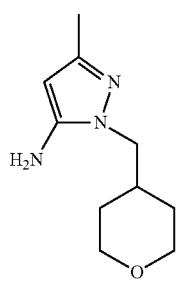<br>From intermediate 141' | 1930 | Quant. |
| intermediate 163 | 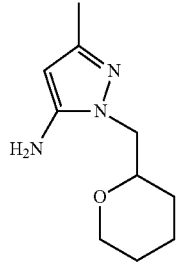<br>From intermediate 162 | 1000 | 90 |
| intermediate 166 | 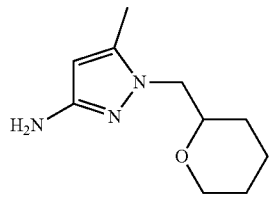<br>From intermediate 162' | 3300 | 98 |

-continued
| Int. number | Structure | Mass (mg) | Yield (%) |
|---|---|---|---|
| intermediate 184 | 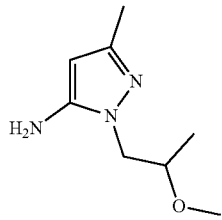 From intermediate 183 | 850 | Quant. |
| intermediate 192 | 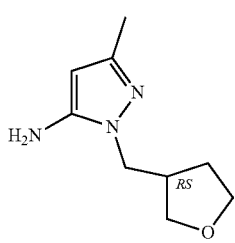 From intermediate 191 | 1100 | Quant. |
| intermediate 200 | 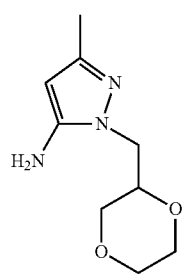 From intermediate 199 | 650 | Quant. |
| intermediate 220 | 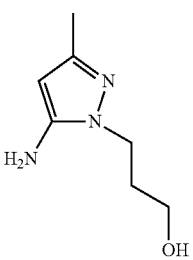 From intermediate 219 | 1400 | 98 |
| intermediate 229 | 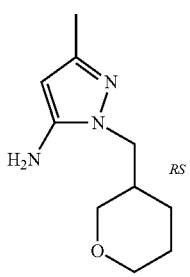 From intermediate 228 | 1530 | Quant. |

| Int. number | Structure | Mass (mg) | Yield (%) |
|---|---|---|---|
| intermediate 276 | 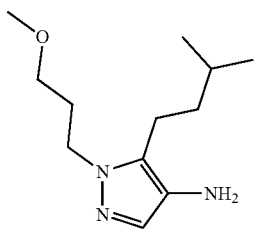 From intermediate 275 | 890 | 96 |
| intermediate 279 | 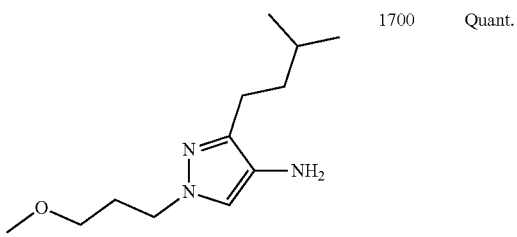 From intermediate 275' | 1700 | Quant. |
| intermediate 293 | 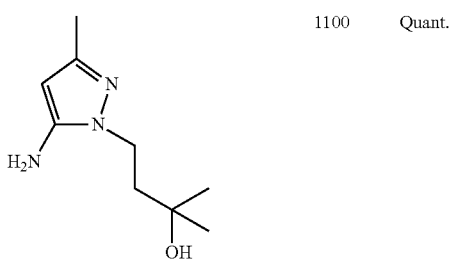 From intermediate 292 | 1100 | Quant. |
| intermediate 296 | 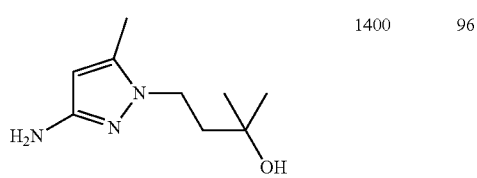 From intermediate 292' | 1400 | 96 |
| intermediate 371 | 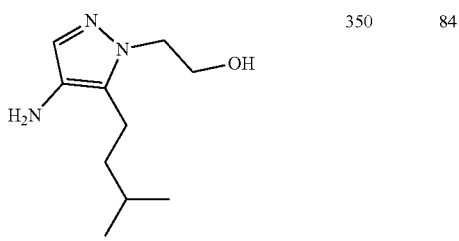 From intermediate 370 | 350 | 84 |
| intermediate 607 | 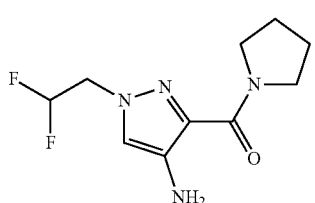 From intermediate 606 | 120 | 70 |

-continued

| Int. number | Structure | Mass (mg) | Yield (%) |
|---|---|---|---|
| intermediate 613 | 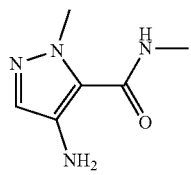<br>From intermediate 612 | 176 | 72 |
| intermediate 617 | <br>From intermediate 616 | 105 | 89 |

Example A20

Preparation of Intermediate 103

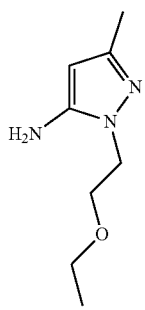

In a sealed glassware, (2-ethoxyethyl)-hydrazine (1.70 g, 9.60 mmol) was added to a solution of 3-aminocrotononitrile (394.12 mg, 4.80 mmol) in a mixture of AcOH (6.3 mL) and EtOH (20.8 mL). The mixture was stirred at 90° C. for 17 h. Water was added and the aqueous layer was extracted with Et$_2$O. The aqueous layer was basified with K$_2$CO$_3$ powder and extracted twice with DCM. The combined organic layers were dried over MgSO$_4$, filtered and evaporated. The residue (400 mg) was purified by column chromatography on silica gel (Irregular SiOH, 40 m, mobile phase DCM/MeOH/NH$_4$OH, gradient from 100% DCM to 95% DCM, 5% MeOH, 0.1% NH$_4$OH). The pure fractions were combined and the solvent was evaporated to give 194 mg of intermediate 103 (24% yield).

Example A21

Preparation of Intermediate 121

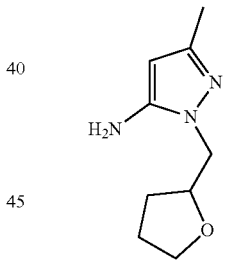

3-aminocrotononitrile (1.91 g, 23.27 mmol) and [(tetrahydro-2-furanyl)methyl]-hydrazine (4.40 g, 23.27 mmol) in EtOH (7.8 mL) were stirred at reflux for 5 h. EtOH was evaporated. The residue was taken up into water, extracted with Et$_2$O twice, basified with K$_2$CO$_3$ powder and extracted with DCM. The organic layer was dried over MgSO$_4$, filtered and evaporated. The residue was purified by column chromatography on silica gel (stationary phase: irregular SiOH 15-40 µm, 80 g, mobile phase: DCM/MeOH/NH$_4$OH, gradient from 100% DCM to 97% DCM, 3% MeOH, 0.1% NH$_4$OH). The fractions containing the product were combined and evaporated to dryness to give 1.6 g of intermediate 121 (38% yield).

The intermediates in the Table below were prepared by using an analogous starting from the respective starting materials.

| Int. number | Structure | Mass (mg) | Yield (%) |
|---|---|---|---|
| Intermediate 156 | 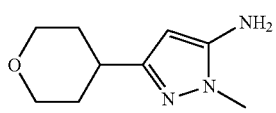<br>From (2-methoxyethyl)-hydrazine and tetrahydro-β-oxo-2H-pyran-4-propanenitrile | 209 | 28 |
| Intermediate 159 | From methylhydrazine and tetrahydro-β-oxo-2H-pyran-4-propanenitrile | 260 | 25 |
| Intermediate 239 + intermediate 239' | From methylhydrazine and 2-[(dimethylamino)methylene]-5-methyl-3-oxo-, methyl ester, (2Z)-hexanoic acid | 3730 (intermediate 239)<br>2230 (intermediate 239') | 22<br><br>13 |

Example A22

Preparation of Intermediate 171

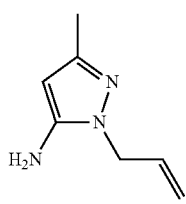

A mixture of intermediate 170 (430.00 mg, 2.57 mmol), $NH_4Cl$ (550.36 mg, 10.29 mmol) and Iron powder (718.31 mg, 12.86 mmol) in a mixture of EtOH (9.82 mL) and distilled water (3.93 mL) was heated at 75° C. for 2 h. The reaction mixture was cooled to rt, poured onto a mixture of 10% aqueous $K_2CO_3$ and DCM, then filtered through a pad of Celite®. The organic layer was decanted, washed with brine, dried over $MgSO_4$, filtered and evaporated to dryness to give 331 mg of intermediate 171 (94% yield, 81% purity based on LC/MS).

The intermediates in the Table below were prepared by using an analogous starting from the respective starting materials. The most relevant minor deviations to the referenced method are indicated as additional information in the column 'Yield (%)'.

| Int. number | Structure | Mass (mg) | Yield (%) |
|---|---|---|---|
| Intermediate 225 | 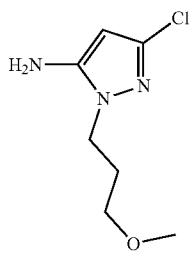<br>From intermediate 224 | 1460 | Quant. |
| Intermediate 308 | 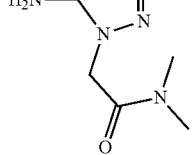<br>From intermediate 307 | 505<br>off-white<br>solid | 81<br>with T = 85° C. |
| Intermediate 324 | 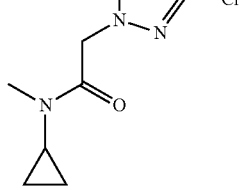<br>From intermediate 323 | 284<br>colorless oil | 67<br>with T = 85° C. |
| Intermediate 332 | 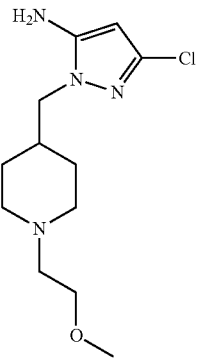<br>From intermediate 331 | 209<br>colorless oil | 70<br>with T = 85° C. |
| Intermediate 420 | <br>From intermediate 419 | 559<br>brown<br>residue | 90<br>with T = 85° C. |

-continued

| Int. number | Structure | Mass (mg) | Yield (%) |
|---|---|---|---|
| Intermediate 461 | 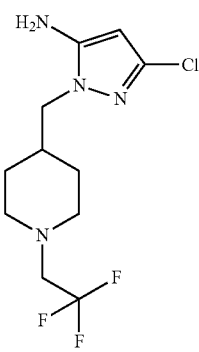<br>From intermediate 460 | 600 | 86<br>with T = 85° C. |
| Intermediate 496 | 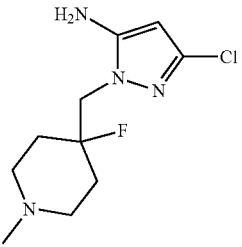<br>From intermediate 495 | 95<br>(86% purity based on LC/MS)<br>colorless oil | 61<br>with T = 85° C. |
| Intermediate 500 | 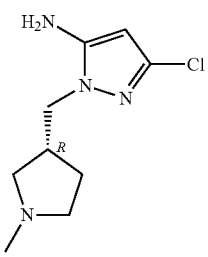<br>From intermediate 499 | 462 | 69<br>with T = 85° C. |
| Intermediate 504 | 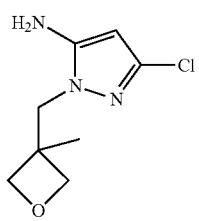<br>From intermediate 503 | 930<br>(79% purity based on LC/MS)<br>colorless oil | 81<br>with T = 85° C. |
| Intermediate 722 | 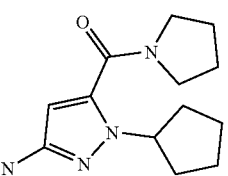<br>From intermediate 721 | 130 | 77<br>with<br>T = 70° C.,<br>30 min |

-continued

| Int. number | Structure | Mass (mg) | Yield (%) |
|---|---|---|---|
| Intermediate 735 | 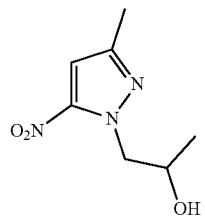<br>From intermediate 734 | 120 | 77<br>with<br>T = 70° C.,<br>30 min |

Example A23

Preparation of Intermediate 182 and intermediate 182'

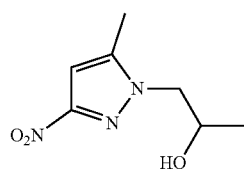

intermediate 182 intermediate 182'

A mixture of 5-methyl-3-nitro-1H-pyrazole (7.00 g, 55.07 mmol) (+/−)-propylene oxide (7.71 mL, 110.15 mmol) in EtOH (64.31 mL) in a sealed tube was stirred at 140° C. for 4 h. The solvent was evaporated and the residue was purified by column chromatography on silica gel (stationary phase: irregular SiOH, 15-40 m, 120 g, mobile phase: heptane/EtOAc, gradient from 80:20 to 50:50). The fractions containing the product were combined to give 2.5 g of intermediate 182 (25% yield) and 7.5 g of intermediate 182' (74% yield).

Preparation of Intermediate 183

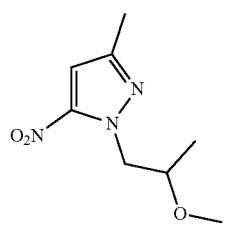

Intermediate 182 (1.00 g, 5.40 mmol) and iodomethane (504.26 μL, 8.10 mmol) in THF (10 mL) were added at 0° C. under $N_2$. Then, NaH (60% dispersion in mineral oil) (259.18 mg, 6.48 mmol) was added and the resulting mixture was stirred at rt for 4 h, poured out onto water, extracted with EtOAc, dried over $MgSO_4$, filtered and evaporated. The residue was purified by column chromatography on silica gel (stationary phase: irregular SiOH, 15-40 μm 40 g, mobile phase: heptane/EtOAc, gradient from 80:20 to 60:40). The fractions containing the product were combined and evaporated to dryness to give 1.01 g of intermediate 183 (94% yield).

Example A24

Preparation of Intermediate 195

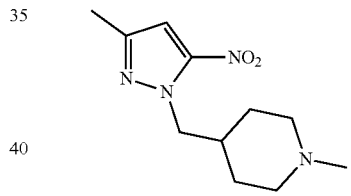

To a solution of 3-methyl-5-nitro-1H-pyrazole (2.46 g, 19.40 mmol) and 1-methyl-4-piperidinemethanol (5.00 g, 38.70 mmol) in dry Me-THF (190 mL). Di-tert-butyl azodicarboxylate (8.91 g, 38.70 mmol) and $PPh_3$ (10.20 g, 38.70 mmol) were added. The solution was heated at 55° C. over the weekend. The reaction mixture was diluted with EtOAc and water. The organic layer was separated and the aqueous layer was extracted thrice with EtOAc. The organic layers were combined, washed with brine, dried over $MgSO_4$, filtered and concentrated. The residue (yellow oil) was purified by column chromatography on silica gel (Irregular SiOH, 15-40 m, 330 g, liquid loading in DCM, mobile phase: DCM/MeOH, gradient from 100:0 to 90:10). The fractions containing the product were combined and evaporated to dryness to give 2.36 g of intermediate 195 (51% yield, yellow oil).

The intermediates in the Table below were prepared by using an analogous starting from the respective starting materials. The most relevant minor deviations to the referenced method are indicated as additional information in the column 'Yield (%)'.

| Int. number | Structure | Mass (mg) | Yield (%) |
|---|---|---|---|
| Intermediate 288 | 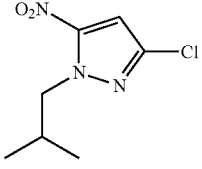<br>From intermediate 224 | 4360<br>yellow oil | 63<br>with T = rt |
| Intermediate 307 | 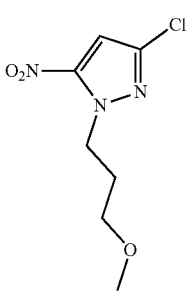<br>From 3-chloro-5-nitro-1H-pyrazole and 3-methoxy-1-propanol | 780<br>yellow oil | 65<br>with T = rt |
| Intermediate 311 | 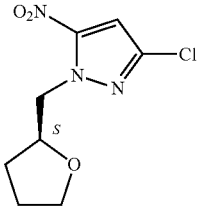<br>From 3-chloro-5-nitro-1H-pyrazole and (S)-tetrahydrofuran-2-yl-methanol | 780<br>colourless oil | 62<br>with T = rt |
| Intermediate 315 | 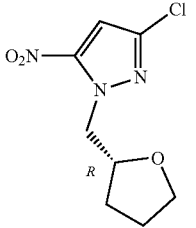<br>From 3-chloro-5-nitro-1H-pyrazole and (R)-tetrahydrofuran-2-yl-methanol | 759<br>yellow oil | 60<br>with T = rt |
| Intermediate 319 | 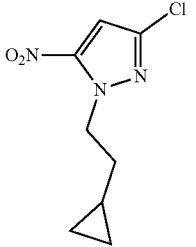<br>From 3-chloro-5-nitro-1H-pyrazole and 2-cyclopropylethanol | 718<br>yellow oil | 71<br>with T = rt |

-continued

| Int. number | Structure | Mass (mg) | Yield (%) |
|---|---|---|---|
| Intermediate 323 | ![structure] From 3-chloro-5-nitro-1H-pyrazole and 2-hydroxy-N,N-dimethylacetamide | 484 white solid | 31 with T = rt |
| Intermediate 331 | ![structure] From 3-chloro-5-nitro-1H-pyrazole and 2-hydroxy-N,N-dimethylacetamide | 847 white solid | 27 with T = rt |
| Intermediate 358 | ![structure] From 3-chloro-5-nitro-1H-pyrazole and 1-methyl-4-piperidine methanol | 274 | 16 with T = rt |
| Intermediate 366 | 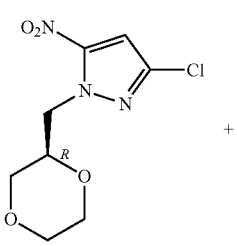 From 3-chloro-5-nitro-1H-pyrazole and (2R)-1,4-dioxane-2-methanol | 1240 colorless oil | 74 colorless oil with T = rt |

-continued

| Int. number | Structure | Mass (mg) | Yield (%) |
|---|---|---|---|
| Intermediate 379 + intermediate 379' | *(3-chloro-5-nitro-1H-pyrazole substituted with (S)-tetrahydrofuran-3-yl-methyl group; mixture of two regioisomers)* From 3-chloro-5-nitro-1H-pyrazole and (S)-tetrahydrofuran-3yl-methanol | 1040 (intermediate 379) colorless oil 426 (intermediate 379') yellow oil | 66 27 with T = rt |
| Intermediate 394 + intermediate 394' | *(3-chloro-5-nitro-1H-pyrazole substituted with (2S)-1,4-dioxan-2-yl-methyl group; mixture of two regioisomers)* From 3-chloro-5-nitro-1H-pyrazole and (2S)-1,4-dioxan-2yl-methanol | 1560 (intermediate 394) colorless oil 730 (intermediate 394') colorless oil | 93 43 with T = rt |
| Intermediate 398 | *(3-chloro-5-nitro-1H-pyrazole substituted with N-Boc-piperidin-4-yl-methyl group)* From 3-chloro-5-nitro-1H-pyrazole and N-Boc-piperidinemethanol | 10600 yellow oil | 75 with T = rt |

-continued

| Int. number | Structure | Mass (mg) | Yield (%) |
|---|---|---|---|
| Intermediate 479 | 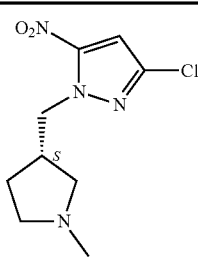<br>From 3-chloro-5-nitro-1H-pyrazole and (S)-3-(hydroxymethyl)-1-methylpyrrolidine | 706<br>yellow oil | 49<br>with T = rt |
| Intermediate 495 | 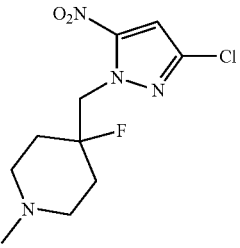<br>From 3-chloro-5-nitro-1H-pyrazole and 4-fluoro-1-methyl-4-piperidinemethanol | 174<br>yellow oil | 13<br>with T = rt |
| Intermediate 499 | 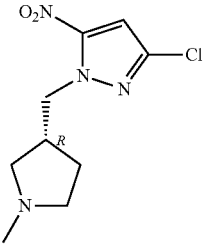<br>From 3-chloro-5-nitro-1H-pyrazole and (R)-(1-methylpyrrolidin-3-yl)methanol | 761<br>yellow oil | 55<br>with T = rt |
| Intermediate 503 | 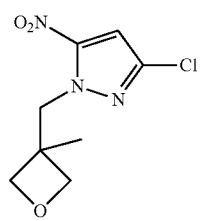<br>From 3-chloro-5-nitro-1H-pyrazole and (3-methyl-3-oxetanemethanol | 1450<br>off-white solid | 92<br>with T = rt |

Example A25

Preparation of Intermediate 211 and intermediate 212

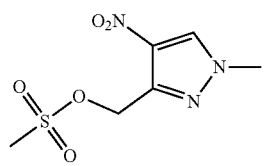
intermediate 211

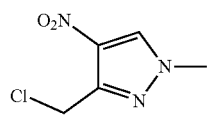
intermediate 212

MsCl (0.36 mL, 4.65 mmol) was added slowly at 0° C. to a solution of 1-methyl-4-nitro-1H-pyrazole-3-methanol (0.62 g, 3.95 mmol) in a mixture of DCM (8 mL) and TEA (1 mL, 7.194 mmol). This reaction was stirred for 2 h at rt. Then, water and an aqueous solution of HCl 3N was added. The aqueous layer was extracted twice with DCM. The organic layer was decanted and the solvent was evaporated until dryness to give 526 mg of a mixture of intermediate 211 and 212 (50:50) which was used directly as it in the next step.

The intermediates in the Table below were prepared by using an analogous starting from the respective starting materials.

| Int. number | Structure | Mass (mg) | Yield (%) |
|---|---|---|---|
| Intermediate 490 | From intermediate 489 | 800 | 86 |
| Intermediate 702 | From intermediate 701 | 500 | 100 |

Example A26

Preparation of Intermediate 213

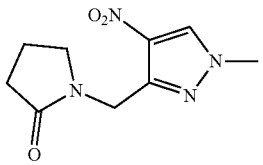 [SMILES: Cn1cc([N+](=O)[O-])c(CN2CCCC2=O)n1]

NaH (60% dispersed in mineral oil) (0.61 g, 15.38 mmol) was added at rt to a solution of pyrrolidinone (1.10 mL, 14.26 mmol) in DMF (35 mL). After 5 min at rt, a mixture of intermediate 211 and 212 (1.83 g, 7.78 mmol) was added and stirred at rt overnight. Then, water and an aqueous solution of $NH_4Cl$ 10% were added and this mixture was extracted twice with EtOAc. The organic layer was decanted and the solvent was evaporated until dryness to give 810 mg of intermediate 213 (46% yield) used as it for the next step.

Example A27

Preparation of Intermediate 224

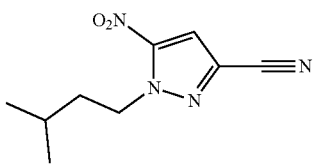

Intermediate 223 (2.30 g, 10.17 mmol) and $CH_3CN$ (15.93 mL, 0.30 mol) in $POCl_3$ (3.78 mL, mL, 40.67 mmol) in a sealed tube were stirred at 140° C. using one single mode microwave (Biotage Initiator EXP 60) with a power output ranging from 0 to 400 W for 5 min. The resulting mixture was poured out onto ice and water, extracted with DCM, dried over $MgSO_4$, filtered and evaporated. The residue was purified by column chromatography on silica gel (stationary phase: irregular SiOH, 15-40 m, 80 g, liquid injection, mobile phase: heptane/EtOAc 90:10). The pure fractions were combined and the solvent was evaporated to give 1.71 g of intermediate 224 (81% yield).

Example A28

Preparation of Intermediate 232 and intermediate 232'

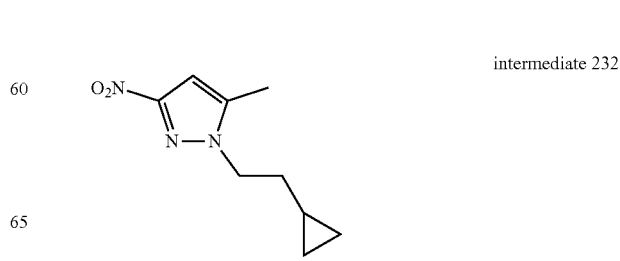
intermediate 232

479
-continued intermediate 232′

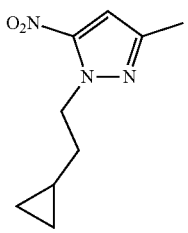

In a sealed tube, 2-(tributylphosphoranylidene)-acetonitrile (7.30 g, 30.25 mmol) was added to a solution of 5-Methyl-3-nitro-1H-pyrazole (2.00 g, 15.74 mmol) and 2-cyclopropylethanol (2.04 g, 23.68 mmol) in toluene (70 mL). The mixture was heated at 60° C. for 19 h. After cooling down to rt, the mixture was diluted with EtOAc and water. The organic layer was decanted and the solvent was evaporated in vacuo. The residue was purified by column chromatography on silica gel (Irregular SiOH, 20-45 m, 40 g, mobile phase: heptane/EtOAc, gradient from 60:40 EtOAc to 50:50). The pure fractions were combined and the solvent was evaporated until dryness to give 2.10 g of intermediate 232′ (68% yield) and 330 mg of intermediate 232 (11% yield).

Example A29

Preparation of Intermediate 240

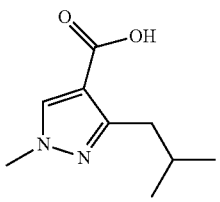

LiOH (1.40 g, 58.46 mmol) was added to a mixture of intermediate 239 (3.73 g, 19.01 mmol) at rt in a mixture of EtOH (20.00 mL), distilled water (20.00 mL) and 1,4-dioxane (20.00 mL). This reaction was stirred at 40° C. for 3 h then at rt 2 nights. The reaction was poured onto water and Et₂O. The organic layer was decanted and the aqueous layer was acidified by an aqueous solution of HCl 3N until pH=4. The aqueous layer was extracted twice with EtOAc and the organic layer was decanted and evaporated until dryness to give 3.71 g of intermediate 240 (quant. yield) used as it in the next step.

The intermediates in the Table below were prepared by using an analogous starting from the respective starting materials.

| Int. number | Structure | Mass (mg) | Yield (%) |
|---|---|---|---|
| Intermediate 245 | 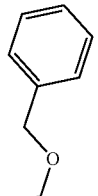<br>From intermediate 239′ | 1600 | 77 |

480
Preparation of Intermediate 241

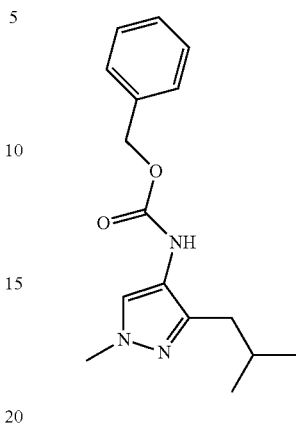

This reaction has been made twice from 1 g of intermediate 240. At rt, diphenyl phosphoryl azide (2.40 mL, 11.16 mmol) followed by benzyl alcohol (2.40 mL, 23.19 mmol) was added to a mixture of intermediate 240 (1.00 g, 5.49 mmol) and TEA (1.60 mL, 11.51 mmol). This reaction was stirred under microwave 160° C. using one single mode microwave (Biotage Initiator EXP 60) with a power output ranging from 0 to 400 W for 15 min. The reaction was cooled down to rt. These reactions were combined with another batch (from 860 mg of intermediate 240) and the solvent was evaporated until dryness. This residue was purified by column chromatography on silica gel (stationary phase: irregular SiOH, 15-40 μm, 120 g, mobile phase: heptane/EtOAc, gradient from 80:20 to 60:40). The pure fractions were collected and the solvent was evaporated until dryness to give 2.58 g of intermediate 241 (57% over 3 batches) which was directly used as it in the next step.

The intermediates in the Table below were prepared by using an analogous starting from the respective starting materials.

| Int. number | Structure | Mass (mg) | Yield (%) |
|---|---|---|---|
| Intermediate 246 | 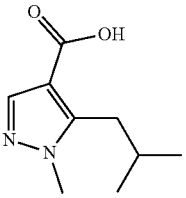<br>From intermediate 245 | 3.1 | Quant. |

Example A30

Preparation of Intermediate 250

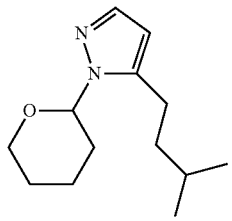 [SMILES: CC(C)CCc1ccnn1C1CCCCO1]

At −78° C. under N$_2$, BuLi (1.6 M in hexane) (8.30 mL, 13.28 mmol) was added over 15 min to a solution of 1-(-2-tetrahydropyranyl)-1H-pyrazole (2.00 g, 13.14 mmol) in THF (20.00 mL). This reaction was stirred at −78° C. for 30 min. 1-bromo-3-methylbutane (1.80 mL, 14.40 mmol) was added dropwise over 10 min to this mixture. After 3 h at −78° C., the reaction mixture was warmed to rt overnight then quenched with water and few drops of an aqueous solution of HCl 3N was added. This mixture was extracted twice with EtOAc and once with DCM. The organic layers were combined and the solvent was evaporated until dryness. The residue was purified by column chromatography on silica gel (stationary phase: irregular SiOH, 15-40 μm, 40 g, mobile phase gradient from: 95% heptane, 5% MeOH to 75% heptane, 25% EtOAc). The pure fractions were collected and the solvent was evaporated until dryness to give: 1.23 g of intermediate 250 (42% yield) (and 60 mg of intermediate 251).

Preparation of Intermediate 251

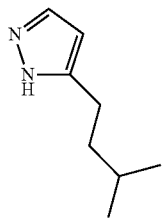

At 0° C., HCl (37% in H$_2$O) (2.50 mL, 29.94 mmol) was added to a mixture of intermediate 250 (1.23 g, 5.53 mmol) in EtOH (55 mL). This reaction was stirred at rt for 5 h. The solvent was evaporated until dryness. This crude was basified by an aqueous solution of NaHCO$_3$ until pH=8. This mixture was extracted twice with Et$_2$O and the organic layer was decanted and the solvent was evaporated until dryness to give 625 mg of intermediate 251 (82% yield) which was directly used as it in the next step. Alternative preparation of intermediate 251: 5-methyl-1-hexyne (10 mL, 76.11 mmol) and (trimethylsilyl)diazomethane (38.06 mL, 2 M, 76.11 mmol) in a sealed glassware were stirred at 135° C. for 2 h then at 100° C. for 12 h. The volatiles were evaporated. The residue was performed by column chromatography on silica gel (stationary phase: irregular SiOH, 15-40 μm, 80 g, mobile phase: gradient from 80% heptane, 20% EtOAc to 60% heptane, 40% EtOAc). The fractions containing the product were combined and evaporated to dryness to give 3.2 g of intermediate 251 (30% yield).

The intermediates in the Table below were prepared by using an analogous starting from the respective starting materials. The most relevant minor deviations to the referenced method are indicated as additional information in the column 'Yield (%)'.

| Int. number | Structure | Mass (mg) | Yield (%) |
| --- | --- | --- | --- |
| Intermediate 678 | From 3-methyl-1-butyne | 4000 | 53<br>135° C. 4 hours |
| Intermediate 684 | From cyclopropyl-acetylene | 8400 | quant<br>135° C. 4 hours |

Preparation of Intermediate 252

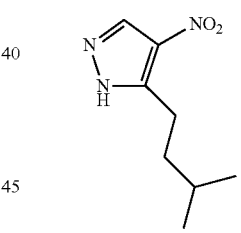

HNO$_3$ (65%) (6.50 mL, 142.35 mmol) was added dropwise to a solution of intermediate 251 (0.62 g, 4.49 mmol) in H$_2$SO$_4$ (6.50 mL, 122.00 mmol) at 0° C. and the reaction was stirred at 0° C. for 3 h and 40 min. HNO$_3$ (65%) (1.50 mL, 32.85 mmol) was added and this reaction was stirred at 0° C. for 2 h. At 0° C., the reaction was poured out onto ice and water, extracted twice with EtOAc and the combined organic layers were washed with saturated NaHCO$_3$ aqueous solution. The organic layer was dried over MgSO$_4$, filtered and evaporated until dryness to give 764 mg of intermediate 252 (93% yield) which was directly used as it in the next step.

The intermediates in the Table below were prepared by using an analogous starting from the respective starting materials. The most relevant minor deviations to the referenced method are indicated as additional information in the column 'Yield (%)'.

| Int. number | Structure | Mass (mg) | Yield (%) |
|---|---|---|---|
| Intermediate 679 | From intermediate 678 | 1410 | 25 |
| Intermediate 685 | From intermediate 684 | 4410 | 37 |

Preparation of Intermediate 261, 262, 253 and 254

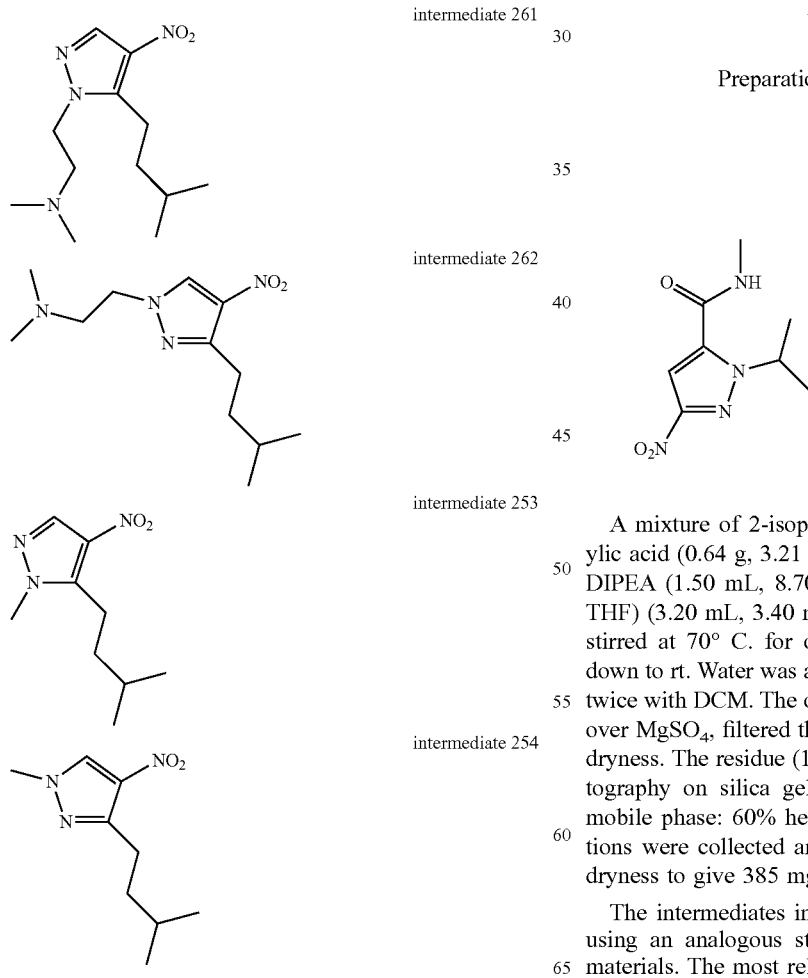

A mixture of intermediate 252 (0.76 g, 4.17 mmol), $K_2CO_3$ (1.10 g, 7.96 mmol) and 2-bromo-N,N-dimethylethylamine hydrobromide (1.13 g, 4.61 mmol) in DMF (8 mL) was stirred in a sealed tube at 120° C. using one single mode microwave (Biotage Initiator EXP 60) with a power output ranging from 0 to 400 W for 60 min. [fixed hold time]. This reaction was performed at 150° C. for 15 min then $K_2CO_3$ added 150° C. for 70 min. Water was added and this mixture was extracted twice with EtOAc. The organic layer was decanted and the solvent was evaporated until dryness. This residue was purified by column chromatography on silica gel (Irregular SiOH, 40 m, 40 g, mobile phase: heptane/EtOAc, gradient from 80:20 to 60:40). The pure fractions were collected and the solvent was evaporated until dryness to give 240 mg of a mixture of intermediates 253 & 254 (29% yield) used as it in the next step. This purification was performed with 95% DCM, 5% MeOH (+10% $NH_4OH$) to 85% DCM, 15% MeOH (+10% $NH_4OH$). The pure fractions were collected and the solvent was evaporated until dryness to give 450 mg of a mixture of intermediates 261 & 262 (42% yield) directly used as it in the next step and a mixture of intermediates 253 & 254 also directly used in the next step.

Example A31

Preparation of Intermediate 269

A mixture of 2-isopropyl-5-nitro-2H-pyrazole-3-carboxylic acid (0.64 g, 3.21 mmol), HATU (1.70 g, 4.47 mmol), DIPEA (1.50 mL, 8.70 mmol) and methylamaine (2M in THF) (3.20 mL, 3.40 mmol) in Me-THF (6.50 mmol) was stirred at 70° C. for overnight. The reaction was cooled down to rt. Water was added and this mixture was extracted twice with DCM. The organic layer was decanted and dried over $MgSO_4$, filtered then the solvent was evaporated until dryness. The residue (1 g) was purified by column chromatography on silica gel (Irregular SiOH, 20-45 m, 40 g, mobile phase: 60% heptane, 40% EtOAc). The pure fractions were collected and the solvent was evaporated until dryness to give 385 mg of intermediate 269 (56% yield).

The intermediates in the Table below were prepared by using an analogous starting from the respective starting materials. The most relevant minor deviations to the referenced method are indicated as additional information in the column 'Yield (%)'.

| Int. number | structure | Mass (mg) | Yield (%) |
|---|---|---|---|
| Intermediate 635 | ![structure] From intermediates 640 and 641 Separation from isomer (intermediate 636) via preparative LC (Stationary phase: irregular SiOH 40 μm 750 g, Mobile phase: 70% heptane, 30% AcOEt) | 10300 | 39 DCM RT, overnight |
| Intermediate 636 | ![structure] From intermediates 640 and 641 Separation from isomer (intermediate 635) via preparative LC (Stationary phase: irregular SiOH 40 μm 750 g, Mobile phase: 70% heptane, 30% AcOEt) | 4900 | 18 DCM RT, overnight |

Example A33

Preparation of Intermediate 289

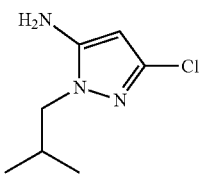

A mixture of intermediate 288 (3.69 g, 18.12 mmol), Zinc (11.85 g, 181.21 mmol) and AcOH (10.37 mL, 181.21 mmol) in MeOH (86 mL) was stirred at rt for 1 h. The mixture was filtered over a pad of Celite® and the filtrate was concentrated under reduced pressure. The resulting residue was diluted with EtOAc and water. The aqueous layer was basified with solid $K_2CO_3$ and the layers were separated. The aqueous layer was extracted twice with EtOAc. The combined organic layers were washed with brine, dried over $MgSO_4$, filtered and the solvent was removed under reduced pressure to give 3.44 g of intermediate 289 as a yellow residue (92% yield) directly used as it in the next step.

The intermediates in the Table below were prepared by using an analogous starting from the respective starting materials. The most relevant minor deviations to the referenced method are indicated as additional information in the column 'Yield (%)'.

| Int. number | Structure | Mass (mg) | Yield (%) |
|---|---|---|---|
| Intermediate 312 | From intermediate 311 | 360 yellow solid | 53 |
| Intermediate 316 | 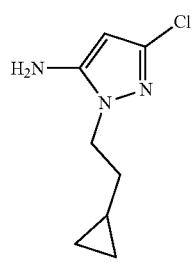 From intermediate 315 | 553 colorless oil | 84 with T = 85° C. |
| Intermediate 320 | From intermediate 319 | 227 yellow oil | 46 with T = 85° C. |
| Intermediate 359 | 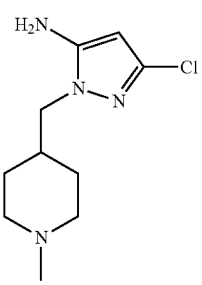 From intermediate 358 | 205 yellow solid | 85 |

| Int. number | Structure | Mass (mg) | Yield (%) |
|---|---|---|---|
| Intermediate 367 | (H₂N, Cl, dioxane, R) From intermediate 366 | 888 yellow solid | 65 |
| Intermediate 380 | (H₂N, Cl, tetrahydrofuran, S) From intermediate 379 | 226 pale yellow solid | 25 |
| Intermediate 395 | (H₂N, Cl, dioxane, S) From intermediate 394 | 1010 yellow oil | 74 |

| Int. number | Structure | Mass (mg) | Yield (%) |
|---|---|---|---|
| Intermediate 401 | (H₂N, Cl, piperidine-CH₂CH₂F) From intermediate 400 | 625 yellow oil | — |
| Intermediate 696 | (H₂N, Cl, morpholine-ethyl) From intermediate 657 | 106 | 10 |

Example A34

Preparation of Intermediate 299

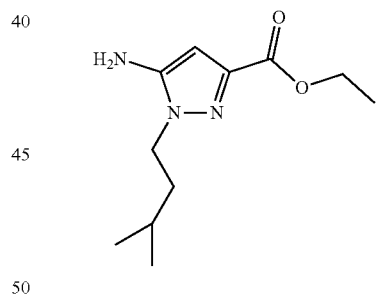

A mixture of 3-cyano-2-oxo-propanoic acid ethyl ester (4.00 g, 22.30 mmol), 3-methylbutyl-hydrazine (2.28 g, 22.32 mmol) and HCl (37% in H$_2$O) (5.50 mL, 65.90 mmol) in EtOH (80 mL) was stirred at 60° C. for 18 h. The mixture was evaporated and an extraction was performed with NaOH (3N) and Et$_2$O. The organic layer was dried over MgSO$_4$, evaporated. The resulting residue was purified by column chromatography on silica gel (stationary phase: irregular SiOH, 15-40 µm, 120 g, mobile phase heptane/EtOAc, gradient from 100:0 to 40:60). The fractions containing the product were combined and evaporated to dryness to give 1.36 g of intermediate 299 (27% yield, yellow solid).

The intermediates in the Table below were prepared by using an analogous starting from the respective starting materials.

| Int. number | Structure | Mass (mg) | Yield (%) |
|---|---|---|---|
| Intermediate 456 | From 3-cyano-2-oxo-propanoic acid ethyl ester and 2-methylpropyl-hydrazine, hydrochloride salt | 723 | 31 |
| Intermediate 464 | From 3-cyano-2-oxo-propanoic acid ethyl ester and (2-methoxyethyl)-hydrazine, hydrochloride hydrate | 397 | 33 |
| Intermediate 475 | From 3-cyano-2-oxo-propanoic acid ethyl ester and isopropyl-hydrazine hydrochloride | 879 (80% purity based on LC/MS) pale yellow solid | 25 |

Preparation of Intermediate 300

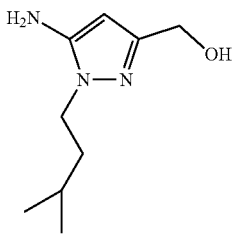

At 0° C., LiAlH$_4$ (230.00 mg, 6.06 mmol) was added slowly to a solution of intermediate 299 (1.36 g, 6.04 mmol) in Et$_2$O (60 mL). The mixture was stirred at rt for 18 h. Further, LiAlH$_4$ (230.00 mg, 6.06 mmol) was added and the mixture was stirred at rt for 2 h. The mixture was placed at 0° C., water (0.5 mL), NaOH (3N, 0.5 mL) and water (1.5 mL) were successively added. The resulting mixture was stirred at rt for 20 min. MgSO$_4$ was added and the mixture was stirred at rt for 1 h. The mixture was filtered and the filtrate was evaporated. The resulting residue was purified by column chromatography on silica gel (irregular SiOH, 15-40 m, 120 g, liquid loading with DCM, mobile phase heptane/EtOAc, gradient from 100:0 to 0:100 in 10 CV then EtOAc/MeOH gradient from 100:0 to 80:20 in 5 CV). The fractions containing the product were combined and evaporated to dryness to give 720 mg of intermediate 300 (65% yield, white solid).

The intermediates in the Table below were prepared by using an analogous starting from the respective starting materials. The most relevant minor deviations to the referenced method are indicated as additional information in the column 'Yield (%)'.

| Int. number | Structure | Mass (mg) | Yield (%) |
|---|---|---|---|
| Intermediate 457 | H₂N–[pyrazole]–CH₂OH, N-isobutyl<br>From intermediate 456 | 400<br>(84% purity based on LC/MS) | 69<br>with THF as solvent |
| Intermediate 465 | H₂N–[pyrazole]–CH₂OH, N-CH₂CH₂OCH₃<br>From intermediate 464 | 243 | 56<br>with THF as solvent |
| Intermediate 476 | H₂N–[pyrazole]–CH₂OH, N-isopropyl<br>From intermediate 475 | 500 | 72<br>with THF as solvent |

Example A35

Preparation of Intermediate 303

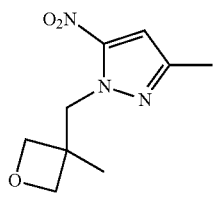

The reaction was performed in 2 batches. In a sealed tube, cyanomethylenetributyl phosphorane (9.28 mL, 35.40 mmol) was added to a solution of 3-methyl-5-nitro-1H-pyrazole (1.50 g, 11.80 mmol) and 3-hydroxymethyl-3-methyloxethane (3.53 mL, 35.40 mmol) in toluene (100 mL). The solution was heated at 60° C. for 18 h. The 2 batches were combined and the solvent was evaporated in vacuo. The residue (black oil) was purified by column chromatography on silica gel (irregular SiOH, 15-40 m, 330 g, liquid loading on DCM, mobile phase: heptane/EtOAc, gradient from 90:10 to 50:50). The fractions containing the product were combined and evaporated to dryness to give 3.95 g of intermediate 303 (79% yield, orange oil) directly used as it in the next step.

The intermediates in the Table below were prepared by using an analogous starting from the respective starting materials. The most relevant minor deviations to the referenced method are indicated as additional information in the column 'Yield (%)'.

| Int. number | Structure | Mass (mg) | Yield (%) |
|---|---|---|---|
| Intermediate 327 | [imidazole-CH₂-pyrazole-NO₂, N-isobutyl]<br>From intermediate 252 and 1-methyl-1H-imidazol-2yl-methanol | 750 | 24 |

-continued

| Int. number | Structure | Mass (mg) | Yield (%) |
|---|---|---|---|
| Intermediate 341 + intermediate 341' | 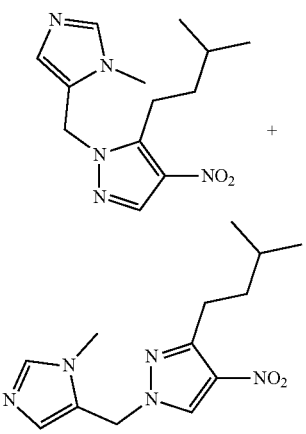 From intermediate 252 and 5-hydroxymethyl-1-methyl-1H-imidazole | 590 (intermediate 341) 900 (intermediate 341') | 19 30 |
| Intermediate 345 | 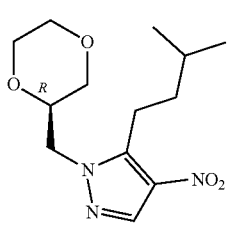 From intermediate 252 and (R)-[1,4]dioxan2-yl-methanol | 407 | 13 |
| Intermediate 362 | 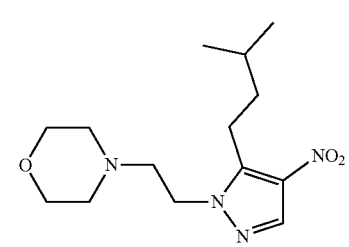 From intermediate 252 and 4-(2-hydroxyethyl)morpholine | 540 | 17 |
| Intermediate 374 | 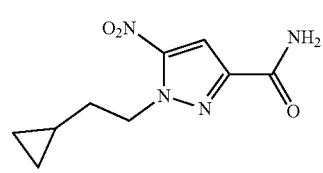 From 5-nitro-1H-pyrazole-3-carboxamide and 2-cyclopropyl ethanol | 2900 | 32 |
| Intermediate 386 | 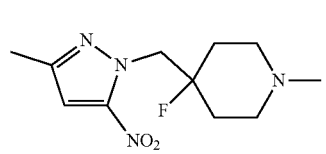 From 5-methyl-3-nitro-1H-pyrazole and 4-fluoro-1-methyl-4-piperidine methanol | 324 (intermediate 386) | 21 |

-continued

| Int. number | Structure | Mass (mg) | Yield (%) |
|---|---|---|---|
| Intermediate 390 | (structure shown) From 3-Methyl-4-nitro-1H-pyrazole and 2,2-difluoroethanol | 856 | 41 |
| Intermediate 407 | (structure shown) From 5-methyl-3-nitro-1H-pyrazole and 1-(tert-butoxycarbonyl)-4-piperidinemethanol | 11100 | 75 |
| Intermediate 417 | (structure shown) From 5-chloro-3-nitro-1H-pyrazole and 1-(tert-butoxycarbonyl)-4-piperidinemethanol | 10600 yellow oil | 75 with T = rt |
| Intermediate 423 | (structure shown) From 3-methyl-5-nitro-1H-pyrazole and (S)-4-methyl-2-(hydroxymethyl)-morpholine | 640 (intermediate 423) | 38 with T = 90° C. |
| Intermediate 427 + intermediate 427' | (structure shown) | 817 (intermediate 427) 870 (intermediate 427') | 22 23 with T = 50° C. |

-continued

| Int. number | Structure | Mass (mg) | Yield (%) |
|---|---|---|---|
| | 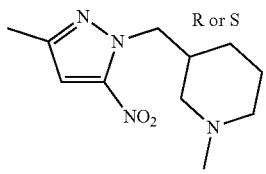 From 3-methyl-5-nitro-1H-pyrazole and 1-methyl-piperidine-3-methanol | | |
| Intermediate 468 | From 5-methyl-3-nitro-1H-pyrazole and 2-(3-methyl-oxetan-3-yl)ethanol | 361 | 92 |
| Intermediate 483 | 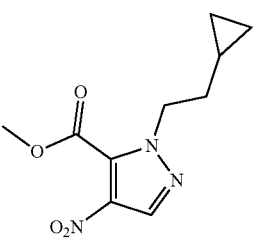 From 5-methyl-3-nitro-1H-pyrazole and (R)-4-methyl-2-hydroxy-methyl-morpholine | 1050 | 63 with T = 90° C. |
| Intermediate 488 | From intermediate 487 | 3320 | 47 |
| Intermediate 517 + intermediate 517' | 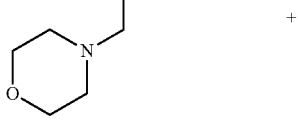 + | 832 (intermediate 517) 405 (intermediate 517') | 63 31 with T = 90° C. |

-continued

| Int. number | Structure | Mass (mg) | Yield (%) |
|---|---|---|---|
| | From 5-methyl-3-nitro-1H-pyrazole and 4-(2-hydroxyethyl)morpholine | | |
| Intermediate 533 | From intermediate 507 and 2,2-Difluoroethanol | 192 (80% purity based on LC/MS) | 22 Procedure with Me-THF |
| Intermediate 537 | From 3-methyl-4-nitro-1H-pyrazole and 4-(2-hydroxyethyl)morpholine | 647 | 11 with T = 90° C. |
| Intermediate 541 | From 3-methyl-5-nitro-1H-pyrazole and 4-hydroxymethyl-1-methyl-2-piperidone | 911 | 76 |
| Intermediate 583 | | 720 | 19 Procedure with Me-THF 8 h |
| Intermediate 583 | From intermediate 582 and 2,2-difluoroethanol | 282 | 6 60° C., 6 h |

-continued

| Int. number | Structure | Mass (mg) | Yield (%) |
|---|---|---|---|
| Intermediate 591 | From 3-methyl-5-nitro-1H-pyrazole and 2,2-difluoroethanol | 372 | 50<br>110° C. μw<br>30 min |
| Intermediate 605 | From intermediate 487 and 2,2-difluoroethanol | 1660 | 17<br>110° C. μw<br>30 min |
| Intermediate 601 | From 3-isopropoxy-4-nitro-1H-pyrazole and 2,2-difluoroethanol | 350 | 68<br>110° C. μw<br>30 min |
| Intermediate 656 | From 4-nitro-1H-pyrazole and 4-(2-hydroxyethyl)morpholine | 700 | 51<br>60° C., 36 h |
| Intermediate 688 | From 5-methyl-3-nitro-1H-pyrazole and 5,6,7,8-tetrahydroimidazo[1,2-A]-pyridin-7-yl)methanol | 1100 | 67<br>90° C., 5 h |
| Intermediate 680 | From intermediate 679 and 2,2-difluoroethanol | 490 | 50<br>60° C., 19 h |

-continued

| Int. number | Structure | Mass (mg) | Yield (%) |
|---|---|---|---|
| Intermediate 686 | 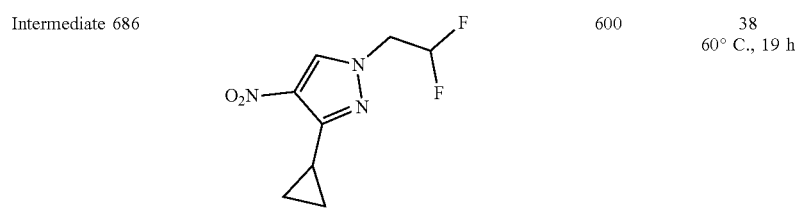 From intermediate 685 and 2,2-difluoroethanol | 600 | 38<br>60° C., 19 h |
| Intermediate 692 | 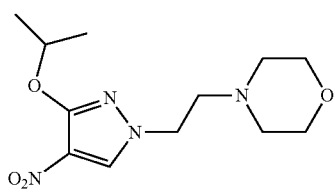 From 3-isopropoxy-4-nitro-1H-pyrazole and 4-(2-hydroxyethyl)-morpholine | 390 | 52<br>RT, 18 h |
| Intermediate 699 | 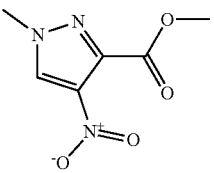 From intermediate 487 and methanol Separation from isomer (intermediate 700) by Normal phase on (Irregular SiOH 40 μm 220 g GRACE). Mobile phase 90% Heptane, 10% AcOEt to 40% Heptane, 60% AcOEt | 680 | 31<br>110° C. μw<br>30 min |
| Intermediate 700 | 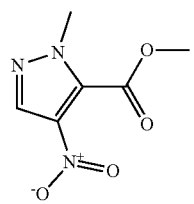 From intermediate 487 and methanol Separation from isomer (intermediate 699) by Normal phase on (Irregular SiOH 40 μm 220 g GRACE). Mobile phase 90% Heptane, 10% AcOEt to 40% Heptane, 60% AcOEt | 1200 | 55<br>110° C. μw<br>30 min |

| Int. number | Structure | Mass (mg) | Yield (%) |
|---|---|---|---|
| Intermediate 742 | 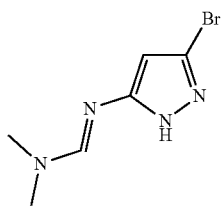<br>From intermediate 741 | 6700 | 79<br>60° C., 12 h |
| Intermediate 747 | 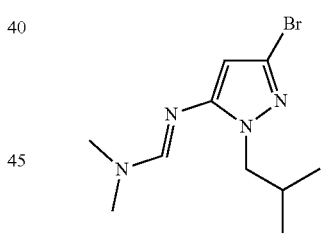<br>From intermediate 746 | 470 | 48<br>60° C., 12 h |

Example A36

Preparation of Intermediate 335

A mixture of 5-bromo-1H-pyrazol-3-amine (790.00 mg, 4.88 mmol) and N,N-dimethyl formamide dimethyl acetal (1.17 mL, 8.78 mmol) in MeOH (12 mL) was refluxed for 2 h. The mixture was evaporated in vacuo. The residual gum was triturated in Et₂O and filtered on a glass-frit to give 617 mg of intermediate 335 (58%, off-white solid). The filtrate was evaporated in vacuo and the residue (380 mg, orange oil) was purified by column chromatography on silica gel (irregular SiOH, 15-40 μm, 10 g, dry loading on Celite®, mobile phase gradient: from heptane 80%, EtOAc 18%, MeOH 2% to heptane 30%, EtOAc 63%, EtOAc 7%). The fractions containing the product were combined and evaporated to dryness to give additional 253 mg of intermediate 335 (24%, white solid).

Preparation of Intermediate 336

To a solution of intermediate 335 (899.00 mg, 4.14 mmol) and 1-iodo-2-methylpropane (0.71 mL, 6.21 mmol) in DMF (42 mL), Cs₂CO₃ (2.70 g, 8.28 mmol) was added and stirred at rt overnight. Further 1-iodo-2-methylpropane (0.24 mL, 2.07 mmol) and Cs₂CO₃ (1.35 g, 4.14 mmol) were added and the mixture was stirred at rt for 1 h. EtOAc was added and the mixture was filtered off. The filtrate was evaporated in vacuo and the residual crude was taken-up in EtOAc and water. The organic layer was washed thrice with brine, dried over MgSO₄, filtered off and evaporated in vacuo. The residue (1.09 g, pale yellow liquid) was purified by column chromatography on silica gel (irregular SiOH, 15-40 m, 50 g, dry loading on Celite®, mobile phase gradient: from heptane 90%, EtOAc 9%, MeOH 1% to heptane 60%, EtOAc 36%, MeOH 4%). The fractions containing the product were combined and evaporated to dryness to give 707 mg of intermediate 336 (62% yield, colorless liquid).

Preparation of Intermediate 337

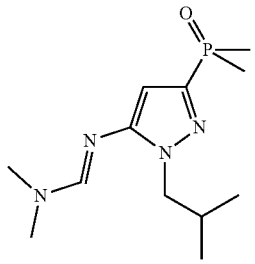

In a sealed tube, a mixture of intermediate 336 (707.00 mg, 2.59 mmol), dimethylphosphine oxide (0.24 g, 2.85 mmol) and $K_3PO_4$ (0.60 g, 2.85 mmol) in DMF was purged with $N_2$. $Pd(OAc)_2$ (58.10 mg, 0.26 mmol) and 4,5-bis(diphenylphosphino)-9,9-dimethylxanthene (149.70 mg, 0.26 mmol) were added. The mixture was purged with $N_2$ and stirred at 130° C. overnight. The mixture was warmed to rt and filtered on a pad of Celite®. The cake was washed with EtOAc and the filtrate was evaporated in vacuo. The residue (920 mg, red oil) was purified by column chromatography on silica gel (irregular SiOH, 15-40 μm, 50 g, dry loading on Celite®, mobile phase: DCM/MeOH, gradient from 100:0 to 95:5). The fractions containing the product were combined and evaporated to dryness to give 330 mg of intermediate 337 (47% yield, reddish solid).

Preparation of Intermediate 338

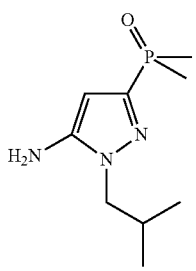

In a sealed tube, to a solution of intermediate 337 (330.00 mg, 1.22 mmol) in EtOH (6 mL) was added HCl (3M in cyclopentyl methyl ether) (6.10 mL, 18.30 mmol). The mixture was stirred at 90° C. overnight. The mixture was evaporated in vacuo to give 501 mg of intermediate 338 (Quant. yield, 77% purity based on NMR, yellow gum).

Example A37

Preparation of Intermediate 349: and intermediate 349'

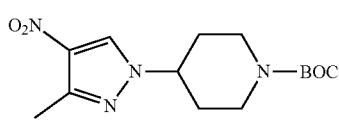

intermediate 349

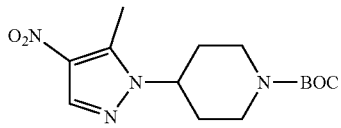

intermediate 349'

A mixture of 3-methyl-4-nitro-1H-pyrazole (1.36 g, 10.71 mmol), tert-butyl-4-iodopiperidine-1-carboxylate (10.00 g, 32.14 mmol) and $K_2CO_3$ (2.96 g, 21.42 mmol) in DMF (16.6 mL) was stirred at reflux for 24 h. The reaction mixture was diluted with EtOAc and water and the layers were separated. The organic layer was washed with brine, dried over $MgSO_4$, filtered and was evaporated under reduced pressure. The residue was purified by column chromatography on silica gel (irregular SiOH 40 m, 80 g, mobile phase: heptane/DCM, gradient from 50:50 to 0:100). The pure fractions were combined and the solvent was evaporated to give a mixture of intermediate 349 and intermediate 349' (540.00 mg, 16% yield).

Preparation of Intermediate 350 and intermediate 350'

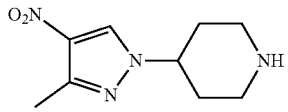

intermediate 350

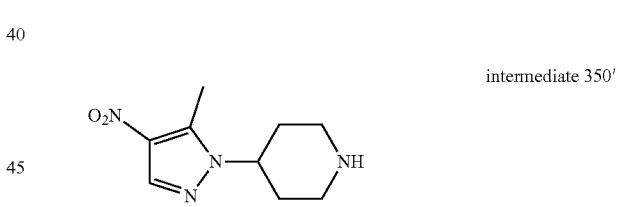

intermediate 350'

At 0° C., HCl (4M in dioxane) (15.00 mL, 60.00 mmol) was added to a solution of a mixture of intermediates 349 and 349' (0.54 g, 1.74 mmol) in 1,4-dioxane (4 mL). The reaction was stirred at rt overnight. The solvent was evaporated until dryness. The residue was taken up into DCM and basified with a 10% aqueous solution of $K_2CO_3$. The organic layer was dried over $MgSO_4$, filtered and the solvent was evaporated until dryness. The residue (817 mg) was purified by column chromatography on silica gel (stationary phase: irregular SiOH, 15-40 μm, 40 g, mobile phase: 98% DCM, 2% MeOH (+10% $NH_4OH$) to 95% DCM, 5% MeOH (+10% $NH_4OH$)). The pure fractions were collected and the solvent was evaporated until dryness to give 0.480 g of a mixture of intermediates 350 and 350' used as it for the next step.

The intermediates in the Table below were prepared by using an analogous starting from the respective starting materials.

| Int. number | Structure | Mass (mg) | Yield (%) |
|---|---|---|---|
| Intermediate 408 | 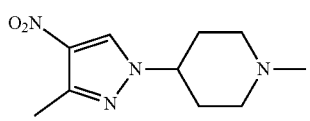<br>From intermediate 407 | 6550 | 85 |

Preparation of Intermediate 351 and intermediate 351'

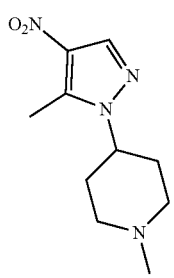

intermediate 351 intermediate 351'

A mixture of intermediates 350 and 350' (0.48 g, 2.28 mmol), formaldehyde (0.21 mL, 2.80 mmol) in MeOH (2.70 mL) and AcOH (0.32 mL, 5.59 mmol) was stirred for 10 min. Then, sodium cyanoborohydride (0.17 g, 2.75 mmol) was added. The reaction was stirred at rt over the weekend. DCM and a 10% solution of $K_2CO_3$ were added. The organic layer was washed with water, dried over $MgSO_4$, filtered and evaporated. The residue (538 mg) was purified by achiral SFC (Stationary phase: CHIRALPAK IC 5 μm 250×20 mm, mobile phase: 75% $CO_2$, 25% MeOH). The pure fractions were collected and the solvent was evaporated until dryness to give: 248 mg of intermediate 351 (49% yield) and 184 mg of intermediate 351' (36% yield).

Example A38

Preparation of Intermediate 375

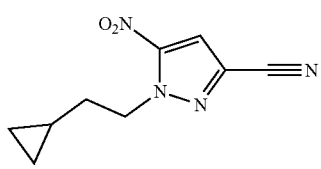 [SMILES: N#Cc1cc([N+](=O)[O-])n(CCC2CC2)n1]

To a solution of intermediate 374 (4.30 g, 19.18 mmol) in DMF (95.9 mL, 0.2 M) at rt was added $SOCl_2$ (2.09 mL, 28.77 mmol) and the resulting solution was stirred at rt overnight. Then, EtOAc was added and the reaction mixture was washed with saturated aqueous sodium bicarbonate solution and water. The combined organic layers were dried over $Na_2SO_4$, filtered and concentrated. The residue (3.1 g) was purified by column chromatography on silica gel (irregular SiOH, 40 μm, 120 g, mobile phase: heptane/EtOAc, gradient from 90:10 to 60:40). The pure fractions were combined and the solvent was evaporated to give 2.11 g of intermediate 375 (53% yield).

Preparation of Intermediate 376

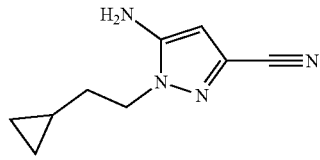

To a solution of intermediate 375 (2.11 g, 10.23 mmol) in a mixture of 1,4-dioxane (30 mL) and distilled water (6 mL), were added iron powder (5.71 g, 102.33 mmol) and iron (II) sulfate heptahydrate (6.22 g, 40.93 mmol). The resulting solution was heated to reflux for 12 h. The reaction mixture was filtered over a pad of Celite®. DCM was added and the organic layer was decanted, dried over $MgSO_4$, filtered and evaporated. DCM was added. The insoluble was filtered and dried with DIPE to give 1.21 g of intermediate 376 (67% yield).

The intermediates in the Table below were prepared by using an analogous starting from the respective starting materials.

| Int. number | Structure | Mass (mg) | Yield (%) |
|---|---|---|---|
| Intermediate 453 | From intermediate 452 | 100 | 22 |

| Int. number | Structure | Mass (mg) | Yield (%) |
|---|---|---|---|
| Intermediate 480 | H₂N–[pyrazole-Cl]–CH₂–[(S)-pyrrolidine-N-Me] From intermediate 479 | 540 yellow oil | 95 |

Example A39

Preparation of Intermediate 399

O₂N–[pyrazole-Cl]–CH₂–[piperidine-NH]

TFA salt

To a solution of intermediate 398 (1.00 g, 2.90 mmol) in DCM (25 mL), TFA (2.50 mL, 32.70 mmol) was added and the reaction mixture was stirred at rt for 16 h. The solvent was removed under reduced pressure. The residue (1.66 g, yellow oil) was triturated with Et₂O to give a white solid. The solid was filtered on a glass frit, washed with Et₂O to give 820 mg of intermediate 399 (79% yield, white solid, TFA salt).

The intermediates in the Table below were prepared by using an analogous starting from the respective starting materials. The most relevant minor deviations to the referenced method are indicated as additional information in the column 'Yield (%)'.

| Int. number | Structure | Mass (mg) | Yield (%) |
|---|---|---|---|
| Intermediate 418 | 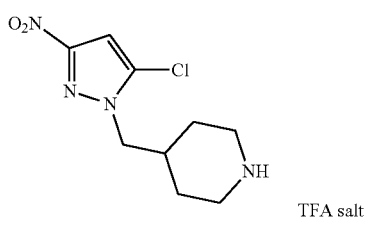 TFA salt From intermediate 417 | 2820 | 90 |

| Int. number | Structure | Mass (mg) | Yield (%) |
|---|---|---|---|
| Intermediate 507 | From intermediate 506 | 4880 | Quant. Procedure with T = 0-5° C. and with DCM/TFA (4:1, v/v) |

Structure for Intermediate 507: O₂N-pyrazole with isobutyl substituent and N-CH₂-piperidine (NH)

Preparation of Intermediate 400

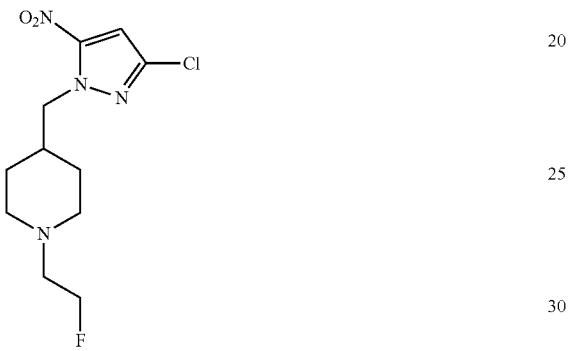

In a sealed tube, a solution of intermediate 399 (1.00 g, 2.79 mmol) in CH₃CN (14 mL) was treated with 1-(4-methylbenzenesulfonate)-2-fluoro-ethanol (0.70 g, 3.21 mmol) and Cs₂CO₃ (2.73 g, 8.36 mmol). The reaction mixture was stirred at 80° C. for 70 h. The crude was diluted with water and a saturated aqueous solution of NaHCO₃ and extracted with EtOAc. The organic layer was dried over MgSO₄, filtered and evaporated in vacuo to give 790 mg of intermediate 400 (97% yield, yellow oil).

The intermediates in the Table below were prepared by using an analogous starting from the respective starting materials.

| Int. number | Structure | Mass (mg) | Yield (%) |
|---|---|---|---|
| Intermediate 460 | From intermediate 399 and 2,2,2-trifluoroethyl trifluoromethane-sulfonate | 790 | 87 |

Example A40

Preparation of Intermediate 409

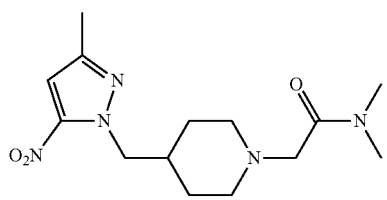 [SMILES: Cc1cc([N+](=O)[O-])n(CC2CCN(CC(=O)N(C)C)CC2)n1]

In a sealed tube a mixture of intermediate 408 (0.50 g, 2.23 mmol), 2-chloro-N,N-dimethylacetamide (0.25 mL, 2.43 mmol) and DIPEA (0.95 mL, 5.51 mmol) in DMF (15 mL) was stirred at 80° C. for overnight. The reaction was cooled down to rt. Water was added and this mixture was extracted twice with EtOAc and twice with DCM. These organic layers were combined and the solvent was evaporated until dryness. The residue was purified by column chromatography on silica gel (irregular SiOH, 40 μm, 40 g, mobile phase gradient from 98% DCM, 2% MeOH (+10% NH₄OH) to 94% DCM, 6% MeOH (+10% NH₄OH)). The pure fractions were collected and the solvent was evaporated until dryness to give 189 mg of intermediate 409 (27% yield) used directly as it in the next step.

The intermediates in the Table below were prepared by using an analogous starting from the respective starting materials. The most relevant minor deviations to the referenced method are indicated as additional information in the column 'Yield (%)'.

| Int. number | Structure | Mass (mg) | Yield (%) |
|---|---|---|---|
| Intermediate 413 | From intermediate 408 and 2,2,2-trifluoroethyl trifluoromethane-sulfonate | 537 | 79 under microwave activation with T = 70° C. |
| Intermediate 419 | From intermediate 418 and 2-bromoethyl methyl ether | 710 (70% purity based on LC/MS) | 84 |
| Intermediate 471 | From intermediate 408 and 2-bromoethyl methyl ether | 530 | 84 |
| Intermediate 508 | From intermediate 507 and 2,2,2-trofluoro-ethyl trifluoromethansulfonate | 840 (61% purity based on LC/MS) | 91 under microwave activation with T = 70° C. |
| Intermediate 529 | From intermediate 507 and 1-fluoro-2-iodoethane | 122 | 15 |
| Intermediate 545 | From intermediate 408 and 1-fluoro-2-iodoethane | 683 | 81 |

-continued

| Int. number | Structure | Mass (mg) | Yield (%) |
|---|---|---|---|
| Intermediate 725 | From intermediate 408 and methyl bromoacetate | 824 | 89 |

Example A41

Preparation of Intermediate 452

Intermediate 211 (0.729 g, 3.10 mmol), morpholine (540.15 mg, 6.20 mmol) and TEA (1.29 mL, 9.30 mmol) in $CH_3CN$ (8.10 mL, 155.00 mmol) were stirred at 60° C. for 1 h. The solvent was evaporated. The residue was purified by column chromatography on silica gel (stationary phase: irregular SiOH, 15-40 μm, 80 g, mobile phase: gradient from 100% DCM to 98% DCM, 2% MeOH, 0.1% $NH_4OH$). The fractions were combined and evaporated to dryness to give 520 mg of intermediate 452 (74% yield).

The intermediates in the Table below were prepared by using an analogous starting from the respective starting materials.

| Int. number | Structure | Mass (mg) | Yield (%) |
|---|---|---|---|
| Intermediate 491 | From intermediate 490 | 450 | Quant. |
| Intermediate 521 | From intermediate 211 | 275 | 49 |
| Intermediate 525 | From Intermediate 490 and 1-methyl piperazine | 390 | 91 |
| Intermediate 703 | From intermediate 702 and 1-methyl piperazone | 396 | 98 |

Example A42

Preparation of Intermediate 487

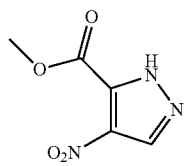

SOCl$_2$ (4.62 mL, 63.66 mmol) was added dropwise over 5 min approximately to a solution of 4-Nitro-1H-pyrazole-3-carboxylic acid (5.00 g, 31.83 mmol) in MeOH (50 mL) at 0° C. The resulting clear solution was stirred at 0° C. for 30 min, followed by rt for 16 h. Solvent was evaporated under reduced pressure to obtain 5.4 of intermediate 487 (99% yield, white solid).

The intermediates in the Table below were prepared by using an analogous starting from the respective starting materials. The most relevant minor deviations to the referenced method are indicated as additional information in the column 'Yield (%)'.

| Int. number | Structure | Mass (mg) | Yield (%) |
|---|---|---|---|
| Intermediate 730 | ![structure] From 5-nitro-3-pyrazolecarboxylic acid | 4800 | 99 Reflux, 5 h |

Example A43

Preparation of Intermediate 489

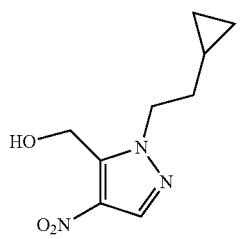 [SMILES: O=[N+]([O-])c1cnn(CCC2CC2)c1CO]

To a solution of intermediate 488 (2.26 g, 9.45 mmol) in dry DCM (25.4 mL) was added dropwise diisobutylaluminium hydride (3.62 mL, 20.31 mmol) at −50° C. The reaction mixture was stirred at −50° C. for 3 h then at rt for 2 h. The mixture was acidified at 0° C. with a 3N aqueous solution of HCl and diluted with Et$_2$O. The organic layer was separated, washed with a 1N aqueous solution of HCl, then twice with brine, dried over MgSO$_4$ and evaporated in vacuo. The residue (2.17 g) was purified by column chromatography on silica gel (irregular SiOH, 40 m, 40 g, mobile phase: heptane/EtOAc, gradient from 100:0 to 60:40). The pure fractions were combined and the solvent was evaporated to give 536 mg of intermediate 489 (27% yield).

The intermediates in the Table below were prepared by using an analogous starting from the respective starting materials. The most relevant minor deviations to the referenced method are indicated as additional information in the column 'Yield (%)'.

| Int. number | Structure | Mass (mg) | Yield (%) |
|---|---|---|---|
| Intermediate 701 | ![structure] From intermediate 700 | 266 | 25 −20° C. 18 h, then 0° C. 2 h |

Example A44

Preparation of Intermediate 512

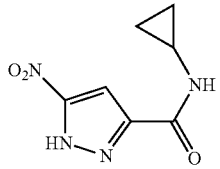 [SMILES: O=C(NC1CC1)c1cc([N+](=O)[O-])[nH]n1]

At 0° C., oxalyl chloride (9.5 mL, 19.00 mmol) was added to a solution of 5-nitro-1H-pyrazole-3-carboxylic acid (1.50 g, 9.55 mmol) in a mixture of DCM (30 mL) and Me-THF (0.85 mL). Then, one drop of DMF was added at 0° C. and this mixture was stirred at rt for 3 h. The solvent was evaporated until dryness. This product was taken up into DCM (45 mL) and a mixture of cyclopropylamine (13 mL), DCM (3 mL) and pyridine (1.50 mL) was added over a period of 10 min. This reaction was stirred over the weekend at rt. This mixture was concentrated in vacuo and purified by column chromatography on silica gel (irregular SiOH, 20-45 m, 80 g, mobile phase gradient from: 100% DCM to 90% DCM, 10% MeOH (+10% NH$_4$OH)). The fractions containing the product were combined and the solvent was evaporated until dryness. The residue (1.80 g) was purified by column chromatography on silica gel (irregular SiOH, 20-45 m, 24 g, mobile phase: heptane/EtOAc, gradient from 70:30 to 50:50). The pure fractions were collected and the solvent was evaporated until dryness to give 1.30 g of intermediate 512 (69% yield).

Example A45

Preparation of Intermediate 558

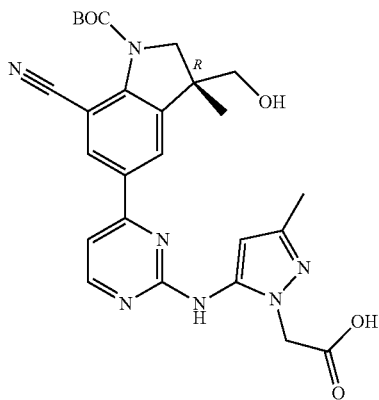

A mixture of intermediate 186 in dioxane (18 mL) was stirred with lithium hydroxide monohydrate (55 mg, 1.31 mmol) and distilled water (2.5 mL) at rt for 2 h. Then, TFA (3.0 mL, 39.3 mmol) was added and the mixture was stirred at rt for 30 min. The reaction mixture was evaporated under reduced pressure and a dry load on Celite® was prepared. The residue was purified by column chromatography on silica gel (irregular SiOH, 15-40 µm, 30 g, dry load on Celite®, mobile phase gradient: from DCM 100% to DCM 90%, MeOH (+AcOH 10%) 10%). The fractions containing the product were combined and evaporated to dryness to give 697 mg of intermediate 558 (67% purity based on LC/MS) as a yellow residue used as it in the next step.

Preparation of Intermediate 559

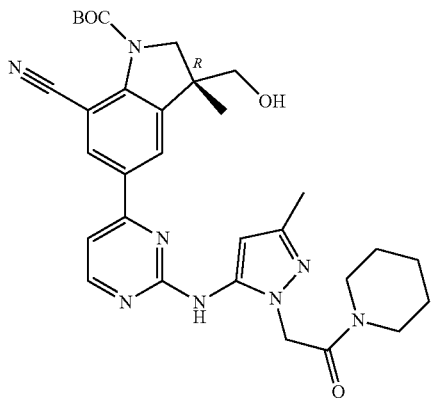

In a sealed tube, intermediate 558 (434.00 mg, 0.84 mmol) and piperidine (99.20 µL, 1.00 mmol) were diluted in dry DMF (10.6 mL). Then, HATU (698.90 mg, 1.84 mmol) and DIPEA (0.36 mL, 2.09 mmol) were added and the mixture was stirred at 70° C. for 17 h. The reaction mixture was evaporated under reduced pressure and purified by column chromatography on silica gel (irregular SiOH, 40 g, dry load on Celite®, mobile phase gradient: from DCM 100% to DCM 90%, MeOH (+aq. $NH_3$ 5%) 10%). The fractions containing the product were combined and evaporated to dryness. The residue (512 mg, yellow residue) was triturated in $Et_2O$ and the solid was filtered on a glass frit to give two batches of intermediate 559 (batch 1, 85 mg, 17% yield, yellow solid; batch 2, 90 mg, 18% yield, yellow residue) directly used as it in the next step.

Example A 46

Preparation of Intermediate 560

DMA-DMF (10.00 mL; 74.69 mmol) was added dropwise to methyl 5-methoxy-3-oxopentanoate (10.00 mL; 68.68 mmol) in DCM (50.00 mL) at room temperature. This reaction was stirred at room temperature for overnight. The solvent was evaporated until dryness to give 15.54 g of intermediate 560 (quantitative) directly used in the next step without any further treatment.

The intermediates in the table below were prepared by using an analogous method starting from the respective starting materials. The most relevant minor deviations to the referenced method are indicated as additional information in the column 'Yield (%)'.

| Int. number | Structure | Mass (mg) | Yield (%) |
| --- | --- | --- | --- |
| Intermediate 755 | From intermediate 754 | 820 | 97 Neat, rt, overnight |

Preparation of Intermediate 561

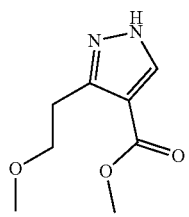

Hydrazine monohydrate (8.00 mL; 164.73 mmol) was added to a solution of intermediate 560 (15.54 g; 72.19 mmol) in EtOH (230 mL). This reaction was stirred at reflux for 6 hours (T=95° C.) then cooled down to room temperature. The solvent was evaporated until dryness. The crude was purified by silica gel chromatography (Irregular SiOH 15-40 m 220 g, mobile phase gradient from: 80% Heptane, 20% EtOAc to 45% Heptane, 55% EtOAc). The pure fractions were collected and the solvent was evaporated until dryness to give 2 fractions of intermediate 561: Fraction A: 3.54 g (27% yield); Fraction B: 7.34 g (55% yield).

These two fractions were directly used in the next step without any further treatment.

The intermediates in the table below were prepared by using an analogous method starting from the respective starting materials. The most relevant minor deviations to the referenced method are indicated as additional information in the column 'Yield (%)'.

| Int. number | Structure | Mass (mg) | Yield (%) |
|---|---|---|---|
| Intermediate 756 | (structure) | 438 | 62 95° C., 2 h then rt, overnight |

From intermediate 755

Preparation of Intermediate 562 and intermediate 563

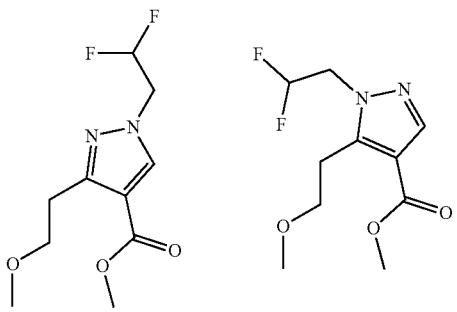 [SMILES: COCCc1nn(CC(F)F)cc1C(=O)OC ; COCCc1c(C(=O)OC)cnn1CC(F)F]

In a sealed tube, 2-(tributylphosphoranylidene)acetonitrile (8.70 mL; 33.16 mmol) was added to a solution of intermediate 561 (3.40 g; 18.46 mmol) and 2,2-difluoroethanol (1.40 mL; 22.11 mmol) in toluene (50.00 mL). This reaction was heated at 70° C. overnight. The reaction was cooled down to room temperature. Water was added and this mixture was extracted twice with EtOAc. The organic layer was decanted and the solvent was evaporated until dryness. This crude was purified by silica gel chromatography (Irregular SiOH 15-40 μm 120 g GraceResolv, mobile phase gradient from: 80% Heptane, 20% EtOAc to 60% Heptane, 40% EtOAc). The pure fractions were collected and the solvent was evaporated until dryness to give 3.26 g of impure intermediate 563 and 1.47 g of impure intermediate 562.

Impure intermediate 563 (3.26 g) was repurified by silica gel chromatography (Irregular SiOH 15-40 m 80 g, mobile phase Gradient from: 90% Heptane, 10% EtOAc to 60% Heptane, 40% EtOAc). The fractions containing the product were collected and the solvent was evaporated until dryness to give 1.2 g (26%) of intermediate 563 and 1 g (22%) of intermediate 562.

Impure intermediate 562 (1.47 g) was repurified by silica gel chromatography (Irregular SiOH 15-40 m 80 g GraceResolv, mobile phase Gradient from: 90% Heptane, 10% EtOAc to 60% Heptane, 40% EtOAc). The pure fractions were collected and the solvent was evaporated until dryness to give 0.53 g (11%) of intermediate 562.

In total 1.53 g of intermediate 562 were obtained.

The intermediates in the table below were prepared by using an analogous method starting from the respective starting materials. The most relevant minor deviations to the referenced method are indicated as additional information in the column 'Yield (%)'.

| Int. number | Structure | Mass (mg) | Yield (%) |
|---|---|---|---|
| Intermediate 757 | (structure) | 395 | 69 |

From intermediate 756

Preparation of Intermediate 564

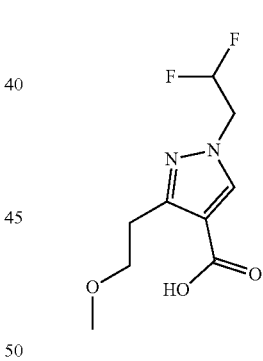

Lithium hydroxide 98% (0.33 g; 13.49 mmol) was added to a solution of intermediate 562 (1.53 g; 6.16 mmol) in ethanol (9.00 mL), water (9.00 mL) and 1,4-dioxane (9.00 mL). The reaction was stirred for 60 minutes at 95° C., then was cooled down to room temperature. Water was added and the mixture was acidified with an aqueous solution of HCl 3N. The aqueous layer was extracted twice with EtOAc. The organic layers were mixed, dried over MgSO$_4$, filtered and the solvent was evaporated until dryness to give 1.41 g of intermediate 564 (98% yield) which was directly engaged in the next step without any further treatment The intermediates in the table below were prepared by using an analogous method starting from the respective starting materials. The most relevant minor deviations to the referenced method are indicated as additional information in the column 'Yield (%)'.

| Int. number | Structure | Mass (mg) | Yield (%) |
|---|---|---|---|
| Intermediate 565 | 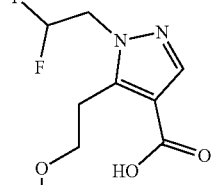 From intermediate 563 | 273 | 91 45° C. for 3 hours then, room temperature overnight |
| Intermediate 758 | 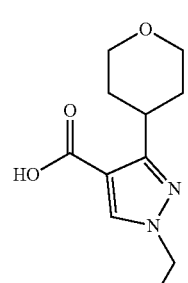 From intermediate 757 | 234 | quant |

Preparation of Intermediate 566

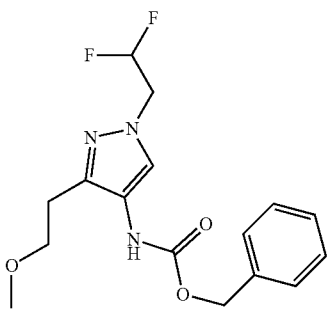 [SMILES: COCCc1nn(CC(F)F)cc1NC(=O)OCc1ccccc1]

A mixture of intermediate 564 (1.42 g; 6.06 mmol), diphenylphosphoryl azide (2.40 mL), triethylamine (1.6 mL; 11.51 mmol) and benzyl alcohol (2.4 mL; 23.19) was stirred at 160° C. using one single mode microwave (Biotage Initiator EXP 60)® with a power output ranging from 0 to [400 W] for 15 minutes. The reaction was cooled down to room temperature and the solvent was evaporated until dryness. The crude was purified by silica gel chromatography (Irregular SiOH 20-45 m 80 g, mobile phase Gradient from: 90% Heptane, 10% EtOAc to 50% Heptane, 50% EtOAc). The pure fractions were collected and the solvent was evaporated until dryness to give:

Fraction A: 0.92 g of intermediate 566 (45% yield)

Fraction B: 0.88 g of impure intermediate 566. Fraction B was repurified by silica gel chromatography (Irregular SiOH, 20-45 m, 40 g, mobile phase gradient from: 90%

Heptane, 10% EtOAc to 50% Heptane, 50% EtOAc). The pure fractions were collected and the solvent was evaporated until dryness to give:

Fraction C: 0.64 g of intermediate 566 (31% yield).

Fraction A and fraction C were combined to give 1.56 g of intermediate 566 (76% yield) which was directly used in the next step.

The intermediates in the table below were prepared by using an analogous method starting from the respective starting materials. The most relevant minor deviations to the referenced method are indicated as additional information in the column 'Yield (%)'.

| Intermediate number | Structure | Mass (mg) | Yield (%) |
|---|---|---|---|
| Intermediate 567 | 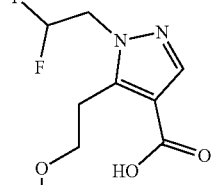 From intermediate 565 | 285 | 72 |
| Intermediate 759 | 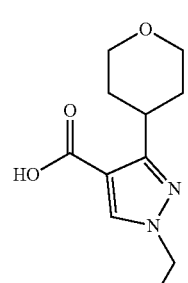 From intermediate 758 | 200 | 61 Anton Parr μw |

Preparation of Intermediate 568

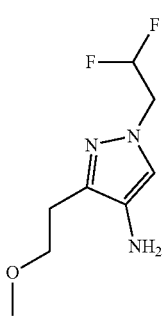

Intermediate 566 (1.56 g; 4.60 mmol) was hydrogenated at room temperature in MeOH (25.00 mL) and EtOAc (20.00 mL) with Pd/C 10% (0.330 g; 0.31 mmol) as a catalyst for 2 hours at atmospheric pressure. The catalyst was filtered over Celite® and the solvent was evaporated until dryness to give 916 mg of intermediate 568 (97% yield) directly used in the next step.

The intermediates in the table below were prepared by using an analogous method starting from the respective starting materials. The most relevant minor deviations to the referenced method are indicated as additional information in the column 'Yield (%)'.

| Intermediate number | Structure | Mass (mg) | Yield (%) |
|---|---|---|---|
| Intermediate 569 | From intermediate 565 | 156 | 91 |
| Intermediate 576 | From intermediate 517' | 187 | 53 |
| Intermediate 580 | From intermediate 579 | 4340 | 100 |

Example A48

Preparation of Intermediate 577

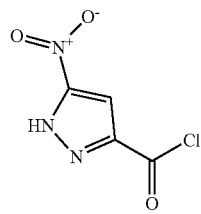 [SMILES: O=C(Cl)c1cc([N+](=O)[O-])[nH]n1]

At 0° C. oxalyl chloride (2M in DCM) (70 mL; 140 mmol) was added slowly to mixture of 5-nitro-3-pyrazole-caboxilic acid (14.50 g, 92.31 mmol) and dimethylformamide (0.200 mL, 2.58 mmol) in DCM (100 mL). The reaction mixture was stirred at room temperature overnight. The precipitate was filtered and the filtrate was evaporated until dryness to give 7.5 g (47%) of intermediate 577 directly used in the next steps without any further purification.

Preparation of Intermediate 578

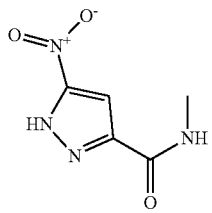

Intermediate 577 (7.52 g; 42.84 mmol) was dissolved in THF (110.00 mL) at room temperature. Then a solution of methylamine (2M in THF) (28.00 mL; 56.00 mmol) in THF (20.00 mL) and trimethylamine (17.00 mL; 122.30 mmol) was added slowly (temperature increased). This reaction mixture was stirred for 4 hours at room temperature, then poured onto a mixture of a 10% aqueous solution of $NH_4Cl$ and EtOAc (100 mL). The aqueous layer was extracted three times with EtOAc (3*200 mL). The organic layers were combined and the solvent was evaporated.

The crude residue was taken up with DCM and triturated. The precipitate was filtered and dried until dryness to give 825 mg (11%) of intermediate 578.

The filtrate was purified via silica gel chromatography (Gradient: 98% DCM, 2% MeOH, 0.2% $NH_4OH$ to 93% DCM, 7% MeOH, 0.7% $NH_4OH$).

The desired fractions were collected and the solvent was evaporated to give 0.126 g of intermediate 578 (impure).

The aqueous layer was acidified until pH 5 with a 10% aqueous solution of HCl and was extracted twice with EtOAc (2*200 mL). The organic layers were mixed and the solvent was evaporated to give 3.46 g (47%) of intermediate 578.

A total of 4.28 g (59%) of intermediate 578 was obtained and directly used in the next reaction step without further purification.

Preparation of Intermediate 579 and intermediate 269

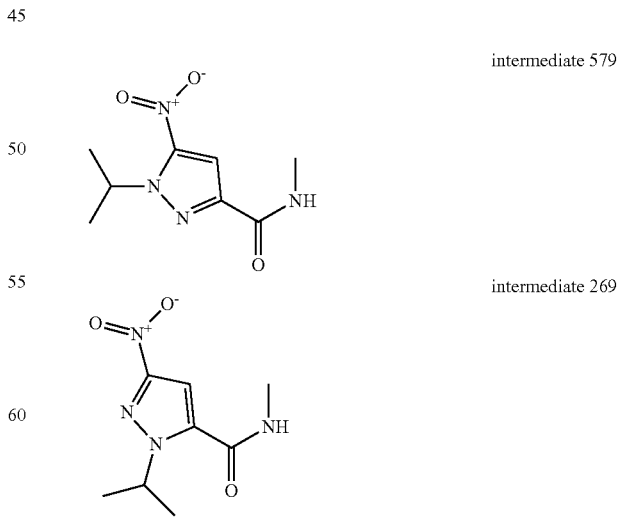

intermediate 579 intermediate 269

In sealed tube, a mixture of intermediate 578 (4.28 g; 25.16 mmol), potassium carbonate (6.81 g; 50.03 mmol) and 2-iodopropane (3.00 mL) in DMF (50 mL) was stirred at 120° C. for 2 hours and 20 minutes. Additional 2-iodopropane (1.00 mL; 10.00 mmol) was added and this reaction was stirred for 2 more hours at 120° C. The mixture was poured onto a mixture of water and a saturated solution of NH$_4$Cl. Then, this mixture was extracted three times with DCM. The organic layer were mixed and the solvent was evaporated until dryness.

The residue (6.34 g) was purified via silica gel chromatography (Stationary phase: irregular SiOH 40 m 330 g, Mobile phase: Gradient from 70% heptane, 30% EtOAc to 60% heptane, 40% EtOAc). The pure fractions were collected and the solvent was evaporated until dryness to give:

1.30 g (24%) of intermediate 269

2.50 g (47%) of intermediate 579 which was combined with another batch of 2.42 g, coming from another reaction, and engaged in the next reaction step.

Example A49

Preparation of Intermediate 582

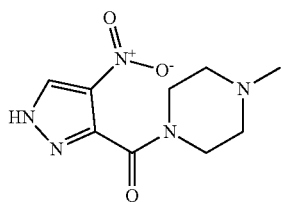 [SMILES: CN1CCN(C(=O)c2n[nH]cc2[N+](=O)[O-])CC1]

To a suspension of 4-nitro-3-pyrazole carboxylic acid (6 g, 38.196 mmol) and DMF (73.938 µL, 0.944 g/mL, 0.955 mmol) in DCM (48.93 mL) at 0° C. was added dropwise a solution of oxalyl chloride 2M in DCM (36 mL, 2 M, 72 mmol) and the reaction mixture was stirred at ambient temperature for 18 h. The reaction mixture was concentrated in vacuo and the residue was dissolved in 20 mL of DCM and 1-methylpiperazine (6.355 mL, 0.903 g/mL, 57.294 mmol) was added slowly at 0° C. The reaction mixture was then allowed to warm to rt and stirred at rt overnight. DCM was removed in vacuo and the resulting slurry was diluted with DCM and a little MeOH. The insoluble residue was filtered off to give 5 g (54%) of intermediate 582.

The filtrate was concentrated in vacuo and purified by Normal phase flash chromatography (Irregular SiOH 40 m 40 g GRACE). Mobile phase 98% DCM, 2% MeOH, 0.2% NH$_4$OH to 90% DCM, 10% MeOH, 1% NH$_4$OH. The pure fractions were combined and the solvent was evaporated to give a further 2.7 g (30%) of intermediate 582.

Example A50

Preparation of Intermediate 584

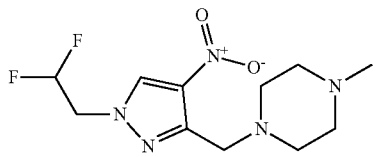 [SMILES: CN1CCN(Cc2nn(CC(F)F)cc2[N+](=O)[O-])CC1]

Borane tetrahydrofuran complex, 1.0M in THF (8.30 mL; 1 M, 8.31 mmol) was added dropwise over 1 h to a stirred suspension of intermediate 583 (630 mg, 2.08 mmol) in THF (4.40 mL, 0.886 g/mL, 54.01 mmol) at 0° C. The reaction mixture was stirred at 0° C. for 2 h and then at rt overnight. Then H$_2$O was added (2.077 mL), and the mixture extracted with DCM. The organic layers were decanted, dried over MgSO$_4$, filtered and evaporated. The crude product was purified by Normal phase flash chromatography (Irregular SiOH 40 m 80 g GRACE). Mobile phase 100% DCM to 90% DCM, 10% MeOH, 1% NH$_4$OH. The pure fractions were combined and the solvent was evaporated to give 337 mg of material. This material was further purified by Normal phase flash chromatography (Irregular SiOH 40 µm 40 g GRACE). Mobile phase 80% Heptane, 20% AcOEt to 40% Heptane, 50% AcOEt, 10% MeOH, 0.1% NH$_4$OH. The pure fractions were combined in 2 batches and the solvent was evaporated to give respectively 113 mg (19%) of intermediate 584 (19%) and 120 mg of intermediate 584 (20%).

Example A51

Preparation of Intermediate 632, intermediate 633 and intermediate 634

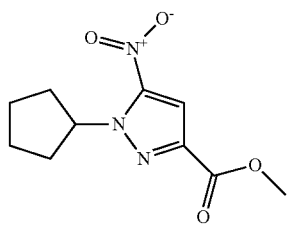

intermediate 632

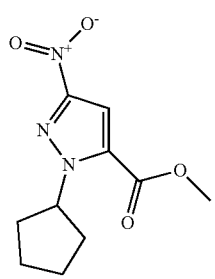 [SMILES: COC(=O)c1cc([N+](=O)[O-])nn1C1CCCC1]

intermediate 633

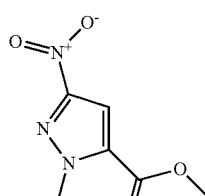

intermediate 634

A mixture of intermediate 730 (800 mg, 4.68 mmol), cyclopentyl bromide (0.600 mL, 5.60 mmol) and K$_2$CO$_3$ (1.25 g, 9.04 mmol) in DMF (5.50 mL) was stirred in a sealed tube at 120° C. using one single mode microwave (Biotage Initiator EXP 60) with a power output ranging from 0 to 400 W for 30 min. [fixed hold time]. The reaction was cooled down to room temperature. The mixture was poured out onto water and DCM. The mixture was decanted and the solvent was evaporated until dryness. The crude was purified by Normal phase flash chromatography (Irregular SiOH 15-40 m 40 g GraceResolv®). Mobile phase 90% Heptane, 10% AcOEt to 60% Heptane, 40% AcOEt. The pure fractions were combined and the solvent was evaporated to give 142 mg (10%) of intermediate 634 and 670 mg of a mixture of the intermediates (60%), which was used directly in the next step.

Alternative Preparation of Intermediate 633

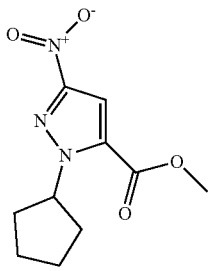

Cyclopentyl iodide (0.608 ml; 5.26 mmol) was added to a solution of intermediate 730 (600 mg; 3.506 mmol) in DMF (12 ml) under N₂ atmosphere. The mixture was stirred at rt for 15 minutes and K₂CO₃ (969.2 mg; 7.013 mmol) was added. The reaction was stirred at rt for overnight. The reaction mixture was diluted with ice water (5 mL). The precipitate was filtered off and washed with water and dried in vacuo. The product was taken forward directly in the next step.

Preparation of Intermediate 640 and intermediate 641 intermediate 640 intermediate 641

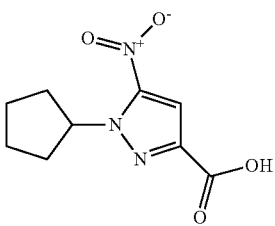

Lithium hydroxide monohydrate (5.80 g; 137.94 mmol) and water (35.4 mL) were added to a solution of the mixture of intermediates 632, 633 and 634 (30 g; 125.40 mmol) in THF (430 mL) and MeOH (430 mL). The reaction mixture was stirred at rt for overnight. The volume of the solution was reduced in vacuo and the solution was poured onto an aqueous solution HCl 3N (500 mL). The resultant precipitate was filtered, washed with aqueous solution of HCl 1M and dissolved in DCM (400 mL). The organic layer was dried over MgSO₄, filtered and the solvent was evaporated to give 25.16 g of a mixture of the intermediates 640 and 641. The product (675 mg; 80%) was used without purification for the next step.

Alternative Preparation of Intermediate 641

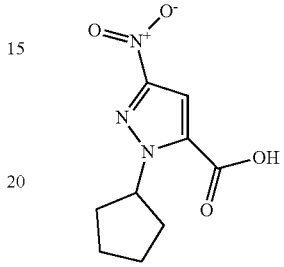

Intermediate 633 (650 mg; 2.717 mmol) was dissolved in a mixture of MeOH (7 ml) and THF (7 ml). To this solution, was added H₂O (0.5 ml) and Lithium hydroxide monohydrate (125.4 mg; 2.989 mmol) and the mixture was stirred until the starting material had disappeared on the TLC. The solution was concentrated in vacuo, the residue was then dissolved in H₂O and acidified with 1M HCl (aq). The resultant precipitate was filtered, washed with aq. 1M HCl and dried in vacuo. The product (250 mg; 41%) was taken forward directly in the next step.

Preparation of Intermediate 721

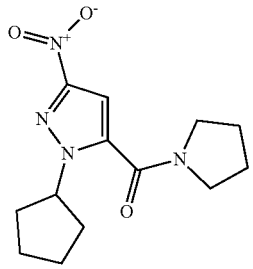 [SMILES: O=C(c1cc([N+](=O)[O-])nn1C1CCCC1)N1CCCC1]

Intermediate 641 (210 mg, 0.933 mmol) was dissolved in DCM (10 mL) and TEA (0.26 mL, 1.865 mmol) was added. To the stirred solution, pyrrolidine (0.156 mL, 1.865 mmol), EDC hydrochloride (357.5 mg, 1.865 mmol) and HOBT (285.6 mg, 1.865 mmol) were added. The resulting suspension was stirred at rt overnight. The reaction mixture was quenched by addition of water (10 ml). The organic layer was washed with brine and the layers were separated. The organic layer was dried over MgSO₄, filtered and the solvent was removed under reduced pressure. The residue was purified by column chromatography on silica gel (irregular SiOH, 15-40 μm, mobile phase: Heptane/EtOAc 50:50). The fractions containing the product were combined and evaporated to dryness to give 210 mg of intermediate 721 (81% yield).

Example A52 intermediate 595

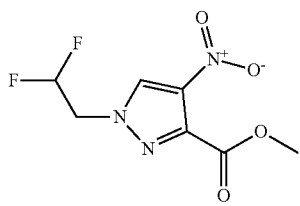

intermediate 596

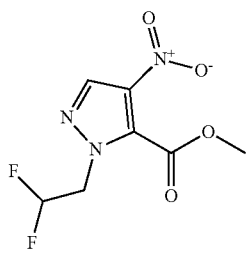

Preparation of Intermediate 595 and 596

Cyanomethylenetributylphosphorane (19.769 mL, 0.92 g/mL, 75.354 mmol) was added to a solution of intermediate 487 (7 g, 40.909 mmol) and 2,2-difluoroethanol, 97% (4.68 g, 57.034 mmol) in toluene (195.641 mL, 0.867 g/mL, 1840.895 mmol) in a sealed tube. The reaction mixture was stirred at 110° C. using one single mode microwave (Masterwave BTR Anton Paar) with a power output ranging from 0 to 1700 W for 30 min. [fixed hold time]. The reaction mixture was diluted with EtOAc washed with a solution 10% of $K_2CO_3$ (aq), water and a solution of saturated NaCl. The layers were separated and the organic layer was dried over $MgSO_4$, filtered and the solvent was removed under reduced pressure. The crude was purified by Normal phase flash chromatography (Irregular SiOH 40 m 330 g GRACE). Mobile phase 90% Heptane, 10% AcOEt to 40% Heptane, 60% AcOEt. The pure fractions were combined and the solvent was evaporated to give 1.77 g of pre-purified intermediate 596 (18%) and 2.9 g of pre-purified intermediate 595 (30%).

The 1.77 g was further purified by Normal phase flash chromatography (Irregular SiOH 40 μm 80 g GRACE). Mobile phase 80% DCM, 20% Heptane to 99% DCM, 1% MeOH, 0.1% $NH_{40}OH$. The pure fractions were combined and the solvent was evaporated to give 1 μg of intermediate 596 (11%).

The 2.9 g was further purified by Normal phase flash chromatography (Irregular SiOH 40 μm 120 g GRACE). Mobile phase 80% DCM, 20% Heptane to 99% DCM, 1% MeOH, 0.1% $NH_4OH$. The pure fractions were combined and the solvent was evaporated to give 1.66 g of intermediate 595 (17%).

The intermediates in the table below were prepared by using an analogous method starting from the respective starting materials. The most relevant minor deviations to the referenced method are indicated as additional information in the column 'Yield (%)'.

| Int. number | structure | Mass (mg) | Yield (%) |
|---|---|---|---|
| Mixture of Intermediates 644 + 645 | ![structures] | 1270 | 40 |

From intermediate 730

Example A53

Preparation of Intermediate 597

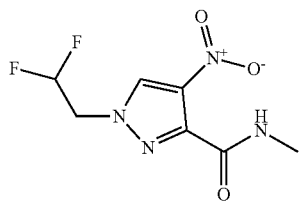 [SMILES: CNC(=O)c1nn(CC(F)F)cc1[N+](=O)[O-]]

Intermediate 595 (0.6 g, 2.55 mmol) in methyl amine 40% in THF (6.40 mL, 2 M, 12.76 mmol) and $^i$PrOH (3.90 mL, 0.785 g/mL, 51.03 mmol) in a sealed tube were stirred at 120° C. using one single mode microwave (Biotage Initiator EXP 60) with a power output ranging from 0 to 400 W for 30 min. [fixed hold time]. The volatiles were evaporated. The crude residue was purified via preparative LC (Stationary phase: irregular SiOH 15-40 μm 40 g GraceResolv®, Mobile phase: gradient from 100% DCM to 97% DCM, 3% MeOH (2% $NH_4OH$))

The pure fractions were collected and the solvent was evaporated until dryness to give intermediate 597 (418 mg, 70%)

The intermediates in the table below were prepared by using an analogous method starting from the respective starting materials. The most relevant minor deviations to the referenced method are indicated as additional information in the column 'Yield (%)'.

| Int. number | structure | Mass (mg) | Yield (%) |
|---|---|---|---|
| Intermediate 606 | From intermediate 605 and pyrrolidine | 192 | 34 |
| Intermediate 612 | From intermediate 610 and methylamine | 293 | 59 |
| Intermediate 616 | From intermediate 610 and pyrrolidine | 136 | 22 Procedure in MeOH 80° C. 10 min |
| Intermediate 635 | From intermediates 632, 633, 634 and methylamine Isomer separation by preparative LC (Stationary phase: irregular SiOH 15-40 μm 40 g GraceResolv®, Mobile phase gradient from 100% DCM to 97% DCM, 3% MeOH (2% NH4OH) | 210 | 31 |
| Intermediate 636 | From intermediates 632, 633, 634 and methylamine Isomer separation by preparative LC (Stationary phase: irregular SiOH 15-40 μm 40 g GraceResolv®, Mobile phase gradient from 100% DCM to 97% DCM, 3% MeOH (2% NH4OH) | 131 | 20 |
| Intermediate 646 | From mixture of intermediate 644 + 645 and methylamine | 670 | 53 |
| Intermediate 666 | From intermediate 651 and methylamine | 359 | 99 Neat Procedure in methyl-amine RT 30 min |

Example A54

Preparation of Intermediate 654

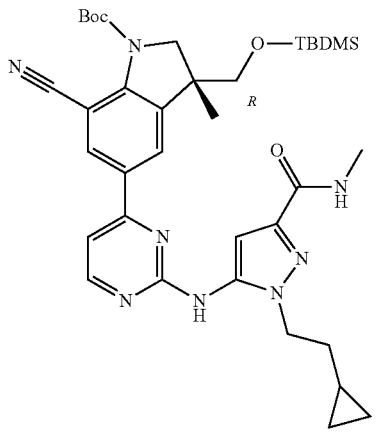

A mixture of intermediate 653 and methylamine solution (33 wt % in EtOH) was stirred at rt for 1 h. The volatiles were removed under reduced pressure, without heating, to afford intermediate 654 (161 mg, 88%). The material was used directly in the next step.

Example A55

Preparation of Intermediate 620 intermediate 610 intermediate 611

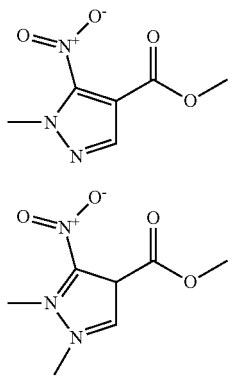

A solution of 4-nitro-3-pyrazole carboxylic acid (5 g, 31.83 mmol), iodomethane (3.963 mL, 2.28 g/mL, 63.66 mmol) and K₂CO₃ (8.798 g, 63.66 mmol) in DMF (60 mL) was stirred rt overnight. Ethyl acetate and water were added to the mixture. The organic layer was dried over MgSO₄, filtered and concentrated. A purification was performed via preparative LC (Stationary phase: irregular SiOH 15-40 µm 220 g grace, Mobile phase: gradient from 90% Heptane, 10% AcOEt to 40% Heptane, 60% AcOEt. The pure fractions were combined and the solvent was evaporated to give 1.43 g of intermediate 610 (24%) and 2.5 g of intermediate 611 (42%).

Example A56

Preparation of Intermediate 620

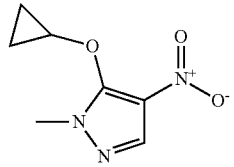

KO$^t$Bu (938 mg, 8.36 mmol) was added to a stirred solution of 5-chloro-1-methyl-4-nitro-1H-pyrazole (900 mg, 5.57 mmol) and cyclopropanol (970.713 mg, 16.713 mmol) in MeCN (7.27 mL) at rt. Addition was done portionwise. The mixture was stirred at rt for 3 hours. Water was added and the mixture acidified with 3N HCl(aq). The reaction mixture was extracted with DCM, dried over MgSO₄, filtered and evaporated. A purification was performed via preparative LC (Stationary phase: irregular SiOH 15-40 µm 80 g GraceResolv®, Mobile phase: gradient from 100% DCM to 98% DCM, 2% MeOH, 0.1% NH₄OH) to afford intermediate 620 (470 mg, yield 46%).

The intermediates in the table below were prepared by using an analogous method starting from the respective starting materials. The most relevant minor deviations to the referenced method are indicated as additional information in the column 'Yield (%)'.

| Int. number | structure | Mass (mg) | Yield (%) |
|---|---|---|---|
| Intermediate 624 | 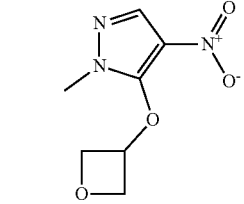<br>From 5-chloro-1-methyl-4-nitro-1H-pyrazole and 3-hydroxyoxetane | 235 | 19<br>140° C.<br>20 min |
| Intermediate 628 | 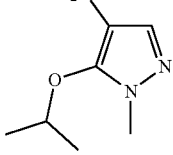<br>From 5-chloro-1-methyl-4-nitro-1H-pyrazole and isopropanol | 407 | 58<br>Procedure in $^i$PrOH, reflux, 12 h |

-continued

| Int. number | structure | Mass (mg) | Yield (%) |
|---|---|---|---|
| Intermediate 741 | 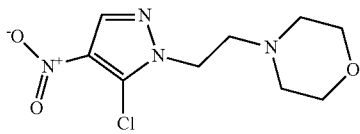 From 3-chloro-4-nitro-1H-pyrazole | 3300 | 65 |

Example A57

Preparation of Intermediate 657

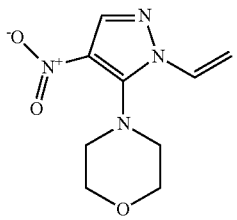

Lithium bis(trimethylsilyl)amide (3.713 mL, 1 M, 3.713 mmol) was added dropwise to a stirred solution of intermediate 656 (700 mg, 3.094 mmol) in THF (9.282 mL, 0.886 g/mL, 114.055 mmol) at −70° C. under nitrogen. The reaction mixture was stirred at −70° C. for 2 hours then hexachloroethane (878.997 mg, 3.713 mmol) in THF (1.856 mL, 0.886 g/mL, 22.811 mmol) was added dropwise. The resulting mixture was allowed to stir at rt and stirred for 1 hour. A diluted solution of NH$_4$Cl was added and the aqueous layer was extracted with DCM and the combined layers were dried over MgSO$_4$. After filtration and removal of the solvent in vacuo, 550 mg of intermediate 657 (68%. yield) were obtained and directly used in the next steps without any further treatment.

Preparation of Intermediate 658

Intermediate 657 (420 mg, 1.611 mmol) in $^i$PrOH (2.965 mL, 0.785 g/mL, 38.726 mmol) in a sealed tube were stirred at 165° C. using one single mode microwave (Biotage Initiator EXP 60) with a power output ranging from 0 to 400 W for 10 min. [fixed hold time]. Sodium Isopropoxide (396.724 mg, 4.834 mmol) was added. Then the resulting mixture was stirred at 165° C. using one single mode microwave (Biotage Initiator EXP 60) with a power output ranging from 0 to 400 W for 5 min. [fixed hold time]. The reaction mixture was poured onto water and an extraction was performed with DCM. The organic layer was washed with brine and the layers were separated. The organic layer was dried over MgSO$_4$, filtered and the solvent was removed under reduced pressure. The residue was purified by column chromatography on silica gel (irregular SiOH, 15-40 m, 40 g, GraceResolv®), mobile phase: DCM/(MeOH(+10% aq. NH$_4$OH)), gradient from 100:0 to 96:4). The fractions containing the product were combined and evaporated to dryness to give 285 mg of intermediate 658 (79% yield).

Example A58

Preparation of Intermediate 662

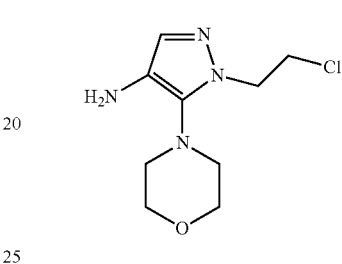

Intermediate 657 (990 mg, 3.798 mmol) was stirred in $^i$PrOH for 20 minutes at 165° C. in a sealed tube. $^i$PrOH was evaporated to give the nitro pre-cursor to the targeted amino pyrazole. The residue was taken up into MeOH (18.045 mL, 0.791 g/mL, 445.47 mmol). AcOH (2.143 mL, 1.049 g/mL, 37.432 mmol) then zinc (2.483 g, 37.978 mmol) were added and the reaction mixture was stirred at rt for 1 hour.

The resulting mixture was filtered on a pad of Celite® and the solvent was concentrated under reduced pressure. A diluted solution of 10% K$_2$CO$_3$ (aq) was added and the aqueous layer was extracted with DCM and the combined layers were dried over MgSO$_4$. After filtration and removal of the solvent in vacuo, 437 mg of intermediate 662 (50%) were obtained and directly used in the next steps without any further treatment.

Preparation of Intermediate 663

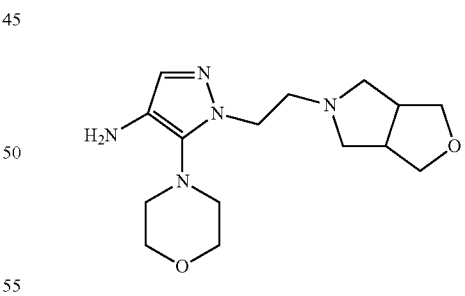

Intermediate 662 (384 mg, 1.665 mmol) and hexahydro-1H-furo[3,4-C]pyrrole (470.891 mg, 4.161 mmol) in $^i$PrOH (3.063 mL, 0.785 g/mL, 40.009 mmol) in a sealed tube were stirred at 165° C. using one single mode microwave (Biotage Initiator EXP 60) with a power output ranging from 0 to 400 W for 10 min. [fixed hold time]. The residue was purified by column chromatography on silica gel (irregular SiOH 15-40 m, 40 g GraceResolv®, mobile phase: DCM/(MeOH(+2% aq. NH$_4$OH)), gradient from 100:0 to 90:10). The fractions containing the product were combined and evaporated to dryness to give 371 mg of intermediate 663 (73% yield).

Example A59

Preparation of Intermediate 672

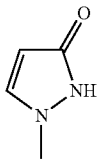

Methyl alpha-chloroacrylate (25 g, 1.189 g/mL, 207.408 mmol) in THF (70 mL) and methylhydrazine (22.083 mL, 0.86 g/mL, 412.217 mmol) in THF (70 mL) were added dropwise at the same rate to THF (10 mL) at rt. The reaction mixture was stirred at rt for 16 h then was heated at 50° C. for 1 hour. The resulting mixture was diluted with water. The aqueous layer was extracted with EtOAc (4×) and the layers were separated. The organic layer was dried over $MgSO_4$, filtered and the solvent was removed under reduced pressure to give 15.7 g intermediate 672 (77%, yield) which was used directly for the next step>yligny_4508_1

Preparation of Intermediate 673

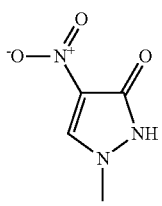

$H_2SO_4$ (39.369 mL, 1.84 g/mL, 738.569 mmol) was cooled down to −5° C. Intermediate 672 (3 g, 30.58 mmol) was added and the solution was stirred for 15 minutes at 0° C. $HNO_3$ (43.306 mL, 1.38 g/mL, 948.406 mmol) was added dropwise. The reaction was stirred at 0-5° C. for 2 hours. The reaction mixture was poured out onto ice and water, stirred for 20 min and the precipitate was filtered off and dried, affording intermediate 673 (2.3 g, yield 52.6%).

Preparation of Intermediate 674

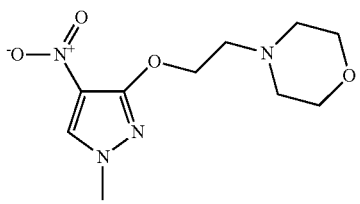

Cyanomethylenetributyl phosphorane (3.483 mL, 0.92 g/mL, 13.277 mmol) was added to a solution of intermediate 673 (1 g, 6.988 mmol) and 4-(2-hydroxyethyl)morpholine (1.273 mL, 1.08 g/mL, 10.482 mmol) in toluene (30.449 mL) at rt. The mixture was stirred at rt for 18 hours. The solvent was evaporated and the residue was purified by preparative LC (Irregular SiOH 20-45 m 40 g GraceResolv®, mobile phase Gradient from 80% Heptane, 20% AcOEt to 40% Heptane, 50% AcOEt, 10% MeOH (2% $NH_4OH$)). The pure fractions were combined and the solvent was evaporated to afford intermediate 674 (1.52 g, yield 84.9%).

Example A60

Preparation of Intermediate 707

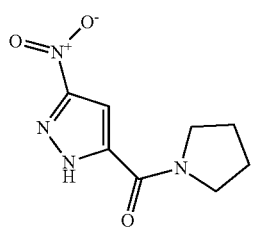 [SMILES: O=C(c1cc([N+](=O)[O-])n[nH]1)N1CCCC1]

Intermediate 577 (2.00 g; 11.39 mmol) was dissolved in THF (30.00 mL). Then a solution of pyrrolidine (15.00 mL; 13.00 mmol), triethylamine (4.50 mL; 32.37 mmol) in THF (10.00 mL) was added slowly to this mixture and the reaction was stirred overnight at room temperature. Water was added and this mixture was extracted twice with EtOAc. The organic layer was decanted and the solvent was evaporated until dryness to give 1.10 g (46%) of intermediate 707. The aqueous layer was acidified with 3N HCl(aq) and extracted twice with EtOAc. The organic layer was decanted and the solvent was evaporated until dryness to give a further 0.90 g (38%) of intermediate 707. The two fractions were combined to give 2.00 g (84%) of intermediate 707 which was used directly in the next step.

The intermediates in the table below were prepared by using an analogous method starting from the respective starting materials. The most relevant minor deviations to the referenced method are indicated as additional information in the column 'Yield (%)'.

| Intermediate number | Structure | Mass (mg) | Yield (%) |
| --- | --- | --- | --- |
| Intermediate 712 | From intermediate 577 and cyclopropylmethylamine | 2140 | 89 Procedure in $Et_3N$, THF RT, o/n |

Example A61

Preparation of Intermediate 729

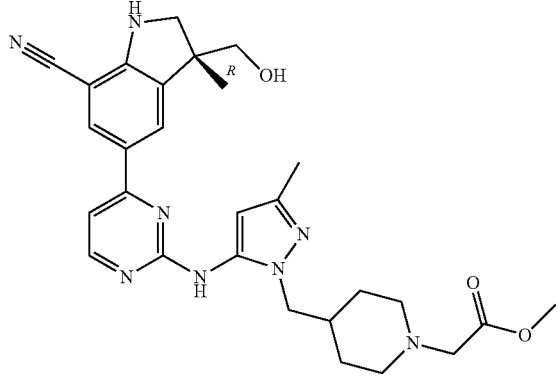

A mixture of intermediate 728 (0.165 g; 0.26 mmol), SiO$_2$ 35-70 m (0.500 g) in toluene (4.00 mL) was stirred at 120° C. for 2 hours. The reaction was cooled down to room temperature. SiO$_2$ was filtered off and washed four times with a mixture of EtOAc/MeOH (85%/15%). The solvent was evaporated until dryness. The crude was purified by preparative LC (Irregular SiOH 20-45 m 40 g GraceResolv®, mobile phase: 98% DCM, 2% MeOH to 94% DCM 6% MeOH). The pure fractions were collected and the solvent was evaporated until dryness to afford intermediate 729 (0.066 g; 48%) which was used directly for the next step.

Example A62

Preparation of Intermediate 732

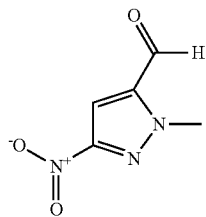

A solution of intermediate 731 (1.22 g, 6.59 mmol) in dry DCM (30 mL) was cooled to −78° C. The reaction mixture was purged with N$_2$, then DIBAL-H (1M solution in DCM) (7.25 mL, 7.249 mmol) was added dropwise. The resulting mixture was stirred at −78° C. for 1.5 h. A saturated NH$_4$Cl solution (1 mL) was added, followed by 1 M HCl (1 mL). The mixture was extracted with DCM. The organic layer was washed with brine and the layers were separated. The organic layer was dried over MgSO$_4$, filtered and the solvent was removed under reduced pressure. The residue was purified by column chromatography on silica gel (irregular SiOH, 15-40 μm, mobile phase: Heptane/EtOAc 70:30). The fractions containing the product were combined and evaporated to dryness to give intermediate 732 (530 mg; 52% yield).

Preparation of Intermediate 733

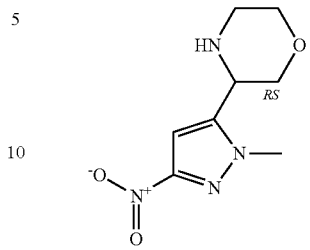

To a solution of SnAP reagent (2-[(tributylstannyl)methoxy]-ethanamine) (0.995 mL, 3.417 mmol) in DCM (15 mL) at rt was added intermediate 732 (530 mg, 3.417 mmol) and Molecular Sieves 4A (100 mg/mmol, 341 mg). The resulting suspension was stirred at rt for 2 hours, filtered and concentrated under reduced pressure to afford the imine. Separately, 2,6-lutidine (0.398 mmol, 3.417 mmol) was added in one portion to a suspension of HFIP (10 mL) and Cu(OTf)$_2$ (1.236 g, 3.417 mmol). A solution of the imine in DCM (6 mL) was added in one portion and the resulting mixture was stirred at rt overnight. The reaction was quenched by addition of 10% aq NH$_4$OH (5 ML) and was extracted with DCM. The organic layer was washed with brine and the layers were separated. The organic layer was dried over MgSO$_4$, filtered and the solvent was removed under reduced pressure to give. The crude was purified by column chromatography on silica gel (irregular SiOH 15-40 m, mobile phase: DCM/(MeOH), gradient from 100:0 to 98:2). The fractions containing the product were combined and evaporated to dryness to give 270 mg of intermediate 733 (37% yield).

Preparation of Intermediate 734

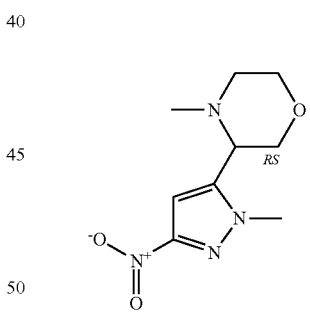

To a solution of intermediate 733 (250 mg, 1.178 mmol) in MeOH (10 mL) were added formaldehyde (0.191 mL, 2.356 mmol) and then formic acid (0.444 μL, 0.0118 mmol). The reaction mixture was stirred at rt 1 hour. Then, sodium triacetoxyborohydride (312.1 mg, 1.473 mmol) was added and the reaction mixture was stirred for 1 hour. Then, the reaction mixture was carefully quenched by addition of saturated NaHCO$_3$ (aq) (2 mL). The organic layer was washed with brine and the layers were separated. The organic layer was dried over MgSO$_4$, filtered and the solvent was removed under reduced pressure. The residue was purified by column chromatography on silica gel (irregular SiOH, 15-40 μm, mobile phase: EtOAc 100%). The fractions containing the product were combined and evaporated to dryness to give 180 mg of intermediate 734 (68% yield).

Example A63

Preparation of Intermediate 738

DIPEA (0.385 mL; 2.24 mmol) was added to a solution of 1-methyl-1H-pyrazol-3-amine (0.159 mL; 2 mmol) and 2,4-dichloro, 1,3,5-triazine (0.3 g; 2 mmol) in acetone (9 mL) at 0° C. The reaction mixture was allowed to warm up to rt, was purged with $N_2$ and was stirred for 3 h. A diluted solution of $NH_4Cl$ was added and the aqueous layer was extracted twice with EtOAc and the combined layers were dried over $MgSO_4$. After filtration and removal of the solvent in vacuo, 660 mg of intermediate 738 (quantitative recovery, purity 57%) were obtained and used directly in the next step without any further treatment.

Preparation of Intermediate 739

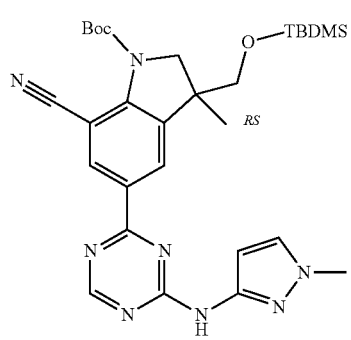

To a solution of intermediate 5 (0.6 g; 0.772 mmol), intermediate 738 (0.285 g; 0.772 mmol) and cesium carbonate (0.755 g; 2.32 mmol) in 1,4-dioxane (3.9 mL) and distilled water (0.4 mL) was added tetrakis(triphenylphosphine)palladium(0) (0.045 g; 0.0386 mmol). The reaction mixture was heated at 95° C. overnight. The reaction mixture was poured into ice and extracted with EtOAc. The organic layer was washed with brine and the layers were separated. The organic layer was dried over $MgSO_4$, filtered and the solvent was removed under reduced pressure. The crude residue was purified by column chromatography on silica gel (irregular SiOH, 15-40 m, 40 g, mobile phase: Heptane/EtOAc gradient from 100:0 to 0:100). The fractions containing the product were combined and evaporated to dryness to give 60 mg of intermediate 739 (13% yield).

Example A64

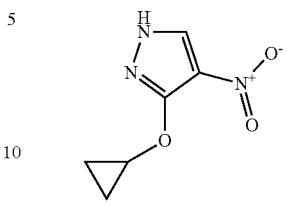

Preparation of Intermediate 746

At 0° C. and under nitrogen flux, NaH (60% dispersion in mineral oil) (0.510 g; 12.8 mmol) was added portionwise to a solution of cyclopropanol (0.64 mL, 12.74 mmol) in Me-THF (24 mL). The reaction was stirred at room temperature for 10 minutes.

At −78° C., the above described suspension was added dropwise to a solution of 1,4-dinitro-1H-pyrazole (3.00 g; 18.98 mmol) in Me-THF (6.50 mL, 64.9 mmol). The reaction mixture was stirred at −78° C. for 1 h then allowed to stir at rt for 5 hours. The reaction mixture was poured out onto water, made acidic with 3N HCl(aq), extracted with DCM, dried over $MgSO_4$, filtered and evaporated. The crude was purified via preparative LC (Stationary phase irregular SiOH 15-40 m 24 g GraceResolv®, Mobile phase: gradient from 80% Heptane, 20% EtOAc to 40% heptane, 60% EtOAc). The pure fractions were collected and the solvent was evaporated to give 466 mg of intermediate 746 (22%).

Example A65

Preparation of Intermediate 754

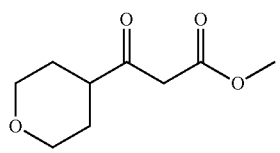

NaH (60% dispersion in mineral oil) (0.340 g; 8.5 mmol) was added to a solution of dimethyl carbonate (0.83 mL; 9.85 mmol) in 1,4-dioxane (4.00 mL) The mixture was heated at 90° C. and 1-(tetrahydro-2H-pyran-4-yl) ethanone (0.5 g; 3.90 mmol) in 1,4-dioxane (1.00 mL) was added to the suspension. The reaction mixture was stirred at reflux for 3 hours. Water was added and few drops of an aqueous solution of 3N HCl.

The mixture was extracted twice with ethylic ether. The organic layer was decanted and the solvent was evaporated until dryness to give 0.65 g of intermediate 754 (89%).

Example A66

Preparation of Intermediate 762

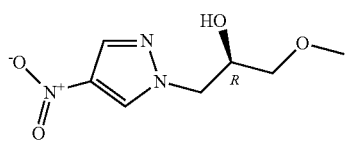

In a sealed tube, 4-nitro-1H-pyrazole (1.9 g, 16.5 mmol), (R)-glycidyl methyl ether (1.6 g, 18.2 mmol) and K$_2$CO$_3$ (3.4 g, 24.8 mmol) in DMF (17.9 mL, 231 mmol) were stirred at 130° C. using one single mode microwave (Masterwave BTR Anton Paar) with a power output ranging from 0 to 1700 W for 5 min. [fixed hold time]. The reaction mixture was poured out onto water, made acidic with 3N HCl(aq), extracted twice with AcOEt and the combined organic layers were washed with water, dried over MgSO$_4$, filtered and evaporated. The residue was purified by Normal phase on (Irregular SiOH 40 µm 40 g GraceResolv®). Mobile phase gradient from 80% heptane, 20% AcOEt to 60% heptane, 40% AcOEt. The pure fractions were combined and the solvent was evaporated to give 1.52 g of intermediate 762 (46%).

Preparation of Intermediate 763

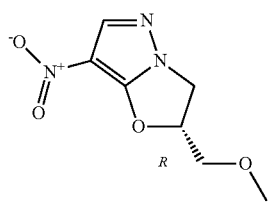

Lithium bis(trimethylsilyl)amide (1M in THF) (18 mL, 1 M, 18 mmol) was added dropwise to a stirred solution of intermediate E5 (1.5 g, 7.5 mmol) in THF (22 mL) at −70° C. under nitrogen. The reactive mixture was stirred at −70° C. for 1 hour and hexachloroethane (2.1 g, 8.9 mmol) in THF (4.5 mL) was added dropwise. The reactive mixture was allowed to stir at rt for 2 h. Water and 3N HCl(aq) were added and the solution was extracted with DCM. The organic layer was dried over MgSO$_4$, filtered and evaporated. The crude residue was purified via silica gel chromatography (Stationary phase: irregular SiOH 15-40 µm, 80 g, mobile phase: gradient from 80% heptane, 20% AcOEt to 60% heptane, 40% AcOEt) to give 700 mg of intermediate 763 (47% yield).

Example A67

Preparation of Intermediate 767

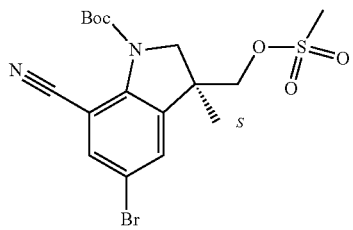

A solution of intermediate 4S (3.85 g; 8 mmol) in dry THF (50 mL) was treated with TBAF (1M in THF) (9 mL; 9 mmol) and allowed to stir at room temperature. The reaction mixture was stirred for 30 min, diluted with EtOAc and washed with brine (3×). The organic layer was dried over MgSO$_4$, filtered, concentrated, and dried overnight under high-vacuum to yield 3.36 g of intermediate 767 (greater than quantitative recovery, pure at 67%).

Preparation of Intermediate 768

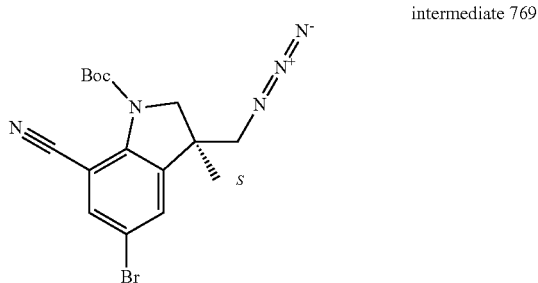

A solution of intermediate 767 (3.36 g; 6.12 mmol) and DIPEA (3 mL; 17.4 mmol) in CH$_2$Cl$_2$ (50 mL) was cooled down to 0° C. and treated with mesyl chloride (1 mL; 12.9 mmol). The reaction mixture was allowed to warm to room temperature and stirred for 30 minutes. The volatiles were evaporated. The residue was redissolved in CH$_2$Cl$_2$ and purified via Flash column chromatography (330 g SiO$_2$, 25-75% EtOAc/Hex over 5 Column Volumes). The desired fractions were combined, concentrated, and dried under high-vac to yield 2.56 g of intermediate 768 (93% yield, 92% purity) as a pale yellow/off-white solid.

Preparation of Intermediate 769 and 769' intermediate 769 intermediate 769'

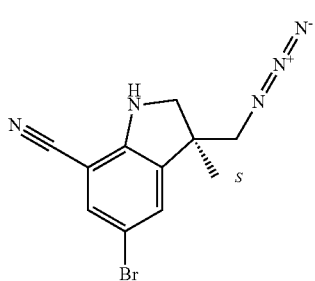

Preparation of Intermediate 771

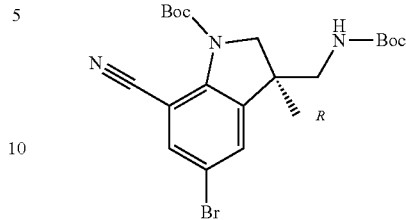

A heterogeneous solution of intermediate 768 (2.48 g; 5.13 mmol) and sodium azide (0.74 g; 11.2 mmol) in dry DMF (20 mL) was heated overnight at 115° C. while stirring under $N_2$. The reaction mixture was cooled to room temperature, diluted with EtOAc and washed with water followed by brine (2×). The organic layer was dried (MgSO$_4$), filtered, concentrated, and dried under high-vacuum to give 1.68 g of a mixture of intermediate 769 and intermediate 769' (in a ratio of 3/1).

Preparation of Intermediate 770 and 770' intermediate 770

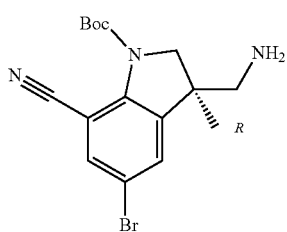

intermediate 770'

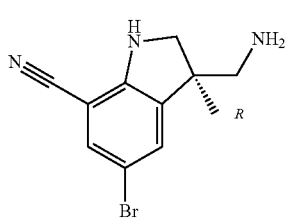

A homogeneous solution of the mixture of intermediate 769 and intermediate 769' (1.68 g; 4.3 mmol) in dry THF (25 mL) was treated with triphenylphosphine (1.68 g; 6.4 mmol) and allowed to stir overnight at room temperature. Next day, Water (5 mL; 277 mmol) was added and the reaction mixture was stirred at 50° C. for 18 hours. Next day, the reaction mixture was cooled down to room temperature, diluted with EtOAc and washed with brine (3×). The organic layer was dried (MgSO$_4$), filtered, concentrated, and dried under high-vacuum. The crude residue was re-dissolved in a minimal amount of CH$_2$Cl$_2$ and purified via Flash Column Chromatography (120 g SiO$_2$, 0-10% 2N NH$_3$/MeOH/EtOAc over 10 Column Volumes, flushing with MeOH). The desired fractions were combined, concentrated, and dried under high-vacuum to give 2.03 g of intermediate 770 (129%, pure at 38%) and 0.38 g of intermediate 770' (32%).

A homogeneous solution of intermediate 770 (2.03 g, 2.1 mmol) in CH$_2$Cl$_2$ (20 mL) was treated with di-tert-butyl dicarbonate (1 mL; 4.7 mmol) at room temperature. The reaction mixture was stirred for 1 hour. The volatiles were evaporated. The residue was re-dissolved in a minimal amount of CH$_2$Cl$_2$ and purified via Flash Column Chromatography (40 g SiO$_2$, 0-50% EtOAc/Hex over 10 Column Volumes). The desired fractions were combined, concentrated, and dried under high-vacuum to yield 1 g of intermediate 771 (quant, based on purity of starting material) as a white solid.

Preparation of Intermediate 772

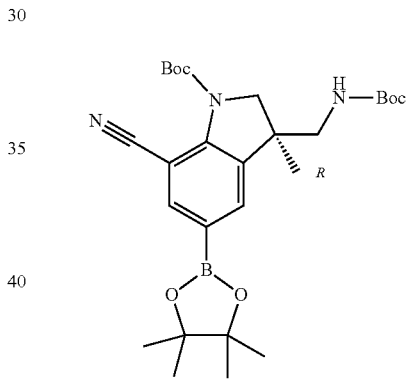

In a 20 mL vial, intermediate 771 (0.395 g; 0.847 mmol), bis(pinacolato)diboron (0.326 g; 1.284 mmol), potassium acetate (0.262 g; 2.67 mmol) and 2nd generation Xphos precatalyst (chloro(2-dicyclohexylphosphino-2',4',6'-triisopropyl-1,1'-biphenyl) [2-(2'-amino-1,1'-biphenyl)]palladium(II)) (0.035 g; 0.0445 mmol) together with a stirbar were added and the vessel capped. The atmosphere was evacuated and purged with N$_2$ (3×) and then the vial was charged with dry, freshly degassed 1,4-dioxane (5 ml). Heating was started directly at 80° C. After 30 min, the reaction mixture had turned heterogeneous black and HPLC indicated complete consumption of intermediate 771. The filtrate was concentrated and dried under high-vacuum to yield crude intermediate 772 as a dark yellow oil. The material used directly in the next step (quantitative conversion assumed).

The intermediate in the table below was prepared by using an analogous 6 step sequence as applied for intermediate 772, but starting from the enantiomeric starting material, 4R.

| Intermediate number | Structure | Mass (mg) | Yield (%) |
|---|---|---|---|
| Intermediate 773 | 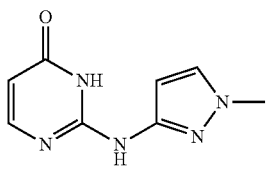<br>From intermediate 4R | 218 (used without further purification) | |

Example A68

Preparation of Intermediate 774

1-Methyl-1H-pyrazol-3-amine (70.0 g, 721 mmol) and 2-(methylthio)pyrimidin-4(3H)-one (63.0 g, 443 mmol) were added to a 250 mL round-bottomed flask. The resulting mixture was then stirred and heated at 180° C. for 2 hours before a yellow solid was formed. The resulting mixture was cooled to room-temperature. The residue was triturated with ethanol (300 mL), filtered, to afford intermediate 774 (80 g, 94.3%) as a white solid, which was used in the next step without further purification.

Preparation of Intermediate 775

Intermediate 774 (80.0 g, 418 mmol) and phosphoryl trichloride (256.6 g, 1674 mmol) were added to a 500 mL flask. The reaction mixture was stirred at 100° C. for 2 hours. After cooling to r.t., the mixture was concentrated to dryness under reduced pressure. The residue was redissolved in dichloromethane (500 mL) and H$_2$O (500 mL), neutralised cautiously with saturated aqueous NaHCO$_3$ to pH=7.0. The mixture was extracted with dichloromethane (500 mL×3). The combined organic extracts were dried over anhydrous Na$_2$SO$_4$, filtered and concentrated to dryness under reduced pressure to afford intermediate 775 (81 g, 89%) as a yellow solid.

Example A69

Preparation of Intermediate 776

In a 25 mL round bottomed flask were added intermediate 773 (0.218 g; 0.425 mmol), intermediate 775 (0.189 g; 0.902 mmol), potassium phosphate (tribasic) (0.482 g; 2.203 mmol), 2nd generation Xphos precatalyst (chloro(2-dicyclohexylphosphino-2',4',6'-triisopropyl-1,1'-biphenyl)[2-(2'-amino-1,1'-biphenyl)]palladium(II)) (0.022 g; 0.028 mmol) together with a stirbar. The vessel was sealed and the atmosphere evacuated and purged with N$_2$ (3×). The vessel was then charged with freshly degassed solvents: dioxane (5 mL) and de-ionized H$_2$O (1 mL). Heating was started directly at 80° C. After 1 hour 30 min the reaction was cooled to room temp, diluted with EtOAc, and washed with de-ionized H$_2$O (3×). The organic layer was dried (MgSO$_4$), filtered, concentrated, and dried under high-vacuum to yield a dark yellow oil. The crude material was dissolved in a minimal amount of CH$_2$Cl$_2$ and purified via Flash Column Chromatography (40 g, 0-100% EtOAc/CH$_2$Cl$_2$ over 10 Column Volumes). The desired fractions were combined, concentrated, and dried under high-vacuum to yield 172 mg of intermediate 776 (63% yield; 88% purity) as a yellow solid.

The intermediate in the table below was prepared by using an analogous method starting from the respective R enantiomer, intermediate 772. The most relevant minor deviations to the referenced method are indicated as additional information in the column 'Yield (%)'.

| Intermediate number | Structure | Mass (mg) | Yield (%) |
|---|---|---|---|
| Intermediate 777 | 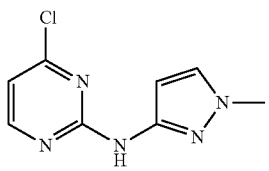<br>From intermediate 772 | 240 | 95 |

Example A70

Preparation of Intermediate 778 and 778'

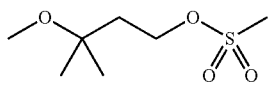
intermediate 778

intermediate 778'

Methanesulfonyl chloride (6.683 mL, 1.48 g/mL, 86.338 mmol) was added to a solution of 3-methoxy-3-methylbutanol (5 g, 42.31 mmol) and $Et_3N$ (17.661 mL, 0.728 g/mL, 127.059 mmol) in DCM (477.33 mL, 1.326 g/mL, 7452.28 mmol) at rt and the reaction mixture was stirred for 18 h. Water was added. The organic layer was separated, washed with 1N HCl(aq) then with brine before drying over $MgSO_4$. The organic layer was filtered and evaporated to afford a mixture on intermediate 778 and 778' (10.3 g, quantitative yield) that was used directly in the next step.

Example A71

Preparation of Intermediate 779

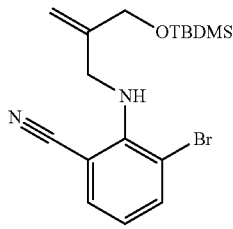 [SMILES: C=C(CNc1c(Br)cccc1C#N)CO[Si](C)(C)C(C)(C)C]

To a solution of 2-Amino-3-bromobenzonitrile (30.0 g) in THF (240 mL) was added sodium tert-butoxide (1.1 eq.) and the mixture was stirred at −5 to 50° C. for 1 hour. A solution of intermediate 3a in THF (85.0 g) was then added dropwise and the mixture was stirred for 2-4 hours monitoring the conversion by HPLC. Water (210 mL) was then added dropwise and the mixture was concentrated to remove most of THF. Heptane (300 mL) was then added and the mixture was stirred for 30 min. After phase separation, the organic layer was washed with water (210 mL), concentrated to 2-3 volumes and filtered through a pad of silica gel (60 g), washing the pad with heptane (300 mL), affording 63.3 g of intermediate 779.

Preparation of Intermediate 780

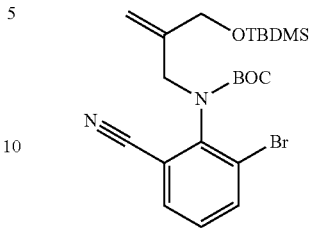

To a solution of intermediate 779 (50.0 g) in dry THF (500 mL) was added dimethylaminopyridine (0.5 eq.) and the temperature was adjusted to 65-70° C. Di-tert-butyldicarbonate (2.2 eq.) was then added and the mixture was stirred for 2 hours (monitoring by HPLC). Water (350 mL) was added and the mixture was concentrated to 350-400 mL. Heptane (500 mL) was added and the pH was adjusted by addition of 20% aqueous AcOH to 4-6. The layers were separated and water (350 mL) was added. After pH adjustment to 7-8 with aqueous 8% $NaHCO_3$, the layers were separated and the organic layer was washed with water (350 mL) and concentrated to afford 64 g (quantitative) of intermediate 780.

B. Preparation of the Final Compounds

Example B 1

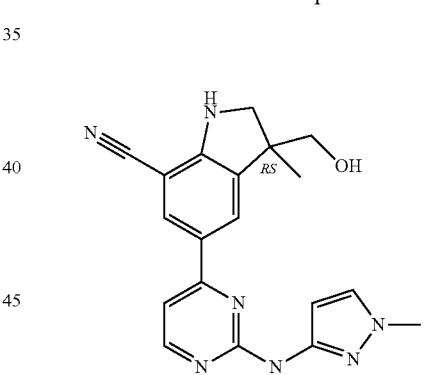

Preparation of Compound 1

A mixture of intermediate 8 (1.09 g, 2.29 mmol) and TBAF (1M in THF) (2.50 mL, 2.50 mmol) in Me-THF (20 mL) was stirred at rt for 18 h. The reaction mixture was directly purified by column chromatography on silica gel (irregular SiOH 15-40 m, 120 g, liquid injection with a mixture of Me-THF/DCM, mobile phase: DCM/(MeOH (10% aq $NH_3$)), gradient from 100:0 to 90:10 in 10 CV). The fractions containing the product were combined and concentrated under vacuum to give 650 mg of compound 1 (78% yield, yellow solid). 255 mg of compound 1 was solubilized in a mixture of $CH_3CN/H_2O$ (1:1) and freeze-dried overnight then dried at 50° C. under reduced pressure to give 255 mg of compound 1 (31%, yellow fluffy solid).

Preparation of Compound 19

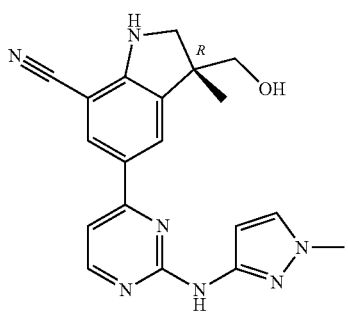

A mixture of intermediate 47 (0.35 g, 0.74 mmol) and TBAF (1M in THF) (0.80 mL, 0.80 mmol) in THF (6 mL) was stirred at rt for 18 h. The reaction mixture was directly (without evaporation) purified by column chromatography on silica gel (irregular SiOH, 15-40 m, 120 g, liquid injection (THF/DCM), mobile phase gradient: DCM/(MeOH (10% aq. NH$_3$)) from 100:0 to 90:10 in 15 CV). The fractions containing the product were combined and evaporated to dryness to give 231 mg of compound 19 (87% yield, yellow solid).

Preparation of Compound 42

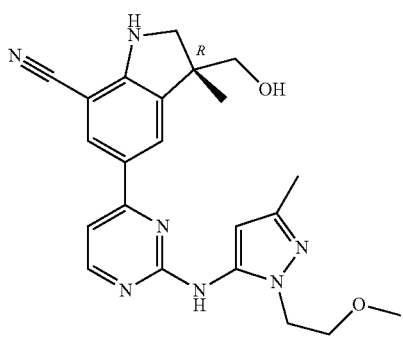

At rt, intermediate 100 (7.60 mL, 7.60 mmol) was added to a solution of TBAF (1M in THF) (2.72 g, 5.10 mmol) in Me-THF (50 mL) and stirred at rt overnight. Water was added and this mixture was extracted twice with EtOAc. The organic layer was decanted and the solvent was evaporated until dryness. The residue was taken up into EtOH and this precipitate was triturated and filtered. The product was dried until dryness to give 1.27 g of compound 42 (56% yield).

Preparation of Compound 49

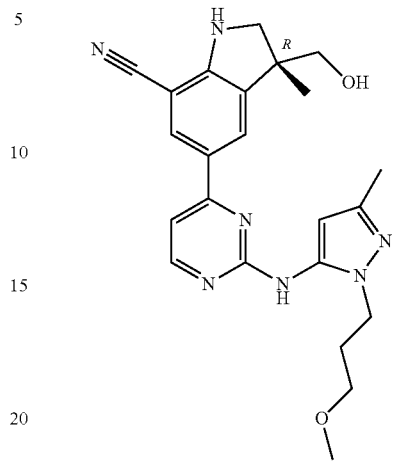

This reaction was done twice on the same quantities of intermediate 117 (12 g, 21.91 mmol). A mixture of intermediate 117 (12.00 g, 21.9 mmol) and TBAF (1M in THF) (48.19 mL, 48.19 mmol) in Me-THF (231.5 mL) was stirred at rt for 12 h. The reaction mixtures were mixed and diluted with EtOAc and water and the layers were separated. The organic layer was washed with brine, dried over MgSO$_4$, filtered and was evaporated under reduced pressure. The residue was purified by column chromatography on silica gel (irregular SiOH, 40 m, 330 g mobile phase from 99% DCM, 1% MeOH, 0.1% NH$_4$OH to 97% DCM, 3% MeOH, 0.3% NH$_4$OH). The pure fractions were combined and the solvent was evaporated. The residue (12.900 g) was crystallized with CH$_3$CN to give 11.565 g of compound 49 (60% yield). M.P=164° C. (K).

Preparation of Compound 107

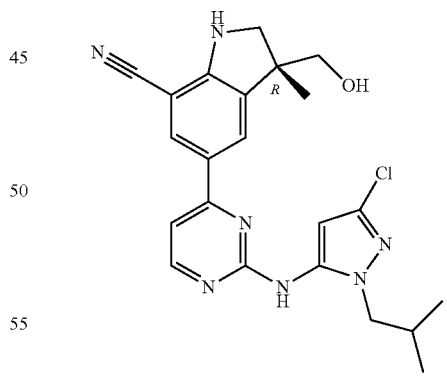

To a solution of intermediate 291 (2.86 g, 5.18 mmol) in Me-THF (60 mL) was added TBAF (1M in THF) (5.95 mL, 5.95 mmol) and the mixture was stirred at rt overnight and combined with another batch (from 270 mg of intermediate 291). The residue was purified by column chromatography on silica gel (irregular SiOH, 15-40 m, 120 g, dry load on Celite®, mobile phase: DCM/MeOH (aq. NH$_3$ 5%), gradient from 100:0 to 90:10). The fractions containing the product were combined and evaporated to dryness. The residue (1480 mg) was taken up with water, triturated and sonicated at 45° C. for 1 h. The mixture was then filtered on a glass frit and the resulting solid was then washed twice with Et₂O, collected and dried under reduced pressure at 50° C. for 16 h to give 1.23 g of compound 107 (54% yield, white solid).

Preparation of Compound 113

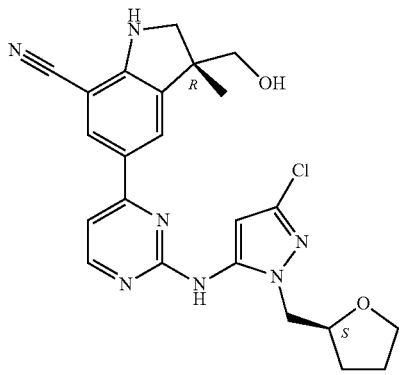

A mixture of intermediate 314 (425.00 mg, 0.73 mmol) and TBAF (1M in THF) (0.81 mL, 0.81 mmol) in dry Me-THF (10 mL) was stirred at rt for 17 h. The reaction mixture was diluted with EtOAc and washed with water. The organic layer was dried over MgSO₄, filtered and evaporated under reduced pressure. The residue was purified by column chromatography on silica gel (irregular SiOH, 15-40 m, 24 g, liquid injection in DCM, mobile phase: DCM/iPrOH, gradient from 100:0 to 90:10). The fractions containing the product were combined and evaporated to dryness. The residue (247 mg, yellow solid) was dried at 50° C. under reduced pressure for 17 h to give 205 mg of a yellow powder. This residue was dried again at 50° C. under reduced pressure for 72 h. Then, it was solubilized in MeOH (1 mL), extended with water (8 mL) and freeze-dried to afford 164 mg of compound 113 (48% yield, white fluffy solid).

Preparation of Compound 114

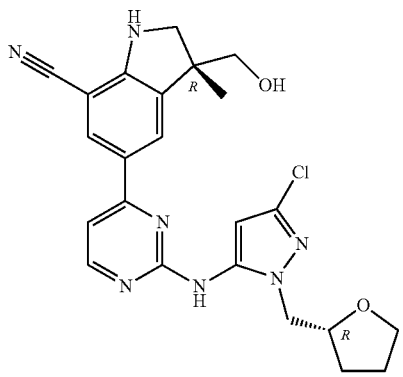

A mixture of intermediate 318 (511.00 mg, 0.88 mmol) and TBAF (1M in THF) (0.97 mL, 0.97 mmol) in Me-THF (12.5 mL) was stirred at rt for 17 h. The reaction mixture was diluted with DCM and washed with water. The organic layer was dried over MgSO₄, filtered, and the solvent was removed under reduced pressure. The residue was purified by column chromatography on silica gel (irregular SiOH, 15-40 m, 24 g, liquid injection in DCM, mobile phase: DCM/MeOH, gradient from 100:0 to 90:10). The fractions containing the product were combined and evaporated to dryness. The residue (275 mg, yellow oil) was purified by reverse phase (stationary phase: X-Bridge-C18, 10 m, 30×150 mm, mobile phase gradient: from 65% aq. NH₄HCO₃ (0.2%), 35% CH₃CN to 25% aq. NH₄HCO₃ (0.2%), 75% CH₃CN). The fractions containing the product were combined and evaporated to dryness. The residue (173 mg, pale yellow residue) was solubilized in MeOH (1 mL), extended with water (8 mL) and freeze-dried to afford 153 mg of compound 114 (37% yield, white fluffy solid).

Preparation of Compound 118

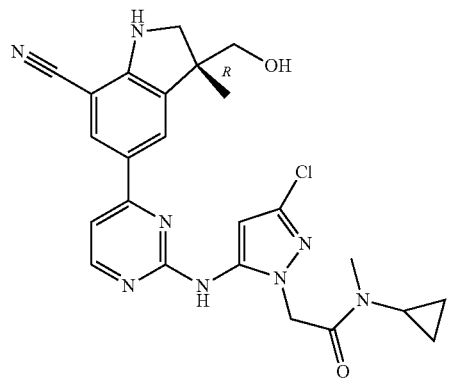

A solution of intermediate 334 (209.00 mg, 0.34 mmol) in Me-THF (4 mL) was treated with TBAF (1M in THF) (0.38 mL, 0.38 mmol) and stirred at rt for 17 h. Celite® was added and the crude mixture was evaporated in vacuo to give a dry load which was purified by column chromatography on silica gel (irregular SiOH, 15-40 m, 40 g, mobile phase gradient: from DCM 98%, MeOH (+5% aq. NH₃) 2% to DCM 90%, MeOH (+5% aq. NH₃) 10%). The fractions containing the product were combined and evaporated to dryness. The residue was recrystallized from EtOH. After cooling down to rt, the mixture was filtered on a glass frit and the solid was washed with Et₂O, collected and dried in vacuo. This residue (102 mg, white solid) was warmed in EtOH (mainly insoluble) and sonicated during 15 min. The mixture was evaporated in vacuo to give a solid which was dried in vacuo to afford 90 mg of compound 118 (53% yield, off-white solid).

Preparation of Compound 120

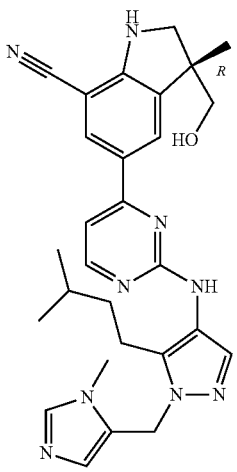

A mixture of intermediate 344 (260.00 mg, 0.41 mmol) and TBAF (1M in THF) (0.62 mL, 0.62 mmol) in Me-THF (6.7 mL) was stirred for 12 h. The resulting mixture was directly purified (injection of the solution) by column chromatography on silica gel (stationary phase: irregular SiOH, 15-40 µm, 80 g, mobile phase: gradient from 100% DCM to 91% DCM, 9% MeOH, 0.1% NH$_4$OH). The fractions containing the product were combined and the solvent was evaporated. The residue was crystallized from CH$_3$CN to give 143 mg of compound 120 (67% yield).

Preparation of Compound 132

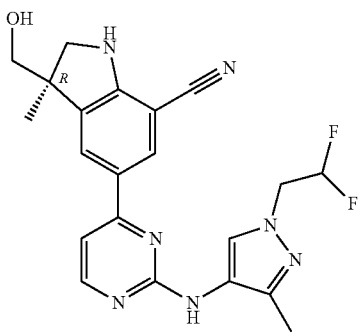

A mixture of intermediate 393 (582.00 mg, 0.98 mmol) and TBAF (1M in THF) (1.07 mL, 1.07 mmol) in Me-THF (14 mL) was stirred at rt for 17 h. The reaction mixture was diluted with DCM and washed with water. The organic layer was dried over MgSO$_4$, filtered, and the solvent was removed under reduced pressure. The residue was purified by column chromatography on silica gel (irregular SiOH, 15-40 m, 40 g, liquid injection in DCM, mobile phase gradient: from DCM 100% to 90%, MeOH (+aq. NH$_3$ 5%) 10%). The fractions containing the product were combined and evaporated to dryness. The residue (318 mg, brown residue) was purified by reverse phase (stationary phase: YMC-actus Triart-C18, 10 m, 30×150 mm, mobile phase gradient: from 75% aq. NH$_4$HCO$_3$ (0.2%), 25% CH$_3$CN to 35% aq. NH$_4$HCO$_3$ (0.2%), 65% CH$_3$CN). The fractions containing the product were combined and evaporated to dryness. The residue (275 mg, yellow oil) was solubilized in MeOH (1 mL), extended with water (8 mL) and freeze-dried to afford 246 mg of compound 132 (52% yield, white fluffy solid).

Preparation of Compound 145

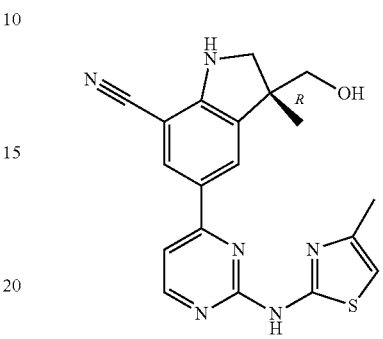

A solution of intermediate 443 (138.00 mg, 0.28 mmol) in Me-THF (5 mL) was treated with TBAF (1M in THF) (0.308 mL, 0.31 mmol) and stirred at rt for 17 h. Celite® was added and the crude mixture was evaporated in vacuo. The residue was purified by column chromatography on silica gel (irregular SiOH, 15-40 m, 40 g, mobile phase gradient: from DCM 98%, MeOH (+5% aq. NH$_3$) 2% to DCM 90%, MeOH (+5% aq. NH3) 10%). The fractions containing the product were combined and evaporated to dryness. The solid was recrystallized from EtOH. After cooling down to rt, the supernatent was removed with a pipette. The solid was triturated in Et$_2$O. The supernatant was removed with a pipette and the solid was dried in vacuo to afford 53 mg of compound 145 (50% yield, pale yellow solid).

Preparation of Compound 156

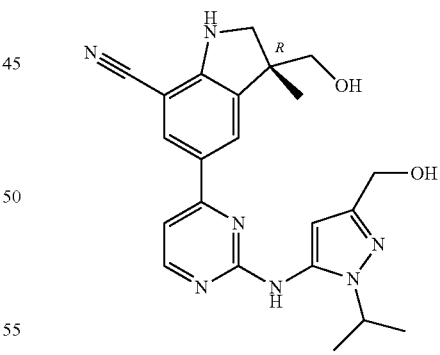

A mixture of intermediate 478 (271.00 mg, 0.51 mmol) and TBAF (1 M in THF) (1.00 mL, 1 mmol) in Me-THF (7 mL) was stirred at rt for 4 h. The reaction mixture was concentrated then directly purified by column chromatography on silica gel (irregular SiOH, 15-40 µm, 120 g, liquid injection (Me-THF/DCM), mobile phase gradient: DCM/(MeOH/10% aq. NH$_3$) from 100:0 to 90:10 in 10 CV). The fractions containing the product were combined and evaporated to dryness to give 192 mg of compound 156 (90% yield, white solid).

Preparation of Compound 164

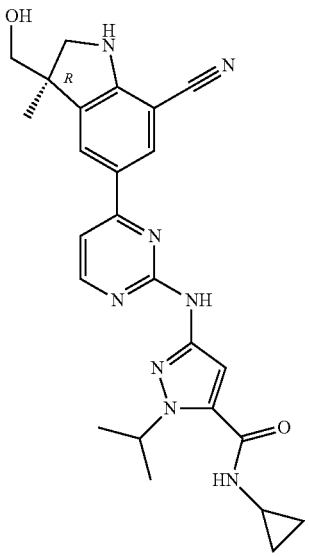

TBAF (1M in THF) (1.00 mL, 1.00 mmol) was added to a solution of intermediate 516 (0.40 g, 0.69 mmol) in Me-THF (5 mL) and this reaction was stirred overnight at rt. This mixture was poured onto water and a 10% aqueous solution of $K_2CO_3$. This mixture was extracted twice with EtOAc. The organic layer was decanted and the solvent was evaporated until dryness. The residue was purified by column chromatography on silica gel (irregular SiOH, 45 μm, 40 g, mobile phase gradient from: 98% DCM, 2% MeOH (+10% $NH_4OH$) to 92% DCM, 8% MeOH (+10% $NH_4OH$)). The pure fractions were collected and the solvent was evaporated until dryness. The residue was taken up into $CH_3CN$, triturated and the precipitate was filtered and dried until dryness to give: 224 mg of compound 164 (69% yield).

Preparation of Compound 180

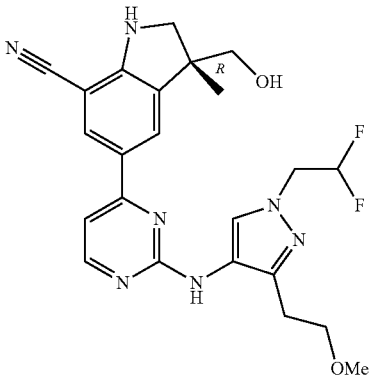

At room temperature, TBAF (1M in THF) (9.00 mL; 9.00 mmol) was added to a solution of intermediate 572 (3.15 g; 5.40 mmol) in THF (50 mL). This reaction was stirred at room temperature for 1 hour. Water and a 10% aqueous solution of $K_2CO_3$ were added and this mixture was extracted twice with EtOAc. The organic layer was mixed, dried over $MgSO_4$, filtered and the solvent was evaporated until dryness. The crude was purified by silica gel chromatography (Irregular SiOH 15-40 m 120 g, mobile phase Gradient from: 99% DCM, 1% MeOH, 0.1% $NH_4OH$ to 93% DCM, 7% MeOH, 0.7% $NH_4OH$). The pure fractions were collected and the solvent was evaporated until dryness to give 1.71 g of compound 180 (67% yield). This quantity of compound 180 was mixed with 510 mg of another batch (obtained from a reaction performed on 710 mg of intermediate 572), taken up into a small amount of ACN, totally dissolved with a hot bath (60° C.) and then, triturated. The solution was cooled to room temperature and a crystalline product appeared after 1 night. This solid was triturated, filtered, washed once with cold ACN and dried until dryness (1 h and 20 min) under vacuum (70° C.) to give 1.22 g of fraction A of compound 180 (MP: 131° C., DSC).

The filtrate was evaporated until dryness and the resulting product was taken up into ACN, totally dissolved, and triturated (initiating crystallization with some crystal coming from fraction A). After several minutes the product crystallized. A small amount of cold isopropylic ether was added and this cristal product was filtered, washed once with cold isopropylic ether then dried until dryness (70° C. under vacuum) to give after 40 minutes 0.67 g of fraction B of compound 180. Fraction B was taken up into ACN, totally solubilized with a hot bath (60° C.) then cooled to room temperature overnight. The cristal product was filtered, washed once with cold isopropylic ether and dried until dryness (70° C. under vacuum) to give 501 mg of fraction B of compound 180 (MP: 150° C., DSC).

Preparation of Compound 183

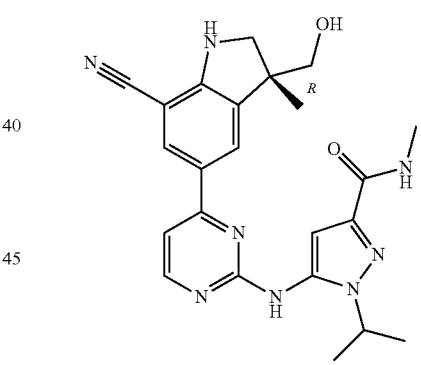

TBAF (1M in THF) (8.00 mL 8.00 mmol) was added slowly to a solution of intermediate 581 (2.44 g; 4.35 mmol) in tetrahydrofurane (40.00 mL) This reaction was stirred at room temperature for 3 hours and 40 minutes and was purified (without treatment) by silica gel chromatography (Irregular SiOH 15-40 m 220 g, mobile phase Gradient from: 100% DCM to 93% DCM, 7% MeOH, 0.7% $NH_4OH$). The pure fractions were collected and the solvent was evaporated until dryness to give 1.7 g (88%) of compound 183.

This material was combined with another batch (1.74 g) of compound 183 obtained from a reaction performed on 2.41 g of intermediate 581 to give 3.44 g of compound 183 which were totally dissolved in ACN (57 mL) and MeOH (34 mL) at 90° C.

This solution was cooled down to room temperature and let for crystallization overnight. The precipitate was filtered and dried C under vacuum until dryness at 900 during 3 hours to give 1.25 g (36%) of compound 183. M.P.=256° C. (DSC).

The filtrate was evaporated until dryness and the residue (1.72 g) was dissolved totally in MeOH (38 mL) at 70° C. (bath oil). The solution was cooled down to room temperature overnight. The precipitate was filtered and dried for 2 hours and 30 minutes at 90° C. under vacuum to give 0.77 g (22%) of compound 183 (not crystalline). This material (0.77 g) was dissolved in a mixture of ACN (12 mL) and MeOH (7 mL) at 95° C. (bath oil). The solution was cooled down to room temperature and let for crystallization overnight. The precipitate was filtered to give 303 mg (9%) of compound 183. M.P.=255° C. (DSC).

The compounds in the Table below were prepared by using an analogous method than the one used for the preparation of compound 1 starting from the respective starting materials. The most relevant minor deviations to the referenced method are indicated as additional information in the column 'Yield (%)'.

| Compound number | Structure | Mass (mg) | Yield (%) |
| --- | --- | --- | --- |
| Compound 4 | 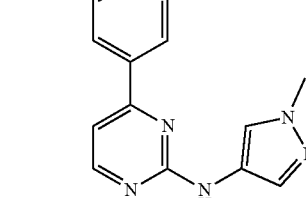<br>From intermediate 14 | 99 | 79<br>Procedure with 1.1 equiv. of TBAF |
| Compound 7 | 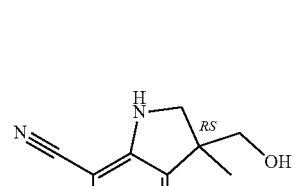<br>From intermediate 22 | 74<br>white solid | 67<br>Procedure with 1.1 equiv. of TBAF |
| Compound 11 | 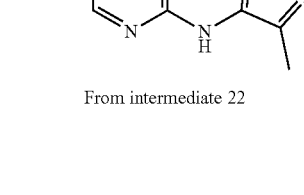<br>From intermediate 30 | 128<br>off-white solid | 19<br>Procedure with 2.2 equiv. of TBAF |

-continued

| Compound number | Structure | Mass (mg) | Yield (%) |
|---|---|---|---|
| Compound 12 | From intermediate 34 | 70 | 28 Procedure with 3 equiv. of TBAF |
| Compound 13 | From intermediate 35 | 67 pale yellow solid | 34 Procedure with 1.1 equiv. of TBAF |
| Compound 14 | From intermediate 37 | 34 off-white solid | 10 Procedure with 1.3 equiv. of TBAF |

-continued
| Compound number | Structure | Mass (mg) | Yield (%) |
|---|---|---|---|
| Compound 16 | 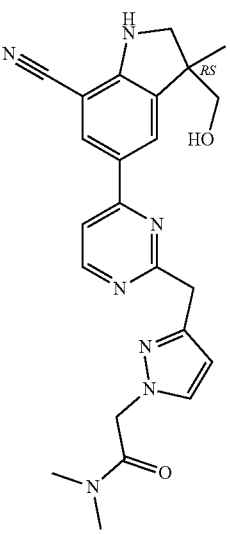 From intermediate 41 | 161 | 54 Procedure with 1.9 equiv. of TBAF |
| Compound 17 | From intermediate 43 | 140 | 53 Procedure with 2 equiv. of TBAF |
| Compound 18 | 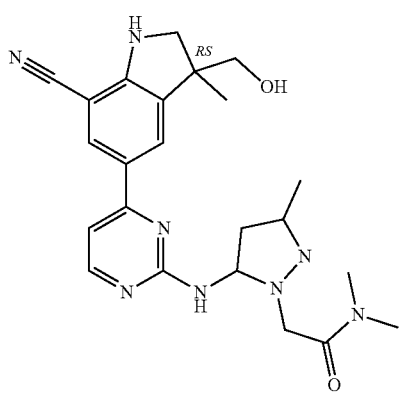 From intermediate 45 | 72 yellow solid | 43 Procedure with 2.2 equiv. of TBAF |

-continued
| Compound number | Structure | Mass (mg) | Yield (%) |
|---|---|---|---|
| Compound 20 | 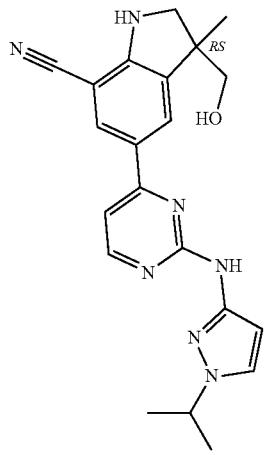<br>From intermediate 49 | 174 | 97<br>Procedure with 1.5 equiv. of TBAF |
| Compound 21 | 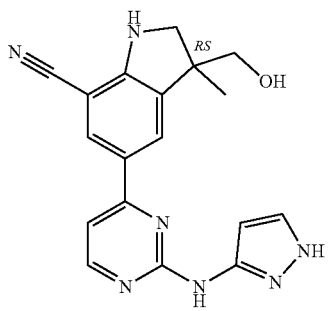<br>From intermediate 51 | 45<br>pale yellow solid | 23<br>Procedure with 1.1 equiv. of TBAF |
| Compound 22 | 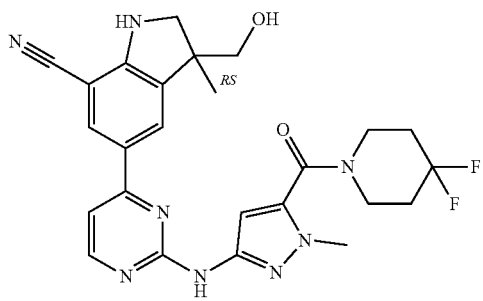<br>From intermediate 55 | 37 | 42<br>Procedure with 1.5 equiv. of TBAF |

-continued

| Compound number | Structure | Mass (mg) | Yield (%) |
|---|---|---|---|
| Compound 23 | From intermediate 59 | 89 | 33 Procedure with 1.5 equiv. of TBAF |
| Compound 24 | From intermediate 61 | 107 | 48 Procedure with 1.5 equiv. of TBAF |
| Compound 25 | From intermediate 64 | 62 | 62 Procedure with 1.5 equiv. of TBAF |

-continued

| Compound number | Structure | Mass (mg) | Yield (%) |
|---|---|---|---|
| Compound 27 | From intermediate 69 | 114 | 65 Procedure with 1.7 equiv. of TBAF |
| Compound 28 | From intermediate 72 | 42 | 46 Procedure with 1.5 equiv. of TBAF |
| Compound 29 | From intermediate 74 | 123 | 45 Procedure with 1.5 equiv. of TBAF |

-continued
| Compound number | Structure | Mass (mg) | Yield (%) |
|---|---|---|---|
| Compound 30 | 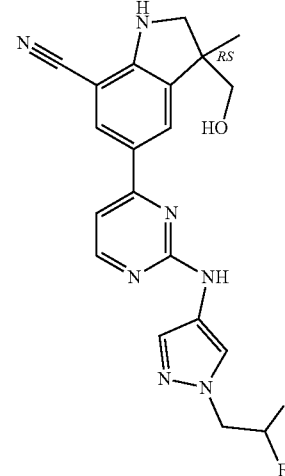<br>From intermediate 76 | 12 | 37<br>Procedure with 1.5 equiv. of TBAF |
| Compound 31 | 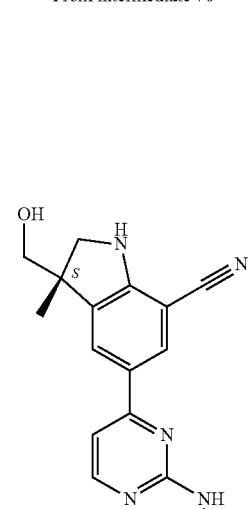<br>From intermediate 78 | 45 | 52<br>Procedure with 1.5 equiv. of TBAF |
| Compound 32 | 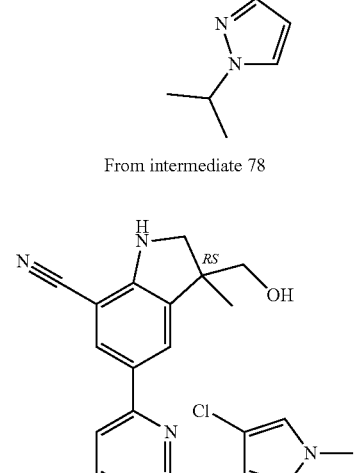<br>From intermediate 80 | 94 | 45<br>Procedure with 1.1 equiv. of TBAF |

-continued

| Compound number | Structure | Mass (mg) | Yield (%) |
|---|---|---|---|
| Compound 33 (obtained as a mixture of 2 diastereoisomers) | From intermediate 82 | 69 | 48 Procedure with 1.5 equiv. of TBAF |
| Compound 34 | From intermediate 8 | 1250 | 63 Procedure with 1.1 equiv. of TBAF |
| Compound 35 | From intermediate 86 | 55 | 28 Procedure with 1.5 equiv. of TBAF |

-continued

| Compound number | Structure | Mass (mg) | Yield (%) |
|---|---|---|---|
| Compound 36 | From intermediate 88 | 27 | 33 Procedure with 1.5 equiv. of TBAF |
| Compound 37 | From intermediate 90 | 59 | 44 Procedure with 1.1 equiv. of TBAF |
| Compound 38 | From intermediate 92 | 43 | 26 Procedure with 1.1 equiv. of TBAF |
| Compound 39 | From intermediate 94 | 186 | 55 Procedure with 1.1 equiv. of TBAF |

-continued

| Compound number | Structure | Mass (mg) | Yield (%) |
|---|---|---|---|
| Compound 40 | From intermediate 96 | 160 | 69<br>Procedure with 1.1 equiv. of TBAF |
| Compound 41 | From intermediate 98 | 44<br>orange solid | 43<br>Procedure with 1.1 equiv. of TBAF |
| Compound 43 | From intermediate 102 | 128 | 75<br>Procedure with 1.5 equiv. of TBAF |
| Compound 44 | From intermediate 105 | 45 | 27<br>Procedure with 1.5 equiv. of TBAF |

-continued

| Compound number | Structure | Mass (mg) | Yield (%) |
|---|---|---|---|
| Compound 45 | From intermediate 107 | 185 | 67 Procedure with 1.5 equiv. of TBAF |
| Compound 46 | From intermediate 109 | 490 | 38 Procedure with 1.5 equiv. of TBAF |
| Compound 47 | From intermediate 111 | 243 | 41 Procedure with 2.2 equiv. of TBAF |

-continued
| Compound number | Structure | Mass (mg) | Yield (%) |
|---|---|---|---|
| Compound 48 | 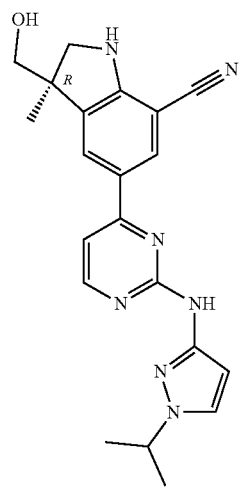<br>From intermediate 113 | 51 | 45<br>Procedure with 1.5 equiv. of TBAF |
| Compound 50 | 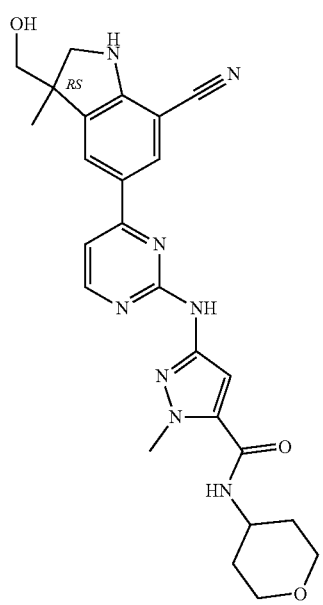<br>From intermediate 120 | 35 | 37<br>Procedure with 1.5 equiv. of TBAF |

-continued
| Compound number | Structure | Mass (mg) | Yield (%) |
|---|---|---|---|
| Compound 51 | 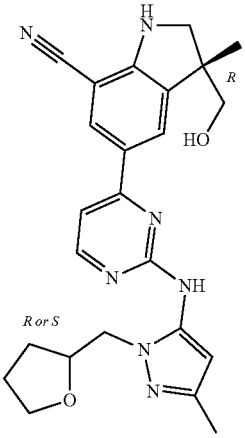<br>From intermediate 123 | 100 | 16<br>Procedure with 1.5 equiv. of TBAF |
| Compound 52 | 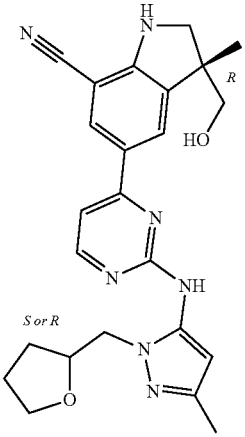<br>From intermediate 123 | 97 | 15<br>Procedure with 1.5 equiv. of TBAF |
| Compound 53 | 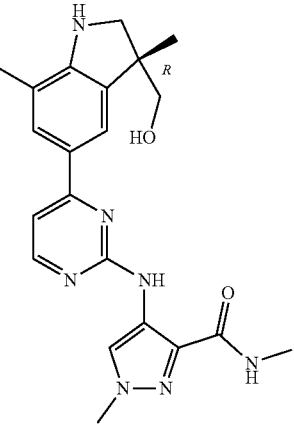<br>From intermediate 125 | 145 | 68<br>Procedure with 1.5 equiv. of TBAF |

-continued

| Compound number | Structure | Mass (mg) | Yield (%) |
|---|---|---|---|
| Compound 54 | From intermediate 127 | 153 | 32 Procedure with 2.2 equiv. of TBAF |
| Compound 55 | From intermediate 129 | 54 | 40 Procedure with 2.2 equiv. of TBAF |
| Compound 56 | From intermediate 131 | 9 | 16 Procedure with 1 equiv. of TBAF |

| Compound number | Structure | Mass (mg) | Yield (%) |
|---|---|---|---|
| Compound 57 | 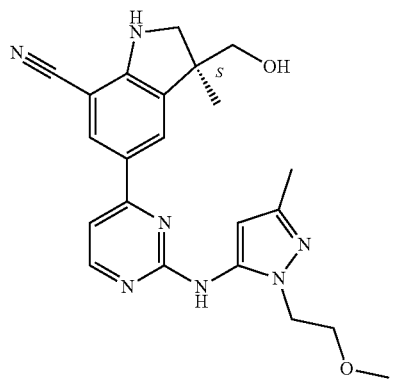<br>From intermediate 133 | 150 | 30<br>Procedure with 1.5 equiv. of TBAF |
| Compound 58 | 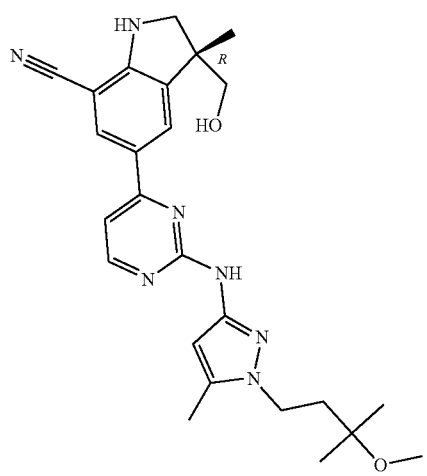<br>From intermediate 137 | 150 | 51<br>Procedure with 1.5 equiv. of TBAF |
| Compound 59 | 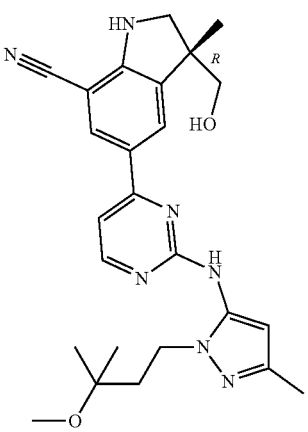<br>From intermediate 140 | 130 | 71<br>Procedure with 1.5 equiv. of TBAF |

-continued

| Compound number | Structure | Mass (mg) | Yield (%) |
|---|---|---|---|
| Compound 60 | From intermediate 144 | 81 | 34<br>Procedure with 2.2 equiv. of TBAF |
| Compound 61 | From intermediate 147 | 113 | 65<br>Procedure with 2.2 equiv. of TBAF |
| Compound 62 | From intermediate 149 | 58 | 43<br>Procedure with 2.2 equiv. of TBAF |

-continued
| Compound number | Structure | Mass (mg) | Yield (%) |
|---|---|---|---|
| Compound 63 | 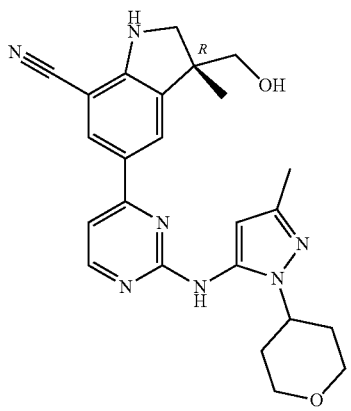<br>From intermediate 151 | 131 | 46<br>Procedure with 2.2 equiv. of TBAF |
| Compound 64 | 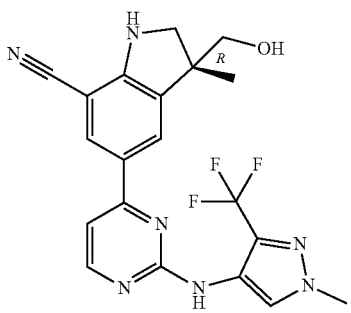<br>From intermediate 153 | 71 | 50<br>Procedure with 1.5 equiv. of TBAF |
| Compound 65 | 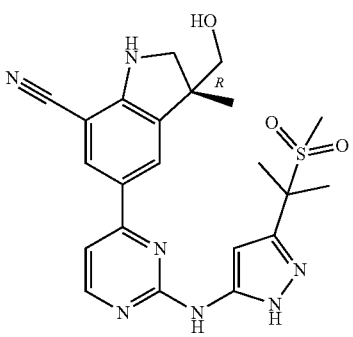<br>From intermediate 155 | 25 | 48<br>Procedure with 1.5 equiv. of TBAF |

-continued

| Compound number | Structure | Mass (mg) | Yield (%) |
|---|---|---|---|
| Compound 66 | From intermediate 158 | 111 white foam | 55 Procedure with 1.5 equiv. of TBAF |
| Compound 67 | From intermediate 161 | 203 | 68 Procedure with 1.6 equiv. of TBAF |
| Compound 68 | From intermediate 165 | 78 | 24 Procedure with 2.2 equiv. of TBAF |

-continued
| Compound number | Structure | Mass (mg) | Yield (%) |
|---|---|---|---|
| Compound 69 | 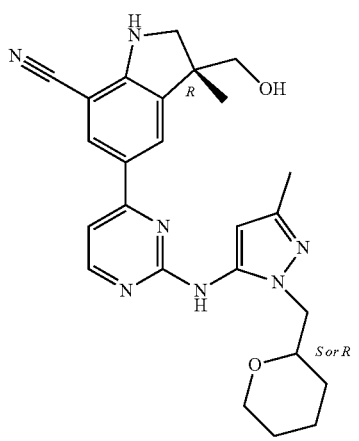<br>From intermediate 165 | 77 | 24<br>Procedure with 2.2 equiv. of TBAF |
| Compound 70 | 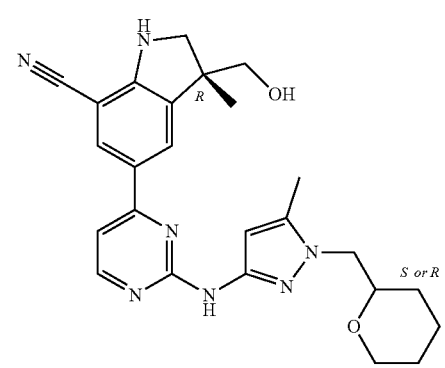<br>From intermediate 167 | 95 | 28<br>Procedure with 2.2 equiv. of TBAF |
| Compound 71 | 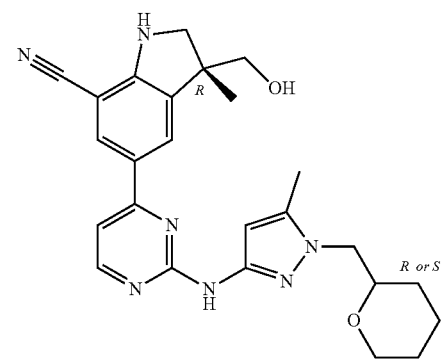<br>From intermediate 167 | 106 | 31<br>Procedure with 2.2 equiv. of TBAF |

-continued

| Compound number | Structure | Mass (mg) | Yield (%) |
|---|---|---|---|
| Compound 72 | From intermediate 169 | 31 | 35<br>Procedure with 1.5 equiv. of TBAF |
| Compound 73 | From intermediate 173 | 59 | 39<br>Procedure with 1.5 equiv. of TBAF |
| Compound 74 | From intermediate 175 | 65 | 58<br>Procedure with 1.5 equiv. of TBAF |

-continued
| Compound number | Structure | Mass (mg) | Yield (%) |
|---|---|---|---|
| Compound 75 | 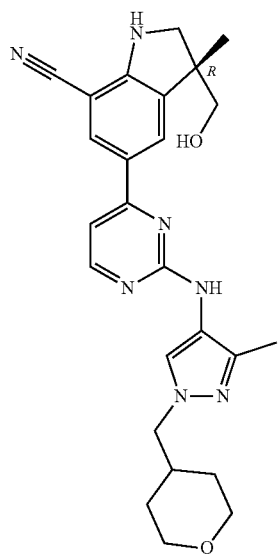<br>From intermediate 179 | 92 | 56<br>Procedure with 1.5 equiv. of TBAF |
| Compound 76 | 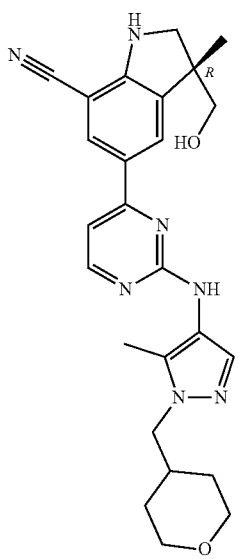<br>From intermediate 181 | 42 | 29<br>Procedure with 1.5 equiv. of TBAF |

-continued
| Compound number | Structure | Mass (mg) | Yield (%) |
|---|---|---|---|
| Compound 77 | 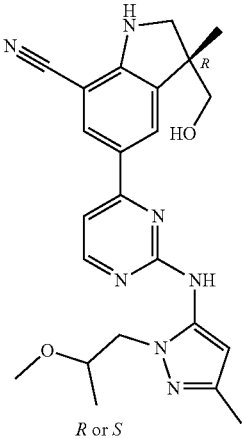<br>R or S<br>From intermediate 185 | 57 | 28<br>Procedure with 1.5 equiv. of TBAF |
| Compound 78 | 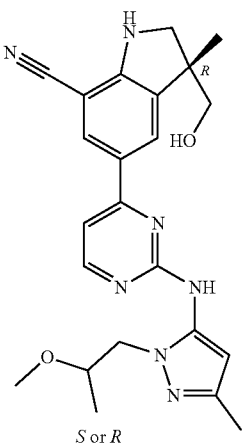<br>S or R<br>From intermediate 185 | 58 | 28<br>Procedure with 1.5 equiv. of TBAF |
| Compound 79 | 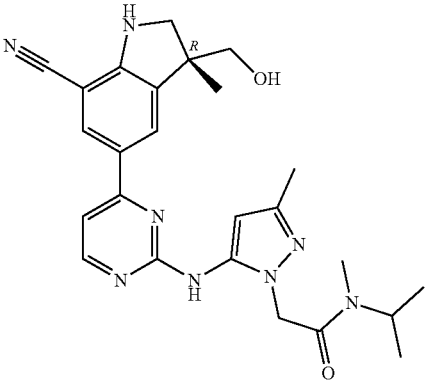<br>From intermediate 188 | 58 | 48<br>Procedure with 1.1 equiv. of TBAF |

-continued

| Compound number | Structure | Mass (mg) | Yield (%) |
|---|---|---|---|
| Compound 80 | From intermediate 190 | 52 | 52 Procedure with 1.1 equiv. of TBAF |
| Compound 81 | From intermediate 194 | 58 | 33 Procedure with 2.2 equiv. of TBAF |
| Compound 82 | From intermediate 194 | 55 | 32 Procedure with 2.2 equiv. of TBAF |

-continued

| Compound number | Structure | Mass (mg) | Yield (%) |
|---|---|---|---|
| Compound 83 | From intermediate 198 | 77 orange powder | 36 Procedure with 1.1 equiv. of TBAF |
| Compound 84 | From intermediate 202 | 66 | 11 Procedure with 1.5 equiv. of TBAF |
| Compound 85 | From intermediate 202 | 66 | 11 Procedure with 1.5 equiv. of TBAF |

-continued

| Compound number | Structure | Mass (mg) | Yield (%) |
|---|---|---|---|
| Compound 86 | For intermediate 204 | 110 | 90 Procedure with 1.8 equiv. of TBAF |
| Compound 87 | From intermediate 206 | 26 pink solid | 19 Procedure with 1.1 equiv. of TBAF |
| Compound 88 | From intermediate 208 | 105 beige solid | 72 Procedure with 1.1 equiv. of TBAF |

-continued

| Compound number | Structure | Mass (mg) | Yield (%) |
|---|---|---|---|
| Compound 89 | From intermediate 210 | 85 pink solid | 63 Procedure with 1.1 equiv. of TBAF |
| Compound 90 | From intermediate 216 | 49 | 36 Procedure with 1.5 equiv. of TBAF |
| Compound 91 | From intermediate 218 | 68 | 35 Procedure with 1.5 equiv. of TBAF |

-continued

| Compound number | Structure | Mass (mg) | Yield (%) |
|---|---|---|---|
| Compound 92 | From intermediate 222 | 1230 | 78 Procedure with 1.5 equiv. of TBAF |
| Compound 93 | From intermediate 227 | 321 | 38 Procedure with 1.5 equiv. of TBAF |
| Compound 94 (obtained as a mixture of 2 diastereoisomers) | From intermediate 231 | 60 | 17 Procedure with 2.2 equiv. of TBAF |

-continued

| Compound number | Structure | Mass (mg) | Yield (%) |
|---|---|---|---|
| Compound 95 | From intermediate 235 | 124 | 62 Procedure with 1.5 equiv. of TBAF |
| Compound 96 | From intermediate 238 | 813 | 67 Procedure with 1.6 equiv. of TBAF |
| Compound 97 | From intermediate 244 | 1500 | 68 Procedure with 1.5 equiv. of TBAF |

-continued
| Compound number | Structure | Mass (mg) | Yield (%) |
|---|---|---|---|
| Compound 98 | 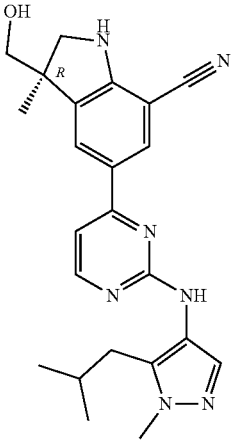<br>From intermediate 249 | 1000 | 62<br>Procedure with 1.6 equiv. of TBAF |
| Compound 99 | 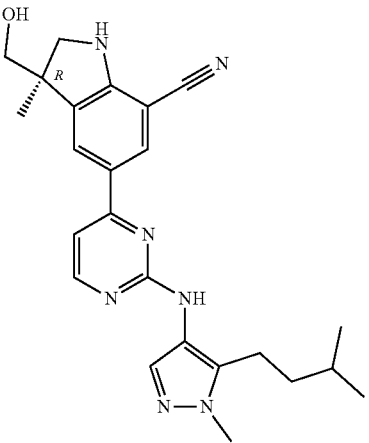<br>From intermediate 258 | 15 | 63<br>Procedure with 1.6 equiv. of TBAF |
| Compound 100 | 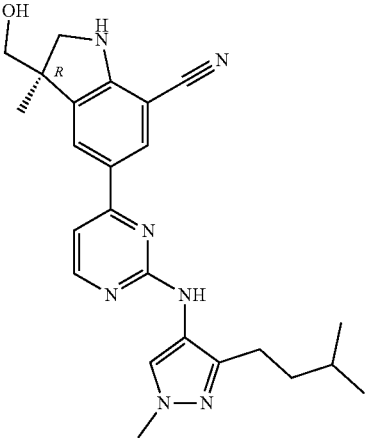<br>From intermediate 260 | 36 | 88<br>Procedure with 2.5 equiv. of TBAF |

-continued

| Compound number | Structure | Mass (mg) | Yield (%) |
|---|---|---|---|
| Compound 101 | (From intermediate 267) | 50 | 32<br>Procedure with 1.7 equiv of TBAF |
| Compound 102 | (From intermediate 267) | 20 | 13<br>Procedure with 1.7 equiv of TBAF |
| Compound 104 | (From intermediate 278) | 327 | 57<br>Procedure with 2.2 equiv. of TBAF |

-continued

| Compound number | Structure | Mass (mg) | Yield (%) |
|---|---|---|---|
| Compound 105 | From intermediate 281 | 312 | 36 Procedure with 2.2 equiv. of TBAF |
| Compound 108 | From intermediate 295 | 137 | 56 Procedure with 2.2 equiv. of TBAF |
| Compound 109 | From intermediate 298 | 103 | 54 Procedure with 2.2 equiv. of TBAF |

-continued

| Compound number | Structure | Mass (mg) | Yield (%) |
|---|---|---|---|
| Compound 111 | From intermediate 306 | 127 | 34 (over 2 steps) Procedure with 1 equiv. of TBAF |
| Compound 112 | From intermediate 310 | 218 | 51 Procedure with 1.1 equiv. of TBAF |
| Compound 115 | From intermediate 322 | 12 off-white solid | 13 Procedure with 1.1 equiv. of TBAF |

-continued

| Compound number | Structure | Mass (mg) | Yield (%) |
|---|---|---|---|
| Compound 116 | From intermediate 326 | 112 off-white solid | 57 Procedure 1.1 equiv. of TBAF |
| Compound 117 | From intermediate 330 | 205 | 60 Procedure with 1.5 equiv. of TBAF |
| Compound 119 | From intermediate 340 | 40 white fluffy solid | 43 Procedure with 1.1 equiv. of TBAF |

-continued

| Compound number | Structure | Mass (mg) | Yield (%) |
|---|---|---|---|
| Compound 121 | From intermediate 348 | 85 | 20 Procedure with 1.5 equiv. of TBAF |
| Compound 122 | Intermediate 354 | 106 | 79 Procedure with 1.5 equiv. of TBAF |
| Compound 123 | Intermediate 357 | 19 | 20 Procedure with 1.5 equiv. of TBAF |

-continued

| Compound number | Structure | Mass (mg) | Yield (%) |
|---|---|---|---|
| Compound 124 | From intermediate 361 | 56 white fluffy solid | 43 Procedure with 1.1 equiv. of TBAF |
| Compound 125 | From intermediate 365 | 114 | 33 Procedure with 2 equiv. of TBAF |
| Compound 126 | From intermediate 369 | 85 white fluffy solid | 36 Procedure with 1.1 equiv. of TBAF |

-continued
| Compound number | Structure | Mass (mg) | Yield (%) |
|---|---|---|---|
| Compound 127 | 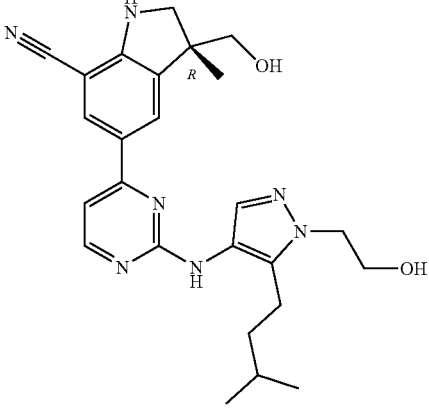<br>From intermediate 373 | 75 | 33<br>Procedure with 2 equiv. of TBAF |
| Compound 128 | 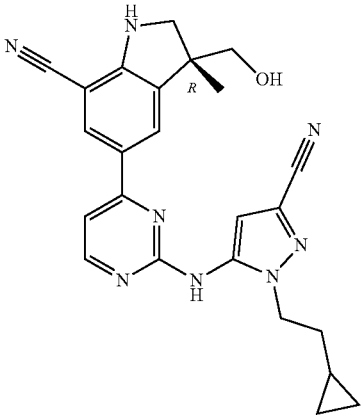<br>From intermediate 378 | 592 | 46<br>Procedure with 2 equiv. of TBAF |
| Compound 129 | 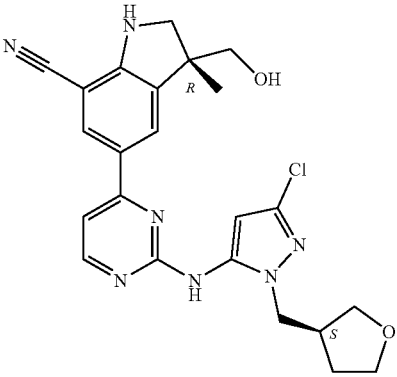<br>From intermediate 382 | 61<br>white solid | 88<br>Procedure with 2 equiv. of TBAF |

-continued
| Compound number | Structure | Mass (mg) | Yield (%) |
|---|---|---|---|
| Compound 130 | 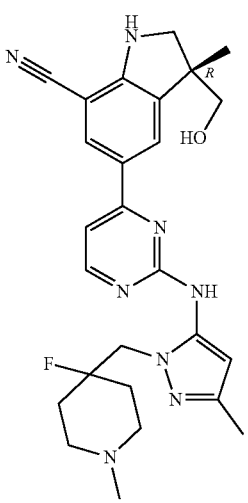<br>From intermediate 385 | 246 | 58<br>Procedure with 2 equiv. of TBAF |
| Compound 131 | 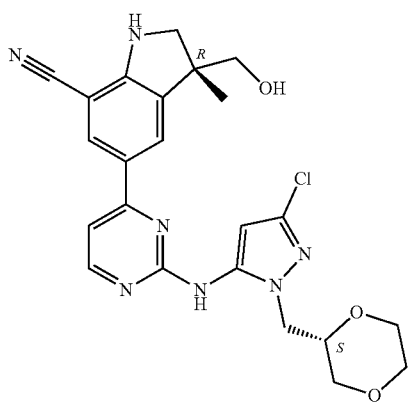<br>From intermediate 389 | 144 | 53<br>Procedure with 2 equiv. of TBAF |
| Compound 133 | From intermediate 397 | 246<br>white fluffy solid | 52<br>Procedure with 1.1 equiv. of TBAF |

-continued

| Compound number | Structure | Mass (mg) | Yield (%) |
|---|---|---|---|
| Compound 134 | From intermediate 403 | 134 yellow solid | 57 Procedure with 1.1 equiv. of TBAF |
| Compound 135 | From intermediate 406 | 88 yellow fluffy solid | 62 with 2.2 equiv. of TBAF |
| Compound 136 | From intermediate 412 | 50 | 57 Procedure with 1.5 equiv. of TBAF |

-continued

| Compound number | Structure | Mass (mg) | Yield (%) |
|---|---|---|---|
| Compound 137 | From intermediate 416 | 210 | 56<br>Procedure with 1.6 equiv. of TBAF |
| Compound 138 | From intermediate 422 | 114<br>white fluffy solid | 66<br>Procedure with 1.1 equiv. of TBAF |
| Compound 139 | From intermediate 426 | 152 | 73<br>Procedure with 2 equiv. of TBAF |

-continued

| Compound number | Structure | Mass (mg) | Yield (%) |
|---|---|---|---|
| Compound 140 | From intermediate 430 | 271 | 76 Procedure with 2 equiv. of TBAF |
| Compound 141 | From intermediate 434 | 163 | 79 Procedure with 2 equiv. of TBAF |
| Compound 143 | From intermediate 438 | 78 | 32 Procedure with 1.5 equiv. of TBAF |

-continued

| Compound number | Structure | Mass (mg) | Yield (%) |
|---|---|---|---|
| Compound 144 | From intermediate 442 | 130 | 61 Procedure with 1.5 equiv. of TBAF |
| Compound 146 | From intermediate 445 | 138 pinkish solid | 73 Procedure with 1.1 equiv. of TBAF |
| Compound 147 | From intermediate 447 | 17 off-white solid | 10 Procedure with 1.7 equiv. of TBAF and a mixture of DCM/THF (3:2, v/v) as solvent |
| Compound 148 | From intermediate 449 | 73 yellow solid | 48 Procedure with 1.8 equiv. of TBAF |

-continued

| Compound number | Structure | Mass (mg) | Yield (%) |
|---|---|---|---|
| Compound 149 | From intermediate 451 | 172 off-white solid | 54 Procedure with 1.1 equiv. of TBAF |
| Compound 150 | From intermediate 455 | 53 | 41 Procedure with 2 equiv. of TBAF |
| Compound 151 | From intermediate 459 | 274 | 76 Procedure with 2 equiv. of TBAF |

-continued

| Compound number | Structure | Mass (mg) | Yield (%) |
|---|---|---|---|
| Compound 152 | From intermediate 463 | 157 | 78 Procedure with 1.1 equiv. of TBAF |
| Compound 153 | From intermediate 467 | 176 white solid | 95 Procedure with 2.1 equiv. of TBAF |
| Compound 154 | From intermediate 470 | 164 off-white solid | 45 (over 2 steps) Procedure with 1.1 equiv. of TBAF |

-continued
| Compound number | Structure | Mass (mg) | Yield (%) |
|---|---|---|---|
| Compound 155 | 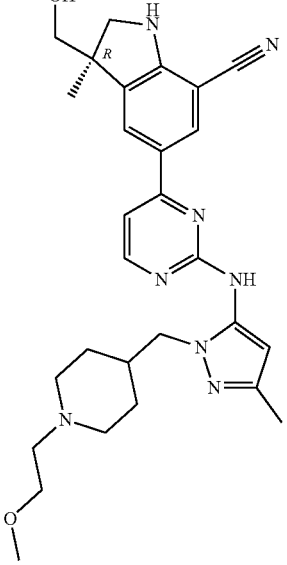<br>From intermediate 474 | 70 | 19<br>Procedure with 1.5 equiv. of TBAF |
| Compound 156 | 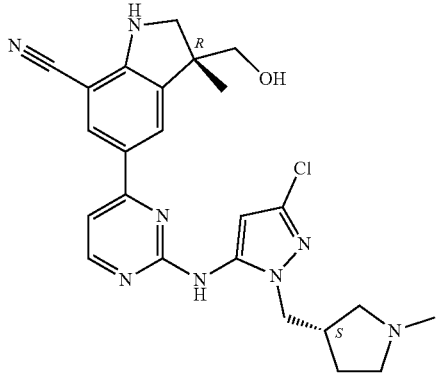<br>From intermediate 482 | 47 | 15<br>Procedure with 1.1 equiv. of TBAF |
| Compound 157 | 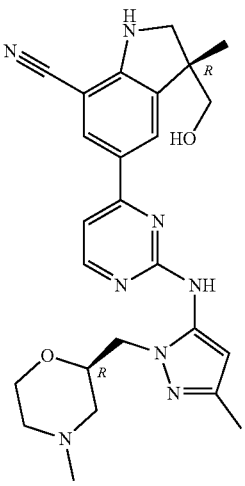<br>From intermediate 486 | 172 | 74<br>Procedure with 2.5 equiv. of TBAF |

-continued

| Compound number | Structure | Mass (mg) | Yield (%) |
|---|---|---|---|
| Compound 158 | From intermediate 494 | 179 | 33 Procedure with 2 equiv. of TBAF |
| Compound 160 | From intermediate 498 | 29 yellow fluffy solid | 47 Procedure with 1.1 equiv. of TBAF |
| Compound 161 | From intermediate 502 | 132 white solid | 53 Procedure with 2.1 equiv. of TBAF |

-continued

| Compound number | Structure | Mass (mg) | Yield (%) |
|---|---|---|---|
| Compound 162 | From intermediate 505 | 70 white fluffy-solid | 24 Procedure with 1.1 equiv. of TBAF |
| Compound 163 | From intermediate 511 | 64 | 27 Procedure with 2 equiv. of TBAF |
| Compound 165 | From intermediate 520 | 154 | 69 Procedure with 1.5 equiv. of TBAF |

-continued

| Compound number | Structure | Mass (mg) | Yield (%) |
|---|---|---|---|
| Compound 166 | From intermediate 524 | 137 | 65 Procedure with 2 equiv. of TBAF |
| Compound 167 | From intermediate 528 | 84 | 49 Procedure with 2 equiv. of TBAF |
| Compound 168 | From intermediate 532 | 27 | 25 Procedure with 2 equiv. of TBAF |

-continued

| Compound number | Structure | Mass (mg) | Yield (%) |
|---|---|---|---|
| Compound 169 | From intermediate 536 | 21 | 21 Procedure with 2 equiv. of TBAF |
| Compound 170 | From intermediate 540 | 119 | 34 Procedure with 2 equiv. of TBAF |
| Compound 171 (obtained as a mixture of 2 diastereoisomers) | From intermediate 544 | 274 | 49 Procedure with 1.5 equiv. of TBAF |

-continued

| Compound number | Structure | Mass (mg) | Yield (%) |
|---|---|---|---|
| Compound 172 | From intermediate 548 | 37 | 18 Procedure with 1.5 equiv. of TBAF |
| Compound 181 | From intermediate 573 | 106 | 61 |
| Compound 182 | From intermediate 574 | 72 | 54 Procedure with 1.5 eq. of TBAF |

-continued

| Compound number | Structure | Mass (mg) | Yield (%) |
|---|---|---|---|
| Compound 184 | From intermediate 587 | 68 | 75<br>Procedure with 2 eq of TBAF<br>Me—THF<br>3 h |
| Compound 185 | From intermediate 590 | 63 | 64<br>Procedure with 2 eq. of TBAF |
| Compound 186 | From intermediate 594 | 228 | 47<br>Procedure with 2 eq. of TBAF |

-continued

| Compound number | Structure | Mass (mg) | Yield (%) |
|---|---|---|---|
| Compound 187 | From intermediate 600 | 740 | 63<br>Procedure with 2 eq. of TBAF |
| Compound 188 | From intermediate 604 | 70 | 23<br>Procedure with 2 eq. of TBAF |
| Compound 189 | From intermediate 609 | 140 | 46<br>Procedure with 2 eq. of TBAF<br>Me—THF<br>12 h |
| Compound 190 | From intermediate 615 | 114 | 65<br>Procedure with 2 eq. of TBAF |

-continued
| Compound number | Structure | Mass (mg) | Yield (%) |
|---|---|---|---|
| Compound 191 | 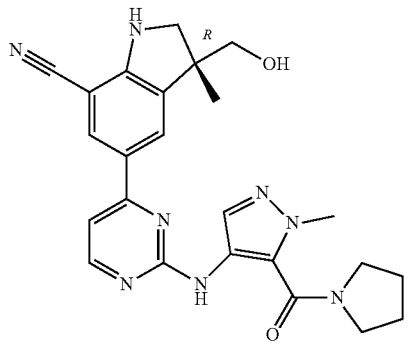<br>From intermediate 619 | 119 | 60<br>Procedure<br>with 2 eq of<br>TBAF<br>Me—THF<br>4 h |
| Compound 192 | 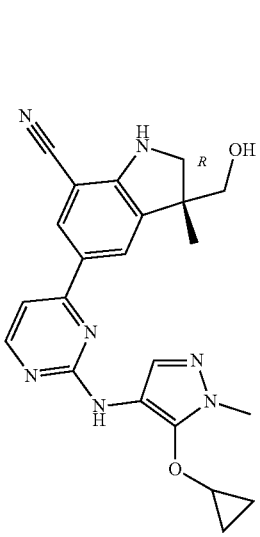<br>From intermediate 623 | 90 | 57<br>Procedure<br>with 2 eq of<br>TBAF<br>Me—THF<br>12 h |
| Compound 193 | 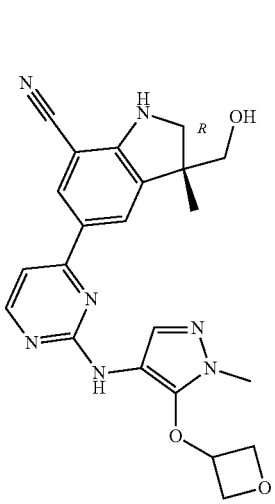<br>From intermediate 627 | 22 | 41<br>Procedure<br>with 2 eq of<br>TBAF<br>Me—THF<br>8 h |

-continued
| Compound number | Structure | Mass (mg) | Yield (%) |
|---|---|---|---|
| Compound 194 | From intermediate 631 | 217 | 44 Procedure with 2 eq of TBAF Me—THF 8 h |
| Compound 195 | 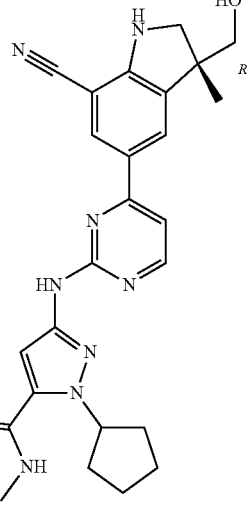 From intermediate 639 | 73 | 51 Procedure with 1.6 eq of TBAF THF 2 h |
| Compound 196 | 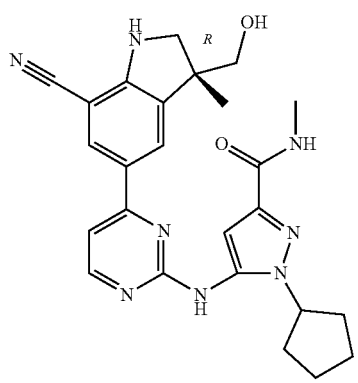 From intermediate 643 | 1850 | 55 Procedure with 2 eq of TBAF THF |

-continued
| Compound number | Structure | Mass (mg) | Yield (%) |
|---|---|---|---|
| Compound 197 | 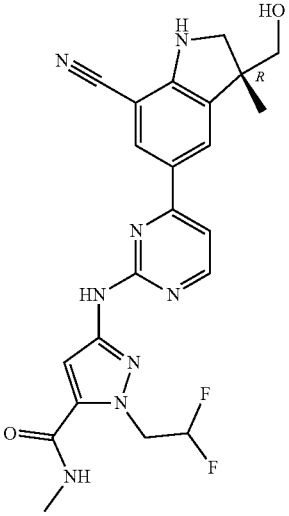<br>From intermediate 649 | 166 | 32<br>Procedure with 1.54 eq of TBAF<br>Me—THF |
| Compound 198 | 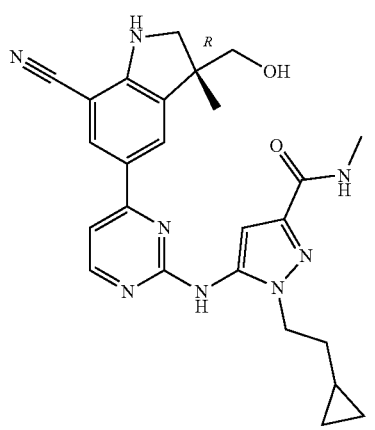<br>From intermediate 655 | 55 | 58<br>Procedure with 1.2 eq of TBAF<br>Me—THF<br>18 h |
| Compound 199 | 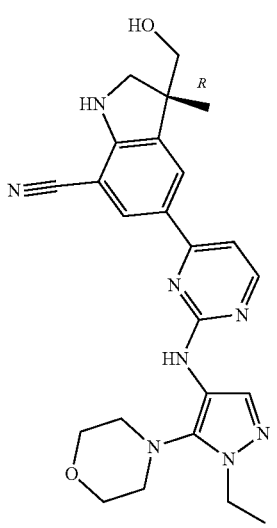<br>From intermediate 661 | 114 | 35<br>Procedure with 2 eq of TBAF<br>Me—THF<br>8 h |

-continued
| Compound number | Structure | Mass (mg) | Yield (%) |
|---|---|---|---|
| Compound 200 | 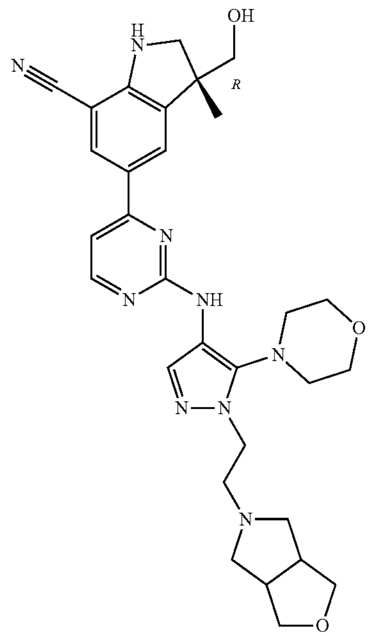 | 75 | 26 Procedure with 2 eq of TBAF Me—THF 2 h |
| | From intermediate 665 | | |
| Compound 202 | 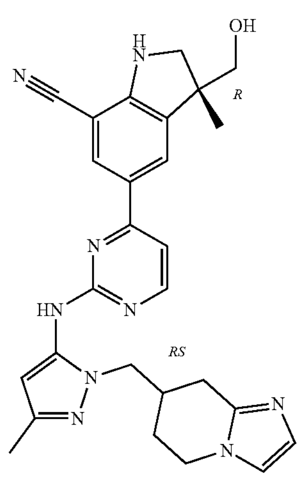 | 45 | 25 Procedure with 1.55 eq of TBAF THF 5 h |
| | 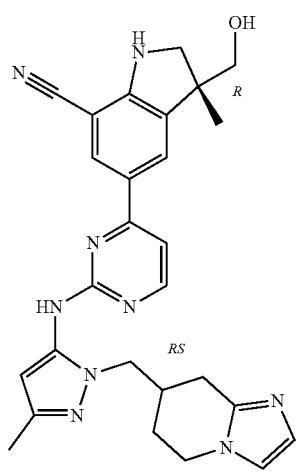<br>From intermediate 671 | | |

-continued

| Compound number | Structure | Mass (mg) | Yield (%) |
|---|---|---|---|
| Compound 203 | From intermediate 677 | 164 | 53<br>Procedure with 2 eq of TBAF<br>Me—THF<br>4 h |
| Compound 204 | From intermediate 683 | 328 | 68<br>Procedure with 1.5 eq of TBAF<br>THF<br>12 h |
| Compound 205 | From intermediate 689 | 30 | 44<br>Procedure with 1.51 eq of TBAF<br>Me—THF<br>12 h |
| Compound 206 | From intermediate 691 | 96 | 52<br>Procedure with 1.5 eq of TBAF<br>THF<br>5 h |

-continued

| Compound number | Structure | Mass (mg) | Yield (%) |
|---|---|---|---|
| Compound 207 | From intermediate 695 | 129 | 41 Procedure with 2 eq of TBAF Me—THF 8 h |
| Compound 208 | From intermediate 698 | 21 | 15 Procedure with 2 eq of TBAF Me—THF 8 h |
| Compound 209 | From intermediate 706 | 159 | 66 Procedure with 2 eq. of TBAF |

| Compound number | Structure | Mass (mg) | Yield (%) |
|---|---|---|---|
| Compound 210 | From intermediate 711 | 104 | 83 Procedure with 1.6 eq of TBAF THF 12 h |
| Compound 211 | From intermediate 717 | 25 | 37 Procedure with 1.45 eq of TBAF THF 12 h |
| Compound 212 | From intermediate 720 | 176 | 54 Procedure with 1.5 eq of TBAF THF 2 h |

-continued

| Compound number | Structure | Mass (mg) | Yield (%) |
|---|---|---|---|
| Compound 213 | From intermediate 724 | 87 | 63 Procedure with 1.2 eq of TBAF Me—THF 3 h |
| Compound 215 | From intermediate 737 | 23 | 64 Procedure with 1.2 eq of TBAF Me—THF 3 h |
| Compound 216 | From intermediate 740 | 17 | 35 Procedure with 1.43 eq of TBAF THF 18 h |
| Compound 217 | From intermediate 745 | 2100 | 64 Procedure with 2 eq TBAF |

-continued
| Compound number | Structure | Mass (mg) | Yield (%) |
| --- | --- | --- | --- |
| Compound 218 | 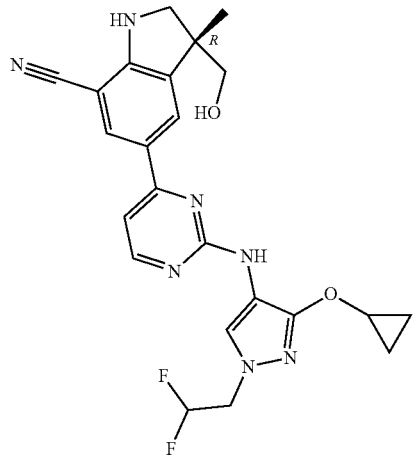<br>From intermediate 749 | 65<br>28 | 27<br>11<br>Procedure with 1.5 eq TBAF |
| Compound 219 | 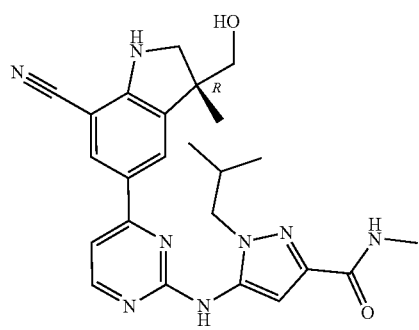<br>From intermediate 753 | 2400 | 69<br>Procedure with 2 eq TBAF |

-continued

| Compound number | Structure | Mass (mg) | Yield (%) |
|---|---|---|---|
| Compound 220 | From intermediate 761 | 37 | 41 Procedure with 1.6 eq TBAF |
| Compound 221 | From intermediate 766 | 36 | 40 Procedure with 2 eq TBAF |

Example B2

Preparation of Compound 2

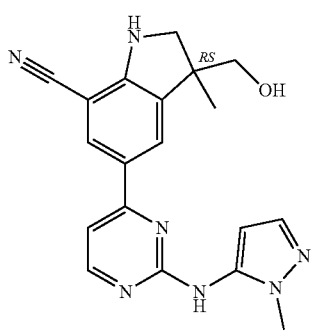 [SMILES: Cn1nccc1Nc1nccc(-c2cc(C#N)c3c(c2)C(C)(CO)CN3)n1]

A mixture of intermediate 10 (268.00 mg, 0.58 mmol) in a mixture of TFA (2 mL) and DCM (5 mL) was stirred at rt for 1 h. The mixture was basified with saturated aqueous solution of NaHCO$_3$. An extraction was performed with DCM. The organic layer was washed with brine, dried over MgSO$_4$, evaporated and purified by column chromatography on silica gel (irregular SiOH 15-40 m, 120 g, liquid injection with DCM, mobile phase: DCM/(MeOH(10% aq. NH$_3$)), gradient from 100:0 to 90:10 in 15 CV). The fractions containing the product were combined and concentrated to give 70 mg of compound 2 (33% yield over 3 steps, white solid).

Preparation of Compound 103

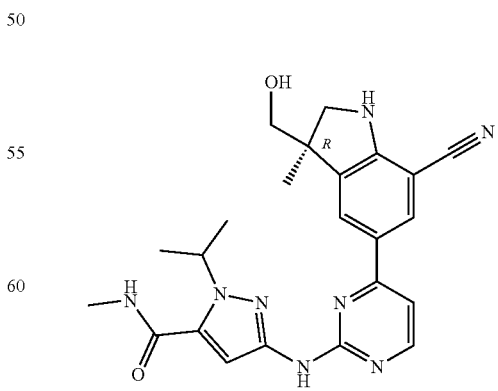

At 0° C., TFA (1.73 mL; 22.61 mmol) was added dropwise to a mixture of intermediate 272 (0.618 g; 1.13 mmol)

in DCM (10.00 mL). This reaction was stirred for 1 hour at 0° C. Water and a 10% aqueous solution of $K_2CO_3$ were added. This mixture was extracted twice with DCM. The organic layer was decanted and the solvent was evaporated until dryness. The crude was purified (solid deposit) by silica gel chromatography (Irregular SiOH 20-45 m 40 g, mobile phase: gradient from 98% DCM, 2% MeOH to 92% DCM, 8% MeOH (+10% $NH_4OH$)). The fractions containing the product were collected and the solvent was evaporated until dryness. The product was taken up into ethylic ether and the precipitate was filtered to give 140 mg of compound 103 (23% yield)

The compounds in the Table below were prepared by using an analogous procedure than the one used for the preparation of compound 2 or 103 starting from the respective starting materials. The most relevant minor deviations to the referenced method are indicated as additional information in the column 'Yield (%)'.

| Compound number | Structure | Mass (mg) | Yield (%) |
|---|---|---|---|
| Compound 3 | From intermediate 12 | 130 white solid | 36% (over 3 step) Procedure with DCM/TFA (8:3, v/v) |
| Compound 5 | From intermediate 17 | 66 | 41 Procedure with DCM/TFA (4:1, v/v) |
| Compound 6 | From intermediate 20 | 54 | 37 Procedure with DCM/TFA (4:1, v/v) |

-continued
| Compound number | Structure | Mass (mg) | Yield (%) |
|---|---|---|---|
| Compound 7 | 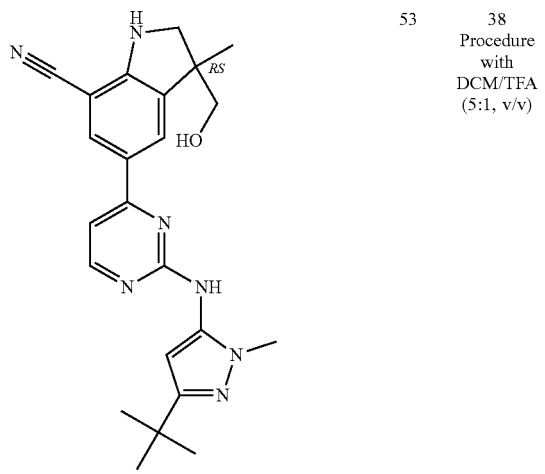<br>From intermediate 24 | 53 | 38<br>Procedure with DCM/TFA (5:1, v/v) |
| Compound 9 | 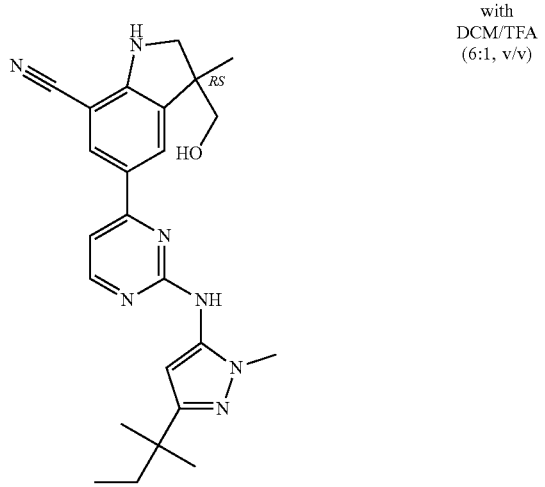<br>From intermediate 26 | 65 | 32<br>Procedure with DCM/TFA (6:1, v/v) |
| Compound 10 | 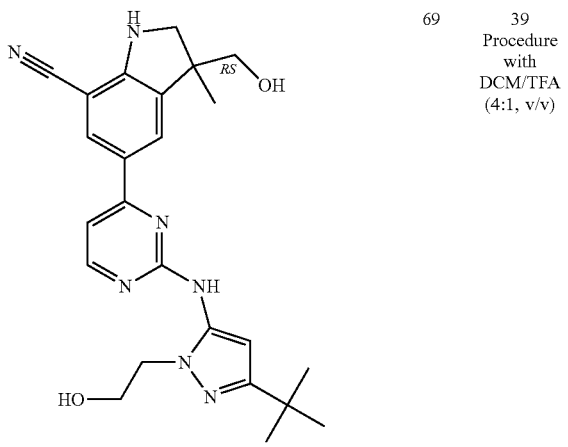<br>From intermediate 28 | 69 | 39<br>Procedure with DCM/TFA (4:1, v/v) |

-continued
| Compound number | Structure | Mass (mg) | Yield (%) |
|---|---|---|---|
| Compound 11 | 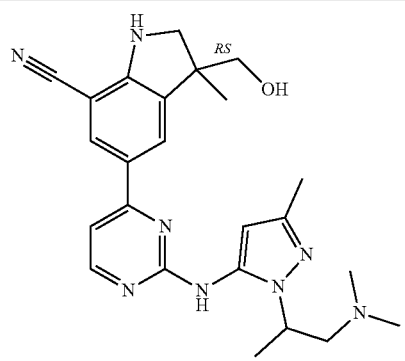<br>From intermediate 32 | 18 | 9<br>Procedure with DCM/TFA (5:2, v/v) |
| Compound 15 | 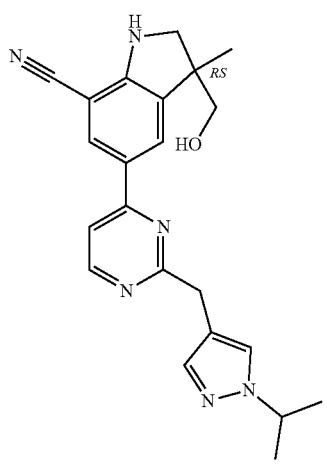<br>From intermediate 39 | 15 | 11<br>Procedure with DCM/TFA (5:1, v/v) |
| Compound 26 | 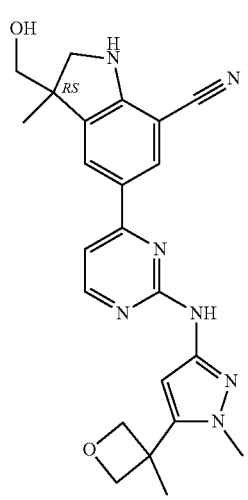<br>From intermediate 66 | 8 | 13<br>Procedure with DCM/TFA (6:1, v/v) |

-continued

| Compound number | Structure | Mass (mg) | Yield (%) |
|---|---|---|---|
| Compound 110 | 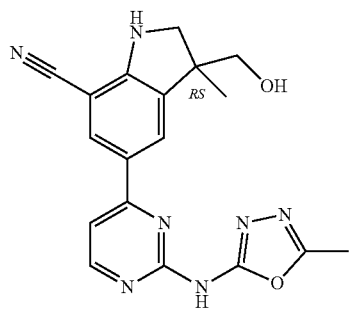  From intermediate 302 | 200 | 45 Procedure with DCM/TFA (10:1, v/v) |
| Compound 142 | From intermediate 435 | 17 | 8 Procedure with DCM/TFA (5:1, v/v) |

Example B3

Preparation of Compound 173

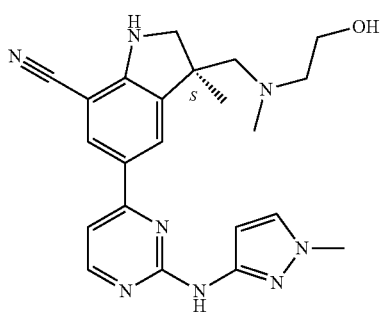

HCl (3M in $H_2O$) (0.80 mL, 2.40 mmol) was added to a solution of intermediate 551 (152.00 mg, 0.24 mmol) in MeOH (3.7 mL) and the reaction mixture was stirred at reflux overnight. The reaction mixture was cooled to rt, poured onto a 10% aqueous solution of $K_2CO_3$ and extracted with DCM. The organic layer was decanted, dried over $MgSO_4$, filtered and evaporated to dryness. The residue (75 mg, orange powder) was purified by column chromatography on silica gel (irregular SiOH, 12 g, mobile phase: gradient from 0% $NH_4OH$, 0% MeOH, 100% DCM to 0.8% $NH_4OH$, 8% MeOH, 92% DCM). The fractions containing the product were collected and evaporated to dryness. The residue (39 mg) was taken up with $Et_2O$ to provide 15 mg of compound 173 (yellow powder).

The compounds in the Table below were prepared by using an analogous starting from the respective starting materials.

| Compound number | Structure | Mass (mg) | Yield (%) |
|---|---|---|---|
| Compound 174 | 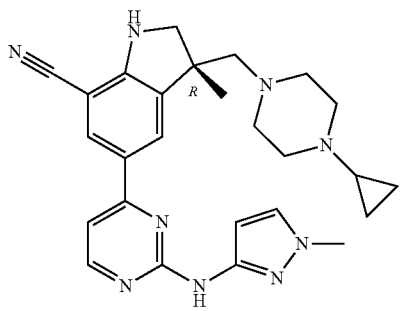<br>From intermediate 555 | 21<br>yellow oil | 34 |

Example B4

Preparation of Compound 176

TFA (0.40 mL, 5.29 mmol) was added at 5° C. to a solution of intermediate 557 (201.00 mg, 0.35 mmol) in DCM (3.84 mL). The reaction mixture was stirred at 5° C. for 1 h and 30 min. The residue was diluted with DCM and poured onto a 10% aqueous solution of $K_2CO_3$, dried over $MgSO_4$, filtered, evaporated to dryness (500 m, yellow powder) and purified by column chromatography on silica gel (irregular SiOH, 24 g, mobile phase: gradient from 100% DCM to 90% DCM, 10% MeOH, 1% $NH_4OH$). The fractions containing the product were collected and evaporated to dryness. The residue (151 mg, light yellow powder) was purified by reverse phase (stationary phase: X-Bridge-C18, 5 m, 30×150 mm, mobile phase: gradient from 75% $NH_4HCO_3$ 0.2%, 25% $CH_3CN$ to 35% $NH_4HCO_3$ 0.2%, 65% $CH_3CN$). The fractions containing the product were combined and evaporated. The residue (31 mg, colorless oil) was taken up with $Et_2O$ to provide 27 mg of compound 176 (16% yield, white powder).

The compounds in the Table below were prepared by using an analogous starting from the respective starting materials.

| Compound number | Structure | Mass (mg) | Yield (%) |
|---|---|---|---|
| Compound 175 | 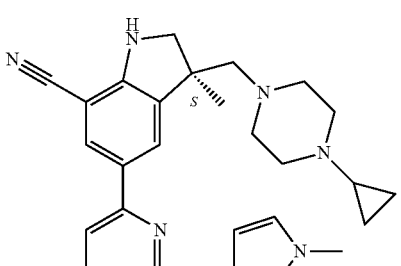<br>From intermediate 556 | 57<br>white powder | 23 |

Example B5

Preparation of Compound 179

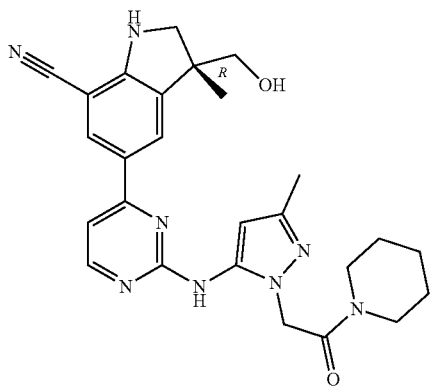

In a sealed tube, a mixture of intermediate 559 (90.00 mg, 153 μmol) and TFA (583.00 μL, 7.62 mmol) in dry DCM (3 mL) was stirred at rt for 1 h. The reaction mixture was diluted with DCM and basified with a saturated aqueous solution of NaHCO$_3$. The layers were separated and the organic layer was combined with another batch (from 75 mg of intermediate 559), dried over MgSO$_4$, filtered and the solvent was removed under reduced pressure. The residue (155 mg, yellow residue) was purified by column chromatography on silica gel (irregular SiOH, 15-40 μm, 10 g, liquid injection in DCM, mobile phase gradient: from DCM 100% to DCM 90%, MeOH (+aq. NH$_3$ 5%) 10%). The fractions containing the product were combined and evaporated to dryness. The residue (55 mg, yellow oil) was triturated in EtOH and the solvent was removed under reduced pressure. The residue (48 mg, yellow solid) was dried 17 h at 50° C. under reduced pressure to give 36 mg of compound 179 (26% yield, yellow powder).

Example B6

Preparation of Compound 214

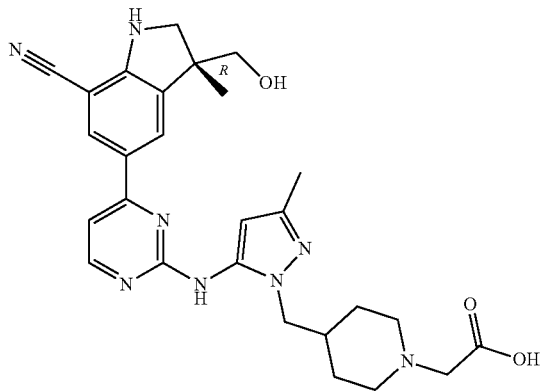

Lithium hydroxide monohydrate (0.011 g; 0.26 mmol) was added slowly to a mixture of intermediate 729 (0.066 g; 0.12 mmol) in H$_2$O (0.250 mL) and 1,4-dioxane (0.500 mL). The reaction was stirred at 100° C. for 1 hour then room temperature overnight. Water was added and this mixture was acidified with an aqueous solution of HCl 3N. This mixture was extracted twice with EtOAc. The solvent was evaporated until dryness to give: 86 mg of crude product. Purification was performed via Reverse phase (Stationary phase: YMC-actus Triart-C18 10 μm 30*150 mm, Mobile phase: Gradient from 85% H$_2$O, 15% ACN to 45% H$_2$O, 55% ACN). The pure fractions were collected and the solvent was evaporated until dryness. The product was taken up into ACN/Water (2 mL/5 mL) and freeze-dried overnight to afford compound 214 (10 mg, 16%).

Example B7

Preparation of Compound 201

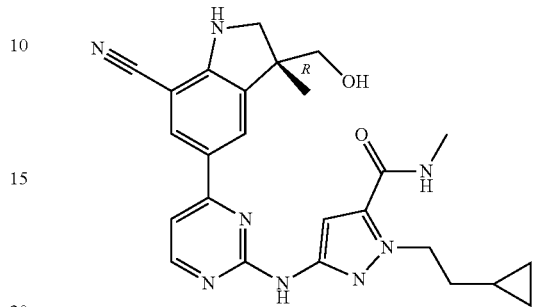

A mixture of intermediate 6R (415.5 mg; 0.81 mmol) and intermediate 667 (252 mg; 1.21 mmol) in 1,4-dioxane (4.40 mL) was added p-toluensulfonic acid monohydrate (236 mg; 1.37 mmol). The resulting mixture was stirred at 95° C. for 15 h. Then the reaction was quenched with a solution of 10% K$_2$CO$_3$ (aq), and extracted with a mixture of DCM-MeOH 9:1. The crude was purified using a silica gel column (DCM:MeOH 90:10) to afford compound 201 (60 mg, 16%).

Example B8

Preparation of Compound 222

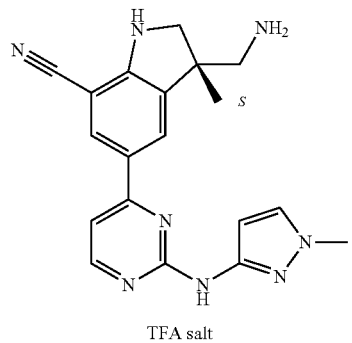

TFA salt

To a homogeneous solution of intermediate 776 (0.172 g; 0.27 mmol) in dry toluene (10 ml) was added SiO$_2$ (0.5 g; 40-63 μm) and the reaction heated at reflux (~120° C.) overnight (16 h). The reaction mixture was cooled to room temp and filtered through celite, rinsing the SiO$_2$ with THF followed by CH$_2$Cl$_2$. The filtrate was concentrated to dryness, redissolved in MeOH, and purified via acidic prep-HPLC (Shimadzu pumps with Gilson fraction collector, DAD. Column: Inertsil ODS-3 (5 uM, 30×50 mm). Mobile phase: A=0.05% TFA in H$_2$O, B=0.05% TFA in CH$_3$CN. Gradient: 5% B for 1 min to 95% B over 12 min, held at 95% B for 2 min. Flow: 80 mL/min. Run time: 15 min). Desired fractions were combined, frozen, and lyophilized to yield 23.6 mg (18% yield) of compound 222 as a yellow solid TFA salt.

The compound in the table below was prepared by using an analogous method starting from the respective R enantiomer, intermediate 777. The most relevant minor deviations to the referenced method are indicated as additional information in the column 'Yield (%)'.

| Compound number | Structure | Mass (mg) | Yield (%) |
|---|---|---|---|
| Compound 223 | 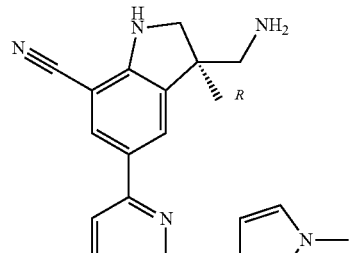<br>TFA salt<br>From intermediate 777 | 47 | 33 |

Example C1

Preparation of Compound 177

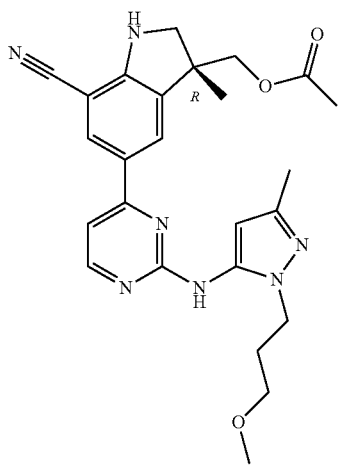

A mixture of compound 49 (50.00 mg, 0.11 mmol), AcOH (6.60 μL, 0.11 mmol), HATU (57.01 mg, 0.15 mmol), DIPEA (70.50 μL, 0.40 mmol) in DMF (2 mL) was stirred 12 h at rt. Water and DCM were added. The mixture was extracted with DCM. The organic layer was washed with brine, dried over MgSO$_4$, filtered and the solvent was evaporated. The residue (690 mg) was purified by column chromatography on silica gel (irregular SiOH, 40 m, 40 g, mobile phase 100% DCM to 98% DCM, 2% MeOH, 0.2% NH$_4$OH). The pure fractions were combined and the solvent was evaporated. The residue (237 mg) was purified again by column chromatography on silica gel (irregular SiOH, 40 μm, 40 g, mobile phase 100% DCM to 99% DCM, 1% MeOH, 0.1% NH$_4$OH). The pure fractions were combined and the solvent was evaporated. The residue (185 mg) was freeze-dried with CH$_3$CN and water. The residue (169 mg) was further purified by reverse phase (Stationary phase: X-Bridge-C18, 10 m, 30×150 mm, mobile phase: gradient from 75% H$_2$O, 25% CH$_3$CN to 35% H$_2$O, 65% CH$_3$CN). The fractions containing the product were combined and evaporated to dryness. The residue (122 mg) was freeze-dried with CH$_3$CN and water to give 101 mg of compound 177 (18% yield). M.P.=70° C. (K, gum).

The intermediates in the Table below were prepared by using an analogous starting from the respective starting materials.

| Compound number | Structure | Mass (mg) | Yield (%) |
|---|---|---|---|
| Compound 178 | 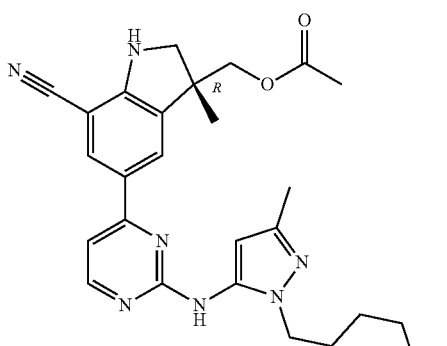<br>From compound 83 | 45 | 24 |

Analytical Part

LCMS (Liquid Chromatography/Mass Spectrometry)

The High Performance Liquid Chromatography (HPLC) measurement was performed using a LC pump, a diode-array (DAD) or a UV detector and a column as specified in the respective methods. If necessary, additional detectors were included (see table of methods below).

Flow from the column was brought to the Mass Spectrometer (MS) which was configured with an atmospheric pressure ion source. It is within the knowledge of the skilled person to set the tune parameters (e.g. scanning range, dwell time . . . ) in order to obtain ions allowing the identification of the compound's nominal monoisotopic molecular weight (MW). Data acquisition was performed with appropriate software. Compounds are described by their experimental retention times ($R_t$) and ions. If not specified differently in the table of data, the reported molecular ion corresponds to the $[M+H]^+$ (protonated molecule) and/or $[M-H]^-$ (deprotonated molecule). In case the compound was not directly ionizable the type of adduct is specified (i.e. $[M+NH_4]^+$, $[M+HCOO]^-$, etc. . . . ). For molecules with multiple isotopic patterns (Br, Cl.), the reported value is the one obtained for the lowest isotope mass. All results were obtained with experimental uncertainties that are commonly associated with the method used. Hereinafter, "SQD" means Single Quadrupole Detector, "RT" room temperature, "BEH" bridged ethylsiloxane/silica hybrid, "HSS" High Strength Silica, "DAD" Diode Array Detector.

Table: LCMS Method codes (Flow expressed in mL/min; column temperature (T) in ° C.; Run time in minutes).

| Method code | Instrument | Column | Mobile phase | gradient | Flow Column T | Run time |
|---|---|---|---|---|---|---|
| Method 1 | Waters: Acquity UPLC ® - DAD and Quattro Micro ™ | Waters: BEH C18 (1.7 μm, 2.1 × 100 mm) | A: 95% CH$_3$COONH$_4$ 7 mM/5% CH$_3$CN, B: CH$_3$CN | 84.2% A for 0.49 min, to 10.5% A in 2.18 min, held for 1.94 min, back to 84.2% A in 0.73 min, held for 0.73 min. | 0.343 40 | 6.2 |
| Method 2 | Waters: Acquity UPLC ® H - Class - DAD and SQD 2 | Waters: BEH C18 (1.7 μm, 2.1 × 100 mm) | A: 95% CH$_3$COONH$_4$ 7 mM/5% CH$_3$CN, B: CH$_3$CN | From 84.2% A to 10.5% A in 2.18 min, held for 1.94 min, back to 84.2% A in 0.73 min, held for 0.73 min. | 0.343 40 | 6.1 |
| Method 3 | Agilent 1260 Series - DAD VL+ and Agilent G6120B ESI-SQD Quadrupole LC/MS | ACE EXCEL 3 C18-AR (3 uM, 3.0 × 50 mm) | A: 0.05% TFA in H$_2$O, B: 100% CH$_3$CN | 1% B to 99% B over 2.5 min, held at 99% for 0.5 min, then back to 10% B over 0.5 min | 1.5 50 | 3.5 |
| Method 4 | Agilent 1100 HPLC DAD LC/MS G1956A | YMC-pack ODS-AQ C18 (50 × 4.6 mm, 3 μm) | A: 0.1% HCOOH in H$_2$O B: CH$_3$CN | From 95% A to 5% A in 4.8 min, held for 1.0 min, to 95% A in 0.2 min. | 2.6 35 | 6.2 |
| Method 5 | Agilent 1290 Infinity DAD TOF-LC/MS G6224A | YMC-pack ODS-AQ C18 (3 μm, 4.6 × 50 mm) | A: 0.1% HCOOH in water B: CH$_3$CN | From 94.51% A to 5% A in 4.8 min, held for 1.0 min, to 95% A in 0.2 min | 2.6 35 | 6.0 |

NMR

The NMR experiments were carried out using a Bruker Avance 500 III using internal deuterium lock and equipped with reverse triple-resonance ($^1$H, $^{13}$C, $^{15}$N TXI) probe head or using a Bruker Avance DRX 400 spectrometer at ambient temperature, using internal deuterium lock and equipped with reverse double-resonance ($^1$H, $^{13}$C, SEI) probe head with z gradients and operating at 400 MHz for the proton and 100 MHz for carbon. Chemical shifts (δ) are reported in parts per million (ppm). J value are expressed in Hertz (Hz).

Compound 19: $^1$H NMR (400 MHz, DMSO-d$_6$): δ 9.56 (s, 1H), 8.36 (d, J=5.6 Hz, 1H), 8.08 (d, J=1.0 Hz, 1H), 7.98 (d, J=1.0H, 1H), 7.57 (d, J=2.0 Hz, 1H), 7.36 (s, 1H), 7.25 (d, J=5.0 Hz, 1H), 6.60 (d, J=2.0 Hz, 1H), 5.00 (t, J=5.3 Hz, 1H), 3.75 (s, 3H), 3.68 (d, J=10.1 Hz, 1H), 3.41-3.47 (m, 1H) 3.34-3.40 (m, 1H), 3.28 (m, 1H, partially obscured by solvent peak), 1.28 (s, 3H)

Compound 42: $^1$H NMR (500 MHz, DMSO-d$_6$): δ 9.17 (s, 1H), 8.38 (d, J=5.4 Hz, 1H), 8.07 (d, J=1.6 Hz, 1H), 7.97 (d, J=1.6 Hz, 1H), 7.42 (s, 1H), 7.35 (d, J=5.4 Hz, 1H), 6.14 (s, 1H), 5.02 (t, J=5.4 Hz, 1H), 4.13 (t, J=5.6 Hz, 2H), 3.67 (d, J=9.8 Hz, 1H), 3.63 (t, J=9.8 Hz, 2H), 3.40-3.46 (m, 1H) 3.35-3.40 (m, 1H), 3.30 (d, J=9.8 Hz, 1H), 3.22 (s, 3H), 2.13 (s, 3H), 1.27 (s, 3H)

Compound 145: $^1$H NMR (500 MHz, DMSO-d$_6$): δ 11.51 (br s, 1H), 8.53 (d, J=5.4 Hz, 1H), 8.23 (d, J=1.6 Hz, 1H), 8.15 (s, 1H), 7.45-7.53 (m, 2H), 6.71 (s, 1H), 5.02 (t, J=5.2 Hz, 1H), 3.70 (d, J=9.8 Hz, 1H), 3.43-3.49 (m, 1H) 3.37-3.42 (m, 1H), 3.31 (m, 1H, partially obscured by solvent peak), 2.26 (s, 3H), 1.30 (s, 3H)

Compound 49: $^1$H NMR (500 MHz, DMSO-d$_6$): δ 9.14 (s, 1H), 8.36 (d, J=5.4 Hz, 1H), 8.06 (d, J=1.9 Hz, 1H), 7.95 (d, J=1.3 Hz, 1H), 7.39 (s, 1H), 7.32 (d, J=5.4 Hz, 1H), 6.07 (s, 1H), 4.99 (t, J=5.4 Hz, 1H), 3.98 (t, J=7.1 Hz, 2H), 3.67 (d, J=9.5 Hz, 1H), 3.40-3.45 (m, 1H) 3.34-3.39 (m, 1H) 3.31 (m, 1H, partially obscured by solvent peak), 3.27 (t, J=6.3 Hz, 2H), 3.16 (s, 3H), 2.13 (s, 3H), 1.92 (q, J=6.6 Hz, 2H), 1.27 (s, 3H)

Compound 107: $^1$H NMR (400 MHz, DMSO-d$_6$): δ 9.54 (s, 1H), 8.41 (d, J=5.1 Hz, 1H), 8.07 (s, 1H), 7.93 (s, 1H), 7.41 (s, 1H), 7.38 (d, J=5.0 Hz, 1H), 6.40 (s, 1H), 4.98 (t, J=5.0 Hz, 1H), 3.87 (d, J=7.6 Hz, 2H), 3.69 (br d, J=10.1 Hz, 1H), 3.40-3.48 (m, 1H) 3.33-3.39 (m, 1H), 3.29 (m, 1H, partially obscured by solvent peak), 2.04-2.18 (m, 1H), 1.27 (s, 3H), 0.81 (d, J=6.6 Hz, 6H)

Compound 113: $^1$H NMR (400 MHz, DMSO-d$_6$): δ 9.41 (s, 1H), 8.43 (d, J=5.6 Hz, 1H), 8.07 (s, 1H), 7.95 (s, 1H), 7.40-7.42 (m, 2H), 6.46 (s, 1H), 4.96 (t, J=5.3 Hz, 1H), 4.24-4.12 (m, 3H), 3.78-3.60 (m, 3H), 3.34-3.47 (m, 2H), 3.31 (m, 1H, partially obscured by solvent peak), 1.94-1.88 (m, 1H), 1.81-1.74 (m, 2H), 1.67-1.57 (m, 1H), 1.28 (s, 3H)

Compound 114: $^1$H NMR (400 MHz, DMSO-d$_6$): δ 9.44 (s, 1H), 8.43 (d, J=5.0 Hz, 1H), 8.07 (d, J=2.0 Hz, 1H), 7.95 (d, J=1.5 Hz, 1H), 7.45-7.38 (m, 2H), 6.46 (s, 1H), 4.99 (t, J=5.0 Hz, 1H), 4.24-4.10 (m, 3H), 3.83-3.53 (m, 3H), 3.34-3.47 (m, 2H), 3.30 (m, 1H, partially obscured by solvent peak), 1.98-1.84 (m, 1H), 1.82-1.77 (m, 2H), 1.67-1.57 (m, 1H), 1.28 (s, 3H)

Compound 118: $^1$H NMR (500 MHz, DMSO-d$_6$): δ 9.84 (s, 1H), 8.39 (d, J=5.4 Hz, 1H), 8.09 (d, J=1.6 Hz, 1H), 7.99 (d, J=1.3 Hz, 1H), 7.41 (s, 1H), 7.32 (d, J=5.4 Hz, 1H), 6.80 (s, 1H), 5.13 (s, 2H), 5.02 (s, 1H), 3.68 (d, J=9.7 Hz, 1H), 3.47-3.29 (m, 3H, partially obscured by solvent peak), 2.90-2.86 (m, 1H), 2.83 (s, 3H), 1.29 (m, 3H), 0.83-0.95 (s, 4H)

Compound 120: $^1$H NMR (500 MHz, DMSO-d$_6$): δ 8.53 (s, 1H), 8.26 (d, J=5.0 Hz, 1H), 8.00 (s, 1H), 7.88 (s, 1H), 7.61-7.50 (m, 2H), 7.33 (s, 1H), 7.15 (d, J=5.0 Hz, 1H), 6.85 (s, 1H), 5.31 (s, 2H), 5.03 (t, J=5.4 Hz, 1H), 3.66 (d, J=9.5 Hz, 1H), 3.60 (s, 3H), 3.33-3.44 (m, 2H), 3.27 (d, J=9.5 Hz, 1H), 2.67 (t, J=8.2 Hz, 2H), 1.52-1.44 (m, 1H), 1.28-1.21 (m, 5H), 0.79 (d, J=6.6 Hz, 6H)

Compound 132: $^1$H NMR (500 MHz, DMSO-d$_6$): δ 8.77 (s, 1H), 8.34 (d, J=5.4 Hz, 1H), 8.10-7.93 (m, 3H), 7.35 (s, 1H), 7.21 (d, J=5.4 Hz, 1H), 6.32 (tt, J=55.1, 3.7 Hz, 1H), 5.01 (t, J=5.4 Hz, 1H), 4.49 (td, J=15.0, 3.8 Hz, 2H), 3.67 (d, J=9.8 Hz, 1H), 3.35-3.35 (m, 2H), 3.29 (d, J=9.5 Hz, 1H), 2.17 (s, 3H), 1.28 (s, 3H)

Compound 156: $^1$H NMR (400 MHz, DMSO-d$_6$): δ 9.15 (s, 1H), 8.34 (d, J=5.0 Hz, 1H), 8.05 (d, J=1.0 Hz, 1H), 7.93 (s, 1H), 7.38 (s, 1H), 7.32 (d, J=5.6 Hz, 1H), 6.14 (s, 1H), 4.98 (t, J=5.3 Hz, 1H), 4.93 (t, J=5.8 Hz, 1H), 4.49 (q, J=6.4 Hz, 1H), 4.37 (d, J=6.1 Hz, 2H), 3.68 (d, J=10.1 Hz, 1H), 3.32-3.46 (m, 2H), 3.28 (m, 1H, partially obscured by solvent peak), 1.31 (d, J=6.6 Hz, 6H), 1.26 (s, 3H)

Compound 164: $^1$H NMR (500 MHz, DMSO-d$_6$): δ 9.75 (s, 1H), 8.52 (d, J=4.1 Hz, 1H), 8.37 (d, J=5.4 Hz, 1H), 8.10 (s, 1H), 7.98 (s, 1H), 7.38 (s, 1H), 7.29 (d, J=5.4 Hz, 1H), 7.12 (s, 1H), 5.41 (q, J=6.6 Hz, 1H), 4.98 (t, J=5.4 Hz, 1H), 3.70 (d, J=10.1 Hz, 1H), 3.34-3.48 (m, 2H), 3.29 (d, J=9.8 Hz, 1H), 2.78-2.85 (m, 1H), 1.38 (dd, J=6.6, 2.2 Hz, 6H), 1.28 (s, 3H), 0.70-0.64 (m, 2H), 0.63-0.58 (m, 2H)

Compound 177: $^1$H NMR (500 MHz, DMSO-d$_6$): δ 9.16 (s, 1H), 8.38 (d, J=5.4 Hz, 1H), 8.11 (d, J=1.3 Hz, 1H), 8.04 (d, J=1.3 Hz, 1H), 7.51 (s, 1H), 7.35 (d, J=5.4 Hz, 1H), 6.07 (s, 1H), 4.12 (d, J=10.7 Hz, 1H), 4.04 (d, J=11.0 Hz, 1H), 3.98 (t, J=7.1 Hz, 2H), 3.63 (d, J=10.1 Hz, 1H), 3.40 (d, J=10.1 Hz, 1H), 3.26 (t, J=6.1 Hz, 2H), 3.15 (s, 3H), 2.13 (s, 3H), 1.98 (s, 3H), 1.91 (q, J=6.6 Hz, 2H), 1.34 (s, 3H)

Compound 103: $^1$H NMR (500 MHz, DMSO-d$_6$) δ ppm 9.76 (s, 1H) 8.42 (q, J=4.4 Hz, 1H) 8.38 (d, J=5.4 Hz, 1H) 8.11 (d, J=1.9 Hz, 1H) 8.01 (d, J=1.6 Hz, 1H) 7.37 (s, 1H) 7.29 (d, J=5.4 Hz, 1H) 7.17 (s, 1H) 5.43 (quin, J=6.6 Hz, 1H) 5.00 (t, J=5.5 Hz, 1H) 3.70 (d, J=9.1 Hz, 1H) 3.42-3.48 (m, 1H) 3.35-3.40 (m, 1H) 3.29 (d, J=9.5 Hz, 1H) 2.75 (d, J=4.7 Hz, 3H) 1.38 (dd, J=6.6, 0.9 Hz, 6H) 1.28 (s, 3H)

Compound 180 (fraction B): $^1$H NMR (500 MHz, DMSO-d$_6$) δ ppm 8.78 (s, 1H) 8.35 (d, J=5.0 Hz, 1H) 8.06 (br s, 2H) 7.96 (s, 1H) 7.37 (s, 1H) 7.23 (d, J=5.4 Hz, 1H) 6.09-6.48 (m, 1H) 5.02 (br t, J=5.0 Hz, 1H) 4.40-4.65 (m, 2H) 3.67 (br d, J=10.1 Hz, 1H) 3.57 (t, J=6.9 Hz, 2H) 3.41-3.48 (m, 1H) 3.35-3.41 (m, 1H) 3.29 (br d, J=10.1 Hz, 1H) 3.27 (s, 3H) 2.87 (br t, J=6.9 Hz, 2H) 1.28 (s, 3H)

Compound 183: $^1$H NMR (500 MHz, DMSO-d$_6$) δ 9.35 (s, 1H), 8.38 (d, J=5.4 Hz, 1H), 8.05 (s, 1H), 7.94 (s, 1H), 7.88 (q, J=4.4 Hz, 1H), 7.42 (s, 1H), 7.36 (d, J=5.4 Hz, 1H), 6.58 (s, 1H), 5.00 (t, J=5.2 Hz, 1H), 4.57-4.66 (m, 1H), 3.68 (d, J=9.8 Hz, 1H), 3.40-3.46 (m, 1H), 3.34-3.38 (m, 1H), 3.29 (br d, J=10.1 Hz, 1H), 2.76 (d, J=4.7 Hz, 3H), 1.38 (d, J=6.6 Hz, 6H), 1.26 (s, 3H)

OR

Optical Rotation is measured with a polarimeter such as e.g. 341 Perkin Elmer, an Autopol IV automatic polarimeter (Rodolph research analytical) or a P-2000 (Jasco).

Specific rotation(OR): $[\alpha]^\theta_\lambda = (100*\alpha)/(c*l)$

α (measured rotation) is the angle through which plane polarized light is rotated by a solution of c (mass concentration) and l (path length). Concentration is in grams per 100 mL; path length is in decimeters and is 1.000 decimeter.

θ is the temperature (° C.) and a the wavelength of the light used.

Unless otherwise indicated, temperature is 20° C., and the sodium D line is used (589 nanometer).

Or Data:

Solvent: DMF (unless otherwise indicated); temperature: 20° C. (unless otherwise indicated); wavelength: 589 nm (unless otherwise indicated); 'Conc.' means concentration of the sample in grams per 100 mL; 'OR' means optical rotation (specific rotation); 'N°' means compound number

| N° | OR (°) | Concentration (g/100 mL) |
|---|---|---|
| 19 | +19.82 | 0.202 |
| 31 | −15.60 | 0.250 |
| 34 | −19.41 | 0.232 |
| 37 | +7.92 | 0.240 |
| 38 | +9.52 | 0.210 |
| 39 | +14.78 | 0.230 |
| 40 | +17.14 | 0.210 |
| 41 | +16.92 | 0.260 |
| 42 | +11.20 | 0.250 |
| 43 | +17.58 | 0.330 |
| 44 | +12.96 | 0.270 |
| 45 | +14.07 | 0.270 |
| 46 | +14.21 | 0.218 |
| 47 | −17.24 | 0.273 |
| 48 | +16.94 | 0.310 |
| 49 | +16.06 | 0.330 |
| 51 | −11.00 | 0.264 |
| 52 | +39.24 | 0.273 |
| 53 | +31.17 | 0.231 |
| 54 | −17.59 | 0.290 |
| 55 | +14.83 | 0.290 |
| 57 | −12.54 | 0.311 |
| 58 | +15.29 | 0.340 |
| 59 | +13.93 | 0.280 |
| 60 | +13.87 | 0.310 |
| 61 | +12.69 | 0.260 |
| 62 | +14.80 | 0.250 |
| 63 | +13.70 | 0.270 |
| 64 | +4.46 | 0.269 |
| 65 | +21.20 | 0.250 |
| 66 | +16.45 | 0.274 |
| 67 | +16.45 | 0.310 |
| 72 | +10.88 | 0.340 |
| 73 | +15.52 | 0.290 |
| 74 | +4.62 | 0.238 |
| 75 | +4.14 | 0.290 |
| 76 | +14.62 | 0.260 |
| 79 | +13.79 | 0.290 |
| 80 | +10.40 | 0.250 |
| 83 | +9.60 | 0.271 |
| 86 | +19.66 | 0.290 |
| 87 | +8.93 | 0.280 |
| 88 | +12.50 | 0.280 |
| 89 | +14.00 | 0.250 |
| 90 | −4.52 | 0.310 |
| 91 | +13.64 | 0.330 |
| 92 | +14.07 | 0.270 |
| 93 | +15.15 | 0.330 |
| 94 | +48.33 | 0.300 |
| 95 | +10.00 | 0.290 |
| 96 | +8.30 | 0.253 |
| 97 | −6.71 | 0.298 |
| 98 | +11.48 | 0.248 |
| 101 | +20.5 | 0.317 |
| 103 | +9.00 | 0.300 |
| 104 | +10.65 | 0.310 |
| 105 | +31.90 | 0.210 |
| 107 | +20.69 | 0.242 |
| 108 | +12.52 | 0.192 |
| 109 | +10.43 | 0.192 |
| 110 | +14.40 | 0.250 |
| 111 | +13.29 | 0.241 |
| 112 | +17.42 | 0.258 |
| 113 | +21.50 | 0.200 |
| 114 | −7.86 | 0.242 |
| 115 | +16.89 | 0.225 |
| 116 | +14.71 | 0.258 |
| 117 | +11.08 | 0.217 |
| 118 | +14.48 | 0.242 |
| 119 | −29.77 | 0.215 |
| 120 | +4.80 | 0.250 |
| 122 | −9.60 | 0.250 |
| 123 | +18.58 | 0.258 |
| 124 | +16.14 | 0.242 |
| 125 | +14.83 | 0.283 |
| 126 | +12.86 | 0.233 |
| 127 | +11.46 | 0.148 |
| 128 | +16.55 | 0.242 |
| 129 | +20.80 | 0.250 |
| 130 | +5.45 | 0.275 |
| 131 | +14.48 | 0.242 |
| 132 | +6.43 | 0.233 |
| 133 | +15.31 | 0.242 |
| 134 | +19.29 | 0.233 |
| 135 | +11.67 | 0.300 |
| 136 | +11.63 | 0.215 |
| 137 | +9.55 | 0.262 |
| 138 | +11.11 | 0.225 |
| 142 | +24.22 | 0.244 |
| 145 | +27.81 | 0.241 |
| 146 | +8.85 | 0.260 |
| 147 | +16.09 | 0.230 |
| 148 | +29.33 | 0.150 |
| 149 | +30.38 | 0.260 |
| 150 | +22.91 | 0.183 |
| 151 | +16.40 | 0.250 |
| 152 | +11.58 | 0.242 |
| 153 | +16.73 | 0.275 |
| 154 | +15.74 | 0.235 |
| 155 | +9.34 | 0.289 |
| 156 | +13.82 | 0.275 |
| 157 | +17.20 | 0.250 |
| 159 | +17.50 | 0.200 |
| 160 | +15.60 | 0.250 |
| 161 | +18.08 | 0.260 |
| 162 | +11.11 | 0.270 |
| 163 | +8.50 | 0.200 |
| 164 | +26.07 | 0.280 |
| 165 | +18.48 | 0.330 |
| 166 | +32.69 | 0.260 |
| 167 | +9.62 | 0.260 |
| 168 | +7.20 | 0.250 |
| 169 | +9.58 | 0.240 |
| 170 | +8.33 | 0.300 |
| 172 | +9.06 | 0.309 |
| 173 | −13.95 | 0.251 |
| 174 | +18.48 | 0.233 |
| 175 | −30.99 | 0.284 |
| 176 | +39.18 | 0.268 |
| 177 | +35.99 | 0.192 |
| 178 | +29.12 | 0.364 |
| 179 | +12.59 | 0.270 |
| 180 | +8.26 | 0.363 |
| 181 | +12.99 | 0.254 |
| 182 | +14.52 | 0.31 |
| 183 | +10.71 | 0.252 |
| 184 | +11.72 | 0.290 |
| 185 | +11.11 | 0.270 |
| 186 | +10.91 | 0.330 |
| 187 | +12.17 | 0.230 |
| 188 | +9.58 | 0.240 |
| 189 | +11.74 | 0.230 |
| 190 | +15.71 | 0.210 |
| 192 | +13.6 | 0.250 |
| 194 | +16.94 | 0.366 |
| 195 | +4.72 | 0.254 |
| 196 | +8.97 | 0.290 |
| 197 | +13.15 | 0.251 |
| 198 | +18.60 | 0.07 (MeOH @ 23° C.) |
| 199 | +7.17 | 0.279 |
| 200 | +10.29 | 0.272 |
| 201 | +4.2 | 0.1 (MeOH @ 23° C.) |

| N° | OR (°) | Concentration (g/100 mL) |
|---|---|---|
| 203 | +4.36 | 0.390 |
| 204 | +4.68 | 0.278 |
| 205 | +30.0 | 0.220 |
| 206 | +11.63 | 0.301 |
| 207 | +5.18 | 0.251 |
| 208 | +7.39 | 0.230 |
| 209 | +13.48 | 0.230 |
| 210 | +9.35 | 0.278 |
| 211 | +5.65 | 0.230 |
| 212 | +7.27 | 0.289 |
| 213 | +12.4 | 0.06 (MeOH @ 23° C.) |
| 217 | +7.69 | 0.260 |
| 218 | +5.81 | 0.241 |
| 219 | +11.55 | 0.251 |
| 220 | +9.13 | 0.230 |

Melting Point (DSC, MP50, or K)

For a number of compounds, melting points (MP) were determined with a DSC1 (Mettler-Toledo) (indicated with DSC in the analytical table). Melting points were measured with a temperature gradient of 10° C./minute. Maximum temperature was 350° C. Values are peak values."

For a number of compounds, melting points were obtained with a Kofler hot bench, consisting of a heated plate with linear temperature gradient, a sliding pointer and a temperature scale in degrees Celsius (indicated with K in the analytical table).

For a number of compounds, melting points were obtained with a Mettler Toledo MP50 apparatus (indicated with MP50 in the analytical table). Melting points were measured with a temperature gradient of 10° C. per minute starting from 50° C. (waiting time 10 seconds) to a maximum value of 300° C.

Table: N° means compound number; MP means melting point (° C.); $R_t$ means retention time (min)

| N° | MP (° C.) | MP method | Rt | [M + H]$^+$ | LC/MS Method |
|---|---|---|---|---|---|
| 1 | 212 | DSC | 2.15 | 362 | 1 |
| 2 | 208 | DSC | 2.08 | 362 | 1 |
| 3 | 232 | DSC | 2.15 | 376 | 1 |
| 4 | 252 | DSC | 2.10 | 362 | 1 |
| 5 | — | — | 2.14 | 432 | 1 |
| 6 | >260 | K | 2.74 | 444 | 1 |
| 7 | 227 | DSC | 2.04 | 376 | 2 |
| 8 | — | — | 2.37 | 418 | 2 |
| 9 | — | — | 1.91 | 434 | 2 |
| 10 | — | — | 2.17 | 448 | 2 |
| 11 | 206 | DSC | 2.14 | 433 | 1 |
| 12 | 203 | K | 1.66 | 445 | 2 |
| 13 | 260 | DSC | 1.97 | 375 | 2 |
| 14 | — | — | 2.01 | 420 | 1 |
| 15 | — | — | 2.33 | 390 | 1 |
| 16 | — | — | 2.21 | 406 | 1 |
| 17 | — | — | 2.00 | 433 | 1 |
| 18 | — | — | 2.08 | 447 | 1 |
| 19 | 199 | DSC | 2.15 | 362 | 1 |
| 20 | 215 | DSC | 2.45 | 390 | 1 |
| 21 | 233 | DSC | 2.02 | 348 | 1 |
| 22 | — | — | 2.40 | 509 | 1 |
| 23 | — | — | 2.30 | 420 | 1 |
| 24 | — | — | 2.28 | 390 | 1 |
| 25 | — | — | 2.05 | 489 | 1 |
| 26 | — | — | 2.18 | 432 | 1 |
| 27 | — | — | 2.24 | 420 | 1 |
| 28 | — | — | 2.39 | 509 | 1 |
| 29 | 150 (gum) | K | 2.42 | 402 | 1 |
| 30 | — | — | 2.25 | 412 | 1 |
| 31 | — | — | 2.45 | 390 | 1 |
| 32 | 163 | K | 2.19 | 396 | 1 |
| 33 | 250 | K | 2.33 | 480 | 1 |
| 34 | 200 | DSC | 2.14 | 362 | 1 |
| 35 | <260 | K | 2.35 | 517 | 1 |
| 36 | — | — | 2.04 | 376 | 1 |
| 37 | >260 | K | 1.94 | 445 | 1 |
| 38 | 249 | K | 1.90 | 445 | 1 |
| 39 | 170 | K | 2.13 | 461 | 1 |
| 40 | 221 | K | 2.45 | 402 | 1 |
| 41 | 208 | DSC | 2.34 | 396 | 1 |
| 42 | — | — | 2.30 | 420 | 1 |
| 43 | 240 | K | 2.44 | 396 | 1 |
| 44 | — | — | 2.41 | 434 | 1 |
| 45 | — | — | 2.03 | 433 | 1 |
| 46 | 166 | K | 2.18 | 420 | 1 |
| 47 | 174 | K | 2.18 | 420 | 1 |
| 48 | — | — | 2.38 | 390 | 1 |
| 49 | 162 | DSC | 2.34 | 767 | 1 |
| 50 | — | — | 2.14 | 489 | 1 |
| 51 | 192 | K | 2.47 | 446 | 1 |
| 52 | 173 | K | 2.46 | 446 | 1 |
| 53 | 260 | K | 2.33 | 419 | 1 |
| 54 | 159 | K | 2.32 | 434 | 1 |
| 55 | 200 | K | 2.50 | 418 | 1 |
| 56 | — | — | 1.95 | 419 | 1 |
| 57 | — | — | 2.29 | 420 | 1 |
| 58 | 228 | K | 2.60 | 462 | 1 |
| 59 | — | — | 2.45 | 462 | 1 |
| 60 | >260 | K | 2.39 | 460 | 1 |
| 61 | 138 (gum) | K | 2.24 | 460 | 1 |
| 62 | 192 | K | 2.00 | 459 | 1 |
| 63 | >250 | K | 2.21 | 446 | 1 |
| 64 | — | — | 2.58 | 430 | 1 |
| 65 | — | — | 2.07 | 468 | 1 |
| 66 | — | — | 2.32 | 490 | 1 |
| 67 | — | — | 2.17 | 446 | 1 |
| 68 | 142 | K | 2.64 | 460 | 1 |
| 69 | 138 (gum) | K | 2.65 | 460 | 1 |
| 70 | 214 | K | 2.63 | 460 | 1 |
| 71 | 150 (gum) | K | 2.63 | 460 | 1 |
| 72 | 167 | K | 2.17 | 446 | 1 |
| 73 | — | — | 2.32 | 402 | 1 |
| 74 | 191 | K | 2.20 | 446 | 1 |
| 75 | 203 | K | 2.24 | 460 | 1 |
| 76 | 134 (gum) | K | 2.21 | 460 | 1 |
| 77 | 123 (gum) | K | 2.44 | 434 | 1 |
| 78 | 117 (gum) | K | 2.44 | 434 | 1 |
| 79 | — | — | 2.31 | 475 | 1 |
| 80 | 304 | DSC | 2.35 | 499 | 1 |
| 81 | 124 (gum) | K | 2.22 | 446 | 1 |
| 82 | 140 (gum) | K | 2.22 | 446 | |
| 83 | — | — | 2.00 | 473 | 1 |
| 84 | 140 (gum) | K | 2.28 | 462 | 1 |
| 85 | 141 (gum) | K | 2.28 | 462 | 1 |
| 86 | 152 | K | 2.03 | 433 | 1 |
| 87 | — | — | 2.26 | 495 | 1 |
| 88 | — | — | 2.19 | 473 | 1 |
| 89 | — | — | 2.25 | 473 | 1 |
| 90 | 118 (gum) | K | 2.00 | 459 | 1 |

| N° | MP (° C.) | MP method | Rt | [M + H]+ | LC/MS Method |
|---|---|---|---|---|---|
| 91 | — | — | 2.40 | 474 | 1 |
| 92 | — | — | 2.08 | 420 | 1 |
| 93 | — | — | 2.89 | 443 | 1 |
| 94 | — | — | 2.33 | 460 | 1 |
| 95 | 222 | DSC | 2.74 | 430 | 1 |
| 96 | 182 | DSC | 2.54 | 430 | 1 |
| 97 | — | — | 2.52 | 418 | 1 |
| 98 | 248 | DSC | 2.48 | 418 | 1 |
| 99 | — | — | 2.61 | 432 | 1 |
| 100 | — | — | 2.66 | 432 | 1 |
| 101 | — | — | 2.49 | 489 | 1 |
| 102 | — | — | 2.44 | 489 | 1 |
| 103 | — | — | 2.08 | 447 | 1 |
| 104 | — | — | 2.74 | 490 | 1 |
| 105 | 150 | K | 2.80 | 490 | 1 |
| 107 | 202 | DSC | 2.80 | 438 | 1 |
| 108 | 186 | K | 2.21 | 448 | 1 |
| 109 | 230 | K | 2.30 | 448 | 1 |
| 110 | — | — | 2.31 | 448 | 1 |
| 111 | 227 | DSC | 2.24 | 446 | 1 |
| 112 | 190 | DSC | 2.62 | 454 | 1 |
| 113 | — | — | 2.75 | 466 | 1 |
| 114 | — | — | 2.74 | 466 | 1 |
| 115 | 202 | DSC | 2.81 | 450 | 1 |
| 116 | 277 | DSC | 2.23 | 467 | 1 |
| 117 | 206 | K | 2.43 | 512 | 1 |
| 118 | 238 | DSC | 2.46 | 493 | 1 |
| 119 | — | — | 2.16 | 480 | 1 |
| 120 | 189 | K | 2.37 | 512 | 1 |
| 121 | 189 | K | 2.63 | 518 | 1 |
| 122 | — | — | 1.97 | 459 | 1 |
| 123 | — | — | 1.93 | 459 | 1 |
| 124 | — | — | 2.19 | 493 | 1 |
| 125 | 194 | K | 2.52 | 531 | 1 |
| 126 | — | — | 2.54 | 482 | 1 |
| 127 | 178 | K | 2.37 | 462 | 1 |
| 128 | 184 | K | 2.76 | 441 | 1 |
| 129 | — | — | 2.48 | 466 | 1 |
| 130 | 226 | K | 2.51 | 512 | 1 |
| 131 | 139 | K (gum) | 2.15 | 491 | 1 |
| 132 | — | — | 2.30 | 426 | 1 |
| 133 | — | — | 2.54 | 482 | 1 |
| 134 | — | — | 2.45 | 525 | 1 |
| 135 | — | — | 1.69 | 420 | 1 |
| 136 | — | — | 2.07 | 544 | 1 |
| 137 | — | — | 2.64 | 541 | 1 |
| 138 | — | — | 2.29 | 537 | 1 |
| 139 | — | — | 2.21 | 475 | 1 |
| 140 | — | — | 2.03 | 473 | 1 |
| 141 | 129 | K (gum) | 2.04 | 473 | 1 |
| 142 | — | — | 1.89 | 364 | 1 |
| 143 | >250 | K | 2.31 | 380 | 1 |
| 144 | >250 | K | 2.31 | 380 | 1 |
| 145 | — | — | 2.40 | 379 | 1 |
| 146 | 222 | DSC | 2.43 | 379 | 1 |
| 147 | — | — | 2.10 | 363 | 1 |
| 148 | 285 | DSC | 2.55 | 393 | 1 |
| 149 | — | — | 2.14 | 450 | 1 |
| 150 | >260 | K | 2.21 | 461 | 1 |
| 151 | 227 | DSC | 2.19 | 434 | 1 |
| 152 | 257 | DSC | 2.93 | 561 | 1 |
| 153 | 199 | DSC | 1.98 | 436 | 1 |
| 154 | — | — | 2.24 | 460 | 1 |
| 155 | 197 | DSC | 2.07 | 517 | 1 |
| 156 | 219 | DSC | 2.05 | 420 | 1 |
| 157 | — | — | 2.18 | 479 | 1 |
| 158 | 141 | K (gum) | 2.21 | 475 | 1 |
| 159 | 183 | K | 2.63 | 515 | 1 |
| 160 | — | — | 2.36 | 511 | 1 |
| 161 | 243 | DSC | 2.18 | 479 | 1 |
| 162 | 211 | DSC | 2.49 | 466 | 1 |
| 163 | 191 | K | 3.17 | 597 | 1 |
| 164 | 262 | DSC | 2.50 | 473 | 1 |
| 165 | — | — | 2.35 | 475 | 1 |
| 166 | 245 | K | 1.96 | 474 | 1 |
| 167 | 165 | K | 2.33 | 528 | 1 |
| 168 | 126 | K | 2.21 | 559 | 1 |
| 169 | 147 | K (gum) | 2.95 | 579 | 1 |
| 170 | 177 | K | 2.08 | 475 | 1 |
| 171 | — | — | 2.12 | 487 | 1 |
| 172 | — | — | 1.95 | 503 | 1 |
| 173 | 110 | K (gum) | 2.22 | 419 | 1 |
| 174 | 110 | K (gum) | 2.22 | 419 | 1 |
| 175 | 260 | K | 2.67 | 470 | 1 |
| 176 | 264 | K | 2.67 | 470 | 1 |
| 177 | 70 | K (gum) | 2.63 | 476 | 1 |
| 178 | — | — | 2.28 | 515 | 1 |
| 179 | — | — | 2.34 | 487 | 1 |
| 180 | 131 170 | DSC DSC | 2.43 | 470 | 1 |
| 181 | 182 | DSC | 2.41 | 470 | 1 |
| 182 | 271 | DSC | 2.23 | 475 | 1 |
| 183 | 255-256 | DSC | 2.24 | 447 | 1 |
| 184 | 148 | K (gum) | 2.38 | 538 | 1 |
| 185 | 154 | K (gum) | 2.00 | 524 | 2 |
| 186 | 240 | K | 2.36 | 426 | 1 |
| 187 | 267 | DSC | 2.47 | 469 | 1 |
| 188 | 107 | K (gum) | 2.74 | 470 | 1 |
| 189 | 238 | K | 2.81 | 509 | 1 |
| 190 | 250 | K | 2.03 | 419 | 1 |
| 191 | 192 | K | 2.15 | 459 | 1 |
| 192 | 204 | K | 2.27 | 418 | 1 |
| 193 | 128 | K (gum) | 1.98 | 434 | 1 |
| 194 | 250 | K | 2.34 | 420 | 1 |
| 195 | 292 | DSC | 2.47 | 473 | 2 |
| 196 | 217 | DSC | 2.49 | 473 | 1 |
| 197 | 304 | DSC | 2.33 | 469 | 1 |
| 198 | 158 | MP50 | 2.86 | 473 | 4 |
| 199 | 226 | K | 2.25 | 461 | 1 |
| 200 | 138 | K (gum) | 2.06 | 572 | 1 |
| 201 | 290 | MP50 | 2.32 | 473 | 5 |
| 202 | 158 | K (gum) | 2.12 | 496 | 1 |
| 203 | 112 | K (gum) | 2.15 | 491 | 1 |
| 204 | — | — | 2.60 | 454 | 1 |
| 205 | — | — | 2.53 | 452 | 1 |
| 206 | 212 | DSC | 2.11 | 447 | 1 |
| 207 | 126 | K | 2.45 | 519 | 1 |
| 208 | 129 | K (gum) | 2.25 | 495 | 1 |
| 209 | 254 | K | 1.78 | 474 | 2 |
| 210 | 179 | DSC | 2.54 | 487 | 1 |
| 211 | | | 2.44 | 487 | 1 |
| 212 | 275 | DSC | 2.53 | 487 | 1 |
| 213 | 299 | MP50 | 2.08 | 513 | 4 |
| 214 | — | — | 1.88 | 517 | 1 |
| 215 | 230 | MP50 | 1.99 | 461 | 4 |
| 216 | — | — | 2.06 | 363 | 1 |
| 217 | 156 | DSC | 2.46 | 486 | 1 |
| 218 | 183 | DSC | 2.56 | 468 | 1 |
| 219 | 173 | DSC | 2.37 | 461 | 1 |
| 220 | — | — | 2.36 | 496 | 1 |
| 221 | — | — | 2.03 | 466 | 1 |
| 222 | — | — | 1.61 | 361 | 3 |
| 223 | — | — | 1.61 | 361 | 3 |

SFC-MS Method

The SFC measurement was performed using an Analytical Supercritical fluid chromatography (SFC) system composed by a binary pump for delivering carbon dioxide ($CO_2$) and modifier, an autosampler, a column oven, a diode array detector equipped with a high-pressure flow cell standing up to 400 bars. If configured with a Mass Spectrometer (MS) the flow from the column was brought to the (MS). It is within the knowledge of the skilled person to set the tune parameters (e.g. scanning range, dwell time . . . ) in order to obtain ions allowing the identification of the compound's nominal monoisotopic molecular weight (MW). Data acquisition was performed with appropriate software.

Table: Analytical SFC-MS Methods (flow expressed in mL/min; column temperature (T) expressed in ° C.; run time expressed in minutes, backpressure (BPR) expressed in bars.

| Method | column | mobile phase | gradient | Flow Col T | Run time BPR |
|---|---|---|---|---|---|
| Method 1 | Chiralpak ® AD-H column (5 μm, 150 × 4.6 mm) | A: $CO_2$ B: iPrOH (0.3% $iPrNH_2$) | 30% B hold 7 min, | 3 35 | 7 100 |
| Method 2 | Chiralcel ® OJ-H column (5 μm, 150 × 4.6 mm) | A: $CO_2$ B: MeOH (0.3% $iPrNH_2$) | 40% B hold 7 min, | 3 35 | 7 100 |
| Method 3 | Chiralpak ® AD-3 column (3 μm, 100 × 4.6 mm) | A: $CO_2$ B: EtOH (0.3% $iPrNH_2$) | 30% B hold 3 min, | 3.5 35 | 3 103 |
| Method 4 | Chiralcel ® OJ-H column (5 μm, 150 × 4.6 mm) | A: $CO_2$ B: MeOH (0.3% $iPrNH_2$) | 15% B hold 6 min, | 3.5 35 | 6 103 |
| Method 5 | Chiralpak ® AD-3 column (3 μm, 100 × 4.6 mm) | A: $CO_2$ B: EtOH (0.3% $iPrNH_2$) | 40% B hold 3 min, | 3.5 35 | 3 103 |
| Method 6 | Chiralpak ® AD-3 column (3 μm, 100 × 4.6 mm) | A: $CO_2$ B: iPrOH (0.3% $iPrNH_2$) | 35% B hold 3 min, | 3.5 35 | 3 103 |
| Method 7 | Chiralpak ® IC3 column (3 μm, 100 × 4.6 mm) | A: $CO_2$ B: iPrOH (0.3% $iPrNH_2$) | 35% B hold 3 min, | 3.5 35 | 3 103 |
| Method 8 | Lux cellulose 4 column (3 μm, 100 × 4.6 mm) | A: $CO_2$ B: EtOH (0.3% $iPrNH_2$) | 40% B hold 3 min, | 3.5 35 | 3 103 |

Table: Analytical SFC data ($R_t$ means retention time (in minutes), $[M+H]^+$ means the protonated mass of the compound, method refers to the method used for SFC-MS analysis of enantiomerically pure compounds; N° means compound number).

| N° | Rt | $[M + H]^+$ | Chiral purity UV Area % | Method |
|---|---|---|---|---|
| 68 | 2.96 | 460 | 100 | 1 |
| 69 | 3.54 | 460 | 99.10 | 1 |
| 70 | 4.16 | 460 | 100 | 2 |
| 71 | 2.31 | 460 | 100 | 2 |
| 77 | 1.01 | 434 | 100 | 3 |
| 78 | 1.14 | 434 | 99.12 | 3 |
| 81 | 2.31 | 446 | 99.39 | 4 |
| 82 | 2.70 | 446 | 98.12 | 4 |
| 84 | 1.00 | 462 | 100 | 5 |
| 85 | 1.56 | 462 | 100 | 5 |
| 121 | 0.99 | 518 | 97.2 | 6 |
| 139 | 1.69 | 475 | 100 | 7 |
| 140 | 1.52 | 473 | 100 | 8 |
| 141 | 2.05 | 473 | 98.63 | 8 |
| 158 | 2.31 | 475 | 100 | 7 |

Pharmacological Part

Biological Assay a

Inhibition of auto-phosphorylation of recombinant human NF-kappaB-inducing kinase (NIK/MAP3K14) activity (AlphaScreen®)

NIK/MAP3K14 auto-phosphorylation activity was measured using the AlphaScreen® (αscreen) format (Perkin Elmer). All compounds tested were dissolved in dimethyl sulfoxide (DMSO) and further dilutions were made in assay buffer. Final DMSO concentration was 1% (v/v) in assays. Assay buffer was 50 mM Tris pH 7.5 containing 1 mM EGTA (ethylene glycol tetraacetic acid), 1 mM DTT (dithiothreitol), 0.1 mM $Na_3VO_4$, 5 mM $MgCl_2$, 0.01% Tween® 20. Assays were carried out in 384 well Alphaplates (Perkin Elmer). Incubations consisted of compound, 25 microM Adenosine-5'-triphosphate (ATP), and 0.2 nM NIK/MAP3K14. Incubations were initiated by addition of GST-tagged NIK/MAP3K14 enzyme, carried out for 1 h at 25° C. and terminated by addition of stop buffer containing anti-phospho-IKK Ser176/180 antibody. Protein A Acceptor and Glutathione-Donor beads were added before reading using an EnVision® Multilabel Plate Reader (Perkin Elmer). Signal obtained in the wells containing blank samples was subtracted from all other wells and $IC_{50}$'s were determined by fitting a sigmoidal curve to % inhibition of control versus $Log_{10}$ compound concentration.

Biological assay B

Effect of compounds on P-IKKα levels in L363 (NIK translocated multiple myeloma) cells All compounds tested were dissolved in DMSO and further dilutions were made in culture medium. Final DMSO concentration was 1% (v/v) in cell assays. The human L363 cells (ATCC) were cultured in RPMI 1640 medium supplemented with GlutaMax and 10% fetal calf serum (PAA). Cells were routinely maintained at densities of $0.2 \times 10^6$ cells per ml-$1 \times 10^6$ cells per ml at 37° C. in a humidified 5% $CO_2$ atmosphere. Cells were passaged twice a week splitting back to obtain the low density. Cells were seeded in 96 well plates (Nunc 167008) at $2 \times 10^6$ per ml media in a volume of 75 μl per well plus 25 μl 1 μg/ml recombinant human B-cell activating factor (BAFF/BLyS/TNFSF13B). Seeded cells were incubated at 37° C. in a humidified 5% $CO_2$ atmosphere for 24 hr. Drugs and/or solvents were added (20 μl)

to a final volume of 120 µl. Following 2 hr treatment plates were removed from the incubator and cell lysis was achieved by the addition of 30 µl 5× lysis buffer followed by shaking on a plate shaker at 4° C. for 10 min. At the end of this incubation lysed cells were centrifuged at 800×g for 20 min at 4° C. and the lysate was assessed for P-IKKα levels by sandwich immuno-assay carried out in anti-rabbit antibody coated Mesoscale plates. Within an experiment, the results for each treatment were the mean of 2 replicate wells. For initial screening purposes, compounds were tested using an 8 point dilution curve (serial 1:3 dilutions). For each experiment, controls (containing MG132 and BAFF but no test drug) and a blank incubation (containing MG132 and BAFF and 10 µM ADS125117, a test concentration known to give full inhibition) were run in parallel. The blank incubation value was subtracted from all control and sample values. To determine the $IC_{50}$ a sigmoidal curve was fitted to the plot of % inhibition of control P-IKKα levels versus $Log_{10}$ compound concentration.

Biological assay C

Determination of antiproliferative activity on JJN-3 (NIK translocated) and KMS12-BM (NIK WT) multiple myeloma cells All compounds tested were dissolved in DMSO and further dilutions were made in culture medium. Final DMSO concentration was 0.3% (v/v) in cell proliferation assays. Viability was assessed using CellTiter-Glo cell viability assay kit (Promega). The human JJN-3 and KMS12-BM cells (DSMZ) were cultured in RPMI 1640 medium supplemented with 2 mM L-glutamine, and 10% fetal calf serum (PAA). Cells were routinely kept as suspension cells at 37° C. in a humidified 5% $CO_2$ atmosphere. Cells were passaged at a seeding density of $0.2 \times 10^6$/ml twice a week. Cells were seeded in black tissue culture treated 96-well plates (Perkin Elmer). Densities used for plating ranged from 15000 (JJN3) to 20000 (KMS12BM) cells per well in a total volume of 135 µl medium. Drugs and/or solvents were added (15 µl) to a final volume of 150 µl. Following 96 hr of treatment, plates were removed from the incubator and allowed to equilibrate to room temperature for approx 10 min. 75 µl CellTiter-Glo reagent was added to each well that was then covered (Perkin Elmer Topseal) and shaken on plate shaker for 10 min. Luminescence was measured on a HTS Topcount (Perkin Elmer). Within an experiment, the results for each treatment were the mean of 2 replicate wells. For initial screening purposes, compounds were tested using a 9 point dilution curve (serial 1:3 dilutions). For each experiment, controls (containing no drug) and a blank incubation (containing cells read at the time of compound addition) were run in parallel. The blank value was subtracted from all control and sample values. For each sample, the mean value for cell growth (in relative light units) was expressed as a percentage of the mean value for cell growth of the control.

Data for the compounds of the invention in the above assays are provided in Table A (the values in Table are averaged values over all measurements on all batches of a compound). ('n.c.' means not calculated)

TABLE A

| Compound | Auto-phosphorylation inhibition of NIK (IC50 (nM)) | Inhibition of pIKKα_L-363 (IC50 (nM)) | KMS-12 Proliferation inhibition (IC50 (nM)) | JJN-3 Proliferation inhibition (IC50 (nM)) |
| --- | --- | --- | --- | --- |
| 1 | 4.0 | n.c. | 2434 | 250 |
| 2 | 6.9 | n.c. | 794 | 141 |
| 3 | 4.2 | n.c. | ~1230 | 407 |
| 4 | 2.5 | n.c. | 162 | ~55 |
| 5 | 5.4 | n.c. | >10000 | 708 |
| 6 | 7.6 | n.c. | >10000 | 347 |
| 7 | 3.2 | 2 | ~1738 | 112 |
| 8 | 5.5 | n.c. | 7943 | 129 |
| 9 | 5.1 | n.c. | >10000 | 832 |
| 10 | 13 | n.c. | >10000 | 724 |
| 11 | 21 | n.c. | 3702 | 576 |
| 12 | 3.6 | n.c. | ~213.8 | ~45 |
| 13 | 3.4 | n.c. | ~2512 | 162 |
| 14 | 7.1 | n.c. | ~7244 | 234 |
| 15 | 5.4 | n.c. | 437 | 191 |
| 16 | 2.8 | n.c. | 7079 | 525 |
| 17 | 10 | n.c. | 4169 | 4365 |
| 18 | 11 | n.c. | >10000 | 1862 |
| 19 | 2.2 | n.c. | 2717 | 163 |
| 20 | 3.4 | n.c. | 2512 | 229 |
| 21 | 2.9 | n.c. | 1023 | 813 |
| 22 | 18 | n.c. | >10000 | 2344 |
| 23 | 4.9 | n.c. | 3890 | 295 |
| 24 | 10 | n.c. | >10000 | 646 |
| 25 | 8.1 | n.c. | 1514 | 1905 |
| 26 | 10 | n.c. | ~2951 | 457 |
| 27 | 13 | n.c. | ~4571 | 389 |
| 28 | ~17 | n.c. | >10000 | 2570 |
| 29 | 4.4 | n.c. | 1445 | ~603 |
| 30 | 3.2 | n.c. | ~170 | 47 |
| 31 | 14 | n.c. | >10000 | 589 |
| 32 | 27 | n.c. | >10000 | 7762 |
| 33 | 9.1 | n.c. | ~6166 | 1259 |
| 34 | 10 | n.c. | ~10000 | 1175 |
| 35 | 7.9 | 4 | >10000 | 209 |
| 36 | 2.6 | n.c. | 7586 | 174 |
| 37 | 2.0 | n.c. | 182 | 162 |
| 38 | 47 | n.c. | 3890 | 3981 |
| 39 | 32 | n.c. | >10000 | 1445 |
| 40 | 2.2 | n.c. | 562 | 295 |
| 41 | 2.1 | n.c. | ~479 | 78 |
| 42 | 4.2 | 68 | 5976 | 398 |
| 43 | 2.6 | n.c. | 933 | 234 |
| 44 | 4.5 | n.c. | 8710 | 324 |
| 45 | 7.6 | n.c. | 4169 | 1318 |
| 46 | 6.6 | n.c. | 2399 | 158 |
| 47 | 44 | n.c. | >10000 | 1549 |
| 48 | 5.1 | n.c. | 263 | 89 |
| 49 | 4.0 | 11 | 2089 | 134 |
| 50 | 3.8 | n.c. | >10000 | 316 |
| 51 | 4.1 | n.c. | ~1905 | ~59 |
| 52 | 6.9 | n.c. | >10000 | 115 |
| 53 | 3.5 | n.c. | ~5012 | 851 |
| 54 | 11 | n.c. | >10000 | 525 |
| 55 | 4.4 | n.c. | ~2041.74 | 59 |
| 56 | 3.1 | n.c. | ~1412.54 | ~363 |
| 57 | 28 | n.c. | >10000 | ~933 |
| 58 | 1.5 | n.c. | 468 | 69 |
| 59 | 5.0 | n.c. | 1950 | 68 |
| 60 | 2.0 | 5 | ~501.19 | 72 |
| 61 | 4.4 | n.c. | 355 | 162 |
| 62 | 23 | n.c. | 269 | 204 |
| 63 | 9.8 | n.c. | 6310 | 692 |
| 64 | 1.9 | n.c. | 3236 | 240 |
| 65 | 10 | n.c. | >10000 | ~1412 |
| 66 | 13 | n.c. | >10000 | 324 |
| 67 | 1.6 | n.c. | 912 | 141 |
| 68 | 5.3 | n.c. | >10000 | 38 |
| 69 | 5.8 | n.c. | >10000 | 78 |
| 70 | 3.8 | 6 | 1862 | 209 |
| 71 | 2.8 | 4 | 813 | 102 |
| 72 | 2.9 | 3 | 724 | 102 |
| 73 | 1.9 | 2 | 1318 | 195 |
| 74 | 3.0 | n.c. | ~3890 | 324 |
| 75 | 13 | n.c. | ~6026 | 2089 |
| 76 | 1.2 | 2 | 741 | 141 |
| 77 | 13 | n.c. | 1585 | 309 |
| 78 | 9.8 | n.c. | 9120 | 457 |

TABLE A-continued

| Compound | Auto-phosphorylation inhibition of NIK (IC50 (nM)) | Inhibition of pIKKα_L-363 (IC50 (nM)) | KMS-12 Proliferation inhibition (IC50 (nM)) | JJN-3 Proliferation inhibition (IC50 (nM)) |
|---|---|---|---|---|
| 79 | 8.3 | n.c. | >10000 | 2239 |
| 80 | 3.9 | n.c. | 6166 | 1096 |
| 81 | 4.3 | 11 | 851 | 195 |
| 82 | ~5.0 | 13 | 380 | 182 |
| 83 | 10 | 514 | 148 | 111 |
| 84 | 11 | 11 | >10000 | 437 |
| 85 | 9.8 | 31 | ~4898 | 380 |
| 86 | 2.6 | 15 | ~3715 | 871 |
| 87 | ~6.5 | 34 | >10000 | 3236 |
| 88 | 6.8 | 9 | >10000 | 2138 |
| 89 | 3.7 | ~85 | >10000 | 427 |
| 90 | 5.7 | n.c. | 5129 | 1549 |
| 91 | 5.5 | 13 | >10000 | 324 |
| 92 | 3.5 | 7 | 1514 | ~224 |
| 93 | 11 | 37 | 457 | 182 |
| 94 | 5.6 | 7 | 4169 | 178 |
| 95 | 1.6 | 4 | 871 | 100 |
| 96 | 1.6 | 12 | 3802 | 76 |
| 97 | 2.0 | 2 | >10000 | 309 |
| 98 | 2.0 | 5 | >10000 | 1023 |
| 99 | 2.9 | 3 | 9772 | 288 |
| 100 | 2.1 | ~15 | >10000 | 54 |
| 101 | 6.0 | 234 | 5248 | 1513 |
| 102 | 2.2 | 12 | ~6457 | 112 |
| 103 | 2.6 | 4 | 3020 | 71 |
| 104 | 3.4 | 15 | >10000 | 117 |
| 105 | 5.5 | 20 | >10000 | 447 |
| 107 | 3.8 | 9 | 1349 | 55 |
| 108 | 4.1 | 14 | ~3162 | ~724 |
| 109 | 3.6 | 11 | 468 | 50 |
| 110 | 3.0 | 4 | 2042 | 138 |
| 111 | 9.3 | ~331 | 5129 | 355 |
| 112 | 2.9 | 13 | 8913 | 69 |
| 113 | 6.2 | 42 | 3020 | 69 |
| 114 | 6.0 | 30 | 1072 | 151 |
| 115 | 4.6 | 10 | 4266 | 62 |
| 116 | 9.3 | 269 | n.c. | n.c. |
| 117 | 6.0 | 11 | >10000 | 269 |
| 118 | 4.0 | 33 | >10000 | 447 |
| 119 | 9.6 | 43 | >10000 | 3162 |
| 120 | ~29 | 3 | 5012 | 126 |
| 121 | 5.0 | 25 | >10000 | 282 |
| 122 | 6.8 | 1023 | ~1660 | 479 |
| 123 | 1.6 | 20 | ~447 | 195 |
| 124 | 6.8 | 219 | 832 | 49 |
| 125 | 3.5 | 1 | >10000 | 120 |
| 126 | 4.8 | 170 | >10000 | 468 |
| 127 | 2.0 | 25 | >10000 | 617 |
| 128 | 3.7 | ~41 | 1905 | 417 |
| 129 | 3.8 | 28 | 2042 | 251 |
| 130 | 6.0 | 115 | >10000 | 1000 |
| 131 | 5.9 | 166 | >10000 | 224 |
| 132 | 1.0 | 2 | ~1862 | 58 |
| 133 | 6.9 | 65 | 6607 | 389 |
| 134 | 4.8 | 107 | 2239 | 47 |
| 135 | 5.1 | 229 | >10000 | >10000 |
| 136 | 7.2 | 562 | >10000 | 724 |
| 137 | 6.3 | 36 | >10000 | 676 |
| 138 | 8.3 | 178 | 2570 | 44 |
| 139 | 13 | 182 | >10000 | 1122 |
| 140 | 8.3 | 145 | 6457 | 174 |
| 141 | 42 | 813 | >10000 | 79 |
| 142 | 42 | n.c. | ~9772 | >10000 |
| 143 | 1.3 | n.c. | 204 | ~81 |
| 144 | 2.0 | n.c. | 44 | 36 |
| 145 | 1.5 | n.c. | ~3388 | 71 |
| 146 | 1.3 | n.c. | 589 | 102 |
| 147 | 9.6 | n.c. | ~5012 | ~436 |
| 148 | 0.8 | n.c. | 282 | 93 |
| 149 | 0.7 | 8 | ~741 | 50 |
| 150 | 15 | 170 | >10000 | 2399 |
| 151 | 2.0 | 13 | 7079 | 871 |
| 152 | 17 | 135 | 7943 | 646 |
| 153 | 4.3 | 28 | >10000 | 1445 |
| 154 | 4.9 | 15 | 2291 | 646 |
| 155 | 9.3 | 126 | >10000 | 59 |
| 156 | 3.6 | 14 | ~7244 | 1259 |
| 157 | 12 | 182 | 141 | 45 |
| 158 | 10 | 123 | >10000 | 339 |
| 159 | 10 | 91 | >10000 | 1514 |
| 160 | 3.6 | 34 | ~5012 | 69 |
| 161 | 4.3 | 83 | 2239 | 204 |
| 162 | 7.2 | 35 | 2630 | 832 |
| 163 | 12 | 5 | >10000 | 309 |
| 164 | 2.6 | <0.66 | 4677 | 132 |
| 165 | 8.5 | 48 | >10000 | 1622 |
| 166 | 13 | 151 | >10000 | 37 |
| 167 | 13 | 62 | >10000 | 83 |
| 168 | 2.3 | 3 | 7586 | 631 |
| 169 | 3.9 | 16 | ~7079 | 389 |
| 170 | 2.2 | 7 | ~1778 | 417 |
| 171 | 6.2 | 1445 | n.c. | n.c. |
| 172 | 4.6 | ~10000 | n.c. | n.c. |
| 173 | 162 | n.c. | ~6310 | 6026 |
| 174 | 35 | n.c. | 3162 | 1549 |
| 175 | n.c. | n.c. | >10000 | 4074 |
| 176 | 32 | 76 | ~3311.31 | 65 |
| 177 | 10 | 28 | >10000 | 81 |
| 178 | 20 | 141 | 2344 | 98 |
| 179 | 6.2 | n.c. | ~10000 | 832 |
| 180 | 4.7 | 2 | ~6719 | 46 |
| 181 | 3.3 | 11 | ~9120 | 87 |
| 182 | 1.7 | 1 | 1380 | 151 |
| 183 | 22 | 35 | ~9772 | 1412 |
| 184 | 5.4 | 17 | >10000 | 224 |
| 185 | 6.0 | 20 | >10000 | 91 |
| 186 | 6.5 | 3 | 617 | 151 |
| 187 | 7.2 | 11 | >10000 | ~1380 |
| 188 | 2.9 | 4 | ~8128 | 138 |
| 189 | 17.0 | 51 | n.c. | n.c. |
| 190 | 11.7 | 110 | n.c. | n.c. |
| 191 | 107 | 4467 | n.c. | n.c. |
| 192 | 8.1 | 6 | >10000 | 91 |
| 193 | 25.1 | 91 | n.c. | n.c. |
| 194 | 3.1 | 29 | >10000 | 407 |
| 195 | 4.9 | 1 | >10000 | 158 |
| 196 | 8.3 | 36 | 5248 | 554 |
| 197 | 2.1 | 4 | ~2239 | 204 |
| 198 | 6.8 | 20 | >10000 | 112 |
| 199 | 3.5 | 25 | >10000 | 1905 |
| 200 | 5.9 | 20 | >10000 | 3548 |
| 201 | 3.4 | 2 | >10000 | 100 |
| 202 | 7.2 | 1950 | n.c. | n.c. |
| 203 | 4.0 | 25 | >10000 | 339 |
| 204 | 1.1 | 2 | ~6026 | 16 |
| 205 | 2.2 | 1 | ~4898 | 5 |
| 206 | 2.9 | 31 | n.c. | n.c. |
| 207 | 15.5 | 93 | n.c. | n.c. |
| 208 | 2.0 | 4 | ~4786 | 48 |
| 209 | 28.2 | 141 | n.c. | n.c. |
| 210 | 6.3 | 71 | >10000 | 1585 |
| 211 | 14.8 | 204 | n.c. | n.c. |
| 212 | 11.7 | 98 | >10000 | 257 |
| 213 | 5.6 | 27 | >10000 | 95 |
| 214 | 18.6 | 2630 | n.c. | n.c. |
| 215 | 168 | 3490 | n.c. | n.c. |
| 216 | 7.8 | n.c. | 2630 | 537 |
| 217 | 4.6 | 11 | ~7623 | 154 |
| 218 | 2.8 | 7 | ~7431 | 38 |
| 219 | 9.5 | 100 | n.c. | 214 |
| 220 | 5.6 | 11 | >10000 | 195 |
| 221 | 14.8 | ~105 | >10000 | 2291 |
| 222 | 12.0 | 15 | n.c. | n.c. |
| 223 | 224 | 269 | n.c. | n.c. |

Prophetic Composition Examples

"Active ingredient" (a.i.) as used throughout these examples relates to a compound of Formula (I), including any tautomer or stereoisomeric form thereof, or a pharmaceutically acceptable addition salt, or a solvate thereof; in particular to any one of the exemplified compounds.

Typical examples of recipes for the formulation of the invention are as follows:

1. Tablets

| | | |
|---|---|---|
| Active ingredient | 5 to 50 | mg |
| Di-calcium phosphate | 20 | mg |
| Lactose | 30 | mg |
| Talcum | 10 | mg |
| Magnesium stearate | 5 | mg |
| Potato starch | ad 200 | mg |

2. Suspension

An aqueous suspension is prepared for oral administration so that each milliliter contains 1 to 5 mg of active ingredient, 50 mg of sodium carboxymethyl cellulose, 1 mg of sodium benzoate, 500 mg of sorbitol and water ad 1 ml.

3. Injectable

A parenteral composition is prepared by stirring 1.5% (weight/volume) of active ingredient in 0.9% NaCl solution or in 10% by volume propylene glycol in water.

4. Ointment

| | | |
|---|---|---|
| Active ingredient | 5 to 1000 | mg |
| Stearyl alcohol | 3 | g |
| Lanoline | 5 | g |
| White petroleum | 15 | g |
| Water | ad 100 | g |

In this Example, active ingredient can be replaced with the same amount of any of the compounds according to the present invention, in particular by the same amount of any of the exemplified compounds.

The invention claimed is:
1. A compound of Formula (I):

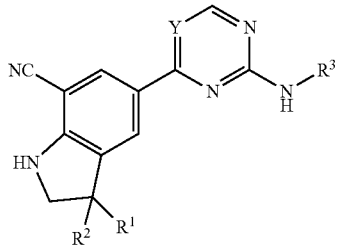

(I)

a tautomer or a stereoisomeric form thereof, wherein
$R^1$ represents $C_{1-4}$alkyl;
$R^2$ represents $C_{1-6}$alkyl, $C_{1-6}$alkyl substituted with one $R^5$, or $C_{1-6}$alkyl substituted with one, two or three fluoro atoms;
Y represents $CR^4$;
$R^4$ represents hydrogen or halo;
$R^5$ represents $Het^{3a}$, $-NR^{6a}R^{6b}$, or $-OR^7$;
$R^{6a}$ represents hydrogen or $C_{1-4}$alkyl;
$R^{6b}$ represents hydrogen; $C_{1-4}$alkyl; $C_{3-6}$cycloalkyl; $-C(=O)-C_{1-4}$alkyl; $-C(=O)-Het^4$; $-S(=O)_2-C_{1-4}$alkyl; $-C(=O)-C_{1-4}$alkyl substituted with one substituent selected from the group consisting of $-OH$ and $-NR^{16a}R^{16b}$; or $C_{1-4}$alkyl substituted with one substituent selected from the group consisting of $-OH$ and $-S(=O)_2-C_{1-4}$alkyl;
$R^7$ represents hydrogen, $C_{1-4}$alkyl, $-C_{1-4}$alkyl-$NR^{8a}R^{8b}$, $-C(=O)-R^9$, $-S(=O)_2-OH$, $-P(=O)_2-OH$, $-(C=O)-CH(NH_2)-_{1-4}$alkyl-$Ar^1$, or $-C_{1-4}$alkyl-$Het^{3b}$;
$R^{8a}$ represents hydrogen or $C_{1-4}$alkyl;
$R^{8b}$ represents hydrogen, $C_{1-4}$alkyl, or $C_{3-6}$cycloalkyl;
$R^9$ represents $C_{1-6}$alkyl, or $C_{1-6}$alkyl substituted with one substituent selected from the group consisting of $-NH_2$, $-COOH$, and $Het^6$;
$R^{16a}$ and $R^{16b}$ each independently represents hydrogen, $C_{1-4}$alkyl or $C_{3-6}$cycloalkyl;
$R^3$ represents a 5-membered heteroaromatic ring containing one, two or three heteroatoms each independently selected from O, S, and N;
wherein said 5-membered heteroaromatic ring may optionally be substituted, where possible, on one ring N-atom with a substituent selected from the group consisting of $C_{1-6}$alkyl; $C_{3-6}$cycloalkyl; $Het^{1a}$; $R^{18}$; $R^{21}$; $C_{1-4}$alkyl substituted with one, two or three halo atoms; $C_{1-5}$alkyl substituted with one, two or three $-OH$ substituents; $C_{1-6}$alkyl substituted with one $R^{13}$; $-C_{1-4}$alkyl-O-$C_{1-4}$alkyl substituted with one or two $-OH$ substituents; $C_{1-4}$alkyl substituted with one $R^{18}$; $C_{2-6}$alkenyl; and $C_{2-6}$alkenyl substituted with one $R^{13}$; provided that when $Het^{1a}$ or $R^{18}$ are directly attached to the N-atom of the 5-membered heteroaromatic ring, said $Het^{1a}$ or $R^{18}$ are attached to the N-atom via a ring carbon atom; and
wherein said 5-membered heteroaromatic ring may optionally be substituted on the ring carbon atoms with in total one or two substituents each independently selected from the group consisting of halo; cyano; $C_{1-6}$alkyl; $-O-C_{1-4}$alkyl; $-C(=O)-R^{10}$; $-S(=O)_2-C_{1-4}$alkyl; $-S(=O)(=N-R^{20a})-C_{1-4}$alkyl; $-O-C_{1-4}$alkyl substituted with one, two or three halo atoms; $-O-C_{1-4}$alkyl-$R^{12}$; $C_{3-6}$cycloalkyl; $-O-C_{3-6}$cycloalkyl; $Het^{1a}$; $-O-Het^{1b}$; $R^{18}$; $R^{21}$; $-P(=O)-(C_{1-4}$alkyl$)_2$; $-NH-C(=O)-C_{1-4}$alkyl; $-NH-C(=O)-Het^{1g}$; $-NR^{17a}R^{17b}$; $C_{1-4}$alkyl substituted with one, two or three halo atoms; $C_{1-4}$alkyl substituted with one, two or three $-OH$ substituents; $C_{1-6}$alkyl substituted with one $R^{13}$; $C_{1-4}$alkyl substituted with one $R^{18}$; $C_{2-6}$alkenyl; and $C_{2-6}$alkenyl substituted with one $R^{13}$;
$R^{10}$ represents $-OH$, $-O-C_{1-4}$alkyl, $-NR^{11a}R^{11b}$ or $Het^2$;
$R^{18}$ represents a 5-membered aromatic ring containing one, two or three N-atoms; wherein said 5-membered aromatic ring may optionally be substituted with one substituent selected from the group consisting of $C_{1-4}$alkyl and $C_{3-6}$cycloalkyl;
$R^{21}$ represents 3,6-dihydro-2H-pyran-4-yl or 1,2,3,6-tetrahydro-4-pyridinyl, wherein 1,2,3,6-tetrahydro-4-pyridinyl may optionally be substituted on the N-atom with $C_{1-4}$alkyl or $C_{3-6}$cycloalkyl;
$Het^{1a}$, $Het^{1c}$ and $Het^{1d}$ each independently represents a 4- to 7-membered monocyclic saturated heterocyclyl containing one or two heteroatoms each independently selected from O, S, $S(=O)_p$ and N; or a 6- to 11-membered bicyclic saturated heterocyclyl, including fused, spiro and bridged cycles, containing one, two or three heteroatoms each independently selected from O, S, $S(=O)_p$ and N;

wherein said 4- to 7-membered monocyclic saturated heterocyclyl or said 6- to 11-membered bicyclic saturated heterocyclyl may optionally be substituted, where possible, on one, two or three ring N-atoms with a substituent each independently selected from the group consisting of $C_{1-4}$alkyl, $C_{3-6}$cycloalkyl, $C_{1-4}$alkyl substituted with one, two or three halo atoms, and $C_{1-4}$alkyl substituted with one substituent selected from the group consisting of —OH, —C(=O)—OH, —C(=O)—$NR^{22a}R^{22b}$ and —O—$C_{1-4}$alkyl; and wherein said 4- to 7-membered monocyclic saturated heterocyclyl or said 6- to 11-membered bicyclic saturated heterocyclyl may optionally be substituted on one, two or three ring C-atoms with one or two substituents each independently selected from the group consisting of —OH, oxo, halo, $C_{1-4}$alkyl, cyano, —C(=O)—$C_{1-4}$alkyl, —$NH_2$, —$NH(C_{1-4}$alkyl), and —$N(C_{1-4}$alkyl$)_2$;

$Het^{1b}$, $Het^{1e}$, $Het^{1g}$ and $Het^4$ each independently represents a 4- to 7-membered monocyclic saturated heterocyclyl, attached to the remainder of the molecule of Formula (I) through any available ring carbon atom, said $Het^{1b}$, $Het^{1e}$, $Het^{1g}$ and $Het^4$ containing one or two heteroatoms each independently selected from O, S, $S(=O)_p$ and N; wherein said 4- to 7-membered monocyclic saturated heterocyclyl may optionally be substituted, where possible, on one or two ring N-atoms with a substituent each independently selected from the group consisting of $C_{1-4}$alkyl, $C_{3-6}$cyloalkyl, and $C_{1-4}$alkyl substituted with one substituent selected from the group consisting of —OH and —O—$C_{1-4}$alkyl; and wherein said 4- to 7-membered monocyclic saturated heterocyclyl may optionally be substituted on one, two or three ring C-atoms with one or two substituents each independently selected from the group consisting of —OH, halo, $C_{1-4}$alkyl, cyano, —C(=O)—$C_{1-4}$alkyl, —O—$C_{1-4}$alkyl, —$NH_2$, —$NH(C_{1-4}$alkyl), and —$N(C_{1-4}$alkyl$)_2$;

$Het^2$ represents a heterocyclyl of formula (b-1):

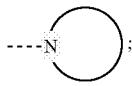

(b-1)

(b-1) represents a N-linked 4- to 7-membered monocyclic saturated heterocyclyl optionally containing one additional heteroatom selected from O, S, $S(=O)_p$ and N, or a N-linked 6- to 11-membered bicyclic saturated heterocyclyl, including fused, spiro and bridged cycles, optionally containing one or two additional heteroatoms each independently selected from O, S, $S(=O)_p$ and N;

wherein in case (b-1) contains one or two additional N-atoms, said one or two N-atoms may optionally be substituted with $C_{1-4}$alkyl; and wherein (b-1) may optionally be substituted on one, two or three ring C-atoms with one or two substituents each independently selected from the group consisting of halo, —OH, cyano, $C_{1-4}$alkyl, —O—$C_{1-4}$alkyl, —$NH_2$, —$NH(C_{1-4}$alkyl), —$N(C_{1-4}$alkyl$)_2$, and $C_{1-4}$alkyl-OH;

$R^{11b}$ represents hydrogen; $Het^{1e}$; $C_{1-4}$alkyl; $C_{1-4}$alkyl-$Het^5$; $C_{1-4}$alkyl substituted with one, two or three substituents each independently selected from the group consisting of halo, —OH and —O—$C_{1-4}$alkyl; $C_{3-6}$cycloalkyl; or $C_{3-6}$cycloalkyl substituted with one, two or three substituents each independently selected from the group consisting of halo, —OH and —O—$C_{1-4}$ alkyl;

$R^{13}$ represents —O—$C_{1-4}$alkyl, —C(=O)OH, —C(=O)$NR^{15a}R^{15b}$, —$NR^{19a}R^{19b}$, $C_{3-6}$cycloalkyl, $Het^{1d}$, $Het^7$, —S(=O)$_2$—$C_{1-4}$alkyl, —S(=O)(=N—$R^{20c}$)—$C_{1-4}$ alkyl, or —C(=O)—$Het^{1f}$;

$R^{12}$ represents —OH, —O—$C_{1-4}$alkyl, —$NR^{14a}R^{14b}$, —C(=O)$NR^{14c}R^{14d}$, —S(=O)$_2$—$C_{1-4}$alkyl, —S(=O)(=N—$R^{20b}$)—$C_{1-4}$alkyl, $C_{3-6}$cycloalkyl, $Ar^2$, or $Het^{1c}$;

$A^1$ represents phenyl optionally substituted with one hydroxy;

$Ar^2$ represents phenyl optionally substituted with one $C_{1-4}$alkyl;

$Het^{3a}$, $Het^{3b}$, $Het^5$, $Het^6$ and $Het^{1f}$ each independently represents a heterocyclyl of formula (c-1):

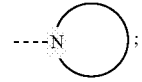

(c-1)

(c-1) represents a N-linked 4- to 7-membered monocyclic saturated heterocyclyl optionally containing one additional heteroatom selected from O, S, $S(=O)_p$ and N; wherein in case (c-1) contains one additional N-atom, said additional N-atom may optionally be substituted with $C_{1-4}$alkyl or $C_{3-6}$cycloalkyl; and wherein (c-1) may optionally be substituted on one or two ring C-atoms atoms with one or two substituents each independently selected from the group consisting of halo, $C_{1-4}$alkyl, and $C_{3-6}$cycloalkyl;

$Het^7$ represents 5,6,7,8-tetrahydro-imidazo[1,2-a]pyridinyl;

$R^{11a}$, $R^{14a}$, $R^{14c}$, $R^{15a}$, $R^{17a}$, $R^{19a}$ and $R^{22a}$ each independently represents hydrogen, $C_{1-4}$alkyl, or $C_{3-6}$cycloalkyl;

$R^{14b}$, $R^{14d}$, $R^{15b}$, $R^{17b}$, $R^{19b}$ and $R^{22b}$ each independently represents hydrogen; $C_{1-4}$alkyl; $C_{3-6}$cycloalkyl; or $C_{1-4}$alkyl substituted with one substituent selected from the group consisting of halo, —OH and —O—$C_{1-4}$ alkyl;

$R^{20a}$, $R^{20b}$ and $R^{20c}$ each independently represents hydrogen; $C_{1-4}$alkyl; $C_{3-6}$cycloalkyl; or $C_{1-4}$alkyl substituted with one substituent selected from the group consisting of —OH and —O—$C_{1-4}$alkyl;

p represents 1 or 2;

or a pharmaceutically acceptable addition salt, or a solvate thereof.

2. The compound according to claim 1, wherein $R^2$ represents $C_{1-6}$alkyl, or $C_{1-6}$alkyl substituted with one $R^5$;

Y represents $CR^4$;

$R^3$ represents a 5-membered heteroaromatic ring containing one, two or three heteroatoms each independently selected from O, S, and N;

wherein said 5-membered heteroaromatic ring may optionally be substituted, where possible, on one ring N-atom with a substituent selected from the group consisting of $C_{1-6}$alkyl; $C_{3-6}$cycloalkyl; Het$^{1a}$; R$^{18}$; R$^{21}$; $C_{1-4}$alkyl substituted with one, two or three halo atoms; $C_{1-4}$alkyl substituted with one, two or three —OH substituents; $C_{1-6}$alkyl substituted with one R$^{13}$; $C_{1-4}$alkyl substituted with one R$^{18}$; $C_{2-6}$alkenyl; and $C_{2-6}$alkenyl substituted with one R$^{13}$; provided that when Het$^{1a}$ or R$^{18}$ are directly attached to the N-atom of the 5-membered heteroaromatic ring, said Het$^{1a}$ or R$^{18}$ are attached to the N-atom via a ring carbon atom; and wherein said 5-membered heteroaromatic ring may optionally be substituted on the ring carbon atoms with in total one or two substituents each independently selected from the group consisting of halo; cyano; $C_{1-6}$alkyl; —O—$C_{1-4}$alkyl; —C(=O)—R$^{10}$; —S(=O)$_2$—$C_{1-4}$alkyl; —S(=O)(=N—R$^{20a}$)—$C_{1-4}$alkyl; —O—$C_{1-4}$alkyl substituted with one, two or three halo atoms; —O—$C_{1-4}$alkyl-R$^{12}$; $C_{3-6}$cycloalkyl; —O—$C_{3-6}$cycloalkyl; Het$^{1a}$; —O-Het$^{1b}$; R$^{18}$; R$^{21}$; —P(=O)—($C_{1-4}$alkyl)$_2$; —NH—C(=O)—$C_{1-4}$alkyl; —NH—C(=O)-Het$^{1g}$; —NR$^{17a}$R$^{17b}$; $C_{1-4}$alkyl substituted with one, two or three halo atoms; $C_{1-4}$alkyl substituted with one, two or three —OH substituents; $C_{1-6}$alkyl substituted with one R$^{13}$; $C_{1-4}$alkyl substituted with one R$^{18}$; $C_{2-6}$alkenyl; and $C_{2-6}$alkenyl substituted with one R$^{13}$;

R$^{13}$ represents —O—$C_{1-4}$alkyl, —C(=O)OH, —C(=O)NR$^{15a}$R$^{15b}$; —NR$^{19a}$R$^{19b}$, $C_{3-6}$cycloalkyl, Het$^{1d}$, —S(=O)$_2$—$C_{1-4}$alkyl, —S(=O)(=N—R$^{20c}$)—$C_{1-4}$alkyl, or —C(=O)—Het$^{1f}$.

3. The compound according to claim 1, wherein
R$^2$ represents $C_{1-6}$alkyl substituted with one R$^5$;
R$^{6b}$ represents hydrogen; or $C_{1-4}$alkyl substituted with one —OH substituent;
R$^7$ represents hydrogen or —C(=O)—R$^9$;
R$^9$ represents $C_{1-6}$alkyl;
R$^3$ represents a 5-membered heteroaromatic ring containing one, two or three heteroatoms each independently selected from O, S, and N;
wherein said 5-membered heteroaromatic ring may optionally be substituted, where possible, on one ring N-atom with a substituent selected from the group consisting of $C_{1-6}$alkyl; $C_{3-6}$cycloalkyl; Het$^{1a}$; $C_{1-4}$alkyl substituted with one, two or three halo atoms; $C_{1-5}$alkyl substituted with one, two or three —OH substituents; $C_{1-6}$alkyl substituted with one R$^{13}$; —$C_{1-4}$alkyl-O—$C_{1-4}$alkyl substituted with one or two —OH substituents; $C_{1-4}$alkyl substituted with one R$^{18}$; and $C_{2-6}$alkenyl; provided that when Het$^{1a}$ is directly attached to the N-atom of the 5-membered heteroaromatic ring, said Het$^{1a}$ is attached to the N-atom via a ring carbon atom; and
wherein said 5-membered heteroaromatic ring may optionally be substituted on the ring carbon atoms with in total one or two substituents each independently selected from the group consisting of halo; cyano; $C_{1-6}$alkyl; —O—$C_{1-4}$alkyl; —C(=O)—R$^{12}$; $C_{3-6}$cycloalkyl; —O—$C_{3-6}$cycloalkyl; Het$^{1a}$; —O-Het$^{1b}$; —P(=O)—($C_{1-4}$alkyl)$_2$; $C_{1-4}$alkyl substituted with one, two or three halo atoms; $C_{1-4}$alkyl substituted with one, two or three —OH substituents; and $C_{1-6}$alkyl substituted with one R$^{13}$;

R$_{10}$ represents —NR$^{11a}$R$^{11b}$ or Het$^2$;
Het$^{1a}$, Het$^{1c}$ and Het$^{1d}$ each independently represents a 4- to 7-membered monocyclic saturated heterocyclyl containing one or two heteroatoms each independently selected from O, S, S(=O)$_p$ and N; or a 6- to 11-membered bicyclic saturated heterocyclyl, including fused cycles, containing one, two or three heteroatoms each independently selected from O and N;

wherein said 4- to 7-membered monocyclic saturated heterocyclyl or said 6- to 11-membered bicyclic saturated heterocyclyl may optionally be substituted, where possible, on one, two or three ring N-atoms with a substituent each independently selected from the group consisting of $C_{1-4}$alkyl, $C_{1-4}$alkyl substituted with one, two or three halo atoms, and $C_{1-4}$alkyl substituted with one substituent selected from the group consisting of —C(=O)—OH, —C(=O)—NR$^{22a}$R$^{22b}$ and —O—$C_{1-4}$alkyl; and wherein said 4- to 7-membered monocyclic saturated heterocyclyl or said 6- to 11-membered bicyclic saturated heterocyclyl may optionally be substituted on one, two or three ring C-atoms with one or two substituents each independently selected from the group consisting of oxo, halo and $C_{1-4}$alkyl;

Het$^{1b}$ and Het$^{1a}$ each independently represents a 4- to 7-membered monocyclic saturated heterocyclyl, attached to the remainder of the molecule of Formula (I) through any available ring carbon atom, said Het$^{1b}$ and Het$^{1c}$ containing one or two O-atoms;

Het$^2$ represents a heterocyclyl of formula (b-1):

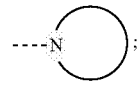

(b-1)

(b-1) represents a N-linked 4- to 7-membered monocyclic saturated heterocyclyl optionally containing one additional N-atom;
wherein in case (b-1) contains one additional N-atom, said N-atom may optionally be substituted with $C_{1-4}$alkyl;
R$^{11b}$ represents Het$^{1e}$; $C_{1-4}$alkyl; or $C_{3-6}$cycloalkyl;
R$^{13}$ represents —O—$C_{1-4}$alkyl, —C(=O)OH, —C(=O)NR$^{15a}$R$^{15b}$, —NR$^{19a}$R$^{19b}$ $C_{3-6}$cycloalkyl, Het$^{1d}$, Het$^7$, —S(=O)$_2$—$C_{1-4}$alkyl, or —C(=O)—Het$^{1f}$;
R$^{12}$ represents —O—$C_{1-4}$alkyl or Het$^{1e}$;
Het$^{3a}$ and Het$^{1f}$ each independently represents a heterocyclyl of formula (c-1):

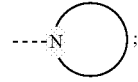

(c-1)

(c-1) represents a N-linked 4- to 7-membered monocyclic saturated heterocyclyl optionally containing one additional N-atom;
wherein in case (c-1) contains one additional N-atom, said additional N-atom may optionally be substituted with $C_{3-6}$cycloalkyl; and
wherein (c-1) may optionally be substituted on one or two ring C-atoms atoms with one or two halo substituents;
R$^{11a}$, R$^{15a}$, R$^{19a}$ and R$^{22a}$ each independently represents hydrogen, $C_{1-4}$alkyl, or $C_{3-6}$cycloalkyl;
R$^{15b}$, R$^{19b}$ and R$^{22b}$ each independently represents $C_{1-4}$alkyl or $C_{3-6}$cycloalkyl;
p represents 2.

4. The compound according to claim 1 or 2, wherein
$R^{6b}$ represents hydrogen; $C_{1-4}$alkyl; $C_{3-6}$cycloalkyl; —C(=O)—$C_{1-4}$alkyl; —C(=O)—$C_{1-4}$alkyl substituted with one substituent selected from the group consisting of —OH and —$NR^{16a}R^{16b}$; or $C_{1-4}$alkyl substituted with one —OH substituent;
$R^7$ represents hydrogen, $C_{1-4}$alkyl, —$C_{1-4}$alkyl-$NR^{8a}R^{8b}$, or —C(=O)—$R^9$;
$R^9$ represents $C_{1-6}$alkyl, or $C_{1-6}$alkyl substituted with one substituent selected from the group consisting of —$NH_2$, and —COOH;
$R^3$ represents a 5-membered heteroaromatic ring containing one, two or three heteroatoms each independently selected from O, S, and N;
wherein said 5-membered heteroaromatic ring may optionally be substituted, where possible, on one ring N-atom with a substituent selected from the group consisting of $C_{1-6}$alkyl; $C_{3-6}$cycloalkyl; $Het^{1a}$; $R^{18}$; $C_{1-4}$alkyl substituted with one, two or three halo atoms; $C_{1-4}$alkyl substituted with one, two or three —OH substituents; $C_{1-6}$alkyl substituted with one $R^{13}$; $C_{1-4}$alkyl substituted with one $R^{18}$; $C_{2-6}$alkenyl; and $C_{2-6}$alkenyl substituted with one $R^{13}$; provided that when $Het^{1a}$ or $R^{18}$ are directly attached to the N-atom of the 5-membered heteroaromatic ring, said $Het^{1a}$ or $R^{18}$ are attached to the N-atom via a ring carbon atom; and
wherein said 5-membered heteroaromatic ring may optionally be substituted on the ring carbon atoms with in total one or two substituents each independently selected from the group consisting of halo; cyano; $C_{1-6}$alkyl; —O—$C_{1-4}$alkyl; —C(=O)—$R^{10}$; —O—$C_{1-4}$alkyl substituted with one, two or three halo atoms; —O—$C_{1-4}$alkyl-$R^{12}$; $C_{3-6}$cycloalkyl; —O—$C_{3-6}$ cycloalkyl; $Het^{1a}$; —O—$Het^{1b}$; $R^{18}$; —P(=O)—$(C_{1-4}$ alkyl$)_2$; —NH—C(=O)—$C_{1-4}$alkyl; —NH—C(=O)-$Het^{1g}$; —$NR^{17a}R^{17b}$; $C_{1-4}$alkyl substituted with one, two or three halo atoms; $C_{1-4}$alkyl substituted with one, two or three —OH substituents; $C_{1-6}$alkyl substituted with one $R^{13}$; $C_{1-4}$alkyl substituted with one $R^{18}$; $C_{2-6}$alkenyl; and $C_{2-6}$alkenyl substituted with one $R^{13}$;
$Het^{1a}$, and $Het^{1d}$ each independently represents a 4- to 7-membered monocyclic saturated heterocyclyl containing one or two heteroatoms each independently selected from O, S, S(=O)$_p$ and N;
wherein said 4- to 7-membered monocyclic saturated heterocyclyl may optionally be substituted, where possible, on one, two or three ring N-atoms with a substituent each independently selected from the group consisting of $C_{1-4}$alkyl, $C_{3-6}$cycloalkyl, substituted with one, two or three halo atoms, and $C_{1-4}$alkyl substituted with one substituent selected from the group consisting of —OH, —C(=O)—OH, —C(=O)—$NR^{22a}R^{22b}$ and —O—$C_{1-4}$alkyl; and
wherein said 4- to 7-membered monocyclic saturated heterocyclyl may optionally be substituted on one, two or three ring C-atoms with one or two substituents each independently selected from the group consisting of —OH, oxo, halo, $C_{1-4}$alkyl, cyano, —C(=O)—$C_{1-4}$alkyl, —O—$C_{1-4}$alkyl, —$NH_2$, —NH($C_{1-4}$alkyl), and —N($C_{1-4}$alkyl)$_2$;
$Het^{1b}$, $Het^{1e}$, and $Het^{1g}$ each independently represents a 4- to 7-membered monocyclic saturated heterocyclyl, attached to the remainder of the molecule of Formula (I) through any available ring carbon atom, said $Het^{1b}$, $Het^{1e}$, and $Het^{1g}$ containing one or two heteroatoms each independently selected from O, S, S(=O)$_p$ and N;

wherein said 4- to 7-membered monocyclic saturated heterocyclyl may optionally be substituted, where possible, on one or two ring N-atoms with a substituent each independently selected from the group consisting of $C_{1-4}$alkyl, $C_{3-6}$cycloalkyl, and $C_{1-4}$alkyl substituted with one substituent selected from the group consisting of —OH and —O—$C_{1-4}$alkyl; and
wherein said 4- to 7-membered monocyclic saturated heterocyclyl may optionally be substituted on one, two or three ring C-atoms with one or two substituents each independently selected from the group consisting of —OH, halo, $C_{1-4}$alkyl, cyano, —C(=O)—$C_{1-4}$alkyl, —O—$C_{1-4}$alkyl, —$NH_2$, —NH($C_{1-4}$alkyl), and —N($C_{1-4}$alkyl)$_2$;
$Het^2$ represents a heterocyclyl of formula (b-1):

(b-1) represents a N-linked 4- to 7-membered monocyclic saturated heterocyclyl optionally containing one additional heteroatom selected from O, S, S(=O)$_p$ and N; wherein in case (b-1) contains one additional N-atom, said N-atom may optionally be substituted with $C_{1-4}$alkyl; and
wherein (b-1) may optionally be substituted on one, two or three ring C-atoms with one or two substituents each independently selected from the group consisting of halo, —OH, cyano, $C_{1-4}$alkyl, —O—$C_{1-4}$alkyl, —$NH_2$, —NH($C_{1-4}$alkyl), —N($C_{1-4}$alkyl)$_2$, and $C_{1-4}$alkyl-OH;
$R^{11b}$ represents hydrogen; $Het^{1e}$; $C_{1-4}$alkyl; $C_{1-4}$alkyl substituted with one, two or three substituents each independently selected from the group consisting of halo, —OH and —O—$C_{1-4}$alkyl; $C_{3-6}$cycloalkyl; or $C_{3-6}$cycloalkyl substituted with one, two or three substituents each independently selected from the group consisting of halo, —OH and —O—$C_{1-4}$alkyl;
$R^{13}$ represents —O—$C_{1-4}$alkyl, —C(=O)OH, —C(=O)$NR^{15a}R^{15b}$, —$NR^{19a}R^{19b}$, $C_{3-6}$cycloalkyl, $Het^{1d}$, —S(=O)$_2$—$C_{1-4}$alkyl, or —C(=O)—$Het^{1f}$;
$R^{12}$ represents —OH, —O—$C_{1-4}$alkyl, —$NR^{14a}R^{14b}$, —C(=O)$NR^{14c}R^{14d}$, —S(=O)$_2$—$C_{1-4}$alkyl, $C_{3-6}$cycloalkyl;
$Het^{3a}$, and $Het^{1f}$ each independently represents a heterocyclyl of formula (c-1):

(c-1) represents a N-linked 4- to 7-membered monocyclic saturated heterocyclyl optionally containing one additional heteroatom selected from O, S, S(=O)$_p$ and N; wherein in case (c-1) contains one additional N-atom, said additional N-atom may optionally be substituted with $C_{1-4}$alkyl or $C_{3-6}$cycloalkyl; and
wherein (c-1) may optionally be substituted on one or two ring C-atoms atoms with one or two substituents each independently selected from the group consisting of halo, $C_{1-4}$alkyl, and $C_{3-6}$cycloalkyl.

5. The compound according to claim 1 or 2, wherein
$R^2$ represents $C_{1-6}$alkyl substituted with one $R^5$;
$R^5$ represents $Het^{3a}$, $-NR^{6a}R^{6b}$, or $-OR^7$;
$R^{6a}$ represents $C_{1-4}$alkyl;
$R^{6b}$ represents $C_{1-4}$alkyl substituted with one $-OH$ substituent;
$R^7$ represents hydrogen, or $-C(=O)-R^9$;
$R^9$ represents $C_{1-6}$alkyl;
$R^3$ represents a 5-membered heteroaromatic ring containing two or three heteroatoms each independently selected from O, S, and N;
wherein said 5-membered heteroaromatic ring may optionally be substituted, where possible, on one ring N-atom with a substituent selected from the group consisting of $C_{1-6}$alkyl; $Het^{1a}$; $C_{1-4}$alkyl substituted with one, two or three halo atoms; $C_{1-4}$alkyl substituted with one, two or three $-OH$ substituents; $C_{1-6}$alkyl substituted with one $R^{13}$; substituted with one $R^{18}$; and $C_{2-6}$alkenyl; provided that when $Het^{1a}$ is directly attached to the N-atom of the 5-membered heteroaromatic ring, said $Het^{1a}$ is attached to the N-atom via a ring carbon atom; and
wherein said 5-membered heteroaromatic ring may optionally be substituted on the ring carbon atoms with in total one or two substituents each independently selected from the group consisting of halo; cyano; $C_{1-6}$alkyl; $-O-C_{1-4}$alkyl; $-C(=O)-R^{10}$; $C_{3-6}$cycloalkyl; $Het^{1a}$, $-P(=O)-(C_{1-4}alkyl)_2$; $C_{1-4}$alkyl substituted with one, two or three halo atoms; $C_{1-4}$alkyl substituted with one, two or three $-OH$ substituents; and substituted with one $R^{13}$;
$R^{10}$ represents $-NR^{11a}R^{11b}$ or $Het^2$;
$R^{18}$ represents a 5-membered aromatic ring containing one, two or three N-atoms;
wherein said 5-membered aromatic ring may optionally be substituted with one $C_{1-4}$alkyl;
$Het^{1a}$, and $Het^{1d}$ each independently represents a 4- to 7-membered monocyclic saturated heterocyclyl containing one or two heteroatoms each independently selected from O, S, $S(=O)_p$ and N;
wherein said 4- to 7-membered monocyclic saturated heterocyclyl may optionally be substituted, where possible, on one ring N-atom with a substituent each independently selected from the group consisting of $C_{4-4}$alkyl, $C_{1-4}$alkyl substituted with one, two or three halo atoms, and $C_{1-4}$alkyl substituted with one substituent selected from the group consisting of $-C(=O)-NR^{22a}R^{22b}$ and $-O-C_{1-4}$alkyl; and
wherein said 4- to 7-membered monocyclic saturated heterocyclyl may optionally be substituted on one, two or three ring C-atoms with one or two substituents each independently selected from the group consisting of oxo, halo, and $C_{1-4}$alkyl;
$Het^{1e}$ represents a 4- to 7-membered monocyclic saturated heterocyclyl, attached to the remainder of the molecule of Formula (I) through any available ring carbon atom, said $Het^{1e}$ containing one or two O-atoms;
$Het^2$ represents 1-piperidinyl;
$R^{11b}$ represents $Het^{1e}$; $C_{1-4}$alkyl; $C_{3-6}$cycloalkyl;
$R^{13}$ represents $-O-C_{1-4}$alkyl, $-C(=O)OH$, $-C(=O)NR^{15a}R^{15b}$, $-NR^{19a}R^{19b}$, $C_{3-6}$cycloalkyl, $Het^{1d}$, $-S(=O)_2-C_{1-4}$alkyl, or $-C(=O)-Het^{1f}$;
$Het^{3a}$, and $Het^{1f}$ each independently represents a heterocyclyl of formula (c-1):

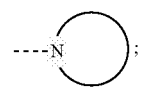

(c-1) represents a N-linked 4- to 7-membered monocyclic saturated heterocyclyl optionally containing one additional N-atom;
wherein in case (c-1) contains one additional N-atom, said additional N-atom may optionally be substituted with $C_{3-6}$cycloalkyl; and
wherein (c-1) may optionally be substituted on one or two ring C-atoms atoms with one or two halo substituents;
$R^{15b}$, $R^{19b}$ and $R^{22b}$ each independently represents $C_{1-4}$alkyl; or $C_{3-6}$cycloalkyl;
p represents 2.
6. The compound according to claim 1 or 2, wherein
$R^2$ represents $C_{1-6}$alkyl substituted with one $R^5$;
$R^4$ represents hydrogen;
$R^5$ represents $-OR^7$;
$R^7$ represents hydrogen, or $-C(=O)-R^9$;
$R^9$ represents $C_{1-6}$ alkyl;
$R^3$ represents a 5-membered heteroaromatic ring containing two or three heteroatoms each independently selected from S, and N;
wherein said 5-membered heteroaromatic ring may optionally be substituted, where possible, on one ring N-atom with a substituent selected from the group consisting of $C_{1-6}$alkyl; $C_{1-4}$alkyl substituted with one, two or three halo atoms; $C_{1-6}$alkyl substituted with one $R^{13}$; and $C_{1-4}$alkyl substituted with one $R^{18}$; and
wherein said 5-membered heteroaromatic ring may optionally be substituted on the ring carbon atoms with in total one or two substituents each independently selected from the group consisting of halo; $C_{1-6}$alkyl; $-C(=O)-R^{10}$; and $C_{1-4}$alkyl substituted with one, two or three $-OH$ substituents;
$R^{10}$ represents $-NR^{11a}R^{11b}$;
$R^{18}$ represents a 5-membered aromatic ring containing two N-atoms; wherein said 5-membered aromatic ring may optionally be substituted with one $C_{1-4}$alkyl;
$Het^{1d}$ represents a 4- to 7-membered monocyclic saturated heterocyclyl containing one or O-atom;
$R^{11}$ b represents $C_{1-4}$alkyl or $C_{3-6}$cycloalkyl;
$R^{13}$ represents $-O-C_{1-4}$alkyl, $-C(=O)NR^{15a}R^{15b}$, or $Het^{1d}$;
$R^{11a}$ and $R^{15a}$ each independently represents hydrogen or $C_{1-4}$alkyl;
$R^{15b}$ represents $C_{3-6}$cycloalkyl.
7. The compound according to any one of claims 1 to 6, wherein
$R^1$ represents methyl;
$R^2$ represents methyl or $-CH_2-OH$.
8. The compound according to any one of claims 1 to 5, wherein
$R^4$ is hydrogen or fluoro.
9. The compound according to any one of claims 1 to 5, wherein
$R^4$ is hydrogen.
10. The compound according to any one of claims 1 to 6, wherein
$R^5$ represents $-OR^7$; and
$R^7$ represents hydrogen.

11. The compound according to claim 1 or 2, wherein $R^3$ represents pyrazolyl optionally substituted on one ring N-atom with a substituent selected from the group consisting of $C_{1-6}$alkyl; $C_{3-6}$cycloalkyl; Het$^{1a}$; $R^{18}$; $R^{21}$; $C_{1-4}$alkyl substituted with one, two or three halo atoms; $C_{1-4}$alkyl substituted with one, two or three —OH substituents; $C_{1-6}$alkyl substituted with one $R^{13}$; $C_{1-4}$alkyl substituted with one $R^{18}$; $C_{2-6}$alkenyl; and $C_{2-6}$alkenyl substituted with one $R^{13}$; provided that when Het$^{1a}$ or $R^{18}$ are directly attached to the N-atom of the 5-membered heteroaromatic ring, said Het$^{1a}$ or $R^{18}$ are attached to the N-atom via a ring carbon atom; and wherein said 5-membered heteroaromatic ring may optionally be substituted on the ring carbon atoms with in total one or two substituents each independently selected from the group consisting of halo; cyano; $C_{1-6}$alkyl; —O—$C_{1-4}$alkyl; —C(=O)—$R^{10}$; —S(=O)$_2$—$C_{1-4}$alkyl; —S(=O)(=N—$R^{20a}$)—$C_{1-4}$alkyl; —O—$C_{1-4}$alkyl substituted with one, two or three halo atoms; —O—$C_{1-4}$alkyl-$R^{12}$; $C_{3-6}$cycloalkyl; —O—$C_{3-6}$cycloalkyl; Het$^{1a}$; —O-Het$^{1b}$; $R^{18}$; $R^{21}$; —P(=O)—($C_{1-4}$alkyl)$_2$; —NH—C(=O)—$C_{1-4}$alkyl; —NH—C(=O)-Het$^{1g}$; —NR$^{17a}$R$^{17b}$; $C_{1-4}$alkyl substituted with one, two or three halo atoms; $C_{1-4}$alkyl substituted with one, two or three —OH substituents; $C_{1-6}$alkyl substituted with one $R^{13}$; $C_{1-4}$alkyl substituted with one $R^{18}$; $C_{2-6}$alkenyl; and $C_{2-6}$alkenyl substituted with one $R^{13}$.

12. The compound according to claim 1, wherein the compound is selected from

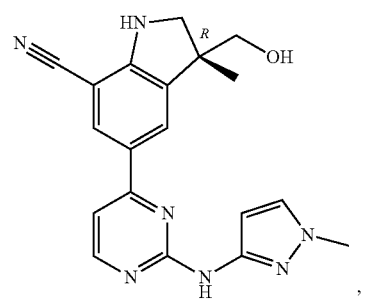

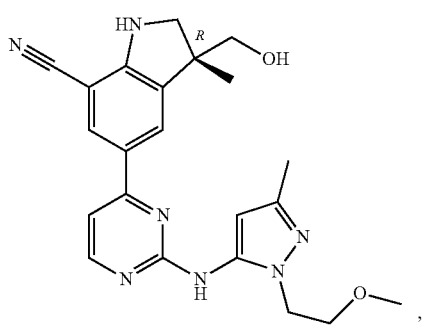

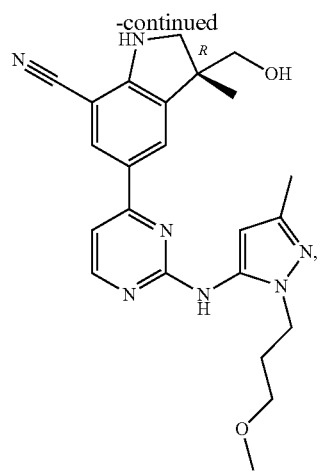

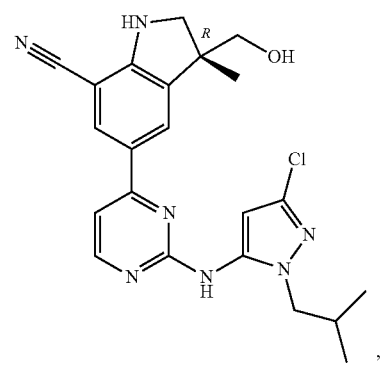

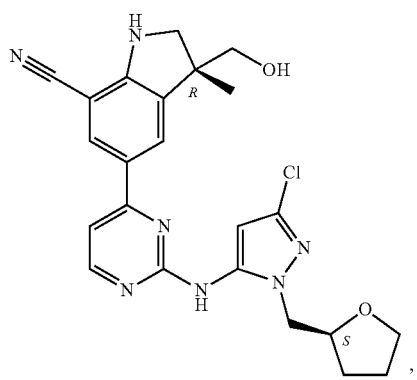

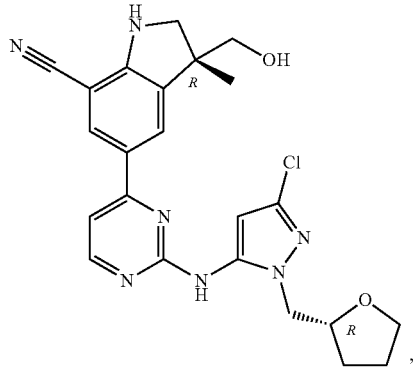

727
-continued
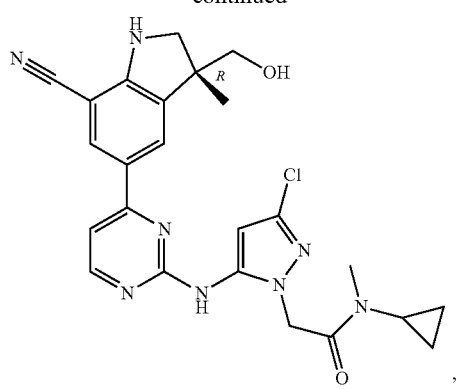
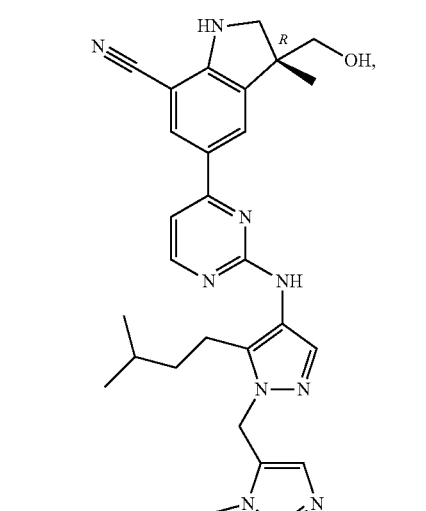
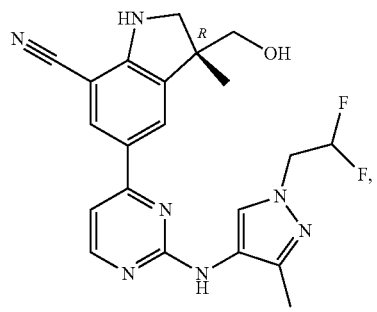
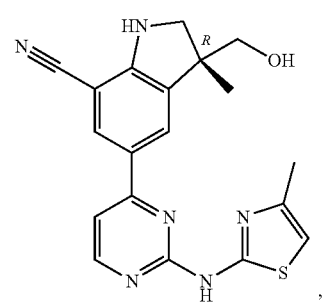
728
-continued
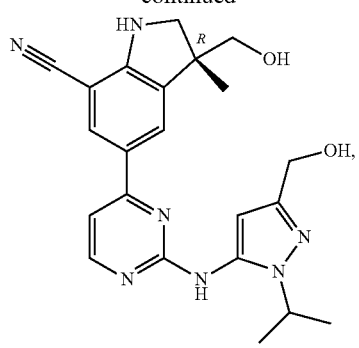
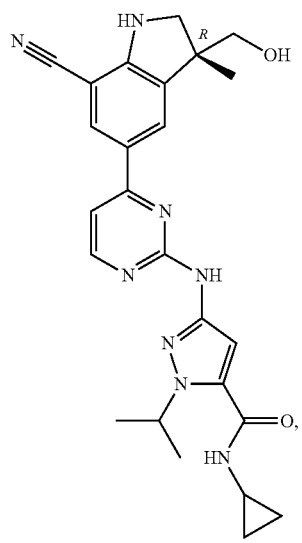
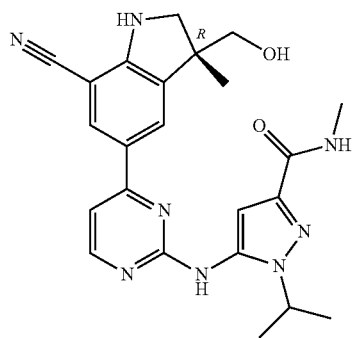
and
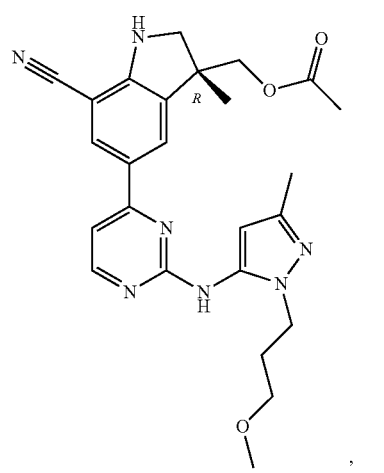

tautomers and stereoisomeric forms thereof, and the pharmaceutically acceptable addition salts, and the solvates thereof.

13. A pharmaceutical composition comprising a compound of claim 1 and a pharmaceutically acceptable carrier or diluent.

14. A method of treating a B-cell malignancy selected from multiple myeloma, hodgkins lymphoma, mantle cell lymphoma, diffuse large B-cell lymphoma and chronic lymphocytic leukemia in a warm-blooded animal comprising administering to said animal an effective amount of a compound as claimed in claim 1.

15. The method of claim 14 wherein the B-cell malignancy is multiple myeloma.

* * * * *